(12) United States Patent
Lander et al.

(10) Patent No.: US 6,727,063 B1
(45) Date of Patent: Apr. 27, 2004

(54) SINGLE NUCLEOTIDE POLYMORPHISMS IN GENES

(75) Inventors: Eric S. Lander, Cambridge, MA (US); Michele Cargill, Gaithersburg, MD (US); James S. Ireland, Gaithersburg, MD (US); Stacey Bolk, West Roxbury, MA (US); George Q. Daley, Weston, MA (US); Jeanette J. McCarthy, San Diego, CA (US)

(73) Assignees: Millennium Pharmaceuticals, Inc., Cambridge, MA (US); Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 09/657,472

(22) Filed: Sep. 7, 2000

Related U.S. Application Data

(60) Provisional application No. 60/220,947, filed on Jul. 26, 2000, provisional application No. 60/225,724, filed on Aug. 16, 2000, and provisional application No. 60/153,357, filed on Sep. 10, 1999.

(51) Int. Cl.[7] .............................. C12Q 1/68; C12P 19/34
(52) U.S. Cl. .......................... 435/6; 435/91.1; 435/91.2
(58) Field of Search .......................... 435/6, 91.1, 91.2; 536/23.1, 24.3

(56) References Cited

U.S. PATENT DOCUMENTS

| | | | |
|---|---|---|---|
| 5,279,966 A | 1/1994 | Jessell et al. | 435/320.1 |
| 5,750,502 A | 5/1998 | Jessell et al. | 514/12 |

OTHER PUBLICATIONS

Crawford et al., Cell; vol. 93, pp 1159–1170, 1998.*
LA Lange et al., Arterioscler Thromb Vasc Biol., "Autosomal Genome–Wide Scan for Coronary Artery Calcification Loci in Sibships at High Risk for Hypertension,"2002, 22:418–423.*
Accession No. AF102887, Oct. 1999.*
Accession No. X89963, Jan. 1998.*
Accession No. Z19091, Jun. 1993.*
Polymeropoulos, M.H., et al., "Dinucleotide Repeat Polymorphism at the Human Thrombospondin Gene THBS1," *Nucleic Acids Research*, 18(24):7467 (1990).
Wang, D.G., et al., "Large–Scale Identification, mapping, and Genotyping of Single–Nucleotide Polymorphisms in the Human Genome," *Science*, 280: 1077–1082 (1998).
Fan, J., et al., "Genetic mapping: Finding and Analyzing Single–Nucleotide Polymorphisms With High–Density DNA Arrays," American Journal of Human Genetics, 61 (4; suppl.): 1601 (1997).
Kalka, C., et al., "Novel Genes Containing the Thrombospondin Type 1 Domain Suppress the Development of Angiogenesis in an in–vivo Model of Peripheral Vascular Ischemia," *Circulation*, American Heart Association, Abstract No. 3825 from the 71st Scientific Sessions, Dallas, Texas, (Nov. 8–11, 1998).
Schymkowitz, J.W.H., et al., "Sequence Conservation Provides the Best Prediction of the Role of Proline Residues in p13sucl," *J. Mol. Biol., 301*:199–204 (2000).
Kyriakides, T.R., "Mice That Lack Thrombospondin 2 Display Connective Tissue Abnormalities That Are Associated with Disordered Collagen Fibrillogenesis, and Increased Vascular Density, and a Bleeding Diathesis," *J. Cell Biol., 140*(2) :419–430 (1998).
Yang, Z., et al., "Matricellular Proteins as Modulators of Cell–Matrix Interactions: Adhesive Defect in Thrombospondin 2–null Fibroblasts in a Consequence of Increased Levels of Matrix Metalloproteinase–2," *Mol. Biol. Cell, 11*(10) :3353–3364 (2000).
Lawler, J., et al., "Characterization of Human Thrombospondin–4*," *J. Biol. Chem.* 270(6) :2809–2814 (1995).

* cited by examiner

*Primary Examiner*—Jehanne Souaya
(74) *Attorney, Agent, or Firm*—Hamilton, Brook, Smith & Reynolds, P.C.

(57) ABSTRACT

The invention provides nucleic acid segments of the human genome, particularly nucleic acid segments from a gene, including polymorphic sites. Allele-specific primers and probes hybridizing to regions flanking or containing these sites are also provided. The nucleic acids, primers and probes are used in applications such as phenotype correlations, forensics, paternity testing, medicine and genetic analysis. A role for the thrombospondin gene(s) in vascular disease is also disclosed. Use of single nucleotide polymorphisms in the thrombospondin gene(s) for diagnosis, prediction of clinical course and treatment response, development of therapeutics and development of cell-culture-based and animal models for research and treatment are disclosed.

4 Claims, 8 Drawing Sheets

HT1220 Report

RECORD INFORMATION

| | |
|---|---|
| Gene ID: | 1220 |
| Sequence ID: | 1220 |
| Protein ID: | 1220 |
| Sequence name: | thrombospondin 1, alt. transcript 1 |
| Genome: | nucleus |
| Taxon: | Homo sapiens |
| Locus: | 1220 |
| Common Name: | thrombospondin 1 |
| Role ID: | 40 |

| | |
|---|---|
| Coding sequence length: | 3513 nt |
| Transcript sequence length: | 5722 nt |
| Expression data: | THC201673 |

ACCESSION DATA

HT1220 is derived from accessions(s):

SP:P07996 (THROMBOSPONDIN 1 PRECURSOR.)
GB:X04665 (Human mRNA for thrombospondin)
GB:X14787 (Human mRNA for thrombospondin)
GB:U12471 (thrombospondin-p50 {Homo sapiens})
GB:M99425 (Human thrombospondin mRNA, 3' end.)
PIR:G01478 (thrombospondin-p50 - human (fragment))
GB:U12471 (Human thrombospondin-1 gene, partial cds.)
GB:J04835 (Human thrombospondin gene, exons 1, 2 and 3.)
GB:M25631 (Homo sapiens (clone lambda-TS-33) thrombospondin (THBS) mRNA, 5' end.)

ALTERNATIVE SPLICE INFORMATION

Alternative splice forms for this gene:

HT3987 thrombospondin 1, alt. transcript 2

MAPPING DATA

GDB accession(s) for this gene:

GDB ID:   Symbol
-------------------

Figure 1A gdb:120438    THBS1 cDNA FEATURES

| Feature | End 5 | End 3 |
|---|---|---|
| coding_seq | 112 | 3624 |
| 3'UT | 3625 | 5722 |
| spjunc_h | 1235 | 1236 |

SEQUENCE nucleotide:

```
ggacgcacaggcattccccgcgcccctccagccctcgccgccctcgccaccgctcccggc
cgccgcgctccggtacacacaggatccctgctgggcaccaacagctccaccatggggctg
gcctggggactaggcgtcctgttcctgatgcatgtgtgtggcaccaaccgcattccagag
tctggcggagacaacagcgtgtttgacatctttgaactcaccgggccgccgcaagggg
tctgggcgccgactggtgaagggccccgaccttccagcccagctttccgcatcgaggat
gccaacctgatcccctgtgcctgatgacaagttccaagacctggtggatgctgtgcgg
gcagaaaagggttcctccttctggcatccctgaggcagatgaagaaccgggcacg
ctgctggccctggagcggaagaccactctggccaggtcttcagcgtggtgtccaatggc
aaggcgggcaccctggacctcagcctgaccgtccaaggaaagcagcacgtggtgtctgtg
gaagaagctctcctggcaaccggccagtggaagagcatccctgtttgtgcaggaagac
agggcccagctgtacatcgactgtgaaaagatggagaatgctgagttggacgtccccatc
caaagcgtcttcaccagagacctggccagcatcgccagactccgcatcgcaaagggggc
gtcaatgacaattcccaggggtgctgcagaatgtgaggttgtctttggaaccacacca
gaagacatcctcaggaacaaaggctgctccagctctaccagtgtcctcctcaccttgac
aacaacgtggtgaatggttccagccctgccatccgcactaactacattggccacaagaca
aagcacttgcaagccatctgcggcatctcctgtgatgagctgtccagcatggtcctggaa
ctcaggggcctgcgcaccattgtgaccacgctgcaggacagcatccgcaaagtgactgaa
gagaacaaagagttggccaatgagctgaggcggcctcccctatgctatcacaacggagtt
cagtacagaaataacgaggaatggactgttgatagctgcactgagtgtcactgtcagaac
tcagttaccatctgcaaaaaggtgtcctgccccatcatgccctgctccaatgccacagtt
cctgatggagaatgctgtcctcgctgttggccagcgactctgcggacgatggctggtct
ccatggtccgagtggacctcctgttctacgagctgtggcaatggaattcagcagcgcggc
cgctcctgcgatagcctcaacaaccgatgtgagggctcctcggtccagacacggacctgc
cacattcaggagtgtgacaaaagatttaaacaggatggtggctggagccactggtccccg
tggtcatcttgttctgtgacatgtggtgatggtgtgatcacaaggatccggctctgcaac
tctcccagccccagatgaatgggaaaccctgtgaaggcgaagcgcgggagaccaaagcc
tgcaagaaagacgcctgccccatcaatggaggctgggtccttggtcaccatgggacatc
tgttctgtcacctgtggaggaggggtacagaaacgtagtcgtctctgcaacaaccccgca
ccccagtttggaggcaaggactgcgttggtgatgtaacagaaaaccagatctgcaacaag
caggactgtccaattgatggatgcctgtccaatccctgctttgccggcgtgaagtgtact
agctaccctgatggcagctgcaaatgtggtgcttgtccccctggttacagtggaaatggc
atccagtgcacagatgttgatgagtgcaaagaagtgcctgatgcctgcttcaaccacaat
ggagagcaccggtgtgagaacacggaccccggctacaactgcctgcctgccccccacgc
ttcaccggctcacagcccttcggccaggtgtcgaacatgccacggccaacaaacaggtg
tgcaagccccgtaaccctgcacggatgggacccacgactgcaacaagaacgccaagtgc
aactacctgggccactatagcgacccatgtaccgctgcgagtgcaagcctggctacgct
ggcaatggcatcatctgcggggaggacacagacctggatggctggcccaatgagaacctg
gtgtgcgtggccaatgcgacttaccactgcaaaaaggataattgcccaaccttcccaac
tcagggcaggaagactatgacaaggatggaattggtgatgcctgtgatgatgacgatgac
aatgataaaattccagatgacagggacaactgtccattccattacaacccagctcagtat
gactatgacagagatgatgtgggagaccgctgtgacaactgtccctacaaccacaacccca
```

Figure 1B

```
gatcaggcagacacagacaacaatggggaaggagacgcctgtgctgcagacattgatgga
gacggtatcctcaatgaacgggacaactgccagtacgtctacaatgtggaccagagagac
actgatatggatggggttggagatcagtgtgacaattgcccttggaacacaatccggat
cagctggactctgactcagaccgcattggagatacctgtgacaacaatcaggatattgat
gaagatggccaccagaacaatctggacaactgtccctatgtgcccaatgccaaccaggct
gaccatgacaaagatggcaaggagatgcctgtgaccacgatgatgacaacgatggcatt
cctgatgacaaggacaactgcagactcgtgcccaatcccgaccagaaggactctgacggc
gatggtcgaggtgatgcctgcaaagatgattttgaccatgacagtgtgccagacatcgat
gacatctgtcctgagaatgttgacatcagtgagaccgatttccgccgattccagatgatt
cctctggacccaaagggacatcccaaaatgaccctaactgggttgtacgccatcagggt
aaagaactcgtccagactgtcaactgtgatcctggactcgctgtaggttatgatgagttt
aatgctgtggacttcagtggcaccttcttcatcaacaccgaaagggacgatgactatgct
ggatttgtctttggctaccagtccagcagccgcttttatgttgtgatgtggaagcaagtc
acccagtcctactgggacaccaaccccacgagggctcagggatactcgggcctttctgtg
aaagttgtaaactccaccacagggcctggcgagcacctgcggaacgccctgtggcacaca
ggaaacacccctggccaggtgcgcaccctgtggcatgaccctcgtcacataggctggaaa
gatttcacgcctacagatggcgtctcagccacaggccaaagacgggtttcattagagtg
gtgatgtatgaagggaagaaaatcatggctgactcaggacccatctatgataaaacctat
gctggtggtagactagggttgtttgtcttctctcaagaaatggtgttcttctctgacctg
aaatacgaatgtagagatccctaatcatcaaattgttgattgaaagactgatcataaacc
aatgctggtattgcaccttctggaactatgggcttgagaaaaccccaggatcacttctc
cttggcttccttctttttctgtgcttgcatcagtgtggactcctagaacgtgcgacctgcc
tcaagaaaatgcagttttcaaaaacagactcatcagcattcagcctccaatgaataagac
atcttccaagcatataaacaattgctttggtttccttttgaaaaagcatctacttgcttc
agttgggaaggtgcccattccactctgcctttgtcacagagcagggtgctattgtgaggc
catctctgagcagtggactcaaaagcatttcaggcatgtcagagaagggaggactcact
agaattagcaaacaaaaccaccctgacatcctccttcaggaacacggggagcagaggcca
aagcactaagggcagggcgcatacccgagacgattgtatgaagaaaatatggaggaactg
ttacatgttcggtactaagtcattttcaggggattgaaagactattgctggatttcatga
tgctgactggcgttagctgattaacccatgtaaataggcacttaaatagaagcaggaaag
ggagacaaagactggcttctggacttcctccctgatccccacccttactcatcaccttgc
agtggccagaattagggaatcagaatcaaaccagtgtaaggcagtgctggctgccattgc
ctggtcacattgaaattggtggcttcattctagatgtagcttgtgcagatgtagcaggaa
aataggaaaacctaccatctcagtgagcaccagctgcctcccaaaggaggggcagccgtg
cttatatttttatggttacaatggcacaaaattattatcaacctaactaaaacattcctt
ttctctttttccgtaattactaggtagttttctaattctctcttttggaagtatgattt
ttttaaagtcttttacgatgtaaaatatttatttttttacttattctggaagatctggctga
aggattattcatggaacaggaagaagcgtaaagactatccatgtcatctttgttgagagt
cttcgtgactgtaagattgtaaatacagattatttattaactctgttctgcctgaaatt
taggcttcatacggaaagtgtttgagagcaagtagttgacatttatcagcaaatctcttg
caagaacagcacaaggaaaatcagtctaataagctgctctgcccttgtgctcagagtgg
atgttatgggattcctttttctctgtttatcttttcaagtggaattagttggttatcc
atttgcaaatgttttaaattgcaaagaaagccatgaggtcttcaatactgttttacccca
tcccttgtgcatatttccagggagaaggaaagcatatacactttttcttcatttttcc
aaaagagaaaaaatgacaaaaggtgaaacttacatacaaatattacctcatttgttgtg
tgactgagtaaagaatttttggatcaagcggaaagagtttaagtgtctaacaaacttaaa
gctactgtagtacctaaaaagtcagtgttgtacatagcataaaaactctgcagagaagta
ttcccaataaggaaatagcattgaaatgttaaatacaattctgaaagttatgtttcttt
tctatcatctggtataccattgctttattttataaattatttctcattgccattggaa
tagaatattcagattgtgtagatatgctatttaaataatttatcaggaaatactgcctgt
agagttagtatttctattttatataatgtttgcacactgaattgaagaattgttggttt
tttcttttcttgttttctttttttttcttttttttttgcttttgacctcccatttta
ctatttgccaataccttttctaggaatgtgctttttttgtacacattttatccattt
tacattctaaagcagtgtaagttgtatattactgtttcttatgtacaaggaacaacaata
aatcatatggaaatttatattc
``` protein:

MGLAWGLGVLFLMHVCGTNRIPESGGDNSVFDIFELTGAARKGSGRRLVKGPDPSSPAFR

Figure 1C

```
IEDANLIPPVPDDKFQDLVDAVRAEKGFLLLASLRQMKKTRGTLLALERKDHSGQVFSVV
SNGKAGTLDLSLTVQGKQHVVSVEEALLATGQWKSITLFVQEDRAQLYIDCEKMENAELD
VPIQSVFTRDLASIARLRIAKGGVNDNFQGVLQNVRFVFGTTPEDILRNKGCSSSTSVLL
TLDNNVVNGSSPAIRTNYIGHKTKDLQAICGISCDELSSMVLELRGLRTIVTTLQDSIRK
VTEENKELANELRRPPLCYHNGVQYRNNEEWTVDSCTECHCQNSVTICKKVSCPIMPCSN
ATVPDGECCPRCWPSDSADDGWSPWSEWTSCSTSCGNGIQQRGRSCDSLNNRCEGSSVQT
RTCHIQECDKRFKQDGGWSHWSPWSSCSVTCGDGVITRIRLCNSPSPQMNGKPCEGEARE
TKACKKDACPINGGWGPWSPWDICSVTCGGGVQKRSRLCNNPAPQFGGKDCVGDVTENQI
CNKQDCPIDGCLSNPCFAGVKCTSYPDGSWKCGACPPGYSGNGIQCTDVDECKEVPDACF
NHNGEHRCENTDPGYNCLPCPPRFTGSQPFGQGVEHATANKQVCKPRNPCTDGTHDCNKN
AKCNYLGHYSDPMYRCECKPGYAGNGIICGEDTDLDGWPNENLVCVANATYHCKKDNCPN
LPNSGQEDYDKDGIGDACDDDDDNDKIPDDRDNCPFHYNPAQYDYDRDDVGDRCDNCPYN
HNPDQADTDNNGEGDACAADIDGDGILNERDNCQYVYNVDQRDTDMDGVGDQCDNCPLEH
NPDQLDSDSDRIGDTCDNNQDIDEDGHQNNLDNCPYVPNANQADHDKDGKGDACDHDDDN
DGIPDDKDNCRLVPNPDQKDSDGDGRGDACKDDFDHDSVPDIDDICPENVDISETDFRRF
QMIPLDPKGTSQNDPNWVVRHQGKELVQTVNCDPGLAVGYDEFNAVDFSGTFFINTERDD
DYAGFVFGYQSSSRFYVVMWKQVTQSYWDTNPTRAQGYSGLSVKVVNSTTGPGEHLRNAL
WHTGNTPGQVRTLWHDPRHIGWKDFTAYRWRLSHRPKTGFIRVVMYEGKKIMADSGPIYD
KTYAGGRLGLFVFSQEMVFFSDLKYECRDP
```

Figure 1D

HT2143 Report

RECORD INFORMATION

| | |
|---|---|
| Gene ID: | 2081 |
| Sequence ID: | 2143 |
| Protein ID: | 2125 |
| Sequence name: | thrombospondin 4 |
| Genome: | nucleus |
| Taxon: | Homo sapiens |
| Locus: | 2081 |
| Common Name: | thrombospondin 4 |
| Role ID: | 40 |

| | |
|---|---|
| Coding sequence length: | 2886 nt |
| Transcript sequence length: | 3074 nt |
| Expression data: | THC168897 |

ACCESSION DATA

HT2143 is derived from accessions(s):

SP:P35443 (THROMBOSPONDIN 4 PRECURSOR.)
GB:Z19585(thrombospondin-4 {Homo sapiens})
GB:Z19585(H.sapiens mRNA for thrombospondin-4)
PIR:A55710 (thrombospondin 4 precursor - human)

cDNA FEATURES

| Feature | End 5 | End 3 |
|---|---|---|
| coding_seq | 28 | 2913 |
| 3'UT | 2914 | 3074 |

SEQUENCE nucleotide:

gaattccggggagcaggaagagccaacatgctggccccgcgcggagccgccgtcctcctg
ctgcacctggtcctgcagcggtggctagcggcaggcgccaggccaccccccaggtcttt
gacttctcccatcttccagtcagaggctaaacccaggcgctctgctgccagtcctgaca
gaccccgccctgaatgatctctatgtgatttccaccttcaagctgcagactaaaagttca
gccaccatcttcggtctttactcttcaactgacaacagtaaatattttgaatttactgtg
atgggacgcttaagcaaagccatcctccgttacctgaagaacgatgggaaggtgcatttg

Figure 2A

```
gtggttttcaacaacctgcagctggcagacggaaggcggcacaggatcctcctgaggctg
agcaatttgcagcgagggggccggctccctagagctctacctggactgcatccaggtggat
tccgttcacaatctccccagggcctttgctggcccctcccagaaacctgagaccattgaa
ttgaggactttccagaggaagccacaggacttcttggaagagctgaagctggtggtgaga
ggctcactgttccaggtggccagcctgcaagactgcttcctgcagcagagtgagccactg
gctgccacaggcacaggggactttaaccggcagttcttgggtcaaatgacacaattaaac
caactcctgggagaggtgaaggaccttctgagacagcaggttaaggaaacatcatttttg
cgaaacaccatagctgaatgccaggcttgcggtcctctcaagtttcagtctccgacccca
agcacggtggtcgcccggctccccctgcaccgccaacacgcccacctcgtcggtgtgac
tccaacccatgtttccgaggtgtccaatgtaccgacagtagagatggcttccagtgtggg
ccctgccccgagggctacacaggaaacgggatcacctgtattgatgttgatgagtgcaaa
taccatccctgctacccgggcgtgcactgcataaatttgtctcctggcttcagatgtgac
gcctgcccagtgggcttcacagggcccatggtgcagggtgttgggatcagttttgccaag
tcaaacaagcaggtctgcactgacattgatgagtgtcgaaatggagcgtgcgttcccaac
tcgatctgcgttaatactttgggatcttaccgctgtgggccttgtaagccggggtatact
ggtgatcagataaggggatgcaaagtggaaagaaactgcagaaacccagagctgaaccct
tgcagtgtgaatgcccagtgcattgaagagaggcaggggatgtgacatgtgtgtgtgga
gtcggttgggctggagatggctatatctgtggaaaggatgtggacatcgacagttacccc
gacgaagaactgccatgctctgccaggaactgtaaaaaggacaactgcaaatatgtgcca
aattctggccaagaagatgcagacagagatggcattggcgacgcttgtgacgaggatgct
gacggagatgggatcctgaatgagcaggataactgtgtcctgattcataatgtggaccaa
aggaacagcgataaagatatctttggggatgcctgtgataactgcctgagtgtcttaaat
aacgaccagaaagacaccgatggggatggaagaggagatgcctgtgatgatgacatggat
ggagatgggaataaaaaaacattctggacaactgcccaaaatttcccaatcgtgaccaacgg
gacaaggatggtgatggtgtgggggatgcctgtgacagttgtcctgatgtcagcaaccct
aaccagtctgatgtggataatgatctggttggggactcctgtgacaccaatcaggacagt
gatggagatgggcaccaggacagcacagacaactgccccaccgtcattaacagtgcccag
ctggacaccgataaggatggaattggtgacgagtgtgatgatgatgatgacaatgatggt
atcccagacctggtgcccctggaccagacaactgccggctggtccccaacccagcccag
gaggatagcaacagcgacggagtgggagacatctgtgagtctgactttgaccaggaccag
gtcatcgatcggatcgacgtctgcccagagaacgcagaggtcacctgaccgacttcagg
gcttaccagaccgtgggcctggatcctgaaggggatgcccagatcgatcccaactgggtg
gtcctgaaccagggcatggagattgtacagaccatgaacagtgatcctggcctggcagtg
gggtacacagcttttaatggagttgacttcgaagggaccttccatgtgaatacccagaca
gatgatgactatgcaggctttatctttggctaccaagatagctccagcttctacgtggtc
atgtggaagcagacggagcagacatattggcaagccacccattccgagcagttgcagaa
cctggcattcagctcaaggctgtgaagtctaagacaggtccaggggagcatctccggaac
tccctgtggcacacgggggacaccagtgaccaggtcaggctgctgtggaaggactccagg
aatgtgggctggaaggacaaggtgtcctaccgctggttcctacagcacaggccccaggtg
ggctacatcagggtacgattttatgaaggctctgagttggtggctgactctggcgtcacc
atagacaccacaatgcgtggaggccgacttggcgttttctgcttctctcaagaaaacatc
atctggtccaacctcaagtatcgctgcaatgacaccatccctgaggacttccaagagttt
caaacccagaatttcgaccgcttcgataattaaaccaaggaagcaatctgtaactgcttt
tcggaacactaaaaccatatatatttaacttcaattttctttagcttttaccaacccaa
atatatcaaaacgttttatgtgaatgtggcaataaggagaagagatcattttaaaaaa
aaaaaaaaaaaaa protein:

MLAPRGAAVLLLHLVLQRWLAAGAQATPQVFDLLPSSSQRLNPGALLPVLTDPALNDLYV
ISTFKLQTKSSATIFGLYSSTDNSKYFEFTVMGRLSKAILRYLKNDGKVHLVVFNNLQLA
DGRRHRILLRLSNLQRGAGSLELYLDCIQVDSVHNLPRAFAGPSQKPETIELRTFQRKPQ
DFLEELKLVVRGSLFQVASLQDCFLQQSEPLAATGTGDFNRQFLGQMTQLNQLLGEVKDL
LRQQVKETSFLRNTIAECQACGPLKFQSPTPSTVVAPAPPAPPTRPPRRCDSNPCFRGVQ
CTDSRDGFQCGPCPEGYTGNGITCIDVDECKYHPCYPGVHCINLSPGFRCDACPVGFTGP
MVQGVGISFAKSNKQVCTDIDECRNGACVPNSICVNTLGSYRCGPCKPGYTGDQIRGCKV
ERNCRNPELNPCSVNAQCIEERQGDVTCVCGVGWAGDGYICGKDVDIDSYPDEELPCSAR
NCKKDNCKYVPNSGQEDADRDGIGDACDEDADGDGILNEQDNCVLIHNVDQRNSDKDIFG
DACDNCLSVLNNDQKDTDGDGRGDACDDDMDGDGIKNILDNCPKFPNRDQRDKDGDVGD
```

Figure 2B

```
ACDSCPDVSNPNQSDVDNDLVGDSCDTNQDSDGDGHQDSTDNCPTVINSAQLDTDKDGIG
DECDDDDDNDGIPDLVPPGPDNCRLVPNPAQEDSNSDGVGDICESDFDQDQVIDRIDVCP
ENAEVTLTDFRAYQTVGLDPEGDAQIDPNWVVLNQGMEIVQTMNSDPGLAVGYTAFNGVD
FEGTFHVNTQTDDDYAGFIFGYQDSSSFYVVMWKQTEQTYWQATPFRAVAEPGIQLKAVK
SKTGPGEHLRNSLWHTGDTSDQVRLLWKDSRNVGWKDKVSYRWFLQHRPQVGYIRVRFYE
GSELVADSGVTIDTTMRGGRLGVFCFSQENIIWSNLKYRCNDTIPEDFQEFQTQNFDRFD
N
```

Figure 2C

| Poly ID | Sequence ID | Position | Gene Description | Flanking Seq | Mutation Type | Re/ NT | Alt NT | Ref AA | Alt AA |
|---|---|---|---|---|---|---|---|---|---|
| G3344 | HT111220_mRNA | 2210 | THBS1, thrombospondin 1 | TGGATGGCTGGCCCAAGTGAGAACCTGGTGTG | Missense | A | G | N | S |
| G3955i2 | HTHT2143_mRNA | 1186 | THBS4, thrombospondin 4 | GAGTGTCGAAATGGAG/C CGTGCGTTCCCAACT | Missense | G | C | A | P |

SINGLE NUCLEOTIDE POLYMORPHISMS IN GENES

RELATED APPLICATIONS

This application claims the benefit of U.S. Provisional Application Serial No. 60/153,357, filed Sep. 10, 2000, U.S. Provisional Application Serial No. 60/220,947, filed Jul. 26, 2000, and U.S. Provisional Application Serial No. 60/225,724, filed Aug. 16, 2000, the entire teachings of all of which are incorporated herein by reference.

BACKGROUND OF THE INVENTION

The genomes of all organisms undergo spontaneous mutation in the course of their continuing evolution, generating variant forms of progenitor nucleic acid sequences (Gusella, Ann. Rev. Biochem. 55, 831–854 (1986)). The variant form may confer an evolutionary advantage or disadvantage relative to a progenitor form, or may be neutral. In some instances, a variant form confers a lethal disadvantage and is not transmitted to subsequent generations of the organism. In other instances, a variant form confers an evolutionary advantage to the species and is eventually incorporated into the DNA of many or most members of the species and effectively becomes the progenitor form. In many instances, both progenitor and variant form(s) survive and co-exist in a species population. The coexistence of multiple forms of a sequence gives rise to polymorphisms.

Several different types of polymorphism have been reported. A restriction fragment length polymorphism (RFLP) is a variation in DNA sequence that alters the length of a restriction fragment (Botstein et al., Am. J. Hum. Genet. 32, 314–331 (1980)). The restriction fragment length polymorphism may create or delete a restriction site, thus changing the length of the restriction fragment. RFLPs have been widely used in human and animal genetic analyses (see WO 90/13668; WO90/11369; Donis-Keller, Cell 51, 319–337 (1987); Lander et al., Genetics 121, 85–99 (1989)). When a heritable trait can be linked to a particular RFLP, the presence of the RFLP in an individual can be used to predict the likelihood that the animal will also exhibit the trait.

Other polymorphisms take the form of short tandem repeats (STRs) that include tandem di-, tri- and tetra-nucleotide repeated motifs. These tandem repeats are also referred to as variable number tandem repeat (VNTR) polymorphisms. VNTRs have been used in identity and paternity analysis (U.S. Pat. No. 5,075,217; Armour et al., FEBS Lett. 307, 113–115 (1992); Horn et al., WO 91/14003; Jeffreys, EP 370,719), and in a large number of genetic mapping studies.

Other polymorphisms take the form of single nucleotide variations between individuals of the same species. Such polymorphisms are far more frequent than RFLPs, STRs and VNTRs. Some single nucleotide polymorphisms (SNP) occur in protein-coding nucleic acid sequences (coding sequence SNP (cSNP)), in which case, one of the polymorphic forms may give rise to the expression of a defective or otherwise variant protein and, potentially, a genetic disease. Examples of genes in which polymorphisms within coding sequences give rise to genetic disease include β-globin (sickle cell anemia), apoE4 (Alzheimer's Disease), Factor V Leiden (thrombosis), and CFTR (cystic fibrosis). cSNPs can alter the codon sequence of the gene and therefore specify an alternative amino acid. Such changes are called "missense" when another amino acid is substituted, and "nonsense" when the alternative codon specifies a stop signal in protein translation. When the cSNP does not alter the amino acid specified the cSNP is called "silent".

Other single nucleotide polymorphisms occur in noncoding regions. Some of these polymorphisms may also result in defective protein expression (e.g., as a result of defective splicing). Other single nucleotide polymorphisms have no phenotypic effects.

Single nucleotide polymorphisms can be used in the same manner as RFLPs and VNTRs, but offer several advantages. Single nucleotide polymorphisms occur with greater frequency and are spaced more uniformly throughout the genome than other forms of polymorphism. The greater frequency and uniformity of single nucleotide polymorphisms means that there is a greater probability that such a polymorphism will be found in close proximity to a genetic locus of interest than would be the case for other polymorphisms. The different forms of characterized single nucleotide polymorphisms are often easier to distinguish than other types of polymorphism (e.g., by use of assays employing allele-specific hybridization probes or primers).

Only a small percentage of the total repository of polymorphisms in humans and other organisms has been identified. The limited number of polymorphisms identified to date is due to the large amount of work required for their detection by conventional methods. For example, a conventional approach to identifying polymorphisms might be to sequence the same stretch of DNA in a population of individuals by dideoxy sequencing. In this type of approach, the amount of work increases in proportion to both the length of sequence and the number of individuals in a population and becomes impractical for large stretches of DNA or large numbers of persons.

SUMMARY OF THE INVENTION

Work described herein pertains to the identification of polymorphisms which can predispose individuals to disease, by resequencing large numbers of genes in a large number of individuals. Various genes from a number of individuals have been resequenced as described herein, and SNPs in these genes have been discovered (see the Table and FIG. 3). Some of these SNPs are cSNPs which specify a different amino acid sequence, some of the SNPs are silent cSNPs and some of these cSNPs specify a stop signal in protein translation. Some of the identified SNPs were located in non-coding regions.

The invention relates to a gene which comprises a single nucleotide polymorphism at a specific location. In a particular embodiment the invention relates to the variant allele of a gene having a single nucleotide polymorphism, which variant allele differs from a reference allele by one nucleotide at the site(s) identified in the Table and FIG. 3. Complements of these nucleic acid sequences are also included. The nucleic acid molecules can be DNA or RNA, and can be double- or single-stranded. Nucleic acid molecules can be, for example, 5–10, 5–15, 10–20, 5–25, 10–30, 10–50 or 10–100 bases long.

The invention further provides allele-specific oligonucleotides that hybridize to the reference or variant allele of a gene comprising a single nucleotide polymorphism or to the complement thereof. These oligonucleotides can be probes or primers.

The invention further provides a method of analyzing a nucleic acid from an individual. The method determines which base is present at any one of the polymorphic sites shown in the Table and/or FIG. 3. Optionally, a set of bases occupying a set of the polymorphic sites shown in the Table and/or FIG. 3 is determined. This type of analysis can be performed on a number of individuals, who are tested for the presence of a disease phenotype. The presence or absence of disease phenotype is then correlated with a base or set of bases present at the polymorphic site or sites in the individuals tested.

Thus, the invention further relates to a method of predicting the presence, absence, likelihood of the presence or absence, or severity of a particular phenotype or disorder associated with a particular genotype. The method comprises obtaining a nucleic acid sample from an individual and determining the identity of one or more bases (nucleotides) at polymorphic sites of genes described herein, wherein the presence of a particular base is correlated with a specified phenotype or disorder, thereby predicting the presence, absence, likelihood of the presence or absence, or severity of the phenotype or disorder in the individual.

The thrombospondins are a family of extracellular matrix (ECM) glycoproteins that modulate many cell behaviors including adhesion, migration, and proliferation. Thrombospondins (also known as thrombin sensitive proteins or TSPs) are large molecular weight glycoproteins composed of three identical disulfide-linked polypeptide chains. The results described herein also reveal an important association between alterations, particularly SNPs, in TSP genes, particularly TSP-1 and TSP-4, and vascular disease. In particular, SNPs in these genes which are associated with premature coronary artery disease (CAD)(or coronary heart disease) and myocardial infarction (MI) have been identified and represent a potentially vital marker of upstream biology influencing the complex process of atherosclerotic plaque generation and vulnerability.

Thus, the invention relates to the TSP gene SNPs identified as described herein, both singly and in combination, as well as to the use of these SNPs, and others in TSP genes, particularly those nearby in linkage disequilibrium with these SNPs, for diagnosis, prediction of clinical course and treatment response for vascular disease, development of new treatments for vascular disease based upon comparison of the variant and normal versions of the gene or gene product, and development of cell-culture based and animal models for research and treatment of vascular disease. The invention further relates to novel compounds and pharmaceutical compositions for use in the diagnosis and treatment of such disorders. In preferred embodiments, the vascular disease is CAD or MI.

The invention relates to isolated nucleic acid molecules comprising all or a portion of the variant allele of TSP-1 (e.g., as exemplified by SEQ ID NO: 1), and to isolated nucleic acid molecules comprising all or a portion of the variant allele of TSP-4 (e.g., as exemplified by SEQ ID NO: 3). Preferred portions are at least 10 contiguous nucleotides and comprise the polymorphic site, e.g., a portion of SEQ ID NO: 1 which is at least 10 contiguous nucleotides and comprises the "G" at position 2210, or a portion of SEQ ID NO: 3 which is at least 10 contiguous nucleotides and comprises the "C" at position 1186. The invention further relates to isolated gene products, e.g., polypeptides or proteins, which are encoded by a nucleic acid molecule comprising all or a portion of the variant allele of TSP-1 or TSP-4 (e.g., SEQ ID NO: 1 or SEQ ID NO: 3, respectively). The invention also relates to nucleic acid molecules which hybridize to and/or share identity with the variant alleles identified herein (or their complements) and which also comprise the variant nucleotide at the SNP site.

The invention further relates to isolated proteins or polypeptides comprising all or a portion of the variant amino acid-sequence of TSP-1 (e.g., as exemplified by SEQ ID NO: 2), and to isolated proteins or polypeptides comprising all or a portion of the variant amino acid sequence of TSP-4 (e.g., as exemplified by SEQ ID NO: 4). Preferred polypeptides are at least 10 contiguous amino acids and comprise the polymorphic amino acid, e.g., a portion of SEQ ID NO: 2 which is at least 10 contiguous amino acids and comprises the serine at residue 700, or a portion of SEQ ID NO: 4 which is at least 10 contiguous amino acids and comprises the proline at residue 387. The invention further relates to isolated nucleic acid molecules encoding such proteins and polypeptides, as well as to antibodies which bind, e.g., specifically, to such proteins and polypeptides.

The invention further relates to a method of diagnosing or aiding in the diagnosis of a disorder associated with the presence of one or more of (a) a G at nucleotide position 2210 of SEQ ID NO: 1; or (b) a C at nucleotide position 1186 of SEQ ID NO: 3 in an individual. The method comprises obtaining a nucleic acid sample from the individual and determining the nucleotide present at one or more of the indicated nucleotide positions, wherein presence of one or more of (a) a G at nucleotide position 2210 of SEQ ID NO: 1; or (b) a C at nucleotide position 1186 of SEQ ID NO: 3 is indicative of increased likelihood of said disorder in the individual as compared with an appropriate control, e.g., an individual having the reference nucleotide at one or more of said positions. In a particular embodiment the disorder is a vascular disease selected from the group consisting of atherosclerosis, coronary heart or artery disease, MI, stroke, peripheral vascular diseases, venous thromboembolism and pulmonary embolism. In a preferred embodiment, the vascular disease is selected from the group consisting of CAD and M.

The invention further relates to a method of diagnosing or aiding in the diagnosis of a disorder associated with one or more of (a) a G at nucleotide position 2210 of SEQ ID NO: 1; or (b) a C at nucleotide position 1186 of SEQ ID NO: 3 in an individual. The method comprises obtaining a nucleic acid sample from the individual and determining the nucleotide present at one or more of the indicated nucleotide positions, wherein presence of one or more of (a) an A at nucleotide position 2210 of SEQ ID NO: 1; or (b) a G at nucleotide position 1186 of SEQ ID NO: 3 is indicative of decreased likelihood of said disorder in the individual as compared with an appropriate control, e.g., an individual having the variant nucleotide at said position. In a particular embodiment the disorder is a vascular disease selected from the group consisting of atherosclerosis, coronary heart or artery disease, MI, stroke, peripheral vascular diseases, venous thromboembolism and pulmonary embolism. In a preferred embodiment, the vascular disease is selected from the group consisting of CAD and MI.

In one embodiment, the invention relates to a method for predicting the likelihood that an individual will have a vascular disease (or aiding in the diagnosis of a vascular disease), comprising the steps of obtaining a DNA sample from an individual to be assessed and determining the nucleotide present at one or more of nucleotide positions 2210 of SEQ ID NO: 1 or 1186 of SEQ ID NO: 3. The presence of the reference nucleotide at one or more of these positions indicates that the individual has a lower likelihood of having a vascular disease than an individual having the variant nucleotide at one or more of these positions, or a lower likelihood of having severe symptomology. In a particular embodiment, the individual is an individual at risk for development of a vascular disease.

The invention further relates to a method of diagnosing or aiding in the diagnosis of a disorder associated with the presence of one or more of (a) a serine at amino acid position 700 of SEQ ID NO: 2; or (b) a proline at amino acid position 387 of SEQ ID NO: 4 in an individual. The method comprises obtaining a biological sample containing the TSP-1 and/or TSP-4 protein or relevant portion thereof from the individual and determining the amino acid present at one or more of the indicated amino acid positions, wherein presence of one or more of (a) a serine at amino acid position 700 of SEQ ID NO: 2; or (b) a proline at amino acid position 387 of SEQ ID NO: 4 is indicative of increased likelihood of said disorder in the individual as compared with an appropriate control, e.g., an individual having the reference amino acid at one or more of said positions.

The invention further relates to a method of diagnosing or aiding in the diagnosis of a disorder associated with one or more of (a) a serine at amino acid position 700 of SEQ ID NO: 2; or (b) a proline at amino acid position 387 of SEQ ID NO: 4 in an individual. The method comprises obtaining a biological sample containing the TSP-1 and/or TSP-4 protein or relevant portion thereof from the individual and determining the amino acid present at one or more of the indicated amino acid positions, wherein presence of one or more of (a) an asparagine at amino acid position 700 of SEQ ID NO: 2; or (b) an alanine at amino acid position 387 of SEQ ID NO: 4 is indicative of decreased likelihood of said disorder in the individual as compared with an appropriate control, e.g., an individual having the variant amino acid at one or more of said positions.

In one embodiment, the invention relates to a method for predicting the likelihood that an individual will have a vascular disease (or aiding in the diagnosis of a vascular disease), comprising the steps of obtaining a biological sample comprising the TSP-1 and/or TSP-4 protein or relevant portion thereof from an individual to be assessed and determining the amino acid present at one or more of amino acid positions 700 of SEQ ID NO: 2 or 387 of SEQ ID NO: 4. The presence of the reference amino acid at one or more of these positions indicates that the individual has a lower likelihood of having a vascular disease than an individual having the variant amino acid at one or more of these positions, or a lower likelihood of having severe symptomology. In a particular embodiment, the individual is an individual at risk for development of a vascular disease.

In another embodiment, the invention relates to pharmaceutical compositions comprising a reference TSP-1 and/or TSP-4 gene or gene product, or active portion thereof, for use in the treatment of vascular diseases. The invention further relates to the use of agonists and antagonists of TSP-1 and TSP-4 activity for use in the treatment of vascular diseases. In a particular embodiment the vascular disease is selected from the group consisting of atherosclerosis, coronary heart or artery disease, MI, stroke, peripheral vascular diseases, venous thromboembolism and pulmonary embolism. In a preferred embodiment, the vascular disease is selected from the group consisting of CAD and MI.

BRIEF DESCRIPTION OF THE DRAWINGS

FIGS. 1A–1D show the reference nucleotide (SEQ ID NO: 1) and amino acid (SEQ ID NO: 2) sequences for TSP-1.

FIGS. 2A–2C show the reference nucleotide (SEQ ID NO: 3) and amino acid (SEQ ID NO: 4) sequences for TSP4.

FIG. 3 shows a table providing detailed information about the SNPs identified herein. Column one shows the internal polymorphism identifier. Column two shows the accession number for the reference sequence in the TIGR database which can be found on the world wide web at tigr.org/tdb/hgi/searching/hgi_reports.html. Column three shows the nucleotide position for the SNP site. Column four shows the gene in which the polymorphism was identified. Column five shows the polymorphic site and additional flanking sequence on each side of the polymorphism. Column six shows the type of mutation produced by the polymorphism. Columns seven and eight show the reference and alternate (variant) nucleotides, respectively, for the SNP. Columns nine and ten show the reference and alternate (variant) amino acids, respectively, encoded by the alleles of the gene.

DETAILED DESCRIPTION OF THE INVENTION

The present invention relates to a gene which comprises a single nucleotide polymorphism (SNP) at a specific location. The gene which includes the SNP has at least two alleles, referred to herein as the reference allele and the variant allele. The reference allele (prototypical or wild type allele) has been designated arbitrarily and typically corresponds to the nucleotide sequence of the gene which has been deposited with GenBank or TIGR under a given Accession number. The variant allele differs from the reference allele by one nucleotide at the site(s) identified in the Table. The present invention also relates to variant alleles of the described genes and to complements of the variant alleles. The invention also relates to nucleic acid molecules which hybridize to and/or share identity with the variant alleles identified herein (or their complements) and which also comprise the variant nucleotide at the SNP site.

The invention further relates to portions of the variant alleles and portions of complements of the variant alleles which comprise (encompass) the site of the SNP and are at least 5 nucleotides in length. Portions can be, for example, 5–10, 5–15, 10–20, 5–25, 10–30, 10–50 or 10–100 bases long. For example, a portion of a variant allele which is 21 nucleotides in length includes the single nucleotide polymorphism (the nucleotide which differs from the reference allele at that site) and twenty additional nucleotides which flank the site in the variant allele. These nucleotides can be on one or both sides of the polymorphism. Polymorphisms which are the subject of this invention are defined in the Table with respect to the reference sequence deposited in GenBank or TIGR under the Accession number indicated. For example, the invention relates to a portion of a gene (e.g., AT3) having a nucleotide sequence as deposited in GenBank (e.g., U11270) comprising a single nucleotide polymorphism at a specific position (e.g., nucleotide 11918). The reference nucleotide for AT3 is shown in column 8, and the variant nucleotide is shown in column 9 of the Table. The nucleotide sequences of the invention can be double- or single-stranded.

The invention further provides allele-specific oligonucleotides that hybridize to the reference or variant allele of a gene comprising a single nucleotide polymorphism or to the complement thereof. These oligonucleotides can be probes or primers.

The invention further provides a method of analyzing a nucleic acid from an individual. The method determines which base is present at any one of the polymorphic sites shown in the Table and/or FIG. 3. Optionally, a set of bases occupying a set of the polymorphic sites shown in the Table and/or FIG. 3 is determined. This type of analysis can be performed on a number of individuals, who are tested for the presence of a disease phenotype. The presence or absence of disease phenotype is then correlated with a base or set of bases present at the polymorphic site or sites in the individuals tested.

Thus, the invention further relates to a method of predicting the presence, absence, likelihood of the presence or absence, or severity of a particular phenotype or disorder associated with a particular genotype. The method comprises obtaining a nucleic acid sample from an individual and determining the identity of one or more bases (nucleotides) at polymorphic sites of genes described herein, wherein the presence of a particular base is correlated with a specified phenotype or disorder, thereby predicting the presence, absence, likelihood of the presence or absence, or severity of the phenotype or disorder in the individual.

DEFINITIONS

A nucleic acid molecule or oligonucleotide can be DNA or RNA, and single- or double-stranded. Nucleic acid molecules and oligonucleotides can be naturally occurring or synthetic, but are typically prepared by synthetic means. Preferred nucleic acid molecules and oligonucleotides of the invention include segments of DNA, or their complements, which include any one of the polymorphic sites shown in the Table. The segments can be between 5 and 250 bases, and, in specific embodiments, are between 5–10, 5–20, 10–20, 10–50, 20–50 or 10–100bases. For example, the segment can be 21 bases. The polymorphic site can occur within any position of the segment. The segments can be from any of the allelic forms of DNA shown in the Table.

As used herein, the terms "nucleotide", "base" and "nucleic acid" are intended to be equivalent. The terms "nucleotide sequence", "nucleic acid sequence", "nucleic acid molecule" and "segment" are intended to be equivalent.

Hybridization probes are oligonucleotides which bind in a base-specific manner to a complementary strand of nucleic acid. Such probes include peptide nucleic acids, as described in Nielsen et al., *Science* 254, 1497–1500 (1991). Probes can be any length suitable for specific hybridization to the target nucleic acid sequence. The most appropriate length of the probe may vary depending upon the hybridization method in which it is being used; for example, particular lengths may be more appropriate for use in microfabricated arrays, while other lengths may be more suitable for use in classical hybridization methods. Such optimizations are known to the skilled artisan. Suitable probes and primers can range from about 5 nucleotides to about 30 nucleotides in length. For example, probes and primers can be 5, 6, 8, 10, 12, 14, 16, 18, 20, 22, 24, 25, 26, 28 or 30 nucleotides in length. The probe or primer preferably overlaps at least one polymorphic site occupied by any of the possible variant nucleotides. The nucleotide sequence can correspond to the coding sequence of the allele or to the complement of the coding sequence of the allele.

As used herein, the term "primer" refers to a single-stranded oligonucleotide which acts as a point of initiation of template-directed DNA synthesis under appropriate conditions (e.g., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template. The term primer site refers to the area of the target DNA to which a primer hybridizes. The term primer pair refers to a set of primers including a 5' (upstream) primer that hybridizes with the 5' end of the DNA sequence to be amplified and a 3' (downstream) primer that hybridizes with the complement of the 3' end of the sequence to be amplified.

As used herein, linkage describes the tendency of genes, alleles, loci or genetic markers to be inherited together as a result of their location on the same chromosome. It can be measured by percent recombination between the two genes, alleles, loci or genetic markers.

As used herein, polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic or biallelic polymorphism has two forms. A triallelic polymorphism has three forms.

Work described herein pertains to the resequencing of large numbers of genes in a large number of individuals to identify polymorphisms which can predispose individuals to disease. For example, polymorphisms in genes which are expressed in liver may predispose individuals to disorders of the liver. By altering amino acid sequence, SNPs may alter the function of the encoded proteins. The discovery of the SNP facilitates biochemical analysis of the variants and the development of assays to characterize the variants and to screen for pharmaceutical that would interact directly with on or another form of the protein. SNPs (including silent SNPs) also enable the development of specific DNA, RNA, or protein-based diagnostics that detect the presence or absence of the polymorphism in particular conditions.

A single nucleotide polymorphism occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele. Typically the polymorphic site is occupied by a base other than the reference base. For example, where the reference allele contains the base "T" at the polymorphic site, the altered allele can contain a "C", "G" or "A" at the polymorphic site.

The invention also relates to nucleic acid molecules which hybridize to the variant alleles identified herein (or their complements) and which also comprise the variant nucleotide at the SNP site. Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25–30° C., or equivalent conditions, are suitable for allele-specific probe hybridizations. Equivalent conditions can be determined by varying one or more of the parameters given as an example, as known in the art, while maintaining a similar degree of identity or similarity between the target nucleotide sequence and the primer or probe used.

The invention also relates to nucleic acid molecules which share substantial sequence identity to the variant alleles identified herein (or their complements) and which also comprise the variant nucleotide at the SNP site. Particularly preferred are nucleic acid molecules and fragments which have at least about 60%, preferably at least about 70, 80 or 85%, more preferably at least about 90%, even more preferably at least about 95%, and most preferably at least about 98% identity with nucleic acid molecules described herein. The percent identity of two nucleotide or amino acid sequences can be determined by aligning the sequences for optimal comparison purposes (e.g., can be introduced in the sequence of a first sequence). The nucleotides or amino acids at corresponding positions are then compared, and the percent identity between the two sequences is a function of the number of identical positions shared by the sequences (i.e., % identity=# of identical positions/total # of positions× 100). In certain embodiments, the length of a sequence aligned for comparison purposes is at least 30%, preferably at least 40%, more preferably at least 60%, and even more preferably at least 70%, 80% or 90% of the length of the reference sequence. The actual comparison of the two sequences can be accomplished by well-known methods, for example, using a mathematical algorithm. A preferred, non-limiting example of such a mathematical algorithm is described in Karlin et al., *Proc. Natl. Acad. Sci. USA*, 90:5873–5877 (1993). Such an algorithm is incorporated into the NBLAST and XBLAST programs (version 2.0) as described in Altschul et al., *Nucleic Acids Res.*, 25:389–3402 (1997). When utilizing BLAST and Gapped BLAST programs, the default parameters of the respective programs (e.g., NBLAST) can be used. See the world wide web at ncbi.nlm.nih.gov. In one embodiment, parameters for sequence comparison can be set at score=100, wordlength= 12, or can be varied (e.g., W=5 or W=20).

The term "isolated" is used herein to indicate that the material in question exists in a physical milieu distinct from that in which it occurs in nature. For example, an isolated nucleic acid of the invention may be substantially isolated with respect to the complex cellular milieu in which it naturally occurs. In some instances, the isolated material will form part of a composition (for example, a crude extract containing other substances), buffer system or reagent mix. In other circumstance, the material may be purified to essential homogeneity, for example as determined by PAGE or column chromatography such as HPLC. Preferably, an isolated nucleic acid comprises at least about 50, 80 or 90 percent (on a molar basis) of all macromolecular species present.

I. Novel Polymorphisms of the Invention

Some of the novel polymorphisms of the invention are shown in the Table. Columns one and two show designations for the indicated polymorphism. Column three shows the Genbank or TIGR Accession number for the wild type (or reference) allele. Column four shows the location of the polymorphic site in the nucleic acid sequence with reference to the Genbank or TIGR sequence shown in column three. Column five shows common names for the gene in which the polymorphism is located. Column six shows the polymorphism and a portion of the 3' and 5' flanking sequence of the gene. Column seven shows the type of mutation; N, nonsense, S, silent, M, missense. Columns eight and nine show the reference and alternate nucleotides, respectively, at the polymorphic site. Columns ten and eleven show the reference and alternate amino acids, respectively, encoded by the reference and variant, respectively, alleles. Other novel polymorphisms of the invention are shown in FIG. 3.

II. Analysis of Polymorphisms

A. Preparation of Samples

Polymorphisms are detected in a target nucleic acid from an individual being analyzed. For assay of genomic DNA, virtually any biological sample (other than pure red blood cells) is suitable. For example, convenient tissue samples include whole blood, semen, saliva, tears, urine, fecal material, sweat, buccal, skin and hair. For assay of cDNA or mRNA, the tissue sample must be obtained from an organ in which the target nucleic acid is expressed. For example, if the target nucleic acid is a cytochrome P450, the liver is a suitable source.

Many of the methods described below require amplification of DNA from target samples. This can be accomplished by e.g., PCR. See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et a., *PCR Methods and Applications* 1, 17 (1991); PCR (eds. McPherson et al., IRL Press, Oxford); and U.S. Pat. No. 4,683,202.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

B. Detection of Polymorphisms in Target DNA

There are two distinct types of analysis of target DNA for detecting polymorphisms. The first type of analysis, sometimes referred to as de novo characterization, is carried out to identify polymorphic sites not previously characterized (i.e., to identify new polymorphisms). This analysis compares target sequences in different individuals to identify points of variation, i.e., polymorphic sites. By analyzing groups of individuals representing the greatest ethnic diversity among humans and greatest breed and species variety in plants and animals, patterns characteristic of the most common alleles/haplotypes of the locus can be identified, and the frequencies of such alleles/haplotypes in the population can be determined. Additional allelic frequencies can be determined for subpopulations characterized by criteria such as geography, race, or gender. The de novo identification of polymorphisms of the invention is described in the Examples section. The second type of analysis determines which form(s) of a characterized (known) polymorphism are present in individuals under test. There are a variety of suitable procedures, which are discussed in turn.

1. Allele-Specific Probes

The design and use of allele-specific probes for analyzing polymorphisms is described by e.g., Saiki et al., *Nature* 324, 163–166 (1986); Dattagupta, EP 235,726, Saiki, WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15-mer at the 7 position; in a 16-mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

2. Tiling Arrays

The polymorphisms can also be identified by hybridization to nucleic acid arrays, some examples of which are described in WO 95/11995. One form of such arrays is described in the Examples section in connection with de novo identification of polymorphisms. The same array or a different array can be used for analysis of characterized polymorphisms. WO 95/11995 also describes subarrays that are optimized for detection of a variant form of a precharacterized polymorphism. Such a subarray contains probes designed to be complementary to a second reference sequence, which is an allelic variant of the first reference sequence. The second group of probes is designed by the same principles as described in the Examples, except that the probes exhibit complementarity to the second reference sequence. The inclusion of a second group (or further groups) can be particularly useful for analyzing short subsequences of the primary reference sequence in which multiple mutations are expected to occur within a short distance commensurate with the length of the probes (e.g., two or more mutations within 9 to 21 bases).

3. Allele-Specific Primers

An allele-specific primer hybridizes to a site on target DNA overlapping a polymorphism and only primes amplification of an allelic form to which the primer exhibits perfect complementarity. See Gibbs, *Nucleic Acid Res.* 17, 2427–2448 (1989). This primer is used in conjunction with a second primer which hybridizes at a distal site. Amplification proceeds from the two primers, resulting in a detectable product which indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer (see, e.g., WO 93/22456).

4. Direct-Sequencing

The direct analysis of the sequence of polymorphisms of the present invention can be accomplished using either the dideoxy chain termination method or the Maxam—Gilbert method (see Sambrook et al., *Molecular Cloning, A Laboratory Manual* (2nd Ed., CSHP, New York 1989); Zyskind et al., *Recombinant DNA Laboratory Manual*, (Acad. Press, 1988)).

5. Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., PCR *Technology, Principles and Applications for DNA Amplification*, (W. H. Freeman and Co, New York, 1992), Chapter 7.

6. Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et at., *Proc. Nat. Acad. Sci.* 86, 2766–2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence differences between alleles of target sequences.

7. Single-Base Extension

An alternative method for identifying and analyzing polymorphisms is based on single-base extension (SBE) of a fluorescently-labeled primer coupled with fluorescence resonance energy transfer (FRET) between the label of the added base and the label of the primer. Typically, the method, such as that described by Chen et al., (*PNAS* 94:10756–61 (1997), incorporated herein by reference) uses a locus-specific oligonucleotide primer labeled on the 5' terminus with 5-carboxyfluorescein (FAM). This labeled primer is designed so that the 3' end is immediately adjacent to the polymorphic site of interest. The labeled primer is hybridized to the locus, and single base extension of the labeled primer is performed with fluorescently labeled dideoxyribonucleotides (ddNTPs) in dye-terminator sequencing fashion, except that no deoxyribonucleotides are present. An increase in fluorescence of the added ddNTP in response to excitation at the wavelength of the labeled primer is used to infer the identity of the added nucleotide.

III. Methods of Use

After determining polymorphic form(s) present in an individual at one or more polymorphic sites, this information can be used in a number of methods.

A. Forensics

Determination of which polymorphic forms occupy a set of polymorphic sites in an individual identifies a set of polymorphic forms that distinguishes the individual. See generally National Research Council, *The Evaluation of Forensic DNA Evidence* (Eds. Pollard et al., National Academy Press, DC, 1996). The more sites that are analyzed, the lower the probability that the set of polymorphic forms in one individual is the same as that in an unrelated individual. Preferably, if multiple sites are analyzed, the sites are unlinked. Thus, polymorphisms of the invention are often used in conjunction with polymorphisms in distal genes. Preferred polymorphisms for use in forensics are biallelic because the population frequencies of two polymorphic forms can usually be determined with greater accuracy than those of multiple polymorphic forms at multi-allelic loci.

The capacity to identify a distinguishing or unique set of forensic markers in an individual is useful for forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers does match, one can conclude that the DNA from the suspect is consistent with that found at the crime scene. If frequencies of the polymorphic forms at the loci tested have been determined (e.g., by analysis of a suitable population of individuals), one can perform a statistical analysis to determine the probability that a match of suspect and crime scene sample would occur by chance.

p(ID) is the probability that two random individuals have the same polymorphic or allelic form at a given polymorphic site. In biallelic loci, four genotypes are possible: AA, AB, BA, and BB. If alleles A and B occur in a haploid genome of the organism with frequencies x and y, the probability of each genotype in a diploid organism is (see WO 95/12607):

Homozygote: $p(AA)=x^2$

Homozygote: $p(BB)=y^2=(1-x)^2$

Single Heterozygote: $p(AB)=p(BA)=xy=x(1-x)$

Both Heterozygotes: $p(AB+BA)=2xy=2x(1-x)$

The probability of identity at one locus (i.e, the probability that two individuals, picked at random from a population will have identical polymorphic forms at a given locus) is given by the equation:

$$p(ID)=(x^2)^2+(2xy)^2+(y^2)^2.$$

These calculations can be extended for any number of polymorphic forms at a given locus. For example, the probability of identity p(ID) for a 3-allele system where the alleles have the frequencies in the population of x, y and z, respectively, is equal to the sum of the squares of the genotype frequencies:

$$p(ID)=x^4+(2xy)^2+(2yz)^2+(2yz)^2+z^4+y^4$$

In a locus of n alleles, the appropriate binomial expansion is used to calculate p(ID) and p(exc).

The cumulative probability of identity (cum p(ID)) for each of multiple unlinked loci is determined by multiplying the probabilities provided by each locus.

cum p(ID)=p(ID1)p(ID2)p(ID3) . . . p(IDn)

The cumulative probability of non-identity for n loci (i.e. the probability that two random individuals will be different at 1 or more loci) is given by the equation:

cum p(nonID)=1−cum p(ID).

If several polymorphic loci are tested, the cumulative probability of non-identity for random individuals becomes very high (e.g., one billion to one). Such probabilities can be taken into account together with other evidence in determining the guilt or innocence of the suspect.

B. Paternity Testing

The object of paternity testing is usually to determine whether a male is the father of a child. In most cases, the mother of the child is known and thus, the mother's contribution to the child's genotype can be traced. Paternity testing investigates whether the part of the child's genotype not attributable to the mother is consistent with that of the putative father. Paternity testing can be performed by analyzing sets of polymorphisms in the putative father and the child.

If the set of polymorphisms in the child attributable to the father does not match the set of polymorphisms of the putative father, it can be concluded, barring experimental error, that the putative father is not the real father. If the set of polymorphisms in the child attributable to the father does match the set of polymorphisms of the putative father, a statistical calculation can be performed to determine the probability of coincidental match.

The probability of parentage exclusion (representing the probability that a random male will have a polymorphic form at a given polymorphic site that makes him incompatible as the father) is given by the equation (see WO 95/12607):

$$p(exc)=xy(1-xy)$$

where x and y are the population frequencies of alleles A and B of a biallelic polymorphic site.

(At a triallelic site $p(exc)=xy(1-xy)+yz(1-yz)+xz(1-xz)+3xyz(1-xyz)$), where x, y and z and the respective population frequencies of alleles A, B and C).

The probability of non-exclusion is p(non-exc)=1−p(exc)

The cumulative probability of non-exclusion (representing the value obtained when n loci are used) is thus:

cum p(non-exc)=p(non-exc1)p(non-exc2)p(non-exc3) . . . p(non-excn)

The cumulative probability of exclusion for n loci (representing the probability that a random male will be excluded) cum p(exc)=1−cum p(non-exc).

If several polymorphic loci are included in the analysis, the cumulative probability of exclusion of a random male is very high. This probability can be taken into account in assessing the liability of a putative father whose polymorphic marker set matches the child's polymorphic marker set attributable to his/her father.

C. Correlation of Polymorphisms with Phenotypic Traits

The polymorphisms of the invention may contribute to the phenotype of an organism in different ways. Some polymorphisms occur within a protein coding sequence and contribute to phenotype by affecting protein structure. The effect may be neutral, beneficial or detrimental, or both beneficial and detrimental, depending on the circumstances. For example, a heterozygous sickle cell mutation confers resistance to malaria, but a homozygous sickle cell mutation is usually lethal. Other polymorphisms occur in noncoding regions but may exert phenotypic effects indirectly via influence on replication, transcription, and translation. A single polymorphism may affect more than one phenotypic trait. Likewise, a single phenotypic trait may be affected by polymorphisms in different genes. Further, some polymorphisms predispose an individual to a distinct mutation that is causally related to a certain phenotype.

Phenotypic traits include diseases that have known but hitherto unmapped genetic components (e.g., agammaglobulimenia, diabetes insipidus, Lesch-Nyhan syndrome, muscular dystrophy, Wiskott-Aldrich syndrome, Fabry's disease, familial hypercholesterolemia, polycystic kidney disease, hereditary spherocytosis, von Willebrand's disease, tuberous sclerosis, hereditary hemorrhagic telangiectasia, familial colonic polyposis, Ehlers-Danlos syndrome, osteogenesis imperfecta, and acute intermittent porphyria). Phenotypic traits also include symptoms of, or susceptibility to, multifactorial diseases of which a component is or may be genetic, such as autoimmune diseases, inflammation, cancer, diseases of the nervous system, and infection by pathogenic microorganisms. Some examples of autoimmune diseases include rheumatoid arthritis, multiple sclerosis, diabetes (insulin-dependent and nonindependent), systemic lupus erythematosus and Graves disease. Some examples of cancers include cancers of the bladder, brain, breast, colon, esophagus, kidney, leukemia, liver, lung, oral cavity, ovary, pancreas, prostate, skin, stomach and uterus. Phenotypic traits also include characteristics such as longevity, appearance (e.g., baldness, obesity), strength, speed, endurance, fertility, and susceptibility or receptivity to particular drugs or therapeutic treatments.

The correlation of one or more polymorphisms with phenotypic traits can be facilitated by knowledge of the gene product of the wild type (reference) gene. The genes in which cSNPs of the present invention have been identified are genes which have been previously sequenced and characterized in one of their allelic forms.

Correlation is performed for a population of individuals who have been tested for the presence or absence of a phenotypic trait of interest and for polymorphic markers sets. To perform such analysis, the presence or absence of a set of polymorphisms (i.e. a polymorphic set) is determined for a set of the individuals, some of whom exhibit a particular trait, and some of which exhibit lack of the trait. The alleles of each polymorphism of the set are then reviewed to determine whether the presence or absence of a particular allele is associated with the trait of interest. Correlation can be performed by standard statistical methods such as a U-squared test and statistically significant correlations between polymorphic form(s) and phenotypic characteristics are noted. For example, it might be found that the presence of allele A1 at polymorphism A correlates with heart disease. As a further example, it might be found that the combined presence of allele A1 at polymorphism A and allele B1 at polymorphism B correlates with increased milk production of a farm animal.

Such correlations can be exploited in several ways. In the case of a strong correlation between a set of one or more polymorphic forms and a disease for which treatment is available, detection of the polymorphic form set in a human or animal patient may justify immediate administration of treatment, or at least the institution of regular monitoring of the patient. Detection of a polymorphic form correlated with serious disease in a couple contemplating a family may also be valuable to the couple in their reproductive decisions. For example, the female partner might elect to undergo in vitro fertilization to avoid the possibility of transmitting such a polymorphism from her husband to her offspring. In the case of a weaker, but still statistically significant correlation between a polymorphic set and human disease, immediate therapeutic intervention or monitoring may not be justified. Nevertheless, the patient can be motivated to begin simple life-style changes (e.g., diet, exercise) that can be accomplished at little cost to the patient but confer potential benefits in reducing the risk of conditions to which the patient may have increased susceptibility by virtue of variant alleles. Identification of a polymorphic set in a patient correlated with enhanced receptiveness to one of several treatment regimes for a disease indicates that this treatment regime should be followed.

For animals and plants, correlations between characteristics and phenotype are useful for breeding for desired characteristics. For example, Beitz et al., U.S. Pat. No. 5,292,639 discuss use of bovine mitochondrial polymorphisms in a breeding program to improve milk production in cows. To evaluate the effect of mtDNA D-loop sequence polymorphism on milk production, each cow was assigned a value of 1 if variant or 0 if wildtype with respect to a prototypical mitochondrial DNA sequence at each of 17 locations considered. Each production trait was analyzed individually with the following animal model:

$$Y_{ijkpn} = \mu + YS_i + P_j + X_k \beta_1 + \ldots \beta_{17} + PE_n + a_n + e_p$$

where $Y_{ijknp}$ is the milk, fat, fat percentage, SNF, SNF percentage, energy concentration, or lactation energy record; $\mu$ is an overall mean; $YS_i$ is the effect common to all cows calving in year-season; $X_k$ is the effect common to cows in either the high or average selection line; $\beta_1$ to $\beta_{17}$ are the binomial regressions of production record on mtDNA D-loop sequence polymorphisms; $PE_n$ is permanent environmental effect common to all records of cow n; $a_n$ is effect of animal n and is composed of the additive genetic contribution of sire and darn breeding values and a Mendelian sampling effect; and $e_p$ is a random residual. It was found that eleven of seventeen polymorphisms tested influenced at least one production trait. Bovines having the best polymorphic forms for milk production at these eleven loci are used as parents for breeding the next generation of the herd.

D. Genetic Mapping of Phenotypic Traits

The previous section concerns identifying correlations between phenotypic traits and polymorphisms that directly or indirectly contribute to those traits. The present section describes identification of a physical linkage between a genetic locus associated with a trait of interest and polymorphic markers that are not associated with the trait, but are in physical proximity with the genetic locus responsible for the trait and co-segregate with it. Such analysis is useful for mapping a genetic locus associated with a phenotypic trait to a chromosomal position, and thereby cloning gene(s) responsible for the trait. See Lander et al., *Proc. Natl. Acad. Sci.* (*USA*) 83, 7353–7357 (1986); Lander et al., *Proc. Natl. Acad. Sci.* (*USA*) 84, 2363–2367 (1987); Donis-Keller et al., *Cell* 51, 319–337 (1987); Lander et al., *Genetics* 121, 185–199 (1989)). Genes localized by linkage can be cloned by a process known as directional cloning. See Wainwright, *Med. J. Australia* 159, 170–174 (1993); Collins, *Nature Genetics* 1,3–6 (1992).

Linkage studies are typically performed on members of a family. Available members of the family are characterized for the presence or absence of a phenotypic trait and for a set of polymorphic markers. The distribution of polymorphic markers in an informative meiosis is then analyzed to determine which polymorphic markers co-segregate with a phenotypic trait. See, e.g., Kerem et al., *Science* 245, 1073–1080 (1989); Monaco et al., *Nature* 316, 842 (1985); Yamoka et al., *Neurology* 40, 222–226 (1990); Rossiter et al., *FASEB Journal* 5, 21–27 (1991).

Linkage is analyzed by calculation of LOD (log of the odds) values. A lod value is the relative likelihood of obtaining observed segregation data for a marker and a genetic locus when the two are located at a recombination fraction θ, versus the situation in which the two are not linked, and thus segregating independently (Thompson & Thompson, *Genetics in Medicine* (5th ed, W. B. Saunders Company, Philadelphia, 1991); Strachan, "Mapping the human genome" in *The Human Genome* (BIOS Scientific Publishers Ltd, Oxford), Chapter 4). A series of likelihood ratios are calculated at various recombination fractions (θ), ranging from θ=0.0 (coincident loci) to θ=0.50 (unlinked). Thus, the likelihood at a given value of θ is: probability of data if loci linked at θ to probability of data if loci unlinked. The computed likelihoods are usually expressed as the $\log_{10}$ of this ratio (i.e., a lod score). For example, a lod score of 3 indicates 1000:1 odds against an apparent observed linkage being a coincidence. The use of logarithms allows data collected from different families to be combined by simple addition. Computer programs are available for the calculation of lod scores for differing values of θ (e.g., LIPED, MLINK (Lathrop, *Proc. Nat. Acad. Sci.* (*USA*) 81, 3443–3446 (1984)). For any particular lod score, a recombination fraction may be determined from mathematical tables. See Smith et al., *Mathematical tables for research workers in human genetics* (Churchill, London, 1961); Smith, *Ann. Hum. Genet.* 32, 127–150(1968). The value of θ at which the lod score is the highest is considered to be the best estimate of the recombination fraction.

Positive lod score values suggest that the two loci are linked, whereas negative values suggest that linkage is less likely (at that value of θ) than the possibility that the two loci are unlinked. By convention, a combined lod score of +3 or greater (equivalent to greater than 1000:1 odds in favor of linkage) is considered definitive evidence that two loci are linked. Similarly, by convention, a negative lod score of −2 or less is taken as definitive evidence against linkage of the two loci being compared. Negative linkage data are useful in excluding a chromosome or a segment thereof from consideration. The search focuses on the remaining non-excluded chromosomal locations.

IV. Modified Polypeptides and Gene Sequences

The invention further provides variant forms of nucleic acids and corresponding proteins. The nucleic acids comprise one of the sequences described in the Table, column 5, in which the polymorphic position is occupied by one of the alternative bases for that position. Some nucleic acids encode full-length variant forms of proteins. Similarly, variant proteins have the prototypical amino acid sequences encoded by nucleic acid sequences shown in the Table, column 5, (read so as to be in-frame with the full-length coding sequence of which it is a component) except at an amino acid encoded by a codon including one of the polymorphic positions shown in the Table. That position is occupied by the amino acid coded by the corresponding codon in any of the alternative forms shown in the Table.

Variant genes can be expressed in an expression vector in which a variant gene is operably linked to a native or other promoter. Usually, the promoter is a eucaryotic promoter for expression in a mammalian cell. The transcription regulation sequences typically include a heterologous promoter and optionally an enhancer which is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The means of introducing the expression construct into a host cell varies depending upon the particular construction and the target host. Suitable means include fusion, conjugation, transfection, transduction, electroporation or injection, as described in Sambrook, supra. A wide variety of host cells can be employed for expression of the variant gene, both prokaryotic and eukaryotic. Suitable host cells include bacteria such as *E. coli*, yeast, filamentous fungi, insect cells, mammalian cells, typically immortalized, e.g., mouse, CHO, human and monkey cell lines and derivatives thereof Preferred host cells are able to process the variant gene product to produce an appropriate mature polypeptide. Processing includes glycosylation, ubiquitination, disulfide bond formation, general post-translational modification, and the like. As used herein, "gene product" includes mRNA, peptide and protein products.

The protein may be isolated by conventional means of protein biochemistry and purification to obtain a substantially pure product, i.e., 80, 95 or 99% free of cell component contaminants, as described in Jacoby, *Methods in Enzymology* Volume 104, Academic Press, New York (1984); Scopes, *Protein Purification, Principles and Practice*, 2nd Edition, Springer-Verlag, New York (1987); and Deutscher (ed), *Guide to Protein Purification, Methods in Enzymology*, Vol. 182 (1990). If the protein is secreted, it can be isolated from the supernatant in which the host cell is grown. If not secreted, the protein can be isolated from a lysate of the host cells.

The invention further provides transgenic nonhuman animals capable of expressing an exogenous variant gene and/or having one or both alleles of an endogenous variant gene inactivated. Expression of an exogenous variant gene is usually achieved by operably linking the gene to a promoter and optionally an enhancer, and microinjecting the construct into a zygote. See Hogan et al., "Manipulating the Mouse Embryo, A Laboratory Manual," Cold Spring Harbor Laboratory. Inactivation of endogenous variant genes can be achieved by forming a transgene in which a cloned variant gene is inactivated by insertion of a positive selection marker. See Capecchi, *Science* 244, 1288–1292 (1989). The transgene is then introduced into an embryonic stem cell, where it undergoes homologous recombination with an endogenous variant gene. Mice and other rodents are preferred animals. Such animals provide useful drug screening systems.

In addition to substantially full-length polypeptides expressed by variant genes, the present invention includes biologically active fragments of the polypeptides, or analogs thereof, including organic molecules which simulate the interactions of the peptides. Biologically active fragments include any portion of the full-length polypeptide which confers a biological function on the variant gene product, including ligand binding, and antibody binding. Ligand binding includes binding by nucleic acids, proteins or polypeptides, small biologically active molecules, or large cellular structures.

Polyclonal and/or monoclonal antibodies that specifically bind to variant gene products but not to corresponding prototypical gene products are also provided. Antibodies can be made by injecting mice or other animals with the variant gene product or synthetic peptide fragments thereof Monoclonal antibodies are screened as are described, for example, in Harlow & Lane, *Antibodies, A Laboratory Manual*, Cold Spring Harbor Press, New York (1988); Goding, *Monoclonal antibodies, Principles and Practice* (2d ed.) Academic Press, New York (1986). Monoclonal antibodies are tested for specific immunoreactivity with a variant gene product and lack of immunoreactivity to the corresponding prototypical gene product. These antibodies are useful in diagnostic assays for detection of the variant form, or as an active ingredient in a pharmaceutical composition.

V. Kits

The invention further provides kits comprising at least one allele-specific oligonucleotide as described herein. Often, the kits contain one or more pairs of allele-specific oligonucleotides hybridizing to different forms of a polymorphism. In some kits, the allele-specific oligonucleotides are provided immobilized to a substrate. For example, the same substrate can comprise allele-specific oligonucleotide probes for detecting at least 10, 100 or all of the polymorphisms shown in the Table. Optional additional components of the kit include, for example, restriction enzymes, reverse-transcriptase or polymerase, the substrate nucleoside triphosphates, means used to label (for example, an avidin-enzyme conjugate and enzyme substrate and chromogen if the label is biotin), and the appropriate buffers for reverse transcription, PCR, or hybridization reactions. Usually, the kit also contains instructions for carrying out the methods.

The thrombospondins are a family of extracellular matrix (ECM) glycoproteins that modulate many cell behaviors including adhesion, migration, and proliferation. Thrombospondins (also known as thrombin sensitive proteins or TSPs) are large molecular weight glycoproteins composed of three identical disulfide-linked polypeptide chains. TSPs are stored in the alpha-granules of platelets and secreted by a variety of mesenchymal and epithelial cells (Majack et al., *Cell Membrane* 3:57–77 (1987)). Platelets secrete TSPs when activated in the blood by such physiological agonists such as thrombin. TSPs have lectin properties and a broad function in the regulation of fibrinolysis and as a component of the ECM, and are one of a group of ECM proteins which have adhesive properties. TSPs bind to fibronectin and fibrinogen (Lahav et al., *Eur J Biochem* 145:151–6 (1984)), and these proteins are known to be involved in platelet adhesion to substratum and platelet aggregation (Leung, *J Clin Invest* 74:1764–1772 (1986)).

Recent work has implicated TSPs in response of cells to growth factors. Submitogenic doses of PDGF induce a rapid but transitory, increase in TSP synthesis and secretion by rat aortic smooth muscle cells (Majack et al., *J Biol Chem* 101:1059–70 (1985)). PDGF responsiveness to TSP synthesis in glial cells has also been shown (Asch et al, *Proc Natl Acad Sci* 83:2904–8 (1986)). TSP mRNA levels rise rapidly in response to PDGF (Majack et al., *J Biol Chem* 262:8821–5 (1987)). TSPs act synergistically with epidermal growth factor to increase DNA synthesis in smooth muscle cells (Majack et al., *Proc Natl Acad Sci* 83:9050–4 (1986)), and monoclonal antibodies to TSPs inhibit smooth muscle cell proliferation (Majack et al., *J Biol Chem* 106:415–22 (1988)). TSPs modulate local adhesions in endothelial cells, and TSPs, particularly TSP-1 primarily derived from platelet granules, are known to be an important activator of transforming growth factor beta-1 (TGFB-1) (Crawford et al., *Cell* 93:1159 (1998)) and appear to be a potential link between platelet-thrombosis and development of atherosclerosis.

To determine pivotal genes associated with premature coronary artery disease, we analyzed DNA from 347 patients with MI or coronary revascularization before age 40 (men) or 45 (women) and 422 general population controls. Cases were drawn (one per family) from a retrospective collection of sibling pairs with premature CAD. Controls were ascertained through random-digit dialing. Both cases and controls were Caucasian. A complete database of phenotypic and laboratory variables for the affected patients afforded logistic regression to control for age, diabetes, body mass index, gender.

Thrombospondin (TSP) 4 and 1 emerged as important SNPs associated with premature CAD and MI. For CAD, 148 of 347 patients carried at least one copy of the TSP-4 variant compared with 142 of 422 control subjects; adjusted odds ratio 1.47, p=0.01. For premature MI, the association was even stronger: 91 of 187 cases vs. 142 of 422 controls had the variant; adjusted odds ratio 2.08, p=0.0003. The TSP-1 SNP was rare. Nonetheless, homozygosity for the variant allele gave an adjusted odds ratio of 9.5, p=0.04.

Specific reference nucleotide (SEQ ID NO: 1) and amino acid (SEQ ID NO: 2) sequences for TSP-1 are shown in FIGS. 1A–1D. Specific reference nucleotide (SEQ ID NO: 3) and amino acid (SEQ ID NO: 4) sequences for TSP-4 are shown in FIGS. 2A–2C. It is understood that the invention is not limited by these exemplified reference sequences, as variants of these sequences which differ at locations other than the SNP sites identified herein can also be utilized. The skilled artisan can readily determine the SNP sites in these other reference sequences which correspond to the SNP sites identified herein by aligning the sequence of interest with the reference sequences specifically disclosed herein, and programs for performing such alignments are commercially available. For example, the ALIGN program in the GCG software package can be used, utilizing a PAM120 weight residue table, a gap length penalty of 12 and a gap penalty of 4, for example.

Two SNPs have been specifically studied as described herein. The first (G334u4) is a change from A (reference nucleotide) to G (alternate or variant nucleotide) at nucleotide position 2210 of the nucleic acid sequence of TSP-1 (FIGS. 1A–1D), resulting in a missense amino acid mutation from asparagine (reference) to serine (alternate) at amino acid 700. The second SNP (G355u2) is a change from G (reference) to C (alternate) at nucleotide position 1186 of the nucleic acid sequence of TSP-4 (FIGS. 2A–2C), resulting in a missense amino acid alteration from alanine (reference) to proline (alternate) at amino acid 387. With respect to the G355u2 SNP, individuals with CAD carried at least one copy of the variant "C" allele more frequently than control individuals (43% as compared with 34%). With respect to the G355u2 SNP, individuals with MI carried at least one copy of the variant "C" allele more frequently than control individuals (49% as compared with 34%). With respect to the G334u4 SNP, individuals with CAD carried two copies of the variant "G" allele more frequently than control individuals (1.7% as compared with 0.2%). With respect to the G334u4 SNP, individuals with MI carried two copies of the variant "G" allele more frequently than control individuals (2% as compared with 0.2%).

As used herein, the term "polymorphism" refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair, in which case it is referred to as a single nucleotide polymorphism (SNP).

Thus, the invention relates to a method for predicting the likelihood that an individual will have a vascular disease, or for aiding in the diagnosis of a vascular disease, or predicting the likelihood of having altered symptomology associated with a vascular disease, comprising the steps of obtaining a DNA sample from an individual to be assessed and determining the nucleotide present at one or more of nucleotide positions 2210 of the TSP-1 gene or 1186 of the TSP-4 gene. In a preferred embodiment, the nucleotides present at both of these nucleotide positions are determined. In one embodiment the TSP-1 gene has the nucleotide sequence of SEQ ID NO: 1 and the TSP-4 gene has the nucleotide sequence of SEQ ID NO: 3. The presence of one or more of a G (the variant nucleotide) at position 2210 of SEQ ID NO: 1 or a C (the variant nucleotide) at position 1186 of SEQ ID NO: 1186 indicates that the individual has a greater likelihood of having a vascular disease, or a greater likelihood of having severe symptomology associated with a vascular disease, than if that individual had the reference nucleotide at one or more of these positions. Conversely, the presence of one or more of an A (the reference nucleotide) at position 2210 of SEQ ID NO: 1 or a G (the reference nucleotide) at position 1186 of SEQ ID NO: 3 indicates that the individual has a reduced likelihood of having a vascular disease or a likelihood of having reduced symptomology associated with a vascular disease than if that individual had the variant nucleotide at one or more of these positions.

In a particular embodiment, the individual is an individual at risk for development of a vascular disease. In another embodiment the individual exhibits clinical symptomology associated with a vascular disease. In one embodiment, the individual has been clinically diagnosed as having a vascular disease. Vascular diseases include, but are not limited to, atherosclerosis, coronary heart disease, myocardial infarction (MI), stroke, peripheral vascular diseases, venous thromboembolism and pulmonary embolism. In preferred embodiments, the vascular disease is CAD or MI.

The genetic material to be assessed can be obtained from any nucleated cell from the individual. For assay of genomic DNA, virtually any biological sample (other than pure red blood cells) is suitable. For example, convenient tissue samples include whole blood, semen, saliva, tears, urine, fecal material, sweat, skin and hair. For assay of cDNA or mRNA, the tissue sample must be obtained from a tissue or organ in which the target nucleic acid is expressed.

Many of the methods described herein require amplification of DNA from target samples. This can be accomplished by e.g., PCR. See generally PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. No. 4,683,202.

Other suitable amplification methods include the ligase chain reaction (LCR) (see Wu and Wallace, Genomics 4, 560 (1989), Landegren et al., Science 241, 1077 (1988), transcription amplification (Kwoh et al., Proc. Natl. Acad. Sci. USA 86, 1173 (1989)), and self-sustained sequence replication (Guatelli et al., Proc. Nat. Acad. Sci. USA, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The nucleotide which occupies the polymorphic site of interest (e.g., nucleotide position 2210 in TSP-1 and/or nucleotide position 1186 in TSP-4) can be identified by a variety of methods, such as Southern analysis of genomic DNA; direct mutation analysis by restriction enzyme digestion; Northern analysis of RNA; denaturing high pressure liquid chromatography (DHPLC); gene isolation and sequencing; hybridization of an allele-specific oligonucleotide with amplified gene products; single base extension (SBE). In a preferred embodiment, determination of the allelic form of TSP is carried out using SBE-FRET methods as described herein, or using chip-based oligonucleotide arrays as described herein.

The invention also relates to a method for predicting the likelihood that an individual will have a vascular disease, or for aiding in the diagnosis of a vascular disease, or predicting the likelihood of having altered symptomology associated with a vascular disease, comprising the steps of obtaining a biological sample comprising TSP-1 and/or TSP-4 protein or relevant portion thereof from an individual to be assessed and determining the amino acid present at one or more of amino acid positions 700 of the TSP-1 gene product (e.g., as exemplified by SEQ ID NO: 2) or 387 of the TSP-4 gene product (e.g., as exemplified by SEQ ID NO: 4). In a preferred embodiment, the amino acids present at both of these amino acid positions are determined. As used herein, the term "relevant portion" of the TSP-1 and TSP-4 proteins is intended to encompass any portion of the protein which comprises the polymorphic amino acid positions. The presence of one or more of a serine (the variant amino acid) at position 700 of SEQ ID NO: 2, or a proline (the variant amino acid) at position 387 of SEQ ID NO: 4 indicates that the individual has a greater likelihood of having a vascular disease, or a greater likelihood of having severe symptomology associated with a vascular disease, than if that individual had the reference amino acid at one or more of these positions. Conversely, the presence of one or more of an asparagine (the reference amino acid) at position 700 of SEQ ID NO: 2, or an alanine (the reference amino acid) at position 387 of SEQ ID NO: 4 indicates that the individual has a reduced likelihood of having a vascular disease or a likelihood of having reduced symptomology associated with a vascular disease, than if that individual had the varaint amino acid at one or more of these positions.

In a particular embodiment, the individual is an individual at risk for development of a vascular disease. In another embodiment the individual exhibits clinical symptomology associated with a vascular disease. In one embodiment, the individual has been clinically diagnosed as having a vascular disease.

In this embodiment of the invention, the biological sample contains protein molecules from the test subject. In vitro techniques for detection of protein include enzyme linked immunosorbent assays (ELISAs), Western blots, immunoprecipitations and immunofluorescence. Furthermore, in vivo techniques for detection of protein include introducing into a subject a labeled anti-protein antibody. For example, the antibody can be labeled with a radioactive marker whose presence and location in a subject can be detected by standard imaging techniques. Polyclonal and/or monoclonal antibodies that specifically bind to variant gene products but not to corresponding reference gene products, and vice versa, are also provided. Antibodies can be made by injecting mice or other animals with the variant gene product or synthetic peptide fragments thereof comprising the variant portion. Monoclonal antibodies are screened as are described, for example, in Harlow & Lane, Antibodies, A Laboratory Manual, Cold Spring Harbor Press, New York (1988); Goding, Monoclonal antibodies, Principles and Practice (2d ed.) Academic Press, New York (1986). Monoclonal antibodies are tested for specific immunoreactivity with a variant gene product and lack of immunoreactivity to the corresponding prototypical gene product. These antibodies are useful in diagnostic assays for detection of the variant form, or as an active ingredient in a pharmaceutical composition.

The polymorphisms of the invention may be associated with vascular disease in different ways. The polymorphisms may exert phenotypic effects indirectly via influence on replication, transcription, and translation. Additionally, the described polymorphisms may predispose an individual to a distinct mutation that is causally related to a certain phenotype, such as susceptibility or resistance to vascular disease and related disorders. The discovery of the polymorphisms and their correlation with CAD and MI facilitates biochemical analysis of the variant and reference forms and the development of assays to characterize the variant and reference forms and to screen for pharmaceutical agents that interact directly with one or another form of the protein.

Alternatively, these particular polymorphisms may belong to a group of two or more polymorphisms in the TSP gene(s) which contributes to the presence, absence or severity of vascular disease. An assessment of other polymorphisms within the TSP gene(s) can be undertaken, and the separate and combined effects of these polymorphisms, as well as alternations in other, distinct genes, on the vascular disease phenotype can be assessed.

Correlation between a particular phenotype, e.g., the CAD or MI phenotype, and the presence or absence of a particular allele is performed for a population of individuals who have been tested for the presence or absence of the phenotype. Correlation can be performed by standard statistical methods such as a Chi-squared test and statistically significant correlations between polymorphic form(s) and phenotypic characteristics are noted. This correlation can be exploited in several ways. In the case of a strong correlation between a particular polymorphic form, e.g., the variant allele for TSP-1 and/or TSP-4, and a disease for which treatment is available, detection of the polymorphic form in an individual may justify immediate administration of treatment, or at least the institution of regular monitoring of the individual. Detection of a polymorphic form correlated with a disorder in a couple contemplating a family may also be valuable to the couple in their reproductive decisions. For example, the female partner might elect to undergo in vitro fertilization to avoid the possibility of transmitting such a polymorphism from her husband to her offspring. In the case of a weaker, but still statistically significant correlation between a polymorphic form and a particular disorder, immediate therapeutic intervention or monitoring may not be justified. Nevertheless, the individual can be motivated to begin simple life-style changes (e.g., diet modification, therapy or counseling) that can be accomplished at little cost to the individual but confer potential benefits in reducing the risk of conditions to which the individual may have increased susceptibility by virtue of the particular allele. Furthermore, identification of a polymorphic form correlated with enhanced receptiveness to one of several treatment regimes for a disorder indicates that this treatment regimen should be followed for the individual in question.

Furthermore, it may be possible to identify a physical linkage between a genetic locus associated with a trait of interest (e.g., CAD or MI) and polymorphic markers that are or are not associated with the trait, but are in physical proximity with the genetic locus responsible for the trait and co-segregate with it. Such analysis is useful for mapping a genetic locus associated with a phenotypic trait to a chromosomal position, and thereby cloning gene(s) responsible for the trait. See Lander et al., *Proc. Natl. Acad. Sci.* (*USA*) 83, 7353–7357 (1986); Lander et al., *Proc. Natl. Acad. Sci.* (*USA*) 84, 2363–2367 (1987); Donis-Keller et al., Cell 51, 319–337 (1987); Lander et al., *Genetics* 121, 185–199 (1989)). Genes localized by linkage can be cloned by a process known as directional cloning. See Wainwright, *Med. J Australia* 159, 170–174 (1993); Collins, *Nature Genetics* 1,3–6 (1992). Linkage studies are discussed in more detail above.

In another embodiment, the invention relates to pharmaceutical compositions comprising a reference TSP-1 and/or TSP-4 gene or gene product for use in the treatment of vascular disease, e.g., CAD and MI. As used herein, a reference TSP gene product is intended to mean gene products which are encoded by the reference allele of the TSP gene. In addition to substantially full-length polypeptides expressed by the genes, the present invention includes biologically active fragments of the polypeptides, or analogs thereof, including organic molecules which simulate the interactions of the peptides. Biologically active fragments include any portion of the full-length polypeptide which confers a biological function on the variant gene product, including ligand binding, and antibody binding. Ligand binding includes binding by nucleic acids, proteins or polypeptides, small biologically active molecules, or large cellular structures.

For instance, the polypeptide or protein, or fragment thereof, of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to procedures well known to medicinal chemists, and will depend on the ultimate pharmaceutical formulation desired. Methods of introduction of exogenous peptides at the site of treatment include, but are not limited to, intradermal, intramuscular, intraperitoneal, intravenous, subcutaneous, oral and intranasal. Other suitable methods of introduction can also include rechargeable or biodegradable devices and slow release polymeric devices. The pharmaceutical compositions of this invention can also be administered as part of a combinatorial therapy with other agents and treatment regimens.

The invention further pertains to compositions, e.g., vectors, comprising a nucleotide sequence encoding reference or variant TSP-1 and/or TSP-4 gene products. For example, reference genes can be expressed in an expression vector in which a reference gene is operably linked to a native or other promoter. Usually, the promoter is a eukaryotic promoter for expression in a mammalian cell. The transcription regulation sequences typically include a heterologous promoter and optionally an enhancer which is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The means of introducing the expression construct into a host cell varies depending upon the particular construction and the target host. Suitable means include fusion, conjugation, transfection, transduction, electroporation or injection, as described in Sambrook, supra. A wide variety of host cells can be employed for expression of the variant gene, both prokaryotic and eukaryotic. Suitable host cells include bacteria such as *E. coli*, yeast, filamentous fungi, insect cells, mammalian cells, typically immortalized, e.g., mouse, CHO, human and monkey cell lines and derivatives thereof Preferred host cells are able to process the variant gene product to produce an appropriate mature polypeptide. Processing includes glycosylation, ubiquitination, disulfide bond formation, general post-translational modification, and the like.

It is also contemplated that cells can be engineered to express the reference allele of the invention by gene therapy methods. For example, DNA encoding the reference TSP gene product, or an active fragment or derivative thereof, can be introduced into an expression vector, such as a viral vector, and the vector can be introduced into appropriate cells in an animal. In such a method, the cell population can be engineered to inducibly or constitutively express active reference TSP gene product. In a preferred embodiment, the vector is delivered to the bone marrow, for example as described in Corey et al. (*Science* 244:1275–1281(1989)).

The invention further relates to the use of compositions (i.e., agonists) which enhance or increase the activity of the reference (or variant) TSP (e.g., TSP-1 or TSP-4) gene product, or a functional portion thereof, for use in the treatment of vascular disease. The invention also relates to the use of compositions (i.e., antagonists) which reduce or decrease the activity of the variant (or reference) TSP (e.g., TSP-1 or TSP-4) gene product, or a functional portion thereof, for use in the treatment of vascular disease.

The invention also relates to constructs which comprise a vector into which a sequence of the invention has been inserted in a sense or antisense orientation. For example, a vector comprising a nucleotide sequence which is antisense to the variant TSP-1 or TSP-4 allele may be used as an antagonist of the activity of the TSP-1 or TSP-4 variant allele. Alternatively, a vector comprising a nucleotide sequence of the TSP-1 or TSP-4 reference allele may be used therapeutically to treat vascular diseases. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses) that serve equivalent functions.

Preferred recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc.

The expression vectors of the invention can be introduced into host cells to thereby produce proteins or peptides, including fusion proteins or peptides, encoded by nucleic acids as described herein. The recombinant expression vectors of the invention can be designed for expression of a polypeptide of the invention in prokaryotic or eukaryotic cells, e.g., bacterial cells such as *E. coli*, insect cells (using baculovirus expression vectors), yeast cells or mammalian cells. Suitable host cells are discussed further in Goeddel, supra. Alternatively, the recombinant expression vector can be transcribed and translated in vitro, for example using T7 promoter regulatory sequences and T7 polymerase.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a nucleic acid of the invention can be expressed in bacterial cells (e.g., *E. coli*), insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAB-dextran-mediated transfection, lipofection, or electroporation. Suitable methods for transforming or transfecting host cells can be found in Sambrook, et al (supra), and other laboratory manuals.

A host cell of the invention, such as a prokaryotic or eukaryotic host cell in culture, can be used to produce (i.e., express) a polypeptide of the invention. Accordingly, the invention further provides methods for producing a polypeptide using the host cells of the invention. In one embodiment, the method comprises culturing the host cell of the invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a nucleic acid of the invention has been introduced. Such host cells can then be used to create non-human transgenic animals in which exogenous nucleotide sequences have been introduced into their genome or homologous recombinant animals in which endogenous nucleotide sequences have been altered. Such animals are useful for studying the function and/or activity of the nucleotide sequence and polypeptide encoded by the sequence and for identifying and/or evaluating modulators of their activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid of the invention into the male pronuclei of a fertilized oocyte, e.g., by microinjection, retroviral infection, and allowing the oocyte to develop in a pseudopregnant female foster animal. The sequence can be introduced as a transgene into the genome of a non-human animal. Intronic sequences and polyadenylation signals can also be included in the transgene to increase the efficiency of expression of the transgene. A tissue-specific regulatory sequence(s) can be operably linked to the transgene to direct expression of a polypeptide in particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of mRNA in tissues or cells of the animals. A transgenic founder animal can then be used to breed additional animals carrying the transgene. Moreover, transgenic animals carrying a transgene encoding the transgene can further be bred to other transgenic animals carrying other transgenes.

The invention also relates to the use of the variant and reference gene products to guide efforts to identify the causative mutation for vascular diseases or to identify or synthesize agents useful in the treatment of vascular diseases, e.g., CAD and MI. Amino acids that are essential for function can be identified by methods known in the art, such as site-directed mutagenesis or alanine-scanning mutagenesis (Cunningham et al., *Science*, 244:1081–1085 (1989)). The latter procedure introduces single alanine mutations at every residue in the molecule. The resulting mutant molecules are then tested for biological activity in vitro, or in vitro activity. Sites that are critical for polypeptide activity can also be determined by structural analysis such as crystallization, nuclear magnetic resonance or photoaffinity labeling (Smith et al, *J Mol. Biol.*, 224:899–904 (1992); de Vos et al. *Science*, 255:306–312 (1992)).

Another aspect of the invention pertains to monitoring the influence of agents (e.g., drugs, compounds) on the expression or activity of proteins of the invention in clinical trials. An exemplary method for detecting the presence or absence of proteins or nucleic acids of the invention in a biological sample involves obtaining a biological sample from a test subject and contacting the biological sample with a compound or an agent capable of detecting the protein, or nucleic acid (e.g., mRNA, genomic DNA) that encodes the protein, such that the presence of the protein or nucleic acid is detected in the biological sample. A preferred agent for detecting mRNA or genomic DNA is a labeled nucleic acid probe capable of hybridizing to mRNA or genomic DNA sequences described herein, preferably in an allele-specific manner. The nucleic acid probe can be, for example, a full-length nucleic acid, or a portion thereof, such as an oligonucleotide of at least 15, 30, 50, 100, 250 or 500 nucleotides in length and sufficient to specifically hybridize under stringent conditions to appropriate mRNA or genomic DNA. Other suitable probes for use in the diagnostic assays of the invention are described herein.

The invention also encompasses kits for detecting the presence of proteins or nucleic acid molecules of the invention in a biological sample. For example, the kit can comprise a labeled compound or agent (e.g., nucleic acid probe) capable of detecting protein or mRNA in a biological sample; means for determining the amount of protein or mRNA in the sample; and means for comparing the amount of protein or mRNA in the sample with a standard. The compound or agent can be packaged in a suitable container. The kit can further comprise instructions for using the kit to detect protein or nucleic acid.

The following Examples are offered for the purpose of illustrating the present invention and are not to be construed to limit the scope of this invention. The teachings of all references cited herein are hereby incorporated herein by reference.

EXAMPLES

Identification of Single Nucleotide Polymorphisms

The polymorphisms shown in the Table were identified by resequencing of target sequences from individuals of diverse ethnic and geographic backgrounds by hybridization to probes immobilized to microfabricated arrays. The strategy and principles for design and use of such arrays are generally described in WO 95/11995.

A typical probe array used in this analysis has two groups of four sets of probes that respectively tile both strands of a reference sequence. A first probe set comprises a plurality of probes exhibiting perfect complementarily with one of the reference sequences. Each probe in the first probe set has an interrogation position that corresponds to a nucleotide in the reference sequence. That is, the interrogation position is aligned with the corresponding nucleotide in the reference sequence, when the probe and reference sequence are aligned to maximize complementarily between the two. For each probe in the first set, there are three corresponding probes from three additional probe sets. Thus, there are four probes corresponding to each nucleotide in the reference sequence. The probes from the three additional probe sets are identical to the corresponding probe from the first probe set except at the interrogation position, which occurs in the same position in each of the four corresponding probes from the four probe sets, and is occupied by a different nucleotide in the four probe sets. In the present analysis, probes were 25 nucleotides long. Arrays tiled for multiple different references sequences were included on the same substrate.

Publicly available sequences for a given gene were assembled into Gap4, which can be found on the world wide web at biozentrum.unibas.ch/~biocomp/staden/Overview.html. PCR primers covering each exon were designed using Primer 3, which can be found on the world wide web at genome.wi.mit.edu/cgi-bin/primer/primer3.cgi. Primers were not designed in regions where there were sequence discrepancies between reads. Genomic DNA was amplified in at least 50 individuals using 2.5 pmol each primer, 1.5 mM $MgCl_2$, 100 μM dNTPs, 0.75 μM AmpliTaq GOLD polymerase, and 19 ng DNA in a 15 μl reaction. Reactions were assembled using a PACKARD MultiPROBE robotic pipetting station and then put in MJ 96-well tetrad thermocyclers (96° C. for 10 minutes, followed by 35 cycles of 96° C. for 30 seconds, 59° C. for 2 minutes, and 72° C. for 2 minutes). A subset of the PCR assays for each individual were run on 3% NuSieve gels in 0.5× TBE to confirm that the reaction worked.

For a given DNA, 5 μl (about 50 ng) of each PCR or RT-PCR product were pooled (Final volume=150–200 1 μl). The products were purified using QiaQuick PCR purification from Qiagen. The samples were eluted once in 35 μl sterile water and 4 μl 10× One-Phor-All buffer (Pharmacia). The pooled samples were digested with 0.2 μ DNaseI (Promega) for 10 minutes at 37° C. and then labeled with 0.5 nmols biotin-N6-ddATP and 15μ Terminal Transferase (GibcoBRL Life Technology) for 60 minutes at 37° C. Both fragmentation and labeling reactions were terminated by incubating the pooled sample for 15 minutes at 100° C.

Low-density DNA chips (Affymetrix,CA) were hybridized following the manufacturer's instructions. Briefly, the hybridization cocktail consisted of 3M TMACl, 10 mM Tris pH 7.8, 0.01% Triton X-100, 100 mg/ml herring sperm DNA (Gibco BRL), 200 pM control biotin-labeled oligo. The processed PCR products were denatured for 7 minutes at 100° C. and then added to prewarmed (37° C.) hybridization solution. The chips were hybridized overnight at 44° C. Chips were washed in 1×SSPET and 6×SSPET followed by staining with 2 μg/ml SARPE and 0.5 mg/ml acetylated BSA in 200 μl of 6×SSPET for 8 minutes at room temperature. Chips were scanned using a Molecular Dynamics scanner.

Chip image files were analyzed using Ulysses (Affymetrix, Calif.) which uses four algorithms to identify potential polymorphisms. Candidate polymorphisms were visually inspected and assigned a confidence value: high confidence candidates displayed all three genotypes, while likely candidates showed only two genotypes (homozygous for reference sequence and heterozygdus for reference and variant). Some of the candidate polymorphisms were confirmed by ABI sequencing. Identified polymorphisms were compared to several databases to determine if they were novel. Results arc shown in the Table.

Association of Thrombospondin Gene Polymorphisms with Vascular Disease To determine pivotal genes associated with premature coronary artery disease, we analyzed DNA from 347 patients with MI or coronary revascularization before age 40 (men) or 45 (women) and 422 general population controls. Cases were drawn (one per family) from a retrospective collection of sibling pairs with premature CAD. Controls were ascertained through random-digit dialing. Both cases and controls were Caucasian. A complete database of phenotypic and laboratory variables for the affected patients afforded logistic regression to control for age, diabetes, body mass index, gender.

Thrombospondin (TSP) 4 and 1 emerged as important SNPs associated with premature CAD and MI. For CAD, 148 of 347 patients carried at least one copy of the TSP4 variant compared with 142 of 422 control subjects; adjusted odds ratio 1.47, p=0.01. For premature MI, the association was even stronger: 91 of 187 cases vs. 142 of 422 controls had the variant; adjusted odds ratio 2.08, p=0.0003. The TSP-1 SNP was rare. Nonetheless, homozygosity for the variant allele gave an adjusted odds ratio of 9.5, p=0.04.

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| AT3a7 | WIAF-13246 | U11270 | 11918 | AT3, antithrombin III | CTGCAGGAGT[G/A]GCTGGATGAA | N | G | A | W | * |
| DRD5u22 | WIAF-12913 | M67439 | 310 | DRD1, dopamine receptor D1 | CATCTGGACC[C/T]TGCTGGCCAA | S | C | T | L | L |
| DRD5u23 | WIAF-12914 | M67439 | 332 | DRD1, dopamine receptor D1 | GTGCTGCTGT[G/C]CGGCAGCCAT | M | G | C | C | S |
| DRD5u24 | WIAF-12915 | M67439 | 369 | DRD1, dopamine receptor D1 | TGCGCGCCAA[C/G]ATGACCAACG | M | C | G | N | K |
| DRD5u25 | WIAF-12916 | M67439 | 522 | DRD1, dopamine receptor D1 | TGTGCTCCAC[T/C]GCCTCCATCC | S | T | C | T | T |
| DRD5u26 | WIAF-12917 | M67439 | 953 | DRD1, dopamine receptor D1 | GCAGAGCACG[C/T]GCAGAGCTGC | M | C | T | T | V |
| DRD5u27 | WIAF-12918 | M67439 | 635 | DRD1, dopamine receptor D1 | ATGGTCGCAC[T/C]GGATGGACC | M | T | C | A | P |
| DRD5u28 | WIAF-12919 | M67439 | 606 | DRD1, dopamine receptor D1 | GCAAGATGAC[T/C]CAGCGCATGG | S | T | C | L | L |
| DRD5u29 | WIAF-12920 | M67439 | 845 | DRD1, dopamine receptor D1 | TCGCTCATCA[G/A]CTTCTACATC | M | G | A | S | N |
| DRD5u30 | WIAF-12921 | M67439 | 720 | DRD1, dopamine receptor D1 | GGGGCCGGCT[G/T]GACCTGCCAA | S | G | T | L | L |
| DRD5u31 | WIAF-12922 | M67439 | 1044 | DRD1, dopamine receptor D1 | AGACCCTGTC[G/A]GTGATCATGG | M | G | A | S | S |
| DRD5u32 | WIAF-12923 | M67439 | 766 | DRD1, dopamine receptor D1 | GGAGGAGGAC[T/G]TTTGGGAGCC | S | T | G | V | V |
| DRD5u33 | WIAF-12924 | M67439 | 777 | DRD1, dopamine receptor D1 | TTTGGGAGCC[C/T]GACGTGAATG | S | C | T | P | P |
| DRD5u34 | WIAF-12925 | M67439 | 786 | DRD1, dopamine receptor D1 | CCGACGTGAA[T/G]GCAGAGAACT | M | T | G | N | K |
| DRD5u35 | WIAF-12926 | M67439 | 887 | DRD1, dopamine receptor D1 | ACCTACACGC[G/A]CATCTACCGC | M | G | A | R | H |
| DRD5u36 | WIAF-12927 | M67439 | 1279 | DRD1, dopamine receptor D1 | GTGCAGCCAC[T/G]TCTGCTCCCG | M | T | G | F | V |
| DRD5u37 | WIAF-12928 | M67439 | 1370 | DRD1, dopamine receptor D1 | GAAATCGCAG[C/T]TGCCTACATC | M | C | T | A | V |
| DRD5u38 | WIAF-12929 | M67439 | 1500 | DRD1, dopamine receptor D1 | ACCCTGTTGC[T/A]GAGTCTGTCT | S | T | A | A | A |
| DRD5u39 | WIAF-12930 | M67439 | 1338 | DRD1, dopamine receptor D1 | TCTCCTACAA[C/T]CAAGACATCG | S | C | T | N | N |
| DRD5u40 | WIAF-12931 | M67439 | 1215 | DRD1, dopamine receptor D1 | CACTCAACCC[C/A]GTCATCTATG | S | C | A | P | P |
| DRD5u41 | WIAF-12932 | M67439 | 1242 | DRD1, dopamine receptor D1 | ACGCCGACTT[T/C]CAGAAGGTGT | S | T | C | F | F |
| DRD5u42 | WIAF-12933 | M67439 | 1441 | DRD1, dopamine receptor D1 | CGAGGAGGAG[G/A]GTCCTTTCGA | M | G | A | G | S |
| DRD5u43 | WIAF-12934 | M67439 | 1460 | DRD1, dopamine receptor D1 | GATCGCATGT[T/C]CCAGATCTAT | M | T | C | F | S |
| DRD5u44 | WIAF-12960 | M67439 | 399 | DRD1, dopamine receptor D1 | TGTCTCTGGC[C/T]GTCTCTGACC | S | C | T | A | A |
| DRD5u45 | WIAF-12961 | M67439 | 162 | DRD1, dopamine receptor D1 | TGCCGCCAGG[C/G]AGCAACGGCA | S | C | G | G | G |
| DRD5u46 | WIAF-12962 | M67439 | 195 | DRD1, dopamine receptor D1 | GGCAGTTCGC[T/G]CTATACCAGC | M | T | G | A | G |
| DRD5u47 | WIAF-12963 | M67439 | 264 | DRD1, dopamine receptor D1 | TGGGGCCCTC[A/G]CAGGTGGTCA | S | A | G | A | A |
| DRD5u48 | WIAF-12964 | M67439 | 465 | DRD1, dopamine receptor D1 | TGGCCCGTTA[C/T]TGGCCCTTTG | S | C | T | Y | Y |
| DRD5u49 | WIAF-12965 | M67439 | 511 | DRD1, dopamine receptor D1 | CTTCGACATC[A/T]TGTGCTCCAC | M | A | T | M | L |
| DRD5u50 | WIAF-12966 | M67439 | 557 | DRD1, dopamine receptor D1 | ATCAGCTGGA[A/G]CCCTACTGG | M | A | G | D | G |
| DRD5u51 | WIAF-12967 | M67439 | 476 | DRD1, dopamine receptor D1 | TGGCCCTTTG[G/A]AGCGTTCTGC | M | G | A | G | E |
| DRD5u52 | WIAF-12968 | M67439 | 1004 | DRD1, dopamine receptor D1 | AGCCTGCCGC[C/T]TTCCATCAAG | M | C | T | A | V |
| DRD5u53 | WIAF-12969 | M67439 | 1036 | DRD1, dopamine receptor D1 | GGTTCTCAAG[A/C]CCCTGTCGGT | M | A | C | T | P |
| DRD5u54 | WIAF-12970 | M67439 | 859 | DRD1, dopamine receptor D1 | CTACATCCCC[G/A]TTGCCATCAT | M | G | A | V | I |
| DRD5u55 | WIAF-12971 | M67439 | 931 | DRD1, dopamine receptor D1 | GATTTCCTCC[C/T]TGGAGAGGGC | S | C | T | L | L |
| G10u1 | WIAF-10234 | J04111 | 1308 | JUN, v-jun avian sarcoma virus 17 oncogene homolog | CCCTCAACGC[C/T]TCGTTCCTCC | M | C | T | A | A |
| G10u2 | WIAF-10235 | J04111 | 1471 | JUN, v-jun avian sarcoma virus 17 oncogene homolog | GCTGCTCAAG[C/T]TGGCGTGCC | S | C | T | L | L |
| G10u3 | WIAF-10253 | J04111 | 2010 | JUN, v-jun avian sarcoma virus 17 oncogene homolog | TGGAGTCCCA[G/A]GAGCGGATCA | S | G | A | Q | Q |
| G1001u1 | WIAF-13746 | D26135 | 993 | DGKG, diacylglycerol kinase, gamma (90 kD) | CCCCAGTGGT[G/A]TACCTGAAGG | S | G | A | V | V |
| G1001u2 | WIAF-13764 | D26135 | 2313 | DGKG, diacylglycerol kinase, gamma (90 kD) | ATGTGATGAG[A/T]GAGAAACATC | M | A | T | R | S |
| G1002u1 | WIAF-13918 | X57206 | 334 | ITPKB, inositol 1,4,5-trisphosphate 3-kinase B | CCCCAAGATC[A/C]GGACAAGCCT | M | A | C | Q | P |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G1002u2 | WIAF-13925 | X57206 | 575 | ITPKB, inositol 1,4,5-trisphosphate 3-kinase B | CCAACTCAGC[T/C]TTCCTGCATA | S | T | C | A | A |
| G1004u1 | WIAF-13567 | L36151 | 1854 | PIK4CA, phosphatidylinositol 4-kinase, catalytic, alpha polypeptide | GCCGCTCAGA[C/T]TCCGAGGATG | S | C | T | D | D |
| G1006u1 | WIAF-12375 | HT2690 | 858 | PRKCA, protein kinase C, alpha | GGTACAAGTT[G/A]CTTAACCAAG | S | G | A | L | L |
| G1008u1 | WIAF-12397 | HT2136 | 300 | PRKCZ, protein kinase C, zeta | CTGGCCTGCC[A/G]TGTCCGGAAG | S | A | G | P | P |
| G1008u2 | WIAF-12398 | HT2136 | 246 | PRKCZ, protein kinase C, zeta | AGTGCAGGGA[T/C]GAAGGCCTCA | S | T | C | D | D |
| G1008u3 | WIAF-12399 | HT2136 | 504 | PRKCZ, protein kinase C, zeta | GCTGCCACGG[C/T]CTCGTCCCGC | S | C | T | G | G |
| G1008u4 | WIAF-12403 | HT2136 | 807 | PRKCZ, protein kinase C, zeta | AGAAGAATGA[C/T]CAAATTTACG | S | C | T | D | D |
| G1008u5 | WIAF-12404 | HT2136 | 1514 | PRKCZ, protein kinase C, zeta | GGATTTTCTG[A/T]CATCAAGTCG | M | A | T | D | V |
| G1008u6 | WIAF-12412 | HT2136 | 166 | PRKCZ, protein kinase C, zeta | CAAGTGGGTG[G/A]ACAGCGAAGG | M | G | A | D | N |
| G1008u7 | WIAF-12418 | HT2136 | 560 | PRKCZ, protein kinase C, zeta | TCCCAAGAGC[C/T]TCCAGTAGAC | S | C | T | P | L |
| G1009u1 | WIAF-12396 | L05186 | 2495 | PTK2, PTK2 protein tyrosine kinase 2 | TCATCAACAA[G/A]ATGAAACTGG | S | G | A | K | K |
| G1011u1 | WIAF-11988 | X07876 | 1250 | WNT2, wingless-type MMTV integration site family member 2 | TCCCATGTCA[C/A]CCGATGACC | M | C | A | N | N |
| G1011u2 | WIAF-11997 | X07876 | 788 | WNT2, wingless-type MMTV integration site family member 2 | GACTATGGGA[T/C]CAAATTGCC | M | T | C | I | T |
| G1011u3 | WIAF-12014 | X07876 | 1338 | WNT2, wingless-type MMTV integration site family member 2 | TGCACACATG[C/A]AAGGCCCCA | N | C | A | C | * |
| G1011u4 | WIAF-13475 | X07876 | 856 | WNT2, wingless-type MMTV integration site family member 2 | CCTGATGAAT[C/T]TTCACACAA | M | C | T | L | F |
| G1011u5 | WIAF-13476 | X07876 | 958 | WNT2, wingless-type MMTV integration site family member 2 | GACATGCTGG[C/T]TGGCCATGGC | S | C | T | L | L |
| G1011u6 | WIAF-13477 | X07876 | 789 | WNT2, wingless-type MMTV integration site family member 2 | ACTATGGGAT[C/T]AAATTTGCCC | S | C | T | I | I |
| G1011u7 | WIAF-13478 | X07876 | 823 | WNT2, wingless-type MMTV integration site family member 2 | TGCAAAGGAA[A/G]GGGAAGGAAA | M | A | G | R | G |
| G1012u1 | WIAF-12408 | HT48910 | 1574 | WNT2B, wingless-type MMTV integration site family, member 2B | ATACTTGCAA[A/G]GCCCCAAGA | S | A | G | K | K |
| G1016a1 | WIAF-12125 | Z22534 | 793 | ACVR1, activin A receptor, type I | GGCAAGGGGA[A/G]AATGTTGCCG | S | A | G | E | E |
| G1016u2 | WIAF-12392 | Z22534 | 373 | ACVR1, activin A receptor, type I | CTGGCCAAGC[T/C]GTGGAGTGCT | S | T | C | A | A |
| G1018u1 | WIAF-12413 | X74210 | 1150 | ADCY2, adenylate cyclase 2 (brain) | CAAATTGCGA[G/T]TGGGTATTAA | M | G | T | V | L |
| G1019u1 | WIAF-12394 | U83867 | 5475 | SPTAN1, spectrin, alpha, non-erythrocytic 1 (alpha-fodrin) | GGGACCTAAC[T/C]GGCCTGCAGA | S | T | C | T | T |
| G1019u2 | WIAF-12406 | U83867 | 1223 | SPTAN1, spectrin, alpha, non-erythrocytic 1 (alpha-fodrin) | GCCCTCATCA[A/G]TGCAGATGAG | M | A | G | N | S |
| G1019u3 | WIAF-12409 | U83867 | 3555 | SPTAN1, spectrin, alpha, non-erythrocytic 1 (alpha-fodrin) | CTGAAGGTCT[T/C]ATGCCAGAGG | S | T | C | L | L |
| G1019u4 | WIAF-12415 | U83867 | 3369 | SPTAN1, spectrin, alpha, non-erythrocytic 1 (alpha-fodrin) | TCCGTGAAGC[G/A]AATGAACTAC | S | G | A | A | A |
| G1019u5 | WIAF-12417 | U83867 | 5839 | SPTAN1, spectrin, alpha, non-erythrocytic 1 (alpha-fodrin) | TGAGACAGAC[T/A]TCACCGTCCA | M | T | A | F | I |
| G1022u1 | WIAF-12393 | U45945 | 631 | ATP1B2, ATPase, Na+/Ka+ transporting, beta 2 polypeptide | CATGAATGTT[A/G]CCTGTGCTGG | M | A | G | T | A |
| G1022u2 | WIAF-12400 | U45945 | 432 | ATP182, ATPase, Na+/K+ transporting, beta 2 polypeptide | GCCGCCCTGG[G/A]CGCTATTACG | S | G | A | G | G |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G1023u1 | WIAF-12401 | D89722 | 395 | ARNTL, aryl hydrocarbon receptor nuclear translocator-like | AACATTAAGA[G/C]GTGCCACCAA | M | G | C | G | R |
| G1023u2 | WIAF-12407 | D89722 | 681 | ARNTL, aryl hydrocarbon receptor nuclear translocator-like | CTCATACATG[C/T]AAAAACTGGA | M | C | T | A | V |
| G1024u1 | WIAF-12410 | U85946 | 731 | Homo sapiens brain secretory protein hsec10p (HSEC10) mRNA, complete cds. | GATAGATTTT[C/T]AGAAGTTAAA | M | C | T | S | L |
| G1027u1 | WIAF-12402 | L47647 | 1135 | CKB, creatine kinase, brain | TCGAGATGGA[A/G]CAGCGGCTGG | S | A | G | E | E |
| G1027u2 | WIAF-12405 | L47647 | 499 | CKB, creatine kinase, brain | GGGAGCGCCG[A/C]GCCATCGAGA | S | A | C | R | R |
| G103u1 | WIAF-10427 | HT2269 | 335 | ERCC5, excision repair cross-complementing rodent repair deficiency, complementation group 5 (xeroderma pigmentosum, complementation group G (Cockayne syndrome)) | GGGATCGCCA[T/C]GGGAACTCAA | S | T | C | H | H |
| G103u2 | WIAF-10429 | HT2269 | 1221 | ERCC5, excision repair cross-complementing rodent repair deficiency, complementation group 5 (xeroderma pigmentosum, complementation group G (Cockayne syndrome)) | CCCTCCTTCT[C/T]CAAGAACTTT | M | C | T | P | S |
| G103u3 | WIAF-10431 | HT2269 | 1783 | ERCC5, excision repair cross-complementing rodent repair deficiency, complementation group 5 (xeroderma pigmentosum, complementation group G (Cockayne syndrome)) | TCTCCAACTT[G/C]TACAAATTCT | M | G | C | C | S |
| G103u4 | WIAF-10432 | HT2269 | 2077 | ERCC5, excision repair cross-complementing rodent repair deficiency, complementation group 5 (xeroderma pigmentosum, complementation group G (Cockayne syndrome)) | ACTGAATCTG[C/A]AGGCCAGAT | M | C | A | A | E |
| G103u5 | WIAF-10446 | HT2269 | 3338 | ERCC5, excision repair cross-complementing rodent repair deficiency, complementation group 5 (xeroderma pigmentosum, complementation group G (Cockayne syndrome)) | AATTTGAGCT[A/T]CTTGATAAGG | S | A | T | L | L |
| G103u6 | WIAF-10447 | HT2269 | 3487 | ERCC5, excision repair cross-complementing rodent repair deficiency, complementation group 5 (xeroderma pigmentosum, complementation group G (Cockayne syndrome)) | TCAGAATCAT[C/T]TGATGGATCT | M | C | T | S | F |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G103u7 | WIAF-10448 | HT2269 | 3507 | ERCC5, excision repair cross-complementing rodent repair deficiency, complementation group 5 (xeroderma pigmentosum, complementation group G (Cockayne syndrome)) | TTCAAGTGAA[C/G]ATGCTGAAAG | M | C | G | H | D |
| G103u8 | WIAF-10457 | HT2269 | 1388 | ERCC5, excision repair cross-complementing rodent repair deficiency, complementation group 5 (xeroderma pigmentosum, complementation group G (Cockayne syndrome)) | CTCTTGACGA[T/G]GACGAAGATG | M | T | G | D | E |
| G103u9 | WIAF-10458 | HT2269 | 1362 | ERCC5, excision repair cross-complementing rodent repair deficiency, complementation group 5 (xeroderma pigmentosum, complementation group G (Cockayne syndrome)) | CCGGACTCTT[T/C]CAGCCATTAA | M | T | C | S | P |
| G103u10 | WIAF-10459 | HT2269 | 2357 | ERCC5, excision repair cross-complementing rodent repair deficiency, complementation group 5 (xeroderma pigmentosum, complementation group G (Cockayne syndrome)) | CTGAGAAAGA[T/C]GCGGAAGATT | S | T | C | D | D |
| G103u11 | WIAF-10462 | HT2269 | 3109 | ERCC5, excision repair cross-complementing rodent repair deficiency, complementation group 5 (xeroderma pigmentosum, complementation group G (Cockayne syndrome)) | TGGAACAGAA[C/T]GAAGACAGAT | M | C | T | T | M |
| G103u12 | WIAF-10463 | HT2269 | 3138 | ERCC5, excision repair cross-complementing rodent repair deficiency, complementation group 5 (xeroderma pigmentosum, complementation group G (Cockayne syndrome)) | GTTTCCTGTA[T/C]TAAAGCAACT | S | T | C | L | L |
| G103u14 | WIAF-10484 | HT2269 | 3553 | ERCC5, excision repair cross-complementing rodent repair deficiency, complementation group 5 (xeroderma pigmentosum, complementation group G (Cockayne syndrome)) | AGAACAGCTG[C/T]GAAAGAGCCA | M | C | T | A | V |
| G103u15 | WIAF-10485 | HT2269 | 1429 | ERCC5, excision repair cross-complementing rodent repair deficiency, complementation group 5 (xeroderma pigmentosum, complementation group G (Cockayne syndrome)) | GATGTGCAGA[C/T]GGGAGGCCA | M | C | T | T | M |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G103a16 | WIAF-12097 | HT2269 | 3335 | ERCC5, excision repair cross-complementing rodent repair deficiency, complementation group 5 (xeroderma pigmentosum, complementation group G (Cockayne syndrome)) | AAGAATTTGA[G/T]CTACTTGATA | | G | T | E | D |
| G1030u1 | WIAF-12411 | U07358 | 203 | ZPK, zipper (leucine) protein kinase | ACACTTCTGA[C/T]TGCACTCCCG | S | C | T | D | D |
| G1030u2 | WIAF-12416 | U07358 | 1806 | ZPK, zipper (leucine) protein kinase | GCCACCCCAT[G/T]AACCTGAGG | N | G | T | E | * |
| G1031a1 | WIAF-12124 | U87460 | 2825 | GPR37, G protein-coupled receptor 37 (endothelin receptor type B-like) | GAGTCCACCAC[C/T]TTCACCTTAT | S | C | T | T | T |
| G1032u1 | WIAF-12381 | U57911 | 926 | C11ORF8, chromosome 11 open reading frame 8 | ACGTACATCA[A/C]TGCCTCGACG | M | A | C | N | T |
| G1033u1 | WIAF-12437 | M65188 | 431 | GJA1, gap junction protein, alpha 1, 43 kD (connexin 43) | TCTGTACCCA[C/T]ACTCTTGTAC | M | C | T | T | I |
| G1033u2 | WIAF-12438 | M65188 | 169 | GJA1, gap junction protein, alpha 1, 43 kD (connexin 43) | AGGCAACATG[G/C]GTGACTGAAG | M | G | C | G | R |
| G1033u3 | WIAF-12439 | M65188 | 467 | GJA1, gap junction protein, alpha 1, 43 kD (connexin 43) | TATGTGATGC[G/A]AAAGGAAGAG | M | G | A | R | Q |
| G1033u4 | WIAF-12440 | M65188 | 263 | GJA1, gap junctiono protein, alpha 1, 43 kD (connexin 43) | TTTCATTTTCC[G/A]AATCCTGCTG | M | G | A | R | Q |
| G1033u5 | WIAF-12441 | M65188 | 218 | GJA1, gap junction protein, alpha 1, 43 kD (connexin 43) | CAAGCCTACT[C/T]AACTGCTGA | M | C | T | S | L |
| G1033u6 | WIAF-12442 | M65188 | 498 | GJA1, gap junction protein, alpha 1, 43 kD (connexin 43) | AGAAAGAGGA[A/G]GAACTCAAGG | S | A | G | E | E |
| G1033u7 | WIAF-12465 | M65188 | 550 | GJA1, gap junction protein, alpha 1, 43 kD (connexin 43) | GCACTTGAAG[C/A]AGATTGAGAT | M | C | A | Q | K |
| G1033u8 | WIAF-12466 | M65188 | 548 | GJA1, gap junction protein, alpha 1, 43 kD (connexin 43) | ATGCACTTGA[A/G]GCAGATTGAG | M | A | G | K | R |
| G1033u9 | WIAF-12486 | M65188 | 933 | GJA1, gap junction protein, alpha 1, 43 kD (connexin 43) | CGCTGAGCCC[T/C]GCCAAAGACT | S | T | C | P | P |
| G1033u10 | WIAF-12487 | M65188 | 990 | GJA1, gap junction protein, alpha 1, 43 kD (connexin 43) | CCTCACCAAC[C/T]GCTCCCCTCT | S | C | T | P | T |
| G1033u11 | WIAF-12488 | M65188 | 1034 | GJA1, gap junction protein, alpha 1, 43 kD (connexin 43) | AAGCTGGTTA[C/A]TGGCGACAGA | M | C | A | T | N |
| G1033u12 | WIAF-12489 | M65188 | 1158 | GJA1, gap junction protein, alpha 1, 43 kD (connexin 43) | CTAACTCCCA[T/C]GCACAGCCTT | S | T | C | H | H |
| G1033u13 | WIAF-12490 | M65188 | 1222 | GJA1, gap junction protein, alpha 1, 43 kD (connexin 43) | TGGACATGAA[T/C]TACAGCCACT | S | T | C | L | L |
| G1033u14 | WIAF-12491 | M65188 | 1069 | GJA1, gap junction protein, alpha 1, 43 kD (connexin 43) | CCGCAATTAC[A/G]ACAAGCAAGC | M | A | G | N | D |
| G1033u15 | WIAF-12492 | M65188 | 1250 | GJA1, gap junction protein, alpha 1, 43 kD (connexin 43) | TATTTGTGTC[T/C]GTACCCACAC | S | T | C | S | S |
| G1033u16 | WIAF-12496 | M65188 | 423 | GJA1, gap junction protein, alpha 1, 43 kD (connexin 43) | TATTTGTGTC[T/C]GTACCCACAC | S | T | C | S | S |
| G1033u17 | WIAF-12503 | M65188 | 880 | GJA1, gap junction protein, alpha 1, 43 kD (connexin 43) | CGTTAAGGAT[C/T]GGGTTAAGGG | M | C | T | R | W |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G1033u18 | WIAF-12504 | M65188 | 855 | GJA1, gap junction protein, alpha 1, 43 kD (connexin 43) | AACTCTTCTA[T/C]GTTTTCTTCA | S | T | C | Y | Y |
| G1033u19 | WIAF-12505 | M65188 | 576 | GJA1, gap junction protein, alpha 1, 43 kD (connexin 43) | AGTTCAAGTA[C/T]GGTATTGAAG | S | C | T | Y | Y |
| G1033u20 | WIAF-12512 | M65188 | 1255 | GJA1, gap junction protein, alpha 1, 43 kD (connexin 43) | CCAGCGACCT[T/G]CAAGCAGAGC | M | T | G | S | A |
| G1033u21 | WIAF-12513 | M65188 | 1078 | GJA1, gap junction protein, alpha 1, 43 kD (connexin 43) | CAACAAGCAA[G/A]CAAGTGAGCA | M | G | A | A | T |
| G1033u22 | WIAF-12514 | M65188 | 1097 | GJA1, gap junction protein, alpha 1, 43 kD (connexin 43) | CAAAACTGGG[C/G]TAATTACAGT | M | C | G | A | G |
| G1034u1 | WIAF-12443 | J03544 | 1201 | PYGB, phosphorylase, glycogen; brain | AGACCTGTGC[A/G]TACCACACC | M | A | G | A | A |
| G1034u2 | WIAF-12469 | J03544 | 771 | PYGB, phosphorylase, glycogen; brain | GACACCCCAG[T/C]GCCCGGCTAC | S | T | C | A | A |
| G1034u3 | WIAF-12470 | J03544 | 1465 | PYGB, phosphorylase, glycogen; brain | TCCACTCGGA[G/C]ATCGTGAAAC | M | G | C | V | D |
| G1034u4 | WIAF-12471 | J03544 | 1583 | PYGB, phosphorylase, glycogen; brain | GGGGCTGGCC[G/A]AATACCATCGT | M | G | A | D | N |
| G1034u5 | WIAF-12472 | J03544 | 1774 | PYGB, phosphorylase, glycogen; brain | CCATGTTCGA[T/C]GTGCATGTGA | S | T | C | D | D |
| G1034u6 | WIAF-12474 | J03544 | 2449 | PYGB, phosphorylase, glycogen; brain | AGGTGGACCA[G/A]CTGTACCGGA | S | G | A | Q | Q |
| G1034u7 | WIAF-12508 | J03544 | 718 | PYGB, phosphorylase, glycogen; brain | CCCCCGACGG[C/T]GTGAAGTGGC | S | C | T | G | G |
| G1035u1 | WIAF-12484 | U97105 | 1962 | DPYSL2, dihydropyrimidinase-like 2 | GCAGAGGAGC[A/G]GCAGAGGATC | M | A | G | Q | R |
| G1035u2 | WIAF-12485 | U97105 | 2842 | DPYSL2, dihydropyrimidinase-like 2 | ATGACGGACC[T/C]GTGTGTGAAG | S | T | C | P | P |
| G1035u3 | WIAF-12511 | U97105 | 2062 | DPYSL2, dihydropyrimidinase-like 2 | CCATCACCAT[C/T]GCCAACCAGA | S | C | T | I | I |
| G1036u1 | WIAF-12444 | D88460 | 311 | WASL, Wiskott-Aldrich syndrome-like | ACGTGGGGTC[C/T]CTGTTGCTCA | S | C | T | S | S |
| G1038u1 | WIAF-12445 | HT2746 | 994 | PCTK2, PCTAIRE protein kinase 2 | TAGAAGAAAG[G/A]TATTGCATCG | M | G | A | V | I |
| G1039u1 | WIAF-12429 | HT2747 | 955 | serine/threonine kinase, PCTAIRE-3 | ATCCAAGAGT[C/T]GCATGTCAGC | M | C | T | R | C |
| G1039u2 | WIAF-12458 | HT2747 | 808 | serine/threonine kinase, PCTAIRE-3 | CACAGAGAG[A/T]CGTGGCCCGG | M | A | T | T | S |
| G1041u1 | WIAF-12459 | X72886 | 544 | H. sapiens TYRO3 mRNA. | CAAGTGGCCG[G/C]CCCTGAAAC | M | G | C | A | P |
| G1041u2 | WIAF-12460 | X72886 | 693 | H. sapiens TYRO3 mRNA. | TTGGCGGGAA[C/T]CGCCTGAAAC | S | C | T | T | P |
| G1041u3 | WIAF-12502 | X72886 | 561 | H. sapiens TYRO3 mRNA. | AGAGCCTGGC[C/T]GACAACCTGT | S | C | T | N | N |
| G1043u1 | WIAF-12448 | M94055 | 5481 | Human voltage-gated sodium channel mRNA, complete cds. | CTCTGAGTGA[G/A]GATGACTTTG | S | G | A | E | E |
| G1043u2 | WIAF-12449 | M94055 | 5205 | Human voltage-gated sodium channel mRNA, complete cds. | TTTGAGACCT[T/C]GGCAACAGCA | S | T | C | F | F |
| G1043u3 | WIAF-12450 | M94055 | 5224 | Human voltage-gated sodium channel mRNA, complete cds. | CATGATCTGC[C/T]TGTTCCAAAT | S | C | T | L | L |
| G1043u4 | WIAF-12451 | M94055 | 5514 | Human voltage-gated sodium channel mRNA, complete cds. | AGGTTTGGGA[G/A]AAGTTTGATC | S | G | A | E | E |
| G1043u5 | WIAF-12452 | M94055 | 5217 | Human voltage-gated sodium channel mRNA, complete cds. | GCAACAGCAT[G/C]ATCTGCCTGT | M | G | C | M | I |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G1043u6 | WIAF-12453 | M94055 | 5334 | Human voltage-gated sodium channel mRNA, complete cds. | GCTCAGTTAA[A/G]GGAGACTGTG | S | A | G | K | K |
| G1043u7 | WIAF-12454 | M94055 | 5424 | Human voltage-gated sodium channel mRNA, complete cds. | TGTACATCGC[G/C]GTCATCCTGG | S | G | C | A | A |
| G1043u8 | WIAF-12455 | M94055 | 5322 | Human voltage-gated sodium channel mRNA, complete cds. | ATCACCCTGG[A/C]AGCTCAGTTA | S | A | C | G | G |
| G1043u9 | WIAF-12456 | M94055 | 1200 | Human voltage-gated sodium channel mRNA, complete cds. | ATGGCTACAG[G/A]AGCTTTGACA | S | G | A | T | T |
| G1043u10 | WIAF-12499 | M94055 | 1170 | Human voltage-gated sodium channel mRNA, complete cds. | TCTGTGTGAA[G/T]GCTGGTAGAA | M | G | T | K | N |
| G1046a1 | WIAF-13187 | U50352 | 267 | ACCN1, amiloride-sensitive cation channel 1, neuronal (degenerin) | TCCCAGCTGT[G/A]ACCCTCTGTA | S | G | A | V | V |
| G1046a2 | WIAF-13188 | U50352 | 282 | ACCN1, amiloride-sensitive cation channel 1, neuronal (degenerin) | TCTGTAACCT[C/g]AATGGCTTCC | S | C | g | L | L |
| G1046a3 | WIAF-13189 | U50352 | 315 | ACCN1, amiloride-sensitive cation channel 1, neuronal (degenerin) | TCACCACCAA[C/t]GACCTGTACC | S | C | t | N | N |
| G1046a4 | WIAF-13190 | U50352 | 386 | ACCN1, amiloride-sensitive cation channel 1, neuronal (degenerin) | CCCCATCTGG[C/a]TGACCCCTCC | M | C | a | A | D |
| G1046a5 | WIAF-13191 | U50352 | 417 | ACCN1, amiloride-sensitive cation channel 1, neuronal (degenerin) | CCCTGCGGCA[G/A]AAGGCCAACT | S | G | A | Q | Q |
| G1048u1 | WIAF-12641 | HT5174S | 3214 | REST, RE1-silencing transcription factor | CAGTCAAAGC[G/A]GCTAAGGAG | S | G | A | A | A |
| G1048u2 | WIAF-12642 | HT5174S | 3199 | REST, RE1-silencing transcription factor | CAAAGGAAGC[C/G]TTGGCAGTCA | S | C | G | A | A |
| G1048u3 | WIAF-12657 | HT5174S | 2125 | REST, RE1-silencing transcription factor | CTCCCATGGA[G/T]ACTGCTCAGA | M | G | T | S | D |
| G1048u4 | WIAF-12660 | HT5174S | 2333 | REST, RE1-silencing transcription factor | GGAACCTGTT[A/C]AGATAGAGCT | M | A | C | K | Q |
| G1051u1 | WIAF-12431 | HT28321 | 658 | SCNN1G, sodium channel, nonvoltage-gated 1, gamma | ATGACACCTC[C/T]GACTGTGCCA | S | C | T | S | S |
| G1051u2 | WIAF-12434 | HT28321 | 1735 | SCNN1G, sodium channel, nonvoltage-gated 1, gamma | AAGCCAAGGA[G/A]TGGTGCGCCT | S | G | A | E | S |
| G1051u3 | WIAF-12473 | HT28321 | 409 | SCNN1G, sodium channel, nonvoltage-gated 1, gamma | AGTCCCTGTA[T/C]GGCTTTCCAG | S | T | C | Y | Y |
| G1051u4 | WIAF-12475 | HT28321 | 953 | SCNN1G, sodium channel, nonvoltage-gated 1, gamma | AGTCATTTTG[T/C]ACATAAACGA | M | T | C | Y | H |
| G1051u5 | WIAF-12476 | HT28321 | 975 | SCNN1G, sodium channel, nonvoltage-gated 1, gamma | GAGGAATACA[A/G]CCCATTCCTC | M | A | G | N | S |
| G1051u6 | WIAF-12477 | HT28321 | 1192 | SCNN1G, sodium channel, nonvoltage-gated 1, gamma | CTGCCTACTC[G/A]CTCCAGATCT | S | G | A | S | S |
| G1053a1 | WIAF-13192 | HT2201 | 4085 | SCN5A, sodium channel, voltage-gated, type V, alpha polypeptide (long (electrocardiographic) QT syndrome 3) | CGTCCTCTGA[G/A]AGCTCTGTCA | N | G | A | R | K |
| G1053a2 | WIAF-13193 | HT2201 | 5607 | SCN5A, sodium channel, voltage-gated, type v, alpha polypeptide (long (electrocardiographic) QT syndrome 3) | ACTTTGCCGA[C/T]GCCCTGTCTG | S | C | T | D | D |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G1053a3 | WIAF-13194 | HT2201 | 5828 | SCN5A, sodium channel, voltage-gated, type v, alpha polypeptide (long (electrocardiographic) QT syndrome 3) | GAGCCCATCA[C/T]CACCACTC | M | C | T | T | I |
| G1053a4 | WIAF-13202 | HT2201 | 713 | SCN5A, sodium channel, voltage-gated, type v, alpha polypeptide (long (electrocardiographic) QT syndrome 3) | GCGTTCACTT[T/A]CCTTCGGGAC | M | T | A | F | Y |
| G1053a5 | WIAF-13203 | HT2201 | 6148 | SCN5A, sodium channel, voltage-gated, type v, alpha polypeptide (long (electrocardiographic) QT syndrome 3) | CCACACAGTGAA[G/T]ATCTCGCCGA | M | G | T | D | Y |
| G1053a6 | WIAF-13204 | HT2201 | 6217 | SCN5A, sodium channel, voltage-gated, type v, alpha polypeptide (long (electrocardiographic) QT syndrome 3) | GGCCTGGCTG[G/T]CCAGGACACA | — | G | T | — | — |
| G1053a7 | WIAF-13205 | HT2201 | 6324 | SCN5A, sodium channel, voltage-gated, type v, alpha polypeptide (long (electrocardiographic) QT syndrome 3) | AATGGGCCTC[G/A]GCCCCGCGGA | — | G | A | — | — |
| G1054u1 | WIAF-12419 | HT2202 | 2252 | SCN4A, sodium channel, voltage-gated, type IV, alpha polypeptide | TTGGGAAGAG[C/T]TACAAGGAGT | S | C | T | S | S |
| G1054u2 | WIAF-12423 | HT2202 | 4559 | SCN4A, sodium channel, voltage-gated, type IV, alpha polypeptide | TGGTCATGTT[C/T]ATCTACTCCA | S | C | T | F | F |
| G1054u3 | WIAF-12424 | HT2202 | 4856 | SCN4A, sodium channel, voltage-gated, type IV, alpha polypeptide | TGAACATGTA[C/G]ATCGCCATCA | N | C | G | Y | * |
| G1054u4 | WIAF-12425 | HT2202 | 4777 | SCN4A, sodium channel, voltage-gated, type IV, alpha polypeptide | GTGAAGGGTG[A/G]CTGCGGAAAC | M | A | G | D | G |
| G1054u5 | WIAF-12426 | HT2202 | 4863 | SCN4A, sodium channel, voltage-gated, type IV, alpha polypeptide | GTACATCGCC[A/G]TCATCCTGA | M | A | G | I | V |
| G1054u6 | WIAF-12427 | HT2202 | 4566 | SCN4A, sodium channel, voltage-gated, type IV, alpha polypeptide | GTTCATCTAC[T/G]CCATCTTCGG | M | T | G | S | A |
| G1054u7 | WIAF-12428 | HT2202 | 4923 | SCN4A, sodium channel, voltage-gated, type IV, alpha polypeptide | TGGTGAAGAT[G/T]ACTTTGAGAT | M | G | T | D | Y |
| G1054u8 | WIAF-12446 | HT2202 | 3595 | SCN4A, sodium channel, voltage-gated, type IV, alpha polypeptide | TTCTGGCTGA[T/C]CTTCAGCATC | M | T | C | I | T |
| G1054u9 | WIAF-12447 | HT2202 | 4203 | SCN4A, sodium channel, voltage-gated, type IV, alpha polypeptide | GGAGACAGAC[G/A]ACCAGAGCCA | M | G | A | D | N |
| G1054u10 | WIAF-12495 | HT2202 | 4811 | SCN4A, sodium channel, voltage-gated, type IV, alpha polypeptide | TCTGCTTCTT[C/A]TGCAGCTATA | N | C | A | F | L |
| G1054u11 | WIAF-12497 | HT2202 | 5555 | SCN4A, sodium channel, voltage-gated, type IV, alpha polypeptide | CAGGGCAGAC[T/G]GTGCGCCCAG | S | T | G | T | T |
| G1054u12 | WIAF-12498 | HT2202 | 5480 | SCN4A, sodium channel, voltage-gated, type IV, alpha polypeptide | CAGGGGACGC[C/T]GGACCCACTA | S | C | T | A | A |
| G1059u1 | WIAF-12432 | HT33704 | 112 | APLP1, amyloid beta (A4) precursor-like protein 1 | CGCTGCTGCT[G/A]CCACTATTGC | S | G | A | L | L |
| G1059u2 | WIAF-12433 | HT33704 | 140 | APLP1, amyloid beta (A4) precursor-like protein 1 | TCTGCCGCCG[C/T]AGCCCGCCAT | N | C | T | Q | * |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G1059u3 | WIAF-12435 | HT33704 | 1344 | APLP1, amyloid beta (A4) precursor-like protein 1 | CAGCATGTGG[C/T]CGCCGTGAT | M | C | T | A | V |
| G1059u4 | WIAF-12457 | HT33704 | 1687 | APLP1, amyloid beta (A4) precursor-like protein 1 | ATGAGCCAAA[G/A]GTGAATGCGT | S | G | A | K | K |
| G1059u5 | WIAF-12500 | HT33704 | 976 | APLP1, amyloid beta (A4) precursor-like protein 1 | GGTTCCTGAG[A/G]GCCAAGATGG | S | A | G | R | R |
| G1059u6 | WIAF-12501 | HT33704 | 1786 | APLP1, amyloid beta (A4) precursor-like protein 1 | GTGAGGCTGT[A/G]TCGGGTCTGC | S | A | G | V | V |
| G1060u1 | WIAF-12436 | HT1418 | 1744 | APLP2, amyloid beta (A4) precursor-like protein 2 | CGAAGAAATT[C/G]AAGAGAAAT | M | C | G | Q | E |
| G1060u2 | WIAF-12467 | HT1418 | 2213 | APLP2, amyloid beta (A4) precursor-like protein 2 | ATCAGCCTGG[T/G]GATGCTGAGG | M | T | G | V | G |
| G1060u3 | WIAF-12468 | HT1418 | 2256 | APLP2, amyloid beta (A4) precursor-like protein 2 | GCCACGGGAT[C/T]GTGGAGTTG | S | C | T | H | H |
| G1066a1 | WIAF-13195 | HT3538 | 566 | CCKBR, cholecystokinin B receptor | CTTTGGCACC[G/A]TCATCTGCAA | M | G | A | V | I |
| G1066a2 | WIAF-13196 | HT3538 | 607 | CCKBR, cholecystokinin B receptor | GGGTGTCTGT[G/A]AGTGTGTCCA | S | G | A | V | V |
| G1066a3 | WIAF-13206 | HT3538 | 864 | CCKBR, cholecystokinin B receptor | CTGCTGCTTC[T/A]GCTCTTGTTC | M | T | A | L | Q |
| G1067u1 | WIAF-12478 | HT0830 | 684 | KCNA1, potassium voltage-gated channel, shaker-related subfamily, member 1 (episodic ataxia with myokymia) | AAACGCTGTG[C/T]ATCATCTGGT | S | C | T | C | C |
| G1067u2 | WIAF-12479 | HT0830 | 722 | KCNA1, potassium voltage-gated channel, shaker-related subfamily, member 1 (episodic ataxia with myokymia) | GTGCGCGTTCT[T/C]CGCCTGCCCC | M | T | C | F | S |
| G1067u3 | WIAF-12480 | HT0830 | 804 | KCNA1, potassium voltage-gated channel, shaker-related subfamily, member 1 (episodic ataxia with myokymia) | ATTTCATCAC[C/G]CTGGGCACCG | S | C | G | T | T |
| G1067u4 | WIAF-12509 | HT0830 | 690 | KCNA1, potassium voltage-gated channel, shaker-related subfamily, member 1 (episodic ataxia with myokymia) | TGTGCATCAT[C/T]TTGGTTCCT | S | C | T | H | H |
| G1068u1 | WIAF-12493 | HT0831 | 774 | KCNA2, potassium voltage-gated channel, shaker-related subfamily, member 2 | TGAAACATCAT[T/A]GACATTGTGG | S | T | A | H | H |
| G1070a1 | WIAF-13197 | HT27728 | 522 | KCNJ6, potassium inwardly-rectifying channel, subfamily J, member 6 | CACAGTGACC[T/C]GGCTCTTTTT | M | T | C | W | R |
| G1070a2 | WIAF-13201 | HT27728 | 1244 | KCNJ6, potassium inwardly-rectifying channel, subfamily J, member 6 | CCCTGAGGA[T/C]GGGTTCTACG | S | T | C | D | D |
| G1070a3 | WIAF-13207 | HT27728 | 707 | KCNJ6, potassium inwardly-rectifying channel, subfamily J, member 6 | ATAAATGCCC[G/A]GAGGGAATTA | S | G | A | P | P |
| G1071u1 | WIAF-12422 | HT38672 | 1534 | KCNJ3, potassium inwardly-rectifying channel, subfamily J, member 3 | TTCCGGGCAA[C/T]TCAGAAGAAA | S | C | T | N | N |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G1073u1 | WIAF-12461 | HT4556 | 1127 | KCNJ1, potassium inwardly-rectifying channel, subfamily J, member 1 | CACTGTGCCA[T/C]GTGCCTTTAT | M | T | C | M | T |
| G1074u1 | WIAF-12462 | HT27804 | 289 | KCNAB2, potassium voltage-gated channel, shaker-related subfamily, beta member 2 | ACCTCTTCGA[T/C]ACAGCAGAAG | S | T | C | D | D |
| G1079u1 | WIAF-12463 | HT27383 | 1130 | potassium channel, inwardly rectifing (GB:D50582) | ACCTGGCCGA[T/A]GAGATCCTGT | M | T | A | D | E |
| G1079u2 | WIAF-12464 | HT27383 | 1192 | potassium channel, inwardly rectifing (GB:D50582) | CGTTACTCTG[T/G]GGACTACTCC | M | T | G | V | G |
| G1079u3 | WIAF-12481 | HT27383 | 708 | potassium channel, inwardly rectifing (GB:D50582) | GCTTGGCTAC[A/G]TCTTCATGAA | M | A | G | I | V |
| G1079u4 | WIAF-12482 | HT27383 | 779 | potassium channel, inwardly rectifing (GB:D50582) | CGGTGATCGC[T/C]CTGCGCCACG | S | T | C | A | A |
| G1079u5 | WIAF-12483 | HT27383 | 276 | potassium channel, inwardly rectifing (GB:D50582) | GGACCCTGCC[G/A]AGCCCAGGTA | M | G | A | E | K |
| G1079u6 | WIAF-12510 | HT27383 | 489 | potassium channel, inwardly rectifing (GB:D50582) | GTGGCTCATC[G/A]CCTTCGCCCA | M | G | A | A | T |
| G1080u1 | WIAF-12536 | HT4412 | 1099 | KCNJ4, potassium inwardly-rectifying channel, subfamily J, member 4 | TGGACTACTC[A/G]CGTTTTCACA | S | A | G | S | S |
| G1080u2 | WIAF-12537 | HT4412 | 1050 | KCNJ4, potassium inwardly-rectifying channel, subfamily J, member 4 | GGCCACCGCT[T/A]TGAGCCTGTG | M | T | A | F | Y |
| G1081u1 | WIAF-12538 | HT27724 | 1090 | KCNJ2, potassium inwardly-rectifying channel, subfamily J, member 2 | GGCCACCGCT[A/T]TGAGCCTGTG | M | A | T | Y | F |
| G1082u1 | WIAF-12662 | HT28319 | 768 | potassium channel, inwardly rectifying, high conductance, alpha subunit | CGCGGGTCAC[C/T]GAGGAGGCT | S | C | T | T | T |
| G1082u2 | WIAF-12663 | HT28319 | 854 | potassium channel, inwardly rectifying, high conductance, alpha subunit | CTGGTGTCGC[C/T]CATCACCATC | M | C | T | P | L |
| G1082u3 | WIAF-12679 | HT28319 | 471 | potassium channel, inwardly rectifying, high conductance, alpha subunit | TCTCCATCGA[G/C]ACGCAGACCA | M | G | C | E | D |
| G1084a1 | WIAF-13198 | HT0383 | 2028 | KCNB1, potassium voltage-gated channel, Shab-related subfamily, member 1 | CACTCCCCAG[C/A]AAGACTGGGG | M | C | A | S | R |
| G1084a2 | WIAF-13199 | HT0383 | 2033 | KCNB1, potassium voltage-gated channel, Shab-related subfamily, member 1 | CCCAGCAAGA[C/G]TGGGGCAGC | M | C | G | T | S |
| G1084a3 | WIAF-13200 | HT0383 | 2321 | KCNB1, potassium voltage-gated channel, Shab-related subfamily, member 1 | GAGTGTGCCA[C/A]GCTTTTGAC | M | C | A | T | K |
| G1084a4 | WIAF-13208 | HT0383 | 870 | KCNB1, potassium voltage-gated channel, Shab-related subfamily, member 1 | ACAACCCCCA[G/A]CTGGCCACG | S | G | A | Q | Q |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G1088u1 | WIAF-12516 | HT0522 | 1503 | KCNA5, potassium voltage-gated channel, shaker-related subfamily, member 5 | TCCTGGGCAA[G/A]ACCTTGCAGG | S | G | A | K | K |
| G1088u2 | WIAF-12519 | HT0522 | 1249 | KCNA5, potassium voltage-gated channel, shaker-related subfamily, member 5 | CGAGCTGCTC[G/A]TGCGGTTCTT | M | G | A | V | M |
| G1088u3 | WIAF-12520 | HT0522 | 973 | KCNA5, potassium voltage-gated channel, shaker-related subfamily, member 5 | CTCTGGGTCC[G/A]CGCGGGCCAT | M | G | A | A | T |
| G1088u4 | WIAF-12521 | HT0522 | 1013 | KCNA5, potassium voltage-gated channel, shaker-related subfamily, member 5 | GTTATCCTCA[T/C]CTCCATCATC | M | T | C | I | T |
| G1090u1 | WIAF-12651 | HT1497 | 1836 | KCNA6, potassium voltage-gated channel, shaker-related subfamily, member 6 | CAACCAGCCA[G/A]TGGAGGAGGC | M | G | A | S | N |
| G1091u1 | WIAF-12714 | HT0222 | 843 | KCNA3, potassium voltage-gated channel, shaker-related subfamily, member 3 | CATCATCTGG[T/C]TCTCCTTCGA | M | T | C | F | L |
| G1094a1 | WIAF-13218 | HT27381 | 1280 | KCNJ8, potassium inwardly-rectifying channel, subfamily J. member 8 | GTGTATTCTG[G/a]GGATTACTCC | M | T | a | V | E |
| G1095u1 | WIAF-12532 | HT2629 | 765 | KCNMA1, potassium large conductance calcium-activated channel, subfamily M, alpha member 1 | TTCTCTACTT[C/T]GGCTTGCGGT | S | C | T | F | F |
| G1095u2 | WIAF-12533 | HT2629 | 2441 | KCNMA1, potassium large conductance calcium-activated channel, subfamily M, alpha member 1 | GTGGGTCGCA[T/C]CTTTGGCGAC | M | T | C | I | T |
| G1095u3 | WIAF-12534 | HT2629 | 2714 | KCNMA1, potassium large conductance calcium-activated channel, subfamily M, alpha member 1 | GATGATACTT[C/G]GCTGCAGGAC | M | C | G | S | W |
| G1095u4 | WIAF-12535 | HT2629 | 2439 | KCNMA1, potassium large conductance calcium-activated channel, subfamily M, alpha member 1 | TCGTGGTCTG[C/T]ATCTTGGGCG | S | C | T | C | C |
| G1095u5 | WIAF-12539 | HT2629 | 3048 | KCNMA1, potassium large conductance calcium-activated channel, subfamily M, alpha member 1 | CACTCATGAG[C/T]GCGACCTACT | S | C | T | S | S |
| G1095u6 | WIAF-12544 | HT2629 | 2352 | KCNMA1, potassium large conductance calcium-activated channel, subfamily M, alpha member 1 | GGATGTTTCA[C/T]TGGTGTGCAC | S | C | T | H | H |
| G1095u7 | WIAF-12545 | HT2629 | 2392 | KCNMA1, potassium large conductance calcium-activated channel, subfamily M, alpha member 1 | CATCCTGACT[C/T]GAAGTGAAGC | N | C | T | R | * |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G1095u8 | WIAF-12546 | HT2629 | 2295 | KCNMA1, potassium large conductance calcium-activated channel, subfamily M, alpha member 1 | CTGGCAATGA[T/C]CAGATTGACA | S | T | C | D | D |
| G1095u9 | WIAF-12548 | HT2629 | 2949 | KCNMA1, potassium large conductance calcium-activated channel, subfamily M, alpha member 1 | AGTTTTTGGA[C/T]CAAGACGATG | S | C | T | D | D |
| G1095u10 | WIAF-12549 | HT2629 | 2865 | KCNMA1, potassium large conductance calcium-activated channel, subfamily M, alpha member 1 | TGCACGGGAT[G/A]TTACGTCAAC | M | G | A | M | I |
| G1096u1 | WIAF-12547 | L26318 | 930 | PRKM8, protein kinase mitogen-activated 8 (MAP kinase) | TGCTGGTAAT[A/T]GATGCATCTA | S | A | T | I | I |
| G1098u1 | WIAF-12515 | L19711 | 2650 | DAG1, dystroglycan 1 (dystrophin-associated glycoprotein 1) | TCTACCTGCA[C/T]ACAGTCATTC | S | C | T | H | H |
| G1110u1 | WIAF-10385 | HT27392 | 230 | meiosis-specific recA homolog, HsLim15 | CAAAGTATA[C/T]AGATGACAAC | N | T | C | Q | * |
| G1110u2 | WIAF-10397 | HT27392 | 1050 | meiosis-specific recA homolog, HsLim15 | CCTGAAAATG[A/G]AGCCACCTTC | M | A | G | E | G |
| G1110u3 | WIAF-10399 | HT27392 | 674 | meiosis-specific recA homolog, HsLim15 | TGAACATCAG[A/G]TGGAGCTACT | M | A | G | M | V |
| G1106u1 | WIAF-12647 | HT5073 | 5781 | MAP1B, microtubule-associated protein 1B | ACTATGAGAG[G/A]ATAGAGAA | S | G | A | K | K |
| G1106u2 | WIAF-12648 | HT5073 | 5916 | MAP1B, microtubule-associated protein 1B | CTGAAGAGGG[C/T]GGGTACTCAT | S | C | T | G | G |
| G1106u3 | WIAF-12650 | HT5073 | 1837 | MAP1B, microtubule-associated protein 1B | AGACAAGCCA[G/A]TAAAAACAGA | M | G | A | V | I |
| G1106u4 | WIAF-12653 | HT5073 | 2476 | MAP1B, microtubule-associated protein 1B | CACCACAGCA[G/A]CTGTCATGGC | M | G | A | A | T |
| G1106u5 | WIAF-12656 | HT5073 | 3913 | MAP1B, microtubule-associated protein 1B | GCCCAATGAG[A/G]TTAAAGTCTC | M | A | G | I | V |
| G1106u6 | WIAF-12667 | HT5073 | 559 | MAP1B, microtubule-associated protein 1B | GATTTTCACC[G/A]ATCAAGAGAT | M | G | A | D | N |
| G1106u7 | WIAF-12668 | HT5073 | 570 | MAP1B, microtubule-associated protein 1B | ATCAAGAGAT[C/T]GGGGAGTTAC | S | C | T | I | I |
| G1106u8 | WIAF-12669 | HT5073 | 6175 | MAP1B, microtubule-associated protein 1B | TACTTCCACA[T/C]ACTGTTACGA | M | T | C | Y | H |
| G1106u9 | WIAF-12670 | HT5073 | 1215 | MAP1B, microtubule-associated protein 1B | TCACTCTCCA[G/C]TACCTAAACA | M | G | C | Q | H |
| G1106u10 | WIAF-12672 | HT5073 | 1821 | MAP1B, microtubule-associated protein 1B | AGGTAATGGT[G/A]AAAAAGACA | S | G | A | V | V |
| G1106u11 | WIAF-12673 | HT5073 | 2727 | MAP1B, microtubule-associated protein 1B | GTCGTGCCGA[G/T]TCCCCTGATG | M | G | T | E | D |
| G1106u12 | WIAF-12674 | HT5073 | 2739 | MAP1B, microtubule-associated protein 1B | CCCCTGATGA[G/A]GGAATCACTA | S | G | A | E | E |
| G1106u13 | WIAF-12676 | HT5073 | 3643 | MAP1B, microtubule-associated protein 1B | AGATGCCACT[G/A]ATGGCAAGGA | M | G | A | D | N |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G1106u14 | WIAF-12677 | HT5073 | 3609 | MAP1B, microtubule-associated protein 1B | CACCGCTCAA[C/T]GGATTTTCTG | S | C | T | N | N |
| G1106u15 | WIAF-12682 | HT5073 | 4752 | MAP1B, microtubule-associated protein 1B | TTCCAGAGCC[A/T]ACAACAGATG | S | A | T | P | P |
| G1110u1 | WIAF-12517 | HT1096 | 1527 | myelin aesociated glycoprotein | GCGGCCTCGT[G/C]CTCACCAGCA | S | G | C | V | V |
| G1110u2 | WIAF-12518 | HT1096 | 1678 | myelin asecociated glycoprotein | TGTGGGCGCC[G/T]TGGTCGCCTT | M | G | T | V | L |
| G1110u3 | WIAF-12522 | HT1096 | 1271 | myelin associated glycoprotein | GCCGTGTCAC[C/T]CGAGGATGAT | M | C | T | P | L |
| G1113u1 | WIAF-12523 | HT2242 | 353 | myelin transcription factor 1 | AATTCCCATC[G/T]GATCCTCAGG | M | G | T | R | L |
| G1116a1 | WIAF-13217 | HT28451 | 417 | myelin oligodendrocyte glycoprotein (MOG) | CAAGCTTATC[G/A]AGACCCTCTC | S | G | A | S | S |
| G1116a2 | WIAF-13219 | HT28451 | 913 | myelin oligodendrocyte glycoprotein (MOG) | GCAGATCACT[C/G]TTGGCCTCGT | S | C | G | L | V |
| G1116a3 | WIAF-13220 | HT28451 | 922 | myelin oligodendrocyte glycoprotein (MOG) | TCTTGGCCTC[G/A]TCTTCCTCTG | M | G | A | V | I |
| G1120u1 | WIAF-12525 | HT3695 | 1200 | neurofilament, subunit H | TAGAGATAGC[T/C]GCTTACAGAA | S | T | C | A | A |
| G1123u1 | WIAF-12542 | HT2569 | 2269 | OMG, oligodendrocyte myelin glycoprotein | CAGCTGCAAC[T/C]CTAACTATTC | S | T | C | T | T |
| G1126u1 | WIAF-12526 | HT28354 | 626 | PSEN2, presenilin 2 (Alzheimer disease 4) | GAGCGAAGCA[T/C]GTGATCATGC | S | T | C | H | H |
| G1126u2 | WIAF-12527 | HT28354 | 494 | PSEN2, presenilin 2 (Alzheimer disease 4) | ATGGAGAGAA[T/C]ACTGCCCAGT | S | T | C | N | N |
| G1126u3 | WIAF-12528 | HT28354 | 434 | PSEN2, presenilin 2 (Alzheimer disease 4) | TAATGTCGGC[C/T]GAGAGCCCCA | S | C | T | A | A |
| G1126u4 | WIAF-12543 | HT28354 | 550 | PSEN2, presenilin 2 (Alzheimer disease 4) | GACCCTGACC[G/A]CTATGTCTGT | M | G | A | R | H |
| G117u1 | WIAF-10391 | HT27765 | 156 | GTBP, G/T mismatch-binding protein | ACTTCTCACC[A/G]GGAGATTTGG | S | A | G | P | P |
| G117u2 | WIAF-10392 | HT27765 | 420 | GTBP, G/T mismatch-binding protein | AACGTGCAGA[T/C]GAAGCCTTAA | S | T | C | D | D |
| G117u3 | WIAF-10407 | HT27765 | 939 | GTBP, G/T mismatch-binding protein | CCCACGTTAG[T/C]GGAGGTGGTG | S | T | C | S | S |
| G117u4 | WIAF-10411 | HT27765 | 1622 | GTBP, G/T mismatch-binding protein | CATTGTTCGA[G/A]ATTTAGGACT | M | G | A | R | K |
| G117u5 | WIAF-10412 | HT27765 | 2405 | GTBP, G/T mismatch-binding protein | GACAGCAGGG[C/T]TATAATGTAT | M | C | T | A | V |
| G117u6 | WIAF-10413 | HT27765 | 2387 | GTBP, G/T mismatch-binding protein | AAGAGTCAGA[A/T]CCACCCAGAC | M | A | T | N | I |
| G125u1 | WIAF-10371 | HT28632 | 1999 | ATM, ataxia telangiectasia mutated (includes complementation groups A, C and D) | CAGTAATTTT[C/T]CTCATCTTGT | M | C | T | P | S |
| G125u2 | WIAF-10372 | HT28632 | 2631 | ATM, ataxia telangiectasia mutated (includes complementation groups A, C and D) | TAATGAATGA[C/A]ATTGCAGATA | M | C | A | D | E |
| G125u3 | WIAF-10373 | HT28632 | 3084 | ATM, ataxia telangiectasia mutated (includes complementation groups A, C and D) | CAATGGAAGA[T/C]GTTCTTGAAC | M | T | G | D | E |
| G125u5 | WIAF-10375 | HT28632 | 4767 | ATM, ataxia telangiectasia mutated (includes complementation groups A, C and D) | CACTTATACC[C/T]CTTGTGTATG | S | C | T | P | P |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G125u6 | WIAF-10383 | HT28632 | 8713 | ATM, ataxia telangiectasia mutated (includes complementation groups A, C and D) | ATTCTTGGAT[C/T]CAGCTATTTG | M | C | T | P | S |
| G125u7 | WIAF-10396 | HT28632 | 1825 | ATM, ataxia telangiectasia mutated (includes complementation groups A, C and D) | GACTTTGGCA[C/G]TGACCACCAG | M | C | G | L | V |
| G125u8 | WIAF-10398 | HT28632 | 2924 | ATM, ataxia telangiectasia mutated (includes complementation groups A, C and D) | ACTACTGCTC[A/G]CACCAATACT | M | A | G | Q | R |
| G125u9 | WIAF-10405 | HT28632 | 8967 | ATM, ataxia telangiectasia mutated (includes complementation groups A, C and D) | TTGAAGGTGT[C/T]TTCAGAAGAT | S | C | T | V | V |
| G125u10 | WIAF-10408 | HT28632 | 6954 | ATM, ataxia telangiectasia mutated (includes complementation groups A, C and D) | CCAAACACCT[T/C]GTAGAACTCT | S | T | C | L | L |
| G125u11 | WIAF-10409 | HT28632 | 6855 | ATM, ataxia telangiectasia mutated (includes complementation groups A, C and D) | TTCAGGAGCC[T/C]ATCATGGCTC | S | T | C | P | P |
| G125u12 | WIAF-10410 | HT28632 | 6801 | ATM, ataxia telangiectasia mutated (includes complementation groups A, C and D) | TATATATTAA[G/T]TGGCAGAAAC | M | G | T | K | N |
| G125u13 | WIAF-10421 | HT28632 | 335 | ATM, ataxia telangiectasia mutated (includes complementation groups A, C and D) | CATTCAGATT[C/G]CAAACAAGGA | M | C | G | S | C |
| G125u14 | WIAF-11607 | HT28632 | 3966 | ATM, ataxia telangiectasia mutated (includes complementation groups A, C and D) | TTCCACATCT[G/A]GTGATTAGAA | S | G | A | L | L |
| G125a15 | WIAF-13130 | HT28632 | 8642 | ATM, ataxia telangiectasia mutated (includes complementation groups A, C and D) | GAGAAATATG[A/C]AGTCTTCATG | M | A | C | E | A |
| G136u1 | WIAF-10388 | HT3337 | 535 | MLH1, mutL (E. coli) homolog 1 (colon cancer, nonpolyposis type 2) | AGGAGAAAAG[C/T]TTTAAAAAAT | M | C | T | A | V |
| G136u2 | WIAF-10389 | HT3337 | 769 | MLH1, mutL (E. coli) homolog 1 (colon cancer, nonpolyposis type 2) | TTCAAAATGA[A/G]TGGTTACATA | M | A | G | N | S |
| G144u1 | WIAF-11638 | HT3625 | 1129 | FOS, v-fos FBJ murine osteosarcoma viral oncogene homolog | CCTGTGCACT[C/T]CGGTGGTCAC | M | C | T | P | S |
| G1461u1 | WIAF-12562 | HT0329 | 684 | pRB-binding protein | TTGCCAAGAA[G/A]TCCAAGAACC | S | G | A | K | K |
| G1466u1 | WIAF-12571 | HT27849 | 2128 | API2, apoptosis inhibitor 2 | ATGATCCATG[G/C]GTAGAACATG | M | G | C | W | C |
| G1468u1 | WIAF-12563 | HT4986 | 1928 | apoptosis inhibitor, neuronal | CCACCAGACC[A/T]GACGAGGGC | S | A | T | P | P |
| G1468u2 | WIAF-12564 | HT4986 | 3057 | apoptosis inhibitor, neuronal | TTTGCAATTC[C/G]TTCAAGGGAG | M | C | G | L | V |
| G1472u1 | WIAF-12565 | HT28478 | 242 | BAK1, BCL2-antagonist/killer 1 | GGCAGCCATG[C/T]GGAGAGCCTG | S | C | T | C | C |
| G1472u2 | WIAF-12572 | HT28478 | 509 | BAK1, BCL2-antagonist/killer 1 | TGCAGCCCAG[C/A]GCAGAGAATG | S | G | A | T | T |
| G1473u1 | WIAF-12568 | HT28606 | 394 | CASP6, caspase 6, apoptosis-related cysteine protease | GGTGTCAAGT[G/C]TTAGCCACGG | M | G | C | V | L |
| G1473u2 | WIAF-12576 | HT28606 | 411 | CASP6, caspase 6, apoptosis-related cysteine protease | ACGCAGATGC[C/T]GATTGCTTTG | S | C | T | A | A |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G1479u1 | WIAF-12550 | Y09077 | 711 | ATR, ataxia telangiectasia and Rad3 related | AGTTTATTAA[T/C]GGTTCTTACT | M | T | C | M | T |
| G1479u2 | WIAF-12551 | Y09077 | 4303 | ATR, ataxia telangiectasia and Rad3 related | TTGCGTATGC[T/C]GATAATAGCC | S | T | C | A | A |
| G1479u3 | WIAF-12552 | Y09077 | 1894 | ATR, ataxia telangiectasia and Rad3 related | ATTCTGATGA[T/C]GGCTGTTTAA | S | T | C | D | D |
| G1479u4 | WIAF-12553 | Y09077 | 1855 | ATR, ataxia telangiectasia and Rad3 related | ATTTATGTGG[T/A]ATGCTCTCAC | S | T | A | G | G |
| G1479u5 | WIAF-12558 | Y09077 | 5287 | ATR, ataxia telangiectasia and Rad3 related | TCATTGATTA[T/C]CATGGTGTAG | S | T | C | Y | Y |
| G1479u6 | WIAF-12559 | Y09077 | 5539 | ATR, ataxia telangiectasia and Rad3 related | CAGCTTTTTA[T/C]GACTCACTGA | S | T | C | Y | Y |
| G1479u7 | WIAF-12569 | Y09077 | 1540 | ATR, ataxia telangiectasia and Rad3 related | ATCCTGTTAT[T/C]GAGATGTTAG | S | T | C | I | I |
| G1479u8 | WIAF-12570 | Y09077 | 2521 | ATR, ataxia telangiectasia and Rad3 related | ATTTAATGGA[A/G]GATCCAGACA | S | A | G | E | E |
| G1482u1 | WIAF-12560 | HT27870 | 3176 | BLM, Bloom syndrome | AAAATATAAC[G/A]GAATGCAGGA | S | G | A | T | T |
| G1482u2 | WIAF-12561 | HT27870 | 3605 | BLM, Bloom syndrome | GAAATAAAGC[C/A]CAAACTGTAC | S | C | A | A | A |
| G1482u3 | WIAF-12573 | HT27870 | 2677 | BLM, Bloom syndrome | TATGTATTAC[C/T]GAAAAAGCCT | S | C | T | P | L |
| G1483u1 | WIAF-12597 | HT1470 | 1910 | MYBL2, v-myb avian myeloblastosis viral oncogene homolog-like 2 | GGATGAGGAT[G/A]TGAAGCTGAT | M | G | A | V | M |
| G1483u2 | WIAF-12610 | HT1470 | 244 | MYBL2, v-myb avian myeloblastosis viral oncogene homolog-like 2 | ATGAGGAGGA[C/T]GAGCAGCTGA | S | C | T | D | D |
| G1483u3 | WIAF-12611 | HT1470 | 1406 | MYBL2, v-myb avian myeloblastosis viral oncogene homolog-like 2 | CACTGAGAAT[A/G]GCACCAGTCT | M | A | G | S | G |
| G1485u1 | WIAF-12581 | HT1432 | 1941 | BCR, breakpoint cluster region | TGGAGATGAG[A/G]AAATGGGTCC | S | A | G | R | R |
| G1485u2 | WIAF-12582 | HT1432 | 3144 | BCR, breakpoint cluster region | TGACCATCAA[T/C]AAGGAAGATG | S | T | C | N | N |
| G1485u3 | WIAF-12583 | HT1432 | 3777 | BCR, breakpoint cluster region | ATAACAAGGA[T/C]GTGTCGGTGA | S | T | C | D | D |
| G1485u4 | WIAF-12603 | HT1432 | 2831 | BCR, breakpoint cluster region | CAGATCAAGA[G/A]TGACATCCAG | M | G | A | S | N |
| G1485u5 | WIAF-12608 | HT1432 | 4217 | BCR, breakpoint cluster region | ATCCCTGCCC[C/T]GGACAGCAAG | M | C | T | P | L |
| G1486u1 | WIAF-12578 | HT33770 | 1909 | BRCA2, breast cancer 2, early onset | ATTGATAATG[G/A]AAGCTGGCCA | M | G | A | G | E |
| G1486u2 | WIAF-12579 | HT33770 | 3623 | BRCA2, breast cancer 2, early onset | AGTTTAGAAA[A/G]CCAAGCTACA | S | A | G | K | K |
| G1486u3 | WIAF-12586 | HT33770 | 1341 | BRCA2, breast cancer 2, early onset | AAATGTAGCA[A/C]ATCAGAAGCC | M | A | C | N | H |
| G1486u4 | WIAF-12594 | HT33770 | 446 | BRCA2, breast cancer 2, early onset | CTTATAATCA[G/A]CTGGCTTCAA | S | G | A | Q | Q |
| G1486u5 | WIAF-12598 | HT33770 | 3013 | BRCA2, breast cancer 2, early onset | ACCATGTTT[T/C]ATATGGAGAC | M | T | C | L | S |
| G1486u6 | WIAF-12599 | HT33770 | 3187 | BRCA2, breast cancer 2, early onset | CAAAAAAATA[A/T]TGATTACATG | M | A | T | N | I |
| G1486u7 | WIAF-12604 | HT33770 | 4971 | BRCA2, breast cancer 2, early onset | AGCATGTGAG[A/C]CCATTGAGAT | M | A | C | T | P |
| G1486u8 | WIAF-12607 | HT33770 | 4034 | BRCA2, breast cancer 2, early onset | ATGATTCTGT[C/T]GTTTCAATGT | S | C | T | V | V |
| G1487u1 | WIAF-12584 | HT27632 | 2536 | BRCA1, breast cancer 1, early onset | AGTCAGTGTG[C/G]AGCATTTGAA | M | C | G | A | G |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G1487u2 | WIAF-12587 | HT27632 | 4697 | BRCA1, breast cancer 1, early onset | CATCTCAAGA[G/C]GAGCTCATTA | M | G | C | E | D |
| G1487u3 | WIAF-12595 | HT27632 | 469 | BRCA1, breast cancer 1, early onset | TCTCCTGAAC[A/G]TCTAAAGAT | M | A | G | H | R |
| G1487u4 | WIAF-12600 | HT27632 | 3667 | BRCA1, breast cancer 1, early onset | AGCGTCCACA[A/G]AGGAGAGCTT | M | A | G | K | R |
| G1487u5 | WIAF-12601 | HT27632 | 3537 | BRCA1, breast cancer 1, early onset | TATGGGAAGT[A/G]GTCATGCATC | M | A | G | S | G |
| G1487u6 | WIAF-12602 | HT27632 | 4956 | BRCA1, breast cancer 1, early onset | ATCTGCCCAG[A/G]GTCCAGCTGC | M | A | G | S | G |
| G1487u7 | WIAF-12605 | HT27632 | 2090 | BRCA1, breast cancer 1, early onset | AGTACACCA[A/G]ATGCCAGTCA | S | A | G | Q | Q |
| G1487u8 | WIAF-12614 | HT27632 | 233 | BRCA1, breast cancer 1, early onset | TCTCCACAAA[G/A]TGTGACACCA | S | G | A | K | K |
| G1492u1 | WIAF-12585 | HT3506 | 3912 | cell death-associated kinase | TCCAGGTCCG[T/C]CGGCCTGGAGA | S | T | C | R | R |
| G1492u2 | WIAF-12593 | HT3506 | 4352 | cell death-associated kinase | TACAACACCA[A/G]TAACGGGGCT | M | A | G | N | S |
| G1492u3 | WIAF-12606 | HT3506 | 2127 | cell death-associated kinase | GCAATTTGGA[C/T]ATCTCCAACA | S | C | T | D | D |
| G1492u4 | WIAF-12612 | HT3506 | 1605 | cell death-associated kinase | TGAAATTTCT[C/T]AGTGAGAACA | S | C | T | L | L |
| G1494u1 | WIAF-12589 | HT28507 | 366 | cell death-inducing protein Bik | TTCACCACAC[T/C]TAAGGAGAGA | M | T | C | L | P |
| G1495u1 | WIAF-12580 | HT27803 | 759 | CSE1L, chromosome segregation 1 (yeast homolog)-like | TTTCTTCCCT[G/C]ATCCTGATCT | S | G | C | L | L |
| G1501u1 | WIAF-13502 | HT1949 | 1181 | MCC, mutated in colorectal cancers | CAGCAATGAC[A/C]TTCCCATCGC | M | A | C | I | L |
| G1501u2 | WIAF-13503 | HT1949 | 1753 | MCC, mutated in colorectal cancers | CAGCTGAGAA[C/T]GCTGCCAAGG | S | C | T | N | N |
| G1501u3 | WIAF-13504 | HT1949 | 2344 | MCC, mutated in colorectal cancers | TGTCCCTAGC[T/C]GAACTCAGGA | S | T | C | A | A |
| G1501u4 | WIAF-13521 | HT1949 | 445 | MCC, mutated in colorectal cancers | AGCGAACGAC[G/A]CTTCGCTATG | S | G | A | T | T |
| G1501u5 | WIAF-13522 | HT1949 | 1504 | MCC, mutated in colorectal cancers | AAAGCAATGC[T/C]GAGAGGATGA | S | T | C | A | A |
| G1501u6 | WIAF-13527 | MT1949 | 2511 | MCC, mutated in colorectal cancers | TTCGTGAATG[A/G]GACTGCCTCC | M | A | G | D | G |
| G1502u1 | WIAF-12633 | HT1547 | 870 | CCND1, cyclin D1 (PRAD1: parathyroid adenomatosis 1) | AGTGTGACCC[A/G]GACTGCCTCC | S | A | G | P | P |
| G1503u1 | WIAF-13741 | U37022 | 1151 | CDK4, cyclin-dependent kinase 4 | CATGCCAATT[G/A]CATCGTTCAC | M | G | A | C | Y |
| G1503u2 | WIAF-13742 | U37022 | 1410 | CDK4, cyclin-dependent kinase 4 | CTGAAGCCGA[C/T]CAGTGGGCA | S | C | T | D | D |
| G1503u3 | WIAF-13743 | U37022 | 1328 | CDK4, cyclin-dependent kinase 4 | TATGCAACAC[C/T]TGTGGACATG | M | C | T | P | L |
| G1503u4 | WIAF-13780 | U37022 | 1194 | CDK4, cyclin-dependent kinase 4 | TTCTGGTGAC[A/G]AGTGGTGGAA | S | A | G | T | T |
| G1503u5 | WIAF-13781 | U37022 | 1443 | CDK4, cyclin-dependent kinase 4 | TGATTGGGCT[G/A]CCTCCAGAGG | M | G | A | L | L |
| G1503u6 | WIAF-13787 | U37022 | 1633 | CDK4, cyclin-dependent kinase 4 | CTCTTATCTA[C/T]ATAAGGATGA | M | C | T | H | Y |
| G1517u1 | WIAF-12618 | HT1132 | 3894 | ERBB3, v-erb-b2 avian erythroblastic leukemia viral oncogene homolog 3 | CAGACCTCAG[T/C]GCCTCTCTGG | S | T | C | S | S |
| G152u1 | WIAF-11608 | HT3854 | 1673 | HSPA1L, heat shock 70 kD protein-like 1 | GTGAGTGATG[A/C]AGGTTTGAAG | M | A | C | E | A |
| G152u2 | WIAF-11629 | HT3854 | 1683 | HSPA1L, heat shock 70 kD protein-like 1 | AAGGTTTGAA[G/A]GGCAAGATTA | S | G | A | K | K |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G152u3 | WIAF-11609 | HT3854 | 1478 | HSPA1L, heat shock 70 kD protein-like 1 | GTCACAGCCA[C/T]GGACAAGAGC | M | C | T | T | M |
| G152u4 | WIAF-11610 | HT3854 | 1443 | HSPA1L, heat shock 70 kD protein-like 1 | TGACGTTTGA[C/T]ATTGATGCCA | S | C | T | D | D |
| G1520u1 | WIAF-12162 | HT1175 | 2211 | DNA excision repair protein ERCC2, 5' end | TGACCGTGGA[C/T]GAGGGTGTCC | S | C | T | D | D |
| G1520u2 | WIAF-12166 | HT1175 | 546 | DNA excision repair protein ERCC2, 5' end | CCCACTGCCG[A/C]TTCTATGAGG | S | A | C | R | R |
| G1527u1 | WIAF-12168 | HT0086 | 577 | GSTM2, glutathione S-transferase M2 (muscle) | TCATCTCCCG[A/C]TTTGAGGGCT | S | A | C | R | R |
| G1527u2 | WIAF-12169 | HT0086 | 644 | GSTM2, glutathione S-transferase M2 (muscle) | ACCTGTGTTC[A/T]CAAAGATGGC | M | A | T | T | S |
| G1527u3 | WIAF-12171 | HT0086 | 100 | GSTM2, glutathione S-transferase M2 (muscle) | ACTCAAGCTA[C/T]GAGGAAAAGA | S | C | T | Y | Y |
| G1527u4 | WIAF-12172 | HT0086 | 41 | GSTM2, glutathione S-transferase M2 (muscle) | CGGGTACTGG[A/G]ACATCCGCGG | M | A | G | N | D |
| G1527u5 | WIAF-12173 | HT0086 | 215 | GSTM2, glutathione S-transferase M2 (muscle) | GATTGATGGG[A/G]CTGAGAAGAT | M | A | G | T | A |
| G1527u6 | WIAF-12194 | HT0086 | 238 | GSTM2, glutathione S-transferase M2 (muscle) | CCGAGAGCAA[T/C]GCCATCGTGC | S | T | C | N | N |
| G1528u1 | WIAF-11950 | HT1811 | 529 | GSTM3, glutathione S-transferase M3 (brain) | GTATATTTGA[C/G]CCCAAGTGCC | M | C | G | D | E |
| G1528u2 | WIAF-11951 | HT1811 | 674 | GSTM3, glutathione S-transferase M3 (brain) | CAACAGACCT[G/A]TATGCTGAGC | M | G | A | V | I |
| G1528u3 | WIAF-11989 | HT1811 | 572 | GSTM3, glutathione S-transferase M3 (brain) | GGCTTTGATG[T/G]GCCGTTTTGA | M | T | G | C | G |
| G1528u4 | WIAF-13470 | HT1811 | 240 | GSTM3, glutathione S-transferase M3 (brain) | GAGAGGAATG[C/A]CATCTTGCGC | M | C | A | A | D |
| G1529u1 | WIAF-14146 | HT2006 | 797 | GSTM4, glutathione S-transferase M4 | TGGACGCCTT[C/T]CCAAATGTGA | S | C | T | F | F |
| G1530u1 | WIAF-12163 | HT3856 | 1212 | HSPA1B, heat shock 70 kD protein 1 | TGGGGCTGGA[G/A]ACGGCCGGAG | S | G | A | E | E |
| G1530u2 | WIAF-12182 | HT3856 | 676 | HSPA1B, heat shock 70 kD protein 1 | GGCGGGGAC[A/G]CCCACCTGGG | M | A | G | T | A |
| G1530u3 | WIAF-12183 | HT3856 | 1695 | HSPA1B, heat shock 70 kD protein 1 | TCAGCGAGGC[C/G]GACAAGAAGA | S | C | G | A | A |
| G1530u4 | WIAF-12189 | HT3856 | 330 | HSPA1B, heat shock 70 kD protein 1 | AGAAGGGGA[G/C]ACCAAGGCAT | M | G | C | E | D |
| G1530u5 | WIAF-12190 | HT3856 | 1053 | HSPA1B, heat shock 70 kD protein 1 | AGCTGCTGGA[A/G]GACTTCTTGA | S | A | G | Q | Q |
| G1530u1 | WIAF-11964 | HT3010 | 673 | GSTM5, glutathione S-transferase M5 | ATTCCTCCGA[G/A]GTCTTTTGTT | M | G | A | G | S |
| G1530u2 | WIAF-11995 | HT3010 | 593 | GSTM5, glutathione S-transferase M5 | GACGCCTTCC[T/C]AAACTTGAAG | M | T | C | L | P |
| G1530u3 | WIAF-13473 | HT3010 | 693 | GSTM5, glutathione S-transferase M5 | TTGGAAAGTC[A/G]GCTACACATGGA | S | A | G | S | S |
| G1533u1 | WIAF-13458 | HT27460 | 543 | GSTT2, glutathione S-transferase theta 2 | CTCTCGGCTA[C/T]GAACTGTTTG | S | C | T | Y | Y |
| G1533u2 | WIAF-13460 | HT27460 | 417 | GSTT2, glutathione S-transferase theta 2 | GGACTGCCGAT[G/A]GACCAGGCCC | M | G | A | M | I |
| G1533u3 | WIAF-13461 | HT27460 | 359 | GSTT2, glutathione S-transferase theta 2 | CAGGTGTTGG[G/A]GCCACTCATT | M | G | A | G | E |
| G1533u4 | WIAF-13462 | HT27460 | 363 | GSTT2, glutathione S-transferase theta 2 | TGTTGGGGCC[A/C]CTGATTGGGG | S | A | C | P | P |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G1533u5 | WIAF-13463 | HT27460 | 385 | GSTT2, glutathione S-transferase theta 2 | CCAGGTGCCC[G/A]AGGAGAAGGT | M | G | A | E | K |
| G1535u1 | WIAF-11952 | HT0436 | 517 | HCK, hemopoietic cell kinase | CCGCGTTGAC[T/C]CTCTGGAGAC | M | T | C | S | P |
| G1535u2 | WIAF-12013 | HT0436 | 783 | HCK, hemopoietic cell kinase | TGGACCACTA[C/T]AAGAAGGGGA | S | C | T | Y | Y |
| G1535u3 | WIAF-13464 | HT0436 | 357 | HCK, hemopoietic cell kinase | TCATCGTGGT[T/C]GCCCTGTATG | S | T | C | V | V |
| G1535u4 | WIAF-13465 | HT0436 | 387 | HCK, hemopoietic cell kinase | CCATTCACCA[C/T]GAAGACCTCA | S | C | T | H | H |
| G1535u5 | WIAF-13466 | HT0436 | 471 | HCK, hemopoietic cell kinase | CCCTGGCCAC[C/G]CGGAAGGAGG | S | C | G | T | T |
| G1535u6 | WIAF-13467 | HT0436 | 240 | HCK, hemopoietic cell kinase | CCAGCGCCAG[C/T]CCACACTGTC | S | C | T | S | S |
| G1535u7 | WIAF-13468 | HT0436 | 394 | HCK, hemopoietic cell kinase | CCACGAAGAC[C/T]TCAGCTTCCA | M | C | T | L | F |
| G1537u1 | WIAF-12020 | U04045 | 1514 | MSH2, mutS (E. coli) homolog 2 (colon cancer, nonpolyposis type 1) | GTGAATTAAG[A/G]GAAATAATGA | S | A | G | R | R |
| G1537u2 | WIAF-12044 | U04045 | 599 | MSH2, mutS (E. coli) homolog 2 (colon cancer, nonpolyposis type 1) | GACTGTGTGA[A/T]TTTCCCTGATA | M | A | T | E | D |
| G1537u3 | WIAF-12045 | U04045 | 1452 | MSH2, mutS (E. coli) homolog 2 (colon cancer, nonpolyposis type 1) | AGATATGGAT[C/T]AGGTGGAAAA | N | C | T | Q | * |
| G1537u4 | WIAF-12076 | U04045 | 938 | MSH2, mutS (E. coli) homolog 2 (colon cancer, nonpolyposis type 1) | GACAGTTTGA[A/T]CTGACTACTT | M | A | T | E | D |
| G1537u5 | WIAF-12077 | U04045 | 1878 | MSH2, mutS (E. coli) homolog 2 (colon cancer, nonpolyposis type 1) | TCAGCTAGAT[G/A]CTGTTGTCAG | M | A | T | A | T |
| G1543u1 | WIAF-13856 | J00119 | 553 | MOS, v-mos Moloney murine sarcoma viral oncogene homolog | GAGTTTCTGG[G/T]CTGAGCTCAA | M | G | T | A | S |
| G1543u2 | WIAF-13857 | J00119 | 621 | MOS, v-mos Moloney murine sarcoma viral oncogene homolog | GCACGCCCAC[G/A]CCCGCCAGGT | S | G | A | T | T |
| G1544u1 | WIAF-12018 | U59464 | 3821 | PTCH, patched (Drosophila) homolog | CATCCCGAAT[C/T]CAGGCATCAC | M | C | T | S | F |
| G1544u2 | WIAF-12019 | U59464 | 3618 | PTCH, patched (Drosophila) homolog | GCGTGGTTCCG[C/T]TTCGCCATGC | S | C | T | R | R |
| G1544u3 | WIAF-12027 | U59464 | 1761 | PTCH, patched (Drosophila) homolog | ATTTTGCCAT[G/T]GTTCCTGCTCA | M | G | T | M | I |
| G1544u4 | WIAF-12029 | U59464 | 4074 | PTCH, patched (Drosophila) homolog | CTGCCATGGG[C/T]AGCTCCGTGC | S | C | T | G | G |
| G1544u5 | WIAF-12043 | U59464 | 3845 | PTCH, patched (Drosophila) homolog | CCCTCGAACC[C/T]GAGACAGCAG | M | C | T | P | L |
| G1544u6 | WIAF-12056 | U59464 | 1433 | PTCH, patched (Drosophila) homolog | CTGCTGTGTTG[C/T]ACTGTCAGTG | M | C | T | A | V |
| G1544u7 | WIAF-12058 | U59464 | 3298 | PTCH, patched (Drosophila) homolog | CACCGTTCAC[G/C]TTGCTTTGGC | M | G | C | V | L |
| G1544u8 | WIAF-12062 | U59464 | 3986 | PTCH, patched (Drosophila) homolog | TCTACTGAAG[G/A]GATTCTGGC | M | G | A | G | E |
| G1544u9 | WIAF-13489 | U59464 | 1665 | PTCH, patched (Drosophila) homolog | CCATCAGCAA[T/C]GTCACAGCCT | S | T | C | N | N |
| G1544u10 | WIAF-13490 | U59464 | 2396 | PTCH, patched (Drosophila) homolog | AAATACTTTT[C/T]TTTCTACAAC | M | C | T | S | F |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G1544u11 | WIAF-13491 | U59464 | 2199 | PTCH, patched (Drosophila) homolog | GGACACTCTC[A/G]TCTTTTGCTG | S | A | G | S | S |
| G1544u12 | WIAF-13492 | U59464 | 2222 | PTCH, patched (Drosophila) homolog | AAGCACTATG[C/T]TCCTTTCCTC | M | C | T | A | V |
| G1544u13 | WIAF-13500 | U59464 | 1686 | PTCH, patched (Drosophila) homolog | TCTTCATGGC[C/T]GCGTTAATCC | S | C | T | A | A |
| G1545u1 | WIAF-12032 | HT0473 | 1835 | RAG1, recombination activating gene 1 | GGACATGGAA[G/A]AAGACATCTT | M | G | A | E | K |
| G1545u2 | WIAF-12035 | HT0473 | 2519 | RAG1, recombination activating gene 1 | TGACATTGGC[A/G]ATGCAGCTGA | M | A | G | N | D |
| G1545u3 | WIAF-12046 | HT0473 | 3045 | RAG1, recombination activating gene 1 | CGGAAAATGA[A/G]TGCCAGGCAG | M | A | G | N | S |
| G1545u4 | WIAF-12047 | HT0473 | 3146 | RAG1, recombination activating gene 1 | TCATAATGCA[T/C]TAAAAACCTC | S | T | C | L | L |
| G1545u5 | WIAF-12075 | HT0473 | 2513 | RAG1, recombination activating gene 1 | CCACTGTGAC[A/T]TTTGGCAATGC | M | A | T | I | F |
| G1545u6 | WIAF-13484 | HT0473 | 1322 | RAG1, recombination activating gene 1 | GTCGCTGACT[C/T]GGAGAGCTCA | M | C | T | R | W |
| G1545u7 | WIAF-13494 | HT0473 | 2571 | RAG1, recombination activating gene 1 | GAAGTGTATA[A/G]GAATCCCAAT | M | A | G | K | R |
| G1545u8 | WIAF-13498 | HT0473 | 1018 | RAG1, recombination activating gene 1 | TTCTGGCTGA[C/A]CCTGTGAGA | M | C | A | D | E |
| G1545u9 | WIAF-13499 | HT0473 | 2782 | RAG1, recombination activating gene 1 | ATCTTTACCT[G/C]AAGATGAAAC | S | G | C | L | L |
| G1548u1 | WIAF-12015 | HT4999 | 133 | IFI27, interferon, alpha-inducible protein 27 | CTCTGCCGTA[G/A]TTTTGCCCCT | M | G | A | V | I |
| G1548u2 | WIAF-13482 | HT4999 | 380 | IFI27, interferon, alpha-inducible protein 27 | ATCCTGGGCT[C/T]CATTGGGTCT | M | C | T | S | F |
| G1548u3 | WIAF-13483 | HT4999 | 135 | IFI27, interferon, alpha-inducible protein 27 | CTGCCGTAGT[T/C]TTGCCCCTGG | S | T | C | V | V |
| G1155u1 | WIAF-11634 | HT3962 | 991 | CHC1, chromosome condensation 1 | AGCTGGATGT[G/A]CCTGTGGTAA | S | G | A | V | V |
| G1155u2 | WIAF-11635 | HT3962 | 1271 | CHC1, chromosome condensation 1 | CGGGTTCGGC[C/T]TCTCCAACTA | M | C | T | L | F |
| G1155u3 | WIAF-11636 | HT3962 | 1192 | CHC1, chromosome condensation 1 | GCCGGGGCCA[C/T]GTGAGATTCC | S | C | T | H | H |
| G1155u4 | WIAF-11637 | HT3962 | 1267 | CHC1, chromosome condensation 1 | TGTACGGCTT[C/T]GGCCTCTCCA | S | C | T | F | F |
| G1155u5 | WIAF-11649 | HT3962 | 1657 | CHC1, chromosome condensation 1 | TGATGGGCAA[A/G]CAGCTGGAGA | M | A | G | K | K |
| G1550u1 | WIAF-12057 | M16038 | 611 | LYN, v-yes-1 Yamaguchi sarcoma viral related oncogene homolog | GCAAAGTCCC[T/G]TTTAACAAAA | M | T | G | L | R |
| G1550u2 | WIAF-12061 | M16038 | 1371 | LYN, v-yes-1 Yamaguchi sarcoma viral related oncogene homolog | TGGCATACAT[C/T]GAGCGGAAGA | S | C | T | I | I |
| G1550u3 | WIAF-12080 | M16038 | 1059 | LYN, v-yes-1 Yamaguchi sarcoma viral related oncogene homolog | AAAGGCTTGG[C/G]GCTGGGCAGT | S | C | T | G | G |
| G1550u4 | WIAF-12081 | M16038 | 996 | LYN, v-yes-1 Yamaguchi sarcoma viral related oncogene homolog | AGCCACAGAA[G/A]CCATGGGATA | S | G | A | K | K |
| G1552u1 | WIAF-12030 | HT4578 | 2355 | PMS1, postmeiotic segregation increased (S. cerevisiae) 1 | CCTGCTATTT[A/T]AAAGACTTCT | N | A | T | K | * |
| G1552u2 | WIAF-12031 | HT4578 | 2231 | PMS1, postmeiotic segregation increased (S. cerevisiae) 1 | ACAAAGTTGA[C/T]TTAGAAGAGA | S | C | T | D | D |
| G1552u3 | WIAF-12040 | HT4578 | 617 | PMS1, postmeiotic segregation increased (S. cerevisiae) 1 | TCATGAGCTT[T/C]GGTATCCTTA | S | T | C | F | F |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G1552u4 | WIAF-12063 | HT4578 | 1723 | PMS1, postmeiotic segregation increased (S. cerevisiae) 1 | TCATGTAACA[A/G]AAAATCAAAT | M | A | G | K | R |
| G1552u5 | WIAF-12064 | HT4578 | 1732 | PMS1, postmeiotic segregation increased (S. cerevisiae) 1 | AAAAATCAA[A/G]TGTAATAGAT | M | A | G | N | S |
| G1552u6 | WIAF-12065 | HT4578 | 1660 | PMS1, postmeiotic segregation increased (S. cerevisiae) 1 | TTACCATGTA[A/G]AGTAAGTAAT | M | A | G | K | R |
| G1552u7 | WIAF-12066 | HT4578 | 1975 | PMS1, postmeiotic segregation increased (S. cerevisiae) 1 | GAACGATACA[A/G]TAGTCAAATG | M | A | G | N | S |
| G1552u8 | WIAF-12067 | HT4578 | 1881 | PMS1, postmeiotic segregation increased (S. cerevisiae) 1 | TTTAGAGGAT[G/T]CAACACTACA | M | G | T | A | S |
| G1552u9 | WIAF-12068 | HT4578 | 2454 | PMS1, postmeiotic segregation increased (S. cerevisiae) 1 | TTTAGACGTT[T/A]TATATAAAAT | M | T | A | L | I |
| G1552u10 | WIAF-12069 | HT4578 | 2457 | PMS1, postmeiotic segregation increased (S. cerevisiae) 1 | AGACGTTTTA[T/C]ATAAAATGAC | M | T | C | Y | H |
| G1552u11 | WIAF-12082 | HT4578 | 2557 | PMS1, postmeiotic segregation increased (S. cerevisiae) 1 | ATACCAGGAG[T/C]TTCAATTACT | M | T | C | V | A |
| G1552u12 | WIAF-12083 | HT4578 | 971 | PMS1, postmeiotic segregation increased (S. cerevisiae) 1 | TTTTCTTTCT[G/T]AAAATCGATG | S | G | T | L | L |
| G1554u1 | WIAF-12028 | HT4161 | 1500 | ELK3, ELK3, ETS-domain protein (SRF accessory protein 2) NOTE: Symbol and name provisional. | CTCAGAAATC[C/T]TGATGACCTC | S | C | T | S | S |
| G1554u2 | WIAF-12059 | HT4161 | 1380 | ELK3, ELK3, ETS-domain protein (SRF accessory protein 2) NOTE: Symbol and name provisional. | CTGCCAGGCT[G/A]CAAGGGCCAA | S | G | A | L | L |
| G1554u3 | WIAF-12060 | HT4161 | 1436 | ELK3, ELK3, ETS-domain protein (SRF accessory protein 2) NOTE: Symbol and name provisional. | CACATGCCAG[T/C]GCCAATCCCC | M | T | C | V | A |
| G1562u1 | WIAF-12024 | HT28220 | 804 | PDCD1, programmed cell death 1 | GGGGCTCAGC[T/C]GACGGCCCTC | S | T | C | A | A |
| G1562u2 | WIAF-13488 | HT28220 | 644 | PDCD1, programmed cell death 1 | GACCCCTCAG[C/T]CGTGCCCTGTG | M | C | T | A | V |
| G1563u1 | WIAF-13493 | HT1187 | 1748 | EGFR, epidermal growth factor receptor (avian erythroblastic leukemia viral (v-erb-b) oncogene homolog) | CCGAGCCCCA[G/A]GGACTGCCTC | M | G | A | R | K |
| G1563u2 | WIAF-13497 | HT1187 | 2073 | EGFR, epidermal growth factor receptor (avian erythroblastic leukemia viral (v-erb-b) oncogene homolog) | ACGGATGCAC[T/A]GGGCCAGTC | S | T | A | T | T |
| G1566u1 | WIAF-12016 | HT27594 | 235 | PDCD2, programmed cell death 2 | GCGCCGCCTGC[C/G]TGGCCGCCCG | M | C | G | P | R |
| G1566u2 | WIAF-12033 | HT27594 | 904 | PDCD2, programmed cell death 2 | TTGGAATTCC[A/G]GGTCATGCCT | M | A | G | Q | R |
| G1566u3 | WIAF-12041 | HT27594 | 331 | PDCD2, programmed cell death 2 | AATCAACTAC[C/T]CAGGAAAAAC | M | C | T | P | L |
| G1566u4 | WIAF-12071 | HT27594 | 649 | PDCD2, programmed cell death 2 | CCTGAGTTTG[T/C]GGAAAAGGAA | M | T | C | V | A |
| G1566u5 | WIAF-12072 | HT27594 | 633 | PDCD2, programmed cell death 2 | AGAAGATGAG[A/T]TTTATGCCTGA | M | A | T | H | F |
| G1567u1 | WIAF-12042 | M95936 | 293 | AKT2, v-akt murine thymoma viral oncogene homolog 2 | GAGAGGCCGC[G/A]ACCCAACACC | M | G | A | R | Q |
| G1572u1 | WIAF-12212 | HT3998 | 1894 | proto-oncogene c-abl, tyrosine protein kinase, alt. transcript 2 | TGTTCCAGGA[A/G]TCCAGTATCT | S | A | G | E | E |
| G1572u2 | WIAF-12233 | HT3998 | 3694 | proto-oncogene c-abl, tyrosine protein kinase, alt. transcript 2 | AGCTTCAGAT[C/T]TGCCCGGCGA | S | C | T | I | I |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G1572u3 | WIAF-12234 | HT3998 | 3721 | proto-oncogene c-abl, tyrosine protein kinase, alt. transcript 2 | GCAGTGGTCC[G/A]GCGGCCACTC | S | G | A | P | P |
| G1573u1 | WIAF-12021 | HT0642 | 343 | CBL, Cas-Br-M (murine) ecotropic retroviral transforming sequence | TCATGGACAA[G/C]GTGGTGCCGT | M | G | C | K | N |
| G1573u2 | WIAF-12022 | HT0642 | 363 | CBL, Cas-Br-M (murine) ecotropic retroviral transforming sequence | TTGTGTCAGA[A/T]CCCAAAGCTG | M | A | T | N | I |
| G1573u3 | WIAF-12034 | HT0642 | 2364 | CBL, Cas-Br-M (murine) ecotropic retroviral transforming sequence | AATATTCAGT[C/T]CCAGGCGCCA | M | C | T | S | F |
| G1573u4 | WIAF-12049 | HT0642 | 387 | CBL, Cas-Br-M (murine) ecotropic retroviral transforming sequence | CTAAAGAATA[G/A]CCCACCTTAT | M | G | A | S | N |
| G1573u5 | WIAF-12050 | HT0642 | 947 | CBL, Cas-Br-M (murine) ecotropic retroviral transforming sequence | AACTCATCCT[G/A]GCTACATGGC | M | G | A | G | S |
| G1573u6 | WIAF-12070 | HT0642 | 2740 | CBL, Cas-Br-M (murine) ecotropic retroviral transforming sequence | TCGAGAACCT[C/T]ATGAGTCAGG | S | C | T | L | L |
| G1573u7 | WIAF-12073 | HT0642 | 661 | CBL, Cas-Br-M (murine) ecotropic retroviral transforming sequence | TCTTTCCAAG[T/C]GGACTCTTTC | S | T | C | S | S |
| G1573u8 | WIAF-12074 | HT0642 | 2569 | CBL, Cas-Br-M (murine) ecotropic retroviral transforming sequence | CTCTGGATGG[T/C]GATCCTACAA | S | T | C | G | G |
| G1573u9 | WIAF-13486 | HT0642 | 2006 | CBL, Cas-Br-M (murine) ecotropic retroviral transforming sequence | CCGGCACTCA[C/T]TTTCCATTTC | M | C | T | L | F |
| G1574u1 | WIAF-12037 | HT1508 | 2493 | FES, feline sarcoma (Snyder-Theilen) viral (v-fes)/Fujinami avian sarcoma (PRCII) viral (v-fps) oncogene homolog | AGCGGCCCAG[C/T]TTCAGCACCA | S | C | T | S | S |
| G1574u2 | WIAF-12051 | HT1508 | 189 | FES, feline sarcoma (Snyder-Theilen) viral (v-fes)/Fujinami avian sarcoma (PRCII) viral (v-fps) oncogene homolog | CCCAGCGGCT[C/T]AAGAGTGACA | S | C | T | V | V |
| G1574u3 | WIAF-12052 | HT1508 | 1441 | FES, feline sarcoma (Snyder-Theilen) viral (v-fes)/Fujinami avian sarcoma (PRCII) viral (v-fps) oncogene homolog | GAAGCCCCTG[C/T]ATGAGCAGCT | M | C | T | H | Y |
| G1574u4 | WIAF-12053 | HT1508 | 2202 | FES, feline sarcoma (Snyder-Theilen) viral (v-fes)/Fujinami avian sarcoma (PRCII) viral (v-fps) oncogene homolog | GAGAGGAAGC[C/T]GATGGGTCT | S | C | T | A | A |
| G1574u5 | WIAF-12054 | HT1508 | 2088 | FES, feline sarcoma (Snyder-Theilen) viral (v-fes)/Fujinami avian sarcoma (PRCII) viral (v-fps) oncogene homolog | CTGCTGGCAT[G/T]GAGTACCTGG | M | G | T | M | I |
| G1574u6 | WIAF-12078 | HT1508 | 1577 | FES, feline sarcoma (Snyder-Theilen) viral (v-fes)/Fujinami avian sarcoma (PRCII) viral (v-fps) oncogene homolog | GATGGTCTGC[C/T]CCGGCACTTC | M | C | T | P | L |
| G1574u7 | WIAF-13495 | HT1508 | 579 | FES, feline sarcoma (Snyder-Theilen) viral (v-fes)/Fujinami avian sarcoma (PRCII) viral (v-fps) oncogene homolog | GTGACAAGGC[T/C]AAGGACAAGT | S | T | C | A | A |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G1575u1 | WIAF-12079 | HT1052 | 963 | FGR, Gardner-Rasheed feline sarcoma viral (v-fgr) oncogene homolog | TGGGCACCGG[C/T]TGCTTCGGGG | S | C | T | G | G |
| G1575u2 | WIAF-13487 | HT1052 | 232 | FGR, Gardner-Rasheed feline sarcoma viral (v-fgr) oncogene homolog | CAGAAGCTAC[G/A]GGGCAGCAGA | M | G | A | G | R |
| G1585u1 | WIAF-12017 | HT1675 | 996 | CRK, v-crk avian sarcoma virus CT10 oncogene homolog | TGGATACAACA[G/A]AATCCCGATG | S | G | A | Q | Q |
| G1585u2 | WIAF-12036 | HT1675 | 446 | CRK, v-crk avian sarcoma virus CT10 oncogene homolog | ACTACAACGT[T/C]GATAGAACCA | M | T | C | L | S |
| G1587u1 | WIAF-12023 | HT0590 | 1473 | proto-oncogene dbl | GGCCAATCCA[A/G]TTTGTGGTAC | S | A | G | Q | Q |
| G1587u2 | WIAF-12025 | HT0590 | 2549 | proto-oncogene dbl | GTCCAGGCTT[C/T]TAATGTAGAT | M | C | T | S | F |
| G1587u3 | WIAF-12026 | HT0590 | 2828 | proto-oncogene dbl | GCATCACAAT[C/T]TGCAGAAATC | M | C | T | S | F |
| G1587u4 | WIAF-12038 | HT0590 | 982 | proto-oncogene dbl | AAATTCTCAG[G/C]AGCTATTATC | M | G | C | E | Q |
| G1587u5 | WIAF-12039 | HT0590 | 2343 | proto-oncogene dbl | AACCAATGCA[G/T]CGACACCTTT | M | G | T | Q | H |
| G1587u6 | WIAF-12048 | HT0590 | 683 | proto-oncogene dbl | GACACTGAAG[G/A]AGCTGTCAGT | M | G | A | G | E |
| G1587u7 | WIAF-12055 | HT0590 | 2686 | proto-oncogene dbl | TTCTCTTCAG[C/T]AGAATGATGA | N | C | T | Q | * |
| G1587u8 | WIAF-13485 | HT0590 | 2136 | proto-oncogene dbl | ACTGTGAAGG[T/A]TCTGCTCTGT | S | T | A | G | G |
| G1587u9 | WIAF-13496 | HT0590 | 1566 | proto-oncogene dbl | AAAATCAGAG[C/T]AACTTAAAAA | S | C | T | S | S |
| G159u1 | WIAF-11616 | HT4209 | 1059 | RAD23B, RAD23 (S. cerevisiae) homolog B | AGTACTGGGG[C/T]TCCTCAGTCT | M | C | T | A | V |
| G1590u1 | WIAF-13897 | HT2455 | 1257 | ETS2, v-ets avian erythroblastosis virus E26 oncogene homolog 2 | GCCAGTCTCT[G/C]TGCCTCAATA | S | G | C | L | L |
| G1590u2 | WIAF-13913 | HT2455 | 1107 | ETS2, v-ets avian erythroblastosis virus E26 oncogene homolog 2 | ATTCTGGGAC[T/G]CCCAAAGACC | S | T | G | T | T |
| G1590u3 | WIAF-13914 | HT2455 | 1314 | ETS2, v-ets avian erythroblastosis virus E26 oncogene homolog 2 | GGAGTGACCC[A/G]GTGGAGCAAG | S | A | G | P | P |
| G1591u1 | WIAF-13924 | HT2333 | 417 | HRAS, v-Ha-ras Harvey rat sarcoma viral oncogene homolog | TCCAGAACCA[T/C]TTTGTGGACG | S | T | C | H | H |
| G1595u1 | WIAF-12262 | HT33778 | 1302 | proto-oncogene 1-myc, alt. transcript 1 | GCATACCTCA[G/C]TGGCTACTAA | M | G | C | S | T |
| G1597u1 | WIAF-12243 | HT0410 | 900 | MAS1, MAS1 oncogene | CCATCTTGGT[C/T]GTGAAGATCC | S | C | T | V | V |
| G160u1 | WIAF-11630 | HT4247 | 690 | RAD23A, RAD23 (S. cerevisiae) homolog A | AGAGCCAGGT[A/G]TCGGAGCAGC | S | A | G | V | V |
| G1602u1 | WIAF-14180 | HT1903 | 1321 | proto-oncogene pim-1 | GTCGCCGGGG[C/A]CCAGCAAATA | M | C | A | P | T |
| G1604u1 | WIAF-12319 | HT2788 | 1182 | REL, v-rel avian reticuloendotheliosis viral oncogene homolog | CCTCCCAAAG[T/C]GCTGGGATTA | S | T | C | S | S |
| G1609u1 | WIAF-12358 | HT33646 | 348 | RIPK1, receptor (TNFRSF)-interacting serine-threonine kinase 1 | GACGCAGGGT[C/T]TCCATGACCC | S | C | T | V | V |
| G161u1 | WIAF-11654 | HT4251 | 1522 | DNA repair and recombination homolog RAD52 | TATGATCCAT[C/T]TTAACTGAGG | M | C | T | S | F |
| G1610a1 | WIAF-12101 | HT27727 | 501 | replication protein Rpa4, 30 kDa | TGCAACTCCT[G/A]CTATTAAGAC | M | G | A | A | T |
| G1610a2 | WIAF-12102 | HT27727 | 554 | replication protein Rpa4, 30 kDa | TACCGTGTAA[C/T]GTGAACCAGC | S | C | T | N | N |
| G1610u3 | WIAF-12307 | HT27727 | 450 | replication protein Rpa4, 30 kDa | TTCTGCTGCT[G/A]ATGGAGCCAG | M | G | A | D | N |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G1610u4 | WIAF-12320 | HT27727 | 1037 | replication protein Rpa4, 30 kDa | TGATTCATGA[G/C]TGTCCTCATC | M | G | C | E | D |
| G1610u5 | WIAF-12321 | HT27727 | 857 | replication protein Rpa4, 30 kDa | TAGAGGACAT[G/A]AACGAGTTCA | M | G | A | M | I |
| G1610u6 | WIAF-12343 | HT27727 | 539 | replication protein Rpa4, 30 kDa | GAATTCAGGA[C/T]GTTGTACCGT | S | C | T | D | D |
| G1630u1 | WIAF-12302 | HT3563 | 4312 | DCC, deleted in colorectal carcinoma | ACTCATGAAG[C/T]AGCTTAATGC | N | C | T | Q | * |
| G1632u1 | WIAF-13572 | HT27355 | 742 | tumor suppressor, PDGF receptor beta-like | TTTATGACAT[G/C]AAGCGGGGCT | M | G | C | M | I |
| G1632u2 | WIAF-13584 | HT27355 | 1102 | tumor suppressor, PDGF receptor beta-like | TGGAAGACTT[C/T]GAGACCATTG | S | C | T | F | F |
| G1632u3 | WIAF-13601 | HT27355 | 258 | tumor suppressor, PDGF receptor beta-like | AAGACGCAGT[C/T]TATCATGATG | M | C | T | S | F |
| G1633u1 | WIAF-13957 | HT1778 | 1263 | FER, fer (fpa/fes related) tyrosine kinase (phosphoprotein NCP94) | TTCAGGCAAA[T/C]GAGATCATGT | S | T | C | N | N |
| G1633u2 | WIAF-13958 | HT1778 | 2407 | FER, fer (fpa/fes related) tyrosine kinase (phosphoprotein NCP94) | TATGTTGTAT[C/T]TTCGAGAGTAA | M | C | T | L | F |
| G1634u1 | WIAF-13505 | HT3216 | 1569 | ELK1, ELK1, member of ETS oncogene family | TCTCGACCCC[C/T]GTGGTGCTCT | S | C | T | P | P |
| G1634u2 | WIAF-13858 | HT3216 | 456 | ELK1, ELK1, member of ETS oncogene family | GGCTGTGGGG[A/G]CTACGCAAGA | S | A | G | G | G |
| G1634u3 | WIAF-13859 | HT3216 | 745 | ELK1, ELK1, member of ETS oncogene family | AGGCCCAGGC[G/A]GTTTGGCACG | M | G | A | G | S |
| G1638u1 | WIAF-14172 | HT1224 | 98 | uracil-DNA glycosylase | GCTGGGACCT[G/C]TTCCACAAAT | — | G | C | — | — |
| G1643u1 | WIAF-13517 | HT3751 | 629 | DXS648E, DNA segment on chromosome X (unique) 648 expressed sequence | TACATCCCCA[G/A]TCGTGGCCCT | M | G | A | S | N |
| G1645u1 | WIAF-14087 | D21089 | 363 | XPC, xeroderma pigmentosum, complementation group C | AAAACCTCAA[G/A]GTTATAAAGG | S | G | A | K | K |
| G1645u2 | WIAF-14088 | D21089 | 2166 | XPC, xeroderma pigmentosum, complementation group C | TGCATTCCAG[G/A]GACACGTGGC | S | G | A | R | R |
| G1645u3 | WIAF-14089 | D21089 | 1580 | XPC, xeroderma pigmentosum, complementation group C | GGGAGCCATC[G/A]TAAGGACCCA | M | G | A | R | H |
| G1645u4 | WIAF-14090 | D21089 | 1601 | XPC, xeroderma pigmentosum, complementation group C | AGCTTGCCAG[T/C]GGCATCCTCA | M | T | C | V | A |
| G1645u5 | WIAF-14091 | D21089 | 2920 | XPC, xeroderma pigmentosum, complementation group C | CCCATTTGAG[A/C]AGCTGTGAGC | M | A | C | K | Q |
| G1645u6 | WIAF-14103 | D21089 | 405 | XPC, xeroderma pigmentosum, complementation group C | ATGACCTCAG[G/A]GACTTTCCAA | S | G | A | R | R |
| G1645u7 | WIAF-14104 | D21089 | 151 | XPC, xeroderma pigmentosum, complementation group C | GGGACGCGAA[C/G]TGCGCAGCCA | M | C | G | L | V |
| G1645u8 | WIAF-14105 | D21089 | 2133 | XPC, xeroderma pigmentosum, complementation group C | AAGCGGTCTA[C/T]TCCAGGGATT | S | C | T | Y | Y |
| G167u1 | WIAF-11632 | HT4579 | 83 | PMS2L8, postmeiotic segregation increased 2-like 8 | CCTATTGATC[G/A]GAAGTCAGTC | M | G | A | R | Q |
| G167u2 | WIAF-11633 | HT4579 | 219 | PMS2L8, postmeiotic segregation increased 2-like 8 | GAGTGGATCT[T/C]ATTGAAGTTT | S | T | C | L | L |
| G167u3 | WIAF-11644 | HT4579 | 768 | PMS2L8, postmeiotic segregation increased 2-like 8 | TGCCCCCTAG[T/C]GACTCCGTGT | S | T | C | S | S |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G167u4 | WIAF-11622 | HT4579 | 1645 | PMS2L8, postmeiotic segregation increased 2-like 8 | GAAAGCGCCT[G/A]AAACTGACGA | M | G | A | E | K |
| G167u5 | WIAF-11645 | HT4579 | 1512 | PMS2L8, postmeiotic segregation increased 2-like 8 | ACTCGGGGCA[C/T]GGCAGCACTT | S | C | T | H | H |
| G167u6 | WIAF-11646 | HT4579 | 1619 | PMS2L8, postmeiotic segregation increased 2-like 8 | TCGCAGGAAC[A/G]TGTGGACTCT | M | A | G | H | R |
| G167u7 | WIAF-11647 | HT4579 | 1432 | PMS2L8, postmeiotic segregation increased 2-like 8 | CGTCCTGAGA[C/T]CTCAGAAAGA | M | C | T | P | S |
| G167u8 | WIAF-11625 | HT4579 | 2490 | PMS2L8, postmeiotic segregation increased 2-like 8 | GGACTGCTCT[T/C]AACACAAGCG | S | T | C | L | L |
| G167u9 | WIAF-11619 | HT4579 | 804 | PMS2L8, postmeiotic segregation increased 2-like 8 | TGAGCTGTTC[G/C]GATGCTCTGC | S | G | C | S | S |
| G167u10 | WIAF-11623 | HT4579 | 1555 | PMS2L8, postmeiotic segregation increased 2-like 8 | CATCCCAGA[A/G]CGGGCAGTCA | M | A | G | T | A |
| G167u11 | WIAF-11624 | HT4579 | 2364 | PMS2L8, postmeiotic segregation increased 2-like 8 | CCTTCGGACC[C/T]CAGGACGTCG | S | C | T | P | P |
| G167u12 | WIAF-11626 | HT4579 | 2348 | PMS2L8, postmeiotic segregation increased 2-like 8 | ACTAGTAAAA[A/G]CTGGACTTC | M | A | G | N | S |
| G181u1 | WIAF-11697 | HT48793 | 311 | ERCC4, excision repair cross-complementing rodent repair deficiency, complementation group 4 | ATATTTGCGA[C/T]AAGTAGGATA | M | C | T | T | I |
| G181u2 | WIAF-11698 | HT48793 | 295 | ERCC4, excision repair cross-complementing rodent repair deficiency, complementation group 4 | CACACAAGGT[G/C]GTGTTATATT | M | G | C | G | R |
| G181u3 | WIAF-11699 | HT48793 | 234 | ERCC4, excision repair cross-complementing rodent repair deficiency, complementation group 4 | TTGAACACCT[C/T]CCTCGCCCTG | S | C | T | L | L |
| G181u4 | WIAF-11704 | HT48793 | 808 | ERCC4, excision repair cross-complementing rodent repair deficiency, complementation group 4 | TTTGTGGCAC[C/T]AGCTTGGACC | N | C | T | Q | * |
| G181u5 | WIAF-11705 | HT48793 | 640 | ERCC4, excision repair cross-complementing rodent repair deficiency, complementation group 4 | TTCTATGACA[C/T]CTACCATGCT | M | C | T | P | S |
| G181u6 | WIAF-11670 | HT48793 | 1117 | ERCC4, excision repair cross-complementing rodent repair deficiency, complementation group 4 | AGAAAGCAAC[C/T]CAAAGTGGGA | M | C | T | P | S |
| G185u1 | WIAF-11668 | HT5122 | 319 | ACVR2B, activin A receptor, type IIB | TCTGCAACGA[G/A]CGCTTCACTC | S | G | A | E | E |
| G185u2 | WIAF-11707 | HT5122 | 70 | ACVR2B, activin A receptor, type IIB | AGACACGGGA[G/C]TGCATCTACT | M | G | C | E | D |
| G185u3 | WIAF-11672 | HT5122 | 812 | ACVR2B, activin A receptor, type IIB | CCTCACGGAT[T/C]ACCTCAAGGG | M | T | C | Y | H |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G185u4 | WIAF-13542 | X77533 | 1109 | ACVR2B, activin A receptor, type IIB | GGCTCCTGAG[G/A]TGCTCGAGGG | M | G | A | V | M |
| G185u5 | WIAF-13558 | X77533 | 997 | ACVR2B, activin A receptor, type IIB | TGCTGAAGAG[C/T]GACCTCACAG | S | C | T | S | S |
| G187u1 | WIAF-11669 | HT97400 | 183 | androgen | CCAGAGACAG[C/T]GCCACCCGGA | M | C | T | R | C |
| G191u1 | WIAF-10176 | AF025375 | 414 | CXCR4, chemokine (C-X-C motif), receptor 4 (fusin) | ACCTGGCCAT[C/T]GTCCACGCCA | S | C | T | I | I |
| G193u1 | WIAF-10178 | D29984 | 231 | CCR2, chemokine (C-C motif) receptor 2 | AGTGCTTGAC[T/A]GACATTTACC | S | T | A | T | T |
| G193u2 | WIAF-10179 | D29984 | 190 | CCR2, chemokine (C-C motif) receptor 2 | CATGCTGGTC[G/A]TCCTCATCTT | M | G | A | V | I |
| G194u1 | WIAF-10211 | D43767 | 121 | SCYA17, small inducible cytokine subfamily A (Cys-Cys), member 17 | ACATCCACGC[A/C]GCTCGAGGGA | S | A | C | A | A |
| G197u1 | WIAF-10167 | D50403 | 1515 | NRAMP1, natural resistance-associated macrophage protein 1 (might include Leishmaniasis) | GGTGCTAGTC[T/C]GCCGCCATCAA | M | T | C | C | R |
| G197u2 | WIAF-10173 | D50403 | 1629 | NRAMP1, natural resistance-associated macrophage protein 1 (might include Leishmaniasis) | CACCTACCTG[G/C]TCTGGACCTG | M | G | C | V | L |
| G20u1 | WIAF-10249 | U14722 | 896 | ACVR1B, activin A receptor, type IB | CGGTACACAG[T/C]GACAATTGAG | M | T | C | V | A |
| G20u2 | WIAF-10250 | U14722 | 866 | ACVR1B, activin A receptor, type IB | GAGCACGGGT[C/T]CCTGTTTGAT | M | C | T | S | F |
| G20u3 | WIAF-10251 | U14722 | 1391 | ACVR1B, activin A receptor, type IB | CAGAGTTATG[A/T]GGGCACTGCGG | M | A | T | E | V |
| G20u4 | WIAF-10252 | U14722 | 1236 | ACVR1B, activin A receptor, type IB | TATATTGGGA[G/C]ATTGCTCGAA | M | G | C | E | D |
| G20u5 | WIAF-10261 | U14722 | 518 | ACVR1B, activin A receptor, type IB | GAGATGTGTC[T/C]CTCCAAAGAC | M | T | C | L | P |
| G207a1 | WIAF-10516 | L25259 | 866 | Human CTLA4 counter-receptor (B7-2) mRNA, complete cds. | AGCTGTACTT[C/T]CAACAGTTAT | M | C | T | P | S |
| G208u1 | WIAF-10204 | L31581 | 85 | CCR7, chemokine (C-C motif) receptor 7 | GGGGAAACCA[A/G]TGAAAAGCGT | M | A | G | M | V |
| G211u1 | WIAF-10213 | M24545 | 174 | SCYA2, small inducible cytokine A2 (monocyte chemotactic protein 1, homologous to mouse sig-je) | TCACCTGCTG[T/C]TATAACTTCA | S | T | C | C | C |
| G214u1 | WIAF-10191 | M27533 | 452 | CD80, CD80 antigen (CD28 antigen ligand 1, B7-1 antigen) | TGAAAGAAGT[G/A]GCAACGCTGT | S | G | A | V | V |
| G215u1 | WIAF-11659 | M28393 | 822 | PRF1, perforin 1 (preforming protein) | GCATCTCTGC[C/T]GAAGCCAAGG | S | C | T | A | A |
| G215u2 | WIAF-11723 | M28393 | 159 | PRF1, perforin 1 (preforming protein) | TGACCAGCCT[C/T]CGCCGCTCCG | S | C | T | L | L |
| G215u3 | WIAF-11724 | M28393 | 96 | PRF1, perforin 1 (preforming protein) | CAGAGTGCAA[G/A]CGCAGCCACA | S | G | A | K | K |
| G215u4 | WIAF-11725 | M28393 | 1377 | PRF1, perforin 1 (preforming protein) | ATAACAACCC[C/T]ATCTGGTCAG | S | C | T | P | P |
| G215u5 | WIAF-11726 | M28393 | 1326 | PRF1, perforin 1 (preforming protein) | TGAAGTCTT[C/T]TTTGGTGCC | S | C | T | F | F |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G215u6 | WIAF-11727 | M28393 | 1076 | PRF1, perforin 1 (preforming protein) | CGGCGGGAGG[C/T]ACTGAGGAGG | M | C | T | A | V |
| G217u1 | WIAF-11691 | M31932 | 649 | FCGR2B, Fc fragment of IgG, low affinity IIb, receptor for (CD32) | GCAGCTCTTC[A/G]CCAATGGGGA | S | A | G | S | S |
| G217u2 | WIAF-11692 | M31932 | 625 | FCGR2B, Fc fragment of IgG, low affinity IIb, receptor for (CD32) | TCACTGTCCA[A/G]GTGCCCAGCA | S | A | G | Q | Q |
| G217u3 | WIAF-11712 | M31932 | 332 | FCGR2B, Fc fragment of IgG, low affinity IIb, receptor for (CD32) | GACTGGCCAG[A/C]CCAGCCTCAG | M | A | C | T | P |
| G217u4 | WIAF-11713 | M31932 | 101 | FCGR2B, Fc fragment of IgG, low affinity IIb, receptor for (CD32) | GGCTTCTGCA[G/T]ACAGTCAAGC | M | G | T | D | Y |
| G218u1 | WIAF-10184 | M36712 | 677 | CD8B1, CD8 antigen, beta polypeptide 1 (p37) | TTTTACAAAT[A/G]AGCAGAGAAT | N | A | G | * | * |
| G218u2 | WIAF-10188 | M36712 | 326 | CD8B1, CD8 antigen, beta polypeptide 1 (p37) | GCTGTGTTTC[G/C]GGATGCAAGC | M | G | C | R | P |
| G218u3 | WIAF-10189 | M36712 | 196 | CD8B1, CD8 antigen, beta polypeptide 1 (p37) | CAGTAACATG[C/T]GCATCTACTG | M | C | T | R | C |
| G218u4 | WIAF-10190 | M36712 | 225 | CD8B1, CD8 antigen, beta polypeptide 1 (p37) | AGCGCCAGGC[A/C]CCGAGCAGTG | S | A | C | A | A |
| G218u5 | WIAF-10194 | M36712 | 583 | CD8B1, CD8 antigen, beta polypeptide 1 (p37) | GGTGGCTGGC[G/A]TCCTGGTTCT | M | G | A | V | I |
| G218u6 | WIAF-10208 | M36712 | 372 | CD8B1, CD8 antigen, beta polypeptide 1 (p37) | TGAAGCCGGA[A/G]GACAGTGGCA | S | A | G | E | E |
| G218u7 | WIAF-10209 | M36712 | 400 | CD8B1, CD8 antigen, beta polypeptide 1 (p37) | CTGCATGATC[G/T]TCGGAGCCCC | M | G | T | V | F |
| G218u8 | WIAF-10210 | M36712 | 270 | CD8B1, CD8 antigen, beta polypeptide 1 (p37) | TCTGGGATTC[C/T]GCAAAAGGGA | S | C | T | S | S |
| G218a9 | WIAF-10518 | M36712 | 618 | CD8B1, CD8 antigen, beta polypeptide 1 (p37) | GAGTGGCCAT[C/G]CACCTGTCCT | M | C | G | I | M |
| G218a10 | WIAF-13223 | M36712 | 556 | CD8B1, CD8 antigen, beta polypeptide 1 (p37) | TTGTAGCCCC[A/G]TCACCCTTGG | M | A | G | H | V |
| G218a11 | WIAF-13224 | M36712 | 836 | CD8B1, CD8 antigen, beta polypeptide 1 (p37) | CTGTGTGTGA[T/C]GTCATGGGA | — | T | C | — | — |
| G22u1 | WIAF-10301 | U86136 | 6719 | Human telomerase-associated protein TP-1 mRNA, complete cds. | GGTGGTAACC[G/A]TCCGGCTAGA | M | G | A | V | I |
| G22u2 | WIAF-10302 | U86136 | 7537 | Human telomerase-associated protein TP-1 mRNA, complete cds. | CTGATGGGAT[C/G]CTATGGAACC | M | C | G | I | M |
| G22u3 | WIAF-10311 | U86136 | 1798 | Human telomerase-associated protein TP-1 mRNA, complete cds. | ATGATGCCAT[T/C]GATGCCCTCG | S | T | C | I | I |
| G22u4 | WIAF-10312 | U86136 | 2397 | Human telomerase-associated protein TP-1 mRNA, complete cds. | CTGTCTCTGG[C/T]TGGCCAAAGG | M | C | T | A | V |
| G22u5 | WIAF-10313 | U86136 | 3289 | Human telomerase-associated protein TP-1 mRNA, complete cds. | AGAAAGGGAT[A/C]ACCTGCCCCA | S | A | C | I | I |
| G22u6 | WIAF-10314 | U86136 | 3242 | Human telomerase-associated protein TP-1 mRNA, complete cds. | AGAGGCCGCA[T/C]GTCGGATCTC | M | T | C | C | R |
| G22u7 | WIAF-10315 | U86136 | 4482 | Human telomerase-associated protein TP-1 mRNA, complete cds. | CCGTTTGCCT[G/A]CCTCGTCCAG | M | G | A | C | Y |
| G22u8 | WIAF-10316 | U86136 | 4363 | Human telomerase-associated protein TP-1 mRNA, complete cds. | GTTTGACTGT[G/A]GACCAGTGC | S | G | A | V | V |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G22u9 | WIAF-10317 | U86136 | 4230 | Human telomerase-associated protein TP-1 mRNA, complete cds. | GTGTCTGAGA[G/A]ACTCCGGACC | M | G | A | R | K |
| G22u10 | WIAF-10318 | U86136 | 4419 | Human telomerase-associated protein TP-1 mRNA, complete cds. | GGGACTAAGA[G/C]CTGGGAAGAA | M | G | C | S | T |
| G22u11 | WIAF-10319 | U86136 | 5269 | Human telomerase-associated protein TP-1 mRNA, complete cds. | TCTCCGATGA[T/C]ACACTCTTTC | S | T | C | D | D |
| G22u12 | WIAF-10320 | U86136 | 5015 | Human telomerase-associated protein TP-1 mRNA, complete cds. | GCTGCTCCC[C/T]GGAGATGGCA | M | C | T | R | W |
| G22u13 | WIAF-10321 | U86136 | 5133 | Human telomerase-associated protein TP-1 mRNA, complete cds. | GTGGCCTTCT[C/T]CACCAATGGG | M | C | T | S | F |
| G22u14 | WIAF-10322 | U86136 | 7764 | Human telomerase-associated protein TP-1 mRNA, complete cds. | ACAGCCCTCC[A/G]TGTGCTACCT | M | A | G | H | R |
| G22u15 | WIAF-10323 | U86136 | 7884 | Human telomerase-associated protein TP-1 mRNA, complete cds. | TGCCTGGAAC[C/T]TTGGCTGGGC | M | C | T | P | L |
| G22u16 | WIAF-10324 | U86136 | 7744 | Human telomerase-associated protein TP-1 mRNA, complete cds. | AGATTCACTC[G/A]GGCTCTGCA | S | G | A | S | S |
| G22u17 | WIAF-10337 | U86136 | 1018 | Human telomerase-associated protein TP-1 mRNA, complete cds. | CCATTGCTGC[T/C]TTCTTGCCGG | S | T | C | A | A |
| G22u18 | WIAF-10338 | U86136 | 1000 | Human telomerase-associated protein TP-1 mRNA, complete cds. | TGGCCAATAA[C/A]ATCTTGGCCA | M | C | A | N | K |
| G22u19 | WIAF-10339 | U86136 | 1182 | Human telomerase-associated protein TP-1 mRNA, complete cds. | ATGACGGACA[A/G]ATTGCCCAG | M | A | G | K | R |
| G22u20 | WIAF-10340 | U86136 | 1939 | Human telomerase-associated protein TP-1 mRNA, complete cds. | AGCAGCTTCG[T/G]ATGGCAATGA | S | T | G | R | R |
| G22u21 | WIAF-10341 | U86136 | 2227 | Human telomerase-associated protein TP-1 mRNA, complete cds. | TCACGAGGGC[G/A]GAGCAGTTGG | S | G | A | A | A |
| G22u22 | WIAF-10342 | U86136 | 2776 | Human telomerase-associated protein TP-1 mRNA, complete cds. | GGCGCAGCAT[C/T]CGGCTTTTCA | S | C | T | I | I |
| G22u23 | WIAF-10343 | U86136 | 2877 | Human telomerase-associated protein TP-1 mRNA, complete cds. | GCCCCTCACC[G/A]TATCAGCCTT | M | G | A | R | H |
| G22u24 | WIAF-10344 | U86136 | 3087 | Human telomerase-associated protein TP-1 mRNA, complete cds. | TCAGGGCGCT[C/T]TGTGACAGAG | M | C | T | S | F |
| G22u25 | WIAF-10345 | U86136 | 3662 | Human telomerase-associated protein TP-1 mRNA, complete cds. | CAAGGTGGCA[C/T]CATTAGTCTT | M | C | T | P | S |
| G22u26 | WIAF-10346 | U86136 | 4762 | Human telomerase-associated protein TP-1 mRNA, complete cds. | TTTCGAAGTT[C/T]CTTACCAACC | S | C | T | F | F |
| G22u27 | WIAF-10351 | U86136 | 1737 | Human telomerase-associated protein TP-1 mRNA, complete cds. | CTCCAGCATG[G/C]GAAGTCGGTG | M | G | C | G | A |
| G22u28 | WIAF-10352 | U86136 | 3543 | Human telomerase-associated protein TP-1 mRNA, complete cds. | ACAGTGCAAC[A/G]GCTGATGCTG | M | A | G | Q | R |
| G22u29 | WIAF-10353 | U86136 | 4232 | Human telomerase-associated protein TP-1 mRNA, complete cds. | GTCTGAGAGA[C/T]TCCGGACCCT | M | C | T | L | F |
| G22u30 | WIAF-10354 | U86136 | 4523 | Human telomerase-associated protein TP-1 mRNA, complete cds. | GGAGGGCCCT[C/T]TGGAGCGCCC | S | C | T | L | L |
| G22u31 | WIAF-10355 | U86136 | 5333 | Human telomerase-associated protein TP-1 mRNA, complete cds. | TGGTTGTCGG[G/T]TGCTGCAGAC | M | G | T | V | L |
| G22u32 | WIAF-10356 | U86136 | 6208 | Human telomerase-associated protein TP-1 mRNA, complete cds. | AGCTGCTGAC[G/A]CGGCCACACA | S | G | A | T | T |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G22u33 | WIAF-10357 | U86136 | 7703 | Human telomerase-associated protein TP-1 mRNA, complete cds. | TAGTGAGCCA[A/G]CACCACATCT | M | A | G | T | A |
| G22u34 | WIAF-10360 | U86136 | 3881 | Human telomerase-associated protein TP-1 mRNA, complete cds. | CATCGATGGG[G/A]CTGATAGGTT | M | G | A | A | T |
| G222u1 | WIAF-11700 | M57230 | 697 | IL6ST, interleukin 6 signal transducer (gp130, oncostatin M receptor) | TGAGTGGGAT[G/C]GTGGAAGGGA | M | G | C | G | R |
| G222u2 | WIAF-11701 | M57230 | 708 | IL6ST, interleukin 6 signal transducer (gp130, oncostatin M receptor) | GTGGAAGGGA[A/G]ACACACTTGG | S | A | G | E | E |
| G222u3 | WIAF-11702 | M57230 | 677 | IL6ST, interleukin 6 signal transducer (gp130, oncostatin M receptor) | GAGGGGAAGA[A/G]AATGAGGTGT | M | A | G | K | R |
| G222u4 | WIAF-11706 | M57230 | 1616 | IL6ST, interleukin 6 signal transducer (gp130, oncostatin M receptor) | AAGAAATATA[T/C]ACTTGAGTGG | M | T | C | I | T |
| G222u5 | WIAF-11667 | M57230 | 1444 | IL6ST, interleukin 6 signal transducer (gp130, oncostatin M receptor) | TGATCGCTAT[C/G]TAGCAACCCT | M | C | G | L | V |
| G222u6 | WIAF-11708 | M57230 | 981 | IL6ST, interleukin 6 signal transducer (gp130, oncostatin M receptor) | TCTTAAAATT[G/C]ACATGGACCA | M | G | C | L | F |
| G226u1 | WIAF-11714 | M85079 | 869 | TGFBR2, transforming growth factor, beta receptor II (70-80 kD) | CACTGGGAGT[T/C]GCCATATCTG | S | T | C | V | V |
| G226u2 | WIAF-11715 | M85079 | 1749 | TGFBR2, transforming growth factor, beta receptor II (70-80 kD) | AGATTATGAG[C/T]CTCCATTTGG | M | C | T | P | S |
| G226u3 | WIAF-11716 | M85079 | 1601 | TGFBR2, transforming growth factor, beta receptor II (70-80 kD) | TGGGAACTGC[A/G]AGATACATGG | S | A | G | A | A |
| G226u4 | WIAF-11721 | M85079 | 1256 | TGFBR2, transforming growth factor, beta receptor II (70-80 kD) | TACTCCAGTT[C/G]CTGACGGCTG | M | C | G | F | L |
| G226u5 | WIAF-11722 | M85079 | 1502 | TGFBR2, transforming growth factor, beta receptor II (70-80 kD) | TCGTGAAGAA[C/T]GACCTAACCT | S | C | T | N | N |
| G226u6 | WIAF-11671 | M85079 | 888 | TGFBR2, transforming growth factor, beta receptor II (70-80 kD) | TGTCATCATC[A/C]TCTTCTACTG | M | A | C | I | L |
| G226u7 | WIAF-11674 | M85079 | 1425 | TGFBR2, transforming growth factor, beta receptor II (70-80 kD) | CCTCCACAGT[G/A]ATCACACTCC | M | G | A | D | N |
| G227u1 | WIAF-10197 | M86511 | 685 | CD14, CD14 antigen | CCTGTCTGAC[A/G]ATCCTGGACT | M | A | G | N | D |
| G227u2 | WIAF-10212 | M86511 | 497 | CD14, CD14 antigen | GAAGCCACAG[G/A]ACTTGCACTT | M | G | A | G | E |
| G2278u1 | WIAF-14117 | AF034611 | 959 | CUBN, cubilin (intrinsic factor-cobalamin receptor) | AGATAAATAA[T/C]GGGCGGCTGTT | S | T | C | N | N |
| G2278u2 | WIAF-14118 | AF034611 | 781 | CUBN, cubilin (intrinsic factor-cobalamin receptor) | GGGTGGATGT[C/T]TTCACCCAAC | M | C | T | S | F |
| G2278u3 | WIAF-14119 | AF034611 | 641 | CUBN, cubilin (intrinsic factor-cobalamin receptor) | CTGAGACGTA[C/T]GGACCCCAGT | S | C | T | Y | Y |
| G2278u4 | WIAF-14121 | AF034611 | 1185 | CUBN, cubilin (intrinsic factor-cobalamin receptor) | TGGTTATGGG[C/A]CAAATGGATG | M | C | A | P | T |
| G2278u5 | WIAF-14133 | AF034611 | 1532 | CUBN, cubilin (intrinsic factor-cobalamin receptor) | TCTGGGTTAT[C/G]AAAACTGAAA | M | C | G | I | M |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G2278u6 | WIAF-14134 | AF034611 | 2208 | CUBN, cubilin (intrinsic factor-cobalamin receptor) | GCCTTTCACT[C/T]ACACCAGCA | M | C | T | H | Y |
| G228u1 | WIAF-10199 | U00672 | 586 | IL10RA, interleukin 10 receptor, alpha | GCAAGGTGCC[G/A]GGAAACTTCA | S | G | A | P | P |
| G228u2 | WIAF-10200 | U00672 | 731 | IL10RA, interleukin 10 receptor, alpha | AGAGGAGTGC[A/G]TCTCCCTCAC | M | A | G | I | V |
| G2280u1 | WIAF-13970 | AJ001515 | 1747 | RYR3, ryanodine receptor 3 | CAGGTATCTT[G/A]GAAGTTTTGC | S | G | A | L | L |
| G2280u2 | WIAF-13974 | AJ001515 | 8593 | RYR3, ryanodine receptor 3 | TAGAAGCCAT[T/C]GTCAGCAGTG | S | T | C | H | H |
| G2282u1 | WIAF-12694 | D00726 | 263 | FECH, ferrochelatase (protoporphyria) | ACATGGGAGG[C/T]CCTGAAACTC | S | C | T | G | G |
| G2282u2 | WIAF-12695 | D00726 | 514 | FECH, ferrochelatase (protoporphyria) | TACTATATTG[G/A]ATTTCGGTAC | M | G | A | G | E |
| G2285u1 | WIAF-12688 | D16611 | 673 | CPO, coproporphyrinogen oxidase (coproporphyria, harderoporphyria) | AGAAGACGCT[G/A]TCCATTTTCA | M | G | A | V | I |
| G2285u2 | WIAF-12689 | D16611 | 783 | CPO, coproporphyrinogen oxidase (coproporphyria, harderoporphyria) | ATCGTGGAGA[G/A]CGGCGGGGCA | S | G | A | E | E |
| G2287u1 | WIAF-12687 | D28472 | 502 | PTGER4, prostaglandin E receptor 4 (subtype EP4) | GGGCCTCACG[C/T]TCTTTGCAGT | M | C | T | L | F |
| G2287u2 | WIAF-12691 | D28472 | 1309 | PTGER4, prostaglandin E receptor 4 (subtype EP4) | TGAAAATGGC[C/T]TTTGGAGGCAG | M | C | T | L | F |
| G2287u3 | WIAF-12707 | D28472 | 243 | PTGER4, prostaglandin E receptor 4 (subtype EP4) | AGGAGACGAC[C/T]TTCTACACGC | S | C | T | T | T |
| G2287u4 | WIAF-12710 | D28472 | 1343 | PTGER4, prostaglandin E receptor 4 (subtype EP4) | GGTGCCTG[G/A]CATGGGCCTG | M | G | A | G | D |
| G229u1 | WIAF-10185 | U16752 | 202 | SDF1, stromal cell-derived factor 1 | CATGTTGCCA[G/A]AGCCAACGTC | M | G | A | R | K |
| G2295u1 | WIAF-12727 | D89079 | 613 | LTB4R, leukotriene b4 receptor (chemokine receptor-like 1) | CTATGTCTGC[G/C]GAGTCAGCAT | M | G | C | G | R |
| G2295u2 | WIAF-12728 | D89079 | 1248 | LTB4R, leukotriene b4 receptor (chemokine receptor-like 1) | AGGGCCACGG[T/C]TCCGAGGCGT | S | T | C | G | G |
| G2295u3 | WIAF-12753 | D89079 | 1348 | LTB4R, leukotriene b4 receptor (chemokine receptor-like 1) | CCTCACTGCC[T/G]CCAGCCCTCT | M | T | G | S | A |
| G230u1 | WIAF-10201 | U31628 | 627 | IL15RA, interleukin 15 receptor, alpha | ACAGCCAAGA[A/C]CTGGAACTC | M | A | C | N | T |
| G2300u1 | WIAF-12735 | J02959 | 102 | LTA4H, leukotriene A4 hydrolase | ACCTGGCACCT[G/T]CGCTGCAGCG | S | G | T | L | L |
| G2300u2 | WIAF-12738 | J02959 | 1380 | LTA4H, leukotriene A4 hydrolase | CCTGGCTCTA[C/T]TCTCCTGGAC | S | C | T | Y | Y |
| G2302u1 | WIAF-12741 | J03037 | 627 | CA2, carbonic anhydrase II | TCCTGAATCC[C/T]TGGATTACTG | S | C | T | L | L |
| G2302u2 | WIAF-12742 | J03037 | 819 | CA2, carbonic anhydrase II | GCCACTGAAG[A/G]ACAGGCAAAT | M | A | G | N | D |
| G2303u1 | WIAF-12751 | J03571 | 304 | ALOX5, arachidonate 5-lipoxygenase | CGCTGAAGAC[G/A]CCCCACGGGG | S | G | A | T | T |
| G2303u2 | WIAF-12752 | J03571 | 794 | ALOX5, arachidonate 5-lipoxygenase | AGAGCTGCCC[G/A]AGAAGCTCCC | M | G | A | E | K |
| G2304u1 | WIAF-12772 | J03575 | 840 | PDHA1, pyruvate dehydrogenase (lipoamide) alpha 1 | TCCGAGAGGC[A/G]ACAAGGTTTG | S | A | G | A | A |
| G2304u2 | WIAF-12779 | J03575 | 1044 | PDHA1, pyruvate dehydrogenase (lipoamide) alpha 1 | CCAGTGTGGA[A/C]GAACTAAAGG | M | A | C | E | D |
| G2305u1 | WIAF-12763 | J03576 | 456 | PDHB, pyruvate dehydrogenase (lipoamide) beta | TCTTCAGGGG[A/G]CCCAATGTG | S | A | G | G | G |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G2305u2 | WIAF-12764 | J03576 | 650 | PDHB, pyruvate dehydrogenase (lipoamide) beta | GTTCCTTTG[A/C]ATTTCTCCCG | M | A | C | E | A |
| G231u1 | WIAF-10202 | U32324 | 734 | IL11RA, interleukin 11 receptor, alpha | CCAGGGCCTG[C/T]GGGTAGAGTC | M | C | T | R | W |
| G2312u1 | WIAF-12762 | J05096 | 3726 | ATP1A2, ATPase, Na+/K+ transporting, alpha 2 (+) polypeptide | TCAAGAACCA[C/T]ACAGAGATCG | S | C | T | H | H |
| G2313u1 | WIAF-12760 | J05200 | 6141 | RYR1, ryanodine receptor 1 (skeletal) | TGCAATTCAA[A/G]GATGGTACAG | S | A | G | K | K |
| G2313u2 | WIAF-12767 | J05200 | 3048 | RYR1, ryanodine receptor 1 (skeletal) | CGGCGCAGAC[A/G]ACACTGGTGG | S | A | G | T | T |
| G2313u3 | WIAF-12768 | J05200 | 3084 | RYR1, ryanodine receptor 1 (skeletal) | ATGGGCACAA[C/T]CTGTGGGCCC | S | C | T | N | N |
| G2313u4 | WIAF-12777 | J05200 | 5667 | RYR1, ryanodine receptor 1 (skeletal) | GCATCTTTGG[C/T]GATGAGGATG | S | C | T | G | G |
| G2313u5 | WIAF-12780 | J05200 | 6600 | RYR1, ryanodine receptor 1 (skeletal) | GCTCGCTGCT[C/T]ATCGTGCAGA | S | C | T | L | L |
| G2313u6 | WIAF-12781 | J05200 | 7191 | RYR1, ryanodine receptor 1 (skeletal) | AGCCTGAGTG[C/T]TTCGGACCCG | S | C | T | C | C |
| G2313u7 | WIAF-12782 | J05200 | 7602 | RYR1, ryanodine receptor 1 (skeletal) | ACCACAAGGC[G/A]TCCATGGTGC | S | G | A | A | A |
| G2313u8 | WIAF-12784 | J05200 | 9288 | RYR1, ryanodine receptor 1 (skeletal) | CAGAGCCCCC[A/G]GCTGTGGTCA | S | A | G | P | P |
| G2313u9 | WIAF-12786 | J05200 | 13690 | RYR1, ryanodine receptor 1 (skeletal) | TCCAAAGAAG[G/A]AGGAAGCTGG | M | G | A | E | K |
| G2313u10 | WIAF-12789 | J05200 | 3147 | RYR1, ryanodine receptor 1 (skeletal) | ACATCCCAGC[G/A]CGCCGAAACC | S | G | A | A | A |
| G2314u1 | WIAF-12771 | J05272 | 1920 | IMPDH1, IMP (inosine monophosphate) dehydrogenase 1 | TGAAGATCGC[A/G]CAGGGTGTCT | S | A | G | A | A |
| G2319u1 | WIAF-12814 | K03191 | 651 | CYP1A1, cytochrome P450, subfamily I (aromatic compound-inducible), polypeptide 1 | CCCCTACAGG[T/C]ATGTGGTGGT | M | T | C | Y | H |
| G232u1 | WIAF-11657 | U58917 | 1490 | Homo sapiens IL-17 receptor mRNA, complete cds. | TGAACATGAT[C/T]CTCCCGGACT | S | C | T | I | I |
| G232u2 | WIAF-11677 | U58917 | 1293 | Homo sapiens IL-17 receptor mRNA, complete cds. | GCCAGGCCATC[T/C]CGGAGGCAGG | M | T | C | S | P |
| G232u3 | WIAF-11658 | U58917 | 1132 | Homo sapiens IL-17 receptor mRNA, complete cds. | GGCCTGCCTG[C/T]GGCTGACCTG | M | C | T | A | V |
| G232u4 | WIAF-11679 | U58917 | 905 | Homo sapiens IL-17 receptor mRNA, complete cds. | GCAGCTGCCT[C/T]AATGACTGCC | S | C | T | L | L |
| G232u5 | WIAF-11682 | U58917 | 1794 | Homo sapiens IL-17 receptor mRNA, complete cds. | GTTCGAATGT[G/T]AGAACCTCTA | N | G | T | E | * |
| G232u7 | WIAF-11660 | U58917 | 743 | Homo sapiens IL-17 receptor mRNA, complete cds. | TGACCAGTTT[T/C]CCGCACATGG | S | T | C | F | F |
| G2322u1 | WIAF-12853 | L01406 | 1316 | GHRHR, growth hormone releasing hormone receptor | CTGACATCTA[T/C]GTGCTAGGCT | M | T | C | M | T |
| G2328u1 | WIAF-12845 | L20316 | 1285 | GCGR, glucagon receptor | TGCGGGCACG[G/C]CAGATGCACC | S | G | C | R | R |
| G2329u1 | WIAF-12850 | L22214 | 713 | ADORA1, adenosine A1 receptor | TGCTGCAAT[T/C]GCTGTGACC | S | T | C | I | I |
| G2329u2 | WIAF-12851 | L22214 | 716 | ADORA1, adenosine A1 receptor | TGGCAATTGC[T/G]GTGACCCCT | S | T | G | A | A |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G2335a1 | WIAF-12136 | L32961 | 265 | ABAT, 4-aminobutyrate aminotransferase | CCTAGATCTC[A/G]GGAGTTAATG | M | A | G | Q | R |
| G2335a2 | WIAF-12137 | L32961 | 407 | ABAT, 4-aminobutyrate aminotransferase | TCTCCTCTGT[T/C]CCCATAGGTT | S | T | C | V | V |
| G2335u3 | WIAF-12838 | L32961 | 365 | ABAT, 4-aminobutyrate aminotransferase | TTGATGTGGA[C/T]GGCAACCGAA | S | C | T | D | D |
| G2335u4 | WIAF-12839 | L32961 | 583 | ABAT, 4-aminobutyrate aminotransferase | ATCACCATGG[C/T]CTGCGGCTCC | M | C | T | A | V |
| G2335u5 | WIAF-12841 | L32961 | 1082 | ABAT, 4-aminobutyrate aminotransferase | TGGACAGGT[C/A]CAGACCGAG | S | C | A | V | V |
| G2335u6 | WIAF-12852 | L32961 | 227 | ABAT, 4-aminobutyrate aminotransferase | ATTATGATGG[G/A]CCCTCTGATGA | S | G | A | G | G |
| G2337u1 | WIAF-13577 | L34820 | 149 | ALDH5A1, aldehyde dehydrogenase 5 family, member A1 (succinate-semialdehyde dehydrogenase) | TGTTCTTCGAA[A/G]GAATGCCAAG | M | A | G | K | R |
| G2342a1 | WIAF-12138 | M12530 | 1602 | TF, transferrin | GCCTAAACCT[G/C]TGTGAACCCA | S | G | C | L | L |
| G2342a2 | WIAF-12139 | M12530 | 1795 | TF, transferrin | TACCAGGAAA[C/T]CTGTGGAGGA | M | C | T | P | S |
| G2346u1 | WIAF-12829 | M13928 | 234 | ALAD, aminolevulinate, delta-, dehydratase | TGGCCAGGTA[T/C]GGTGTGAAGC | S | T | C | Y | Y |
| G2346u2 | WIAF-12830 | M13928 | 529 | ALAD, aminolevulinate, delta-, dehydratase | TGAGGTGGCA[T/C]TGGCGTATGC | S | T | C | L | L |
| G2346u3 | WIAF-12843 | M13928 | 480 | ALAD, aminolevulinate, delta-, dehydratase | TGAGTGAAAA[C/T]GGAGCATTCC | S | C | T | N | N |
| G2348u1 | WIAF-12835 | M14016 | 621 | UROD, uroporphyrinogen decarboxylase | CTCTGGTCCC[A/G]TATCTGGTAG | S | A | G | P | P |
| G2351u1 | WIAF-11678 | U83171 | 100 | SCYA22, small inducible cytokine subfamily A (Cys-Cys), member 22 | CAGGCCCCTA[C/T]GGCGCCAACA | S | C | T | Y | Y |
| G2363a1 | WIAF-10519 | M37435 | 596 | CSF1, colony stimulating factor 1 (macrophage) | GACAAGGACT[G/T]GAATATTTTC | M | G | T | W | L |
| G2363a2 | WIAF-13225 | M37435 | 498 | CSF1, colony stimulating factor 1 (macrophage) | AAGAGACATGA[C/T]AAGGCCTGCG | S | C | T | D | D |
| G2363a3 | WIAF-13226 | M37435 | 712 | CSF1, colony stimulating factor 1 (macrophage) | CAGTGACCCG[G/T]CCCTCTGTCTC | M | G | T | A | S |
| G2369u1 | WIAF-12854 | M30773 | 857 | PPP3R1, protein phosphatase 3 (formerly 2B), regulatory subunit B (19 kD), alpha isoform (calcineurin B, type I) | TTGATTTGGA[C/T]AATTCTGGTT | S | C | T | D | D |
| G2369u2 | WIAF-12855 | M30773 | 1274 | PPP3R1, protein phosphatase 3 (formerly 2B), regulatory subunit B (19 kD), alpha isoform (calcineurin B, type I) | ATGTGTGACT[C/T]TTATCAGAGA | — | C | T | — | — |
| G237u1 | WIAF-11662 | U86358 | 311 | SCYA25, small inducible cytokine subfamily A (Cys-Cys), member 25 | CACCCAAACA[T/C]GCAGACCTTC | M | T | C | M | T |
| G237u2 | WIAF-11680 | U86358 | 134 | SCYA25, small inducible cytokine subfamily A (Cys-Cys), member 25 | GTGCTCCGGC[G/A]CGCCTGGACT | M | G | A | R | H |
| G237u3 | WIAF-11681 | U86358 | 133 | SCYA25, small inducible cytokine subfamily A (Cys-Cys), member 25 | TGTGCTCCGG[C/T]GCGCCTGGAC | M | C | T | R | C |
| G237u5 | WIAF-11661 | U86358 | 302 | SCYA25, small inducible cytokine subfamily A (Cys-Cys), member 25 | GCAAAGCTCC[A/G]CCAACAATG | M | A | G | H | R |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G237u6 | WIAF-11663 | U86358 | 378 | SCYA25, small inducible cytokine subfamily A (Cys-Cys), member 25 | AGTTATCATC[A/G]TCCAAGTTTA | S | A | G | S | S |
| G2373u1 | WIAF-12870 | M36035 | 500 | BZRP, benzodiazapine receptor (peripheral) | GCTGGCCTTC[G/A]CGACCACACT | M | G | A | A | T |
| G2376u1 | WIAF-13025 | M57414 | 979 | TACR2, tachykinin receptor 2 | CTGCTGCCCA[T/C]GGGTCACACC | M | T | C | W | R |
| G238u1 | WIAF-10177 | X01394 | 239 | TNF, tumor necrosis factor (TNF superfamily, member 2) | GCTCCAGGCG[G/T]TGCTTGTTCC | S | G | T | R | R |
| G2381u1 | WIAF-12894 | M59941 | 730 | CSF2RB, colony stimulating factor 2 receptor, beta, low-affinity (granulocyte-macrophage) | CAGAGGTTTG[C/T]TGGGACTCCC | S | C | T | C | C |
| G2381u2 | WIAF-12896 | M59941 | 1306 | CSF2RB, colony stimulating factor 2 receptor, beta, low-affinity (granulocyte-macrophage) | GGATCTGGAG[C/T]GAGTGGAGTG | S | C | T | S | S |
| G2381u3 | WIAF-12900 | M59941 | 1972 | CSF2RB, colony stimulating factor 2 receptor, beta, low-affinity (granulocyte-macrophage) | CGATGGGACC[G/A]GGACAGGCCG | S | G | A | P | P |
| G2381u4 | WIAF-12901 | M59941 | 1982 | CSF2RB, colony stimulating factor 2 receptor, beta, low-affinity (granulocyte-macrophage) | GGGACAGGCC[G/A]TGGAAGTGGA | M | G | A | V | M |
| G2381u5 | WIAF-12942 | M59941 | 773 | CSF2RB, colony stimulating factor 2 receptor, beta, low-affinity (granulocyte-macrophage) | CCAGAACCTG[G/C]AGTGCTTCTT | M | G | C | E | Q |
| G2381u6 | WIAF-12946 | M59941 | 2458 | CSF2RB, colony stimulating factor 2 receptor, beta, low-affinity (granulocyte-macrophage) | CCCCACAGCC[C/A]GAGGGCCTCC | S | C | A | P | P |
| G2384u1 | WIAF-12908 | M61831 | 1000 | AHCY, S-adenosylhomocysteine hydrolase | GCCGTGGAGA[A/C]GGTGAACATC | M | A | C | K | T |
| G2387u1 | WIAF-12910 | M63967 | 2585 | ALDH5, aldehyde dehydrogenase 5 | CTGCTGAACC[T/G]CCTGGCAGAC | M | T | G | L | R |
| G2387u2 | WIAF-12911 | M63967 | 2996 | ALDH5, aldehyde dehydrogenase 5 | TATGGCCCAA[C/G]AGCAGGTGCG | M | C | G | T | R |
| G2387u3 | WIAF-12954 | M63967 | 2522 | ALDH5, aldehyde dehydrogenase 5 | GCCCGGGAAG[C/T]CTTCCGCCTG | M | C | T | A | V |
| G2387u4 | WIAF-12955 | M63967 | 2448 | ALDH5, aldehyde dehydrogenase 5 | ACCCTACCAC[C/T]GGGGAGGTCA | S | C | T | T | T |
| G2387u5 | WIAF-12956 | M63967 | 2460 | ALDH5, aldehyde dehydrogenase 5 | GGGAGGTCAT[C/T]CCACAGCAG | S | C | T | H | H |
| G2387u6 | WIAF-12957 | M63967 | 2991 | ALDH5, aldehyde dehydrogenase 5 | CGGGTATGG[C/T]CCAACAGCAG | S | C | T | I | I |
| G2387u7 | WIAF-12958 | M63967 | 3022 | ALDH5, aldehyde dehydrogenase 5 | CGCCAGCAC[A/G]TGGATGTTGA | M | A | G | M | V |
| G2387u8 | WIAF-12959 | M63967 | 2943 | ALDH5, aldehyde dehydrogenase 5 | CCCTCATCAA[G/C]GAGCAGGCT | M | G | C | K | N |
| G2388u1 | WIAF-12888 | M64590 | 588 | GLDC, glycine dehydrogenase (decarboxylating; glycine decarboxylase, glycine cleavage system protein P) | TGCCACAGAC[G/A]ATTTTGCGGA | S | G | A | T | T |
| G2388u2 | WIAF-12889 | M64590 | 651 | GLDC, glycine dehydrogenase (decarboxylating; glycine decarboxylase, glycine cleavage system protein P) | ACCAGCCTGA[G/A]GTGTCTCAGG | S | G | A | E | E |
| G2388u3 | WIAF-12890 | M64590 | 698 | GLDC, glycine dehydrogenase (decarboxylating; glycine decarboxylase, glycine cleavage system protein P) | CAGACCATGG[T/C]GTGTGACATC | M | T | C | V | A |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G2388u4 | WIAF-12891 | M64590 | 557 | GLDC, glycine dehydrogenase (decarboxylating; glycine decarboxylase, glycine cleavage system protein P) | TATATTGGCA[T/C]GGGCTATTAT | M | T | C | M | T |
| G2388u5 | WIAF-12938 | M64590 | 587 | GLDC, glycine dehydrogenase (decarboxylating; glycine decarboxylase, glycine cleavage system protein P) | GTGCCACAGA[C/G]GATTTTGCGG | M | C | G | T | R |
| G2388u6 | WIAF-12939 | M64590 | 518 | GLDC, glycine dehydrogenase (decarboxylating; glycine decarboxylase, glycine cleavage system protein P) | CTGCATGCCA[T/C]TTCAAGCAAA | M | T | C | I | T |
| G2388u7 | WIAF-12940 | M64590 | 810 | GLDC, glycine dehydrogenase (decarboxylating; glycine decarboxylase, glycine cleavage system protein P) | GGAAATTTCT[C/T]GTTGATCCCC | S | C | T | L | L |
| G2388u8 | WIAF-12941 | M64590 | 1481 | GLDC, glycine dehydrogenase (decarboxylating; glycine decarboxylase, glycine cleavage system protein P) | CATTGTGGCT[G/A]CTCAGTGAAG | M | G | A | C | Y |
| G2388u9 | WIAF-12947 | M64590 | 1841 | GLDC, glycine dehydrogenase (decarboxylating; glycine decarboxylase, glycine cleavage system protein P) | AAACTGAACA[G/A]TTCGTCTGAA | M | G | A | S | N |
| G2388u10 | WIAF-12948 | M64590 | 2325 | GLDC, glycine dehydrogenase (decarboxylating; glycine decarboxylase, glycine cleavage system protein P) | GACAGTCTA[C/T]CTAGACGGGG | S | C | T | Y | Y |
| G2388u11 | WIAF-12949 | M64590 | 2362 | GLDC, glycine dehydrogenase (decarboxylating; glycine decarboxylase, glycine cleavage system protein P) | GGTGGGAATC[T/A]GTCGCCCTGG | M | T | A | C | S |
| G2388u12 | WIAF-12950 | M64590 | 3220 | GLDC, glycine dehydrogenase (decarboxylating; glycine decarboxylase, glycine cleavage system protein P) | TTAGTCCTCT[C/G]TCCCTAAGTT | — | C | G | — | — |
| G2391u1 | WIAF-12998 | M69238 | 623 | ARNT, aryl hydrocarbon receptor nuclear translocator | TGGTGTATGT[G/C]TCTGACTCCG | S | G | C | V | V |
| G2391u2 | WIAF-13002 | M69238 | 1072 | ARNT, aryl hydrocarbon receptor nuclear translocator | TGCCTAGTGG[C/T]CATTGGCAGA | M | C | T | A | V |
| G2391u3 | WIAF-13021 | M69238 | 966 | ARNT, aryl hydrocarbon receptor nuclear translocator | ACCTCACTTC[G/A]TGGTGGTCCA | M | G | A | V | M |
| G2394u1 | WIAF-13003 | M73747 | 2061 | TSHR, thyroid stimulating hormone receptor | TTGCTGTAC[T/A]CTTCTATCCA | M | T | A | L | H |
| G2394u2 | WIAF-13004 | M73747 | 2248 | TSHR, thyroid stimulating hormone receptor | TTACCACGA[C/G]ATGAGGCAGG | M | C | G | D | E |
| G2396u1 | WIAF-12995 | M74542 | 1027 | ALDH3, aldehyde dehydrogenase 3 | CCCCAGTCC[C/G]CGGTGATGCA | M | C | G | P | A |
| G2396u2 | WIAF-13019 | M74542 | 1295 | ALDH3, aldehyde dehydrogenase 3 | GGCAAGAAGA[G/A]CTTCGAGACT | M | G | A | S | N |
| G2403u1 | WIAF-13583 | M83670 | 280 | CA4, carbonic anhydrase IV | TACGATAAGA[A/T]GCAAACGTGG | M | A | T | K | M |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G2409u1 | WIAF-10010 | HT2156 | 1268 | AGTR1, angiotensin receptor 1 | CCACTCAAAC[C/T]TTTCAACAAA | M | C | T | L | F |
| G2411u1 | WIAF-13541 | M97759 | 210 | ADORA2B, adenosine A2b receptor | TGGCGGGCAA[C/T]GTGCTGGTGT | S | C | T | N | N |
| G2422u1 | WIAF-14077 | S90469 | 375 | POR, P450 (cytochrome) oxidoreductase | GCAGCCTGCC[A/G]GAGATCGACA | S | A | G | P | P |
| G2422u2 | WIAF-14078 | S90469 | 852 | POR, P450 (cytochrome) oxidoreductase | TCCTGCTGC[A/G]GTCACCACCA | S | A | G | A | A |
| G2422u3 | WIAF-14082 | S90469 | 1496 | POR, P450 (cytochrome) oxidoreductase | AAGGAGCCTG[T/C]CGGGGAGAAC | M | T | C | V | A |
| G2422u4 | WIAF-14099 | S90469 | 1443 | POR, P450 (cytochrome) oxidoreductase | AGACCAAGGC[C/T]GGCCGCATCA | S | C | T | A | A |
| G2422u5 | WIAF-14100 | S90469 | 1704 | POR, P450 (cytochrome) oxidoreductase | GCCGCCGCTC[G/A]GATGAGGACT | S | G | A | S | S |
| G2427u1 | WIAF-14079 | U07919 | 1369 | ALDH6, aldehyde dehydrogenase 6 | ACTATGGACT[C/T]ACAGCAGCCG | S | C | T | L | L |
| G2427u2 | WIAF-14096 | U07919 | 1347 | ALDH6, aldehyde dehydrogenase 6 | ATAAAAAGAG[C/T]GAATAGCACC | M | C | T | A | V |
| G2431u1 | WIAF-11684 | X57522 | 926 | TAP1, transporter 1, ABC (ATP binding cassette) | ATAGCCAGTG[C/G]GAGTGCTGAG | M | C | G | A | G |
| G2431u2 | WIAF-11685 | X57522 | 627 | TAP1, transporter 1, ABC (ATP binding cassette) | ACCCTACCGC[C/T]TTCGTTGTCA | S | C | T | A | A |
| G2431u3 | WIAF-11686 | X57522 | 538 | TAP1, transporter 1, ABC (ATP binding cassette) | CCTGCCGGGA[C/G]TTGCCTTGTT | M | C | G | L | V |
| G2431u4 | WIAF-11687 | X57522 | 798 | TAP1, transporter 1, ABC (ATP binding cassette) | TGGTGGTTCCT[C/G]TCCTCTCTTG | S | C | G | L | L |
| G2431u5 | WIAF-11689 | X57522 | 1465 | TAP1, transporter 1, ABC (ATP binding cassette) | TAGTATTTCA[G/T]GTATGCTGCT | M | G | T | G | C |
| G2431u6 | WIAF-11690 | X57522 | 177 | TAP1, transporter 1, ABC (ATP binding cassette) | AGAGTCCCAG[A/G]CCCGGCCGGG | S | A | G | R | R |
| G2431u7 | WIAF-11693 | X57522 | 1067 | TAP1, transporter 1, ABC (ATP binding cassette) | AACATCATGT[C/T]TCGGGTAACA | M | C | T | S | F |
| G2431u8 | WIAF-11665 | X57522 | 1207 | TAP1, transporter 1, ABC (ATP binding cassette) | GGTCACCCTG[A/G]TCACCCTGCC | M | A | G | I | V |
| G2431u9 | WIAF-11664 | X57522 | 1757 | TAP1, transporter 1, ABC (ATP binding cassette) | CCAAACCGCC[C/T]AGATGTCTTA | M | C | T | P | L |
| G2441u1 | WIAF-10174 | X60592 | 239 | TNFRSF5, tumor necrosis factor receptor superfamily, member 5 | CTTGCGGTGA[A/G]AGCGAATTCC | S | A | G | E | E |
| G2441u1 | WIAF-13682 | U30246 | 1355 | SLC12A2, solute carrier family 12 (sodium/potassium/chloride transporters), member 2 | TGCTTAAGGA[A/G]CATTCCATAC | S | A | G | E | E |
| G2441u2 | WIAF-13714 | U30246 | 2691 | SLC12A2, solute carrier family 12 (sodium/potassium/chloride transporters), member 2 | AGCCAAATAT[C/G]AGCGATGGCT | M | C | G | Q | E |
| G2443u1 | WIAF-14004 | U37143 | 1456 | CYP2J2, cytochrome P450, subfamily IIJ (arachidonic acid epoxygenase) polypeptide 2 | CTGAAGTTTA[G/A]AATGGGTATC | M | G | A | R | K |
| G2443u2 | WIAF-14032 | U37143 | 376 | CYP2J2, cytochrome P450, subfamily IIJ (arachidonic acid epoxygenase) polypeptide 2 | TTTAAGAAAA[A/G]TGGATTGATT | M | A | G | N | S |
| G2443u3 | WIAF-14033 | U37143 | 1502 | CYP2J2, cytochrome P450, subfamily IIJ (arachidonic acid epoxygenase) polypeptide 2 | TCTGCCTGT[T/A]CCTCAGGTGT | S | T | A | V | V |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G2444u1 | WIAF-14065 | U37519 | 771 | ALDH3, aldehyde dehydrogenase 3 | CCCGCAGGGA[A/G]TTGCGTGTG | M | A | G | N | S |
| G2444u2 | WIAF-14066 | U37519 | 1698 | ALDH3, aldehyde dehydrogenase 3 | AAGGAGATCC[G/A]CTACCCACCC | M | G | A | R | H |
| G2445u1 | WIAF-14114 | U38178 | 236 | CNP, 2',3'-cyclic nucleotide 3' phosphodiesterase | TGCCGGGCGC[G/A]CCTCTCGCTG | M | G | A | R | H |
| G2445u2 | WIAF-14115 | U38178 | 849 | CNP, 2',3'-cyclic nucleotide 3' phosphodiesterase | GTGCCCCCGA[A/G]GAAAAAGTGC | S | A | G | E | E |
| G2445u3 | WIAF-14122 | U38178 | 1655 | CNP, 2',3'-cyclic nucleotide 3' phosphodiesterase | GTTATCTTGC[A/T]GAGATCTCTG | M | A | T | Q | L |
| G2445u4 | WIAF-14241 | X95520 | 941 | CNP, 2',3'-cyclic nucleotide 3' phosphodiesterase | TGCAAAATAT[T/C]CAGGAGACCG | ? | T | C | ? | ? |
| G2445u5 | WIAF-14242 | X95520 | 1057 | CNP, 2',3'-cyclic nucleotide 3' phosphodiesterase | TGGAGTTGAT[C/T]TTTCAGTGCT | ? | C | T | ? | ? |
| G2445u6 | WIAF-14243 | X95520 | 1583 | CNP, 2',3'-cyclic nucleotide 3' phosphodiesterase | TCTACTGGCT[C/G]TCTAACTAAT | ? | C | G | ? | ? |
| G2448u1 | WIAF-13973 | U46689 | 1895 | ALDH10, aldehyde dehydrogenase 10 (fatty aldehyde dehydrogenase) | TTGTCAAGGC[A/T]GAATATTACT | S | A | T | A | A |
| G2457u1 | WIAF-13898 | U90277 | 1304 | GRIN2A, glutamate receptor, ionotropic, N-methyl D-aspartate 2A | GGTCCCGATG[C/T]ACACCTTGCA | M | C | T | H | Y |
| G2457u2 | WIAF-13899 | U90277 | 1934 | GRIN2A, glutamate receptor, ionotropic, N-methyl D-aspartate 2A | AAGAAGTAAT[G/T]GCACCGTCTC | M | G | T | G | C |
| G2457u3 | WIAF-13900 | U90277 | 2230 | GRIN2A, glutamate receptor, ionotropic, N-methyl D-aspartate 2A | TCGCTGTCAT[A/G]TTCCTGGCTA | M | A | G | I | M |
| G2457u4 | WIAF-13902 | U90277 | 2916 | GRIN2A, glutamate receptor, ionotropic, N-methyl D-aspartate 2A | GGCATTACA[G/A]CTGCATTCAT | M | G | A | S | N |
| G2457u5 | WIAF-13903 | U90277 | 3251 | GRIN2A, glutamate receptor, ionotropic, N-methyl D-aspartate 2A | CTATGTATTC[C/T]AGGGACAACA | N | C | T | Q | * |
| G2457u6 | WIAF-13917 | U90277 | 2756 | GRIN2A, glutamate receptor, ionotropic, N-methyl D-aspartate 2A | GGACATTGAC[A/G]ACATGGCGGG | M | A | G | N | D |
| G2468u1 | WIAF-13642 | X04011 | 1017 | CYBB, cytochrome b-245, beta polypeptide (chronic granulomatous disease) | AGGTGTCCAA[G/A]CTGGAGTGGC | S | G | A | K | K |
| G2473u1 | WIAF-13670 | X06990 | 1417 | ICAM1, intercellular adhesion molecule 1 (CD54), human rhinovirus receptor | GGTCACCCGC[G/A]AGGTGACCGT | M | G | A | E | K |
| G2473u2 | WIAF-13695 | X06990 | 179 | ICAM1, intercellular adhesion molecule 1 (CD54), human rhinovirus receptor | GACCAGCCCA[A/T]GTTGTTGGGC | M | A | T | K | M |
| G2480u1 | WIAF-14148 | X55330 | 800 | AGA, aspartylglucosaminidase | TTGGCATGGT[T/G]GTAATCCATA | S | T | G | V | V |
| G2480u2 | WIAF-14149 | X55330 | 852 | AGA, aspartylglucosaminidase | AAATGGTATA[A/T]AATTCAAAAT | N | A | T | K | * |
| G2480u3 | WIAF-14158 | X55330 | 616 | AGA, aspartylglucosaminidase | TTATCTACCA[G/C]TGCTTCTCAA | M | G | C | S | T |
| G2485u1 | WIAF-13612 | X59543 | 2301 | RRM1, ribonucleotide reductase M1 polypeptide | ATTGATCAAA[G/A]CCAATCTTTG | M | G | A | S | N |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---------|---------|----------------------------------|----------------------|------------------|--------------|---------------|--------|--------|--------|--------|
| G2485u2 | WIAF-13613 | X59543 | 2410 | RRM1, ribonucleotide reductase M1 polypeptide | ATTTAAGGAC[G/A]AGACCAGCAG | S | G | A | T | T |
| G2485u3 | WIAF-13651 | X59543 | 548 | RRM1, ribonucleotide reductase M1 polypeptide | CAAGTCAACA[T/C]TGGATATTGT | S | T | C | L | L |
| G2485u4 | WIAF-13652 | X59543 | 199 | RRM1, ribonucleotide reductase M1 polypeptide | TGCATGTGAT[C/T]AAGCGAGATG | S | C | T | I | I |
| G2485u5 | WIAF-13653 | X59543 | 1037 | RRM1, ribonucleotide reductase M1 polypeptide | CAACACAGCT[C/A]GATATGTGGA | S | C | A | R | R |
| G2485u6 | WIAF-13660 | X59543 | 1955 | RRM1, ribonucleotide reductase M1 polypeptide | GAAGATTGCA[A/C]AGTATGGTAT | M | A | C | K | Q |
| G2485u7 | WIAF-13877 | X59543 | 860 | RRM1, ribonucleotide reductase M1 polypeptide | GAGTATGAAA[G/C]ATGACAGCAT | M | G | C | D | H |
| G2486u1 | WIAF-14075 | X59618 | 543 | RRM2, ribonucleotide reductase M2 polypeptide | TCAGCACTGG[G/C]AATCCCTGAA | M | G | C | E | Q |
| G2486u2 | WIAF-14076 | X59618 | 189 | RRM2, ribonucleotide reductase M2 polypeptide | TCGCTGCGCC[T/G]CCACTATGCT | - | T | G | - | - |
| G2486u3 | WIAF-14092 | X59618 | 524 | RRM2, ribonucleotide reductase M2 polypeptide | TTTGACCTCTC[C/G]AAGGACATTC | S | C | G | S | S |
| G2488u1 | WIAF-13585 | X63563 | 1633 | POLR2B, polymerase (RNA) II (DNA directed) polypeptide B (140 kD) | CCTTGATGGC[G/A]TATATTTCAG | S | G | A | A | A |
| G2488u2 | WIAF-13586 | X63563 | 2452 | POLR2B, polymerase (RNA) II (DNA directed) polypeptide B (140 kD) | CTGTAGACCG[C/T]GGCTTCTTCA | S | C | T | R | R |
| G2488u3 | WIAF-13587 | X63563 | 2740 | POLR2B, polymerase (RNA) II (DNA directed) polypeptide B (140 kD) | TCAGAACTAG[T/C]GAGACGGGCA | S | T | C | S | S |
| G2488u4 | WIAF-13602 | X63563 | 1411 | POLR2B, polymerase (RNA) II (DNA directed) polypeptide B (140 kD) | GGGGTGATCA[A/G]AAGAAAGCTC | S | A | G | Q | Q |
| G2488u5 | WIAF-13603 | X63563 | 2386 | POLR2B, polymerase (RNA) II (DNA directed) polypeptide B (140 kD) | CAATTGTGGC[C/T]ATTGCATCAT | S | C | T | A | A |
| G2489u1 | WIAF-14181 | X63564 | 1346 | POLR2A, polymerase (RNA) II (DNA directed) polypeptide A (220 kD) | TGGTGGACAA[T/C]GAGCTGCCTG | S | T | C | N | N |
| G2489u2 | WIAF-14236 | X63564 | 1847 | POLR2A, polymerase (RNA) II (DNA directed) polypeptide A (220 kD) | TGAATCTTAG[C/T]GTGACAACTC | ? | C | T | ? | ? |
| G2489u3 | WIAF-14237 | X63564 | 2678 | POLR2A, polymerase (RNA) II (DNA directed) polypeptide A (220 kD) | CTGAATACAA[C/T]AACTTCAAGT | ? | C | T | ? | ? |
| G2489u4 | WIAF-14238 | X63564 | 3059 | POLR2A, polymerase (RNA) II (DNA directed) polypeptide A (220 kD) | AGCTGCCCTA[C/T]GGCGAAGACG | ? | C | T | ? | ? |
| G2489u5 | WIAF-14239 | X63564 | 3827 | POLR2A, polymerase (RNA) II (DNA directed) polypeptide A (220 kD) | TGGGCCAGTC[C/T]GCTCGAGATG | ? | C | T | ? | ? |
| G2489u6 | WIAF-14240 | X63564 | 3827 | POLR2A, polymerase (RNA) II (DNA directed) polypeptide A (220 kD) | TGCCTGACTT[T/C]GATGTGCCCC | ? | T | C | ? | ? |
| G2489u7 | WIAF-14245 | X63564 | 3938 | POLR2A, polymerase (RNA) II (DNA directed) polypeptide A (220 kD) | CCCAGAGCAC[G/A]GTGGTGGCAG | ? | G | A | ? | ? |
| G250u1 | WIAF-11696 | HT0155 | 1113 | IL3RA, interleukin 3 receptor, alpha (low affinity) | CTGTGTCTTC[G/C]TGATCTGCAG | M | G | C | V | L |
| G251u1 | WIAF-11666 | HT0240 | 179 | interleukin 1 beta convertase | TGGATAAGAC[C/T]CGAGCTTTGA | S | C | T | T | T |
| G251u2 | WIAF-11694 | HT0240 | 973 | interleukin 1 beta convertase | GATGCTATTA[A/G]GAAAGCCCAC | M | A | G | K | R |
| G251u3 | WIAF-11695 | HT0240 | 783 | interleukin 1 beta convertase | CCCAGATATA[C/T]TACAACTCAA | S | C | T | L | L |
| G2513u1 | WIAF-13736 | HT27365 | 1721 | PLCB3, phospholipase C, beta 3 (phosphatidylinositol-specific) | AACTATCTAT[G/A]AAAAGCCAAA | M | G | A | M | I |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G2513u2 | WIAF-13737 | HT27365 | 1741 | PLCB3, phospholipase C, beta 3 (phosphatidylinositol-specific) | AACTATTGGG[A/T]AATGTGTTCA | M | A | T | E | V |
| G2513u3 | WIAF-13738 | HT27365 | 1697 | PLCB3, phospholipase C, beta 3 (phosphatidylinositol-specific) | AATCTGTTCA[A/G]TACAGGGATT | S | A | G | Q | Q |
| G2513u4 | WIAF-13739 | HT27365 | 1908 | PLCB3, phospholipase C, beta 3 (phosphatidylinositol-specific) | CTGTCAGATT[G/A]TAGCAATGAA | M | G | A | V | I |
| G2513u5 | WIAF-13740 | HT27365 | 2172 | PLCB3, phospholipase C, beta 3 (phosphatidylinositol-specific) | TATAGAGATA[C/T]ACGGAATTCC | M | C | T | H | Y |
| G2513u6 | WIAF-13744 | HT27365 | 3019 | PLCB3, phospholipase C, beta 3 (phosphatidylinositol-specific) | TTGAAGGGCC[A/G]AGGAGATCTG | M | A | G | Q | R |
| G2513u7 | WIAF-13745 | HT27365 | 3024 | PLCB3, phospholipase C, beta 3 (phosphatidylinositol-specific) | GGGCCAAGGA[G/A]ATCTGTTGAA | M | G | A | D | N |
| G2513u8 | WIAF-13771 | HT27365 | 1079 | PLCB3, phospholipase C, beta 3 (phosphatidylinositol-specific) | ACATTTTTGA[T/C]CCTGAGCAAA | S | T | C | D | D |
| G2513u9 | WIAF-13772 | HT27365 | 1546 | PLCB3, phospholipase C, beta 3 (phosphatidylinositol-specific) | AAGTTGCCTT[C/T]TGATCCAGAT | M | C | T | S | F |
| G2513u10 | WIAF-13773 | HT27365 | 1514 | PLCB3, phospholipase C, beta 3 (phosphatidylinositol-specific) | AATTAAAAAG[A/T]ATGATCATTG | M | A | T | R | S |
| G2513u11 | WIAF-13774 | HT27365 | 1445 | PLCB3, phospholipase C, beta 3 (phosphatidylinositol-specific) | AGGTCTTTGG[C/T]AATAAACTCT | S | C | T | G | G |
| G2513u12 | WIAF-13778 | HT27365 | 2087 | PLCB3, phospholipase C, beta 3 (phosphatidylinositol-specific) | TTCATATCAA[G/A]ATCATCAGTG | S | G | A | K | K |
| G2513u13 | WIAF-13779 | HT27365 | 2367 | PLCB3, phospholipase C, beta 3 (phosphatidylinositol-specific) | TGAATGTTTG[C/T]AGCCTGGATA | N | C | T | Q | * |
| G2513u14 | WIAF-13782 | HT27365 | 2719 | PLCB3, phospholipase C, beta 3 (phosphatidylinositol-specific) | CTCATCACCA[G/A]TGACAATACT | M | G | A | S | N |
| G2513u15 | WIAF-13783 | HT27365 | 2567 | PLCB3, phospholipase C, beta 3 (phosphatidylinositol-specific) | TTTGATGACAT[C/T]TTTAAAATAG | S | C | T | I | I |
| G2513u16 | WIAF-13784 | HT27365 | 2864 | PLCB3, phospholipase C, beta 3 (phosphatidylinositol-specific) | TAGAAATGGC[G/A]GACACAGTCC | S | G | A | A | A |
| G2513u17 | WIAF-13785 | HT27365 | 2571 | PLCB3, phospholipase C, beta 3 (phosphatidylinositol-specific) | TGACATCTTT[A/T]AAATAGCGGT | N | A | T | K | * |
| G2513u18 | WIAF-13786 | HT27365 | 2706 | PLCB3, phospholipase C, beta 3 (phosphatidylinositol-specific) | TCTGTCATCT[C/T]GGCTCATCAC | M | C | T | R | W |
| G252u1 | WIAF-10195 | HT0425 | 397 | FCER2, Fc fragment of IgE, low affinity II, receptor for (CD23A) | GAGGGCTGCC[C/T]GGAACGTCTC | M | C | T | R | W |
| G252u2 | WIAF-10206 | HT0425 | 930 | FCER2, Fc fragment of IgE, low affinity II, receptor for (CD23A) | ATGGGAGCCA[T/C]GTGGACTACA | S | T | C | H | H |
| G253u1 | WIAF-10175 | HT0573 | 228 | IFNB1, interferon, beta 1, fibroblast | GGCTTGAATA[C/T]TGCCTCAAGG | S | C | T | Y | Y |
| G254u1 | WIAF-10196 | HT0611 | 466 | IL4R, interleukin 4 receptor | TCAGTGCGGA[T/C]AACTATACAC | S | T | C | D | D |
| G254u2 | WIAF-10198 | HT0611 | 1474 | IL4R, interleukin 4 receptor | CATGCCTTCT[T/C]CCACCTTCGG | S | T | C | L | L |
| G254u3 | WIAF-10207 | HT0611 | 1902 | IL4R, interleukin 4 receptor | AGTGGCTATC[A/G]GGAGTTTGTA | M | A | G | Q | R |
| G260u1 | WIAF-10186 | HT1090 | 453 | IL1R1, interleukin 1 receptor, type I | TGTTATAATG[C/G]ACAAGCCATA | M | C | G | A | G |
| G261u1 | WIAF-10187 | HT1101 | 434 | IL7R, interleukin 7 receptor | CCTGAGTGTC[A/G]TCTATCGGGA | M | A | G | I | V |
| G261u2 | WIAF-10203 | HT1101 | 517 | IL7R, interleukin 7 receptor | TTTTAATGCA[T/C]GATGTAGCTT | S | T | C | H | H |
| G267u1 | WIAF-11735 | HT1877 | 881 | IL2RB, interleukin 2 receptor, beta | TCCTCGTGGG[C/T]CTCAGCGGGG | S | C | T | G | G |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G267u2 | WIAF-11759 | HT1877 | 379 | IL2RB, interleukin 2 receptor, beta | AGTCAAGCAT[C/T]CTGGCCTGC | M | C | T | S | F |
| G268u1 | WIAF-11758 | HT1985 | 568 | CD19 antigen | GCCTCCGTGT[G/C]TCCCACCGAG | M | G | C | V | L |
| G268u2 | WIAF-11734 | HT1985 | 783 | CD19 antigen | ACGATCGCCC[G/T]GCCAGAGATA | S | G | T | P | P |
| G270u1 | WIAF-11736 | HT2415 | 530 | IL6R, interleukin 6 receptor | AGGAGGTGGC[A/G]GAGAGGCGTGC | S | A | G | A | A |
| G270u2 | WIAF-11760 | HT2415 | 1590 | IL6R, interleukin 6 receptor | CATTGCCATT[G/A]TTCTGAGGTT | M | G | A | V | I |
| G270u3 | WIAF-11737 | HT2415 | 1510 | IL6R, interleukin 6 receptor | CCAGTGCAAG[A/C]TTCTTCTTCA | M | A | C | D | A |
| G270u4 | WIAF-11761 | HT2415 | 1451 | IL6R, interleukin 6 receptor | CTACTAATAA[A/T]GACGATGATA | M | A | T | K | N |
| G270u5 | WIAF-11766 | HT2415 | 1843 | IL6R, interleukin 6 receptor | TTCCCAGAT[A/G]GCTGGCTGGG | N | A | G | * | W |
| G270u6 | WIAF-11767 | HT2415 | 1829 | IL6R, interleukin 6 receptor | ATACAGACTA[C/T]TTCTTCCCCA | S | C | T | Y | Y |
| G271u1 | WIAF-11762 | HT2531 | 577 | CD2, CD2 antigen (p50), sheep red blood cell receptor | TCAGAGGGTC[A/G]TCACACACAA | M | A | G | I | V |
| G271u2 | WIAF-11739 | HT2531 | 861 | CD2, CD2 antigen (p50), sheep red blood cell receptor | GGAAGCCCCA[A/C]CAAATTCCAG | M | A | C | X | H |
| G271u3 | WIAF-11768 | HT2531 | 818 | CD2, CD2 antigen (p50), sheep red blood cell receptor | CTGGAGACAA[G/A]AGCCACAGA | M | G | A | R | K |
| G271u4 | WIAF-11738 | HT2531 | 736 | CD2, CD2 antigen (p50), sheep red blood cell receptor | CCTCTTGATG[G/A]TCTTTGTGGC | M | G | A | V | I |
| G273u1 | WIAF-11763 | HT3139 | 667 | IL2RA, interleukin 2 receptor, alpha | ATCATGGTGC[C/T]TGGCTGCCAG | M | C | T | P | L |
| G273u2 | WIAF-11764 | HT3139 | 956 | IL2RA, interleukin 2 receptor, alpha | AAAGTCCAAT[G/C]CAGCCAGTGG | M | G | C | M | I |
| G273u3 | WIAF-11765 | HT3139 | 701 | IL2RA, interleukin 2 receptor, alpha | ACGATGACCC[G/A]CCAGAGATCC | M | G | A | P | P |
| G273u4 | WIAF-11740 | HT3139 | 1133 | IL2RA, interleukin 2 receptor, alpha | AAATGACCCA[C/T]GGGAAGACAA | S | C | T | H | H |
| G273u5 | WIAF-11769 | HT3139 | 1163 | IL2RA, interleukin 2 receptor, alpha | AGCCCCAGCT[C/A]ATATGCACAG | S | C | A | L | L |
| G276u1 | WIAF-10192 | HT3670 | 644 | CD4 antigen | CTGGTAGTAG[C/G]CCCTCAGTGC | M | C | G | S | R |
| G276u2 | WIAF-10193 | HT3670 | 1535 | CD4 antigen | CCTGCCAGTG[T/C]CCTCACCGGT | S | T | C | C | C |
| G276u3 | WIAF-10205 | HT3670 | 1217 | CD4 antigen | TGATGCTGAG[T/C]TTGAAACTGG | S | T | C | S | S |
| G277u1 | WIAF-10007 | D10232 | 851 | RENBP, renin-binding protein | CACGTGATTG[A/G]CAAGTTCCTA | M | A | G | D | G |
| G277u2 | WIAF-10032 | D10232 | 842 | RENBP, renin-binding protein | CTTCGACCCC[A/G]CGTGATTGAC | M | A | G | H | R |
| G277u3 | WIAF-10042 | D10232 | 634 | RENBP, renin-binding protein | GCTGGCGGGC[A/G]AATACGCAGA | M | A | G | K | E |
| G279u1 | WIAF-10047 | K01740 | 1658 | F8C, coagulation factor VIIIc, procoagulant component (hemophilia A) | ACTGATGTCC[G/A]TCCTTTGTAT | M | G | A | R | H |
| G279u2 | WIAF-10049 | K01740 | 2328 | F8C, coagulation factor VIIIc, procoagulant component (hemophilia A) | CCTTACTGAA[G/A]GTTTCTAGTT | S | G | A | K | K |
| G279u3 | WIAF-10050 | K01740 | 4650 | F8C, coagulation factor VIIIc, procoagulant component (hemophilia A) | CTGTTCTCCC[G/A]AAACCAGACT | S | G | A | P | P |
| G279u4 | WIAF-10061 | K01740 | 6919 | F8C, coagulation factor VIIIc, procoagulant component (hemophilia A) | CCAGAGACA[A/G]TGAAAGTCAC | M | A | G | M | V |
| G279u5 | WIAF-10080 | K01740 | 480 | F8C, coagulation factor VIIIc, procoagulant component (hemophilia A) | TTAAGAACAT[G/A]GCTTCCATC | M | G | A | M | I |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G279u6 | WIAF-10082 | K01740 | 2129 | F8C, coagulation factor VIIIc, procoagulant component (hemophilia A) | TACATTCTAA[G/A]CATTGGAGCA | M | G | A | S | N |
| G279u7 | WIAF-10084 | K01740 | 2533 | F8C, coagulation factor VIIIc, procoagulant component (hemophilia A) | GTTTGCACAC[A/G]GAACACCTAT | M | A | G | R | G |
| G279u8 | WIAF-10086 | K01740 | 6639 | F8C, coagulation factor VIIIc, procoagulant component (hemophilia A) | ACCCTCCAAT[T/C]ATTGCTCGAT | S | T | C | I | I |
| G279u9 | WIAF-10087 | K01740 | 5957 | F8C, coagulation factor VIIIc, procoagulant component (hemophilia A) | GAGAATTATC[G/A]CTTCCATGCA | M | G | A | R | H |
| G279a10 | WIAF-10495 | K01740 | 5829 | F8C, coagulation factor VIIIc, procoagulant component (hemophilia A) | TGACAGTACA[G/A]GAATTTGCTC | S | G | A | Q | Q |
| G279a11 | WIAF-10496 | K01740 | 5852 | F8C, coagulation factor VIIIc, procoagulant component (hemophilia A) | TTTTTCACCA[T/G]CTTTGATGAG | M | T | G | I | S |
| G279a12 | WIAF-10502 | K01740 | 2492 | F8C, coagulation factor VIIIc, procoagulant component (hemophilia A) | ACCACAATTC[C/T]AGAAAATGAC | M | C | T | P | L |
| G279a13 | WIAF-10503 | K01740 | 6906 | F8C, coagulation factor VIIIc, procoagulant component (hemophilia A) | TGCAAGTGGA[C/T]TTCCAGAAGA | S | C | T | P | D |
| G279a14 | WIAF-13120 | K01740 | 1980 | F8C, coagulation factor VIIIc, procoagulant component (hemophilia A) | CAGAGAATAT[A/c]CAACGCTTTC | S | A | c | H | I |
| G279a15 | WIAF-13121 | K01740 | 1982 | F8C, coagulation factor VIIIc, procoagulant component (hemophilia A) | GAGAGAATAC[A/c]ACGCTTTCTC | M | A | c | Q | P |
| G282u1 | WIAF-10067 | L25615 | 976 | AVPR1A, arginine vasopressin receptor 1A | CGCCTTTCTT[C/A]ATCATCCAGA | M | C | A | F | L |
| G282u2 | WIAF-10070 | L25615 | 460 | AVPR1A, arginine vasopressin receptor 1A | TCGGCATGTT[T/C]GCGTCGGCCT | S | T | C | F | F |
| G282u3 | WIAF-10071 | L25615 | 343 | AVPR1A, arginine vasopressin receptor 1A | GCCTGGCCGA[C/T]CTGGCCGTGG | S | C | T | D | D |
| G282u4 | WIAF-10072 | L25615 | 68 | AVPR1A, arginine vasopressin receptor 1A | TCTCTCCGCC[G/A]GTCCCGACGC | M | G | A | G | S |
| G282u5 | WIAF-10073 | L25615 | 535 | AVPR1A, arginine vasopressin receptor 1A | AGACTCTGCA[A/G]CAGCCCGCGC | S | A | G | Q | Q |
| G282u6 | WIAF-10092 | L25615 | 1075 | AVPR1A, arginine vasopressin receptor 1A | CCTTGAATAG[C/A]TGCTGTAATC | M | C | A | S | R |
| G282a7 | WIAF-10499 | L25615 | 1089 | AVPR1A, arginine vasopressin receptor 1A | TGTAATCCCT[G/A]GATATACATG | N | G | A | W | * |
| G284u1 | WIAF-10182 | M16827 | 1179 | ACADM, acyl-Coenzyme A dehydrogenase, C-4 to C-12 straight chain | AATATCCTGT[A/G]GAAAACTAA | S | A | G | V | V |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G284a2 | WIAF-10515 | M16827 | 696 | ACADM, acyl-Coenzyme A dehydrogenase, C-4 to C-12 straight chain | TTGTGAAGC[A/G]GATACCCAG | S | A | G | A | A |
| G285u1 | WIAF-10108 | M28372 | 258 | ZNF9, zinc finger protein 9 (a cellular retroviral nucleic acid binding protein) | CTCTTCCAGA[T/C]ATTTGTTATC | S | T | C | D | D |
| G289u1 | WIAF-10041 | M63012 | 172 | PON1, paraoxonase 1 | CTCTGAAGAC[A/T]TGGAGATACT | M | A | T | M | L |
| G290u1 | WIAF-10085 | M63959 | 354 | LRPAP1, low density lipoprotein-related protein-associated protein 1 (alpha-2-macroglobulin receptor-associated protein 1) | CTCATACGCA[A/G]CCTCAATGTC | M | A | G | N | S |
| G290a2 | WIAF-13122 | M63959 | 223 | LRPAP1, low density lipoprotein-related protein-associated protein 1 (alpha-2-macroglobulin receptor-associated protein 1) | AGCGACTGCA[T/A]CTTCCTCCCG | M | T | A | H | Q |
| G292u1 | WIAF-10180 | M74096 | 1002 | ACADL, acyl-Coenzyme A dehydrogenase, long chain | AGTGCAACAT[A/C]AATTAGCAGA | M | A | C | K | Q |
| G293u1 | WIAF-10068 | M74775 | 723 | LIPA, lipase A, lysosomal acid, cholesterol esterase (Wolman disease) | AAGGACTTAT[T/C]TGGAGACAAA | M | T | C | F | S |
| G293a2 | WIAF-10497 | M74775 | 107 | LIPA, lipase A, lysosomal acid, cholesterol esterase (Wolman disease) | TGAGGGTCT[G/A]GAGGGAAACT | M | G | A | G | R |
| G293a3 | WIAF-10498 | M74775 | 86 | LIPA, lipase A, lysosomal acid, cholesterol esterase (Wolman disease) | GGTTCTCTGG[C/A]CCCTGCATTC | M | C | A | P | T |
| G295u1 | WIAF-10057 | U04270 | 1282 | KCNH2, potassium voltage-gated channel, subfamily H, member 2 | AAAGGACGCA[A/T]CCCACACATGT | S | A | T | T | S |
| G295u2 | WIAF-10062 | U04270 | 1875 | KCNH2, potassium voltage-gated channel, subfamily H, member 2 | CGCACTCGCT[A/G]GCCTGCATCT | S | A | G | L | L |
| G295u3 | WIAF-10064 | U04270 | 2040 | KCNH2, potassium voltage-gated channel, subfamily H, member 2 | ACTTCACCTT[C/T]AGCAGCCTCA | S | C | T | F | F |
| G295u4 | WIAF-10088 | U04270 | 1650 | KCNH2, potassium voltage-gated channel, subfamily H, member 2 | CCGGCCCAT[C/T]GCCGTCCACT | S | C | T | H | H |
| G295u5 | WIAF-10090 | U04270 | 2139 | KCNH2, potassium voltage-gated channel, subfamily H, member 2 | CCCTCATGTA[T/C]GCTAGCATCT | S | T | C | Y | Y |
| G2951u1 | WIAF-14147 | HT0030 | 1334 | ZNF42, zinc finger protein 42 (myeloid-specific retinoic acid-responsive) | CCCTGCTCTG[A/G]TCACCACCCG | M | A | G | H | V |
| G2951u2 | WIAF-14157 | HT0030 | 1558 | ZNF42, zinc finger protein 42 (myeloid-specific retinoic acid-responsive) | ACCAGCTTAC[G/A]CACACCGAGG | S | G | A | T | T |
| G2959u1 | WIAF-13501 | HT0134 | 1014 | GRLF1, glucocorticoid receptor DNA binding factor 1 | GTGGAGAGAC[T/C]CTGCATAGCT | S | T | C | T | T |
| G2959u2 | WIAF-13518 | HT0134 | 1853 | GRLF1, glucocorticoid receptor DNA binding factor 1 | GAGCCATCTT[A/C]CAGCCTGTTT | M | A | C | Y | S |
| G296a1 | WIAF-10514 | U12778 | 961 | ACADSB, acyl-Coenzyme A dehydrogenase, short/branched chain | TATTCCATAT[A/G]TTAAAGAAAG | M | A | G | I | V |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G2968u1 | WIAF-12699 | HT0244 | 1754 | SMARCA1, SWI/SNF related, matrix associated, actin dependent regulator of chromatin, subfamily a, member 1 | CAGAAGAAAC[C/T]AGTACGTGTA | M | C | T | P | L |
| G2968u2 | WIAF-12716 | HT0244 | 2624 | SMARCA1, SWI/SNF related, matrix associated, actin dependent regulator of chromatin, subfamily a, member 1 | TGGGAACGTT[G/T]CAATGAATTA | M | G | T | C | F |
| G297u1 | WIAF-10109 | U16660 | 402 | ECH1, enoyl Coenzyme A hydratase 1, peroxisomal | ACATGGCTTC[G/A]GACATCCTGC | S | G | A | S | S |
| G297u2 | WIAF-10110 | U16660 | 149 | ECH1, enoyl Coenzyme A hydratase 1, peroxisomal | GCACAAGAGG[A/C]GGCTTCCGGA | M | A | C | E | A |
| G2970u1 | WIAF-12746 | HT0281 | 682 | BR140: bromodomain-containing protein, 140 kD (peregrin) | ATGACATGGA[C/T]GAGGAGACT | S | C | T | D | D |
| G2975u1 | WIAF-12729 | HT0334 | 1104 | B-cell-specific transcription factor | AGTTTTCCGG[G/A]AGTCCCTACA | S | G | A | G | G |
| G2975u2 | WIAF-12730 | HT0334 | 1185 | B-cell-specific transcription factor | GCTCCCCCTA[C/T]TATTATAGCG | S | C | T | Y | Y |
| G2976a1 | WIAF-12129 | HT0340 | 1600 | SATB1, special AT-rich sequence binding protein 1 (binds to nuclear matrix/scaffold-associating DNA's) | GTCCTGCCCC[C/A]CTCATCAGCA | S | C | A | P | P |
| G2976u2 | WIAF-12743 | HT0340 | 2116 | SATB1, special AT-rich sequence binding protein 1 (binds to nuclear matrix/scaffold-associating DNA's) | TGGCCCTCTCC[A/G]GCAGAGTCAG | S | A | G | P | P |
| G2978u1 | WIAF-12721 | HT0346 | 1140 | MSX1, msh (Drosophila) homeo box homolog 1 (formerly homeo box 7) | CATAGAGGGT[C/T]CCAGGTCCCC | — | C | T | — | — |
| G298u1 | WIAF-10048 | U33837 | 8995 | Human glycoprotein receptor gp330 precursor, mRNA, complete cds. | CCGGACAGGA[G/A]GTGCATTCCC | M | G | A | R | K |
| G298u2 | WIAF-10051 | U33837 | 13217 | Human glycoprotein receptor gp330 precursor, mRNA, complete cds. | ATGCAGCCAT[C/T]GAACTGCCTA | S | C | T | I | I |
| G298u3 | WIAF-10077 | U33837 | 6298 | Human glycoprotein receptor gp330 precursor, mRNA, complete cds. | AACTCTTTCA[T/C]TGTTGTTTCA | M | T | C | I | T |
| G298u4 | WIAF-10078 | U33837 | 6371 | Human glycoprotein receptor gp330 precursor, mRNA, complete cds. | CCATGGTGCC[G/A]GTGGCAGGCC | S | G | A | P | P |
| G298u5 | WIAF-10079 | U33837 | 6914 | Human glycoprotein receptor gp330 precursor, mRNA, complete cds. | ACTCTGAAGT[G/A]ATTCGTTATG | S | G | A | V | V |
| G298u6 | WIAF-10081 | U33837 | 8718 | Human glycoprotein receptor gp330 precursor, mRNA, complete cds. | GTTCCAATGC[G/A]CATCTGGGCG | M | G | A | A | T |
| G298u7 | WIAF-10083 | U33837 | 9088 | Human glycoprotein receptor gp330 precursor, mRNA, complete cds. | ACTTGCTCTG[A/G]AAATGAATTC | M | A | G | E | G |
| G298u8 | WIAF-10096 | U33837 | 6949 | Human glycoprotein receptor gp330 precursor, mRNA, complete cds. | ACTCCTTATG[G/C]CATCACTGTT | M | G | C | G | A |
| G298u9 | WIAF-10097 | U33837 | 7149 | Human glycoprotein receptor gp330 precursor, mRNA, complete cds. | TTGCTTGAA[A/G]ACAATGGTGG | M | A | G | N | D |
| G298u10 | WIAF-10100 | U33837 | 8590 | Human glycoprotein receptor gp330 precursor, mRNA, complete cds. | TACACAAAAT[G/A]TCATAATTCA | M | G | A | C | Y |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G298u11 | WIAF-10101 | U33837 | 12948 | Human glycoprotein receptor gp330 precursor, mRNA, complete cds. | CATCTTTGAA[G/C]ACCAGTATA | M | G | C | D | H |
| G2980u1 | WIAF-12723 | HT0356 | 437 | TLE1, transducin-like enhancer of split 1, homolog of Drosophila E(sp1) | TCATGGCCAC[G/A]GACCCCAGT | M | G | A | G | R |
| G2980u2 | WIAF-12726 | HT0356 | 2044 | TLE1, transducin-like enhancer of split 1, homolog of Drosophila E(sp1) | AGTGGCTGGC[A/G]GTGGGCATGG | S | A | G | A | A |
| G2980u3 | WIAF-12747 | HT0356 | 379 | TLE1, transducin-like enhancer of split 1, homolog of Drosophila E(sp1) | CCATGGCAGA[G/A]TTGAATGCCA | S | G | A | E | E |
| G2980u4 | WIAF-12748 | HT0356 | 276 | TLE1, transducin-like enhancer of split 1, homolog of Drosophila E(sp1) | ATCGCCAAGA[G/A]ATTGAATACG | M | G | A | R | K |
| G2980u5 | WIAF-12749 | HT0356 | 1876 | TLE1, transducin-like enhancer of split 1, homolog of Drosophila E(sp1) | GCCACACAGA[C/T]GGGAGCCAGCT | S | C | T | D | D |
| G2980u6 | WIAF-12750 | HT0356 | 1759 | TLE1, transducin-like enhancer of split 1, homolog of Drosophila E(sp1) | CCGCCTGCTA[C/T]GCCCTGGCCA | S | C | T | Y | Y |
| G2981u1 | WIAF-12720 | HT0357 | 2206 | TLE2, transducin-like enhancer of split 2, homolog of Drosophila E(sp1) | ACAAATACAT[T/C]GTGACAGGCT | S | T | C | I | I |
| G2981u2 | WIAF-12737 | HT0357 | 1036 | TLE2, transducin-like enhancer of split 2, homolog of Drosophila E(sp1) | CGGACAGCGT[C/T]GCCCTGAGGA | S | C | T | V | V |
| G2981u3 | WIAF-12740 | HT0357 | 2181 | TLE2, transducin-like enhancer of split 2, homolog of Drosophila E(sp1) | CTGAGTTGTG[A/T]CATCTCCAGA | M | A | T | D | V |
| G2983u1 | WIAF-12833 | HT0360 | 636 | TLE3, transducin-like enhancer of split 3, homolog of Drosophila E(sp1) | TGTCACCCTC[G/C]GAAAGCCTCC | S | G | C | S | S |
| G2983u2 | WIAF-12834 | HT0360 | 1944 | TLE3, transducin-like enhancer of split 3, homolog of Drosophila E(sp1) | TGGACAACAC[G/A]GTGCGCTCCT | S | G | A | T | T |
| G2983u3 | WIAF-12848 | HT0360 | 1710 | TLE3, transducin-like enhancer of split 3, homolog of Drosophila E(sp1) | ACCTGGCCTC[G/A]CCCACGCCCC | S | G | A | S | S |
| G2985u1 | WIAF-12724 | HT0421 | 995 | homeotic protein D3 | GGCTTCGCCA[G/A]CGCCAACCTG | M | G | A | S | N |
| G2985u2 | WIAF-12725 | HT0421 | 1003 | homeotic protein D3 | CAGCGCCAAC[C/T]TGCAGGGCAG | S | C | T | L | L |
| G2986u1 | WIAF-14124 | HT0468 | 1197 | CSDA, cold shock domain protein A | GCCGTGGATA[C/T]CGGCGTCCCT | S | C | T | Y | Y |
| G2987u1 | WIAF-12758 | HT0474 | 2068 | ZNF7, zinc finger protein 7 (KOX 4, clone HF.16) | AGTGGTTTTA[C/T]TGAATATGGGA | S | C | T | Y | Y |
| G2987u2 | WIAF-12773 | HT0474 | 985 | ZNF7, zinc finger protein 7 (KOX 4, clone HF.16) | GAGAGAAGCC[G/C]TACGAATGTG | S | G | C | P | P |
| G2987u3 | WIAF-12775 | HT0474 | 1278 | ZNF7, zinc finger protein 7 (KOX 4, clone HF.16) | AGCCAGCAGT[C/T]GCAGCTGGTT | M | C | T | S | L |
| G3005a1 | WIAF-12133 | HT0735 | 1441 | homeotic protein 5.1 | GAGGCAGCGG[C/T]CCCGGGCCTG | S | C | T | G | G |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G3008a1 | WIAF-12134 | HT0753 | 1850 | ATF4, activating transcription factor 4 (tax-responsive enhancer element B67) | TAAAAGAGAG[G/A]GCGGATTCCC | S | G | A | R | R |
| G3008u2 | WIAF-12798 | HT0753 | 946 | ATF4, activating transcription factor 4 (tax-responsive enhancer element B67) | CCCTTCGACC[C/A]GTCGGGTTTG | M | C | A | P | Q |
| G3008u3 | WIAF-12812 | HT0753 | 1482 | ATF4, activating transcription factor 4 (tax-responsive enhancer element B67) | CACTGCTTAC[G/A]TTGCCATGAT | M | G | A | V | I |
| G3008u4 | WIAF-12813 | HT0753 | 1847 | ATF4, activating transcription factor 4 (tax-responsive enhancer element B67) | CTCTAAAAGA[G/C]AGGGCGGATT | M | G | C | E | D |
| G301u1 | WIAF-10127 | U71285 | 3639 | MTR, 5-methyltetrahydrofolate-homocysteine methyltransferase | TGTGGAGACT[C/T]GCAGACATCG | S | C | T | L | L |
| G3012u1 | WIAF-12794 | HT0873 | 402 | MAD, MAX dimerization protein | TGGTGCCACT[G/T]GGACCCGAAT | S | G | T | L | L |
| G3014u1 | WIAF-14183 | HT0899 | 274 | homeotic protein 2, distal-less | AAAAGACTCA[G/A]TACTTGGCCT | S | G | A | Q | Q |
| G3020u1 | WIAF-12797 | HT0956 | 852 | MLLT3, myeloid/lymphoid or mixed-lineage leukemia (trithorax (Drosophila) homolog); translocated to, 3 | GTGCCTTCAA[A/G]GAACCTTCCA | S | A | G | K | K |
| G3023u1 | WIAF-13724 | HT0966 | 381 | zinc finger, X-linked, duplicated A | GCTGCAGCAA[G/A]CAATATGACA | S | G | A | K | K |
| G3023u2 | WIAF-13725 | HT0966 | 220 | zinc finger, X-linked, duplicated A | GGCCAAACTC[G/A]GCCCCCACCA | M | G | A | G | S |
| G3023u3 | WIAF-13726 | HT0966 | 69 | zinc finger, X-linked, duplicated A | AGTCGCACGA[T/C]AAACTGCGGC | S | T | C | D | D |
| G3023u4 | WIAF-13727 | HT0966 | 249 | zinc finger, X-linked, duplicated A | ACTTCGAACC[C/T]GAGAGGCCTT | S | C | T | P | P |
| G3023u5 | WIAF-13765 | HT0966 | 661 | zinc finger, X-linked, duplicated A | CAGGTTCTCT[G/A]CTCGCAGTAG | M | G | A | A | T |
| G3023u6 | WIAF-13766 | HT0966 | 1302 | zinc finger, X-linked, duplicated A | TGACTCCTTC[G/T]AGCACCCTTT | S | G | T | S | S |
| G3027u1 | WIAF-12800 | HT1035 | 124 | HOXB7, homeo box B7 | TTATGCCAAT[G/A]CTTTATTTTC | M | G | A | A | T |
| G3027u2 | WIAF-12816 | HT1035 | 450 | HOXB7, homeo box B7 | GGGACTCGGA[C/T]TTGGCGGCCG | S | C | T | D | D |
| G3028u1 | WIAF-12806 | HT1037 | 701 | homeotic protein C8 | AGACCCTGGA[A/G]CTGGAGAAGG | S | A | G | E | E |
| G3029u1 | WIAF-14153 | HT1100 | 441 | zinc finger protein 8 | TCAGACTCAG[G/A]GAAAACTGCG | S | G | A | R | R |
| G3029u2 | WIAF-14155 | HT1100 | 1416 | zinc finger protein 8 | GGCGTGAACA[A/G]TCCTGAGCA | S | A | G | Q | Q |
| G303u1 | WIAF-10000 | X13916 | 4110 | LRP1, low density lipoprotein-related protein 1 (alpha-2-macroglobulin receptor) | ATGGAGCTGG[G/A]GCCCGACAAC | M | G | A | G | E |
| G303u2 | WIAF-10001 | X13916 | 4012 | LRP1, low density lipoprotein-related protein 1 (alpha-2-macroglobulin receptor) | GCGAGCTCTG[C/T]GACCAGTGCT | S | C | T | C | C |
| G303u3 | WIAF-10002 | X13916 | 4702 | LRP1, low density lipoprotein-related protein 1 (alpha-2-macroglobulin receptor) | GCCTGCCCCG[C/T]ATTGAGGCAG | S | C | T | R | R |
| G303u4 | WIAF-10003 | X13916 | 6395 | LRP1, low density lipoprotein-related protein 1 (alpha-2-macroglobulin receptor) | CTGGATCGCA[G/A]GCAACATCTA | M | G | A | G | S |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G303u5 | WIAF-10004 | X13916 | 6937 | LRP1, low density lipoprotein-related protein 1 (alpha-2-macroglobulin receptor) | AAGGCACCAA[C/T]GTGTGCCGGG | S | C | T | N | N |
| G303u6 | WIAF-10005 | X13916 | 9391 | LRP1, low density lipoprotein-related protein 1 (alpha-2-macroglobulin receptor) | GGCTGAAGGA[T/C]GACGGCCCGA | S | T | C | D | D |
| G303u7 | WIAF-10011 | X13916 | 766 | LRP1, low density lipoprotein-related protein 1 (alpha-2-macroglobulin receptor) | ACTGCATGGA[C/T]GGCTCAGATG | S | C | T | D | D |
| G303u8 | WIAF-10015 | X13916 | 9040 | LRP1, low density lipoprotein-related protein 1 (alpha-2-macroglobulin receptor) | ACCCGACCTG[C/T]GGCCCCAGTG | S | C | T | C | C |
| G303u9 | WIAF-10019 | X13916 | 11749 | LRP1, low density lipoprotein-related protein 1 (alpha-2-macroglobulin receptor) | CCCTGCGCTG[C/T]AACATGTTCG | S | C | T | C | C |
| G303u10 | WIAF-10020 | X13916 | 1917 | LRP1, low density lipoprotein-related protein 1 (alpha-2-macroglobulin receptor) | GACCAGTATG[G/A]GAAGCCGGGT | M | G | A | G | E |
| G303u11 | WIAF-10021 | X13916 | 4810 | LRP1, low density lipoprotein-related protein 1 (alpha-2-macroglobulin receptor) | AGAAGCCGCAT[C/T]CTTTGGATTG | S | C | T | H | H |
| G303u12 | WIAF-10022 | X13916 | 6367 | LRP1, low density lipoprotein-related protein 1 (alpha-2-macroglobulin receptor) | TTGGCCGTGT[G/C]GAGGGCATTG | S | G | C | V | V |
| G303u13 | WIAF-10023 | X13916 | 6247 | LRP1, low density lipoprotein-related protein 1 (alpha-2-macroglobulin receptor) | CTGTCGGCAT[C/T]GACTTCCACG | S | C | T | H | H |
| G303u14 | WIAF-10024 | X13916 | 8371 | LRP1, low density lipoprotein-related protein 1 (alpha-2-macroglobulin receptor) | ACGCCTCAGA[T/C]GAGATGAACT | S | T | C | D | D |
| G303u15 | WIAF-10030 | X13916 | 11395 | LRP1, low density lipoprotein-related protein 1 (alpha-2-macroglobulin receptor) | ACGGCAGCGA[C/T]GAGGAGGCCT | S | C | T | D | D |
| G303u16 | WIAF-10031 | X13916 | 12763 | LRP1, low density lipoprotein-related protein 1 (alpha-2-macroglobulin receptor) | ACGTCTTTGA[G/A]GATTACATCT | S | G | A | E | E |
| G303u17 | WIAF-10035 | X13916 | 640 | LRP1, low density lipoprotein-related protein 1 (alpha-2-macroglobulin receptor) | ACGGATCTGA[C/T]GAGGCCCCTG | S | C | T | D | D |
| G303u18 | WIAF-10037 | X13916 | 1609 | LRP1, low density lipoprotein-related protein 1 (alpha-2-macroglobulin receptor) | GCCGCCTTGT[C/T]TACTGGGCAG | S | C | T | V | V |
| G303u19 | WIAF-10038 | X13916 | 1629 | LRP1, low density lipoprotein-related protein 1 (alpha-2-macroglobulin receptor) | GATGCCTATC[T/G]GGACTATATT | M | T | G | L | R |
| G303u20 | WIAF-10039 | X13916 | 2210 | LRP1, low density lipoprotein-related protein 1 (alpha-2-macroglobulin receptor) | CACCAGCTAC[C/T]TCATTGGCCG | M | C | T | L | F |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G303u21 | WIAF-10043 | X13916 | 7287 | LRP1, low density lipoprotein-related protein 1 (alpha-2-macroglobulin receptor) | GATGGCTCCA[G/A]GAGGATCACC | M | G | A | R | K |
| G303u22 | WIAF-10044 | X13916 | 8258 | LRP1, low density lipoprotein-related protein 1 (alpha-2-macroglobulin receptor) | CTCTGACGAG[A/G]TCCCTTGCAA | M | A | G | I | V |
| G303u23 | WIAF-10045 | X13916 | 11871 | LRP1, low density lipoprotein-related protein 1 (alpha-2-macroglobulin receptor) | GTGCGCACCG[A/G]GAAAGCGGCC | M | A | G | E | G |
| G3031u1 | WIAF-14097 | HT1128 | 611 | PSMC3, proteasome (prosome, macropain) 26S subunit, ATPase, 3 | TGGGGATCCA[A/G]CCTCCAAAAG | S | A | G | Q | Q |
| G3034u1 | WIAF-12836 | HT1182 | 137 | TCF12, transcription factor 12 (HTF4, helix-loop-helix transcription factors 4) | ATAAGGGAGC[G/A]TGAGGAGTCT | M | G | A | R | H |
| G3034u2 | WIAF-12837 | HT1182 | 421 | TCF12, transcription factor 12 (HTF4, helix-loop-helix transcription factors 4) | ATCTTCAATT[A/G]TGGGTTCCTT | M | A | G | M | V |
| G3038u1 | WIAF-12864 | HT1373 | 1700 | NFKB1, nuclear factor of kappa light polypeptide gene enhancer in B-cells 1 (p105) | AGAGAAGGCT[A/G]TGCAGCTTGC | M | A | G | M | V |
| G3038u2 | WIAF-12881 | HT1373 | 1936 | NFKB1, nuclear factor of kappa light polypeptide gene enhancer in B-cells 1 (p105) | TGTACCAGAC[G/A]CCCTTGCACT | S | G | A | T | T |
| G3038u3 | WIAF-12882 | HT1373 | 2641 | NFKB1, nuclear factor of kappa light polypeptide gene enhancer in B-cells 1 (p105) | AGCTGCAGCT[G/C]TATAAGTTAC | S | G | C | L | L |
| G3039u1 | WIAF-13027 | HT1375 | 3761 | GLI3, GLI-Kruppel family member GLI3 (Greig cephalopolysyndactyly syndrome) | AACAGCCCCG[G/T]AAGTGGCACC | M | G | T | G | V |
| G3039u2 | WIAF-13028 | HT1375 | 3963 | GLI3, GLI-Kruppel family member GLI3 (Greig cephalopolysyndactyly syndrome) | CGCCAAATGA[G/T]TCAGCTGCA | M | G | T | E | D |
| G304u1 | WIAF-12242 | HT637 | 158 | FABP3, fatty acid binding protein 3, muscle and heart (mammary-derived growth inhibitor) | CTCACCCTAA[A/G]AACACACAGC | M | A | G | K | R |
| G3043u1 | WIAF-12867 | HT1486 | 842 | IRF2, interferon regulatory factor 2 | GTGCCAGGGG[G/A]CGGCCACACT | M | G | A | G | G |
| G3047u1 | WIAF-12875 | HT1518 | 1233 | transcription factor 1, nucleolar | TCCGTTTCCT[C/T]GAGAGCCTGC | S | C | T | L | L |
| G3047u2 | WIAF-12876 | HT1518 | 1746 | transcription factor 1, nucleolar | GGATTAAGAA[G/A]GCAGCCGAAG | S | G | A | K | K |
| G3047u3 | WIAF-12877 | HT1518 | 1829 | transcription factor 1, nucleolar | TCCAAGAAGA[T/C]GAAATTCCAG | M | T | C | M | T |
| G3048u1 | WIAF-12884 | HT1530 | 628 | transcription factor USF | AGTGGACCGT[C/T]GCCGCCGAGA | S | C | T | R | R |
| G305u1 | WIAF-10150 | HT0034 | 777 | prolyl 4-hydroxylase, beta subunit/protein disulfide isomerase/thyroid hormone-binding protein, alt. transcript 1 | CCCTTGTCAT[C/T]GAGTTCACCG | S | C | T | H | H |
| G305u2 | WIAF-10154 | HT0034 | 186 | prolyl 4-hydroxylase, beta subunit/protein disulfide isomerase/thyroid hormone-binding protein, alt. transcript 1 | TGGCGGCCCA[C/A]AAGTACCTGC | M | C | A | H | Q |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G305u3 | WIAF-10155 | HT0034 | 1428 | prolyl 4-hydroxylase, beta subunit/protein disulfide isomerase/thyroid hormone-binding protein, alt. transcript 1 | GGACGGTCAT[T/C]GATTACAACG | S | T | C | I | I |
| G3050u1 | WIAF-12860 | HT1558 | 2098 | FSRG1: female sterile homeotic-related gene 1 (mouse homolog) | AACATTGCAA[T/C]GGCATTTTGA | S | T | C | N | N |
| G3050u2 | WIAF-12861 | HT1558 | 2845 | FSRG1: female sterile homeotic-related gene 1 (mouse homolog) | TAGGCCCTTC[T/C]GGCTTTGGAC | S | T | C | S | S |
| G3050u3 | WIAF-12862 | HT1558 | 3409 | FSRG1: female sterile homeotic-related gene 1 (mouse homolog) | CCTCGTCGTC[G/A]TCTTCAGACA | S | G | A | S | S |
| G3050u4 | WIAF-12874 | HT1558 | 1699 | FSRG1: female sterile homeotic-related gene 1 (mouse homolog) | TCTCTTCTGT[G/C]TCACACACAG | S | G | C | V | V |
| G3050u5 | WIAF-12878 | HT1558 | 2093 | FSRG1: female sterile homeotic-related gene 1 (mouse homolog) | GTTAAAACAT[T/G]GCAATGGCAT | M | T | G | C | G |
| G3050u6 | WIAF-12879 | HT1558 | 2746 | FSRG1: female sterile homeotic-related gene 1 (mouse homolog) | CTGGGGCCGA[C/T]GAAGATGACA | S | C | T | D | D |
| G3051u1 | WIAF-12866 | HT1569 | 1423 | MEF2B, MADS box transcription enhancer factor 2, polypeptide B (myocyte enhancer factor 2B) | CTTGGCCGAC[G/A]GCTGGCCCCG | S | G | A | T | T |
| G3051u2 | WIAF-13022 | HT1569 | 661 | MEF2B, MADS box transcription enhancer factor 2, polypeptide B (myocyte enhancer factor 2B) | CAGAGTACAG[C/T]GAGCCCCACG | S | C | T | S | S |
| G3057a1 | WIAF-12142 | HT1669 | 5565 | alpha-fetoprotein enhancer-binding protein | AGACTGCTCT[T/C]GAGGCTCATA | S | T | C | L | L |
| G3057a2 | WIAF-12143 | HT1669 | 5634 | alpha-fetoprotein enhancer-binding protein | CTCTGTCTGC[G/A]ATGCTCTTAG | S | G | A | A | A |
| G3057a3 | WIAF-12144 | HT1669 | 5664 | alpha-fetoprotein enhancer-binding protein | GGGGACTCCA[G/T]ATGAAAGGAG | M | G | T | Q | H |
| G3057a4 | WIAF-12145 | HT1669 | 5703 | alpha-fetoprotein enhancer-binding protein | GCTTTTCCCA[C/T]CTACCCCCAA | S | C | T | H | H |
| G3057u5 | WIAF-12885 | HT1669 | 2227 | alpha-fetoprotein enhancer-binding protein | TCTGGAGATC[C/T]ATATGAGGTC | M | C | T | H | Y |
| G3057u6 | WIAF-12892 | HT1669 | 3720 | alpha-fetoprotein enhancer-binding protein | AGACCTTGCC[G/A]GCTCAGCTAC | S | G | A | P | P |
| G3057u7 | WIAF-12893 | HT1669 | 4137 | alpha-fetoprotein enhancer-binding protein | CAAGGTTTAC[G/A]GACTACCAGC | S | G | A | T | T |
| G3057u8 | WIAF-12897 | HT1669 | 4783 | alpha-fetoprotein enhancer-binding protein | GAAGACCAAC[A/C]CTCCCCAGCA | M | A | C | T | P |
| G3057u9 | WIAF-12898 | HT1669 | 5215 | alpha-fetoprotein enhancer-binding protein | TCCAACCTCC[A/C]CAATGAACAC | M | A | C | T | P |
| G3057u10 | WIAF-12904 | HT1669 | 7266 | alpha-fetoprotein enhancer-binding protein | CCCTGCAGGC[C/T]GCCTTGACTT | S | C | T | A | A |
| G3057u11 | WIAF-12907 | HT1669 | 8345 | alpha-fetoprotein enhancer-binding protein | CCAAACAGAC[A/C]CTATTCGGAG | M | A | C | D | A |
| G3057u12 | WIAF-12943 | HT1669 | 4257 | alpha-fetoprotein enhancer-binding protein | TGGTGTGGTT[T/C]CAGAATGCCC | S | T | C | F | F |
| G3057u13 | WIAF-12951 | HT1669 | 7333 | alpha-fetoprotein enhancer-binding protein | ACCAGGCTTT[T/A]CTCCTTATTA | M | T | A | S | T |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G3057u14 | WIAF-13030 | HT1669 | 303 | alpha-fetoprotein enhancer-binding protein | GCAGCCTGTC[G/A]GAGGACGAGT | S | G | A | S | S |
| G3057u15 | WIAF-13031 | HT1669 | 777 | alpha-fetoprotein enhancer-binding protein | GCCTTCCAGA[G/A]GAGGACGAGG | S | G | A | E | E |
| G306u1 | WIAF-10118 | HT0040 | 1618 | CPT2, carnitine palmitoyltransferase II | CTCTACTGCC[G/A]TCCACTTTGA | M | G | A | V | I |
| G307u1 | WIAF-10076 | HT0114 | 110 | EDN2, endothelin 2 | CGTTGGCCTA[G/A]CCCTGCTCGT | M | G | A | A | T |
| G3070u1 | WIAF-12972 | HT2085 | 625 | pre-B-cell leukemia transcription factor 3 | AGAAATATGA[A/G]CAGGCATGTA | S | A | G | E | E |
| G3070u2 | WIAF-12973 | HT2085 | 841 | pre-B-cell leukemia transcription factor 3 | GTAACTTCAG[T/C]AAACAGGCCA | S | T | C | S | S |
| G3071u1 | WIAF-12886 | HT2086 | 995 | AGER, advanced glycosylation end product-specific receptor | CCTGCGAGGC[T/C]GTGATGATCC | S | T | C | A | A |
| G3071u2 | WIAF-12887 | HT2086 | 1475 | AGER, advanced glycosylation end product-specific receptor | GAGGCCAGAT[C/G]TACAGCCCAC | M | C | G | I | M |
| G3071u3 | WIAF-12935 | HT2086 | 933 | AGER, advanced glycosylation end product-specific receptor | ACGCATGGTG[A/G]GCATCATCCA | M | A | G | S | G |
| G3071u4 | WIAF-12936 | HT2086 | 1052 | AGER, advanced glycosylation end product-specific receptor | GTAACTTCAG[C/T]AAACAGGCCA | S | C | T | S | S |
| G3071u5 | WIAF-12937 | HT2086 | 836 | AGER, advanced glycosylation end product-specific receptor | AGAAGTATGA[G/A]CAGGCATGTA | S | G | A | E | E |
| G308u1 | WIAF-10094 | HT0192 | 484 | ANX4, annexin IV (placental anticoagulant protein II) | ATGGACGGAG[C/G]CTTGAAGATG | M | C | G | S | R |
| G308u2 | WIAF-10095 | HT0192 | 333 | ANX4, annexin IV (placental anticoagulant protein II) | GGGATGATGA[C/T]GCCCACGGTG | M | C | T | T | M |
| G3081u1 | WIAF-12997 | HT2188 | 689 | PSMC2, proteasome (prosome, macropain) 26S subunit, ATPase, 2 | GGCATTGAGC[C/T]TCCCAAGGGC | S | C | T | P | L |
| G3083u1 | WIAF-12976 | HT2228 | 106 | IGHMBP2, immunoglobulin mu binding protein 2 | TGCTGGAGCT[T/C]GAGAGAGACG | S | T | C | L | L |
| G3083u2 | WIAF-12985 | HT2228 | 2260 | IGHMBP2, immunoglobulin mu binding protein 2 | TGGAGTTCAT[G/C]GCCAGCAAGA | M | G | C | M | I |
| G3083u3 | WIAF-12986 | HT2228 | 2060 | IGHMBP2, immunoglobulin mu binding protein 2 | GGGACCTGCT[A/G]CGTCCACCAG | M | A | G | T | A |
| G3083u4 | WIAF-12987 | HT2228 | 2365 | IGHMBP2, immunoglobulin mu binding protein 2 | ACGACAGTTC[C/T]GGGGAAGGGA | S | C | T | S | S |
| G3083u5 | WIAF-13005 | HT2228 | 411 | IGHMBP2, immunoglobulin mu binding protein 2 | TTTGATGAGT[C/T]CCACGATTTC | M | C | T | S | F |
| G3083u6 | WIAF-13006 | HT2228 | 272 | IGHMBP2, immunoglobulin mu binding protein 2 | ATACGGGTCC[G/A]CGGCAGCTCT | M | G | A | A | T |
| G3083u7 | WIAF-13010 | HT2228 | 2581 | IGHMBP2, immunoglobulin mu binding protein 2 | TCAGGACCGC[G/A]CAGGGGCAGC | M | G | A | A | A |
| G3083u8 | WIAF-13011 | HT2228 | 2594 | IGHMBP2, immunoglobulin mu binding protein 2 | GGGGCAGCCC[G/A]CCAGCAAGGA | M | G | A | A | T |
| G3088u1 | WIAF-12984 | HT2318 | 884 | HIVEP1, human immunodeficiency virus type I enhancer-binding protein 1 | TGTGGCACTA[C/T]GTCCCCTTCC | S | C | T | T | M |
| G3088u2 | WIAF-12988 | HT2318 | 2469 | HIVEP1, human immunodeficiency virus type I enhancer-binding protein 1 | TCTTGTCACC[A/G]CGTCAAACC | S | A | G | P | P |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G3088u3 | WIAF-12989 | HT2318 | 3066 | HIVEP1, human immunodeficiency virus type I enhancer-binding protein 1 | TTCTTGGTAC[T/C]GGACAGTCCC | S | T | C | T | T |
| G3088u4 | WIAF-12991 | HT2318 | 4008 | HIVEP1, human immunodeficiency virus type I enhancer-binding protein 1 | TTATCCGGCA[G/T]CACAACATCC | M | G | T | Q | H |
| G3088u5 | WIAF-12992 | HT2318 | 4880 | HIVEP1, human immunodeficiency virus type I enhancer-binding protein 1 | CAAATCCATG[C/G]ACCGCCTAGC | M | C | G | A | G |
| G3088u6 | WIAF-12993 | HT2318 | 5148 | HIVEP1, human immunodeficiency virus type I enhancer-binding protein 1 | TTGACACGCAT[G/A]TCTAATTCGC | M | G | A | M | I |
| G3088u7 | WIAF-12999 | HT2318 | 5834 | HIVEP1, human immunodeficiency virus type I enhancer-binding protein 1 | CCAGCTGATA[A/G]TTCATCAACA | M | A | G | N | S |
| G3088u8 | WIAF-13000 | HT2318 | 6065 | HIVEP1, human immunodeficiency virus type I enhancer-binding protein 1 | CAAAGTCAAC[G/A]GCCAGTCACT | M | G | A | R | Q |
| G3088u9 | WIAF-13001 | HT2318 | 7652 | HIVEP1, human immunodeficiency virus type I enhancer-binding protein 1 | CATAGGAATA[C/T]GGTCACAGAA | M | C | T | T | M |
| G3088u10 | WIAF-13008 | HT2318 | 741 | HIVEP1, human immunodeficiency virus type I enhancer-binding protein 1 | TTCTGCAGCA[A/G]CCATCTGAAC | S | A | G | Q | Q |
| G3088u11 | WIAF-13009 | HT2318 | 948 | HIVEP1, human immunodeficiency virus type I enhancer-binding protein 1 | CAGAACTGAG[C/T]ACCTTGTCAC | S | C | T | S | S |
| G3088u12 | WIAF-13012 | HT2318 | 1909 | HIVEP1, human immunodeficiency virus type I enhancer-binding protein 1 | TGAAACTTTA[C/T]TAAAATCAAG | S | C | T | L | L |
| G3088u13 | WIAF-13013 | HT2318 | 2803 | HIVEP1, human immunodeficiency virus type I enhancer-binding protein 1 | TCTTCTGTCT[G/A]TACCTTCACT | M | G | A | V | I |
| G3088u14 | WIAF-13015 | HT2318 | 3342 | HIVEP1, human immunodeficiency virus type I enhancer-binding protein 1 | GCGGTCTGCA[A/G]CCTCAGATTC | S | A | G | Q | Q |
| G3088u15 | WIAF-13016 | HT2318 | 3542 | HIVEP1, human immunodeficiency virus type I enhancer-binding protein 1 | CCTAAACATA[G/A]TGTTACCATA | M | G | A | S | N |
| G3088u16 | WIAF-13017 | HT2318 | 4972 | HIVEP1, human immunodeficiency virus type I enhancer-binding protein 1 | TGGGTCTTCT[A/G]AAAGTGAGGA | M | A | G | K | E |
| G3095u1 | WIAF-12994 | HT2435 | 701 | TCF2, transcription factor 2, hepatic; LF-B3; variant hepatic nuclear factor | CCGCTCTGTA[C/T]ACCTGGTACG | S | C | T | Y | Y |
| G3095u2 | WIAF-13018 | HT2435 | 362 | TCF2, transcription factor 2, hepatic; LF-B3; variant hepatic nuclear factor | GGGCCGAGCC[C/T]GACACCAAGC | S | C | T | P | P |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G3095u3 | WIAF-13020 | HT2435 | 1620 | TCF2, transcription factor 2, hepatic; LF-B3; variant hepatic nuclear factor | CCAGTCTCC[C/T]AGCAGCTGCA | N | C | T | Q | * |
| G3100a1 | WIAF-12147 | HT2483 | 526 | ZNF141, zinc finger protein 141 (clone pHZ-44) | GAATGAGTGT[A/G]AGTTGCAGAA | M | A | G | K | E |
| G3102u1 | WIAF-12975 | HT2508 | 259 | NRF1, nuclear respiratory factor 1 | CGCCTTCTTC[G/T]CCCGAGGACA | S | G | T | S | S |
| G3103u1 | WIAF-13617 | HT2511 | 1106 | E2F2, E2F transcription factor 2 | CCTTGGACCA[G/T]CTCATCCAGA | M | G | T | Q | H |
| G3103u2 | WIAF-13659 | HT2511 | 1154 | E2F2, E2F transcription factor 2 | CTGAGACAA[G/A]GCCAACAAGA | S | G | A | K | K |
| G311u1 | WIAF-10291 | HT0402 | 1339 | A2M, alpha-2-macroglobulin | GTCCCTGTTA[C/T]GGCTACCAGT | S | C | T | Y | Y |
| G311u2 | WIAF-10292 | HT0402 | 1201 | A2M, alpha-2-macroglobulin | TCATATTCAT[C/T]AGAGAAATG | S | C | T | H | H |
| G311u3 | WIAF-10293 | HT0402 | 3041 | A2M, alpha-2-macroglobulin | TACTCCAGAG[G/A]TCAAGTCCAA | M | G | A | V | I |
| G311u4 | WIAF-10294 | HT0402 | 3676 | A2M, alpha-2-macroglobulin | TGACATCCTA[T/C]GTGCTCCTCG | S | T | C | Y | Y |
| G311u5 | WIAF-10296 | HT0402 | 3364 | A2M, alpha-2-macroglobulin | ATATCACCAT[C/T]GCCCTTCTGG | S | C | T | H | H |
| G311u6 | WIAF-10297 | HT0402 | 3203 | A2M, alpha-2-macroglobulin | CCAAGCTCGA[C/T]CCTACATCTT | M | G | T | A | S |
| G311a7 | WIAF-10494 | HT0402 | 1122 | A2M, alpha-2-macroglobulin | TCACACTTTC[G/A]ACAGGAATT | M | G | A | R | Q |
| G3119u1 | WIAF-13947 | HT2654 | 2876 | GLI, glioma-associated oncogene homolog (zinc finger protein) | TTTCTGGGGG[G/A]TTCCCAGTT | S | G | A | G | D |
| G3119u2 | WIAF-13959 | HT2654 | 654 | GLI, glioma-associated oncogene homolog (zinc finger protein) | AGTGCCGGGA[G/A]GAACCCTTGG | S | G | A | E | E |
| G3119u3 | WIAF-13965 | HT2654 | 3376 | GLI, glioma-associated oncogene homolog (zinc finger protein) | TGGGGAAACA[G/C]AATTCCTCAA | M | G | C | E | Q |
| G312u1 | WIAF-10006 | HT0428 | 898 | PLAU, plasminogen activator, urokinase | CTCACCACAA[C/T]GACATTGCCT | S | C | T | N | N |
| G312u2 | WIAF-10029 | HT0428 | 498 | PLAU, plasminogen activator, urokinase | GGCCTAAAGC[C/T]GCTTGTCCAA | M | C | T | P | L |
| G312a3 | WIAF-10521 | HT0428 | 767 | PLAU, plasminogen activator, urokinase | TGATTACCCA[A/C]AGAAGGAGGA | M | A | C | K | Q |
| G3125u1 | WIAF-13675 | HT2674 | 740 | GTF2F2, general transcription factor IIF, polypeptide 2 (30 kD subunit) | ACATCACAAA[A/G]CAACCTGTGG | S | A | G | K | K |
| G313u1 | WIAF-10129 | HT0462 | 3086 | platelet-derived growth factor, alpha polypeptide (GB:M21574) | CATGCGTGTG[G/A]ACTCAGACAA | M | G | A | D | N |
| G313u2 | WIAF-10130 | HT0462 | 1078 | platelet-derived growth factor, alpha polypeptide (GB:M21574) | ATGAGAAAGG[T/G]TTCATTGAAA | S | T | G | G | G |
| G313u3 | WIAF-10133 | HT0462 | 1571 | platelet-derived growth factor, alpha polypeptide (GB:M21574) | GGAGATCCAC[T/C]CCCGAGACAG | M | T | C | S | P |
| G313u4 | WIAF-10135 | HT0462 | 2611 | platelet-derived growth factor, alpha polypeptide (GB:M21574) | CTCGCAACGT[C/T]CTCCTGGCAC | S | C | T | V | V |
| G314u1 | WIAF-10069 | HT0467 | 1890 | ALOX15, arachidonate 15-lipoxygenase | TCAGGAGGA[G/A]CTGGCTGCC | S | G | A | E | E |
| G3141u1 | WIAF-13934 | HT27498 | 878 | NFATC3, nuclear factor of activated T-cells, cytoplasmic 3 | CCAGAGGATA[G/A]CTGGCTACTC | M | G | A | S | N |
| G3141u2 | WIAF-13936 | HT27498 | 1189 | NFATC3, nuclear factor of activated T-cells, cytoplasmic 3 | GCCTGCCTCA[T/C]GCAATGGGAA | S | T | C | C | R |
| G3141u3 | WIAF-13938 | HT27498 | 2241 | NFATC3, nuclear factor of activated T-cells, cytoplasmic 3 | CTCTGCGGGG[T/C]TTCCCTTCAG | S | T | C | G | G |
| G3141u4 | WIAF-13944 | HT27498 | 702 | NFATC3, nuclear factor of activated T-cells, cytoplasmic 3 | ATGCCTCTGA[C/T]GAGGCAGCCC | S | C | T | D | D |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G3159u1 | WIAF-13891 | HT2757 | 523 | SP4, Sp4 transcription factor | CTTCAAAGA[G/A]AATAACGTTT | S | G | A | E | E |
| G3159u2 | WIAF-13892 | HT2757 | 1514 | SP4, Sp4 transcription factor | ACAGAATGTT[C/T]AACTTCAAGC | N | C | T | Q | * |
| G3159u3 | WIAF-13893 | HT2757 | 2236 | SP4, Sp4 transcription factor | TGTTTTGTGG[C/T]TAAAAGATTCA | S | C | T | G | G |
| G3165u1 | WIAF-13860 | HT27636 | 437 | transcription factor B-ATF | AGCAGCTCAC[A/G]GAGGAACTGA | S | A | G | T | T |
| G3165u2 | WIAF-13861 | HT27636 | 512 | transcription factor B-ATF | CCAGCACGCC[C/G]TCGCCCCCG | S | C | G | P | P |
| G3173u1 | WIAF-13556 | HT2772 | 1686 | ZNF74, zinc finger protein 74 (Cos52) | TGCACAGCGA[G/A]GGGAAGCCCT | S | G | A | E | E |
| G3175u1 | WIAF-13948 | HT2776 | 2037 | transcriptional regulator, via glucocorticoid receptor | TGTTCGGACC[A/G]GAAGCACCCA | S | A | G | P | P |
| G3182u1 | WIAF-14036 | HT2783 | 1614 | MHC2TA, MHC class II transactivator | ATCCTAGACG[C/G]CTTCGAGGAG | M | C | G | A | G |
| G3182u2 | WIAF-14037 | HT2783 | 2791 | MHC2TA, MHC class II transactivator | TGAGCGACAC[G/A]GTGCGCTGT | S | G | A | T | T |
| G3182u3 | WIAF-14059 | HT2783 | 1657 | MHC2TA, MHC class II transactivator | TGCACACCAC[G/A]TGCGGACCGG | S | G | A | T | T |
| G3182u4 | WIAF-14060 | HT2783 | 1606 | MHC2TA, MHC class II transactivator | TTCTGCTCAT[C/T]CTAGACGCCT | S | C | T | I | I |
| G3183u1 | WIAF-13950 | HT27861 | 392 | zinc finger protein C2H2-150 | TACTCTAGAG[G/A]AGCCTGTTGG | M | G | A | E | K |
| G3184u1 | WIAF-13864 | HT27862 | 271 | zinc finger protein C2H2-171 | GAAACTCCAG[T/G]TCAAAGACTT | M | T | G | F | V |
| G3184u2 | WIAF-13865 | HT27862 | 248 | zinc finger protein C2H2-171 | CTGCTTGAAT[T/C]CATGTATGAR | M | T | C | F | S |
| G3320u1 | WIAF-10136 | HT0791 | 552 | ANX7, annexin VII (synexin) | CCAACTTCGA[T/C]GCTATAAGAG | S | T | C | D | D |
| G3320u2 | WIAF-10137 | HT0791 | 1350 | ANX7, annexin VII (synexin) | TTGACCTTGT[A/G]CAAATAAAAC | S | A | G | V | V |
| G3208u1 | WIAF-14186 | HT27930 | 485 | zinc finger protein ZNF37A | GTCGAAAGTC[A/G]GCCCTAATTG | S | A | G | S | S |
| G3218u1 | WIAF-13526 | HT28104 | 187 | zinc finger protein ZNF169, Krueppel-type | CCCGACAGCTC[C/T]ATTAAGAAAG | M | C | T | H | Y |
| G3323u1 | WIAF-10066 | HT0915 | 1361 | Homo sapiens inducible nitric oxide synthase (NOS) mRNA, complete cds. | ACTTCTGTGA[C/T]GTCCAGCGCT | S | C | T | D | D |
| G3325u1 | WIAF-10106 | HT0962 | 3817 | FBN1, fibrillin 1 (Marfan syndrome) | TGTGAATGCC[C/T]GCCTGGCCAT | S | C | T | P | L |
| G3325u2 | WIAF-10113 | HT0962 | 722 | FBN1, fibrillin 1 (Marfan syndrome) | AGATAGCTCC[T/G]TCCTGTGCT | S | T | G | P | P |
| G3325u3 | WIAF-10114 | HT0962 | 2022 | FBN1, fibrillin 1 (Marfan syndrome) | GATCTGCAAT[A/C]ATGGACGCTG | M | A | C | N | H |
| G3325u4 | WIAF-10116 | HT0962 | 3603 | FBN1, fibrillin 1 (Marfan syndrome) | GAACTGCACA[G/C]ACATTGACGA | M | G | C | D | H |
| G3325u5 | WIAF-10117 | HT0962 | 2270 | FBN1, fibrillin 1 (Marfan syndrome) | TCTGCATGAA[C/T]GGGCGTTGCG | S | C | T | N | N |
| G3326u1 | WIAF-10036 | HT1009 | 1854 | KLKB1, kallikrein B plasma, (Fletcher factor) 1 | GCAAACACAA[C/T]GGAATGTGGC | S | C | T | N | N |
| G3327u1 | WIAF-10052 | HT1011 | 1599 | HRG, histidine-rich glycoprotein | AAGCCAGACA[A/T]TCAGCCCTTT | M | A | T | N | I |
| G3327u2 | WIAF-10054 | HT1011 | 1083 | HRG, histidine-rich glycoprotein | CCACTATTGC[C/T]CATGTCCTGC | M | C | T | P | L |
| G3327u3 | WIAF-10055 | HT1011 | 1140 | HRG, histidine-rich glycoprotein | GCCCAAAGCA[A/G]TTCATAAT | M | A | G | H | R |
| G3328u1 | WIAF-10145 | HT1087 | 255 | SAA1, serum amyloid A1 | GTGCCTGGGC[T/C]GCAAGTGA | M | T | C | A | A |
| G3328a2 | WIAF-10511 | HT1087 | 248 | SAA1, serum amyloid A1 | CCTGGGGGTG[C/T]TCTGGCTCA | M | C | T | A | V |
| G3328a3 | WIAF-10512 | HT1087 | 305 | SAA1, serum amyloid A1 | TTCTTTGGCC[A/G]TGGTGCGAG | M | A | G | H | R |
| G3328a4 | WIAF-13126 | HT1087 | 295 | SAA1, serum amyloid A1 | TATCCAGAGA[T/C]TCTTTGGCCA | M | T | C | F | L |
| G3328a5 | WIAF-13127 | HT1087 | 82 | SAA1, serum amyloid A1 | CTTGGTCCTG[G/A]GTGTCAGCAG | M | G | A | G | S |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G329u1 | WIAF-10140 | HT1141 | 2514 | PLCG1, phospholipase C, gamma 1 (formerly subtype 148) | CTGACCTTCA[T/C]CAAGAGCCCA | M | T | C | I | T |
| G329u2 | WIAF-10162 | HT1141 | 1036 | PLCG1, phospholipase C, gamma 1 (formerly subtype 148) | TATGCCCGGA[C/A]ACCATGAACA | M | C | A | D | E |
| G329u3 | WIAF-10163 | HT1141 | 911 | PLCG1, phospholipase C, gamma 1 (formerly subtype 148) | GTTCATGCTC[A/G]GCTTCCTCCG | M | A | G | S | G |
| G3295u1 | WIAF-14017 | HT3460 | 1229 | FUBP, far upstream element binding protein | CCATAAAAAG[C/T]ATAAGCCAGC | S | C | T | S | S |
| G3296u1 | WIAF-14168 | HT3466 | 6289 | transcription factor TFIIIC, RNA polymerase III, alpha subunit | CAGCCTGGAC[G/A]AGAGCCCCAT | M | G | A | E | K |
| G3296u2 | WIAF-14179 | HT3466 | 235 | transcription factor TFIIIC, RNA polymerase III, alpha subunit | GGGCATCAGC[T/A]TCTATGAGGA | M | T | A | F | I |
| G3298u1 | WIAF-13523 | HT3504 | 1803 | DNA-binding protein HRFX2 | ACTTTGCCAA[C/T]GTGCAGAGC | S | C | T | N | N |
| G3298u2 | WIAF-13524 | HT3504 | 1743 | DNA-binding protein HRFX2 | GGGCGGTGCT[G/A]CAGAACAGT | S | G | A | L | L |
| G3298u3 | WIAF-13528 | HT3504 | 2002 | DNA-binding protein HRFX2 | GTTCTTGCTG[A/G]AATGGTCCTT | M | A | G | K | E |
| G33u1 | WIAF-10254 | X82540 | 1044 | INHBC, inhibin, beta C | AAGGCCAACA[C/T]AGCTGCAGGC | M | C | T | T | I |
| G33u2 | WIAF-10255 | X82540 | 1136 | INHBC, inhibin, beta C | CAGCAACATT[G/A]TCAAGACTGA | M | G | A | V | I |
| G33u3 | WIAF-10256 | X82540 | 1185 | INHBC, inhibin, beta C | GGGTGCAGTT[A/G]GTCTATGTGT | N | G | A | V | V |
| G33u4 | WIAF-10259 | X82540 | 892 | INHBC, inhibin, beta C | TTTTTGTGGA[C/T]TTTCCTGAGA | S | C | T | * | W |
| G3303u1 | WIAF-13566 | HT3523 | 981 | POU6F1, POU domain, class 6, transcription factor 1 | CAGGCCAGGA[G/A]ATCACTGAAA | S | G | A | D | D |
| G3304u1 | WIAF-13932 | HT3544 | 970 | SP2, Sp2 transcription factor | TCAAACAACCT[C/T]GTGAACCCA | S | C | T | L | L |
| G3304u2 | WIAF-13935 | HT3544 | 1891 | SP2, Sp2 transcription factor | AGAAGCACGT[T/G]TGCCACATCC | S | T | G | V | V |
| G3304u3 | WIAF-13943 | HT3544 | 920 | SP2, Sp2 transcription factor | TGTGGTGAAG[T/C]TGACAGGTGG | S | T | C | L | L |
| G3311u1 | WIAF-13839 | HT3585 | 757 | GATA3, GATA-binding protein 3 | CCCACTCCCG[T/C]GGCAGCATGA | S | T | C | R | R |
| G3311u2 | WIAF-13840 | HT3585 | 901 | GATA3, GATA-binding protein 3 | TCGATGCAAG[G/A]TCCAGGCCCA | S | G | A | K | K |
| G3316u1 | WIAF-13818 | HT3607 | 282 | zinc finger protein HKE-T1, Kruppel-like | AAAGAGTTTC[A/G]GTCAGAGTTC | M | A | G | S | G |
| G3319u1 | WIAF-14214 | HT3613 | 1086 | SMARCA3, SWI/SNF related, matrix associated, actin dependent regulator of chromatin, subfamily a, member 3 | AAACTCTTAC[A/G]GCCATTGCAG | S | A | G | T | T |
| G3319u2 | WIAF-14221 | HT3613 | 1261 | SMARCA3, SWI/SNF related, matrix associated, actin dependent regulator of chromatin, subfamily a, member 3 | TAGATGTAGT[G/C]AACAACCCAG | M | G | C | E | Q |
| G3320u1 | WIAF-13692 | HT3622 | 624 | BCL6, B-cell CLL/lymphoma 6 (zinc finger protein 51) | ATTTGCGGGA[G/C]GGCAACATCA | M | G | C | E | D |
| G3320u2 | WIAF-13717 | HT3622 | 1062 | BCL6, B-cell CLL/lymphoma 6 (zinc finger protein 51) | ACAGCCGGCC[G/A]ACTTTGGAGG | S | G | A | P | P |
| G3321u1 | WIAF-13761 | HT3641 | 235 | STAT2, signal transducer and activator of transcription 2, 113 kD | TCTTGGATCA[G/C]CTGAACTATG | M | G | C | Q | H |
| G3321u2 | WIAF-13762 | HT3641 | 774 | STAT2, signal transducer and activator of transcription 2, 113 kD | CAAAAAGCCT[G/C]CATCAGAGCT | M | G | C | C | S |
| G3328u1 | WIAF-13543 | HT3681 | 1550 | transcription factor znf6 | CCACAATGGT[A/G]TCAGAGGAGG | S | A | G | V | V |
| G3328u2 | WIAF-13544 | HT3681 | 1389 | transcription factor znf6 | AGAGGATTTA[G/C]AGGAAGATGA | M | G | C | E | Q |
| G3336u1 | WIAF-13848 | HT3732 | 216 | XBP1, X-box binding protein 1 | ACCTGAGCCC[C/T]GAGGAGAGG | S | C | T | P | P |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G334u1 | WIAF-10008 | HT1220 | 893 | THBS1, thrombospondin 1 | TACATTGGCC[A/C]CAAGACAAAG | M | A | C | H | P |
| G334u2 | WIAF-10009 | HT1220 | 2000 | THBS1, thrombospondin 1 | TCACAGCCCT[T/C]CGGCCAGGGT | M | T | C | F | S |
| G334u3 | WIAF-10016 | HT1220 | 1521 | THBS1, thrombospondin 1 | CCCAGATGAA[T/C]GGGAAACCCT | S | T | C | N | N |
| G334u4 | WIAF-10017 | HT1220 | 2210 | THBS1, thrombospondin 1 | GGCTGGCCCA[A/G]TGAGAACCTG | M | A | G | N | S |
| G334u5 | WIAF-10018 | HT1220 | 2979 | THBS1, thrombospondin 1 | GTGAGACCGA[T/C]TTCCGCCGAT | S | T | C | D | D |
| G334u6 | WIAF-10033 | HT1220 | 1136 | THBS1, thrombospondin 1 | TGTCACTGTC[A/G]GAACTCAGTT | M | A | G | Q | R |
| G334u7 | WIAF-10034 | HT1220 | 1859 | THBS1, thrombospondin 1 | AGTGGAAATG[G/A]CATCCAGTGC | M | G | A | G | D |
| G3343u1 | WIAF-13545 | HT3770 | 1104 | ZNF76, zinc finger protein 76 (expressed in testis) | GCAGTGCCCA[C/T]GGGCAGCTGG | S | C | T | H | H |
| G3343u2 | WIAF-13561 | HT3770 | 425 | ZNF76, zinc finger protein 76 (expressed in testis) | GAGCAGTATG[C/A]CAGCAAGGTT | M | C | A | A | D |
| G3343u3 | WIAF-13562 | HT3770 | 143 | ZNF76, zinc finger protein 76 (expressed in testis) | CACCAGTGA[C/T]GGTACAGAAA | M | C | T | T | M |
| G3343u4 | WIAF-13563 | HT3770 | 646 | ZNF76, zinc finger protein 76 (expressed in testis) | GAAGAGCCAC[G/T]TTCGTACCCA | M | G | T | V | F |
| G3343u5 | WIAF-13564 | HT3770 | 611 | ZNF76, zinc finger protein 76 (expressed in testis) | AGCTGTGGAA[A/G]GGCCTTTGCC | M | A | G | K | R |
| G3344u1 | WIAF-13664 | HT3772 | 925 | zinc finger protein MAZ | AGCTGTCGCA[C/T]TTCCACAGA | S | C | T | H | H |
| G3345u1 | WIAF-13508 | HT3823 | 315 | TCF6L1, transcription factor 6-like 1 (mitochondrial transcription factor 1-like) | TTCGATTTTC[T/C]AAAGAACAAC | S | T | C | S | S |
| G3345u2 | WIAF-13509 | HT3823 | 167 | TCF6L1, transcription factor 6-like 1 (mitochondrial transcription factor 1-like) | GGCGTGCTGA[G/C]TGCCCTGGGA | M | G | C | S | T |
| G3345u3 | WIAF-13531 | HT3823 | 625 | TCF6L1, transcription factor 6-like 1 (mitochondrial transcription factor 1-like) | TTATAACGTT[T/G]GATGTAGCTGA | M | T | G | Y | D |
| G3352u1 | WIAF-13589 | HT4005 | 1190 | MITF, microphthalmia-associated transcription factor | CTCGGAACTG[G/A]GACTGAGGCC | M | G | A | G | E |
| G3352u2 | WIAF-13604 | HT4005 | 1156 | MITF, microphthalmia-associated transcription factor | TCTCACGGAT[G/A]GCACCATCAC | M | G | A | G | S |
| G3353u1 | WIAF-13937 | HT4010 | 360 | GTF2H3, general transcription factor IIH, polypeptide 3 (34 kD subunit) | ATCTAATGAC[C/A]AAAAGTGACA | S | C | A | T | T |
| G3358u1 | WIAF-13671 | HT4187 | 398 | ETV5, ets variant gene 5 (ets-related molecule) | GATGATGAAC[A/G]GTTTGTCCCA | M | A | G | Q | R |
| G3358u2 | WIAF-13672 | HT4187 | 223 | ETV5, ets variant gene 5 (ets-related molecule) | TCAGCAAGTC[C/T]CTTTTATGGT | S | C | T | P | S |
| G3358u3 | WIAF-13673 | HT4187 | 1236 | ETV5, ets variant gene 5 (ets-related molecule) | GACTGGAAGG[C/G]AAAGTCAAAC | S | C | G | G | G |
| G3358u4 | WIAF-13674 | HT4187 | 1678 | ETV5, ets variant gene 5 (ets-related molecule) | TTACCTCCTG[G/A]ACATGGACCG | M | G | A | D | N |
| G3358u5 | WIAF-13706 | HT4187 | 414 | ETV5, ets variant gene 5 (ets-related molecule) | TCCCAGATTT[T/C]CAGTCTGATA | S | T | C | F | F |
| G3358u6 | WIAF-13707 | HT4187 | 1238 | ETV5, ets variant gene 5 (ets-related molecule) | CTGGAAGGCA[A/G]AGTCAAACAG | M | A | G | K | R |
| G336u1 | WIAF-10152 | HT1258 | 566 | ACAT1, acetyl-Coenzyme A acetyltransferase 1 (acetoacetyl Coenzyme A thiolase) | AGAGCATGTC[C/A]AATGTTCCAT | S | C | A | S | S |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G3369u1 | WIAF-14047 | HT4302 | 614 | zinc finger protein DB1 | ATCTCAATCG[A/G]CACAAGTCT | S | A | G | R | R |
| G337u1 | WIAF-10268 | HT1259 | 464 | EDNRB, endothelin receptor type B | AAAGGAGACA[G/T]GACGGCAGGA | M | G | T | R | M |
| G337u2 | WIAF-10298 | HT1259 | 1281 | EDNRB, endothelin receptor type B | TGAAGCTCAC[T/A]ACTTTATAATC | M | T | A | T | T |
| G3373u1 | WIAF-14203 | HT4342 | 1253 | MTF1, metal-regulatory transcription factor 1 | CTCAACAGAC[A/G]GCTTCCTTGA | S | A | G | T | T |
| G3390u1 | WIAF-14182 | HT4483 | 680 | ZNF133, zinc finger protein 133 (clone pHZ-13) | AGAGCCAGAG[C/T]TCTACCTCGA | M | C | T | L | F |
| G3390u2 | WIAF-14184 | HT4483 | 1026 | ZNF133, zinc finger protein 133 (clone pHZ-13) | GCTCAGACAG[G/A]GAACCCTGAG | M | G | A | G | E |
| G3390u3 | WIAF-14185 | HT4483 | 1423 | ZNF133, zinc finger protein 133 (clone pHZ-13) | AAAAGCCTTA[T/C]GTGTGCCGGG | S | T | C | Y | Y |
| G3390u4 | WIAF-14197 | HT4483 | 811 | ZNF133, zinc finger protein 133 (clone pHZ-13) | CTGGGGATCC[A/G]GGGCCAGGGG | S | A | G | P | P |
| G3390u5 | WIAF-14198 | HT4483 | 1420 | ZNF133, zinc finger protein 133 (clone pHZ-13) | GGGAAAAGCC[T/G]TATGTGTGCC | S | T | G | P | P |
| G3390u6 | WIAF-14199 | HT4483 | 2143 | ZNF133, zinc finger protein 133 (clone pHZ-13) | CAGCTCTAAT[C/T]ACACACAAGC | S | C | T | I | I |
| G3391u1 | WIAF-13631 | HT4484 | 391 | ZNF136, zinc finger protein 136 (clone pHZ-20) | AGCATTGTAT[A/G]TGGAGAAGTC | M | A | G | Y | C |
| G3396u1 | WIAF-13978 | HT4491 | 1283 | ZNF135, zinc finger protein 135 (clone pHZ-17) | CACAGCTCCT[C/T]GCTCAGCCAG | M | C | T | S | L |
| G3396u2 | WIAF-13979 | HT4491 | 1296 | ZNF135, zinc finger protein 135 (clone pHZ-17) | TCAGCCAGCA[C/T]GAAAGGACGC | S | C | T | H | H |
| G3396u3 | WIAF-13980 | HT4491 | 1028 | ZNF135, zinc finger protein 135 (clone pHZ-17) | AGTCACAGCT[C/T]GTCCCTCACC | S | C | T | S | L |
| G3396u4 | WIAF-13981 | HT4491 | 1057 | ZNF135, zinc finger protein 135 (clone pHZ-17) | GCGAATCCAC[A/G]CTGGGGAGAA | M | A | G | T | A |
| G3396u5 | WIAF-13982 | HT4491 | 1152 | ZNF135, zinc finger protein 135 (clone pHZ-17) | CAGGAGAGAA[A/G]CCCTATGAAT | S | A | G | K | K |
| G3396u6 | WIAF-13983 | HT4491 | 1243 | ZNF135, zinc finger protein 135 (clone pHZ-17) | AAAGCCGTAT[G/C]GGTGCAATGA | M | G | C | G | R |
| G3396u7 | WIAF-13984 | HT4491 | 1045 | ZNF135, zinc finger protein 135 (clone pHZ-17) | CACCAAACAT[C/T]AGCGAATCCA | N | C | T | Q | * |
| G340u1 | WIAF-10139 | HT1386 | 459 | CYP27A1, cytochrome P450, subfamily XXVIIA (steroid 27-hydroxylase, cerebrotendinous xanthomatosis), polypeptide 1 | CCTATGGGCC[G/A]TTCACCACGG | S | G | A | P | P |
| G340u2 | WIAF-10160 | HT1386 | 801 | CYP27A1, cytochrome P450, subfamily XXVIIA (steroid 27-hydroxylase, cerebrotendinous xanthomatosis), polypeptide 1 | TCCCCAAGTG[G/A]ACTCGCCCCG | N | G | A | W | * |
| G341u1 | WIAF-10121 | HT1388 | 912 | MUT, methylmalonyl Coenzyme A mutase | GAGCTGGCCT[A/G]TACTTTAGCA | M | A | G | Y | C |
| G341u2 | WIAF-10128 | HT1388 | 2087 | MUT, methylmalonyl Coenzyme A mutase | TGCTGTGGGC[G/A]TAAGCACCCT | M | G | A | V | I |
| G3410u1 | WIAF-13749 | HT4550 | 1720 | zinc finger homeodomain protein | TGAGTCCTCT[G/T]TTTCATCAGC | M | G | T | V | F |
| G3410u2 | WIAF-13750 | HT4550 | 2843 | zinc finger homeodomain protein | AAACATCATT[T/C]GATTGAACAC | M | T | C | L | S |
| G3410u3 | WIAF-13751 | HT4550 | 2745 | zinc finger homeodomain protein | AGATATTCCA[A/T]AAGAGTAGTT | M | A | T | Q | H |
| G3410u4 | WIAF-13775 | HT4550 | 236 | zinc finger homeodomain protein | AGAGAGGGA[A/C]TGCTAAGAAC | M | A | C | N | T |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G3410u5 | WIAF-13776 | HT4550 | 195 | zinc finger homeodomain protein | TGCCAACAGA[C/T]CAGACAGTGT | S | C | T | D | D |
| G3410u6 | WIAF-13777 | HT4550 | 606 | zinc finger homeodomain protein | ATAACTTTAG[T/C]TGCTCCCTGT | S | T | C | S | S |
| G3410u7 | WIAF-13793 | HT4550 | 2073 | zinc finger homeodomain protein | CAGTTTTACC[A/G]GTGGATCAA | S | A | G | P | P |
| G343u1 | WIAF-10120 | HT1552 | 561 | HK1, hexokinase 1 | CTTGCCAACA[A/G]TCCAAATAG | S | A | G | P | Q |
| G343u2 | WIAF-10124 | HT1552 | 159 | HK1, hexokinase 1 | ACAAGTATCT[G/C]TATGCCATGC | S | G | C | Q | L |
| G348u1 | WIAF-10269 | HT1906 | 2212 | PECAM1, platelet/endothelial cell adhesion molecule (CD31 antigen) | TGACGATGTC[A/G]GAAACCATGC | S | A | G | G | G |
| G348u2 | WIAF-10277 | HT1906 | 1656 | PECAM1, platelet/endothelial cell adhesion molecule (CD31 antigen) | GCCATTCCCA[C/T]GCCAAAATGT | S | C | T | H | H |
| G348u3 | WIAF-10283 | HT1906 | 577 | PECAM1, platelet/endothelial cell adhesion molecule (CD31 antigen) | AGAGTACCAG[C/G]TGTTGGTGA | S | C | G | V | V |
| G348a5 | WIAF-13119 | HT1906 | ? | PECAM1, platelet/endothelial cell adhesion molecule (CD31 antigen) | ATTGTTCCC[C/G] | ? | C | G | | |
| G351u1 | WIAF-10123 | HT1990 | 1047 | OSBP, oxysterol binding protein | TGCTGCAGA[G/A]TCAGATGAAT | S | G | A | E | E |
| G351u2 | WIAF-10132 | HT1990 | 1023 | OSBP, oxysterol binding protein | TGGCCAGC[C/A]AAAGCTGTGA | S | C | A | A | A |
| G355u1 | WIAF-10146 | HT2143 | 1670 | THBS4, thrombospondin 4 | AACTGCCTGA[G/A]TGTCTTAAAT | M | G | A | S | N |
| G355u2 | WIAF-10165 | HT2143 | 1186 | THBS4, thrombospondin 4 | TCGAAATGGA[G/C]CGTGCGTTCC | M | G | C | A | P |
| G355a3 | WIAF-10510 | HT2143 | 1962 | THBS4, thrombospondin 4 | ACTGCCCCAC[C/G]GTCATTAACA | S | C | G | T | T |
| G355a4 | WIAF-13125 | HT2143 | 1963 | THBS4, thrombospondin 4 | CTGCCCCACC[G/a]TCATTAACAG | M | G | a | V | H |
| G3552u1 | WIAF-12701 | HT28101 | 1006 | CLCN2, chloride channel 2 | AAGAGACTAT[T/C]ACAGCCCTCT | S | T | C | H | H |
| G3552u2 | WIAF-12731 | HT28101 | 1823 | CLCN2, chloride channel 2 | CCGCCACCAG[C/T]AGTACCGGGT | S | C | T | Q | * |
| G3552u3 | WIAF-12736 | HT28101 | 2254 | CLCN2, chloride channel 2 | GGAGCCCAGA[G/C]TCCGCAGGCA | M | G | C | E | D |
| G3565u1 | WIAF-12744 | HT2896 | 334 | calcyclin | GCCCTCAAGG[G/A]CTGAAAATAA | M | G | A | G | D |
| G357u1 | WIAF-12267 | HT2244 | 4300 | C4B, complement component 4B | ATGAGTACGA[T/C]GAGCTTCCAG | S | T | C | D | D |
| G357u2 | WIAF-12280 | HT2244 | 5095 | C4B, complement component 4B | TCATGGGTCT[G/A]GATGGGCCA | S | G | A | L | L |
| G357u3 | WIAF-10295 | HT2244 | 2996 | C4B, complement component 4B | CTCAGATCCA[T/C]TGGACACTTT | S | T | C | L | L |
| G359u1 | WIAF-10026 | HT2411 | 936 | PLAT, plasminogen activator, tissue | CGCAGGCTGA[A/G]GTGGAGTAC | M | A | G | T | M |
| G359a2 | WIAF-10520 | HT2411 | 1444 | PLAT, plasminogen activator, tissue | AGGGCCTTGTC[T/C]CCTTTCTATT | S | T | C | S | S |
| G3592u1 | WIAF-12759 | HT4214 | 743 | CLCN4, chloride channel 4 | CTTCTAACGA[G/A]ACCACTTTTG | S | G | A | E | E |
| G3592u2 | WIAF-12761 | HT4214 | 835 | CLCN4, chloride channel 4 | GCTTACATTC[T/G]GAATTACTTA | M | T | G | L | R |
| G361u1 | WIAF-10053 | HT2479 | 857 | cystathionine beta synthase, alt. transcript 1 | TGGCTCACTA[C/T]GACACCACCG | S | C | T | Y | Y |
| G361u2 | WIAF-10056 | HT2479 | 1097 | cystathionine beta synthase, alt. transcript 1 | TCATCCCCAC[G/A]GTCGTGGACA | M | G | A | T | T |
| G362u1 | WIAF-10058 | HT2638 | 223 | ADRB2, adrenergic, beta-2-, receptor, surface | GGCACCCAAT[G/A]GAAGCCATGC | M | G | A | G | R |
| G362u2 | WIAF-10059 | HT2638 | 429 | ADRB2, adrenergic, beta-2-, receptor, surface | TCATGGGCCT[G/A]GCAGTGGTGC | S | G | A | L | L |
| G362u3 | WIAF-10060 | HT2638 | 256 | ADRB2, adrenergic, beta-2-, receptor, surface | CGTCACGCAG[G/C]AAAGGACGA | M | G | C | E | Q |
| G362u4 | WIAF-10093 | HT2638 | 1230 | ADRB2, adrenergic, beta-2-, receptor, surface | AGGGCCTATGG[G/C]AATGGCTACT | S | G | C | G | G |
| G3620u1 | WIAF-12808 | HT97200 | 458 | ACATN, acetyl-Coenzyme A transporter | CACTCTCTGG[A/G]TATGAAGAGC | M | A | G | D | G |
| G3627u1 | WIAF-12820 | HT97387 | 347 | NAPG, N-ethylmaleimide-sensitive factor attachment protein, gamma | GCAGAAACTA[C/T]CAGAGGCCGT | M | C | T | P | S |
| G366u1 | WIAF-10046 | HT2764 | 987 | BDKRB2, bradykinin receptor B2 | GCCTCCTTCA[T/C]GGCCTACAGC | M | T | C | M | T |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G366a2 | WIAF-10500 | HT2764 | 820 | BDKRB2, bradykinin receptor B2 | AGATCCAGAC[G/A]GAGAGGAGGG | S | G | A | T | T |
| G366a3 | WIAF-10501 | HT2764 | 961 | BDKRB2, bradykinin receptor B2 | GCATCATCGA[T/C]GTAATCACAC | S | T | C | D | D |
| G367u1 | WIAF-10156 | HT27685 | 6965 | ACACA, acetyl-Coenzyme A carboxylase alpha | ATCATCCATA[T/C]GACGCAGCAC | N | T | C | * | C |
| G370u1 | WIAF-10281 | HT27888 | 3250 | LEPR, leptin receptor | AAAATTCTCC[G/A]TTGAAGGATT | S | G | A | P | P |
| G370u2 | WIAF-10282 | HT27888 | 3229 | LEPR, leptin receptor | TCACCAAGTG[C/T]TTCTCTAGCA | S | C | T | C | C |
| G370u3 | WIAF-10284 | HT27888 | 1005 | LEPR, leptin receptor | CAATATCAAG[T/C]GAAATATTCA | M | T | C | V | A |
| G370u4 | WIAF-10285 | HT27888 | 1894 | LEPR, leptin receptor | CAGAGAATAA[C/T]CTTCAATTCC | S | C | T | N | N |
| G370u5 | WIAF-10299 | HT27888 | 1222 | LEPR, leptin receptor | TTCTGACAAG[T/C]GTTGGGTCTA | S | T | C | S | S |
| G370u6 | WIAF-10300 | HT27888 | 2161 | LEPR, leptin receptor | CTATGAAAAA[G/C]GAGAAAATG | M | G | C | K | N |
| G371a2 | WIAF-10107 | HT27943 | 349 | CRAT, carnitine acetyltransferase | TCATCTACTC[G/C]ACCCAGGCG | S | G | C | S | S |
| G371a3 | WIAF-12093 | HT27943 | 287 | CRAT, carnitine acetyltransferase | GGAGAACTGG[C/T]TGTCTGAGTG | S | C | T | L | L |
| G372a1 | WIAF-10506 | HT28247 | 1099 | HADHA, hydroxyacyl-Coenzyme A dehydrogenase/3-ketoacyl-Coenzyme A thiolase/enoyl-Coenzyme A hydratase (trifunctional protein), alpha subunit | TGGAGCTCCA[C/A]AGAAGGATGT | M | C | A | Q | K |
| G374u1 | WIAF-10103 | HT28496 | 4435 | FASN, fatty acid synthase | CACCTCCCAC[G/A]TCCGGAGGT | M | G | A | V | I |
| G374u2 | WIAF-10104 | HT28496 | 5996 | FASN, fatty acid synthase | CTGGACAGGG[T/C]GACCCGAGAG | M | T | C | V | A |
| G374u3 | WIAF-10105 | HT28496 | 5644 | FASN, fatty acid synthase | CAAGAGTAC[A/G]TCATCGCTGG | M | A | G | I | V |
| G374u4 | WIAF-10115 | HT28496 | 6387 | FASN, fatty acid synthase | TGGCACACAT[C/T]CTGGGCATCC | S | C | T | H | H |
| G374u5 | WIAF-10119 | HT28496 | 567 | FASN, fatty acid synthase | GGGGCATCAA[C/T]GTCCTGCTGA | S | C | T | N | N |
| G374a6 | WIAF-12094 | HT28496 | 5520 | FASN, fatty acid synthase | ACATGGCCCA[A/G]GGGAAGCACA | S | A | G | Q | Q |
| G377u1 | WIAF-10142 | HT2996 | 929 | PCCB, propionyl Coenzyme A carboxylase, beta polypeptide | GGACCCGCT[T/C]CCCTCCGTGA | M | T | C | S | P |
| G377u2 | WIAF-10143 | HT2996 | 1416 | PCCB, propionyl Coenzyme A carboxylase, beta polypeptide | CACCTTTGTG[G/A]TGATACCAAC | S | G | A | G | D |
| G380u1 | WIAF-10122 | HT3159 | 831 | INSR, insulin receptor | TCTACCTGGA[C/T]TGGCAGGTGTG | S | C | T | D | D |
| G380u2 | WIAF-10126 | HT3159 | 1698 | INSR, insulin receptor | GGCAGGATGC[A/G]TGTGGTTCCA | S | A | G | A | A |
| G380u4 | WIAF-11605 | HT3159 | 2382 | INSR, insulin receptor | GCGTGCCCAC[G/A]AGTCCGAGG | S | G | A | T | T |
| G383u1 | WIAF-10125 | HT33546 | 3633 | phospholipase C, beta 3, alt. transcript 2 | AGCAGCGGGC[G/A]AGGCTCCCCC | M | G | A | R | Q |
| G385u1 | WIAF-10141 | HT3383 | 1505 | PRCP, prolylcarboxypeptidase (angiotensinase C) | ATGACAGTGC[A/G]GGAAAGCAGC | S | A | G | A | A |
| G385u2 | WIAF-10157 | HT3383 | 1360 | PRCP, prolylcarboxypeptidase (angiotensinase C) | ATCACAGACA[C/G]TCTGGTTGCA | M | C | G | T | S |
| G387u1 | WIAF-11729 | HT3439 | 2697 | SREBF2, sterol regulatory element binding transcription factor 2 | CACTCTCCAG[G/C]AGCTCCGTGC | M | G | C | R | S |
| G387u2 | WIAF-11770 | HT3439 | 1901 | SREBF2, sterol regulatory element binding transcription factor 2 | GCTGCTGCCG[C/G]CAACCTACAA | M | C | G | A | G |
| G388u1 | WIAF-10270 | HT3440 | 245 | SELPLG, selectin P ligand | CTCCAGAAAT[G/A]CTGAGGAACA | M | G | A | M | I |
| G390u1 | WIAF-10276 | HT3568 | 2049 | NOS3, nitric oxide synthase 3 (endothelial cell) | TTGCTCCTGC[C/G]GTGGACACAC | S | C | G | A | A |
| G391u1 | WIAF-10013 | HT3630 | 6205 | VWF, von Willebrand factor | AGGACCTGGA[G/A]GTGATTCTCC | M | G | A | E | D |
| G391u2 | WIAF-10265 | HT3630 | 4554 | VWF, von Willebrand factor | GCCCCTGAGA[A/G]CAAGGCCTTC | M | A | G | N | S |
| G391u3 | WIAF-10266 | HT3630 | 7489 | VWF, von Willebrand factor | TGGCCTCAAC[C/T]GCCACCAATG | S | C | T | T | T |
| G391u4 | WIAF-10272 | HT3630 | 2470 | VWF, von Willebrand factor | ACTGTACCAT[G/A]AGTGGAGTCC | M | G | A | M | I |
| G391u5 | WIAF-10273 | HT3630 | 2615 | VWF, von Willebrand factor | GCTGAGTGT[A/G]CGAAAACGTG | M | A | G | H | A |
| G391u6 | WIAF-10274 | HT3630 | 2635 | VWF, von Willebrand factor | GCCAGAACTA[T/C]GACTGGAGT | S | T | C | Y | Y |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G391u7 | WIAF-10275 | HT3630 | 4045 | VWF, von Willebrand factor | TCTCGGAACC[C/A]CCGTTGCACG | S | G | A | P | P |
| G391u8 | WIAF-10278 | HT3630 | 4446 | VWF, von Willebrand factor | AACTTTGTCC[G/A]CTACGTCCAG | M | G | A | R | H |
| G391u9 | WIAF-10279 | HT3630 | 5152 | VWF, von Willebrand factor | GCCCTAATGC[C/T]AACGTGCAGG | S | C | T | A | A |
| G391u10 | WIAF-10286 | HT3630 | 3448 | VWF, von Willebrand factor | TTACCAGTGA[C/T]GTCTTCCAGG | S | C | T | D | D |
| G391u11 | WIAF-10287 | HT3630 | 4891 | VWF, von Willebrand factor | ACATGGTGAC[C/T]GTGGAGTACC | S | C | T | T | T |
| G391u12 | WIAF-10288 | HT3630 | 4805 | VWF, von Willebrand factor | CAGGAGCAAG[G/A]AGTTCATGGA | M | G | A | E | K |
| G391u13 | WIAF-10289 | HT3630 | 4943 | VWF, von Willebrand factor | CCTGCACGTG[G/T]TGCGAGAGAT | M | G | T | V | L |
| G391u14 | WIAF-10290 | HT3630 | 4915 | VWF, von Willebrand factor | TCAGCGAGGC[A/C]CAGTCCAAAG | S | A | C | A | A |
| G391u15 | WIAF-10517 | HT3630 | 6194 | VWF, von Willebrand factor | AAACAAGGAG[C/T]AGGACCGGGA | N | C | T | Q | * |
| G391u16 | WIAF-13222 | HT3630 | 6419 | VWF, von Willebrand factor | TCACCTTGGT[C/T]TACATCTTCAC | M | C | T | H | Y |
| G3941u1 | WIAF-14123 | HT3464 | 1265 | mannosidase, alpha, lysosomal | CAGGTGTGCA[A/G]CCAGCTGCAG | M | A | G | N | S |
| G3941u2 | WIAF-14135 | HT3464 | 965 | mannosidase, alpha, lysosomal | ACCAACCACA[C/T]TGTGATGACC | M | C | T | T | I |
| G395u1 | WIAF-10271 | HT4158 | 1627 | ECE1, endothelin converting enzyme 1 | TCACTGCCGA[T/C]CAGCTCAGGA | S | T | C | D | D |
| G395a2 | WIAF-13110 | HT4158 | 1493 | ECE1, endothelin converting enzyme 1 | CATCTACAAC[A/T]TGATAGGATA | M | A | T | M | L |
| G3959u1 | WIAF-13634 | HT4490 | 250 | ADTB1, adaptin, beta 1 (beta prime) | TGAAGAAGCT[G/A]GTATACCTCT | S | G | A | L | L |
| G3959u2 | WIAF-13640 | HT4490 | 2029 | ADTB1, adaptin, beta 1 (beta prime) | TTCTTGCGGG[T/C]GGCCTTGACA | S | T | C | G | G |
| G3959u3 | WIAF-13641 | HT4490 | 2395 | ADTB1, adaptin, beta 1 (beta prime) | AGGTCCACGC[G/A]CCACTCAGCC | S | G | A | A | A |
| G3967u1 | WIAF-13997 | HT2958 | 918 | ACTC, actin, alpha, cardiac muscle | GAGGCACCAC[T/C]ATGTACCCTG | S | T | C | T | T |
| G3968u1 | WIAF-14159 | HT1986 | 1747 | ACTN3, actinin, alpha 3 | CGAGGCTGAC[C/T]GAGAGCGAGG | S | C | T | R | * |
| G3968u2 | WIAF-14164 | HT1986 | 1900 | ACTN3, actinin, alpha 3 | GGTGCCCAGC[C/T]GTGACCAGAC | M | C | T | R | C |
| G3968u3 | WIAF-14165 | HT1986 | 2184 | ACTN3, actinin, alpha 3 | ACACCGTCTA[C/T]AGCATGGAGC | S | C | T | Y | Y |
| G3968u4 | WIAF-14167 | HT1986 | 2557 | ACTN3, actinin, alpha 3 | GATCTTGGCA[G/A]GAGACAAGAA | M | G | A | G | R |
| G3968u5 | WIAF-14175 | HT1986 | 1212 | ACTN3, actinin, alpha 3 | GGCTGCTCTC[G/A]GAGATCCGGC | M | G | A | R | S |
| G3979u1 | WIAF-13884 | HT0623 | 776 | GPC1, glypican 1 | TGCTGCTGCC[T/G]GATGACTACC | S | T | G | P | P |
| G3979u2 | WIAF-13885 | HT0623 | 680 | GPC1, glypican 1 | TGTACTACCG[C/T]GGTGCCAACC | S | C | T | P | P |
| G3979u3 | WIAF-13886 | HT0623 | 1361 | GPC1, glypican 1 | AGCTGCGTCT[T/C]GAAGCCAAGG | M | T | C | R | R |
| G3979u4 | WIAF-13887 | HT0623 | 1163 | GPC1, glypican 1 | AGAGTGTCAT[C/T]GGCAGCGTGC | S | C | T | S | S |
| G3979u5 | WIAF-13888 | HT0623 | 1670 | GPC1, glypican 1 | ACGCCAGTGA[C/T]GACGGCAGCG | M | C | T | H | H |
| G3979u6 | WIAF-13905 | HT0623 | 1069 | GPC1, glypican 1 | CTTGCCAACC[A/T]GGGCGACCTG | S | A | T | I | D |
| G3979u7 | WIAF-13906 | HT0623 | 1514 | GPC1, glypican 1 | TCATGGGTGA[C/T]GGCCTGGCCA | M | C | T | D | D |
| G3979u8 | WIAF-13907 | HT0623 | 1720 | GPC1, glypican 1 | GACCTCTGCG[G/C]CCGGAAGGTC | M | G | C | D | D |
| G3979u9 | WIAF-13908 | HT0623 | 1676 | GPC1, glypican 1 | GTGACGACGG[C/T]AGCGGCTCGG | M | C | T | G | A |
| G3979u10 | WIAF-13909 | HT0623 | 1719 | GPC1, glypican 1 | TGACCTCTGC[G/A]GCCGGAAGGT | M | G | A | G | G |
| G399u1 | WIAF-10102 | HT48511 | 450 | AQP3, aquaporin 3 | TCTGCACTT[T/C]CCTGCACACAG | S | T | C | F | F |
| G399u2 | WIAF-10111 | HT48511 | 192 | AQP3, aquaporin 3 | GCTCCGTGGC[C/T]CAGGTTGTGC | S | C | T | A | A |
| G399u3 | WIAF-10112 | HT48511 | 165 | AQP3, aquaporin 3 | CCCTCATCCT[C/G]GTGATGTTTG | S | C | G | L | L |
| G3997u1 | WIAF-13649 | HT27682 | 473 | MFAP2, microfibrillar-associated protein 2 | TGTGTGCCCA[C/T]GAGGAGCTCC | S | C | T | H | H |
| G3997u2 | WIAF-13650 | HT27682 | 377 | MFAP2, microfibrillar-associated protein 2 | CCATACACAG[G/T]CCTTGGAAAC | M | G | T | R | S |
| G3997u3 | WIAF-13876 | HT27682 | 453 | MFAP2, microfibrillar-associated protein 2 | GGAGATCTGT[G/T]TTCGTACAGT | M | G | T | V | F |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G4022u1 | WIAF-14020 | HT2426 | 240 | TGM1, transglutaminase 1 (K polypeptide epidermal type I, protein-glutamine-gamma-glutamyltransferase) | TGGCTGCTGT[T/C]CATGCCGAAA | M | T | C | S | P |
| G4022u2 | WIAF-14021 | HT2426 | 371 | TGM1, transglutaminase 1 (K polypeptide epidermal type I, protein-glutamine-gamma-glutamyltransferase) | CCCGGGGCAG[C/T]GGTGTCAATG | S | C | T | S | S |
| G4022u3 | WIAF-14022 | HT2426 | 506 | TGM1, transglutaminase 1 (K polypeptide epidermal type I, protein-glutamine-gamma-glutamyltransferase) | ACGAGCTGAT[A/G]GTGCGCCGCG | M | A | G | I | M |
| G4022u4 | WIAF-14031 | HT2426 | 2491 | TGM1, transglutaminase 1 (K polypeptide epidermal type I, protein-glutamine-gamma-glutamyltransferase) | GCTGGAGGTG[A/T]CAGTCACTTA | M | A | T | D | V |
| G4038u1 | WIAF-13998 | HT4211 | 411 | LAMB3, laminin, beta 3 (nicein (125 kD), kalinin (140 kD), BM600 (125 kD)) | GGTGGCAGTC[C/A]CAGAATGATG | S | C | A | S | S |
| G4038u2 | WIAF-13999 | HT4211 | 258 | LAMB3, laminin, beta 3 (nicein (125 kD), kalinin (140 kD), BM600 (125 kD)) | CTTCATCTAC[C/T]TGTGGACTGA | S | C | T | T | T |
| G4038u3 | WIAF-14002 | HT4211 | 1830 | LAMB3, laminin, beta 3 (nicein (125 kD), kalinin (140 kD), BM600 (125 kD)) | GAGGCTACTG[C/T]AATCGCTACC | S | C | T | C | C |
| G4038u4 | WIAF-14003 | HT4211 | 2668 | LAMB3, laminin, beta 3 (nicein (125 kD), kalinin (140 kD), BM600 (125 kD)) | GACCAGGCAG[A/T]TGATTAGGGC | M | A | T | M | L |
| G4038u5 | WIAF-14018 | HT4211 | 248 | LAMB3, laminin, beta 3 (nicein (125 kD), kalinin (140 kD), BM600 (125 kD)) | TTTCTCCGAG[C/T]TTCATCTACC | M | C | T | A | V |
| G4038u6 | WIAF-14019 | HT4211 | 887 | LAMB3, laminin, beta 3 (nicein (125 kD), kalinin (140 kD), BM600 (125 kD)) | CACGGCCATG[C/T]TGATCGCTGC | M | C | T | A | V |
| G4038u7 | WIAF-14023 | HT4211 | 1266 | LAMB3, laminin, beta 3 (nicein (125 kD), kalinin (140 kD), BM600 (125 kD)) | AGTGTGATCC[G/A]GATGGGGCAG | S | G | A | P | P |
| G4038u8 | WIAF-14025 | HT4211 | 1693 | LAMB3, laminin, beta 3 (nicein (125 kD), kalinin (140 kD), BM600 (125 kD)) | CTATGAGAC[G/A]TGGCCACAGG | M | G | A | V | M |
| G4038u9 | WIAF-14026 | HT4211 | 1553 | LAMB3, laminin, beta 3 (nicein (125 kD), kalinin (140 kD), BM600 (125 kD)) | GGCTGTGAAC[C/T]GTGTGCCTGC | M | C | T | P | L |
| G4038u10 | WIAF-14029 | HT4211 | 3562 | LAMB3, laminin, beta 3 (nicein (125 kD), kalinin (140 kD), BM600 (125 kD)) | CCTGACAGGA[C/T]TGGAGAAGCG | S | C | T | L | L |
| G4038u11 | WIAF-14030 | HT4211 | 3546 | LAMB3, laminin, beta 3 (nicein (125 kD), kalinin (140 kD), BM600 (125 kD)) | TGCTGCCCTC[A/G]GCCGACCTGA | S | A | G | S | S |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G4045u1 | WIAF-13571 | HT0652 | 1266 | adducin, beta subunit | TGGAGCAGGA[G/T]AAGCACCGGC | M | G | T | E | D |
| G4050u1 | WIAF-14106 | HT1466 | 1366 | villin | CGTTTGGCAG[G/A]GCAGCCAGGC | M | G | A | G | S |
| G4050u2 | WIAF-14107 | HT1466 | 1468 | villin | GGTCCCAATG[G/A]AGCAAGGAGCC | M | G | A | G | S |
| G4050u3 | WIAF-14108 | HT1466 | 1932 | villin | CCACAGAGAT[C/T]CCTGACTTCA | S | C | T | I | I |
| G4050u4 | WIAF-14110 | HT1466 | 2438 | villin | TTTGGGATGA[C/T]TCCAGCTGCC | M | C | T | T | I |
| G4057u1 | WIAF-13648 | HT33633 | 371 | CNN3, calponin 3, acidic | TTCAGGCTTA[T/C]GGTATGAAGC | S | T | C | Y | Y |
| G4066u1 | WIAF-13676 | HT4301 | 654 | troponin T, beta, skeletal | AGATTGACAA[G/A]TTCGAGTTTG | S | G | A | K | K |
| G4066u2 | WIAF-13677 | HT4301 | 774 | troponin T, beta, skeletal | GCAAAGTCGG[C/T]GGGCGCTGA | S | C | T | G | G |
| G4066u3 | WIAF-13708 | HT4301 | 625 | troponin T, beta, skeletal | GGAGCTCTGG[G/C]AGACCCTGCA | M | G | C | E | Q |
| G4080u1 | WIAF-14142 | HT1396 | 13130 | HSPG2, heparan sulfate proteoglycan 2 (perlecan) | GATTCTCCTC[G/A]GGCATCACAG | S | G | A | S | S |
| G4080u2 | WIAF-14150 | HT1396 | 10340 | HSPG2, heparan sulfate proteoglycan 2 (perlecan) | TTGAGTTCCA[C/T]TGTGCTGTGC | S | C | T | H | H |
| G4080u3 | WIAF-14151 | HT1396 | 12392 | HSPG2, heparan sulfate proteoglycan 2 (perlecan) | AATGCTATGA[T/C]AGCTCCCCAT | S | T | C | D | D |
| G4080u4 | WIAF-14152 | HT1396 | 3416 | HSPG2, heparan sulfate proteoglycan 2 (perlecan) | TGGCTGTGCC[C/T]GAGGAAACCG | S | C | T | P | P |
| G4080u5 | WIAF-14154 | HT1396 | 4588 | HSPG2, heparan sulfate proteoglycan 2 (perlecan) | GTGCCCCTGG[T/C]GGCCAGCATC | M | T | C | V | A |
| G4080u6 | WIAF-14156 | HT1396 | 9582 | HSPG2, heparan sulfate proteoglycan 2 (perlecan) | GGACAGCCAC[G/A]CGTGCTGCA | M | G | A | A | T |
| G4096u1 | WIAF-13890 | HT4237 | 394 | motor protein | CAAAGAAATC[G/A]ATTCAGTGG | S | G | A | S | S |
| G4096u2 | WIAF-13910 | HT4237 | 455 | motor protein | ATCTAAACAC[C/T]CTGCCTCACA | S | C | T | P | P |
| G4096u3 | WIAF-13911 | HT4237 | 1150 | motor protein | CTAAGGTTGT[A/G]TCTCAGTATC | S | A | G | V | V |
| G4109u1 | WIAF-14034 | HT28223 | 1238 | phosphoglucomutase-related protein | TACAGCCTGG[C/T]GAAGACGGAT | M | C | T | A | V |
| G4109u2 | WIAF-14035 | HT28223 | 1043 | phosphoglucomutase-related protein | ATTATTGCTG[C/A]CCGGAAGCAG | M | C | A | A | D |
| G4112u1 | WIAF-13615 | HT4401 | 374 | KIF5A, kinesin family member 5A | AGATGTCCTT[G/A]CTGGCTACAA | M | G | A | A | T |
| G4112u2 | WIAF-13623 | HT4401 | 2767 | KIF5A, kinesin family member 5A | AGAGAGTTAA[G/T]GCCCTGGAGG | M | G | T | K | N |
| G4114u1 | WIAF-14113 | HT4160 | 830 | fibrinogen-like protein pT49 | AACTTCACCA[G/A]AACATGGCAA | M | G | A | R | K |
| G4118u1 | WIAF-14010 | HT0841 | 564 | MYL5, myosin, light polypeptide 5, regulatory | TCGATGTGGC[G/A]GGCAACCTGG | S | G | A | A | A |
| G4118u2 | WIAF-14011 | HT0841 | 368 | MYL5, myosin, light polypeptide 5, regulatory | TTCACCATGT[T/C]TCTGAACCTG | M | T | C | F | S |
| G4118u3 | WIAF-14012 | HT0841 | 533 | MYL5, myosin, light polypeptide 5, regulatory | GAGGTGGACC[A/G]GATGTTCCAG | M | A | G | Q | R |
| G4122u1 | WIAF-13955 | HT97538 | 161 | myosin-I | TCGAGAACCT[A/G]CGGCGGCAT | S | A | G | L | L |
| G4124u1 | WIAF-13895 | HT0925 | 1517 | TGM3, transglutaminase 3 (E polypeptide, protein-glutamine-gamma-glutamyltransferase) | TCGCTGGCAT[G/A]CTGGCAGTAG | M | G | A | M | I |
| G4124u2 | WIAF-13896 | HT0925 | 1433 | TGM3, transglutaminase 3 (E polypeptide, protein-glutamine-gamma-glutamyltransferase) | AACCCAACAC[G/A]CCATTTGCCG | S | G | A | T | T |
| G4126u1 | WIAF-13830 | HT2465 | 1039 | myosin binding protein H | ACTCGTACTC[C/G]TTCCGGGTCT | S | C | G | S | S |
| G4126u2 | WIAF-13853 | HT2465 | 369 | myosin binding protein H | AGAGAGGGAG[C/C]CTCGGACTGG | M | G | C | G | A |
| G4130u1 | WIAF-13614 | HT1657 | 198 | CFL1, cofilin 1 (non-muscle) | CTGTCGACGA[T/C]CCCTACGCCA | S | T | C | D | D |
| G4138u1 | WIAF-13598 | HT33664 | 601 | MAGP2: Microfibril-associated glycoprotein-2 | GAAAGATGAG[C/T]TTTGCCGTCA | M | C | T | L | F |
| G4138u2 | WIAF-13599 | HT33664 | 405 | MAGP2: Microfibril-associated glycoprotein-2 | ATGACTTGGC[C/T]TCCCTCAGTG | S | C | T | A | A |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G4138u3 | WIAF-13600 | HT33664 | 327 | MAGP2: Microfibril-associated glycoprotein-2 | AAGATCCTAA[T/C]CTGGTGAATG | S | T | C | N | N |
| G4159u1 | WIAF-14048 | HT3443 | 1119 | SNL, singed (Drosophila)-like (sea urchin fascin homolog like) | GCTGCTACTT[T/C]GACATCGAGT | S | T | C | F | F |
| G4170u1 | WIAF-13580 | HT5069 | 1131 | Golgi protein, peripheral, brefeldin A-sensitive | GAAATATACC[A/G]TAAGTATGGA | M | A | G | I | V |
| G4170u2 | WIAF-13581 | HT5069 | 930 | Golgi protein, peripheral, brefeldin A-sensitive | GTATAATAAA[C/T]TCCTGGAGTT | M | C | T | L | F |
| G4170u3 | WIAF-13582 | HT5069 | 2312 | Golgi protein, peripheral, brefeldin A-sensitive | AGCACCCTTA[A/G]GCATCTTGGA | N | A | G | * | * |
| G4170u4 | WIAF-13596 | HT5069 | 359 | Golgi protein, peripheral, brefeldin A-sensitive | TCAACCAGCT[T/G]TCTGTGCCTT | S | T | G | L | L |
| G4170u5 | WIAF-13597 | HT5069 | 1007 | Golgi protein, peripheral, brefeldin A-sensitive | AAAAAGGCAA[T/A]ACTGTTCCTG | M | T | A | N | K |
| G4171u1 | WIAF-13688 | HT1587 | 667 | KIF5B, kinesin family member 5B | TTTTTAATTA[T/C]ATTTACTCCA | S | T | C | Y | Y |
| G4171u2 | WIAF-13689 | HT1587 | 1036 | KIF5B, kinesin family member 5B | TTAGTAAAAC[T/C]GGAGCTGAAG | S | T | C | T | T |
| G4176u1 | WIAF-14204 | HT33754 | 130 | TNR, tenascin R (restrictin, janusin) | GCTCATTGGC[G/A]TCAACCTGAT | M | G | A | V | I |
| G4176u2 | WIAF-14205 | HT33754 | 463 | TNR, tenascin R (restrictin, janusin) | CTGTCCATGT[G/T]CCAGTTCAGC | M | G | T | A | S |
| G4176u3 | WIAF-14206 | HT33754 | 249 | TNR, tenascin R (restrictin, janusin) | ACTACAACAC[G/A]TCCAGCAAAG | S | G | A | T | T |
| G4176u4 | WIAF-14208 | HT33754 | 2009 | TNR, tenascin R (restrictin, janusin) | CTGGTCCCCA[G/A]GGGCATTGGT | S | G | A | R | K |
| G4176u5 | WIAF-14209 | HT33754 | 2175 | TNR, tenascin R (restrictin, janusin) | CAGCCTCCTC[G/A]GAGACCTCCA | S | G | A | S | S |
| G4176u6 | WIAF-14210 | HT33754 | 3318 | TNR, tenascin R (restrictin, janusin) | AATCCACCGA[C/T]GGAAGCCCCA | S | C | T | D | D |
| G4176u7 | WIAF-14211 | HT33754 | 3221 | TNR, tenascin R (restrictin, janusin) | CCGGCAAACC[T/C]GACAGCCAGT | M | T | C | L | P |
| G4176u8 | WIAF-14217 | HT33754 | 1635 | TNR, tenascin R (restrictin, janusin) | TCTCGGACAC[C/T]GTGGCTTTTG | S | C | T | T | T |
| G4178u1 | WIAF-14138 | HT0224 | 2827 | ACTN2, actinin, alpha 2 | GCTGCGTTCT[C/T]TTCCGCACTC | M | C | T | S | F |
| G4178u2 | WIAF-14139 | HT0224 | 2818 | ACTN2, actinin, alpha 2 | CTGGATTACG[C/T]TGCGTTCTCT | M | C | T | A | V |
| G4181u1 | WIAF-11750 | L07594 | 2370 | TGFBR3, transforming growth factor, beta receptor III (betaglycan, 300 kD) | GAGTGCGACTT[C/T]CCTATCCCGC | S | C | T | F | F |
| G4181u2 | WIAF-11751 | L07594 | 2586 | TGFBR3, transforming growth factor, beta receptor III (betaglycan, 300 kD) | AGAAGACGTT[C/T]ACCAAGCCCC | S | C | T | F | F |
| G4181u3 | WIAF-11752 | L07594 | 2671 | TGFBR3, transforming growth factor, beta receptor III (betaglycan, 300 kD) | AATTTCTCCA[C/T]CAATTTCCA | M | C | T | P | S |
| G4181u4 | WIAF-11771 | L07594 | 438 | TGFBR3, transforming growth factor, beta receptor III (betaglycan, 300 kD) | TGTGTGAACT[G/T]TCACCTGTCA | S | G | T | L | L |
| G4181u5 | WIAF-11744 | L07594 | 392 | TGFBR3, transforming growth factor, beta receptor III (betaglycan, 300 kD) | CTGATGAGCT[T/C]CTGTTTAGCC | M | T | C | F | S |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G418u6 | WIAF-11772 | L07594 | 1470 | TGFBR3, transforming growth factor, beta receptor III (betaglycan, 300 kD) | AGCTACGGAT[C/T]CTGCTGACC | S | C | T | I | I |
| G418u7 | WIAF-11773 | L07594 | 1170 | TGFBR3, transforming growth factor, beta receptor III (betaglycan, 300 kD) | TCTTGAAGTG[C/A]AAAAAGTCTG | N | C | A | C | * |
| G418u8 | WIAF-11745 | L07594 | 1463 | TGFBR3, transforming growth factor, beta receptor III (betaglycan, 300 kD) | CCTCCTGAGC[T/C]ACGGATCCTG | M | T | C | L | P |
| G418u9 | WIAF-11746 | L07594 | 2211 | TGFBR3, transforming growth factor, beta receptor III (betaglycan, 300 kD) | ATGTTGAGGT[A/G]TCTGTTACTA | S | A | G | V | V |
| G4181u1 | WIAF-14207 | HT2008 | 425 | SPTBN1, spectrin, beta, non-erythrocytic 1 | CTCTGCGCGG[C/T]TTTTTGAGCG | M | C | T | L | F |
| G4181u2 | WIAF-14213 | HT2008 | 3565 | SPTBN1, spectrin, beta, non-erythrocytic 1 | AGACAGCGAT[C/T]GCCTCGGAGG | S | C | T | H | H |
| G4181u3 | WIAF-14218 | HT2008 | 1258 | SPTBN1, spectrin, beta, non-erythrocytic 1 | ACCTTCTGGA[A/G]TGGATTGAAC | S | A | G | E | E |
| G4181u4 | WIAF-14219 | HT2008 | 1780 | SPTBN1, spectrin, beta, non-erythrocytic 1 | AGCTCGAGGC[C/T]GAGAATTACC | S | C | T | A | A |
| G4181u5 | WIAF-14220 | HT2008 | 3637 | SPTBN1, spectrin, beta, non-erythrocytic 1 | ACATCAAGAA[T/C]GAGATCGACA | S | T | C | N | N |
| 64183u1 | WIAF-13976 | HT2640 | 404 | TPM4, tropomyosin 4 | CCAAGCACAT[T/C]GCGGAAGAGG | S | T | C | H | H |
| G4185u1 | WIAF-13554 | HT3451 | 257 | MFAP1, microfibrillar-associated protein 1 | AAGGCCAGAC[T/G]ATGCCCCTAT | M | T | G | Y | D |
| G4185u2 | WIAF-13555 | HT3451 | 1108 | MFAP1, microfibrillar-associated protein 1 | CCAACAAAGC[T/G]GTAAGGCCA | S | T | G | A | A |
| G4185u3 | WIAF-13570 | HT3451 | 274 | MFAP1, microfibrillar-associated protein 1 | CTATGAGTC[C/T]TCAGATGAGG | S | C | T | S | S |
| G4196u1 | WIAF-13665 | HT97558 | 941 | NUP88, nucleoporin 88 kD | GGGTCCATTG[C/A]CCATGCATCT | M | C | A | A | D |
| G4196u2 | WIAF-13666 | HT97558 | 1092 | NUP88, nucleoporin 88 kD | ATGACCACAC[G/A]TCAGAAAAGT | S | G | A | T | T |
| G4196u3 | WIAF-13667 | HT97558 | 1551 | NUP88, nucleoporin 88 kD | TCCATCCAGC[G/A]TCTCCTCCCC | S | G | A | A | T |
| G4196u4 | WIAF-13668 | HT97558 | 2220 | NUP88, nucleoporin 88 kD | AGGGTGAACA[T/C]ATAAGGAAA | S | T | C | H | H |
| G4196u5 | WIAF-13669 | HT97558 | 2205 | NUP88, nucleoporin 88 kD | CCATCCTGAA[A/G]GAGGAGGTG | M | A | G | K | K |
| G4208u1 | WIAF-13921 | HT1122 | 1329 | VCL, vinculin | TGAATCTAAA[G/C]AAAGAGATGA | S | G | C | E | Q |
| G4208u2 | WIAF-13922 | HT1122 | 2438 | VCL, vinculin | CCATCTCCCC[A/C]GATGGTGATGG | M | A | C | P | P |
| G4208u3 | WIAF-13941 | HT1122 | 818 | VCL, vinculin | GGGATGAAGA[T/C]GCCTGGGCCA | S | T | C | P | P |
| G4208u4 | WIAF-13942 | HT1122 | 1556 | VCL, vinculin | AAGCACAGCG[G/A]TGGATTGATA | S | G | A | D | D |
| G4213u1 | WIAF-13605 | HT2813 | 163 | NUP153, nucleoporin 153 kD | GCCAGGGTGG[T/C]TACAAAGATA | S | T | C | R | R |
| G4213u2 | WIAF-13606 | HT2813 | 742 | NUP153, nucleoporin 153 kD | GAATTCTTCA[A/G]TCCTTAAAAC | M | A | G | L | L |
| G4213u3 | WIAF-13609 | HT2813 | 1800 | NUP153, nucleoporin 153 kD | TTAGACCTGC[A/C]GAAATCCTGA | M | A | C | H | V |
| G4213u4 | WIAF-13627 | HT2813 | 1829 | NUP153, nucleoporin 153 kD | AGTGTTCTAG[A/C]TATTCTGAAA | S | A | C | A | A |
| G4213u5 | WIAF-13632 | HT2813 | 3258 | NUP153, nucleoporin 153 kD | CTTTTGCAA[C/T]GTGGAGCCTG | M | C | T | D | N |
| G4213u6 | WIAF-13635 | HT2813 | 4162 | NUP153, nucleoporin 153 kD | CTCTGAACA[A/G]CTCCTAATTC | S | A | G | T | T |
| G4218u1 | WIAF-13854 | HT1681 | 1122 | phosphatidyl-inositol glycan, class A | AACCTTATTA[T/C]TTTATGTGAG | M | T | C | H | T |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G4223u1 | WIAF-14160 | HT1684 | 1434 | CD36L2, CD36 antigen (collagen type I receptor, thrombospondin receptor)-like 2 (lysosomal integral membrane protein II) | ATTAGATGAC[T/C]TTGTTGAAAC | M | T | C | F | L |
| G4223u2 | WIAF-14173 | HT1684 | 696 | CD36L2, CD36 antigen (collagen type I receptor, thrombospondin receptor)-like 2 (lysosomal integral membrane protein II) | GTGGTCCAG[G/A]TGCACTTCCT | M | G | A | V | M |
| G4223u3 | WIAF-14174 | HT1684 | 986 | CD36L2, CD36 antigen (collagen type I receptor, thrombospondin receptor)-like 2 (lysosomal integral membrane protein II) | CAGACAAGTG[C/T]AATATGATTA | S | C | T | C | C |
| G4223u4 | WIAF-14176 | HT1684 | 1437 | CD36L2, CD36 antigen (collagen type I receptor, thrombospondin receptor)-like 2 (lysosomal integral membrane protein II) | AGATGACTTT[G/A]TTGAAACGGG | M | G | A | V | I |
| G4227u1 | WIAF-14056 | HT1929 | 912 | proteoglycan 2 | ATGCCTCCAA[G/A]AAAGATGGGG | S | G | A | K | K |
| G4227u2 | WIAF-14057 | HT1929 | 1254 | proteoglycan 2 | GGAACTTGC[G/A]TACTGGGCTG | S | G | A | A | A |
| G4227u3 | WIAF-14058 | HT1929 | 1321 | proteoglycan 2 | CCGAGGAGGC[T/C]ACTGGCGTCG | S | T | C | Y | H |
| G4229u1 | WIAF-13961 | HT1689 | 74 | SDC4, syndecan 4 (amphiglycan, ryudocan) | GCTGCTGCTG[T/C]TCTTCGTAGG | M | T | C | F | L |
| G4230u1 | WIAF-13525 | HT4995 | 602 | TRAM protein | CCATAACCTG[A/C]TGACATTTCA | M | A | C | M | L |
| G4243u1 | WIAF-14169 | HT2901 | 406 | KRT17, keratin 17 | AGCTGGAGGT[G/A]AAGATCCGTG | M | G | A | V | V |
| G4243u2 | WIAF-14170 | HT2901 | 478 | KRT17, keratin 17 | ACAGGACAAT[T/C]GAGGAGCTGC | S | T | C | H | H |
| G4243u3 | WIAF-14171 | HT2901 | 389 | KRT17, keratin 17 | GGAGGAGGCC[A/G]ACACTGAGCT | M | A | G | I | V |
| G4243u4 | WIAF-14178 | HT2901 | 564 | KRT17, keratin 17 | CTGGCTCTG[A/C]TGACTTCCGC | M | A | C | N | D |
| G4244u1 | WIAF-14086 | HT1056 | 386 | clathrin, light polypeptide a | ATCGATTGCA[G/C]TGAGAGCCTG | M | G | C | D | A |
| G4246u1 | WIAF-14044 | HT97492 | 259 | SLN, sarcolipin | GTCCTATCAG[T/C]ACTGAGAGGC | M | T | C | Q | H |
| G4246u2 | WIAF-14045 | HT97492 | 189 | SLN, sarcolipin | ACACCCGGA[G/A]CTGTTTCTCA | M | G | A | Y | H |
| G4254u1 | WIAF-13546 | HT3393 | 86 | TNNI2, troponin I, skeletal, fast | ACCTGAAGAG[C/T]GTGATGCTGC | M | C | T | E | E |
| G4254u2 | WIAF-13553 | HT3393 | 530 | TNNI2, troponin I, skeletal, fast | TCGAGGAGAA[G/C]TCTGGCATGG | S | G | C | S | S |
| G4255u1 | WIAF-13644 | HT2907 | 562 | CRYAB, crystallin, alpha B | AGTTCCACAG[G/A]AAATACCGGA | S | G | A | K | N |
| G4255u2 | WIAF-13645 | HT2907 | 367 | CRYAB, crystallin, alpha B | CCTCCTTCCT[G/A]CGGGCACCCA | S | G | A | R | R |
| G4255u3 | WIAF-13872 | HT2907 | 271 | CRYAB, crystallin, alpha B | CCAGCCGCCT[C/T]TTTGACCAGT | S | C | T | R | L |
| G4255u4 | WIAF-13873 | HT2907 | 580 | CRYAB, crystallin, alpha B | GGATCCCAGC[T/C]GATGTAGACC | S | T | C | L | L |
| G4257u1 | WIAF-14052 | HT1694 | 394 | PIGF, phosphatidylinositol glycan, class F | TAGAGTTGGC[A/G]TTGGAAACAT | S | A | G | A | A |
| G4257u2 | WIAF-14053 | HT1694 | 252 | PIGF, phosphatidylinositol glycan, class F | TATTAGTAG[T/C]GAAACCAAAT | M | T | C | V | A |
| G4257u3 | WIAF-14069 | HT1694 | 291 | PIGF, phosphatidylinositol glycan, class F | TCATTATCAC[A/G]CAAGGTAACT | M | A | G | H | R |
| G4264u1 | WIAF-13519 | HT0968 | 1720 | TJP1, tight junction protein 1 (zona occludens 1) | CGGTCAGTGG[C/T]TTCCAGCCAG | M | C | T | A | V |
| G4264u2 | WIAF-13520 | HT0968 | 2272 | TJP1, tight junction protein 1 (zona occludens 1) | CATGCTGATG[A/G]TCACACACCT | M | A | G | D | G |
| G4264u3 | WIAF-13529 | HT0968 | 5408 | TJP1, tight junction protein 1 (zona occludens 1) | AGCCTCCTGA[A/T]GCTGATGGTG | M | A | T | E | D |
| G434u1 | WIAF-11748 | M21121 | 286 | SCYA5, small inducible cytokine A5 (RANTES) | TACATCAACT[C/T]TTTGGAGATG | M | C | T | S | F |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G434u2 | WIAF-11749 | M21121 | 137 | SCYA5, small inducible cytokine A5 (RANTES) | GCTTTGCCTA[C/T]ATTGCCCGCC | S | C | T | Y | Y |
| G435u1 | WIAF-11741 | M31933 | 754 | FCGR2B, Fc fragment of IgG, low affinity IIb, receptor for (CD32) | GTCACTGGGA[T/C]TGCTGTAGCG | M | T | C | I | T |
| G435u2 | WIAF-11743 | M31933 | 395 | FCGR2B, Fc fragment of IgG, low affinity IIb, receptor for (CD32) | GGGAGTACAC[G/A]TGCCAGACTG | S | G | A | T | T |
| G435u3 | WIAF-11742 | M31933 | 673 | FCGR2B, Fc fragment of IgG, low affinity IIb, receptor for (CD32) | TACACGCTGT[T/A]CTTCATCCAAG | M | T | A | F | Y |
| G4369u1 | WIAF-13728 | HT0900 | 1176 | GBE1, glucan (1,4-alpha-), branching enzyme 1 (glycogen branching enzyme, Andersen disease, glycogen storage disease type IV) | TTACGTCCAT[G/A]CTTTATCATC | M | G | A | M | I |
| G4369u2 | WIAF-13729 | HT0900 | 1609 | GBE1, glucan (1,4-alpha-), branching enzyme 1 (glycogen branching enzyme, Andersen disease, glycogen storage disease type IV) | GAGTGTCCTG[A/G]CTCCTTTTAC | M | A | G | T | A |
| G4373u1 | WIAF-13559 | HT0940 | 1117 | HSD17B2, hydroxysteroid (17-beta) dehydrogenase 2 | GCCAGCAAGG[A/T]CTTCTCTCCG | M | A | T | D | V |
| G4373u2 | WIAF-13560 | HT0940 | 1195 | HSD17B2, hydroxysteroid (17-beta) dehydrogenase 2 | CCAGGAAAAG[G/A]CGCTTACTTG | M | G | A | G | D |
| G438u1 | WIAF-11830 | M63121 | 583 | TNFRSF1A, tumor necrosis factor receptor superfamily, member 1A | ACCGTGTGTG[G/A]CTGCAGGAAG | M | G | A | G | D |
| G438u2 | WIAF-11790 | M63121 | 618 | TNFRSF1A, tumor necrosis factor receptor superfamily, member 1A | TTATTGGAGT[G/A]AAAACCTTTT | M | G | A | E | K |
| G440u1 | WIAF-11806 | M74447 | 261 | TAP2, transporter 2, ABC (ATP binding cassette) | TGCTAAAGCT[A/G]AGAGGGCTGC | S | A | G | L | L |
| G440u2 | WIAF-11807 | M74447 | 2089 | TAP2, transporter 2, ABC (ATP binding cassette) | CAGGCTCCAG[G/A]CAGTTCAGCG | M | G | A | A | T |
| G440u3 | WIAF-11808 | M74447 | 2155 | TAP2, transporter 2, ABC (ATP binding cassette) | TGCCCAGCTC[C/T]AGGAGGGACA | N | C | T | Q | * |
| G440u4 | WIAF-11818 | M74447 | 1789 | TAP2, transporter 2, ABC (ATP binding cassette) | GAACAACATT[G/A]CTTATGGGCT | M | G | A | A | T |
| G440u5 | WIAF-11819 | M74447 | 1565 | TAP2, transporter 2, ABC (ATP binding cassette) | AAGGGGCTGA[C/T]GTTTACCCTA | M | C | T | T | M |
| G440u6 | WIAF-11820 | M74447 | 1254 | TAP2, transporter 2, ABC (ATP binding cassette) | TGCACTTGGG[G/T]GTGCAGATGC | S | G | T | G | G |
| G440u7 | WIAF-11788 | M74447 | 1231 | TAP2, transporter 2, ABC (ATP binding cassette) | GTACCTGCTC[A/G]TAAGGAGGGT | M | A | G | I | V |
| G440u8 | WIAF-11821 | M74447 | 1404 | TAP2, transporter 2, ABC (ATP binding cassette) | TGCTCAGCAA[C/T]GTGGGAGCTG | S | C | T | N | N |
| G440u9 | WIAF-11783 | M74447 | 2187 | TAP2, transporter 2, ABC (ATP binding cassette) | CCCGCCTGGT[T/G]CAGCAGCGGC | S | T | G | V | V |
| G440u10 | WIAF-11786 | M74447 | 1825 | TAP2, transporter 2, ABC (ATP binding cassette) | TGATAAGGTG[A/G]TGGCGGCTGC | M | A | G | M | V |
| G4400u1 | WIAF-14007 | HT97396 | 839 | A33 | GCCAATCAAA[G/T]GAGGGCTCAC | M | G | T | K | N |
| G4404u1 | WIAF-14013 | HT1215 | 109 | ACP2, acid phosphatase 2, lysosomal | CCGCCACCC[G/A]GGCCCGAGT | M | G | A | R | Q |

-continued

| Poly ID | WIAF ID | Genbank or TIGR Accession Number | Position in Sequence | Gene Description | Mutation Type | Ref NT | Alt NT | Ref AA | Alt AA |
|---|---|---|---|---|---|---|---|---|---|
| G4404u2 | WIAF-14016 | HT1215 | 1271 | ACP2, acid phosphatase 2, lysosomal | S | C | T | V | V |
| G4406u1 | WIAF-13661 | HT3564 | 872 | ACPP, acid phosphatase, prostate | S | T | C | L | L |
| G4406u2 | WIAF-13662 | HT3564 | 839 | ACPP, acid phosphatase, prostate | S | G | A | K | K |
| G4406u3 | WIAF-13881 | HT3564 | 741 | ACPP, acid phosphatase, prostate | N | G | T | E | * |
| G4411u1 | WIAF-10166 | M77349 | 698 | TGFBI, transforming growth factor, beta-induced, 68 kD | S | C | G | L | L |
| G441u2 | WIAF-10168 | M77349 | 1028 | TGFBI, transforming growth factor, beta-induced, 68 kD | S | A | G | V | V |
| G441u3 | WIAF-10169 | M77349 | 1667 | TGFBI, transforming growth factor, beta-induced, 68 kD | S | T | C | F | F |
| G441u4 | WIAF-10171 | M77349 | 1463 | TGFBI, transforming growth factor, beta-induced, 68 kD | S | C | T | L | L |
| G4411u1 | WIAF-14005 | HT97468 | 492 | acyl-CoA | M | A | G | K | E |
| G4411u2 | WIAF-14008 | HT97468 | 1076 | acyl-CoA | S | C | T | T | T |
| G4412u1 | WIAF-13576 | HT1882 | 657 | ACADS, acyl-Coenzyme A dehydrogenase, C-2 to C-3 short chain | M | G | A | G | S |
| G4412u2 | WIAF-13579 | HT1882 | 1022 | ACADS, acyl-Coenzyme A dehydrogenase, C-2 to C-3 short chain | S | C | T | R | R |
| G4415u1 | WIAF-14080 | HT2503 | 2170 | acyl-Coenzyme A:cholesterol acyltransferase | S | C | T | F | F |
| G4415u2 | WIAF-14081 | HT2503 | 1993 | acyl-Coenzyme A:cholesterol acyltransferase | S | C | T | P | P |
| G4415u3 | WIAF-14098 | HT2503 | 2006 | acyl-Coenzyme A:cholesterol acyltransferase | M | C | G | Q | E |
| G4415u4 | WIAF-14101 | HT2503 | 2365 | acyl-Coenzyme A:cholesterol acyltransferase | S | C | T | V | V |
| G4417u1 | WIAF-13819 | HT0542 | 356 | AOAH, acyloxyacyl hydrolase (neutrophil) | M | G | A | D | N |
| G4417u2 | WIAF-13820 | HT0542 | 340 | AOAH, acyloxyacyl hydrolase (neutrophil) | S | G | A | S | S |
| G4417u3 | WIAF-13824 | HT0542 | 1595 | AOAH, acyloxyacyl hydrolase (neutrophil) | M | G | A | D | N |
| G4417u4 | WIAF-13841 | HT0542 | 382 | AOAH, acyloxyacyl hydrolase (neutrophil) | S | G | A | S | S |
| G4417u5 | WIAF-13842 | HT0542 | 458 | AOAH, acyloxyacyl hydrolase (neutrophil) | M | C | A | V | I |
| G4417u6 | WIAF-13843 | HT0542 | 1201 | AOAH, acyloxyacyl hydrolase (neutrophil) | S | C | T | D | D |
| G4417u7 | WIAF-13844 | HT0542 | 1321 | AOAH, acyloxyacyl hydrolase (neutrophil) | S | A | G | K | K |
| G4417u8 | WIAF-13845 | HT0542 | 1404 | AOAH, acyloxyacyl hydrolase (neutrophil) | M | G | A | S | N |
| G4417u9 | WIAF-13846 | HT0542 | 1759 | AOAH, acyloxyacyl hydrolase (neutrophil) | S | C | T | N | N |
| G4417u10 | WIAF-13847 | HT0542 | 1644 | AOAH, acyloxyacyl hydrolase (neutrophil) | M | G | A | S | N |

Flanking Seq:
- G4404u2: ACCGCCACGT[C/T]GCAGATGGGG
- G4406u1: ACAAAAACT[T/C]ATCATGTATT
- G4406u2: ATCACATGAA[G/A]AGAGCAACTC
- G4406u3: AGAATTGTCA[G/T]TAATTGTCCT
- G4411u1: GTGCCCGGCT[C/G]CTGAAAGCCG
- G441u2: GGCTGTCTGT[A/G]GAGACCCTGG
- G441u3: ACACAGTCTT[T/C]GCTCCCACAA
- G441u4: GTAATAGCCT[C/T]TGCATTGAGA
- G4411u1: GCTGACCAAT[A/G]AGGCCACCCT
- G4411u2: TGCCCGAGAC[C/T]GAGGACGAGA
- G4412u1: GCAAAACAAG[G/A]GCATCAGTGC
- G4412u2: TGACCTGGCG[C/T]GCTGCCATGC
- G4415u1: TCATTATATT[C/T]GAGCAGATTC
- G4415u2: TTTCAGTTCC[C/T]TATTTTCTGT
- G4415u3: TTTTCTGTTT[C/G]AACATTGGCG
- G4415u4: GGGGTTATGT[C/T]GCTATGAAGT
- G4417u1: TCCAGCCAAC[G/A]ATGACCAGTC
- G4417u2: TTCAGTCCTC[G/A]GCCTCTCCAG
- G4417u3: GCTAAATAAA[G/A]ACATGACCTA
- G4417u4: CCAGCCTCTC[G/A]AATGGGCACA
- G4417u5: CAACTCGACG[G/A]TCCAGGCCTC
- G4417u6: GATTTCTGGA[C/T]TTCCACTGTTG
- G4417u7: ACCTGAAGAA[A/G]TTTATAGAAA
- G4417u8: GATGTCTGCA[G/A]TGGAAGAGT
- G4417u9: AATTACAAA[C/T]TTCAATCTTT
- G4417u10: CTCCAGGTCA[G/A]CCCCTGCCAC

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G442u1 | WIAF-11828 | M94582 | 933 | IL8RA, interleukin 8 receptor, alpha | CACATGACC[G/A]GGCTCTGGAT | M | G | A | R | Q |
| G442u2 | WIAF-11829 | M94582 | 721 | IL8RA, interleukin 8 receptor, alpha | TCATCGTGCC[A/G]CTGCTGATCA | S | A | G | P | P |
| G442u3 | WIAF-11780 | M94582 | 1027 | IL8RA, interleukin 8 receptor, alpha | GCCATGGACT[C/T]CTCAAGATTC | S | C | T | L | L |
| G442u4 | WIAF-11792 | M94582 | 78 | IL8RA, interleukin 8 receptor, alpha | ATGGAGAGTG[A/G]CAGCTTTGAA | M | A | G | D | G |
| G4423u1 | WIAF-13752 | HT2216 | 71 | ADSL, adenylosuccinate lyase | GCTATGCCAG[C/T]CCGGAGATGT | S | C | T | S | S |
| G4423u2 | WIAF-13794 | HT2216 | 126 | ADSL, adenylosuccinate lyase | ATGGCGGCAG[C/T]TGTGGCTGTG | S | C | T | L | L |
| G4423u3 | WIAF-13795 | HT2216 | 674 | ADSL, adenylosuccinate lyase | AGCTTGACAA[G/A]ATGGTGACAG | S | G | A | K | K |
| G4428u1 | WIAF-13954 | HT97524 | 57 | ADFP, adipose differentiation-related protein; adipophilin | TGGTCAACCT[G/A]CCCTTGGTGA | S | G | A | L | L |
| G4434u1 | WIAF-13506 | HT0863 | 551 | ARF3, ADP-ribosylation factor 3 | TCTGGAGACA[C/T]TACTTCCAGA | S | C | T | H | H |
| G444u1 | WIAF-10172 | U28694 | 398 | CCR3, chemokine (C-C motif) receptor 3 | CGAGATCTTT[T/G]TCATAATCCT | M | T | G | F | V |
| G444u2 | WIAF-10181 | U28694 | 214 | CCR3, chemokine (C-C motif) receptor 3 | TCCTCATAAA[A/G]TACAGGAGGC | S | A | G | K | K |
| G4440u1 | WIAF-14054 | HT1392 | 136 | ADRBK1, adrenergic, beta, receptor kinase 1 | GCAAGAAGAT[A/C]CTGCTGCCCG | S | A | C | I | I |
| G445u1 | WIAF-10183 | U40373 | 319 | Human cell surface glycoprotein CD44, mRNA, complete cds. | TAGAAGGGCA[C/T]GTGGTGATTC | S | C | T | H | H |
| G4456u1 | WIAF-13629 | HT0626 | 796 | ALDOC, aldolase C, fructose-bisphosphate | CCCTGCTCAA[G/A]CCCAACATGG | S | G | A | K | K |
| G446u1 | WIAF-11832 | U64198 | 754 | IL12RB2, interleukin 12 receptor, beta 2 | TGAAGCCTTC[C/G]CATGTAATTT | S | C | G | S | S |
| G446u2 | WIAF-11795 | U64198 | 2569 | IL12RB2, interleukin 12 receptor, beta 2 | TTTTCTCAAC[G/A]CATTACTTCC | S | G | A | T | T |
| G446u3 | WIAF-11833 | U64198 | 2500 | IL12RB2, interleukin 12 receptor, beta 2 | TGCAAGGTAA[A/G]GCCAATTGGA | S | A | G | K | K |
| G446u4 | WIAF-11835 | U64198 | 1918 | IL12RB2, interleukin 12 receptor, beta 2 | CTCCTCGCCA[G/C]GTCTCTGCAA | M | G | C | Q | H |
| G446u5 | WIAF-11793 | U64198 | 991 | IL12RB2, interleukin 12 receptor, beta 2 | GTGGAGCAGA[G/A]ATCTTCGTTG | S | G | A | E | E |
| G446u6 | WIAF-11794 | U64198 | 2469 | IL12RB2, interleukin 12 receptor, beta 2 | AGTTCCCACG[G/C]AAATGAGAGG | M | G | C | G | A |
| G446a7 | WIAF-13128 | U64198 | 1964 | IL12RB2, interleukin 12 receptor, beta 2 | GGTGACTTGG[C/g]AGCCTCCCAG | M | C | g | Q | E |
| G446a8 | WIAF-13129 | U64198 | 2060 | IL12RB2, interleukin 12 receptor, beta 2 | TCTAAACTGG[C/G]TACGGAGTCG | M | C | G | L | V |
| G447u1 | WIAF-11796 | X03663 | 384 | CSF1R, colony stimulating factor 1 receptor, formerly McDonough feline sarcoma viral (v-fms) oncogene homolog | CCAGTGTCCC[C/T]GAGCTGGTCG | S | C | T | P | P |
| G447u2 | WIAF-11836 | X03663 | 1026 | CSF1R, colony stimulating factor 1 receptor, formerly McDonough feline sarcoma viral (v-fms) oncogene homolog | ACAACAACAC[T/C]AAGCTCGCAA | S | T | C | T | T |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G447u3 | WIAF-11837 | X03663 | 886 | CSF1R, colony stimulating factor 1 receptor, formerly McDonough feline sarcoma viral (v-fms) oncogene homolog | GCTGAAAGTG[C/A]AGAAAGTCAT | M | C | A | Q | K |
| G447u4 | WIAF-11797 | X03663 | 2425 | CSF1R, colony stimulating factor 1 receptor, formerly McDonough feline sarcoma viral (v-fms) oncogene homolog | GAAGAAATAT[G/A]TCCGCAGGGA | M | G | A | V | I |
| G4473u1 | WIAF-13904 | HT1352 | 860 | FUCA1, fucosidase, alpha-L-1, tissue | TTCAAGCCAC[A/G]GAGCTTGCCA | M | A | G | Q | R |
| G4473u2 | WIAF-13916 | HT1352 | 440 | FUCA1, fucosidase, alpha-L-1, tissue | ACAAACTGGC[C/T]GAGTCCTGTG | M | C | T | P | L |
| G4479u1 | WIAF-13637 | HT1995 | 2465 | AMPD2, adenosine monophosphate deaminase 2 (isoform L) | GCCTCAATGA[G/T]CCTGGTCCAT | — | G | T | — | — |
| G4479u2 | WIAF-13866 | HT1995 | 1258 | AMPD2, adenosine monophosphate deaminase 2 (isoform L) | TGGATGTGCA[T/C]GCCGACAGGA | S | T | C | H | H |
| G4479u3 | WIAF-13867 | HT1995 | 1280 | AMPD2, adenosine monophosphate deaminase 2 (isoform L) | CACTTTCCAT[C/T]GCTTTGACAA | M | C | T | R | C |
| G4479u4 | WIAF-13868 | HT1995 | 1201 | AMPD2, adenosine monophosphate deaminase 2 (isoform L) | TGCGGGAGGT[C/T]TTTGAGAGCA | S | C | T | V | V |
| G4479u5 | WIAF-13869 | HT1995 | 1579 | AMPD2, adenosine monophosphate deaminase 2 (isoform L) | GTACCAAGGG[C/T]CAGCTGGCCA | S | C | T | G | G |
| G4492u1 | WIAF-14084 | HT3390 | 866 | ANX11, annexin XI (56 kD autoantigen) | CCTGGGGAGT[C/T]GCTCCAACAA | M | C | T | R | C |
| G4492u2 | WIAF-14085 | HT3390 | 850 | ANX11, annexin XI (56 kD autoantigen) | AGGGCCATCAT[T/C]GACTGCCTGG | S | T | C | I | I |
| G450u1 | WIAF-10170 | X85740 | 1196 | CCR4, chemokine (C-C motif) receptor 4 | TCCAAATTTA[C/T]TCTGCTGACA | S | C | T | Y | Y |
| G4502u1 | WIAF-13510 | HT4840 | 165 | ASS, argininosuccinate synthetase | AAGGCTATGA[C/T]GTCATTGCCT | M | C | T | D | H |
| G4502u2 | WIAF-13511 | HT4840 | 369 | ASS, argininosuccinate synthetase | GGCCCTGCAT[C/T]GCCCGCAAAC | S | C | T | H | H |
| G4502u3 | WIAF-13512 | HT4840 | 73 | ASS, argininosuccinate synthetase | AATCCCAGAC[G/A]CTATGTCCAG | — | G | A | — | — |
| G4502u4 | WIAF-13513 | HT4840 | 129 | ASS, argininosuccinate synthetase | TGGACACCTG[C/G]TGCATCCTCG | S | C | G | S | S |
| G4502u5 | WIAF-13514 | HT4840 | 285 | ASS, argininosuccinate synthetase | AGTTTGTGGA[G/A]GAGTTCATCT | M | G | A | E | K |
| G4502u6 | WIAF-13515 | HT4840 | 234 | ASS, argininosuccinate synthetase | AGGGACTGAA[G/A]CTTGGGGCCA | S | G | A | K | K |
| G4502u7 | WIAF-13516 | HT4840 | 316 | ASS, argininosuccinate synthetase | CCAGTCCAGC[G/A]CACTGTATGA | M | G | A | A | T |
| G4502u8 | WIAF-13537 | HT4840 | 426 | ASS, argininosuccinate synthetase | TGTCCCACGG[C/T]GCCACAGGAA | S | C | T | G | G |
| G4502u9 | WIAF-13538 | HT4840 | 530 | ASS, argininosuccinate synthetase | GAATTCTACA[A/G]CCGGTTCAAG | M | A | G | N | S |
| G4502u10 | WIAF-13539 | HT4840 | 750 | ASS, argininosuccinate synthetase | TTCTCCAGAT[C/T]GAGTTCAAAA | S | C | T | I | I |
| G4502u11 | WIAF-13540 | HT4840 | 960 | ASS, argininosuccinate synthetase | ATGCTCATTT[A/G]GACATCGAGG | M | A | G | L | L |
| G4508u1 | WIAF-13663 | HT28557 | 1767 | ARSD, arylsulfatase D | CAGTTTTCCA[T/C]GACCAACATC | S | T | C | M | M |
| G4508u2 | WIAF-13693 | HT28557 | 433 | ARSD, arylsulfatase D | TTCAGTGGAA[C/T]GCAGGCTCAG | M | C | T | N | N |
| G4508u3 | WIAF-13694 | HT28557 | 747 | ARSD, arylsulfatase D | GGTTCTTCCT[C/G]TGTCTCCCGG | S | C | G | S | C |
| G4508u4 | WIAF-13696 | HT28557 | 1012 | ARSD, arylsulfatase D | CCACGACTTG[C/A]GTTCCTGGGA | M | C | A | A | A |
| G4508u5 | WIAF-13697 | HT28557 | 1302 | ARSD, arylsulfatase D | CCAGTGATTG[G/A]AGAGCCCACG | M | G | A | G | E |
| G4508u6 | WIAF-13698 | HT28557 | 1285 | ARSD, arylsulfatase D | GGGTGCTCCC[G/A]GCCGGCCCAG | S | G | A | P | P |
| G4508u7 | WIAF-13699 | HT28557 | 1807 | ARSD, arylsulfatase D | AGCCGTGCTG[C/T]GGACATTTCC | M | C | T | C | C |
| G4508u8 | WIAF-13718 | HT28557 | 483 | ARSD, arylsulfatase D | GCAAGAATCT[T/C]GCAGCAGCAT | S | T | C | L | L |
| G4518u1 | WIAF-13809 | HT3430 | 515 | ASPA, aspartoacylase (aminoacylase 2, Canavan disease) | ACAACCACCA[C/T]TCTAACATGG | S | C | T | T | T |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G4518u2 | WIAF-13810 | HT3430 | 851 | ASPA, aspartoacylase (aminoacylase 2, Canavan disease) | AAGTTGATTA[C/T]CCCGGGATG | S | C | T | Y | Y |
| G4518u3 | WIAF-13811 | HT3430 | 787 | ASPA, aspartoacylase (aminoacylase 2, Canavan disease) | CATCATTTCA[A/G]TGAAGGAAAA | M | A | G | N | S |
| G4518u4 | WIAF-13837 | HT3430 | 618 | ASPA, aspartoacylase (aminoacylase 2, Canavan disease) | ACCCTGCTAC[G/A]TTTATCTGAT | M | G | A | V | I |
| G452a1 | WIAF-10509 | HT0695 | 553 | APOA4, apolipoprotein A-IV | ACCAGTCA[A/G]CACGCAGGCC | M | A | G | N | S |
| G452a2 | WIAF-13124 | HT0695 | 563 | APOA4, apolipoprotein A-IV | ACACGCAGGC[C/T]GAGCAGCTGC | S | C | T | A | A |
| G4524u1 | WIAF-14120 | HT1541 | 726 | ATP5A1, ATP synthase, H+ transporting, mitochondrial F1 complex, alpha subunit, isoform 1, cardiac muscle | CTCAATTGCT[A/G]TTGACACAAT | M | A | G | H | V |
| G4524u2 | WIAF-14131 | HT1541 | 153 | ATP5A1, ATP synthase, H+ transporting, mitochondrial F1 complex, alpha subunit, isoform 1, cardiac muscle | ATCTTTCATT[G/T]CTGCAAGGAA | M | G | T | A | S |
| G4526u1 | WIAF-14130 | HT4994 | 400 | ATP5D, ATP synthase, H+ transporting, mitochondrial F1 complex, delta subunit | TCCATGCGAG[T/C]GAACGCCGAC | M | T | C | V | A |
| G453u1 | WIAF-10138 | HT0768 | 1747 | PDGFRB, platelet-derived growth factor receptor, beta polypeptide | CTGCCGCCCA[C/T]GCTGCTGGGG | M | C | T | T | M |
| G453u2 | WIAF-10147 | HT0768 | 2957 | PDGFRB, platelet-derived growth factor receptor, beta polypeptide | TTTTGCCTTT[A/G]AAGTGGATGG | S | A | G | L | L |
| G453u3 | WIAF-10148 | HT0768 | 3608 | PDGFRB, platelet-derived growth factor receptor, beta polypeptide | AGCCGGAGCC[A/G]GAGCTGGAAC | S | A | G | P | P |
| G453u4 | WIAF-10149 | HT0768 | 457 | PDGFRB, platelet-derived growth factor receptor, beta polypeptide | CAGGGCCTGG[T/G]CGTCACACCC | M | T | G | V | G |
| G453u5 | WIAF-10151 | HT0768 | 1505 | PDGFRB, platelet-derived growth factor receptor, beta polypeptide | AGCTGACACT[G/C]GTTCGCGTGA | S | G | C | L | L |
| G453u6 | WIAF-10153 | HT0768 | 3446 | PDGFRB, platelet-derived growth factor receptor, beta polypeptide | ACCCCAAACC[C/T]GAGGTTGCTG | S | C | T | P | P |
| G453u7 | WIAF-10161 | HT0768 | 2030 | PDGFRB, platelet-derived growth factor receptor, beta polypeptide | TTTGCAGAA[G/A]AAGCCACGTT | S | G | A | K | K |
| G4533u1 | WIAF-13616 | HT1618 | 343 | ATP synthase, H+ transporting, subunit D, vacuolar | GTTACATGAT[C/T]GACAACGTGA | S | C | T | I | I |
| G4534u1 | WIAF-13569 | HT3556 | 654 | ATP6E, ATPase, H+ transporting, lysosomal (vacuolar proton pump) 31 kD | TAAAGTTTC[C/T]AACACCCTGG | S | C | T | S | S |
| G4535u1 | WIAF-13747 | HT27972 | 357 | APT50, ATP synthase, H+ transporting, mitochondrial F1 complex, O subunit (oligomycin sensitivity conferring protein) | TCACTACCAA[C/T]CTGATCAATT | S | C | T | N | N |
| G4535u2 | WIAF-13748 | HT27972 | 144 | APT50, ATP synthase, H+ transporting, mitochondrial F1 complex, O subunit (oligomycin sensitivity conferring protein) | AGGTATACGG[T/C]ATTGAAGGTC | S | T | C | G | G |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G4535u3 | WIAF-13792 | HT27972 | 329 | APT50, ATP synthase, H+ transporting, mitochondrial F1 complex, O subunit (oligomycin sensitivity conferring protein) | ATCAAGCAA[A/G]AGAGAGGTTC | M | A | G | K | R |
| G4539u1 | WIAF-13711 | HT48520 | 288 | ATPase, 14 kDa subunit, vacuolar | TGCCCTGGAC[G/A]CCCACCAGCA | M | G | A | A | T |
| G4548u1 | WIAF-14127 | HT1574 | 3138 | ATPase, Ca2+ transporting, plasma membrane, isoform 2 | CGCAATGTCT[T/C]TGACGGCATC | M | T | C | F | S |
| G4548u2 | WIAF-14137 | HT1574 | 2089 | ATPase, Ca2+ transporting, plasma membrane, isoform 2 | GCACTATCTG[C/T]GTGGCCTACC | S | C | T | C | C |
| G4548u3 | WIAF-14140 | HT1574 | 2924 | ATPase, Ca2+ transporting, plasma membrane, isoform 2 | CAGGACCATG[A/T]TGAAGAACAT | M | A | T | M | L |
| G4549u1 | WIAF-14161 | HT1346 | 524 | ATP2B4, ATPase, Ca+ transporting, plasma membrane 4 | TGCACTGACC[C/T]AGATTAATGT | N | C | T | Q | * |
| G4549u2 | WIAF-14162 | HT1346 | 715 | ATP2B4, ATPase, Ca+ transporting, plasma membrane 4 | ATGTCACGCT[C/T]ATCATCCTGG | S | C | T | L | L |
| G4549u3 | WIAF-14163 | HT1346 | 508 | ATP2B4, ATPase, Ca+ transporting, plasma membrane 4 | AGCTGCTTC[G/A]AGGGATGCAC | S | G | A | S | S |
| G4549u4 | WIAF-14166 | HT1346 | 1084 | ATP2B4, ATPase, Ca+ transporting, plasma membrane 4 | TGATCCAAGG[G/A]AATGATTGA | S | G | A | G | G |
| G4552u1 | WIAF-13630 | HT0867 | 710 | ATP7A, ATPase, Cu++ transporting, alpha polypeptide (Menkes syndrome) | TACTAGCACT[A/G]TTGAAGGAAA | M | A | G | I | V |
| G456u1 | WIAF-10074 | HT2834 | 408 | EDN1, endothelin 1 | CCTGGGGGCT[T/G]CGCCGGTCCA | S | T | G | L | L |
| G456u2 | WIAF-10075 | HT2834 | 585 | EDN1, endothelin 1 | CAGACCCTGA[A/G]AATAGATCCC | S | A | G | E | E |
| G456a3 | WIAF-10507 | HT2834 | 861 | EDN1, endothelin 1 | TGAAAGGCAA[T/G]CCCTCCAGAG | M | T | G | K | N |
| G4565u1 | WIAF-14041 | HT28561 | 320 | ATP1G1, ATPase, Na+/K+ transporting, gamma 1 polypeptide | CGAGGTGCT[G/A]TTACGGCTCA | S | G | A | L | L |
| G4565u2 | WIAF-14062 | HT28561 | 216 | ATP1G1, ATPase, Na+/K+ transporting, gamma 1 polypeptide | CAGTGACGGG[G/A]ACAAAGGTCT | M | G | A | D | N |
| G4565u3 | WIAF-14063 | HT28561 | 315 | ATP1G1, ATPase, Na+/K+ transporting, gamma 1 polypeptide | ACCGCCGAGG[C/A]TGCTGTTACG | M | C | A | L | M |
| G4565u4 | WIAF-14064 | HT28561 | 531 | ATP1G1, ATPase, Na+/K+ transporting, gamma 1 polypeptide | TTTCCCCAGG[T/C]GAATGGGCTG | N | T | C | * | R |
| G4568u1 | WIAF-14212 | HT0082 | 717 | AMFR, autocrine motility factor receptor | TGCCTCATGC[A/G]TACGTCCCAC | M | A | G | I | V |
| G457a1 | WIAF-10489 | HT2903 | 321 | SELL, selectin L (lymphocyte adhesion molecule 1) | ACAAATCTCT[C/T]ACTGAAGAAG | S | C | T | L | L |
| G457a2 | WIAF-10490 | HT2903 | 577 | SELL, selectin L (lymphocyte adhesion molecule 1) | CCAGTGTCAG[T/C]TTGTGATTCA | M | T | C | F | L |
| G457a3 | WIAF-10491 | HT2903 | 601 | SELL, selectin L (lymphocyte adhesion molecule 1) | TGAGCCTTTG[G/C]AGGCCCCAGA | M | G | C | E | Q |
| G457a4 | WIAF-10492 | HT2903 | 637 | SELL, selectin L (lymphocyte adhesion molecule 1) | CTGTACTCAC[C/T]CTTTGGGAAA | M | C | T | P | S |
| G4573u1 | WIAF-13568 | HT28320 | 943 | MGAT2, mannosyl (alpha-1,6-)-glycoprotein beta-1,2-N-acetylglucosaminyltransferase | CGGACAACCT[G/T]ACCTGCGGT | S | G | T | L | L |
| G4574u1 | WIAF-13805 | HT0198 | 163 | beta-1,4 N-acetylgalactosaminyltransferase | CGGCCTCCGG[C/G]TACCTCTTGC | M | C | G | L | V |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G4574u2 | WIAF-13806 | HT0198 | 415 | beta-1,4 N-acetylgalactosaminyltransferase | TGCCACAAGA[G/A]AGCAGGAGTT | M | G | A | E | K |
| G4574u3 | WIAF-13807 | HT0198 | 726 | beta-1,4 N-acetylgalactosaminyltransferase | AACTACAACT[G/T]GTCACTTACA | S | G | T | L | L |
| G4574u4 | WIAF-13836 | HT0198 | 559 | beta-1,4 N-acetylgalactosaminyltransferase | AGGGGCTGAGC[C/A]TTCAGGCAGC | M | C | A | L | I |
| G4575u1 | WIAF-13626 | HT0341 | 1251 | GCNT1, glucosaminyl (N-acetyl) transferase 1, core 2 (beta-1,6-N-acetylglucosaminyltransferase) | AGTATGATCT[A/G]TCTGACATGC | S | A | G | L | L |
| G4577u1 | WIAF-13971 | HT1495 | 1268 | SIAT1, sialyltransferase 1 (beta-galactoside alpha-2,6-sialytransferase) | ATTTCTTTAA[C/T]AACTACAAGA | S | C | T | N | N |
| G458u1 | WIAF-10063 | HT2968 | 1464 | ALB, albumin | GTGCAGAAGA[C/A]TATCTATCCG | M | C | A | D | E |
| G458u2 | WIAF-10089 | HT2968 | 1470 | ALB, albumin | AAGACTATCT[A/C]TCCGTGGTCC | S | A | C | L | L |
| G458u3 | WIAF-10091 | HT2968 | 1707 | ALB, albumin | TTGTTGAGCT[C/T]GTGAAACACA | S | C | T | L | L |
| G458a4 | WIAF-10504 | HT2968 | 889 | ALB, albumin | CAGGGCGAC[C/T]TTTGCCAAGTA | M | C | T | L | F |
| G458a5 | WIAF-10508 | HT2968 | 1475 | ALB, albumin | TATCTATCCG[T/A]GGTCCTGAAC | M | T | A | V | E |
| G458a6 | WIAF-12091 | HT2968 | 1330 | ALB, albumin | CCAGAATGCG[C/T]TATTAGTTCG | S | C | T | L | L |
| G458a7 | WIAF-12092 | HT2968 | 1408 | ALB, albumin | CCTAGGAAAA[G/a]TGGGCAGCAA | M | G | a | V | M |
| G4592u1 | WIAF-14126 | HT2128 | 985 | branched-chain keto acid dehydrogenase E1, alpha polypeptide | ACCAGCCCTT[T/C]CTATCGAGG | S | T | C | F | F |
| G4593u1 | WIAF-13574 | HT97373 | 1743 | BARD1, BRCA1 associated RING domain 1 | GCTAGCCACT[G/C]CTCAGTAATG | M | G | C | C | S |
| G4593u2 | WIAF-13592 | HT97373 | 1167 | BARD1, BRCA1 associated RING domain 1 | TGTTCTTCAC[C/T]AACTTCATGC | M | C | T | P | L |
| G4593u3 | WIAF-13593 | HT97373 | 1591 | BARD1, BRCA1 associated RING domain 1 | AGAATGGGCA[C/T]GTGGATATAG | S | C | T | H | H |
| G4593u4 | WIAF-13594 | HT97373 | 2030 | BARD1, BRCA1 associated RING domain 1 | AAAGTATGAA[A/G]TTCCTGAAGG | M | A | G | I | V |
| G4593u5 | WIAF-13595 | HT97373 | 2006 | BARD1, BRCA1 associated RING domain 1 | AAGAAAAGTA[T/C]GTGAACAGGA | M | T | C | C | R |
| G4599u1 | WIAF-13920 | HT4273 | 1803 | CDH13, cadherin 13, H-cadherin (heart) | TCGTACCCGA[C/T]GTCTCCTACG | S | C | T | D | D |
| G4614u1 | WIAF-13733 | HT4835 | 91 | S100A3, S100 calcium-binding protein A3 | AGGATGCCA[G/A]AGCCTCTGGAG | M | G | A | R | K |
| G4614u2 | WIAF-13734 | HT4835 | 203 | S100A3, S100 calcium-binding protein A3 | TGCTGCAGAA[G/A]GAGCTGGCCA | S | G | A | K | K |
| G4614u3 | WIAF-13769 | HT4835 | 344 | S100A3, S100 calcium-binding protein A3 | TCTACTGCCA[C/T]GAGTACTTCA | S | C | T | H | H |
| G462u1 | WIAF-10134 | HT4753 | 600 | PDGFA, platelet-derived growth factor alpha polypeptide | ACGGGGTCCA[C/T]GCCACTAGC | S | C | T | H | H |
| G4627u1 | WIAF-14042 | HT0771 | 186 | ANX6, annexin VI (p68) | GGAGGCCATA[C/T]TGGACATAAT | S | C | T | L | L |
| G4627u2 | WIAF-14043 | HT0771 | 1664 | ANX6, annexin VI (p68) | CAGAACACC[T/C]AGTGGAGACA | S | T | C | P | P |
| G4627u3 | WIAF-14067 | HT0771 | 1498 | ANX6, annexin VI (p68) | AAGGAGACT[A/G]TCACAAGTCC | M | A | G | Y | C |
| G4644u1 | WIAF-13801 | HT1736 | 1990 | CPS1, carbamoyl-phosphate synthetase 1, mitochondrial | TGGTGAGAA[G/A]TCAGTGACAG | S | G | A | K | K |
| G4644u2 | WIAF-13802 | HT1736 | 1866 | CPS1, carbamoyl-phosphate synthetase 1, mitochondrial | ATTGGCTACC[C/T]AGTGATGATC | M | C | T | P | L |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G4644u3 | WIAF-13803 | HT1736 | 1993 | CPS1, carbamoyl-phosphate synthetase 1, mitochondrial | TGGAGAAGTC[A/C]GTGACAGTT | S | A | C | S | S |
| G4644u4 | WIAF-13804 | HT1736 | 1860 | CPS1, carbamoyl-phosphate synthetase 1, mitochondrial | GACACCATTG[G/A]CTACCCAGTG | M | G | A | G | D |
| G4644u5 | WIAF-13831 | HT1736 | 1087 | CPS1, carbamoyl-phosphate synthetase 1, mitochondrial | AGCCTGTTTT[G/T]AATATCACAA | M | G | T | L | F |
| G4644u6 | WIAF-13835 | HT1736 | 1958 | CPS1, carbamoyl-phosphate synthetase 1, mitochondrial | CACAAAGGCC[T/C]TTGCTATGAC | M | T | C | F | L |
| G4644u7 | WIAF-13855 | HT1736 | 1332 | CPS1, carbamoyl-phosphate synthetase 1, mitochondrial | AAAGCTACCA[C/A]CATTACATCA | M | C | A | T | N |
| G4659u1 | WIAF-14143 | HT1183 | 1830 | CTNNB1, catenin (cadherin-associated protein), beta 1 (88 kD) | GTGCCAACGT[T/C]CCCTCAACCGT | S | T | C | V | V |
| G466u1 | WIAF-10164 | U00968 | 2403 | SREBF1, sterol regulatory element binding transcription factor 1 | AGCAGTGCCC[G/A]CCAGGCCTGC | M | G | A | R | H |
| G4662u1 | WIAF-13710 | HT2142 | 2183 | CTNNB1, catenin (cadherin-associated protein), beta 1 (88 kD) | TTTTGTTCCG[A/C]ATGTCTGAGG | S | A | C | R | R |
| G467a1 | WIAF-13304 | X72861 | 827 | ADRB3, adrenergic, beta-3-, receptor | GGCCATCGCC[T/C]GGACTCCAG | M | T | C | W | R |
| G467a2 | WIAF-13305 | X72861 | 832 | ADRB3, adrenergic, beta-3-, receptor | TCGCCCTGGAC[T/A]CCGAGACTCC | S | T | A | T | T |
| G467a3 | WIAF-13306 | X72861 | 870 | ADRB3, adrenergic, beta-3-, receptor | TTCGTGACTT[C/T]GCTGGCCGCA | S | C | T | S | L |
| G467a4 | WIAF-13307 | X72861 | 1761 | ADRB3, adrenergic, beta-3-, receptor | TGCGCCGCCG[C/T]CCGCCCGCC | M | C | T | A | V |
| G467a5 | WIAF-13308 | X72861 | 1899 | ADRB3, adrenergic, beta-3-, receptor | TCTGTTGATC[A/C]GAACCTGTGG | — | A | C | — | — |
| G4671u1 | WIAF-13956 | HT1925 | 161 | NDUFB7, NADH dehydrogenase (ubiquinone) 1 beta subcomplex, 7 (18 kD, B18) | TGGTGCCAC[A/G]CAGCAGAGA | S | A | G | T | T |
| G4673u1 | WIAF-13889 | HT0191 | 1349 | CDC25A, cell division cycle 25A | TCTGGGCCA[G/C]CCCCAAAGAG | M | G | C | S | T |
| G4674u1 | WIAF-13821 | HT1393 | 261 | CDC25B, cell division cycle 25B | ACGACCTCGC[C/T]GGGCTCCGCA | S | C | T | A | A |
| G4674u2 | WIAF-13822 | HT1393 | 1297 | CDC25B, cell division cycle 25B | GATGGTTGGC[C/T]TATTGACGGG | S | C | T | L | L |
| G4674u3 | WIAF-13823 | HT1393 | 1083 | CDC25B, cell division cycle 25B | ATAAGCGGAG[G/A]CGGAGCGTGA | S | G | A | R | R |
| G4674u4 | WIAF-13827 | HT1393 | 1446 | CDC25B, cell division cycle 25B | AGAGCCCCAT[C/T]GCCGCCTGTA | S | C | T | H | H |
| G468a1 | WIAF-13309 | L37019 | 192 | ASIP, agouti (mouse)-signaling protein | AAATCCAAAC[C/A]GATCGGCAGA | M | C | A | P | Q |
| G4691u1 | WIAF-13753 | HT97602 | 179 | CMKBR9, chemokine (C-C motif) receptor 9 | TATAGCCTGA[T/A]TTTTGTGTTG | M | T | A | I | N |
| G4691u2 | WIAF-13754 | HT97602 | 134 | CMKBR9, chemokine (C-C motif) receptor 9 | AAGGATGCAG[T/C]GGTGTCCTTT | M | T | C | V | A |
| G4691u3 | WIAF-13755 | HT97602 | 193 | CMKBR9, chemokine (C-C motif) receptor 9 | TGTGTTGGGC[C/T]TCAGCGGGAA | M | C | T | L | F |
| G4691u4 | WIAF-13756 | HT97602 | 770 | CMKBR9, chemokine (C-C motif) receptor 9 | AAAAATAGCTG[C/T]AGCCTTGGTG | M | C | T | A | V |
| G4691u5 | WIAF-13759 | HT97602 | 1130 | CMKBR9, chemokine (C-C motif) receptor 9 | TCTGAGAACT[A/C]CCCTAACAAG | M | A | C | Y | S |
| G4691u6 | WIAF-13796 | HT97602 | 482 | CMKBR9, chemokine (C-C motif) receptor 9 | AGGCTGAGGA[C/A]CCGGGCCAAG | M | C | A | T | N |
| G4691u7 | WIAF-13797 | HT97602 | 259 | CMKBR9, chemokine (C-C motif) receptor 9 | GATGGTTGAG[A/G]TCTATCTGCT | M | A | G | I | V |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G4691u8 | WIAF-13798 | HT97602 | 434 | CMKBR9, chemokine (C-C motif) receptor 9 | ATGAGCCTGG[A/G]CAAGTACCTG | M | A | G | D | G |
| G4691u9 | WIAF-13799 | HT97602 | 755 | CMKBR9, chemokine (C-C motif) receptor 9 | CAGGGCCGGG[C/T]TTTAAAAATA | M | C | T | A | V |
| G4699u1 | WIAF-14040 | HT4277 | 1426 | BAAT, bile acid Coenzyme A: amino acid N-acyltransferase (glycine N-choloyltransferase) | TTCCAGATGT[G/T]ACCAGTCAAC | S | G | T | V | V |
| G4726u1 | WIAF-14128 | HT48614 | 1606 | AOC3, amine oxidase, copper containing 3 (vascular adhesion protein 1) | TCCACCCCAG[T/C]GGGGCCATAG | S | T | C | S | S |
| G4726u2 | WIAF-14129 | HT48614 | 2242 | AOC3, amine oxidase, copper containing 3 (vascular adhesion protein 1) | TTCCTAACAC[A/G]GTGACTGTGG | S | A | G | T | T |
| G4726u3 | WIAF-14141 | HT48614 | 659 | AOC3, amine oxidase, copper containing 3 (vascular adhesion protein 1) | CCTGCCCTAT[C/T]ACCGACGCCC | M | C | T | H | Y |
| G4744u1 | WIAF-13683 | HT2599 | 564 | CTH, cystathionase (cystathionine gamma-lyase) | ATATTGTCCA[T/C]AAGCATGGAG | S | T | C | H | H |
| G4748u1 | WIAF-14144 | HT1061 | 242 | CYBA, cytochrome b-245, alpha polypeptide | GGGACAGAAG[C/T]ACATGACCGC | M | C | T | H | Y |
| G4748u2 | WIAF-14145 | HT1061 | 265 | CYBA, cytochrome b-245, alpha polypeptide | TGGTGAAGCT[G/C]TTCGGGCCCT | S | G | C | L | L |
| G4750u1 | WIAF-14116 | HT48417 | 156 | CYB5, cytochrome b-5 | TGAAGTACTA[C/T]ACCCTAGAGG | S | C | T | Y | Y |
| G4751u1 | WIAF-13770 | HT1285 | 495 | UQCRC2, ubiquinol-cytochrome c reductase core protein II | AGAATTTCGT[C/A]GTTGGGAAGT | M | C | A | R | S |
| G4788u1 | WIAF-13931 | HT28249 | 1864 | DSC3, desmocollin 3 | CTGTTGATCC[T/C]GATGAACCTG | S | T | C | R | R |
| G4788u2 | WIAF-13933 | HT28249 | 2000 | DSC3, desmocollin 3 | TGGATTTCAA[G/T]AATATACCAT | N | G | T | E | * |
| G4788u3 | WIAF-13945 | HT28249 | 2524 | DSC3, desmocollin 3 | ACACTTACTC[G/A]GAGTGGCACA | S | G | A | S | S |
| G479u1 | WIAF-12567 | U36310 | 894 | GPD2, glycerol-3-phosphate dehydrogenase 2 (mitochondrial) | GGGAAAGTGC[A/G]TGTGAGCGGC | M | A | G | H | R |
| G479u2 | WIAF-12574 | U36310 | 1657 | GPD2, glycerol-3-phosphate dehydrogenase 2 (mitochondrial) | CTGGCAAAAG[G/T]TGGCCTATTG | M | G | T | R | S |
| G479u3 | WIAF-12575 | U36310 | 1131 | GPD2, glycerol-3-phosphate dehydrogenase 2 (mitochondrial) | GTTATTTTCT[T/C]CTTACCCTGG | M | T | C | F | S |
| G480u1 | WIAF-12575 | HT336 | 250 | GRB2, growth factor receptor-bound protein 2 | AATGAAACCA[C/A]ATCCGTGGTT | M | C | A | H | N |
| G4819u1 | WIAF-13985 | HT97576 | 1804 | EYA1, eyes absent (Drosophila) homolog 1 | CCCTGCACCA[T/C]GCCTTGGAAC | S | T | C | H | H |
| G482u1 | WIAF-12181 | J04501 | 1186 | GYS1, glycogen synthase 1 (muscle) | CTGACGTCTT[T/C]CTGGAGGCAT | S | T | C | F | F |
| G482u2 | WIAF-12195 | J04501 | 1406 | GYS1, glycogen synthase 1 (muscle) | CCTTCCCGAC[A/G]TGAACAAGAT | M | A | G | M | V |
| G4827u1 | WIAF-14177 | HT97477 | 68 | elongation | CGAGCTGGCC[A/G]TGATGGTGAT | M | A | G | H | R |
| G483a1 | WIAF-12113 | HT4341 | 1850 | GSY2 | TTACCAGCAT[G/T]CCAGACACCT | M | G | T | A | S |
| G483u2 | WIAF-12148 | HT4341 | 1130 | GSY2 | GTTTTTCATT[A/C]TGCCTGCCAA | M | A | C | M | L |
| G483u3 | WIAF-12149 | HT4341 | 880 | GSY2 | GCTTGAATGT[T/G]AAGAAATTTT | S | T | G | V | V |
| G483u4 | WIAF-12150 | HT4341 | 1115 | GSY2 | CATCAGGTG[G/A]TTGTGTTTTT | M | G | A | V | M |
| G483u5 | WIAF-12156 | HT4341 | 1230 | GSY2 | GAAAGTTTG[G/A]AAAAAAACTC | M | G | A | G | E |
| G483u6 | WIAF-12159 | HT4341 | 2033 | GSY2 | TGAGAGATAC[G/A]ATGAGGAAGA | M | G | A | D | N |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G483u7 | WIAF-12160 | HT4341 | 1836 | GSY2 | TACTTAGGCA[G/C]ATATTACCAG | M | G | C | R | T |
| G483u8 | WIAF-12161 | HT4341 | 1678 | GSY2 | CTTACGTAT[T/C]TACATCGTTG | S | T | C | I | I |
| G483u9 | WIAF-12177 | HT4341 | 790 | GSY2 | GCGCTCACG[G/C]TTCACCACGG | S | G | C | V | V |
| G483u10 | WIAF-12188 | HT4341 | 1728 | GSY2 | TGCAATCAGC[T/C]GACTAAGTTT | M | T | C | L | P |
| G484u1 | WIAF-12151 | HT5111 | 487 | GSY3 | CATCAAGTG[A/G]TTGCAATGG | M | A | G | I | V |
| G484u2 | WIAF-12187 | HT5111 | 1141 | GSY3 | AACCCGGAA[C/T]AAATCCGAGA | N | C | T | Q | * |
| G489u1 | WIAF-12152 | HT2607 | 1181 | IRS1, insulin receptor substrate 1 | AAGAAGTGGC[G/A]GCACAAGTCG | M | G | A | R | Q |
| G489u2 | WIAF-12184 | HT2607 | 1031 | IRS1, insulin receptor substrate 1 | ATGGCCAGCC[C/T]TCCGGAGAC | M | C | T | P | L |
| G492a1 | WIAF-13345 | L08603 | 307 | MC4R, melanocortin 4 receptor | AGAAACCATT[A/G]TCATCACCCT | M | A | G | I | V |
| G493u1 | WIAF-12154 | X67594 | 346 | MC1R, melanocortin 1 receptor (alpha melanocyte stimulating hormone receptor) | CGCGCTCGTG[G/T]TGGCCACCAT | M | G | T | V | L |
| G493u2 | WIAF-12167 | X67594 | 646 | MC1R, melanocortin 1 receptor (alpha melanocyte stimulating hormone receptor) | GACCCTGCCG[C/T]GGGGCGCGCA | M | C | T | R | W |
| G493u3 | WIAF-12170 | X67594 | 1110 | MC1R, melanocortin 1 receptor (alpha melanocyte stimulating hormone receptor) | AGGTGCTGAC[A/G]TGCTCCTGGT | S | A | G | T | T |
| G493u4 | WIAF-12186 | X67594 | 442 | MC1R, melanocortin 1 receptor (alpha melanocyte stimulating hormone receptor) | CGGGAGCAAC[G/T]TGCTGGAGAC | M | G | T | V | L |
| G498u1 | WIAF-11809 | J04127 | 1305 | CYP19, cytochrome P450, subfamily XIX (aromatization of androgens) | CTTATAGGTA[C/T]TTTCAGCCAT | S | C | T | Y | Y |
| G498u2 | WIAF-11810 | J04127 | 1377 | CYP19, cytochrome P450, subfamily XIX (aromatization of androgens) | TGAAAGCCAT[C/T]CTCGTTACAC | S | C | T | I | I |
| G498u3 | WIAF-11811 | J04127 | 1406 | CYP19, cytochrome P450, subfamily XIX (aromatization of androgens) | CGATTCCACG[T/C]GAAGACATTG | M | T | C | V | A |
| G498u4 | WIAF-11838 | J04127 | 1055 | CYP19, cytochrome P450, subfamily XIX (aromatization of androgens) | ATTGGTGAGA[G/A]AGACATAAAG | M | G | A | R | K |
| G498u5 | WIAF-11800 | J04127 | 1001 | CYP19, cytochrome P450, subfamily XIX (aromatization of androgens) | ATTGCAAAGC[A/G]CCCTAATGTT | M | A | G | H | R |
| G499u1 | WIAF-11785 | HT1439 | 2142 | ESR1, estrogen receptor 1 | TCCCTGCCAC[A/G]GTCGAGAGC | S | A | G | T | T |
| G499u2 | WIAF-11801 | HT1439 | 443 | ESR1, estrogen receptor 1 | CCCCTGAACC[G/A]TCCGCAGCTC | S | G | A | R | H |
| G500u1 | WIAF-11803 | X99101 | 793 | ESR1, estrogen receptor 1 | CATGAGCAGG[T/C]CGGCCAAGAA | M | T | C | W | R |
| G500u2 | WIAF-11816 | X99101 | 489 | ESR1, estrogen receptor 1 | GGAAGTGTTA[C/T]TGAAGTGGAA | S | C | T | Y | Y |
| G500u3 | WIAF-11817 | X99101 | 474 | ESR1, estrogen receptor 1 | AGGCCTGCCG[A/G]CTTCGGAAGT | M | A | G | R | R |
| G505u1 | WIAF-11824 | HT1113 | 1063 | PRLR, prolactin receptor | GCTTTGAAGG[G/A]CTATAGCATG | S | G | A | G | D |
| G505u2 | WIAF-11827 | HT1113 | 2083 | PRLR, prolactin receptor | GCAACATCAA[G/A]TCAAGTCAGT | M | G | A | S | N |
| G505u3 | WIAF-11787 | HT1113 | 582 | PRLR, prolactin receptor | GAGGACATAC[A/G]TCATGATGGT | M | A | G | I | V |
| G505u4 | WIAF-11802 | HT1113 | 792 | PRLR, prolactin receptor | CCTGTATGAA[A/C]TTCGATTAAA | M | A | C | H | L |
| G509u1 | WIAF-11789 | M32313 | 378 | SRD5A1, steroid-5-alpha-reductase, alpha polypeptide 1 (3-oxo-5 alpha-steroid delta 4-dehydrogenase alpha 1) | CACTGTTGGC[A/G]TGTACAATGG | S | A | G | A | A |
| G510a1 | WIAF-13348 | U17280 | 582 | STAR, steroidogenic acute regulatory protein | CCAATGTCAA[G/A]AGAGATCAAGG | S | G | A | K | K |
| G52u1 | WIAF-10224 | HT0488 | 1139 | inhibin, beta B | CCAACATGAT[T/C]GTGGAGGAGT | S | T | C | I | I |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G520u1 | WIAF-13507 | D31770 | 517 | ACVR2, activin A receptor, type II | CTTATTTCC[G/A]GAGATGAAAG | S | G | A | P | P |
| G520u2 | WIAF-13532 | D31770 | 1177 | ACVR2, activin A receptor, type II | CAGCTTGCAT[T/G]GCTGACTTTG | M | T | G | I | M |
| G520u3 | WIAF-13533 | D31770 | 1189 | ACVR2, activin A receptor, type II | CTGACTTTGG[G/C]TTGGCCTTAA | S | G | C | G | G |
| G520u4 | WIAF-13534 | D31770 | 1024 | ACVR2, activin A receptor, type II | TCTCTTGGAA[T/C]GAACTGTGTC | S | T | C | N | N |
| G523u1 | WIAF-12155 | HT4996 | 538 | OXTR, oxytocin receptor | TGAGCGGGAA[C/T]GCGTGTGTGC | S | C | T | N | N |
| G523u2 | WIAF-12180 | HT4996 | 1057 | OXTR, oxytocin receptor | TCTGGCAGAA[C/T]TTGCGGCTCA | S | C | T | N | N |
| G524a1 | WIAF-13349 | L05144 | 190 | PCK1, phosphoenolpyruvate carboxykinase 1 (soluble) | TGGACAGCCT[G/A]CCCCAGGCAG | S | G | A | L | L |
| G528u1 | WIAF-11831 | V00572 | 988 | PGK1, phosphoglycerate kinase 1 | AAGCCACTGT[G/C]GCTTCTGGCA | S | G | C | V | V |
| G53u1 | WIAF-10307 | HT0508 | 723 | DNA repair protein XRCC1 | CCAGCAGCCC[G/A]GCAGGACCTA | S | G | A | P | P |
| G53u2 | WIAF-10308 | HT0508 | 746 | DNA repair protein XRCC1 | TATGCAGCTG[C/T]TACCCTCCAG | M | C | T | A | V |
| G53u3 | WIAF-10309 | HT0508 | 1884 | DNA repair protein XRCC1 | GGGATCCCAG[C/T]TTTGAGGAGG | S | C | T | S | S |
| G53u4 | WIAF-10362 | HT0508 | 425 | DNA repair protein XRCC1 | AACCCCAACC[G/A]CGTTCGCATG | M | G | A | R | H |
| G534a1 | WIAF-13310 | U28281 | 1284 | SCTR, secretin receptor | GCTTCCTCAA[T/C]GGGGAGGTGC | S | T | C | N | N |
| G534a2 | WIAF-13311 | U28281 | 1404 | SCTR, secretin receptor | AGCAGCCCA[G/C]GGCACCTGCA | S | G | C | Q | Q |
| G535u1 | WIAF-12157 | HT5001 | 1158 | SHC1 | ATGCTCTTCG[G/C]GTGCCTCCAC | S | G | C | R | R |
| G535u2 | WIAF-12196 | HT5001 | 774 | SHC1 | ATGAGGAGGA[G/A]GAAGAGCCAC | S | G | A | E | E |
| G536u1 | WIAF-13923 | M20747 | 535 | SLC2A4, solute carrier family 2 (facilitated glucose transporter), member 4 | GCCTGGCCAA[C/T]GCTGCTGCCT | S | C | T | N | N |
| G538u1 | WIAF-11812 | M55531 | 438 | SLC2A5, solute carrier family 2 (facilitated glucose transporter), member 5 | GCAGCAGAGT[C/T]GCCACATCAT | S | C | T | V | V |
| G538u2 | WIAF-11813 | M55531 | 124 | SLC2A5, solute carrier family 2 (facilitated glucose transporter), member 5 | GACGCTTGTG[C/T]TTGCCCTGGC | M | C | T | L | F |
| G538u3 | WIAF-11791 | M55531 | 816 | SLC2A5, solute catalyzed glucose transporter), member 5 | ACAGGGAGGT[G/A]GCCGAGATCC | S | G | A | V | V |
| G539u1 | WIAF-12158 | K03195 | 224 | Human (HepG2) glucose transporter gene mRNA, complete cds. | TCATGCTGGC[T/C]GTGGAGGAG | S | T | C | A | A |
| G539u2 | WIAF-12191 | K03195 | 1244 | Human (HepG2) glucose transporter gene mRNA, complete cds. | CCATGCGCCT[A/G]GCACTGCTGG | S | A | G | L | L |
| G540a1 | WIAF-12114 | HT960 | 1100 | SOS1 | AGTGAAGATC[A/C]AGAAGACAAG | M | A | C | Q | P |
| G540a2 | WIAF-12165 | HT960 | 933 | SOS1 | ATGATCGTTT[C/T]CTTAGTCAGT | S | C | T | F | F |
| G540u3 | WIAF-12178 | HT960 | 399 | SOS1 | TAGTAGCACC[T/C]TTTAGAATACA | S | T | C | V | V |
| G540u4 | WIAF-12193 | HT960 | 195 | SOS1 | CTCAGCCCCG[A/C]AGTGCTTCAG | S | A | C | R | R |
| G540u5 | WIAF-12197 | HT960 | 1329 | SOS1 | GTTGTAATGA[A/G]TTTATAATTGG | S | A | G | E | E |
| G540u6 | WIAF-12198 | HT960 | 1339 | SOS1 | ATTTATAATG[G/A]AAGGAACTCT | M | G | A | E | K |
| G543a1 | WIAF-13312 | J00306 | 1373 | SST, somatostatin | AAGCAGGAAC[T/C]TGGCCAAGTAC | S | T | C | L | P |
| G543a2 | WIAF-13313 | J00306 | 1603 | SST, somatostatin | AGTATTGTCC[A/G]TATCAGACCT | – | A | G | – | I |
| G544u1 | WIAF-12174 | HT27489 | 982 | SUR, sulfonylurea receptor (hyperinsulinemia) | CCATTGACAT[G/C]GCCACGAAAA | M | G | C | M | I |
| G546u1 | WIAF-13618 | HT225 | 426 | TKT, transketolase (Wernicke-Korsakoff syndrome) | GCTACATTGC[C/T]GAGCAGAACA | S | C | T | A | A |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G551u1 | WIAF-11709 | HT1118 | 257 | TNFRSF1B, tumor necrosis factor receptor superfamily, member 1B | GCTGCAGCAA[A/G]TGCTCGCCGG | S | A | G | K | K |
| G551u2 | WIAF-11710 | HT1118 | 449 | TNFRSF1B, tumor necrosis factor receptor superfamily, member 1B | TCTGCACCTG[C/T]AGGCCCGGCT | S | C | T | C | C |
| G551u3 | WIAF-11719 | HT1118 | 648 | TNFRSF1B, tumor necrosis factor receptor superfamily, member 1B | GATCTGCTAAC[G/A]TGGTGGCCAT | M | G | A | V | M |
| G551u4 | WIAF-11673 | HT1118 | 676 | TNFRSF1B, tumor necrosis factor receptor superfamily, member 1B | AATGCAAGCA[T/G]GGATGCAGTC | M | T | G | M | R |
| G551u5 | WIAF-11720 | HT1118 | 808 | TNFRSF1B, tumor necrosis factor receptor superfamily, member 1B | CCAAGCACCT[C/T]CTTCCTGCTC | M | C | T | S | F |
| G552u1 | WIAF-12229 | HT5108 | 384 | TRAP3 | GCCGCTGCCC[G/A]CTTCATGCTGA | S | G | A | P | P |
| G555u1 | WIAF-12211 | U94592 | 478 | UCP2, uncoupling protein 2 (mitochondrial, proton carrier) | CCGCTACAG[T/C]CAGCGCCCAG | M | T | C | V | A |
| G556u1 | WIAF-11804 | AF001787 | 480 | UCP2, uncoupling protein 2 (mitochondrial, proton carrier) | TCGGCCTCTA[T/C]GACTCCGTCA | S | T | C | Y | Y |
| G556u2 | WIAF-11805 | AF001787 | 563 | UCP2, uncoupling protein 2 (mitochondrial, proton carrier) | TGCACCACAG[G/A]AGCCATGGCG | M | G | A | G | E |
| G556u3 | WIAF-11823 | AF001787 | 1113 | UCP2, uncoupling protein 2 (mitochondrial, proton carrier) | TACGGGAATC[A/G]CCGTTTTGAA | S | A | G | S | S |
| G556u4 | WIAF-11782 | AF001787 | 386 | UCP2, uncoupling protein 2 (mitochondrial, proton carrier) | ATCCTGACCA[T/C]GGTGCGGACT | M | T | C | M | T |
| G561a1 | WIAF-12111 | HT1176 | 2430 | IDE, insulin-degrading enzyme | ACTGTGGCAT[C/A]AGAGATATACT | S | C | A | H | H |
| G561u2 | WIAF-12222 | HT1176 | 3099 | IDE, insulin-degrading enzyme | ATATTAACTT[C/G]ATGGCTGCAA | M | C | G | F | L |
| G562u1 | WIAF-12223 | HT27503 | 680 | tumor necrosis factor receptor type 1 associated protein | CCTGTAGTGA[A/C]TCGGCCGCTG | M | A | C | N | T |
| G562u2 | WIAF-12224 | HT27503 | 900 | tumor necrosis factor receptor type 1 associated protein | CGCTGAGCG[C/A]CTGGTGAGG | S | C | A | R | R |
| G573u1 | WIAF-12199 | HT28094 | 469 | SSTR1, somatostatin receptor 1 | GGACCGCTAC[G/C]TGGCCGTGGT | M | G | C | V | L |
| G573u2 | WIAF-12208 | HT28094 | 480 | SSTR1, somatostatin receptor 1 | TGGCCGTGGT[G/A]CATCCCATCA | S | G | A | V | V |
| G573u3 | WIAF-12209 | HT28094 | 879 | SSTR1, somatostatin receptor 1 | TGCAGCTGGT[T/C]AACGTGTTTG | S | T | C | V | V |
| G574u1 | WIAF-11822 | HT4058 | 1054 | SSTR5, somatostatin receptor 5 | GCCACCGAGC[C/T]GCCTCCAGAC | M | C | T | P | L |
| G575u1 | WIAF-12200 | HT28095 | 99 | SSTR3, somatostatin receptor 3 | ACGTGTCGG[C/G]AGGCCAAGCC | M | C | G | A | A |
| G575u2 | WIAF-12217 | HT28095 | 453 | SSTR3, somatostatin receptor 3 | CCACCGCTC[G/A]GCCCCGCTGGC | S | G | A | A | S |
| G585u1 | WIAF-12204 | HT1022 | 1133 | PYGL, phosphorylase, glycogen; liver (Hers disease, glycogen storage disease type VI) | AGCTGAATGA[T/C]ACTCACCCTC | S | T | C | D | D |
| G585u2 | WIAF-12205 | HT1022 | 1988 | PYGL, phosphorylase, glycogen; liver (Hers disease, glycogen storage disease type VI) | AGCTGATCAC[T/C]TCAGTGGCAG | S | T | C | T | T |
| G585u3 | WIAF-12225 | HT1022 | 1883 | PYGL, phosphorylase, glycogen; liver (Hers disease, glycogen storage disease type VI) | TGTACAACCG[C/T]ATTAAGAAAG | S | C | T | R | R |
| G585u4 | WIAF-12226 | HT1022 | 2037 | PYGL, phosphorylase, glycogen; liver (Hers disease, glycogen storage disease type VI) | AAGCAAGTTG[A/G]AAGTCATCTT | M | A | G | K | E |
| G585u5 | WIAF-12231 | HT1022 | 1387 | PYGL, phosphorylase, glycogen; liver (Hers disease, glycogen storage disease type VI) | GATGTGGACC[C/G]TCTGAGAAGG | M | C | G | P | R |
| G586a1 | WIAF-12112 | HT1878 | 2410 | PFKM, phosphofructokinase, muscle | CCGGGAAGC[T/G]GCCGTCTAAA | S | T | G | A | A |

| Poly ID | WIAF ID | Genbank or TIGR Accession Number | Position in Sequence | Gene Description | Flanking Seq | Mutation Type | Ref NT | Alt NT | Ref AA | Alt AA |
|---------|---------|----------------------------------|----------------------|------------------|--------------|---------------|--------|--------|--------|--------|
| G586u2 | WIAF-12206 | HT1878 | 375 | PFKM, phosphofructokinase, muscle | GGACGACTCC[G/A]AGCTGCTAC | M | G | A | R | Q |
| G586u3 | WIAF-12207 | HT1878 | 322 | PFKM, phosphofructokinase, muscle | TGGGAGGCAC[G/A]GTGATTGGAA | S | G | A | T | T |
| G586u4 | WIAF-12227 | HT1878 | 334 | PFKM, phosphofructokinase, muscle | TGATTGGAAG[T/C]GCCGGTGCA | S | T | C | S | S |
| G586u5 | WIAF-12228 | HT1878 | 408 | PFKM, phosphofructokinase, muscle | CGTGGGATCA[C/G]CAATCTCTGT | M | C | G | T | S |
| G586u6 | WIAF-12235 | HT1878 | 717 | PFKM, phosphofructokinase, muscle | CACGTGGAT[A/G]CCTGGCCTT | M | A | G | Y | C |
| G587u1 | WIAF-12615 | HT3847 | 366 | phosphofructokinase, muscle | ATGGCAGCCT[T/C]ACAGGTGCCA | S | T | C | L | L |
| G589u1 | WIAF-12210 | L39211 | 1327 | CPT1A, carnitine palmitoyltransferase I, liver | CAGCGTTCTT[C/T]GTGACGTTAG | S | C | T | F | F |
| G589u2 | WIAF-12215 | L39211 | 2080 | CPT1A, carnitine palmitoyltransferase I, liver | AATATCTCGC[T/C]GTGGAGTCCC | S | T | C | A | A |
| G589u3 | WIAF-12216 | L39211 | 679 | CPT1A, carnitine palmitoyltransferase I, liver | ACTTCAAACG[G/T]TATGACAGCAC | S | G | T | R | R |
| G589u4 | WIAF-12218 | L39211 | 1844 | CPT1A, carnitine palmitoyltransferase I, liver | CCTCACATAC[G/C]AGGCCTCCAT | M | G | C | E | Q |
| G592u1 | WIAF-11814 | X96586 | 1089 | NSMAF, neutral sphingomyelinase (N-SMase) activation associated factor | TCCGGGATCT[C/T]AGTAAGCCAG | S | C | T | L | L |
| G592u2 | WIAF-11815 | X96586 | 2020 | NSMAF, neutral sphingomyelinase (N-SMase) activation associated factor | AAGTATATCA[T/G]TTTCAAATAT | M | T | G | F | V |
| G592u3 | WIAF-11834 | X96586 | 1673 | NSMAF, neutral sphingomyelinase (N-SMase) activation associated factor | GTAGCCATGC[T/C]TACGCAAATC | M | T | C | L | P |
| G592u4 | WIAF-11784 | X96586 | 1889 | NSMAF, neutral sphingomyelinase (N-SMase) activation associated factor | CACGAGCACT[A/G]TAAAATCCAC | M | A | G | Y | C |
| G592u5 | WIAF-11798 | X96586 | 1677 | NSMAF, neutral sphingomyelinase (N-SMase) activation associated factor | CCATGCTTAC[G/A]CAAATCTTGG | S | G | A | T | T |
| G592u6 | WIAF-11799 | X96586 | 2429 | NSMAF, neutral sphingomyelinase (N-SMase) activation associated factor | TGCCATTCAG[G/C]GATTGTATGT | M | G | C | G | A |
| G592a7 | WIAF-13156 | X96586 | 2205 | NSMAF, neutral sphingomyelinase (N-SMase) activation associated factor | ATTCTGCATC[G/A]TGGGACTCTA | S | G | A | S | S |
| G594u1 | WIAF-10065 | HT3921 | 1153 | annexin V, alt. transcript 2 | TTGTGAAATC[T/A]ATTCGAAGTA | S | T | A | S | S |
| G594u2 | WIAF-10098 | HT3921 | 567 | annexin V, alt. transcript 2 | CGAAGTAATG[C/T]TCAGCGCCAG | M | C | T | A | V |
| G594u3 | WIAF-10099 | HT3921 | 774 | annexin V, alt. transcript 2 | ATTGCTTCAA[G/C]GACACCTGAA | M | G | C | R | T |
| G594a4 | WIAF-10505 | HT3921 | 424 | annexin V, alt. transcript 2 | GAGTAGTCGC[C/T]ATGGCACAGG | – | C | T | – | – |
| G594a5 | WIAF-13123 | HT3921 | 571 | annexin V, alt. transcript 2 | GTAATGCTCA[G/C]CGCCAGGAAA | M | G | C | Q | H |
| G595u1 | WIAF-12203 | HT27983 | 1008 | NRIP1, nuclear receptor interacting protein 1 | TGCAAGATTA[C/T]AGGCTGTTGC | N | C | T | Q | * |
| G595u2 | WIAF-12220 | HT27983 | 785 | NRIP1, nuclear receptor interacting protein 1 | CCCTCAGTCA[T/C]GATTCTTTAA | S | T | C | H | H |
| G595u3 | WIAF-12232 | HT27983 | 1231 | NRIP1, nuclear receptor interacting protein 1 | GTTGGCAGTT[A/T]CCAGCTCCCA | M | A | T | Y | F |
| G595u4 | WIAF-12261 | HT27983 | 2048 | NRIP1, nuclear receptor interacting protein 1 | GCAGTACTCA[G/A]TCTGAAAGC | S | G | A | Q | Q |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G595u5 | WIAF-12274 | HT27983 | 2376 | NRIP1, nuclear receptor interacting protein 1 | TCCTGAACCA[G/T]GGCTTTCTGG | M | G | T | G | W |
| G595u6 | WIAF-12275 | HT27983 | 3498 | NRIP1, nuclear receptor interacting protein 1 | ACTATATTAC[A/G]TGCTTCAAAA | M | A | G | M | V |
| G595u7 | WIAF-12276 | HT27983 | 3671 | NRIP1, nuclear receptor interacting protein 1 | ACAATAGCCA[T/C]ATGGAAATA | S | T | C | H | H |
| G595u8 | WIAF-12294 | HT27983 | 2020 | NRIP1, nuclear receptor interacting protein 1 | ATCAAATGGA[A/G]TTCCCACCA | M | A | G | N | S |
| G595u9 | WIAF-12295 | HT27983 | 3140 | NRIP1, nuclear receptor interacting protein 1 | ATTTGTCCCC[G/A]CACAGAGTA | S | G | A | P | P |
| G596u1 | WIAF-10144 | HT3537 | 3299 | PC, pyruvate carboxylase | TGCGGTCCAT[C/T]TTGGTCAAGG | S | C | T | I | I |
| G596u2 | WIAF-10158 | HT3537 | 2662 | PC, pyruvate carboxylase | ACCAACCTGC[A/C]CTTCCAGGCC | M | A | C | H | P |
| G596u3 | WIAF-10159 | HT3537 | 2156 | PC, pyruvate carboxylase | CCATTCATA[C/A]ACGGCGACG | N | C | A | Y | * |
| G598a1 | WIAF-12118 | HT48666 | 5585 | HERC1, hect (homologous to the E6 AP (UBE3A) carboxyl terminus) domain and RCC1 (CHC1)-like domain (RLD) 1 | GGGACCTATG[C/T]TGATAAACTG | M | C | T | A | V |
| G598u2 | WIAF-12236 | HT48666 | 4456 | HERC1, hect (homologous to the E6 AP (UBE3A) carboxyl terminus) domain and RCC1 (CHC1)-like domain (RLD) 1 | CCTGTTAATA[T/C]TAGGAGTAAG | S | T | C | L | L |
| G598u3 | WIAF-12237 | HT48666 | 6356 | HERC1, hect (homologous to the E6 AP (UBE3A) carboxyl terminus) domain and RCC1 (CHC1)-like domain (RLD) 1 | GGTAATGAAG[G/T]CACGTGTGTT | M | G | T | G | V |
| G598u4 | WIAF-12240 | HT48666 | 12219 | HERC1, hect (homologous to the E6 AP (UBE3A) carboxyl terminus) domain and RCC1 (CHC1)-like domain (RLD) 1 | GTACCTTTGT[C/T]ATCCAGGCCA | S | C | T | V | V |
| G598u5 | WIAF-12241 | HT48666 | 12480 | HERC1, hect (homologous to the E6 AP (UBE3A) carboxyl terminus) domain and RCC1 (CHC1)-like domain (RLD) 1 | CCAGGCAGAT[C/G]GAGGCCTTAC | M | C | G | I | M |
| G598u6 | WIAF-12244 | HT48666 | 12975 | HERC1, hect (homologous to the E6 AP (UBE3A) carboxyl terminus) domain and RCC1 (CHC1)-like domain (RLD) 1 | GAGTAATCAT[T/A]GAAGATGTGG | S | T | A | I | I |
| G598u7 | WIAF-12245 | HT48666 | 1424 | HERC1, hect (homologous to the E6 AP (UBE3A) carboxyl terminus) domain and RCC1 (CHC1)-like domain (RLD) 1 | TCCAATAATC[A/T]GTCAACTTTA | M | A | T | Q | L |
| G598u8 | WIAF-12250 | HT48666 | 5854 | HERC1, hect (homologous to the E6 AP (UBE3A) carboxyl terminus) domain and RCC1 (CHC1)-like domain (RLD) 1 | TTCAAAGCA[A/T]TTCAATCAAA | M | A | T | H | F |
| G598u9 | WIAF-12251 | HT48666 | 6754 | HERC1, hect (homologous to the E6 AP (UBE3A) carboxyl terminus) domain and RCC1 (CHC1)-like domain (RLD) 1 | TATTCAGCTC[G/A]TCCGTATCCT | M | G | A | V | I |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G598u10 | WIAF-12252 | HT48666 | 7635 | HERC1, hect (homologous to the E6 AP (UBE3A) carboxyl terminus) domain and RCC1 (CHC1)-like domain (RLD) 1 | ATCTTTACCT[C/T]GGTGCTATGA | S | C | T | L | L |
| G598u11 | WIAF-12254 | HT48666 | 9189 | HERC1, hect (homologous to the E6 AP (UBE3A) carboxyl terminus) domain and RCC1 (CHC1)-like domain (RLD) 1 | GTGGAAATCC[A/G]TATAACCTGT | S | A | G | P | P |
| G598u12 | WIAF-12255 | HT48666 | 10119 | HERC1, hect (homologous to the E6 AP (UBE3A) carboxyl terminus) domain and RCC1 (CHC1)-like domain (RLD) 1 | TTGTGGCATT[G/C]CTAGCAGACA | M | G | C | L | P |
| G598u13 | WIAF-12257 | HT48666 | 11109 | HERC1, hect (homologous to the E6 AP (UBE3A) carboxyl terminus) domain and RCC1 (CHC1)-like domain (RLD) 1 | ATCCATCTAT[T/C]GTAAATGGCA | S | T | C | H | H |
| G598u14 | WIAF-12258 | HT48666 | 13513 | HERC1, hect (homologous to the E6 AP (UBE3A) carboxyl terminus) domain and RCC1 (CHC1)-like domain (RLD) 1 | CTATGGACCT[C/T]AGATAACTGT | N | C | T | Q | * |
| G598u15 | WIAF-12259 | HT48666 | 13697 | HERC1, hect (homologous to the E6 AP (UBE3A) carboxyl terminus) domain and RCC1 (CHC1)-like domain (RLD) 1 | ACCATCACAG[A/G]GATGTGCCAG | M | A | G | E | G |
| G598u16 | WIAF-12265 | HT48666 | 1098 | HERC1, hect (homologous to the E6 AP (UBE3A) carboxyl terminus) domain and RCC1 (CHC1)-like domain (RLD) 1 | CCCTTTACGA[G/A]GCAGCATTAT | S | G | A | E | E |
| G598u17 | WIAF-12272 | HT48666 | 6079 | HERC1, hect (homologous to the E6 AP (UBE3A) carboxyl terminus) domain and RCC1 (CHC1)-like domain (RLD) 1 | TATGTGGGAG[A/G]CACCCATTGC | M | A | G | T | A |
| G598u18 | WIAF-12273 | HT48666 | 9551 | HERC1, hect (homologous to the E6 AP (UBE3A) carboxyl terminus) domain and RCC1 (CHC1)-like domain (RLD) 1 | AAGAGCTCCT[C/T]TGGAGAATA | M | C | T | S | F |
| G598u19 | WIAF-12277 | HT48666 | 666 | HERC1, hect (homologous to the E6 AP (UBE3A) carboxyl terminus) domain and RCC1 (CHC1)-like domain (RLD) 1 | GTCTTTGCAA[C/T]GATGTCATTC | S | C | T | N | N |
| G598u20 | WIAF-12278 | HT48666 | 882 | HERC1, hect (homologous to the E6 AP (UBE3A) carboxyl terminus) domain and RCC1 (CHC1)-like domain (RLD) 1 | GCTCATTGCG[A/G]TATCTTCTTG | S | A | G | R | R |
| G598u21 | WIAF-12279 | HT48666 | 893 | HERC1, hect (homologous to the E6 AP (UBE3A) carboxyl terminus) domain and RCC1 (CHC1)-like domain (RLD) 1 | TATCTTCTTG[A/T]ATGGATAGAA | M | A | T | E | V |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G598u22 | WIAF-12280 | HT48666 | 13276 | HERC1, hect (homologous to the E6 AP (UBE3A) carboxyl terminus) domain and RCC1 (CHC1)-like domain (RLD) 1 | AGAAGTCAGC[A/G]TTCACACGGT | M | A | G | I | V |
| G598u23 | WIAF-12283 | HT48666 | 6519 | HERC1, hect (homologous to the E6 AP (UBE3A) carboxyl terminus) domain and RCC1 (CHC1)-like domain (RLD) 1 | CCTGTGTGTT[A/T]GACATGAAAG | M | A | T | L | F |
| G598u24 | WIAF-12284 | HT48666 | 8386 | HERC1, hect (homologous to the E6 AP (UBE3A) carboxyl terminus) domain and RCC1 (CHC1)-like domain (RLD) 1 | GGGGTTCTCT[C/T]TTCGGCAGAT | M | C | T | L | F |
| G598u25 | WIAF-12286 | HT48666 | 10266 | HERC1, hect (homologous to the E6 AP (UBE3A) carboxyl terminus) domain and RCC1 (CHC1)-like domain (RLD) 1 | CAGCTCAGCA[A/T]CTCGTGCGCA | M | A | T | Q | H |
| G598u26 | WIAF-12287 | HT48666 | 10099 | HERC1, hect (homologous to the E6 AP (UBE3A) carboxyl terminus) domain and RCC1 (CHC1)-like domain (RLD) 1 | CTTTGTTGTA[A/G]CACAGGCCCT | M | A | G | T | A |
| G598u27 | WIAF-12289 | HT48666 | 11835 | HERC1, hect (homologous to the E6 AP (UBE3A) carboxyl terminus) domain and RCC1 (CHC1)-like domain (RLD) 1 | AGAACTGTCT[G/C]CCTGACCCTG | S | G | C | L | L |
| G598u28 | WIAF-12290 | HT48666 | 12689 | HERC1, hect (homologous to the E6 AP (UBE3A) carboxyl terminus) domain and RCC1 (CHC1)-like domain (RLD) 1 | TTAAACCACA[C/T]TTTGGCAGTG | M | C | T | T | I |
| G598u29 | WIAF-12291 | HT48666 | 14655 | HERC1, hect (homologous to the E6 AP (UBE3A) carboxyl terminus) domain and RCC1 (CHC1)-like domain (RLD) 1 | ACGTGGACAA[C/T]GCCGAGGGCT | S | C | T | N | N |
| G598u30 | WIAF-12296 | HT48666 | 393 | HERC1, hect (homologous to the E6 AP (UBE3A) carboxyl terminus) domain and RCC1 (CHC1)-like domain (RLD) 1 | ATTCCCCATT[T/C]GCCGGGCAC | S | T | C | F | F |
| G598u31 | WIAF-12297 | HT48666 | 479 | HERC1, hect (homologous to the E6 AP (UBE3A) carboxyl terminus) domain and RCC1 (CHC1)-like domain (RLD) 1 | GGCAAGTGA[A/G]GCAGCAGCAG | M | A | G | K | R |
| G598u32 | WIAF-12298 | HT48666 | 1197 | HERC1, hect (homologous to the E6 AP (UBE3A) carboxyl terminus) domain and RCC1 (CHC1)-like domain (RLD) 1 | ATGCTCCCAT[T/C]GTCTCCGAAAA | S | T | C | H | H |
| G598u33 | WIAF-12300 | HT48666 | 3595 | HERC1, hect (homologous to the E6 AP (UBE3A) carboxyl terminus) domain and RCC1 (CHC1)-like domain (RLD) 1 | TCCAGAGGAA[C/T]AGGACACTGC | N | C | T | Q | * |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G598u34 | WIAF-12301 | HT48666 | 3661 | HERC1, hect (homologous to the E6 AP (UBE3A) carboxyl terminus) domain and RCC1 (CHC1)-like domain (RLD) 1 | CACTCCTCAA[T/C]TGGATAAATG | S | T | C | L | L |
| G601u1 | WIAF-12246 | HT27734 | 106 | PRKMK5, protein kinase, mitogen-activated, kinase 5 (MAP kinase kinase 5) | TGGAGAACCA[G/A]GTGCTGGTAA | S | G | A | Q | Q |
| G601u2 | WIAF-12247 | HT27734 | 351 | PRKMK5, protein kinase, mitogen-activated, kinase 5 (MAP kinase kinase 5) | GTAAATGGAC[A/G]GTTAATAGAG | M | A | G | Q | R |
| G601u3 | WIAF-12292 | HT27734 | 617 | PRKMK5, protein kinase, mitogen-activated, kinase 5 (MAP kinase kinase 5) | AGCATATCAT[G/C]TCCCGAGTGG | M | G | C | V | L |
| G603u1 | WIAF-12248 | HT4291 | 1336 | mitogen-activated protein (MAP) kinase p38 | AGTCATCAGC[T/C]TTGTGCCACC | M | T | C | F | L |
| G603u2 | WIAF-12281 | HT4291 | 1230 | mitogen-activated protein (MAP) kinase p38 | CTCAGTACCA[C/T]GATCCTGATG | S | C | T | H | H |
| G610u1 | WIAF-12249 | HT48690 | 1012 | protein kinase, mitogen-activated p38Beta (MAP kinase p38Beta) | CCGAGCCATA[T/C]GATGAGAGCG | S | T | C | Y | Y |
| G610u2 | WIAF-12263 | HT48690 | 799 | protein kinase, mitogen-activated p38Beta (MAP kinase p38Beta) | AAATCTCCTC[G/A]GAACACGCCC | S | G | A | S | S |
| G610u3 | WIAF-12264 | HT48690 | 848 | protein kinase, mitogen-activated p38Beta (MAP kinase p38Beta) | GCCCCAGAAG[G/A]ACCTGAGCAG | M | G | A | D | N |
| G610u4 | WIAF-12282 | HT48690 | 439 | protein kinase, mitogen-activated p38Beta (MAP kinase p38Beta) | TCCTGGTTTA[C/T]CAGCTGCTGC | S | C | T | Y | Y |
| G612u1 | WIAF-12344 | HT1436 | 1513 | RAF1, v-raf-1 murine leukemia viral oncogene homolog 1 | TTTGCATGCA[A/G]AGAACATCAT | M | A | G | K | E |
| G614u1 | WIAF-12267 | HT321 | 603 | BRAF, v-raf murine sarcoma viral oncogene homolog B1 | GACAGTCTAA[A/G]GAAAGCACTG | M | A | G | K | R |
| G614u2 | WIAF-12268 | HT321 | 2282 | BRAF, v-raf murine sarcoma viral oncogene homolog B1 | CCAAACAGAG[G/A]ATTTTAGTCT | M | G | A | D | N |
| G614u3 | WIAF-12299 | HT321 | 973 | BRAF, v-raf murine sarcoma viral oncogene homolog B1 | AGGAAGAGGC[G/A]TCCTTAGCAG | S | G | A | A | A |
| G616u1 | WIAF-12253 | HT48746 | 498 | TRAF-interacting protein (I-TRAF) | AAGAGACAA[G/T]TAGGTTTCTTC | N | G | T | E | * |
| G616u2 | WIAF-12269 | HT48746 | 1338 | TRAF-interacting protein (I-TRAF) | GCATATACCT[C/G]GAGTATGTGA | M | C | G | R | G |
| G616u3 | WIAF-12285 | HT48746 | 377 | TRAF-interacting protein (I-TRAF) | ATAACAATTA[T/C]GGCTGTGTCC | S | T | C | Y | Y |
| G616u4 | WIAF-12288 | HT48746 | 1032 | TRAF-interacting protein (I-TRAF) | TGAAATTCAG[G/A]GAATTGACCC | M | G | A | G | R |
| G617u1 | WIAF-12256 | HT1614 | 52 | PPP1CA, protein phosphatase 1, catalytic subunit, alpha isoform | GAAGCTCAAC[C/T]TGGACTCGAT | S | C | T | L | L |
| G617u2 | WIAF-12270 | HT1614 | 792 | PPP1CA, protein phosphatase 1, catalytic subunit, alpha isoform | AAGACGGCTA[C/T]GAGTTCTTTG | S | C | T | Y | Y |
| G618u1 | WIAF-12238 | HT27508 | 1598 | protein phosphatase, 2A B56-alpha subunit | CATTGAACCA[A/C]CACAGTTCAA | M | A | C | T | P |
| G618u2 | WIAF-12271 | HT27508 | 1135 | protein phosphatase, 2A B56-alpha subunit | ATCAGAAATT[C/T]GTACAACAGC | S | C | T | F | F |
| G62u1 | WIAF-10369 | HT0855 | 214 | ERCC6, excision repair cross-complementing rodent repair deficiency, complementation group 6 | AGGAGTACCT[G/C]TCCTTTCGTT | S | G | C | L | L |

-continued

| Poly ID | WIAF ID | Genbank or TIGR Accession Number | Position in Sequence | Gene Description | Mutation Type | Ref NT | Alt NT | Ref AA | Alt AA |
|---|---|---|---|---|---|---|---|---|---|
| G62u2 | WIAF-10370 | HT0855 | 926 | ERCC6, excision repair cross-complementing rodent repair deficiency, complementation group 6 | M | T | C | F | L |
| G62u3 | WIAF-10428 | HT0855 | 2904 | ERCC6, excision repair cross-complementing rodent repair deficiency, complementation group 6 | M | C | T | T | M |
| G62u4 | WIAF-10430 | HT0855 | 3386 | ERCC6, excision repair cross-complementing rodent repair deficiency, complementation group 6 | M | A | G | M | V |
| G62u5 | WIAF-10451 | HT0855 | 1376 | ERCC6, excision repair cross-complementing rodent repair deficiency, complementation group 6 | M | G | A | E | K |
| G62u6 | WIAF-10452 | HT0855 | 3716 | ERCC6, excision repair cross-complementing rodent repair deficiency, complementation group 6 | M | A | G | R | G |
| G62u7 | WIAF-10453 | HT0855 | 3967 | ERCC6, excision repair cross-complementing rodent repair deficiency, complementation group 6 | S | A | C | A | A |
| G62u8 | WIAF-10454 | HT0855 | 4016 | ERCC6, excision repair cross-complementing rodent repair deficiency, complementation group 6 | M | A | G | T | A |
| G62u9 | WIAF-10455 | HT0855 | 3979 | ERCC6, excision repair cross-complementing rodent repair deficiency, complementation group 6 | S | T | C | S | S |
| G62u10 | WIAF-10456 | HT0855 | 3729 | ERCC6, excision repair cross-complementing rodent repair deficiency, complementation group 6 | M | T | G | F | C |
| G62u11 | WIAF-10476 | HT0855 | 1275 | ERCC6, excision repair cross-complementing rodent repair deficiency, complementation group 6 | M | G | A | G | D |
| G62u12 | WIAF-10477 | HT0855 | 2017 | ERCC6, excision repair cross-complementing rodent repair deficiency, complementation group 6 | S | C | T | D | D |
| G62u13 | WIAF-10479 | HT0855 | 3265 | ERCC6, excision repair cross-complementing rodent repair deficiency, complementation group 6 | S | T | C | S | S |

Flanking Seq:
- G62u2: AAAACTGTCT[T/C]TTGAAAGGAA
- G62u3: AGCACGGACA[C/T]GCAGGCCCGG
- G62u4: TGACCCTCAC[A/G]TGAGTAGTAA
- G62u5: TTTCTGGGAA[G/A]AAGCTGAAGC
- G62u6: TAAGCATTGC[A/G]GAGACGCCAA
- G62u7: CCCTGAAAGC[A/C]CTGAGGCTCT
- G62u8: TGGTGTTCCC[A/G]CCTGGACTGG
- G62u9: TGAGGCTCTC[T/C]CGTCAGCGGT
- G62u10: GACGCCAAGT[T/G]TGAAGGAACT
- G62u11: TCTGGAGATG[G/A]TACTGACTAT
- G62u12: TGATCTTGGA[C/T]GAAGGACACA
- G62u13: CTAACATATC[T/C]GTAAATGATG -continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G62u14 | WIAF-10481 | HT0855 | 4317 | ERCC6, excision repair cross-complementing rodent repair deficiency, complementation group 6 | GGGCACCTGC[A/G]GGAAGCTTCT | M | A | G | Q | R |
| G620a1 | WIAF-12116 | HT1943 | 1256 | PPP2CB, protein phosphatase 2 (formerly 2A), catalytic subunit, beta isoform | TATCATGGAA[T/A]TAGATGACAC | M | T | A | L | I |
| G620a2 | WIAF-12117 | HT1943 | 1326 | PPP2CB, protein phosphatase 2 (formerly 2A), catalytic subunit, beta isoform | CCTCATCTTA[C/G]ACGGCGCACC | M | C | G | T | R |
| G620u3 | WIAF-12239 | HT1943 | 819 | PPP2CB, protein phosphatase 2 (formerly 2A), catalytic subunit, beta isoform | TTTTATGATG[A/G]ATGTCTGCGA | M | A | G | E | G |
| G623u1 | WIAF-12260 | HT3979 | 459 | PPP1CB, protein phosphatase 1, catalytic subunit, beta isoform | TTCATGGACA[A/G]TATACAGATT | S | A | G | Q | Q |
| G625u1 | WIAF-12266 | HT1961 | 227 | PPP2R2A, protein phosphatase 2 (formerly 2A), regulatory subunit B (PR 52), alpha isoform | CATTCTGGAG[A/G]ATTACTAGCA | M | A | G | E | G |
| G628a1 | WIAF-12104 | HT2780 | 1104 | PPP1CC, protein phosphatase 1, catalytic subunit, gamma isoform | AGGGGTATGA[T/A]CACAAAGCAA | M | T | A | I | N |
| G628a2 | WIAF-12105 | HT2780 | 973 | PPP1CC, protein phosphatase 1, catalytic subunit, gamma isoform | CCAATTATTG[C/T]GGAGAGTTTG | S | C | T | C | C |
| G628u3 | WIAF-12311 | HT2780 | 888 | PPP1CC, protein phosphatase 1, catalytic subunit, gamma isoform | GATCTTATAT[G/T]TAGAGCCCAT | M | G | T | C | F |
| G630a1 | WIAF-12103 | HT5086 | 704 | protein phosphatase 2A, 130 kDa regulatory subunit | AAAGATGCAG[A/G]TCTGAACTCT | M | A | G | D | G |
| G630a2 | WIAF-12106 | HT5086 | 1015 | protein phosphatase 2A, 130 kDa regulatory subunit | CGATGGGAAC[G/T]CCCCATCCTT | M | G | T | A | S |
| G630a3 | WIAF-12107 | HT5086 | 1024 | protein phosphatase 2A, 130 kDa regulatory subunit | CGCCCCATCC[T/c]TTGGTTTACT | M | T | c | F | L |
| G630a4 | WIAF-12108 | HT5086 | 837 | protein phosphatase 2A, 130 kDa regulatory subunit | ACTTAAAGGA[T/C]ATTGCAGGAG | S | T | C | D | D |
| G630u5 | WIAF-12325 | HT5086 | 1200 | protein phosphatase 2A, 130 kDa regulatory subunit | TAAAGATGTG[C/T]TTGGACATCT | S | C | T | C | C |
| G630u6 | WIAF-12326 | HT5086 | 2810 | protein phosphatase 2A, 130 kDa regulatory subunit | ATGTTCAGGG[C/T]TGCAGGGGGA | M | C | T | A | V |
| G630u7 | WIAF-12351 | HT5086 | 512 | protein phosphatase 2A, 130 kAa regulatory subunit | ATTATGGCAG[C/T]AACTTACAGA | M | C | T | A | V |
| G630u8 | WIAF-12352 | HT5086 | 703 | protein phosphatase 2A, 130 kDa regulatory subunit | CAAAGATGCA[G/A]ATCTGAACTC | M | G | A | D | N |
| G630u9 | WIAF-12353 | HT5086 | 1069 | protein phosphatase 2A, 130 kDa regulatory subunit | ACCTTTGTCT[C/T]ATAGAAACTC | M | C | T | H | Y |
| G634u1 | WIAF-11825 | X04434 | 2283 | IGF1R, insulin-like growth factor 1 receptor | TGCAAGTGGC[C/T]AACACCACCA | S | C | T | A | A |
| G634u2 | WIAF-11826 | X04434 | 2279 | IGF1R, insulin-like growth factor 1 receptor | GTCATGCAAG[T/C]GGCCAACACC | M | T | C | V | A |
| G634u3 | WIAF-11781 | X04434 | 1731 | IGF1R, insulin-like growth factor 1 receptor | ACAAGGACGT[G/A]GAGCCCGGCA | S | G | A | V | V |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G634a4 | WIAF-13106 | X04434 | 948 | IGF1R, insulin-like growth factor 1 receptor | TCCACGACGG[C/A]GAGTGCATGC | S | C | A | G | G |
| G634a5 | WIAF-13107 | X04434 | 1089 | IGF1R, insulin-like growth factor 1 receptor | CTTCTGCTCA[G/C]ATCTCCAAG | M | G | C | Q | H |
| G634a6 | WIAF-13108 | X04434 | 2539 | IGF1R, insulin-like growth factor 1 receptor | AGAAGAGCA[G/A]ATGACATTCC | M | G | A | D | N |
| G634a7 | WIAF-13109 | X04434 | 2606 | IGF1R, insulin-like growth factor 1 receptor | AAGTGGCCGG[A/C]ACCTGAGAAT | M | A | C | E | A |
| G634a8 | WIAF-13113 | X04434 | 1543 | IGF1R, insulin-like growth factor 1 receptor | CTCCACCACC[A/T]CGTCGAAGAA | M | A | T | T | S |
| G634a9 | WIAF-13112 | X04434 | 1549 | IGF1R, insulin-like growth factor 1 receptor | CACCACGTCG[A/G]AGAATCGCAT | M | A | G | K | E |
| G634a10 | WIAF-13113 | X04434 | 1596 | IGF1R, insulin-like growth factor 1 receptor | CCCCTGACTA[C/T]AGGGATCCA | S | C | T | Y | Y |
| G645u1 | WIAF-12332 | HT5191 | 1127 | retinoic acid-binding protein II | TCTGCAGACT[C/T]TTCAGGAGAG | M | C | T | L | F |
| G645u2 | WIAF-12333 | HT5191 | 1048 | retinoic acid-binding protein II | AAGCATTAGA[G/A]GCCTTACAGA | S | G | A | R | E |
| G646u1 | WIAF-12303 | X81479 | 1204 | EMR1, egf-like module containing, mucin-like, hormone receptor-like sequence 1 | CAAATATCCA[T/C]TGTTGACTAAA | M | T | C | M | T |
| G646u2 | WIAF-12304 | X81479 | 1919 | EMR1, egf-like module containing, mucin-like, hormone receptor-like sequence 1 | TTCTGCTGTG[T/G]CGCTCCATCC | M | T | G | C | W |
| G646u3 | WIAF-12316 | X81479 | 590 | EMR1, egf-like module containing, mucin-like, hormone receptor-like sequence 1 | CTTGCCCAGA[G/T]CATGCAACTT | M | G | T | E | D |
| G646u4 | WIAF-12317 | X81479 | 799 | EMR1, egf-like module containing, mucin-like, hormone receptor-like sequence 1 | GCACCAAGCA[G/A]TGACAGTTG | M | G | A | S | N |
| G646u5 | WIAF-12318 | X81479 | 558 | EMR1, egf-like module containing, mucin-like, hormone receptor-like sequence 1 | TGAAGACGTG[A/G]ATGAATGTGC | M | A | G | N | D |
| G646u6 | WIAF-12334 | X81479 | 207 | EMR1, egf-like module containing, mucin-like, hormone receptor-like sequence 1 | TTACTATTGC[A/G]CTTGCAAACA | M | A | G | T | A |
| G646u7 | WIAF-12335 | X81479 | 458 | EMR1, egf-like module containing, mucin-like, hormone receptor-like sequence 1 | TCCACCAGCAG[G/C]GTCTGCCCTG | M | G | C | R | S |
| G646u8 | WIAF-12336 | X81479 | 1308 | EMR1, egf-like module containing, mucin-like, hormone receptor-like sequence 1 | CTCAGCAAAT[G/A]TCACTCCGGC | M | G | A | V | I |
| G646u9 | WIAF-12337 | X81479 | 1285 | EMR1, egf-like module containing, mucin-like, hormone receptor-like sequence 1 | ACACTGCAT[C/T]TTTTTGGAAA | M | C | T | S | F |
| G646u10 | WIAF-12338 | X81479 | 2026 | EMR1, egf-like module containing, mucin-like, hormone receptor-like sequence 1 | GACAACAAGA[C/T]GGGCTGCGCC | M | C | T | T | M |
| G647u1 | WIAF-12339 | HTS190 | 174 | RARA, retinoic acid receptor, alpha | TGCCTCCCTA[C/T]GCCTTCTTCT | S | C | T | Y | Y |
| G648a1 | WIAF-13332 | HT0070 | 469 | retinoic acid receptor, beta | AACGTGAGCC[A/G]GGAGCAGCGT | — | A | G | — | — |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G648a2 | WIAF-13333 | HT0070 | 532 | retinoic acid receptor, beta | ATTGTTTTA[A/G]GGTGAGAAAT | — | A | G | — | — |
| G650u1 | WIAF-12323 | X52773 | 862 | RXRA, retinoid X receptor, alpha | CTCGCCGAAC[G/A]AACCTGTCAC | M | G | A | D | N |
| G650u2 | WIAF-12341 | X52773 | 102 | RXRA, retinoid X receptor, alpha | TCCTGCCGCT[C/T]GATTTCTCCA | S | C | T | L | L |
| G650u3 | WIAF-12348 | X52773 | 673 | RXRA, retinoid X receptor, alpha | GGCCATGGGC[A/G]TGAAGCGGGA | M | A | G | M | V |
| G650u4 | WIAF-12349 | X52773 | 902 | RXRA, retinoid X receptor, alpha | GAGAAACAGC[T/C]TTTCACCCTG | N | T | C | L | P |
| G653a1 | WIAF-13326 | HT1458 | 439 | RARB, retinoic acid receptor, beta | AGGAGAAAGC[T/C]CTGAAAGCAT | S | T | C | A | A |
| G655a1 | WIAF-13327 | J05252 | 1158 | PCSK2, proprotain convertase subtilisin/kexin type 2 | CCTTCAGCAA[C/T]GGGAGGAAAA | S | C | T | N | N |
| G655a2 | WIAF-13334 | J05252 | 678 | PCSK2, proprotein convertase subtilisin/kexin type 2 | CCTATCCTTA[C/A]CCTCGGTACA | N | C | A | Y | * |
| G655a3 | WIAF-13335 | J05252 | 744 | PCSK2, proprotein convertase subtilisin/kexin type 2 | TTTCTGCTGC[C/T]GCCAACAACA | S | C | T | A | A |
| G658u1 | WIAF-11856 | J02943 | 971 | CBG, corticosteroid binding globulin | TCTATGACCT[T/C]GGAGATGTGC | S | T | C | L | L |
| G658u2 | WIAF-13407 | J02943 | 771 | CRG, corticosteroid binding globulin | CCTTCATGAC[T/G]CAGAGCTCCC | M | T | G | S | A |
| G658u3 | WIAF-13408 | J02943 | 773 | CBG, corticosteroid binding globulin | TTCATGACTC[A/G]GAGCTCCCCT | S | A | G | S | S |
| G658u4 | WIAF-13409 | J02943 | 1046 | CSG, corticosteroid binding globulin | TCACCCAGGA[C/T]GCCCAGCTGA | S | C | T | D | D |
| G663u1 | WIAF-13400 | WT3157 | 1202 | TPO, thyroid peroxidase | CGCCACGCGC[G/A]CCTGCGGCCT | S | G | A | A | A |
| G663u2 | WIAF-13401 | HT3157 | 1282 | TPO, thyroid peroxidase | GGCGGCCCCA[G/C]CGAGGTCCCC | M | G | C | S | T |
| G668a1 | WIAF-13350 | U53506 | 350 | D102, deiodinase, iodothyronine, type II | TCGATGCCTA[C/A]AAACAGGTGA | N | C | A | Y | * |
| G668a2 | WIAF-13351 | U53506 | 354 | D102, deiodinase, iodothyronine, type II | TGCCTACAAA[C/A]AGGTGAAATT | M | C | A | Q | K |
| G668a3 | WIAF-13352 | U53506 | 408 | D102, deiodinase, iodothyronine, type II | TGTCTCCAGT[A/G]CAGAAGGAGG | M | A | G | T | A |
| G673a1 | WIAF-13328 | M57464 | 1723 | Human ret proto-oncogene mRNA for tyrosine kinase. | CGAGCCTGGG[G/A]AGCCCCGGGG | S | G | A | E | K |
| G673a2 | WIAF-13336 | M57464 | 1186 | Human ret proto-oncogene mRNA for tyrosine kinase. | GGCTCGCCGA[T/A]TTGCCCAGAT | M | T | A | F | I |
| G673a3 | WIAF-13337 | MS7464 | 3227 | Human ret proto-oncogene rnRNA for tyrosine kinase. | ACTGCCAGGC[G/A]TTCAGTGGCA | S | G | A | A | A |
| G673a4 | WIAF-13338 | M57464 | 2118 | Human ret proto-oncogene mRNA for tyrosine kinase. | TTGGAAAAAC[T/A]CTAGGAGAAG | S | T | A | T | T |
| G673a5 | WIAF-13339 | M57464 | 2238 | Human ret proto-oncogene mRNA for tyrosine kinase. | CGAGTGAGCT[T/G]CGAGACCTGC | S | T | G | L | L |
| G678u1 | WIAF-13353 | D49492 | 1439 | GDF10, growth differentiation factor 10 | TCGGCTGGAA[T/A]GAATGGATAA | M | T | A | N | K |
| G68u1 | WIAF-10434 | HT1115 | 1214 | ERCC3, excision repair cross-complementing rodent repair deficiency, complementation group 3 (xeroderma pigmentosum group B complementing) | CTGTGGAGCA[G/A]TGGAAAGCCC | S | G | A | Q | Q |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G68u2 | WIAF-10435 | HT1115 | 1155 | ERCC3, excision repair cross-complementing rodent repair deficiency, complementation group 3 (xeroderma pigmentosum group B complementing) | TGTGACTGCT[G/C]CATGCACTGT | M | G | C | A | P |
| G68u3 | WIAF-10436 | HT1115 | 1327 | ERCC3, excision repair cross-complementing rodent repair deficiency, complementation group 3 (xeroderma pigmentosum group B complementing) | AGCACCTACT[C/T]CATGCTGGGC | M | C | T | S | F |
| G68u4 | WIAF-10461 | HT1115 | 926 | ERCC3, excision repair cross-complementing rodent repair deficiency, complementation group 3 (xeroderma pigmentosum group B complementing) | AGGAAATGAT[T/C]GAGGAACTCC | S | T | C | H | H |
| G68u5 | WIAF-10464 | HT1115 | 1430 | ERCC3, excision repair cross-complementing rodent repair deficiency, complementation group 3 (xeroderma pigmentosum group B complementing) | AAGTGCACAC[C/T]ATACCAGCCA | S | C | T | T | T |
| G684a1 | WIAF-13359 | X51801 | 712 | BMP7, bone morphogenetic protein 7 (osteogenic protein 1) | GTTTATCAGG[T/G]GCTCCAGGAG | M | T | G | V | G |
| G684a2 | WIAF-13360 | X51801 | 719 | BMP7, bone morphogenetic protein 7 (osteogenic protein 1) | AGGTGCTCCA[G/A]GAGCACTTGG | S | G | A | Q | Q |
| G684a3 | WIAF-13361 | X51801 | 796 | BMP7, bone morphogenetic protein 7 (osteogenic protein 1) | GGCTGGCTGG[T/G]GTTTGACATC | M | T | G | V | G |
| G684a4 | WIAF-13362 | X51801 | 862 | BMP7, bone morphogenetic protein 7 (osteogenic protein 1) | GGCCTGCCAG[T/G]CTCGGTGGAG | M | T | G | L | R |
| G684a5 | WIAF-13363 | X51801 | 658 | BMP7, bone morphogenetic protein 7 (osteogenic protein 1) | ATCTACAAGG[A/G]CTACATCCGG | M | A | G | D | G |
| G684u6 | WIAF-13834 | X51801 | 1421 | BMP7, bone morphogenetic protein 7 (osteogenic protein 1) | GCCACTAGCT[C/T]CTCCGAGAAT | – | C | T | – | – |
| G685a1 | WIAF-13329 | D89675 | 862 | BMPR1B, bone morphogenetic protein receptor, type IB | GTTCCCTTTA[T/G]GATTATCTGA | N | T | G | Y | * |
| G685a2 | WIAF-13330 | D89675 | 920 | BMPR1B, bone morphogenetic protein receptor, type IB | GCTAAATCAA[T/C]GCTGAAGTTA | M | T | C | M | T |
| G685a3 | WIAF-13331 | D89675 | 770 | BMPR1B, bone morphogenetic protein receptor, type IB | TATCAGACAG[T/G]GTTGATGAGG | M | T | G | V | G |
| G685a4 | WIAF-13340 | D89675 | 1303 | BMPR1B, bone morphogenetic protein receptor, type IB | TCCTTATCAT[G/A]ACCTAGTGCC | M | G | A | D | N |
| G685a5 | WIAF-13341 | D89675 | 1372 | BMPR1B, bone morphogenetic protein receptor, type IB | GTTACGCCCC[T/G]CATTCCCAAA | M | T | G | S | A |
| G685a6 | WIAF-13342 | D89675 | 1173 | BMPR1B, bone morphogenetic protein receptor, type IB | TGTTGACGA[G/A]AGCTTGAACA | S | G | A | E | E |
| G6B6u1 | WIAF-13816 | Z48923 | 2705 | BMPR2, bone morphogenetic protein receptor, type II (serine/threonine kinase) | AAATTTGGCA[G/A]CAAGCACAAA | N | G | A | S | N |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G686u2 | WIAF-13817 | Z48923 | 2749 | BMPR2, bone morphogenetic protein receptor, type II (serine/threonine kinase) | TGGAGTGCC[A/T]AGATGAATAC | N | A | T | K | * |
| G687a1 | WIAF-13343 | MT1455 | 626 | CALB1, calbindin 1, (28 kD) | ATGATCAGGA[C/T]GGCAATGGAT | S | C | T | D | D |
| G696u1 | WIAF-11839 | HT27700 | 1075 | calcium-sensing receptor | GGGCACAATT[G/C]CAGCTGATGA | M | G | C | A | P |
| G696u2 | WIAF-11840 | HT27700 | 1551 | calcium-sensing receptor | TACCTGTGGA[C/T]AACTTTCTGA | S | C | T | D | D |
| G696u3 | WIAF-11841 | HT27700 | 1688 | calcium-sensing receptor | TTACGGATAT[C/T]CTACAATGTG | S | C | T | D | D |
| G696u4 | WIAF-11842 | HT27700 | 1698 | calcium-sensing receptor | CCTACAATGT[G/T]TACTTAGCAG | S | G | T | S | F |
| G696u5 | WIAF-11858 | MT27700 | 1767 | calcium-sensing receptor | GGAGAGGGCT[C/T]TTCACCAATG | S | C | T | V | V |
| G696u6 | WIAF-11859 | HT27700 | 1689 | calcium-sensing receptor | TACGGATATC[C/T]TACAATGTGT | S | C | T | L | L |
| G696u7 | WIAF-11860 | MT27700 | 2541 | calcium-sensing receptor | TCGTGCTCTG[C/T]ATCTCATGCA | S | C | T | G | S |
| G696u8 | WIAF-11861 | HT27700 | 2581 | calcium-sensing receptor | TGTCCTCCTG[G/A]TGTTTGAGGC | M | G | A | C | C |
| G696u9 | WIAF-11863 | HT27700 | 3159 | calcium-sensing receptor | TCTCCCGCAA[G/C]CGGTCCAGCA | M | G | C | V | M |
| G696u10 | WIAF-11872 | HT27700 | 562 | calcium-sensing receptor | TCCTATTCAT[T/A]TTGGAGTAGC | M | T | A | K | N |
| G696u11 | WIAF-11878 | HT27700 | 2941 | calcium-sensing receptor | CATTCCAGCT[G/A]GATCCAGCAC | M | G | A | F | I |
| G696u12 | WIAF-13396 | HT27700 | 1145 | calcium-sensing receptor | AGGGATATCT[G/A]CATCGACTTC | M | G | A | H | D |
| G696u13 | WIAF-13395 | HT27700 | 670 | calcium-sensing receptor | GATATTTGCC[A/G]TAGAGGAGAT | M | A | G | C | Y |
| G696u14 | WIAF-13396 | HT27700 | 2243 | calcium-sensing receptor | TTCTGGTCCA[A/G]TGAAACCAC | M | A | G | H | V |
| G696u15 | WIAF-13397 | HT27700 | 2742 | calcium-sensing receptor | AGCTGAGGA[T/C]GAGATCATCT | S | T | C | D | D |
| G698u1 | WIAF-13547 | X61598 | 393 | CBP1, collagen-binding protein 1 | TCAGCAACTC[G/C]ACGCGCGCA | S | G | C | S | S |
| G698u2 | WIAF-13549 | X61598 | 628 | CBP1, collagen-binding protein 1 | CGGCGCCCTG[C/T]TAGTCAACGC | S | C | T | L | L |
| G698u3 | WIAF-13550 | X61598 | 1230 | CBP1, collagen-binding protein 1 | GCGCTCCCT [G/A]CTATTCATTG | S | G | A | A | A |
| G701u1 | WIAF-12382 | HT27657 | 706 | CGRP tyos I receptor | AACGATGTTG[C/A]AGCAGGAACT | M | G | A | E | E |
| G701u2 | WIAF-12391 | HT27657 | 841 | CGRP type I receptor | TGGACAAATT[A/T]TACCAGTGT | M | A | T | Y | F |
| G704u1 | WIAF-14046 | X60382 | 1396 | COL10A1, collagen, type X, alpha 1 (Schmid metaphyseal chondrodysplasia) | AGGCATTCCA[G/A]GATTCCCTGG | M | G | A | G | R |
| G704u2 | WIAF-14070 | X60382 | 1648 | COL10A1, collagen, type X, alpha 1 (Schmid metaphyseal chondrodysplasia) | TGCCAACCAG[G/C]GGGTAACAGG | M | G | C | G | R |
| G704u2 | WIAF-14070 | X60382 | 1648 | COL10A1, collagen, type X, alpha 1 (Schmid metaphyseal chondrodysplasia) | CATACCACGT[G/C]CATGTGAAAG | S | G | C | V | V |
| G704u3 | WIAF-14071 | X60382 | 1824 | COL10A1, collagen, type X, alpha 1 (Schmid metaphyseal chondrodysplasia) | CATACCACGT[G/C]CATGTGAAAG | S | G | C | V | V |
| G704u4 | WIAF-14072 | X60382 | 1582 | COL10A1, collagen, type X, alpha 1 (Schmid metaphyseal chondrodysplasia) | AGTCATCGCCT[G/C]AGGGTTTTAT | M | G | C | E | Q |
| G705a1 | WIAF-13228 | J04177 | 686 | COL11A1, collagen, type XI, alpha 1 | AGAAGAAAAC[T/A]GTGACAATGA | S | T | A | T | T |
| G705e2 | WIAF-13229 | J04177 | 698 | COL11A1, collagen, type XI, alpha 1 | TGACAATGAT[T/A]GTTGATTGTA | S | T | A | I | I |
| G705a3 | WIAF-13230 | J04177 | 888 | COL11A1, collagen, type XI, alpha 1 | TAGTCCAGAC[T/A]GTGACTCTTC | M | T | A | C | S |
| G705a4 | WIAF-13231 | J04177 | 894 | COL11A1, collagen, type XI, alpha 1 | AGACTGTGAC[T/A]CTTCAGCACC | H | T | A | S | T |
| G705a5 | WIAF-13232 | J04177 | 651 | COL11A1, collagen, type XI, alpha 1 | TGACCGGAAG[T/A]GGCATCGGGT | M | T | A | W | R |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G705a6 | WIAF-13233 | J04177 | 661 | COL11A1, collagen, type XI, alpha 1 | TGGCATCGGG[T/A]AGCAATCAGC | M | T | A | V | E |
| G705a7 | WIAF-13234 | J04177 | 1597 | COL11A1, collagen, type XI, alpha 1 | CGTCCTGGCT[T/C]ACCAGGGGCT | M | T | C | L | S |
| G705a8 | WIAF-13235 | J04177 | 2745 | COL11A1, collagen, type XI, alpha 1 | TGGGTTTCCA[G/A]GTGCCAATGG | M | G | A | G | S |
| G705a9 | WIAF-13236 | J04177 | 4385 | COL11A1, collagen, type XI, alpha 1 | GTCCAGAAGG[T/A]CTTCGGGGCA | S | T | A | G | G |
| G705a10 | WIAF-13237 | J04177 | 4576 | COL11A1, collagen, type XI, alpha 1 | GAAAAAGGTG[A/T]CCGAGGGCTC | M | A | T | D | V |
| G705a11 | WIAF-13238 | J04177 | 4306 | COL11A1, collagen, type XI, alpha 1 | GCTAAGGGGG[A/C]AGGAGGTGCA | M | A | C | E | A |
| G705a12 | WIAF-13239 | J04177 | 4837 | COL11A1, collagen, type XI, alpha 1 | AGACATACTG[A/G]AGGCATGCAA | M | A | G | E | G |
| G705a13 | WIAF-13240 | J04177 | 4931 | COL11A1, collagen, type XI, alpha 1 | AACAAGACAT[C/T]GAGCATATGA | S | C | T | H | H |
| G705e14 | WIAF-13346 | J04177 | 299 | COL11A1, collagen, type XI, alpha 1 | AAGCACTAGA[T/G]TTTCACAATT | M | T | G | D | E |
| G705a15 | WIAF-13347 | J04177 | 2225 | COL11A1, collagen, type XI, alpha 1 | GGGAGCCTGG[G/C]CCTCCAGTC | S | G | C | G | G |
| G705u16 | WIAF-13679 | J04177 | 5493 | COL11A1, collagen, type XI, alpha 1 | AATTGATCAA[G/A]TACCTATTGT | M | G | A | V | I |
| G705u17 | WIAF-13700 | J04177 | 3484 | COL11A1, collagen, type XI, alpha 1 | GGAGTTCAAG[G/A]TCCTGTTGGT | M | G | A | G | D |
| G705u18 | WIAF-13709 | J04177 | 5392 | COL11A1, collagen, type XI, alpha 1 | GAGAGTCCTT[A/T]TGACAATAAT | M | A | T | Y | F |
| G707u1 | WIAF-12363 | U32169 | 4996 | COL11A2, collagen, type XI, alpha 2 | TCCCCTGAGA[C/T]TCCGTGGGGC | M | C | T | L | F |
| G707u2 | WIAF-12374 | U32169 | 3580 | COL11A2, collagen, type XI, alpha 2 | CAATGGCGCT[G/A]ATGGCCCACA | M | G | A | D | N |
| G707u3 | WIAF-12385 | U32169 | 2059 | COL11A2, collagen, type XI, alpha 2 | GCCTGGCTCA[G/A]ACGACCCCC | M | G | A | D | N |
| G708a1 | WIAF-13354 | U73778 | 1885 | COL12A1, collagen, type XII, alpha 1 | GCCTCTCCTC[C/T]TGCAGAGACC | M | C | T | P | L |
| G708a2 | WIAF-13355 | U73778 | 3630 | COL12A1, collagen, type XII, alpha 1 | TGTTGGACAA[G/A]AAATGACAAC | M | G | A | E | K |
| G708a3 | WIAF-13356 | U73778 | 3905 | COL12A1, collagen, type XII, alpha 1 | GCTTGTTGCA[A/T]GCTGTGGCAA | M | A | T | Q | H |
| G708a4 | WIAF-13357 | U73778 | 7051 | COL12A1, collagen, type XII, alpha 1 | ATTCCACCAG[C/A]CCGGGATGTA | M | C | A | A | D |
| G708a5 | WIAF-13358 | U73778 | 8036 | COL12A1, collagen, type XII, alpha 1 | IAAGAAGTAAA[G/A]ACATTATTTT | S | G | A | K | K |
| G708a6 | WIAF-13364 | U73778 | 1461 | COL12A1, collagen, type XII, alpha 1 | TGGCTCCTAT[A/T]GCATTGGGAT | M | A | T | S | C |
| G708a7 | WIAF-13365 | U73778 | 2344 | COL12A1, collagen, type XII, alpha 1 | ATTACTTGGA[C/T]TCAAGCTCCA | M | C | T | T | I |
| G708a8 | WIAF-13366 | U73778 | 5207 | COL12A1, collagen, type XII, alpha 1 | CAGATAAGAT[G/A]GAGACCATCT | M | G | A | M | I |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G708a9 | WIAF-13367 | U73778 | 6592 | COL12A1, collagen, type XII, alpha 1 | GAGCCCATGG[A/T]AGCCTTTGTT | M | A | T | E | V |
| G708a10 | WIAF-13368 | U73778 | 7434 | COL12A1, collagen, type XII, alpha 1 | CCAGGATGAG[G/A]TCAAGAAGGC | M | G | A | V | I |
| G708a11 | WIAF-13369 | U73778 | 9108 | COL12A1, collagen, type XII, alpha 1 | ACCTCGGGGG[C/G]TGCCTGGGCC | M | C | G | L | V |
| G708a12 | WIAF-13370 | U73778 | 9111 | COL12A1, collagen, type XII, alpha 1 | TCGGGGCTG[C/T]CTGGGCCCC | M | C | T | P | S |
| G708a13 | WIAF-13371 | U73778 | 9196 | COL12A1, collagen, type XII, alpha 1 | CCCCCTGCC[G/A]TCCTGAAAC | M | G | A | I | H |
| G708u14 | WIAF-13972 | U73778 | 3044 | COL12A1, collagen, type XII, alpha 1 | CAGTATTTGC[C/A]ACTTACAGCA | S | C | A | A | A |
| G708U15 | WIAF-13977 | U73778 | 5853 | COL12A1, collagen, type XII, alpha 1 | TGTGACTGTA[G/C]TTCCCGTTTA | M | G | C | V | L |
| G710u1 | WIAF-12371 | D38163 | 3082 | COL19A1, collagen, type XIX, alpha 1 | AGGAAACAAG[G/T]GCTCCATGGG | M | G | T | G | C |
| G710u2 | WIAF-12388 | D38163 | 2889 | COL19A1, collagen, type XIX, alpha 1 | TCCAGGGACT[C/T]CAGGGAATGA | M | C | T | P | S |
| G711u1 | WIAF-12360 | L25286 | 1449 | COL15A1, collagen, type XV, alpha 1 | TGTGGGTCCA[A/G]GCAGTGAAGA | M | A | G | S | G |
| G711u2 | WIAF-12372 | L25286 | 4001 | COL15A1, collagen, type XV, alpha 1 | ATATTCCAAT[A/G]TACTCCTTTG | M | A | G | I | M |
| G711u3 | WIAF-12373 | L25286 | 3867 | COL15A1, collagen, type XV, alpha 1 | CCATTTGCAA[G/T]ATCTGTCAC | M | G | T | D | Y |
| G711a4 | WIAF-12372 | L25286 | 395 | COL15A1, collagen, type XV, alpha 1 | CCAGCAGCAC[C/T]CGTGGTGGCG | S | C | T | T | T |
| G711a5 | WIAF-12373 | L25286 | 3101 | COL15A1, collagen, type XV, alpha 1 | AAGGCGACCA[G/A]GGAGCCAGG | M | G | A | Q | Q |
| G712u1 | WIAF-13619 | M92642 | 3608 | COL16A1, collagen, type XVI, alpha 1 | GGCGACCAGG[G/A]ATTTCGGC | S | G | A | G | B |
| G712u2 | WIAF-13620 | M92642 | 4944 | COL16A1, collagen, type XVI, alpha 1 | CCATGAAAAC[C/T]ATGAAGGGGC | S | C | T | T | T |
| G712u3 | WIAF-13621 | M92642 | 4707 | COL16A1, collagen, type XVI, alpha 1 | CCAAAGTGA[A/C]AAAGGGACA | M | A | C | E | D |
| G712u4 | WIAF-13654 | M92642 | 421 | COL16A1, collagen, type XVI, alpha 1 | GCCCACGCGA[C/A]GAGTATTCCC | S | C | A | R | R |
| G712u5 | WIAF-13655 | M92642 | 444 | COL16A1, collagen, type XVI, alpha 1 | GGGGTCTCCC[G/A]GAGGAGTTTG | S | G | A | P | P |
| G712u6 | WIAF-13656 | M92642 | 338 | COL16A1, collagen, type XVI, alpha 1 | CTCATGAAGA[A/C]GTCTGCCATC | M | A | C | K | T |
| G712u7 | WIAF-13862 | N92542 | 3227 | COL16A1, collagen, type XVI, alpha 1 | CCTGGTCCTC[C/T]GGGATTGCCA | M | C | T | P | L |
| G712u8 | WIAF-13863 | M92642 | 3199 | COL16A1, collagen, type XVI, alpha 1 | TCCTGGCTGT[G/T]TTTGGAGCCC | M | G | T | V | F |
| G712u9 | WIAF-13678 | N92642 | 318 | COL16A1, collagen, type XVI, alpha 1 | ACCTCATCCA[C/T]CGACTCAGCC | M | C | T | H | H |
| G712u10 | WIAF-13882 | M92642 | 1346 | COL16A1, collagen, type XVI, alpha 1 | ACAGGCCAGA[A/G]GGGCCAGAAA | N | A | G | K | R |
| G712u11 | WIAF-13883 | N92642 | 1309 | COL16A1, collagen, type XVI, alpha 1 | GTCAGGAGC[C/T]GGGGACCCTC | S | C | T | L | L |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G715a1 | WIAF-13344 | Z74615 | 3504 | COL1A1, collagen, type I, alpha 1 | TCCTGGTGAA[C/G]AAGGTCCCTC | M | C | G | Q | E |
| G717u1 | WIAF-12639 | Z74616 | 3988 | COL1A2, collagen, type I, alpha 2 | ATGAGGAGAC[T/C]GGCAAACCTGA | S | T | C | T | T |
| G720u1 | WIAF-12367 | X14420 | 3494 | COL3A1, collagen, type III, alpha 1 (Ehlers-Danlos syndrome type IV, autosomal dominant) | GGTGCAATCG[G/A]CAGTCCAGGA | M | G | A | G | D |
| G720u2 | WIAF-12383 | X14420 | 3035 | COL3A1, collagen, type III, alpha 1 (Ehlers-Danlos syndrome type IV, autosomal dominant) | GGTGTCAAGG[G/A]TGAAAGTGGG | N | G | A | G | D |
| G720a3 | WIAF-13374 | X14420 | 214 | COL3A1, collagen, type III, alpha 1 (Ehlers-Danlos syndrome type IV, autosomal dominant) | TCTTGGTCAG[T/C]CCTATGCGGA | M | T | C | S | P |
| G720a4 | WIAF-13376 | X14420 | 1953 | COL3A1, collagen, type III, alpha 1 (Ehlers-Danlos syndrome type IV, autosomal dominant) | CTGGACCTCA[A/G]GGACCCCAG | S | A | G | Q | Q |
| G720a5 | WIAF-13376 | X14420 | 2194 | COL3A1, collagen, type III, alpha 1 (Ehlers-Danlos syndrome type IV, autosomal dominant) | TAGAGGTGGA[G/A]CTGGTCCCCC | M | G | A | A | T |
| G720a6 | WIAF-13377 | X14420 | 3731 | COL3A1, collagen, type III, alpha 1 (Ehlers-Danlos syndrome type IV, autosomal dominant) | GGGATTGGAG[G/A]TGAAAAAGCT | M | G | A | G | D |
| G722u1 | WIAF-14132 | HT3162 | 140 | COL4A2, collagen, type IV, alpha 2 | GAGATTGGCG[C/T]GACTGGTGAT | M | C | T | A | V |
| G724a1 | WIAF-12120 | X81053 | 3892 | COL4A4, collagen, type IV, alpha 4 | CTCGTGGAAA[G/A]AAAGGTCCCC | S | G | A | K | K |
| G724a2 | WIAF-12121 | X81053 | 4187 | COL4A4, collagen, type IV, alpha 4 | GAAAGGACCA[A/G]TGGGATTCCC | M | A | G | M | V |
| G724a3 | WIAF-12122 | X81053 | 3802 | COL4A4, collagen, type IV, alpha 4 | ATGATGTGGG[G/A]CCACCTGGTC | S | G | A | G | G |
| G724a4 | WIAF-12123 | X81053 | 1838 | COL4A4, collagen, type IV, alpha 4 | ACCAGGAAAG[C/A]ATGGTGCCTC | M | C | A | H | N |
| G724u5 | WIAF-12364 | X81053 | 3516 | COL4A4, collagen, type IV, alpha 4 | CTGTTTGCCA[C/T]TGTGTTCCTG | S | C | T | H | H |
| G724u6 | WIAF-12365 | X81053 | 4288 | COL4A4, collagen, type IV, alpha 4 | TCCAGGGGAT[C/G]ATGAAGATGC | M | C | G | H | D |
| G724u7 | WIAF-12366 | X81053 | 2018 | COL4A4, collagen, type IV, alpha 4 | GCCTTCCCGT[A/G]TTTAGCACGC | S | A | G | V | V |
| G724u8 | WIAF-12377 | X81053 | 4756 | COL4A4, collagen, type IV, alpha 4 | CTGGACCACC[A/G]GGGTGCCCAG | S | A | G | P | P |
| G724u9 | WIAF-12378 | X81053 | 3595 | COL4A4, collagen, type IV, alpha 4 | GGAGCATCCG[G/C]AGAGCAGGGC | M | G | C | G | A |
| G724u10 | WIAF-12379 | X81053 | 3516 | COL4A4, collagen, type IV, alpha 4 | CTGGTCTTCC[A/G]GGTCCCAGAG | S | A | G | P | P |
| G724u11 | WIAF-12380 | X81053 | 4288 | COL4A4, collagen, type IV, alpha 4 | GCCACTTTT[C/A]GCAAATAAGT | M | C | A | F | L |
| G724u12 | WIAF-12387 | X81053 | 5140 | COL4A4, collagen, type IV, alpha 4 | GACTTGCCTG[C/T]GATGTGGTCT | — | C | T | — | — |
| G727u1 | WIAF-12362 | D90279 | 207 | COL5A1, collagen, type V, alpha 1 | TTCAAGGTTT[A/T]TCTGCAACTTC | M | A | T | Y | F |
| G727u2 | WIAF-12369 | D90279 | 5135 | COL5A1, collagen, type V, alpha 1 | AACAGGGTAT[C/T]ACTGGTCCTT | S | C | T | H | H |
| G727u3 | WIAF-12370 | D90279 | 4686 | COL5A1, collagen, type V, alpha 1 | TCGGTCCTCC[G/C]GGTGAACAGG | S | G | C | P | P |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G727a4 | WIAF-13300 | D90279 | 2034 | COL5A1, collagen, type V, alpha 1 | ACGGCCTGGC[T/A]GGGTTGCCAG | S | T | A | A | A |
| G727a5 | WIAF-13301 | D90279 | 2073 | COL5A1, collagen, type V, alpha 1 | GTGACCCTGG[T/C]CCTTCCGGCC | S | T | C | G | G |
| G727a6 | WIAF-13302 | D98279 | 3763 | COL5A1, collagen, type V, alpha 1 | CGGGCAGAAA[G/A]GTGATGAAGG | M | G | A | G | S |
| G729u1 | WIAF-11844 | L02870 | 2345 | COL7A1, collagen, type VII, alpha 1 (epidermolysis bullosa, dystrophic, dominant and recessive) | ATGGACTGGA[G/A]CCAGATACTG | S | G | A | E | E |
| G729u2 | WIAF-11845 | L02870 | 3083 | COL7A1, collagen, type VII, alpha 1 (epidermolysis bullosa, dystrophic, dominant and recessive) | TATCCTCGCG[G/A]CCACTCAGAG | S | G | A | R | R |
| G729u3 | WIAF-11846 | L02870 | 3031 | COL7A1, collagen, type VII, alpha 1 (epidermolysis bullosa, dystrophic, dominant and recessive) | GACTCGTGA[C/T]TTTGGCCTGG | N | C | T | T | I |
| G729u4 | WIAF-11851 | L02870 | 1289 | COL7A1, collagen, type VII, alpha 1 (epidermolysis bullosa, dystrophic, dominant and recessive) | CGGACTATGA[G/T]GTGACCGTGA | W | G | T | E | D |
| G729u5 | WIAF-11852 | L02870 | 1032 | COL7A1, collagen, type VII, alpha 1 (epidermolysis bullosa, dystrophic, dominant and recessive) | CCAAGTGACT[G/T]TGATTGCCCT | N | G | T | V | L |
| G729u6 | WIAF-11853 | L02870 | 1897 | COL7A1, collagen, type VII, alpha 1 (epidermolysis bullosa, dystrophic, dominant and recessive) | CGCCGGGAGC[C/T]GGAAACTCCA | M | C | T | P | L |
| G729u7 | WIAF-11854 | L02870 | 1827 | COL7A1, collagen, type VII, alpha 1 (epidermolysis bullosa, dystrophic, dominant and recessive) | GCTTAGCTAC[A/T]CTCTGCGGGT | M | A | T | T | G |
| G729u8 | WIAF-11855 | L02870 | 1893 | COL7A1, collagen, type VII, alpha 1 (epidermolysis bullosa, dystrophic, dominant and recessive) | TGTCCCGCGG[G/A]AGCCGGAAAC | M | G | A | E | K |
| G729u9 | WIAF-11864 | L02870 | 2142 | COL7A1, collagen, type VII, alpha 1 (epidermolysis bullosa, dystrophic, dominant and recessive) | GGGCCCTGCT[G/A]CAGTCATCGT | M | G | A | A | T |
| G729u10 | WIAF-11865 | L02870 | 2353 | COL7A1, collagen, type VII, alpha 1 (epidermolysis bullosa, dystrophic, dominant and recessive) | GAGCCAGATA[C/T]TGAGTATACG | M | C | T | T | I |
| G729u11 | WIAF-11866 | L02870 | 2221 | COL7A1, collagen, type VII, alpha 1 (epidermolysis bullosa, dystrophic, dominant and recessive) | TCATCTGTCA[C/T]CATTACCTGG | M | C | T | T | I |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G729u12 | WIAF-11869 | L02870 | 6585 | COL7A1, collagen, type VII, alpha 1 (epidermolysis bullosa, dystrophic, dominant and recessive) | ACCAGAGAG[C/T]GTGGTATGGC | M | C | T | R | C |
| G729u13 | WIAF-11870 | L02870 | 8169 | COL7A1, collagen, type VII, alpha 1 (epidermolysis bullosa, dystrophic, dominant and recessive) | GGGTGACCGA[G/T]GCTTTGACGG | M | G | T | G | C |
| G729u14 | WIAF-11877 | L02870 | 438 | COL7A1, collagen, type VII, alpha 1 (epidermolysis bullosa, dystrophic, dominant and recessive) | CGCCATCCGT[G/A]AGCTTAGCTA | M | G | A | E | K |
| G729u15 | WIAF-11882 | L02870 | 3481 | COL7A1, collagen, type VII, alpha 1 (epidermolysis bullosa, dystrophic, dominant and recessive) | AGGATCCGTG[A/T]CATGCCCTAC | M | A | T | D | V |
| G729u16 | WIAF-11883 | L02870 | 5654 | COL7A1, collagen, type VII, alpha 1 (epidermolysis bullosa, dystrophic, dominant and recessive) | ACGGAAACC[T/C]CGGGACCCTG | S | T | C | P | P |
| G729u17 | WIAF-12884 | L02870 | 7124 | COL7A1, collagen, type VII, alpha 1 (epidermolysis bullosa, dystrophic, dominant and recessive) | TGCCCAGGGC[G/C]CGAGGCGAGA | S | G | C | P | P |
| G729u18 | WIAF-11885 | L02870 | 7757 | COL7A1, collagen, type VII, alpha 1 (epidermolysis bullosa, dystrophic, dominant and recessive) | GCTTGGATGG[T/C]GACAAAGGAC | S | T | C | G | G |
| G729u19 | WIAF-13389 | L02870 | 1615 | COL7A1, collagen, type VII, alpha 1 (epidermolysis bullosa, dystrophic, dominant and recessive) | ACCGTGGTTC[C/T]CACTGTACCA | M | C | T | P | L |
| G729u20 | WIAF-13390 | L02870 | 2930 | COL7A1, collagen, type VII, alpha 1 (epidermolysis bullosa, dystrophic, dominant and recessive) | TCCTAGGGCC[G/A]GCTGGAGAAG | S | G | A | P | P |
| G729u21 | WIAF-13399 | L02870 | 5145 | COL7A1, collagen, type VII, alpha 1 (epidermolysis bullosa, dystrophic, dominant and recessive) | CCACGGAGAT[C/T]CTGGAGAGGA | M | C | T | P | S |
| G729u22 | WIAF-13411 | L02870 | 3472 | COL7A1, collagen, type VII, alpha 1 (epidermolysis bullosa, dystrophic, dominant and recessive) | ATCTTGCAAA[G/A]GATCCGTGAC | M | G | A | R | K |
| G730a1 | WIAF-13303 | X57527 | 305 | COL8A1, collagen, type VIII, alpha 1 | ATGGGCAAGG[A/G]AGCCGTTCCC | M | A | G | E | G |
| G732u1 | WIAF-12616 | M95610 | 936 | COL9A2, collagen, type IX, alpha 2 | CAGGCCGGAC[A/G]GCCCGAAGT | S | A | G | T | T |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G732u2 | WIAF-12617 | M95610 | 696 | COL9A2, collagen, type IX, alpha 2 | AAGGGAGAGA[C/T]GGGCCCTCAT | S | C | T | D | D |
| G732u3 | WIAF-12619 | M95610 | 1288 | COL9A2, collagen, type IX, alpha 2 | AAGTGGGTGA[C/T]CCAGGGGTGG | M | C | T | P | S |
| G732u4 | WIAF-12620 | M95610 | 962 | COL9A2, collagen, type IX, alpha 2 | CCACCAGGGC[C/G]TAGCGGGTGT | M | C | G | P | R |
| G737u1 | WIAF-13394 | M13436 | ? | INHBA, inhibin, beta A (activin A, activin AB alpha polypeptide) | TGCTCCCTG[G/T] | ? | G | T | | |
| G738a1 | WIAF-13383 | M58549 | 183 | MGP, matrix Gla protein | ATGGAGAGCT[A/G]AAGTCCAAGA | M | A | G | K | E |
| G738a2 | WIAF-13384 | M58549 | 330 | MGP, matrix Gla protein | GCGCCAGGGG[A/G]CCAAATGAGA | M | A | G | T | A |
| G739u1 | WIAF-11867 | U94332 | 862 | TNFRSF11B, tumor necrosis factor receptor superfamily, member 11b (osteoprotagerin) | TGCTGAAGTT[A/G]TGGAAACATC | S | A | G | L | L |
| G739u2 | WIAF-11874 | U94332 | 1244 | TNFRSF11B, tumor necrosis factor receptor superfamily, member 11b (osteoprotagerin) | GTATCAGAAG[T/C]TATTTTAGA | S | T | C | L | L |
| G743u1 | WIAF-13402 | HT847 | 1669 | PTHR1, parathyroid hormone receptor 1 | CCCTGAGAC[C/A]CTCGAGACCA | S | C | A | T | T |
| G747u1 | WIAF-12414 | J03040 | 123 | SPARC, secreted protein, acidic, cysteine-rich (osteonectin) | CTCAGCAAGA[A/G]GCCCTGCCTG | S | A | G | E | E |
| G748u1 | WIAF-12628 | HT0157 | 117 | VDR, vitamin D (1,25-dihydroxyvitamin D3) receptor | CCTTCAGGGA[T/C]GGAGGCAATG | M | T | C | M | T |
| G748u2 | WIAF-12629 | HT0157 | 1171 | VDR, vitamin D (1,25-dihydroxyvitamin D3) receptor | CCGCGCCGAT[T/C]GAGGCCATCC | S | T | C | I | I |
| G748u3 | WIAF-12640 | HT0157 | 172 | VDR, vitamin D (1,25-dihydroxyvitamin D3) receptor | TTGACCCGAA[C/T]GTGCCCCCGGA | S | C | T | W | N |
| G749u1 | WIAF-11862 | HT3734 | 679 | osteopontin, alt. transcript 1 | ATCACCTCAC[A/T]CATGGAAAGC | M | A | T | H | L |
| G749u2 | WIAF-11875 | HT3734 | 386 | osteopontin, alt. transcript 1 | AAGATGATGA[A/G]GACCATGTGG | S | A | G | D | D |
| G749u3 | WIAF-11876 | HT3734 | 419 | osteopontin, alt. transcript 1 | CCATTGACTC[G/A]AACGACTCTG | S | G | A | A | S |
| G749a4 | WIAF-12084 | HT3734 | 1711 | osteopontin, alt. transcript 1 | TAAACAGGCT[G/A]ATTCTGAAAG | M | G | A | D | N |
| G749u5 | WIAF-13387 | HT3734 | 738 | osteopontin, alt. tranecript 1 | CCAGGACCTG[A/C]ACCGCCTTC | M | A | C | N | H |
| G749u6 | WIAF-13388 | HT3734 | 716 | osteopontin, alt. transcript 1 | CATACAGGGC[C/A]ATCCCCGTTG | S | C | A | A | A |
| G751u1 | WIAF-12631 | HT5036 | 410 | ADM, adrenomedullin | GACACGAGTC[C/G]GGATGCCGCC | M | C | G | P | R |
| G752u1 | WIAF-11843 | HT1782 | 1405 | CHGA, chromogranin A (parathyroid secretory protein 1) | CGGCCATTGA[A/G]CGAGAGCTGG | S | A | G | E | E |
| G752u2 | WIAF-11873 | HT1782 | 1187 | CHGA, chromogranin A (parathyroid secretory protein 1) | GGACACCGG[G/A]ACAGTTCCAT | M | G | A | D | N |
| G754u1 | WIAF-13382 | K02043 | 663 | NPPA, natriuretic peptide precursor A | GTACAATGCC[G/A]TGTCCAACGC | M | G | A | V | M |
| G756u1 | WIAF-12395 | HT3508 | 2086 | SCNN1A, sodium channel, nonvoltage-gated 1 alpha | CAGTTCCTCC[A/C]CCTGTCCTCT | M | A | G | T | A |
| G757u1 | WIAF-12420 | HT28563 | 797 | SCNN1B, sodium channel, nonvoltage-gated 1, beta (Liddle syndrome) | CCTGCAGGCC[A/C]CCAAACATCTT | M | A | C | T | P |
| G757u2 | WIAF-12421 | HT28563 | 1006 | SCNN1B, sodium channel, nonvoltage-gated 1, beta (Liddle syndrome) | GAACTGAATT[C/T]GGCCTGAAGT | S | C | T | F | F |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G757u3 | WIAF-12430 | HT28563 | 1768 | SCNN1B, sodium channel, nonvoltage-gated 1, beta (Liddle syndrome) | TCATCGACTT[T/C]GTGTGGATCA | S | T | C | F | F |
| G757u4 | WIAF-12494 | HT28563 | 662 | SCNN1B, sodium channel, nonvoltage-gated 1, beta (Liddle syndrome) | AAGCAGCTCA[G/C]CATCAGAAAA | M | G | C | A | P |
| G757u5 | WIAF-12506 | HT28563 | 1091 | SCNN1B, sodium channel, nonvoltage-gated 1, beta (Liddle syndrome) | GATGCTTCAC[G/C]AGCAGAGTC | M | G | C | E | Q |
| G757u6 | WIAF-12507 | HT28563 | 1452 | SCNN1B, sodium channel, nonvoltage-gated 1, beta (Liddle syndrome) | ACCTGCATTG[G/T]CATGTGCAAG | M | G | T | G | V |
| G758u1 | WIAF-12621 | HT27856 | 415 | SCNN1D, sodium channel, nonvoltage-gated 1, delta | CGGGAACCCA[C/T]GTCGGCCGAG | M | C | T | R | C |
| G758u2 | WIAF-12632 | HT27856 | 325 | SCNN1D, sodium channel, nonvoltage-gated 1, delta | CCTCTTTGAG[C/T]GTCACTGGCA | M | C | T | R | C |
| G758u3 | WIAF-12634 | HT27856 | 879 | SCNN1D, sodium channel, nonvoltage-gated 1, delta | ATGGCGTCTG[G/A]ACAGCTCAGC | N | G | A | W | * |
| G758u4 | WIAF-12635 | HT27856 | 1138 | SCNN1D, sodium channel, nonvoltage-gated 1, delta | CGTGGAGGTG[G/C]AGCTGCTACA | M | G | C | E | Q |
| G762u1 | WIAF-12622 | HT27531 | 1850 | NPR3, natriuretic peptide receptor C/guanylate cyclase C (atrionatriuretic peptide receptor C) | TAGGAGCTGG[C/T]TTGCTAATGG | S | C | T | G | G |
| G762u2 | WIAF-12623 | HT27531 | 1926 | NPR3, natriuretic peptide receptor C/guanylate cyclase C (atrionatriuretic peptide receptor C) | AGAAGAAAGT[A/G]ACCTTGAAAA | M | A | G | N | D |
| G762u3 | WIAF-12624 | HT27531 | 1791 | NPR3, natriuretic peptide receptor C/guanylate cyclase C (atrionatriuretic peptide receptor C) | CAAATCATCA[G/T]GTGCCTAGA | M | G | T | G | C |
| G762u4 | WIAF-12636 | HT27531 | 1963 | NPR3, natriuretic peptide receptor C/guanylate cyclase C (atrionatriuretic peptide receptor C) | GAAGATTCCA[T/C]CAGATCCCAT | M | T | C | I | T |
| G763u1 | WIAF-12659 | HT3183 | 1633 | NPR2, natriuretic peptide receptor B/guanylate cyclase B (atrionatriuretic peptide receptor B) | CTGGGCCCTT[C/T]CCTGATGAAC | M | C | T | S | F |
| G763u2 | WIAF-12678 | HT3183 | 668 | NPR2, natriuretic peptide receptor B/guanylate cyclase B (atrionatriuretic peptide receptor B) | TGCCATCACT[T/C]CTGCTGTTGG | S | T | C | L | L |
| G763u3 | WIAF-12684 | HT3183 | 2354 | NPR2, natriuretic peptide receptor B/guanylate cyclase B (atrionatriuretic peptide receptor B) | TGTTTGAACT[C/T]AAACATATGA | S | C | T | L | L |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G764u1 | WIAF-12698 | HT1221 | 3021 | NPR1, natriuretic peptide receptor A/guanylate cyclase A (atrionatriuretic peptide receptor A) | CCCCGTTACT[G/T]TCTCTTTGGG | M | G | T | C | F |
| G764u2 | WIAF-12708 | HT1221 | 588 | NPR1, natriuretic peptide receptor A/guanylate cyclase A (atrionatriuretic peptide receptor A) | GAGCGCCAAG[C/T]GCTCATGCTC | M | C | T | A | V |
| G764u3 | WIAF-12709 | HT1221 | 1897 | NPR1, natriuretic peptide receptor A/guanylate cyclase A (atrionatriuretic peptide receptor A) | GTCCCCGTGG[G/A]AGCCTGCAGG | S | G | A | G | G |
| G765u1 | WIAF-10012 | HT2456 | 604 | DCP1, dipeptidyl carboxypeptidase 1 (angiotensin I converting enzyme) | GCTGGCACAA[A/G]GCTGCGGGCA | S | A | G | N | N |
| G765u2 | WIAF-10014 | HT2456 | 2350 | DCP1, dipeptidyl carboxypeptidase 1 (angiotensin I converting enzyme) | TGATGGCCAC[A/G]TCCCGGAAAT | S | A | G | T | T |
| G765u3 | WIAF-10025 | HT2456 | 1668 | DCP1, dipeptidyl carboxypeptidase 1 (angiotensin I converting enzyme) | CCCACTGCAC[C/A]AGTGTGACAT | M | C | A | Q | K |
| G765u4 | WIAF-10027 | HT2456 | 3220 | DCP1, dipeptidyl carboxypeptidase 1 (angiotensin I converting enzyme) | TCCCCCTTCAG[C/T]TACCTCGTCG | S | C | T | S | S |
| G765u5 | WIAF-10028 | HT2456 | 3409 | DCP1, dipeptidyl carboxypeptidase 1 (angiotensin I converting enzyme) | TCAGGTACTT[T/C]GTCAGCTTCA | S | T | C | F | F |
| G765u6 | WIAF-10040 | HT2456 | 775 | DCP1, dipeptidyl carboxypeptidase 1 (angiotensin I converting enzyme) | AGCCCCTCTA[C/T]CTGAACCTCC | S | C | T | Y | Y |
| G772u1 | WIAF-12626 | HT2121 | 1064 | AVPR2, arginine vasopressin receptor 2 (nephrogenic diabetes insipidus) | TCAGCAGCAG[C/T]GTGTCCTCAG | S | C | T | S | S |
| G772u2 | WIAF-12627 | HT2121 | 998 | AVPR2, arginine vasopressin receptor 2 (nephrogenic diabetes insipidus) | CCTTTGTGCT[A/G]CTCATGTTGC | S | A | G | L | L |
| G773u1 | WIAF-12644 | HT2141 | 163 | SLC6A6, solute carrier family 6 (neurotransmitter transporter, taurine), member 6 | CTAGCAAGAT[C/T]GACTTTGTGC | S | C | T | X | T |
| G773u2 | WIAF-12645 | HT2141 | 445 | SLC6A6, solute carrier family 6 (neurotransmitter transporter, taurine), member 6 | TCGTCATCCT[G/C]GCCTGGGCCA | S | G | C | L | L |
| G773u3 | WIAF-12665 | HT2141 | 289 | SLC6A6, solute carrier family 6 (neurotransmitter transporter, taurine), member 6 | TGTTTGGGAG[C/T]GGGCTGCCTG | S | C | T | S | G |
| G773u4 | WIAF-12666 | HT2141 | 382 | SLC6A6, solute carrier family 6 (neurotransmitter transporter, taurine), member 6 | CCTTGTTCTC[T/C]GGTATCGGCT | S | T | C | S | S |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G776u1 | WIAF-11857 | U66088 | 1457 | SLC5A5, solute carrier family 5 (sodium iodide symporter), member 5 | TAGAAGACCT[C/T]ATCAAACCTC | S | C | T | L | L |
| G776u2 | WIAF-11871 | U66088 | 2039 | SLC5A5, solute carrier family 5 (sodium iodide symporter), member 5 | GATTGTGTG[G/C]TGGGACCTCG | M | G | C | W | C |
| G776u3 | WIAF-13398 | U66088 | 1379 | SLC5A5, solute carrier family 5 (sodium iodide symporter), member 5 | GGCTTTTCCT[G/A]GCCTGTGCTT | S | G | A | L | L |
| G777u1 | WIAF-12646 | HT27843 | 4348 | SMRT | ATACAATATC[A/G]GCCAGCCTGG | M | A | G | S | G |
| G777u2 | WIAF-12664 | HT27843 | 2031 | SMRT | CTGAGCTGGG[T/C]AAGCCGCGGC | S | T | C | G | G |
| G777u3 | WIAF-12655 | HT27843 | 2052 | SMRT | AGAGCCCCCT[G/A]ACCTATGAGG | S | G | A | L | L |
| G777u4 | WIAF-12675 | HT27843 | 2205 | SMRT | CTCGTGAGAT[C/T]GCCAAGTCCC | S | C | T | H | H |
| G778u1 | WIAF-14093 | HT1449 | 8212 | TG, thyroglobulin | ATCTCGTCTC[T/C]GAAGACATCT | M | T | C | L | P |
| G778u2 | WIAF-14111 | HT1449 | 6033 | TG, thyroglobulin | ATGTGAACGA[C/T]GGTGCGATGC | M | C | T | R | W |
| G778u3 | WIAF-14112 | HT1449 | 6894 | TG, thyroglobulin | GTATCTCAAT[G/T]TGTTCATCCC | M | G | T | V | L |
| G778u4 | WIAF-14125 | HT1449 | 2375 | TG, thyroglobulin | ATGGGCCTCC[T/C]GAGCAGGTCT | S | T | C | P | P |
| G778u5 | WIAF-14136 | HT1449 | 1931 | TG, thyroglobulin | AGGATGTCGA[A/G]TGCTTTCCG | M | A | G | Q | P |
| G783u1 | WIAF-12649 | X97674 | 4008 | H. sapiens mRNA for transcriptional intermediary factor 2. | CTAGTGGTAT[G/C]CCAGCAACTA | M | G | C | M | I |
| G783u2 | WIAF-12658 | X97674 | 2566 | H. sapiens mRNA for transcriptional intermediary factor 2. | GCCTGGCAGT[G/A]AGCTGGACAA | M | G | A | E | K |
| G783u3 | WIAF-12671 | X97674 | 3828 | H. sapiens mRNA for transcriptional intermediary factor 2. | CTCTGAGGCC[T/C]GGAGTACCAA | S | T | C | P | P |
| G785u1 | WIAF-13385 | HT1291 | 386 | TTR, transthyretin (prealbumin, amyloidosis type I) | CCAACGACTC[C/T]GGCCCCCGCC | S | C | T | S | S |
| G787u1 | WIAF-12652 | HT27477 | 468 | TRIP15: thyroid receptor interacting protein 15 | GAAAATTATA[T/C]TTAGAACCAG | S | T | C | Y | Y |
| G792u1 | WIAF-12661 | HT27476 | 265 | thyroid receptor interactor 14 | CAGCTGGAAC[G/A]TGAAGAGGGC | M | G | A | V | M |
| G793u1 | WIAF-12643 | HT5152 | 458 | thyroid receptor interactor 8 | GGAAGCTTTT[C/G]AAAGAATGTT | M | C | G | S | * |
| G794u1 | WIAF-12664 | HT5136 | 1110 | PSMC5, proteasome (prosome, macropain) 26S subunit, ATPase, 5 | GCGTGTGCAC[G/A]GAAGCTGGCA | S | G | A | T | T |
| G797u1 | WIAF-11847 | HT3919 | 140 | glutamate receptor 3, flip isoform | CTCACGGAGG[A/G]TTCCCCAACA | S | A | G | G | G |
| G797u2 | WIAF-11848 | HT3919 | 759 | glutamate receptor 3, flip isoform | GGTTGTGATC[C/T]TAGGGAAACA | S | C | T | L | L |
| G797u3 | WIAF-11849 | HT3919 | 1253 | glutamate receptor 3, flip isoform | GCTACTGGAA[C/T]GAGTATGAAA | M | C | T | N | N |
| G797u4 | WIAF-11850 | HT3919 | 1770 | glutamate receptor 3, flip isoform | TCTTTTCCTA[G/A]TCAGCAGGTT | M | G | A | V | I |
| G797u5 | WIAF-13404 | HT3919 | 2711 | glutamate receptor 3, flip isoform | GCTAGAACGT[G/A]TATGGAACAG | M | G | A | V | V |
| G797u6 | WIAF-13405 | HT3919 | 2376 | glutamate receptor 3, flip isoform | CTCAGCATTA[G/A]GAACGCCTGT | S | G | A | G | R |
| G798u1 | WIAF-11868 | X77748 | 2655 | GRM3, glutamate receptor, metabotropic 3 | TGCAGACGAC[A/G]ACCATGTGCA | M | A | G | T | T |
| G798u2 | WIAF-11879 | X77748 | 2771 | GRM3, glutamate receptor, metabotropic 3 | CACAGACTGC[A/G]CCTCAACAGG | M | A | G | H | R |
| G798a3 | WIAF-12085 | X77748 | 2699 | GRM3, glutamate receptor, metabotropic 3 | GTGGTCTTGG[G/C]CTGTTTGTTT | M | G | C | G | A |
| G798a4 | WIAF-12086 | X77748 | 2738 | GRM3, glutamate receptor, metabotropic 3 | ATCCTGTTTC[A/G]ACCCCAGAAG | M | A | G | Q | R |
| G798a5 | WIAF-12087 | X77748 | 2072 | GRM3, glutamate receptor, metabotropic 3 | ACACCCTTGG[T/C]CAAAGCATCG | M | T | C | V | A |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G798a6 | WIAF-12088 | X77748 | 2235 | GRM3, glutamate receptor, metabotropic 3 | CCCTGCTGAC[C/T]AAGACAAACT | S | C | T | T | T |
| G798u7 | WIAF-13391 | X77748 | 1131 | GRM3, glutamate receptor, metabotropic 3 | GCGCCAATGC[C/T]TCCTTCACCT | S | C | T | A | A |
| G799u1 | WIAF-11880 | M81883 | 2000 | GAD1, glutamate decarboxylase 1 (brain, 67 kD) | CAACAAATGC[C/T]TGGAACTGGC | S | C | T | L | L |
| G799u2 | WIAF-11881 | M81883 | 1822 | GAD1, glutamate decarboxylase 1 (brain, 67 kD) | AGGGTATATC[C/T]CAAGGATGCA | S | C | T | L | L |
| G799u3 | WIAF-13392 | M81883 | 661 | GAD1, glutamate decarboxylase 1 (brain, 67 kD) | GCGTGGCCCA[T/C]GGATGCACCA | S | T | C | H | H |
| G799u4 | WIAF-13393 | M81883 | 556 | GAD1, glutamate decarboxylase 1 (brain, 67 kD) | AGCTGATGGC[G/A]TCTTCGACCC | S | G | A | A | A |
| G799u5 | WIAF-13410 | M81883 | 1229 | GAD1, glutamate decarboxylase 1 (brain, 67 kD) | CCTCATGGAA[C/T]AAATAACACT | N | C | T | Q | * |
| G801u1 | WIAF-23403 | D49394 | 1596 | HTR3, 5-hydroxytryptamine (serotonin) receptor 3 | TTTACCTGCT[A/G]GCCGTGCTGG | S | A | G | L | L |
| G803a1 | WIAF-13118 | U66406 | 1446 | EFNB3, ephrin-B3 | CTGGGCCTGG[G/A]GGGTGGAGGT | M | G | A | G | E |
| G804u1 | WIAF-11887 | Z26653 | 7237 | LAMA2, laminin, alpha 2 (merosin, congenital muscular dystrophy) | TCACTGATGG[G/T]CACATAAAAG | S | G | T | G | G |
| G804u2 | WIAF-21901 | Z26653 | 9351 | LAMA2, laminin, alpha 2 (merosin, congenital muscular dystrophy) | GCAAGCCACT[G/C]GAGGTTAATT | M | G | C | W | S |
| G804u3 | WIAF-11924 | Z26653 | 8740 | LAMA2, laminin, alpha 2 (merosin, congenital muscular dystrophy) | ACACTACCCG[A/G]AGAATTGGTC | S | A | G | R | R |
| G804u4 | WIAF-11943 | Z26653 | 8577 | LAMA2, laminin, alpha 2 (merosin, congenital muscular dystrophy) | ACCAAAATCA[A/G]TGATGGCCAG | M | A | G | N | S |
| G804a5 | WIAF-12089 | Z26653 | 3372 | LAMA2, laminin, alpha 2 (merosin, congenital muscular dystrophy) | CTCTGTGACT[G/A]CTTCCTCCCT | M | G | A | C | Y |
| G804a6 | WIAF-13227 | Z26653 | 7047 | LAMA2, laminin, alpha 2 (merosin, congenital muscular dystrophy) | GTCAGTCCTC[A/g]GGTGGAAGAT | S | A | g | Q | R |
| G804u7 | WIAF-13437 | Z26653 | 6791 | LAMA2, laminin, alpha 2 (merosin, congenital muscular dystrophy) | TGTGAGAGCC[C/T]TGGATGGACC | S | C | T | L | L |
| G805u1 | WIAF-13416 | U14755 | 799 | LHX1, LIM homeobox protein 1 | AAGTAACAGC[A/G]GTGTTGCCAA | M | A | G | S | G |
| G805u2 | WIAF-13417 | U14755 | 743 | LHX1, LIM homeobox protein 1 | GGGGAGGAAC[T/C]CTACATCATC | M | T | C | L | P |
| G805u3 | WIAF-13428 | U14755 | 639 | LHX1, LIM homeobox protein 1 | GCCGTCAGGG[C/A]ATCTCCCCTA | S | C | A | G | G |
| G806u1 | WIAF-11866 | AF026547 | 2656 | CSPG3, chondroitin sulfate proteoglycan 3 (neurocan) | TTGGAGTTCC[A/G]GCCATGTCTA | S | A | G | P | P |
| G806u2 | WIAF-11895 | AF026547 | 529 | CSPG3, chondroitin sulfate proteoglycan 3 (neurocan) | TGACCTTCGC[T/C]GAGGCCCAGG | S | T | C | A | A |
| G806u3 | WIAF-11896 | AF026547 | 477 | CSPG3, chondroitin sulfate proteoglycan 3 (neurocan) | GAGGTGACAG[G/A]TGTTGTTTC | M | G | A | G | D |
| G806u4 | WIAF-11917 | AF026547 | 89 | CSPG3, chondroitin sulfate proteoglycan 3 (neurocan) | ACAGGATATC[A/G]CCGATGCCAG | M | A | G | T | A |
| G806u5 | WIAF-11918 | AF026547 | 213 | CSPG3, chondroitin sulfate proteoglycan 3 (neurocan) | AGCGCCAGCCC[G/C]AGATGCCCT | M | G | C | R | P |
| G806u6 | WIAF-11929 | AF026547 | 769 | CSPG3, chondroitin sulfate proteoglycan 3 (neurocan) | GCTTTGCCCG[G/A]GAGCTGGGGG | S | G | A | R | R |
| G806u7 | WIAF-11931 | AF026547 | 3148 | CSPG3, chondroitin sulfate proteoglycan 3 (neurocan) | ACATTGATGA[C/T]TGCCTCTGCA | S | C | T | D | D |
| G806u8 | WIAF-11949 | AF026547 | 209 | CSPG3, chondroitin sulfate proteoglycan 3 (neurocan) | GCCAAGCGCA[G/A]CCCGAGATGC | M | G | A | A | T |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G806a9 | WIAF-13114 | AF026547 | 3430 | CSPG3, chondroitin sulfate proteoglycan 3 (neurocan) | ATGAAAACAC[G/A]TGGATCGCC | S | G | A | T | T |
| G806u10 | WIAF-13420 | AF026547 | 2113 | CSPG3, chondroitin sulfate proteoglycan 3 (neurocan) | CCAGGCAGA[C/G]TTCAGAGAAA | M | C | G | D | E |
| G806u11 | WIAF-13431 | AF026547 | 94 | CSPG3, chondroitin sulfate proteoglycan 3 (neurocan) | ATATCACCGA[T/G]GCCAGCAAA | M | T | G | D | E |
| G806u12 | WIAF-13432 | AF026547 | 275 | CSPG3, chondroitin sulfate proteoglycan 3 (neurocan) | ACAGGACTTG[C/T]CCATCCTGGT | M | C | T | P | S |
| G808a1 | WIAF-13117 | Y13276 | 177 | TLX, tailless homolog (Drosophila) | GCATGAGCAA[G/a]CCAGCCGAT | S | G | a | K | K |
| G810u1 | WIAF-11890 | X98248 | 990 | SORT1, sortilin 1 | ATAAGGATAC[C/A]ACAGAAGGA | S | C | A | T | T |
| G810u2 | WIAF-11891 | X98248 | 1093 | SORT1, sortilin 1 | GGCAGCAAAT[G/T]ATGACATGT | M | G | T | D | Y |
| G810u3 | WIAF-11907 | X98248 | 1683 | SORT1, sortilin 1 | CAGACAAAGG[T/G]CAATGCTGGC | S | T | G | G | G |
| G810u4 | WIAF-11908 | X98248 | 1433 | SORT1, sortilin 1 | ATCTCCCAGA[A/C]ACTGAATGTT | M | A | C | K | T |
| G810u5 | WIAF-13909 | X95248 | 1354 | SORT1, sortilin 1 | GAAGCCTCAA[A/G]ACAGTGAATG | M | A | G | N | D |
| G810u6 | WIAF-11910 | X98248 | 2180 | SORT1, sortilin 1 | TACCGGAAAA[T/A]TCCAGGGGAC | M | T | A | I | N |
| G810u7 | WIAF-11911 | X98248 | 2264 | SORT1, sortilin 1 | AACTTTTTGA[G/A]TCCGGAAAAA | M | G | A | S | N |
| G810u8 | WIAF-11925 | X98248 | 1993 | SORT1, sortilin 1 | TCGAGACTAT[G/A]TTGTGACCAA | M | G | A | V | I |
| G810u9 | WIAF-11939 | X98248 | 1351 | SORT1, sortilin 1 | GAGGAGCCCT[G/C]AAAACAGTGA | H | G | C | E | Q |
| G810u10 | WIAF-11940 | X98248 | 2232 | SORT1, sortilin 1 | AAGTAAAAGA[C/T]TTGAAAAGA | S | C | T | D | D |
| G810a11 | WIAF-11915 | X98248 | 1769 | SORT1, sortilin 1 | TCCATGAATA[T/A]CAGCATTTPG | W | T | A | I | N |
| G810a12 | WIAF-13116 | X98248 | 1757 | SORT1, sortilin 1 | CCTGGAGCTA[G/A]GTCCATGAAT | M | G | A | R | K |
| GB11u1 | WIAF-11893 | HT3676 | 900 | synapain I, alt. transcript 1 | TGACCAAGAC[G/A]ATGCCACTG | S | G | A | T | T |
| G811u2 | WIAF-11894 | HT3676 | 758 | synapain I, alt. transcript 1 | ACCTTCTACC[C/T]CAATCACCAA | M | C | T | P | L |
| GB11u3 | WIAF-11927 | HT3676 | 996 | synapain I, alt. transcript 1 | CGTCAGTGTC[A/T]GGGAACTGGA | S | A | T | S | S |
| GB11u4 | WIAF-11928 | HT3676 | 1054 | synapain I, alt. transcript 1 | CATGTCTGAC[A/G]CATACAAGCT | H | A | G | R | G |
| G811u5 | WIAF-13418 | HT3676 | 249 | synapain I, alt. transcript 1 | TGTCCAACGC[G/A]GTCAAGCAGA | S | G | A | A | A |
| G811u6 | WIAF-13419 | HT3676 | 432 | synapain I, alt. transcript 1 | TTAAAGTAGA[G/A]CAGGCCGAAT | S | G | A | E | E |
| G812u1 | WIAF-11898 | HT4564 | 163 | STX1A, syntaxin 1A (brain) | CCAACCCGA[T/C]GAGAAGACGA | S | T | C | D | D |
| G812u2 | WIAF-11942 | HT4564 | 604 | STX1A, syntaxin 1A (brain) | TACAGACCAT[G/T]TTCATGACA | M | G | T | H | H |
| G813u1 | WIAF-11934 | U72508 | 939 | Human B7 mRNA, complete cds. | TATGAGACAG[G/A]ACAGAGGATG | N | G | A | G | E |
| GB13u2 | WIAF-11948 | U72508 | 619 | Human B7 mRNA, complete cds. | GCATCCACAT[G/C]GTGACAGGTC | S | G | C | M | I |
| G816u1 | WIAF-11897 | HT4230 | 151 | HTR2B, 5-hydroxytryptamine (serotonin) receptor 2B | CTAACTGGTC[T/G]GGATTACAGA | S | T | G | S | S |
| G816u2 | WIAF-11930 | HT4230 | 189 | HTR2B, 5-hydroxytryptamine (serotonin) receptor 2B | GAAATGAAAC[A/G]GATTGTTGGG | M | A | G | Q | R |
| G818u1 | WIAF-11902 | HT2694 | 753 | TPH, tryptophan hydroxylase (tryptophan 5-monooxygenase) | CTAACTGGTC[C/T]TGCACTCAAT | S | C | T | H | H |
| G818u2 | WIAF-11903 | HT2694 | 775 | TPH, tryptophan hydroxylase (tryptophan 5-monooxygenase) | TGTGAGACAC[A/G]GTTCAGATCC | M | A | G | S | G |
| G818u3 | WIAF-11904 | HT2694 | 1211 | TPH, tryptophan hydroxylase (tryptophan 5-monooxygenase) | TATAATCCAT[A/C]TACACGGAGT | M | A | C | Y | S |
| G818u4 | WIAF-11905 | HT2694 | 1081 | TPH, tryptophan hydroxylase (tryptophan 5-monooxygenase) | GATTACCTGC[A/C]AACAGGAATG | M | A | C | K | Q |
| G818u5 | WIAF-11933 | HT2694 | 795 | TPH, tryptophan hydroxylase (tryptophan 5-monooxygenase) | CCTTCTATAC[C/T]CCAGAGCCAG | S | C | T | T | T |
| G818u6 | WIAF-11935 | HT2694 | 1239 | TPH, tryptophan hydroxylase (tryptophan 5-monooxygenase) | TCCTGAAAGA[C/T]ACCAAGAGCA | S | C | T | D | D |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G822u1 | WIAF-11906 | HT0207 | 936 | ASMT, acetylserotonin N-methyltransferase | CAGACGGAAA[G/T]TGCTCACACC | M | G | T | K | N |
| G822u2 | WIAF-11919 | HT0207 | 637 | ASMT, acetylserotonin N-methyltransferase | TGGTGGGACA[C/T]GGATAAAGCT | M | C | T | R | W |
| G822u3 | WIAF-11936 | HT0207 | 318 | ASMT, acetylserotonin N-methyltransferase | GAAAAGCTTT[C/T]TATCGAAACA | S | C | T | F | F |
| G822u4 | WIAF-11937 | HT0207 | 116 | ASMT, acetylserotonin N-methyltransferase | AATGACTACG[C/T]CAACGGCTTC | W | C | T | A | V |
| G822u5 | WIAF-11938 | HT0207 | 930 | ASMT, acetylserotonin N-methyltransferase | ACTGGGCAGA[C/T]GGAAAGTGCT | S | C | T | D | D |
| G822u6 | WIAF-13427 | HT0207 | 120 | ASMT, acetylserotonin N-methyltransferase | ACTACGCCAA[C/A]GGCTTCATGG | M | C | A | N | K |
| G825u1 | WIAF-11888 | HT4974 | 236 | ADAR, adenosine deaminase, RNA-specific | GCTCAGATAC[C/T]AGGAGCCTGG | N | C | T | Q | * |
| G825u2 | WIAF-11900 | HT4974 | 3076 | ADAR, adenosine deaminase, RNA-specific | TCTTTGACAA[A/G]TCCTGCAGCG | S | A | G | K | K |
| G825u3 | WIAF-11912 | HT4974 | 2537 | ADAR, adenosine deaminase, RNA-specific | CTTGATTGGG[G/C]AGAAACGAGAA | M | G | C | E | Q |
| G825u4 | WIAF-11941 | HT4974 | 3558 | ADAR, adenosine deaminase, RNA-specific | GATGGCTATG[A/G]CCTGGAGATC | M | A | G | D | G |
| G825a5 | WIAF-12090 | HT4974 | 1305 | ADAR, adenosine deaminase, RNA-specific | CCTGAGACCA[A/G]AAGAAACGCA | M | A | G | K | R |
| G825u6 | WIAF-13426 | HT4974 | 3683 | ADAR, adenosine deaminase, RNA-specific | CCGCAGGGAT[C/T]TACTGAGACT | S | C | T | L | L |
| G826u1 | WIAF-12554 | X99383 | 2109 | ADARB1, adenosine deaminase, RNA-specific, B1 (homolog of rat RED1) | AGATTACCAA[A/G]CCCAACGTGT | S | A | G | K | K |
| G826u2 | WIAF-12566 | X99383 | 1698 | ADARB1, adenosine deaminase, RNA-specific, B1 (homolog of rat RED1) | TGTCCTGCAG[T/G]GACAAGATTG | M | T | G | S | R |
| G829u1 | WIAF-13735 | U49262 | 1404 | DVL3, dishevelled 3 (homologous to Drosophila dsh) | GGGTTGGAGG[T/C]CCGTGACTGC | W | T | C | V | A |
| G83u1 | WIAF-10449 | HT1576 | 133 | DNMT1, DNA (cytosine-5-)methyltransferase 1 | ATGGATGACCC[G/A]TCTCTTGAAG | S | G | A | P | P |
| G83u2 | WIAF-10450 | HT1576 | 1871 | DNMT1, DNA (cytosine-5-)methyltransferase 1 | AAGCTGGTCT[A/G]CCAGATCTTC | M | A | G | Y | C |
| G83u3 | WIAF-10468 | HT1576 | 928 | DNMT1, DNA (cytosine-5-)methyltransferase 1 | AAATCCACAG[A/G]TTTCTGATGA | M | A | G | I | V |
| G83u4 | WIAF-10469 | HT1576 | 1562 | DNMT1, DNA (cytosine-5-)methyltransferase 1 | AATTCCGACT[C/T]GACCTATGAG | M | C | T | S | L |
| G83u5 | WIAF-10471 | HT1576 | 2424 | DNMT1, DNA (cytosine-5-)methyltransferase 1 | GGGCCACGTC[G/A]GACCCTCTGG | S | G | A | S | S |
| G83u6 | WIAF-10473 | HT1576 | 3790 | DNMT1, DNA (cytosine-5-)methyltransferase 1 | GTTCTTCCTC[C/T]TGGAGAATGT | S | C | T | L | L |
| G83u7 | WIAF-10486 | HT1576 | 1581 | DNMT1, DNA (cytosine-5-)methyltransferase 1 | AGGACCTGAT[C/A]AACAAGATCG | S | C | A | I | I |
| G832u1 | WIAF-12577 | L13387 | 1129 | PAFAH1B1, platelet-activating factor acetylhydrolase, isoform 1b, alpha subunit (45 kD) | AGACATTCAC[A/T]GGACACAGAG | S | A | T | T | T |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G835u1 | WIAF-12555 | U38276 | 1311 | SEMA3F, sema domain, immunoglobulin domain (Ig), short basic domain, secreted, 3F | CCTCTGGCTC[C/A]GTGTTCCGAG | S | C | A | S | S |
| G835u2 | WIAF-12556 | U38276 | 1229 | SEMA3F, sema domain, immunoglobulin domain (Ig), short basic domain, secreted, 3F | ACTCACTTTG[A/T]TGAGCTCCAG | M | A | T | D | V |
| G835u3 | WIAF-12557 | U38276 | 1473 | SEMA3F, sema domain, immunoglobulin domain (Ig), short basic domain, secreted, 3F | GAACCTTCAC[G/A]CCATCTATGA | S | G | A | T | T |
| G835a4 | WIAF-13138 | U3B276 | 1726 | SEMA3F, sema domain, immunoglobulin domain (Ig), short basic domain, secreted, 3F | TGACCAGGAG[A/T]TGGAGGAGCT | M | A | T | M | L |
| G836u1 | WIAF-12592 | U28369 | 1056 | SEMA3B, sema domain, immunoglobulin domain (Ig), short basic domain, secreted, 3B | AACGACGTGG[G/A]CGGCCAGCGC | M | G | A | G | D |
| G836u2 | WIAF-12609 | U28369 | 1479 | SEMA3B, sema domain, immunoglobulin domain (Ig), short basic domain, secreted, 3B | GTCCTGCCCA[C/T]TGGGGGCGC | M | C | T | T | I |
| G838u1 | WIAF-12590 | U72671 | 1107 | ICAMS, intercellular adhesion molecule 5, telencephalin | CGCAGCTGGG[A/G]CCCAAGCTCT | M | A | G | T | A |
| G838u2 | WIAF-12591 | U72671 | 966 | ICAMS, intercellular adhesion molecule 5, telencephalin | CAGGCAGTCG[A/G]TCTGCAACGT | M | A | G | I | V |
| G840a1 | WIAF-12109 | HT961 | 2232 | SOS1, son of sevenless (Drosophila) homolog 1 | CTCAGGCAAA[T/C]GGAGTAAGCC | S | T | C | N | N |
| G840a2 | WIAF-12110 | HT961 | 2404 | SOS1, son of sevenless (Drosophila) homolog 1 | ACCGTCTAAA[C/G]TTGTAGGGAG | M | C | G | L | V |
| G840u3 | WIAF-12213 | HT961 | 3813 | SOS1, son of sevenless (Drosophila) homolog 1 | CAAGGTACC[G/A]CGTCGATGCT | S | G | A | P | P |
| G841u1 | WIAF-12153 | HT97420 | 1372 | SMOH, smoothened (Drosophila) homolog | TTTTGGCTTC[C/G]TGGCCTTTGG | M | C | G | L | V |
| G841u2 | WIAF-12179 | HT97420 | 858 | SMOH, smoothened (Drosophila) homolog | CCCAGTTCAT[G/T]GATGGTGGCC | M | G | T | M | I |
| G841u3 | WIAF-12185 | HT97420 | 1164 | SMOH, smoothened (Drosophila) homolog | CTGTGACTGG[C/G]ATTTGTTTTG | S | C | G | G | G |
| G847u1 | WIAF-12588 | L41939 | 2019 | EPHB2, EphB2 | GGTCTCCAGT[G/T]GCCACCTGAA | M | G | T | G | C |
| G847u2 | WIAF-12596 | L41939 | 1806 | EPHB2, EphB2 | GTGTAACAGA[A/C]GACGGGGTTT | M | A | C | R | R |
| G847u3 | WIAF-12613 | L41939 | 2885 | EPHB2, EphB2 | AGGCCATCAA[G/C]ATGGGGCAGT | M | G | C | X | H |
| G848u1 | WIAF-12685 | L40636 | 2484 | EPHB1, EphB1 | GTCAACAGTA[A/G]CCTGGTGTGC | M | A | G | N | S |
| G848u2 | WIAF-12690 | L40636 | 2020 | EPHB1, EphB1 | CCTTCACTTA[T/C]GAGGATCCA | S | T | C | Y | Y |
| G849u1 | WIAF-11920 | D83492 | 1544 | EPHB6. EphB6 | ACCTGTGTGG[C/T]TCATGCAGAG | M | C | T | A | V |
| G849u2 | WIAF-11921 | D83492 | 3301 | EPHB6, EphB6 | CTTTGGGATA[C/T]TCCTTACTAC | M | C | T | L | F |
| G849u3 | WIAF-13412 | D83492 | 1139 | EPHB6, EphB6 | GAGACCTTCA[C/T]CCTTTACTAC | M | C | T | T | I |
| G849u4 | WIAF-13413 | D83492 | 1895 | EPHB6, EphB6 | TTTGAGTGC[A/C]AGGCTCAGCA | M | A | C | Q | P |
| G849u5 | WIAF-13414 | D83492 | 2338 | EPHB6, EphB6 | CTATGACCAG[G/A]CAGAAGACGA | M | G | A | A | T |
| G849u6 | WIAF-13415 | D83492 | 2567 | EPHB6, EphB6 | GGGGCTTTGG[C/G]CTTCCTCCTG | M | C | G | A | G |
| G849u7 | WIAF-13422 | D83492 | 2860 | EPHB6, EphB6 | GGCCATCCAG[G/A]CCCTGTGGGC | M | G | A | A | T |
| G849u8 | WIAF-13423 | D83492 | 2782 | EPHB6, EphB6 | GGAGGTCATT[G/C]GGACAGGCTC | M | G | C | G | R |
| G849u9 | WIAF-13424 | D83492 | 3038 | EPHB6, EphB6 | TTCCTCAGG[A/G]GCGGGAGGGC | S | A | G | Q | R |
| G849u10 | WIAF-13425 | D83492 | 3637 | EPHB6, EphB6 | AGCCATTGGA[C/T]TGGAGTGCTA | S | C | T | L | L |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G856u1 | WIAF-12625 | D45906 | 1323 | LIMK2, LIM domain kinase 2 | AGCTGAACCT[G/C]CTGACAGAGT | S | G | C | L | L |
| G858u1 | WIAF-12630 | U65019 | 864 | MADH2, MAD (mothers against decapentaplegic, Drosophila) homolog 2 | TTTGGTGTTC[G/A]ATAGCATATT | S | G | A | S | S |
| G86u1 | WIAF-10437 | HT1701 | 263 | RAD51, RAD51 (S. cerevisiae) homolog (E coli RecA homolog) | TGAAGCAAAT[G/C]CAGATACTTC | M | G | C | A | P |
| G86u2 | WIAF-10465 | HT1701 | 861 | RAD51, RAD51 (S. cerevisiae) homolog (E coli RecA homolog) | GCATCAGCCA[T/C]GATGGTAGAA | M | T | C | M | T |
| G86u3 | WIAF-10466 | HT1701 | 924 | RAD51, RAD51 (S. cerevisiae) homolog (E coli RecA homolog) | TACAGAACAG[A/G]CTACTCGGGT | M | A | G | D | G |
| G864a1 | WIAF-13139 | X82324 | 183 | POU3F4, POU domain, class 3, transcription factor 4 | CAGCAATGGG[C/+]ATCCCCTCGG | M | C | t | H | Y |
| G866u1 | WIAF-12637 | HT0101 | 2576 | glutamate receptor (GB:M64752) | AAATCCCGTA[G/A]TGAATCCAAG | M | G | A | S | N |
| G866u2 | WIAF-12638 | HT0301 | 1131 | glutamate receptor (GB:M64752) | TAACAGGAAA[C/T]GTGCAGTTTA | S | C | T | N | N |
| G869u1 | WIAF-13406 | HT33620 | 3627 | GRIN2C, glutamate receptor, ionotropic, N-methyl D-aspartate 2C | AGATCAGCAG[G/T]GTAGCCCGTG | M | G | T | R | S |
| G870u1 | WIAF-11889 | HT4468 | 714 | SLC1A1, solute carrier family 1 (neuronal/epithelial high affinity glutamate transporter, system Xag), member 1 | CAGAAGAGTC[C/G]TTCACAGCTG | S | C | G | S | S |
| G870u2 | WIAF-11913 | HT4468 | 314 | SLC1A1, solute carrier family 1 (neuronal/epithelial high affinity glutamate transporter, system Xag), member 1 | CTAGAGAAAT[T/A]CTACTTTGCT | M | T | A | F | Y |
| G870u3 | WIAF-11914 | HT4468 | 579 | SLC1A1, solute carrier family 1 (neuronal/epithelial high affinity glutamate transporter, system Xag), member 1 | AAGTCAGTAC[G/A]GTGGATGCCA | S | G | A | T | T |
| G870u4 | WIAF-11922 | HT4468 | 706 | SLC1A1, solute carrier family 1 (neuronal/epithelial high affinity glutamate transporter, system Xag), member 1 | GAACATGACA[G/A]AAGAGTCCTT | M | G | A | E | K |
| G870u5 | WIAF-11923 | HT4468 | 978 | SLC1A1, solute carrier family 1 (neuronal/epithelial high affinity glutamate transporter, system Xag), member 1 | GGGAGATCAT[A/G]GAAGTTGAAG | M | A | G | I | M |
| G871u1 | WIAF-11892 | HT3187 | 1004 | SLC1A3, solute carrier family 1 (glial high affinity glutamate transporter), member 3 | TTCTCTTAAC[G/C]AAGCCATCAT | M | G | C | E | Q |
| G871u2 | WIAF-11915 | HT3187 | 1154 | SLC1A3, solute carrier family 1 (glial high affinity glutamate transporter), member 3 | TGTTGGCTTA[C/T]TCATTCAGCC | M | C | T | L | F |
| G871u3 | WIAF-11926 | HT3187 | 1412 | SLC1A3, solute carrier family 1 (glial high affinity glutamate transporter), member 3 | GGCTGCCATT[T/G]TCATTGCTCA | M | T | G | F | V |
| G871u4 | WIAF-11944 | HT3187 | 1217 | SLC1A3, solute carrier family 1 (glial high affinity glutamate transporter), member 3 | AAACCCTTGG[G/A]TTTTATTGG | M | G | A | V | I |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G872u1 | WIAF-13433 | HT4077 | 1271 | SLC1A2, solute carrier family 1 (glial high affinity glutamate transporter), member 2 | CTGTTGGAGC[A/C]ACCATTAACA | S | A | C | A | A |
| G879u1 | WIAF-11899 | HT28317 | 1273 | GRM2, glutamate receptor, metabotropic 2 | GACTTTGTGC[T/C]CAACGTCAAG | M | T | C | L | P |
| G879u2 | WIAF-11932 | HT28317 | 2349 | GRM2, glutamate receptor, metabotropic 2 | CTTCTATGTC[A/G]CCTCCAGTGA | M | A | G | T | A |
| G879u3 | WIAF-13421 | HT28317 | 2186 | GRM2, glutamate receptor, metabotropic 2 | ATGCAAGTAT[G/T]TTGGGCTCGC | M | G | T | M | I |
| G879u4 | WIAF-13429 | HT28317 | 2567 | GRM2, glutamate receptor, metabotropic 2 | CCCAGTTTGT[C/T]CCCACTGTTT | S | C | T | V | V |
| G879u5 | WIAF-13436 | HT28317 | 2046 | GRM2, glutamate receptor, metabotropic 2 | ACAGGTGGCC[A/G]TCTGCCTGGC | M | A | G | I | V |
| G879u6 | WIAF-13438 | HT28317 | 2425 | GRM2, glutamate receptor, metabotropic 2 | GTGCTTGGCT[G/T]CCTCTTTGCG | M | G | T | C | F |
| G879u7 | WIAF-13439 | HT28317 | 2463 | GRM2, glutamate receptor, metabotropic 2 | CCTGTTCCAG[C/T]CGCAGAAGAA | M | C | T | P | S |
| G880u1 | WIAF-12164 | HT33719 | 2117 | GRM4, glutamate receptor, metabotropic 4 | AGCCCCGACCT[T/G]GGCACCTGCT | S | T | G | L | L |
| G880u2 | WIAF-12176 | HT33719 | 2427 | GRM4, glutamate receptor, metabotropic 4 | GGACCTGTCG[C/T]TCATCTGCCT | M | C | T | L | F |
| G880u3 | WIAF-12192 | HT33719 | 2372 | GRM4, glutamate receptor, metabotropic 4 | ACCAGGCGGAC[A/G]CTCGACCCCC | M | A | G | T | T |
| G883a1 | WIAF-13140 | HT48863 | 1408 | GRM7, glutamate receptor, metabotropic 7 | ATCGCAAATG[C/a]ACAGGACAGG | M | C | a | C | * |
| G883a2 | WIAF-13141 | HT48863 | 2027 | GRM7, glutamate receptor, metabotropic 7 | TCCTGTCTTC[C/t]TGGCAATGTT | S | C | t | L | L |
| G883a3 | WIAF-13147 | HT48863 | 1813 | GRM7, glutamate receptor, metabotropic 7 | TGTGCACACT[A/g]CCATGTAAGC | S | A | g | L | L |
| G883a4 | WIAF-13148 | HT48863 | 1536 | GRM7, glutamate receptor, metabotropic 7 | TGTGCGGACT[A/t]CCGGGGTGTC | M | A | t | Y | F |
| G883a5 | WIAF-13149 | HT48863 | 2473 | GRM7, glutamate receptor, metabotropic 7 | AAGCCAGAGG[G/a]GTTCTCAAGT | S | G | a | G | G |
| G883a6 | WIAF-13150 | HT48863 | 2434 | GRM7, glutamate receptor, metabotropic 7 | TCATAGACTA[C/t]GATGAACACA | S | C | t | Y | Y |
| G884u1 | WIAF-11916 | U95025 | 1052 | GRM8, glutamate receptor, metabotropic 8 | CGAACTCTTG[C/A]CAATAATCGA | M | C | A | A | D |
| G884u2 | WIAF-11945 | U95025 | 2016 | GRM8, glutamate receptor, metabotropic 8 | AAACAAACCG[T/C]ATCCACCGAA | S | T | C | R | R |
| G884u3 | WIAF-11946 | U95025 | 1852 | GRM8, glutamate receptor, metabotropic 8 | GAGGGCTTCA[G/A]GACGCGAACT | M | G | A | G | R |
| G884u4 | WIAF-11947 | U95025 | 2078 | GRM8, glutamate receptor, metabotropic 8 | ATTAGTCCAG[C/G]ATCTCAGCTG | M | C | G | A | G |
| G884u5 | WIAF-13430 | U95025 | 1897 | GRM8, glutamate receptor, metabotropic 8 | TTTTCTCTGT[T/G]ATTCAATCAC | M | T | G | Y | D |
| G884u6 | WIAF-13435 | U95025 | 2364 | GRM8, glutamate receptor, metabotropic 8 | TTACCATGTA[T/C]ACCACCTGCA | S | T | C | Y | Y |
| G885u1 | WIAF-13434 | AF002700 | 1363 | GFRA2, GDNF family receptor alpha 2 | AACTCAGGCC[C/A]CAGCAGAGCC | M | C | A | P | H |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G886a1 | WIAF-13142 | U95847 | 497 | GFRA1, GDNF family receptor alpha 1 | GAAGTGCTC[T/a]ACAACTGCCG | M | T | a | Y | N |
| G886a2 | WIAF-13143 | U95847 | 1385 | GFRA1, GDNF family receptor alpha 1 | GTCTGAGAAT[G/a]AAATTCCCAC | M | G | a | E | K |
| G886a3 | WIAF-13151 | U95847 | 781 | GFRA1, GDNF family receptor alpha 1 | GCGTGTCCAA[T/c]GATGTCTGCA | G | T | c | N | N |
| G892u1 | WIAF-11956 | U12140 | 798 | NTRK2, neurotrophic tyrosine kinase, receptor, type 2 | TGGGCAATCC[A/G]TTTACATGCT | S | A | G | P | P |
| G892u2 | WIAF-11957 | U12140 | 834 | NTRK2, neurotrophic tyrosine kinase, receptor, type 2 | GGATCAAGAC[T/A]CTCCAAGAGG | S | T | A | T | T |
| G892u3 | WIAF-11958 | U12140 | 956 | NTRK2, neurotrophic tyrosine kinase, receptor, type 2 | GCAAATCTGG[C/T]CGCACCTAAC | M | C | T | A | V |
| G892u4 | WIAF-11960 | U12140 | 1738 | NTRK2, neurotrophic tyrosine kinase, receptor, type 2 | CTCCAAGTTT[G/A]GCATGAAAGG | M | G | A | S | |
| G892u5 | WIAF-11962 | U12140 | 2486 | NTRK2, neurotrophic tyrosine kinase, receptor, type 2 | GTCGGTGGCC[A/G]CACAATGCTG | M | A | G | R | S |
| G892u6 | WIAF-11965 | U12140 | 1106 | NTRK2, neurotrophic tyrosine kinase, receptor, type 2 | TCCTTAAGGA[T/C]AACTAACATT | M | T | C | T | Q |
| G892u7 | WIAF-11966 | U12140 | 2085 | NTRK2, neurotrophic tyrosine kinase, receptor, type 2 | AGGATGCCAG[T/C]GACAATGCAC | S | T | C X | S | |
| G892u8 | WIAF-11967 | U12140 | 2230 | NTRK2, neurotrophic tyrosine kinase, receptor, type 2 | GGACCTCAAC[A/C]AGTTCCTCAG | M | A | C | K | Q |
| G892u9 | WIAF-11968 | U12140 | 2223 | NTRK2, neurotrophic tyrosine kinase, receptor, type 2 | AGCATGGGGA[C/T]CTCAACAAGT | S | C | T | D | D |
| G892u10 | WIAF-11992 | U12140 | 1602 | NTRK2, neurotrophic tyrosine kinase, receptor, type 2 | GTAATGAAAT[c/T]CCTTCCACAG | S | C | T | H | H |
| G892u11 | WIAF-11998 | U12140 | 1354 | NTRK2, neurotrophic tyrosine kinase, receptor, type 2 | TACTAAAATA[C/T]ATGTTACCAA | M | C | T | H | Y |
| G892u12 | WIAF-11999 | U12140 | 1944 | NTRK2, neurotrophic tyrosine kinase, receptor, type 2 | CATTGTTCA[G/C]CACATCAAGC | M | G | C | Q | H |
| G892u13 | WIAF-12000 | U12140 | 2103 | NTRK2, neurotrophic tyrosine kinase, receptor, type 2 | CACGCAAGGA[C/T]TTCCACCGTG | S | C | T | D | D |
| G892u14 | WIAF-12001 | U12140 | 1860 | NTRK2, neurotrophic tyrosine kinase, receptor, type 2 | CTGTCATTAT[T/C]GGAATGACCA | S | T | C | I | I |
| G892a15 | WIAF-13144 | U12140 | 1868 | NTRK2, neurotrophic tyrosine kinase, receptor, type 2 | ATTGGAATGA[C/G]CAAGATCCCT | M | C | G | T | S |
| G892a16 | WIAF-13145 | U12140 | 1903 | NTRK2, neurotrophic tyrosine kinase, receptor, type 2 | CCAGTACTTT[G/T]GCATCACCAA | M | G | T | G | C |
| G892a17 | WIAF-13140 | U12140 | 1965 | NTRK2, neurotrophic tyrosine kinase, receptor, type 2 | CACATAACAT[T/G]GTTCTGAAAA | M | T | G | I | M |
| G892u18 | WIAF-13442 | U12140 | 958 | NTRK2, neurotrophic tyrosine kinase, receptor, type 2 | AAAATCTGGC[G/T]CACCTAACCT | M | G | T | A | S |
| G892u19 | WIAF-13446 | U12140 | 2502 | NTRK2, neurotrophic tyrosine kinase, receptor, type 2 | TGCTGCCCAT[T/C]CGCTGGATGC | S | T | C | I | I |
| G892u20 | WIAF-13447 | U12140 | 2317 | NTRK2, neurotrophic tyrosine kinase, receptor, type 2 | GATGCTGCAT[A/T]TAGCCCAGCA | M | A | T | H | L |
| G892u21 | WIAF-13448 | U12140 | 2364 | NTRK2, neurotrophic tyrosine kinase, receptor, type 2 | CGTCCCAGCA[C/A]TTCGTGCACC | M | C | A | H | Q |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G892u22 | WIAF-13449 | U12140 | 2507 | NTRK2, neurotrophic tyrosine kinase, receptor, type 2 | CCCATTCGCT[G/A]GATGCCTCCA | N | G | A | W | * |
| G892u23 | WIAF-13471 | U12140 | 2389 | NTRK2, neurotrophic tyrosine kinase, receptor, type 2 | TTTGGCCACC[A/C]GGAACTGCCT | S | A | C | R | R |
| G892u24 | WIAF-13472 | U12140 | 2416 | NTRK2, neurotrophic tyrosine kinase, receptor, type 2 | GGAGAACTTG[C/T]TGGTGAAAAT | S | C | T | L | L |
| G892u25 | WIAF-13474 | U12140 | 359 | NTRK2, neurotrophic tyrosine kinase, receptor, type 2 | GGGATGTCGT[C/T]CTGGATAAGG | M | C | T | S | F |
| G892u26 | WIAF-13479 | U12140 | 1044 | NTRK2, neurotrophic tyrosine kinase, receptor, type 2 | TGTATTGGGA[T/C]GTTGGTAACC | S | T | C | D | D |
| G9u1 | WIAF-10222 | J03826 | 1130 | FDXR, ferredoxin reductase | GGTATAAGAG[C/T]CGCCGTGTCG | S | C | T | S | S |
| G9u2 | WIAF-10258 | J03826 | 388 | FDXR, ferredoxin reductase | CCGGAGCTGC[A/G]GGAGGCCTAC | M | A | G | Q | R |
| G900u1 | WIAF-11970 | HT3470 | 497 | STK4A, syntaxin 4A (placental) | TGCAATTCAA[T/C]GCAGTCCGAA | M | T | C | M | T |
| G901u1 | WIAF-11969 | HT27792 | 758 | STX3A, syntaxin 3A | TGCACACAGT[G/A]GACCACGTGG | S | G | A | V | V |
| G901u1 | WIAF-11971 | HT27792 | 317 | STX3A, syntaxin 3A | ACGTCCGGAA[C/A]AAACTGAAGA | M | C | A | N | X |
| G901u3 | WIAF-12002 | HT27792 | 611 | STX3A, syntaxin 3A | AGCAAGCCCT[C/T]AGTGAGATTG | S | C | T | L | L |
| 0901u3 | WIAF-12002 | HT27792 | 611 | STX3A, syntaxin 3A | GCTGAATTAA[G/A]AGTGGCTAAA | I | G | A | - | - |
| G901u4 | WIAF-12003 | HT27792 | 909 | STX3A, syntaxin 3A | ATTGAGGAAA[C/T]TCGGCTTAAC | M | C | T | T | I |
| G901u5 | WIAF-12004 | HT27792 | 163 | STX3A, syntaxin 3A | CAGCTGACAC[A/G]GGATGATGAT | M | A | G | Q | R |
| G901a6 | WIAF-13152 | HT27792 | 62 | STX3A, syntaxin 3A | CCGGAAGAAA[T/C]TGATAATTAT | S | T | C | L | L |
| G901u7 | WIAF-13453 | HT27792 | 828 | STX3A, syntaxin 3A | TACAGTATCA[T/C]TCTGTCTGCA | M | T | C | H | T |
| G901u8 | WIAF-13455 | HT27792 | 226 | STX3A, syntaxin 3A | ACTTCCAGTC[T/A]GTCACCTCCA | S | T | A | S | S |
| G902u1 | WIAF-13454 | HT27744 | 848 | STX5A, syntaxin 5A | ATTTCGTGAG[A/G]GCCAAGGGCA | S | A | G | R | R |
| G902u2 | WIAF-13456 | HT27744 | 338 | STX5A, ayntaxin 5A | TCCAGATCAA[C/T]GTATCCCCA | S | C | T | N | N |
| G905u1 | WIAF-12202 | HT27789 | 487 | CREBL1, cAMP responsive element binding protein-like 1 | ATTCTGGCCT[A/T]GATGAAGTGG | S | A | T | L | L |
| G905u2 | WIAF-12219 | HT27789 | 151 | CREBL1, cAMP responsive element binding protein-like 1 | AGTCCCTGTC[C/G]CCTTCAGGAT | S | C | G | S | S |
| G905u3 | WIAF-12230 | HT27789 | 649 | CREBL1, cAMP responsive element binding protein-like 1 | AAGGGAAGAA[G/A]GTCTGGATAG | S | G | A | K | K |
| G906u1 | WIAF-12214 | HT4372 | 2127 | N-ethylmaleimide-sensitive factor | GGGAGAGCCT[G/A]CGACAGGGAA | M | G | A | A | T |
| G906u2 | WIAF-12221 | HT4372 | 514 | N-ethylmaleimide-sensitive factor | GCCCAAATAC[T/G]GGAAATAAAA | S | T | G | F | T |
| G908u1 | WIAF-12201 | HT3665 | 98 | RAB5A, member RAS oncogene family | TCGTGCGCAA[C/T]GTGCCCTGGG | S | C | T | H | H |
| G91u1 | WIAF-10438 | HT1848 | 496 | ERCC1, excision repair cross-complementing rodent repair deficiency, complementation group 1 (includes overlapping antisense sequence) | | | | | | |
| G91u2 | WIAF-10439 | HT1848 | 367 | ERCC1, excision repair cross-complementing rodent repair deficiency, complementation group 1 (includes overlapping antisense sequence) | CTGGGGCCAC[G/A]TGCCCCACAG | S | G | A | T | T |
| G914a1 | WIAF-13210 | HT3672 | 252 | synaptobrevin 1 | GCAGTGCTGC[C/A]AAGCTAAAGA | S | C | A | A | A |
| G915a1 | WIAF-12115 | D63506 | 1390 | Homo sapiens mRNA for unc-18homologue, complete cds. | TTACCTTGGT[G/A]ATTCCCATTGT | M | G | A | V | I |
| G915u2 | WIAF-12293 | D63506 | 685 | Homo sapiens mRNA for unc-18homologue, complete cds. | ACAGCTTGTT[G/A]AAAAAAGCT | M | G | A | E | K |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G916a1 | WIAF-13209 | HT28523 | 308 | Huntingtin associated protein 1-like protein | GAGCAGTTTT[C/T]GGAGGCCAGC | M | C | T | S | L |
| G916a2 | WIAF-13211 | HT28523 | 762 | Huntingtin associated protein 1-like protein | CGGAGGAGTT[G/C]GTGCCCCAGG | M | G | C | L | F |
| G916a3 | WIAF-13212 | HT28523 | 560 | Huntingtin associated protein 1-like protein | GAGCTCAGAA[C/T]GTCTCTAAGG | M | C | T | T | M |
| G917u1 | WIAF-11972 | U79734 | 1075 | HIP1, huntingtin interacting protein 1 | AGAGCCAGCG[G/A]GTGTGCTGC | S | G | A | R | R |
| G917u2 | WIAF-11973 | U79734 | 1005 | HIP1, huntingtin interacting protein 1 | GACCACTTAA[T/C]TGAGCGACTA | M | T | C | I | T |
| G917u3 | WIAF-11977 | U79734 | 1539 | HIP1, huntingtin interacting protein 1 | CTGCAAGGCA[G/A]CCTGGAAACT | M | G | A | S | N |
| G917u4 | WIAF-12005 | U79734 | 817 | HIP1, huntingtin interacting protein 1 | TGGTGGTTGAT[C/T]CCTGCAGAGG | S | C | T | I | I |
| G917u5 | WIAF-12006 | U79734 | 1906 | HIP1, huntingtin interacting protein 1 | GCTGGAGCCA[G/C]CTATCTGCCT | M | G | C | Q | H |
| G917u6 | WIAF-13157 | U79734 | 993 | HIP1, huntingtin interacting protein 1 | AAGGATGAGA[A/G]GGACCACTTA | M | A | G | K | R |
| G919u1 | WIAF-11974 | D30742 | 707 | CAMK4, calcium/calmodulin-dependent protein kinase IV | ACTGCGCACC[T/C]GAAATTCTTA | S | T | C | P | P |
| G919u2 | WIAF-11991 | D30742 | 1139 | CAMK4, calcium/calmodulin-dependent protein kinase IV | AGAGCCACAA[G/A]GCTAGCCGAG | S | G | A | K | K |
| G919u3 | WIAF-12007 | D30742 | 834 | CAMK4, calcium/calmodulin-dependent protein kinase IV | CATGTTCAGG[A/T]GAATTCTGAA | N | A | T | R | * |
| G919u4 | WIAF-13443 | D30742 | 1088 | CAMK4, calcium/calmodulin-dependent protein kinase IV | TGGCCTCTTC[C/G]CGCCTGGGAA | S | C | G | S | S |
| G920u1 | WIAF-11979 | X78520 | 1952 | CLCN3, chloride channel 3 | ATGACATTCC[T/C]GATCGTCCAG | S | T | C | P | P |
| G920u2 | WIAF-11980 | X78520 | 1819 | CLCN3, chloride channel 3 | ATAGCCTTCC[C/T]TAATCCATAC | M | C | T | P | L |
| G920u3 | WIAF-11981 | X78520 | 2094 | CLCN3, chloride channel 3 | CATTGGAGCG[A/G]TCCAGAGAAG | M | A | G | I | V |
| G920u4 | WIAF-11983 | X78520 | 2822 | CLCN3, chloride channel 3 | ATATTTTCCG[A/G]AAGCTGGGAC | S | A | G | R | R |
| G920u5 | WIAF-11984 | X78520 | 2745 | CLCN3, chloride channel 3 | GCCATTGAAG[C/T]TTCGAAGCAT | M | C | T | L | F |
| G920u6 | WIAF-11987 | X78520 | 2499 | CLCN3, chloride channel 3 | TCCCTTAGCT[G/T]TCCTGACACA | M | G | T | V | F |
| G920u7 | WIAF-12008 | X78520 | 1251 | CLCN3, chloride channel 3 | CATCATCAGA[G/A]GTTACTTGGG | M | G | A | G | S |
| G920u8 | WIAF-12011 | X78520 | 888 | CLCN3, chloride channel 3 | AGTAGTAACA[C/T]TAACAGGATT | S | C | T | L | L |
| G920u9 | WIAF-13459 | X78520 | 2804 | CLCN3, chloride channel 3 | CAATGGAGAT[T/C]GTGGTGATA | S | T | C | H | H |
| G921u1 | WIAF-11954 | J02908 | 931 | CLU, clusterin (complement lysis inhibitor, SP-40,40, sulfated glycoprotein 2, testosterone-repressed prostate message 2, apolipoprotein J) | GAGAGGTTGA[C/T]CAGGAAATAC | M | C | T | T | I |
| G921u2 | WIAF-11955 | J02908 | 880 | CLU, clusterin (complement lysis inhibitor, SP-40,40, sulfated glycoprotein 2, testosterone-repressed prostate message 2, apolipoprotein J) | CCCTCCCAGG[C/T]TAAGCTGCGG | M | C | T | A | V |

-continued

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G921u3 | WIAF-11990 | J02908 | 1051 | CLU, clusterin (complement lysis inhibitor, SP-40,40, sulfated glycoprotein 2, testosterone-repressed prostate message 2, apolipoprotein J) | CTCACGCAAG[G/C]CGAAGACCAG | M | G | C | G | A |
| G921u4 | WIAF-13469 | J02908 | 986 | CLU, clusterin (complement lysis inhibitor, SP-40,40, sulfated glycoprotein 2, testosterone-repressed prostate message 2, apolipoprotein J) | TCAACACCTC[C/T]TCCTTGCTGG | S | C | T | S | S |
| G923u1 | WIAF-11993 | M19650 | 1059 | Human 2',3'-cyclic nucleotide 3'-phosphodiesterase mRNA, complete cs. | GAGCTAAGCC[G/A]GGGCAAGCTC | M | G | A | R | Q |
| G923u2 | WIAF-11994 | M19650 | 1062 | Human 2',3'-cyclic nucleotide 3'-phosphodiesterase mRNA, complete cs. | CTAAGCCGGG[G/T]CAAGCTCTAT | M | G | T | G | V |
| G923u3 | WIAF-13445 | M19650 | 1141 | Human 2',3'-cyclic nucleotide 3'-phosphodiesterase mRNA, complete cs. | TCTTCACGGG[G/A]TACTACGGGA | S | G | A | G | G |
| G925u1 | WIAF-11953 | L11315 | 666 | CAK, cell adhesion kinase | GGGTCATGAG[T/C]GTCTGTCTGC | S | T | C | S | S |
| G925u2 | WIAF-11959 | L11315 | 2562 | CAK, cell adhesion kinase | TGCTGCCCAT[C/T]CGCTGGATGG | S | C | T | T | I |
| G925u3 | WIAF-11996 | L11315 | 2049 | CAK, cell adhesion kinase | AAGATCTGGT[T/C]AGTCTTGATT | S | T | C | V | V |
| G925u4 | WIAF-13440 | L11315 | 1601 | CAK, cell adhesion kinase | TACCAGGAGC[C/T]CCGGCCTCGT | S | C | T | P | L |
| G925u5 | WIAF-13441 | L11315 | 1629 | CAK, cell adhesion kinase | CGCCCACTC[C/T]GCTCCCTGTG | S | C | T | S | S |
| G925u6 | WIAF-13451 | L11315 | 2262 | CAK, cell adhesion kinase | TGGAGAACGG[C/T]GACCTCAACC | S | C | T | G | G |
| G926u1 | WIAF-11961 | AF018956 | 577 | NRP1, neuropilin 1 | TGAAAGCTTT[G/T]ACCTGGAGCC | M | G | T | D | Y |
| G926u2 | WIAF-11963 | AF018956 | 1683 | NRP1, neuropilin 1 | CCACGCGATT[C/G]ATCAGGATCT | M | C | G | F | L |
| G926u3 | WIAF-11975 | AF018956 | 2176 | NRP1, neuropilin 1 | GACCTTCTGG[T/C]CATCACATGC | M | T | C | Y | H |
| G926u4 | WIAF-11976 | AF018956 | 2092 | NRP1, neuropilin 1 | TTCCCAAGCT[G/T]ACGAAAATCA | M | G | T | D | Y |
| G926a5 | WIAF-13158 | AF018956 | 747 | NRP1, neuropilin 1 | TTTTTTACAC[C/T]GACAGCGCGA | S | C | T | T | T |
| G926a6 | WIAF-13159 | AF018956 | 996 | NRP1, neuropilin 1 | ACTTGGGCCT[T/C]CTGCGCTTTG | S | T | C | L | L |
| G926u7 | WIAF-13444 | AF018956 | 644 | NRP1, neuropilin 1 | GAAATCTGGG[A/C]TGGATTCCCT | M | A | C | D | A |
| G926u8 | WIAF-13450 | AF018956 | 1738 | NRP1, neuropilin 1 | CAGAATCGAG[C/G]TGCTGGGCTG | M | C | G | L | V |
| G926u9 | WIAF-13452 | AF018956 | 537 | NRP1, neuropilin 1 | TTGTCTTTGC[G/A]CCAAAGATGT | S | G | A | A | A |
| G926u10 | WIAF-13457 | AF018956 | 2197 | NRP1, neuropilin 1 | TGGGTCCCAC[G/A]TCCGCACACT | M | G | A | V | I |
| G927u1 | WIAF-11978 | AF022860 | 870 | NRP2, neuropilin 2 | GGATTGCTAA[T/C]GAACAGATCA | M | T | C | N | N |
| G927u2 | WIAF-11982 | AF022860 | 1674 | NRP2, neuropilin 2 | ATGACACCCC[T/G]GACATCCCAA | M | T | G | P | P |
| G927u3 | WIAF-11985 | AF022860 | 1250 | NRP2, neuropilin 2 | TGGCACTCAG[G/A]TATCGCCCTC | S | G | A | P | P |
| G927u4 | WIAF-11986 | AF022860 | 1071 | NRP2, neuropilin 2 | ATGGCTACTA[C/T]GTCAAATCCT | S | C | T | Y | Y |
| G927u5 | WIAF-12009 | AF022860 | 726 | NRP2, neuropilin 2 | GTTCATCGAC[G/A]GGGATCCTCT | M | G | A | G | D |
| G927u6 | WIAF-12010 | AF022860 | 2522 | NRP2, neuropilin 2 | GCAACCTCAG[G/T]GTCTGGCGCC | M | G | T | T | T |
| G927u7 | WIAF-12012 | AF022860 | 123 | NRP2, neuropilin 2 | GCTATATCAC[C/T]TCTCCCGTT | S | C | T | G | V |
| G927a8 | WIAF-13160 | AF022860 | 2427 | NRP2, neuropilin 2 | CTTTTGGAGT[G/T]GACATCCCAG | S | G | T | T | T |
| G927a9 | WIAF-13161 | AF022860 | 2430 | NRP2, neuropilin 2 | TTGCAGTGGA[C/G]ATCCCAGAAA | S | C | G | D | E |
| G927a10 | WIAF-13162 | AF022860 | 2463 | NRP2, neuropilin 2 | AAGGATATGA[A/G]GATGAAATTG | S | A | G | E | E |
| G927a11 | WIAF-13163 | AF022860 | 2473 | NRP2, neuropilin 2 | AGATGAAATT[G/T]ATGATGAATA | M | G | T | D | Y |
| G927u12 | WIAF-13480 | AF022860 | 724 | NRP2, neuropilin 2 | TCGTTCATCG[A/T]CGGGGATCCT | M | A | T | T | S |
| G927u13 | WIAF-13481 | AF022860 | 767 | NRP2, neuropilin 2 | ATGGCCGTGG[C/T]CAAGGATGGC | M | C | T | A | V |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G930a1 | WIAF-13164 | HT2608 | 609 | GABRA2, gamma-aminobutyric acid (GABA) A receptor, alpha 2 | ACAATGGAA[G/a]AAATCAGTAG | S | G | a | K | K |
| G931a1 | WIAF-13153 | HT2609 | 1111 | GABRA3, gamma-aminobutyric acid (GABA) A receptor, alpha 3 | ACTGGTTCAT[A/g]GCCGTCTGTT | M | A | g | I | M |
| G931a2 | WIAF-13165 | HT2609 | 1448 | GABRA3, gamma-aminobutyric acid (GABA) A receptor, alpha 3 | TGTCAGCAAG[G/A]TTGACAAAAT | M | G | A | V | I |
| G932a1 | WIAF-13154 | HT27773 | 1077 | GABRA4, gamma-aminobutyric acid (GABA) A receptor, alpha 4 | CAAAAGAAAG[A/G]CATCAAAGCC | M | A | G | T | A |
| G932a2 | WIAF-13155 | HT27773 | 1189 | GABRA4, gamma-aminobutyric acid (GABA) A receptor, alpha 4 | AGAACAAATG[C/A]TTTGGTTCAC | M | C | A | A | D |
| G936u1 | WIAF-12308 | HT3432 | 1027 | GABRB2, gamma-aminobutyric acid (GABA) A receptor, beta 2 | AATTACGATG[C/T]TTCAGCTGCA | M | C | T | A | V |
| G936u2 | WIAF-12327 | HT3432 | 362 | GABRB2, gamma-aminobutyric acid (GABA) A receptor, beta 2 | AAGGCTATGA[C/T]ATTCGTCTGA | S | C | T | D | D |
| G936u3 | WIAF-12328 | HT3432 | 571 | GABRB2, gamma-aminobutyric acid (GABA) A receptor, beta 2 | CTCTGGGTGC[C/T]TGATACCTAT | M | C | T | P | L |
| G939u1 | WIAF-12330 | HT2236 | 1219 | GABRB2, gamma-aminobutyric acid (GABA) receptor, rho 2 | CTGGATGGAA[G/C]CTACAGTGAG | M | G | C | S | T |
| G939u2 | WIAF-12355 | HT2236 | 1003 | GABRB2, gamma-aminobutyric acid (GABA) receptor, rho 2 | ACCACCATCA[T/C]CACGGGCCTG | M | T | C | I | T |
| G939u3 | WIAF-12356 | HT2236 | 1041 | GABRB2, gamma-aminobutyric acid (GABA) receptor, rho 2 | CGTCTCCTAC[G/A]TCAAGGCCGT | M | G | A | V | I |
| G950u1 | WIAF-13622 | U64871 | 785 | Human putative G protein-coupled receptor (GBR19) gene, complete cds. | GTCCTGCTCC[A/C]GTTCACCACT | M | A | C | Q | P |
| G950u2 | WIAF-13624 | U64871 | 443 | Human putative G protein-coupled receptor (GBR19) gene, complete cds. | GATAACAGCA[A/C]GCCACATTTG | M | A | C | K | T |
| G950u3 | WIAF-13625 | U64871 | 818 | Human putative G protein-coupled receptor (GBR19) gene, complete cds. | CTGGGTAGTG[C/T]AACGTGCAAG | M | C | T | A | V |
| G955a1 | WIAF-13166 | HT3860 | 5110 | calcium channel, voltage-gated, alpha 1 subunit, L type, alt. transcript 1 | CTGGCCCTTT[T/c]ACCGTGGAGA | S | T | c | F | F |
| G955a2 | WIAF-33167 | HT3860 | 3842 | calcium channel, voltage-gated, alpha 1 subunit, L type, alt. transcript 1 | CTACCCCAAC[C/a]CAGAAACTAC | M | C | a | P | T |
| G955a3 | WIAF-13168 | HT3860 | 5624 | calcium channel, voltage-gated, alpha 1 subunit, L type, alt. transcript 1 | GTGTGCCCCA[G/a]AGTCCGAGCC | M | G | a | E | K |
| G955a4 | WIAF-13169 | HT3860 | 5703 | calcium channel, voltage-gated, alpha 1 subunit, L type, alt. transcript 1 | ATCAGCTTCT[A/g]CATGCTCTGT | M | A | g | Y | C |
| G955a5 | WIAF-13170 | HT3860 | 5889 | calcium channel, voltage-gated, alpha 1 subunit, L type, alt. transcript 1 | ACCACCTGGA[T/c]GAGTTTAAAA | S | T | c | D | D |
| G955a6 | WIAF-13171 | HT3860 | 6616 | calcium channel, voltage-gated, alpha 1 subunit, L type, alt. transcript 1 | CCGGCTCCAA[C/t]GCCAACATCA | S | C | t | N | N |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G956u1 | WIAF-14187 | HT2199 | 1334 | calcium channel, voltage-gated, alpha 1D subunit, DHP-sensitive | CTTCACATAG[C/T]CCTTTTGTA | M | C | T | A | V |
| G956u2 | WIAF-14188 | HT2199 | 1452 | calcium channel, voltage-gated, alpha 1D subunit, DHP-sensitive | AAGAGGACCC[A/T]GCTCCATGTG | S | A | T | P | P |
| G956u3 | WIAF-14189 | HT2199 | 1614 | calcium channel, voltage-gated, alpha 1D subunit, DHP-sensitive | GCTGGACAGA[C/T]GTGCTCTACT | S | C | T | D | D |
| G956u4 | WIAF-14190 | HT2199 | 2540 | calcium channel, voltage-gated, alpha 1D subunit, DHP-sensitive | GGCAAGTTTA[A/T]TTTTGATGAA | M | A | T | N | I |
| G956u5 | WIAF-14191 | HT2199 | 3210 | calcium channel, voltage-gated, alpha 1D subunit, DHP-sensitive | TGCTGAGCAG[T/C]GCTGCCCTGG | S | T | C | S | S |
| G956u6 | WIAF-14192 | HT2199 | 3326 | calcium channel, voltage-gated, alpha 1D subunit, DHP-sensitive | TTGAAGATGA[C/T]AACTTTTGGA | M | C | T | T | I |
| G956u7 | WIAF-14193 | HT2199 | 3274 | calcium channel, voltage-gated, alpha 1D subunit, DHP-sensitive | ACTGGGTTAC[T/C]TTGACTATGC | M | T | C | F | L |
| G956u8 | WIAF-14194 | HT2199 | 5127 | calcium channel, voltage-gated, alpha 1D subunit, DHP-sensitive | TGCCTGTCAA[C/T]AGTGACGGGA | S | C | T | N | N |
| G956u9 | WIAF-14195 | HT2199 | 5173 | calcium channel, voltage-gated, alpha 1D subunit, DHP-sensitive | TGCTTTGGTT[C/T]GAACGGCTCT | N | C | T | R | * |
| G956u10 | WIAF-14200 | HT2199 | 1437 | calcium channel, voltage-gated, alpha 1D subunit, DHP-sensitive | CAGATATCGT[A/G]GCTGAAGAGG | S | A | G | V | V |
| G956u11 | WIAF-14201 | HT2199 | 2567 | calcium channel, voltage-gated, alpha 1D subunit, DHP-sensitive | ACCAAGCGGA[G/T]CACCTTTGAC | M | G | T | S | I |
| G956u12 | WIAF-14202 | HT2199 | 4464 | calcium channel, voltage-gated, alpha 1D subunit, DHP-sensitive | TCACCTTTTT[C/T]CGTCTTTTCC | S | C | T | F | F |
| G956u13 | WIAF-14215 | HT2199 | 6927 | calcium channel, voltage-gated, alpha 1D subunit, DHP-sensitive | GCTACAGCGA[C/T]CAAGAGCCAG | S | C | T | D | D |
| G956u14 | WIAF-14216 | HT2199 | 6858 | calcium channel, voltage-gated, alpha 1D subunit, DHP-sensitive | CCCGAGCCAA[C/T]GGCGATGTGG | S | C | T | N | N |
| G957u1 | WIAF-12306 | HT4229 | 915 | calcium channel, voltage-gated, alpha 1E subunit, alt. transcript 2 | TACATCCAGC[G/A]TGCTTCATGA | M | G | A | ? | R |
| G957u2 | WIAF-12309 | HT4229 | 3555 | calcium channel, voltage-gated, alpha 1E subunit, alt. transcript 2 | GCCACTACAT[C/T]GTGAACCTGC | S | C | T | I | I |
| G957u3 | WIAF-12310 | HT4229 | 4116 | calcium channel, voltage-gated, alpha 1E subunit, alt. transcript 2 | ATGTAGATCA[C/T]GAGAAAAACA | S | C | T | M | H |
| G957u4 | WIAF-12313 | HT4229 | 5181 | calcium channel, voltage-gated, alpha 1E subunit, alt. transcript 2 | AGAACAGAAA[T/C]GAACGCTGCG | S | T | C | N | N |
| G957u5 | WIAF-12314 | HT4229 | 5971 | calcium channel, voltage-gated, alpha 1E subunit, alt. transcript 2 | TATGGACCCC[G/A]CCGATGACGG | S | G | A | T | T |
| G957u6 | WIAF-12315 | HT4229 | 5985 | calcium channel, voltage-gated, alpha 1E subunit, alt. transcript 2 | ATGACGGACA[G/T]TTCCAAGAAC | M | G | T | Q | M |
| G957u7 | WIAF-12329 | HT4229 | 3100 | calcium channel, voltage-gated, alpha 1E subunit, alt. transcript 2 | GCTGGCAGGA[G/A]GCCTTGATGA | M | G | A | G | S |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G957u8 | WIAF-12331 | HT4229 | 6492 | calcium channel, voltage-gated, alpha 1E subunit, alt. transcript 2 | CCCTCCTTC[C/T]TACAGCTCCC | M | C | T | ? | R |
| G957u9 | WIAF-12354 | HT4229 | 3839 | calcium channel, voltage-gated, alpha 1E subunit, alt. transcript 2 | AACGCTTGG[G/C]AACCAACAAA | M | G | C | G | A |
| G957u10 | WIAF-12357 | HT4229 | 4753 | calcium channel, voltage-gated, alpha 1E subunit, alt. transcript 2 | TGACTTCATC[A/G]CCCTGATTGG | M | A | G | T | A |
| G960u1 | WIAF-12305 | HT3336 | 1246 | CACNB3, calcium channel, voltage-dependent, beta 3 subunit | TTGATGCCCT[C/T]TGATGAGGCC | M | C | T | S | F |
| G960u2 | WIAF-12340 | HT3336 | 1288 | CACNB3, calcium channel, voltage-dependent, beta 3 subunit | TGGACAGGAT[C/T]TTCACAGCGT | M | C | T | S | F |
| G960u3 | WIAF-12345 | HT3336 | 641 | CACNB3, calcium channel, voltage-dependent, beta 3 subunit | AGGCTCTCTT[C/T]GACTTCCTCA | S | C | T | F | F |
| C960u4 | WIAF-12346 | HT3336 | 576 | CACNB3, calcium channel, voltage-dependent, beta 3 subunit | CATGCGGCCT[G/A]GCCGTGCTGT | W | G | A | V | M |
| G961u1 | WIAF-12322 | U95019 | 2037 | CACNB2, calcium channel, voltage-dependent, beta 2 subunit | ACTCTGCCTA[C/T]GTAGAGCGAA | S | C | T | Y | Y |
| G961u2 | WIAF-12347 | U95019 | 2007 | CACNB2, calcium channel, voltage-dependent, beta 2 subunit | CATTGACTC[G/A]GAAACCCAGG | S | G | A | S | S |
| G962u1 | WIAF-12324 | U95020 | 1423 | CACNB4, calcium channel, voltage-dependent, beta 2 subunit | CCAATTGAAA[G/A]ACGAAGTCTA | M | G | A | R | K |
| G962u2 | WIAF-12342 | U95020 | 167 | CACNB4, calcium channel, voltage-dependent, beta 2 subunit | GGAGCAGGTT[G/T]AAAAGATCCG | M | G | T | L | F |
| G962u3 | WIAF-12350 | U95020 | 1571 | CACNB4, calcium channel, voltage-dependent, beta 2 subunit | ACACTTACAA[A/G]CCCCATAGA | S | A | G | K | K |
| G965u1 | WIAF-12312 | U40583 | 1276 | CHRNA7, cholinergic receptor, nicotinic, alpha polypeptide 7 | TCCTGCACGG[T/C]GGGCAACCCC | S | T | C | G | G |
| G968a1 | WIAF-12119 | HT27592 | 1008 | CHRNA1, cholinergic receptor, nicotinic, alpha polypepide 1 (muscle) | ACACACCA[C/T]CGCTCACCCA | S | C | T | H | M |
| G968u2 | WIAF-12368 | HT27592 | 1136 | CHRNA1, cholinergic receptor, nicotinic, alpha polypeptide 1 (muscle) | AAGATTTTTA[C/T]AGAAGACATT | M | C | T | T | I |
| G973a1 | WIAF-13172 | HT48774 | 800 | CHRNA2, cholinergic receptor, nicotinic, alpha polypeptide 2 (neuronal) | ACACTTCAGA[C/t]GTGTGATTG | S | C | t | D | D |
| G973a2 | WIAF-13173 | HT48774 | 927 | CHRNA2, cholinergic receptor, nicotinic, alpha polypeptide 2 (neuronal) | CTGGAACCCC[G/a]CTGATTTTGG | M | G | a | A | T |
| G977u1 | WIAF-13949 | Y08419 | 366 | CHRNA5, cholinergic receptor, nicotinic, alpha polypeptide 5 | AAGTTATACG[T/C]GTTCCTTCAG | S | T | C | R | R |
| G978a1 | WIAF-13179 | Y08417 | 1331 | CHRNB3, cholinergic receptor, nicotinic, beta polypeptide 3 | CCATTAGATA[C/a]ATTTCGAGAC | N | C | a | Y | * |
| G983a1 | WIAF-13214 | HT0374 | 236 | NPY, neuropeptide Y | GATACTACTC[G/A]GCCGTGCGAC | S | G | A | S | S |
| G983a2 | WIAF-13215 | HT0374 | 290 | NPY, neuropeptide Y | GAAAACGATC[C/T]AGCCCAGAGA | S | C | T | S | S |
| G983a3 | WIAF-13216 | HT0374 | 111 | NPY, neuropeptide Y | GCGACTGGGG[C/T]TGTCCGGACT | S | C | T | L | L |
| G987a1 | WIAF-13174 | HT27830 | 159 | PPYR1, pancreatic polypeptide receptor 1 | TGGTCTTCAT[C/T]GTCACTTCCT | S | C | T | I | I |
| G987a2 | WIAF-13175 | HT27830 | 222 | PPYR1, pancreatic polypeptide receptor 1 | TGATGTGTGT[G/A]ACTGTGAGGC | S | G | A | V | V |

| Poly ID | WIAF ID | Genbank or TIGR Accession Number | Position in Sequence | Gene Description | Flanking Seq | Mutation Type | Ref NT | Alt NT | Ref AA | Alt AA |
|---|---|---|---|---|---|---|---|---|---|---|
| G987a3 | WIAF-13176 | HT27830 | 322 | PPYR1, pancreatic polypeptide receptor 1 | GCCGCTGACC[G/T]CCGTCTACAC | M | G | T | A | S |
| G987a4 | WIAF-13177 | HT27830 | 1074 | PPYR1, pancreatic polypeptide receptor 1 | TGGAGGAGTC[G/A]GAGCATCTGC | S | G | A | S | S |
| G987a5 | WIAF-13178 | HT27830 | 975 | PPYR1, pancreatic polypeptide receptor 1 | CCTCCACCTG[C/T]GTCAACCCAT | S | C | T | C | C |
| G987a6 | WIAF-13180 | HT27830 | 615 | PPYR1, pancreatic polypeptide receptor 1 | AGTTCCTGGC[A/g]GATAAGGTGG | S | A | g | A | A |
| G987a7 | WIAF-13181 | HT27830 | 718 | PPYR1, pancreatic polypeptide receptor 1 | GGGCTTCATC[C/T]TGGTCTGTTA | S | C | T | L | L |
| G987a8 | WIAF-13182 | HT27830 | 745 | PPYR1, pancreatic polypeptide receptor 1 | CATCTACCGG[C/t]GCCTCCAGAG | S | C | t | P | C |
| G987e9 | WIAF-13183 | HT27830 | 842 | PPYR1, pancreatic polypeptide receptor 1 | GTGATGGTGG[T/A]GGCCTTTGCC | M | T | A | V | E |
| G987a10 | WIAF-13184 | HT27830 | 852 | PPYR1, pancreatic polypeptide receptor 1 | TGGCCTTTGC[c/T]GTCCTCTGGC | S | C | T | A | A |
| G987a11 | WIAF-13185 | HT27830 | 889 | PPYR1, pancreatic polypeptide receptor 1 | CAACAGCCTG[G/a]AAGACTGGCA | H | G | a | E | K |
| G987a12 | WIAF-13186 | HT27830 | 924 | PPYR1, pancreatic polypeptide receptor 1 | CCATCTGCCA[C/T]GGGAACCTCA | S | C | T | H | H |
| G989u1 | WIAF-13573 | D86519 | 891 | NPY6R, neuropeptide Y receptor Y6 | TGACTCATGC[C/T]TACTGGGCA | S | C | T | A | A |
| G989u2 | WIAF-13588 | D86519 | 465 | NPY6R, neuropeptide Y receptor Y6 | ACCACCCAGC[A/G]TCTAATACAA | S | A | G | R | A |
| G989u3 | WIAF-13591 | D86519 | 980 | NPY6R, neuropeptide Y receptor Y6 | GAGCCCTTCC[G/A]CAACCTCTCT | M | G | A | R | N |
| G991u1 | WIAF-12390 | HT97376 | 336 | Notch2 | AAGGTACTTG[C/T]GTTCAGAAAA | S | C | T | C | C |
| G993u1 | WIAF-12359 | U95299 | 1343 | NOTCH4, Notch (Drosophila) homolog 4 | TCCACACTCT[G/T]CCTGTGTCAG | M | G | T | C | F |
| G993u2 | WIAF-12361 | U95299 | 2020 | NOTCH4, Notch (Drosophila) homolog 4 | TAAGGACCAG[A/G]AAGACAAGGC | H | A | G | K | E |
| G993u3 | WIAF-12384 | U95299 | 5775 | NOTCH4, Notch (Drosophila) homolog 4 | GGGCCTATTC[G/T]CATTGCCGGA | S | G | T | S | S |
| G996a1 | WIAF-13213 | HT3329 | 356 | OPRM1, opioid receptor, mu 1 | CTTAGATGGC[A/G]ACCTGTCCGA | M | A | G | N | D |
| LPLa4 | WIAF-13314 | HT1320 | 443 | LPL, lipoprotein lipase | ATGTATGAGA[G/T]TTGGGTGCCA | M | G | T | S | I |
| LPLa5 | WIAF-13315 | HT1320 | 579 | LPL, lipoprotein lipase | GACAGGATGT[G/A]GCCCGGTTTA | S | G | A | V | V |
| LPLa6 | WIAF-13316 | HT1320 | 609 | LPL, lipoprotein lipase | TGGAGGAGGA[G/A]TTTAACTACC | M | G | A | E | E |
| LPLa7 | WIAF-13317 | HT1320 | 1338 | LPL, lipoprotein lipase | CAAATAAGAC[C/A]TACTCCTTCC | M | C | A | T | T |
| LPLa8 | WIAF-13318 | HT132C | 1117 | LPL, lipoprotein lipase | CAATCTGGCC[T/G]GATGAGATCAA | M | T | G | Y | D |
| LPLa9 | WIAF-13319 | HT1320 | 715 | LPL, lipoprotein lipase | CAGAATTACT[G/A]GCCTCGATCC | M | G | A | G | S |
| LPLa10 | WIAF-13320 | HT1320 | 834 | LPL, lipoprotein lipase | CTGGTCGAAG[C/A]AATTGGAATCC | M | C | A | S | R |
| LPLa11 | WIAF-13321 | HT1320 | 951 | LPL, lipoprotein lipase | GCGTGAGAGT[T/A]GTG&ACCAGC | M | T | A | D | R |
| LPLa12 | WIAF-13322 | HT1320 | 1595 | LPL, lipoprotein lipase | AATAAGAAGT[C/G]AGGCTGAAAC | N | C | G | S | * |
| LPLa13 | WIAF-13323 | HT1320 | 1597 | LPL, lipoprotein lipase | TAAGAAGTCA[G/A]GCTGAAACTG | M | G | A | G | S |
| LPLa14 | WIAF-13324 | HT1320 | 1606 | LPL, lipoprotein lipase | AGGCTGAAAC[T/C]GGGCGAATCT | — | T | C | — | — |
| LPLa15 | WIAF-13325 | HT1320 | 1611 | LPL, lipoprotein lipase | GAAACTGGGC[G/A]AATCTACAGA | — | G | A | — | — |

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for predicting the likelihood that a human will have myocardial infraction, comprising:

determining the nucleotide present at nucleotide position 1186 of the thrombospondin-4 gene having the nucleotide sequence of SEQ ID NO: 3 in a nucleic acid sample obtained from a human, wherein presence of a C at nucleotide position 1186 is indicative of increased likelihood of a myocardial infraction in the human as compared with a human having a G at nucleotide position 1186, thereby predicting the likelihood that a human will have myocardial infraction.

2. A method for predicting the likelihood that a human will have coronary revascularization, comprising:

determining the nucleotide present at nucleotide position 1186 of the thrombospondin-4 gene having the nucleotide sequence of SEQ ID NO: 3 from a nucleic acid sample obtained from a human, wherein presence of a C at nucleotide position 1186 is indicative of increased likelihood of a coronary revascularization in the human as compared with a human having a G at nucleotide position 1186, thereby predicting the likelihood that a human will have coronary revascularization.

3. A method for predicting the likelihood that a human will have myocardial infraction, comprising:

determining the nucleotide present at nucleotide position 1186 of the thrombospondin-4 gene having the nucleotide sequence of SEQ ID NO: 3 in a nucleic acid sample obtained form a human, wherein presence of a G at nucleotide position 1186 is indicative of decreased likelihood of a myocardial infraction in the human as compared with a human having a C at nucleotide position 1186, thereby predicting the likelihood that a human will have myocardial infraction.

4. A method for predicting the likelihood that a human will have coronary revascularization, comprising:

determining the nucleotide present at nucleotide position 1186 of the thrombospondin-4 gene having the nucleotide sequence of SEQ ID NO: 3 from a nucleic acid sample obtained from a human, wherein presence of a G at nucleotide position 1186 is indicative of decreased likelihood of a coronary revascularization in the human as compared with a human having a C at nucleotide position 1186, thereby predicting the likelihood that a human will have coronary revascularization.

* * * * *

UNITED STATES PATENT AND TRADEMARK OFFICE

PATENT NO. : 6,727,063 B1
DATED : April 27, 2004
INVENTOR(S) : Lander et al.

It is certified that error appears in the above-identified patent and that said Letters Patent is hereby corrected as shown below:

Column 907,
Lines 57, 63 and 66, "infraction" should read -- infarction --;

Column 909,
Lines 2, 8 and 11, "infraction" should read -- infarction --.

Signed and Sealed this

Sixteenth Day of November, 2004

JON W. DUDAS
*Director of the United States Patent and Trademark Office*

SEQUENCE LISTING

<160> NUMBER OF SEQ ID NOS: 2551

<210> SEQ ID NO 1
<211> LENGTH: 5722
<212> TYPE: DNA
<213> ORGANISM: Homo sapiens

<400> SEQUENCE: 1

| | | | | | |
|---|---|---|---|---|---|
| ggacgcacag | gcattcccg | cgccctcca | gccctcgccg | ccctcgccac | cgctcccggc | 60 |
| cgccgcgctc | cggtacacac | aggatccctg | ctgggcacca | acagctccac | catggggctg | 120 |
| gcctggggac | taggcgtcct | gttcctgatg | catgtgtgtg | gcaccaaccg | cattccagag | 180 |
| tctggcggag | acaacagcgt | gtttgacatc | tttgaactca | ccggggccgc | ccgcaagggg | 240 |
| tctgggcgcc | gactggtgaa | gggccccgac | ccttccagcc | cagctttccg | catcgaggat | 300 |
| gccaacctga | tccccctgt | gcctgatgac | aagttccaag | acctggtgga | tgctgtgcgg | 360 |
| gcagaaaagg | gtttcctcct | tctggcatcc | ctgaggcaga | tgaagaagac | ccggggcacg | 420 |
| ctgctggccc | tggagcggaa | agaccactct | ggccaggtct | tcagcgtggt | gtccaatggc | 480 |
| aaggcgggca | ccctggacct | cagcctgacc | gtccaaggaa | agcagcacgt | ggtgtctgtg | 540 |
| gaagaagctc | tcctggcaac | cggccagtgg | aagagcatca | ccctgtttgt | gcaggaagac | 600 |
| agggcccagc | tgtacatcga | ctgtgaaaag | atggagaatg | ctgagttgga | cgtccccatc | 660 |
| caaagcgtct | tcaccagaga | cctggccagc | atcgccagac | tccgcatcgc | aaagggggc | 720 |
| gtcaatgaca | atttccaggg | ggtgctgcag | aatgtgaggt | ttgtctttgg | aaccacacca | 780 |
| gaagacatcc | tcaggaacaa | aggctgctcc | agctctacca | gtgtcctcct | cacccttgac | 840 |
| aacaacgtgg | tgaatggttc | cagccctgcc | atccgcacta | actacattgg | ccacaagaca | 900 |
| aaggacttgc | aagccatctg | cggcatctcc | tgtgatgagc | tgtccagcat | ggtcctggaa | 960 |
| ctcagggcc | tgcgcaccat | tgtgaccacg | ctgcaggaca | gcatccgcaa | agtgactgaa | 1020 |
| gagaacaaag | agttggccaa | tgagctgagg | cggcctcccc | tatgctatca | caacggagtt | 1080 |
| cagtacagaa | ataacgagga | atggactgtt | gatagctgca | ctgagtgtca | ctgtcagaac | 1140 |
| tcagttacca | tctgcaaaaa | ggtgtcctgc | cccatcatgc | cctgctccaa | tgccacagtt | 1200 |
| cctgatggag | aatgctgtcc | tcgctgttgg | cccagcgact | ctgcggacga | tggctggtct | 1260 |
| ccatggtccg | agtggaccc | ctgttctacg | agctgtggca | atggaattca | gcagcgcggc | 1320 |
| cgctcctgcg | atagcctcaa | caaccgatgt | gagggctcct | cggtccagac | acggacctgc | 1380 |
| cacattcagg | agtgtgacaa | aagatttaaa | caggatggtg | gctggagcca | ctggtccccg | 1440 |
| tggtcatctt | gttctgtgac | atgtggtgat | ggtgtgatca | caaggatccg | gctctgcaac | 1500 |
| tctcccagcc | cccagatgaa | tgggaaaccc | tgtgaaggcg | aagcgcggga | gaccaaagcc | 1560 |
| tgcaagaaag | acgcctgccc | catcaatgga | ggctgggggc | cttggtcacc | atgggacatc | 1620 |
| tgttctgtca | cctgtggagg | agggggtacag | aaacgtagtc | gtctctgcaa | caaccccgca | 1680 |
| ccccagtttg | gaggcaagga | ctgcgttggt | gatgtaacag | aaaaccagat | ctgcaacaag | 1740 |
| caggactgtc | caattgatgg | atgcctgtcc | aatccctgct | tgccggcgt | gaagtgtact | 1800 |
| agctaccctg | atggcagctg | gaaatgtggt | gcttgtcccc | ctggttacag | tggaaatggc | 1860 |

-continued

```
atccagtgca cagatgttga tgagtgcaaa gaagtgcctg atgcctgctt caaccacaat    1920
ggagagcacc ggtgtgagaa cacggacccc ggctacaact gcctgccctg cccccacgc    1980
ttcaccggct cacagccctt cggccagggt gtcgaacatg ccacggccaa caaacaggtg    2040
tgcaagcccc gtaacccctg cacggatggg acccacgact gcaacaagaa cgccaagtgc    2100
aactacctgg gccactatag cgaccccatg taccgctgcg agtgcaagcc tggctacgct    2160
ggcaatggca tcatctgcgg ggaggacaca gacctggatg gctggcccaa tgagaacctg    2220
gtgtgcgtgg ccaatgcgac ttaccactgc aaaaaggata attgccccaa ccttcccaac    2280
tcagggcagg aagactatga caaggatgga attggtgatg cctgtgatga tgacgatgac    2340
aatgataaaa ttccagatga cagggacaac tgtccattcc attacaaccc agctcagtat    2400
gactatgaca gagatgatgt gggagaccgc tgtgacaact gtccctacaa ccacaaccca    2460
gatcaggcag acacagacaa caatggggaa ggagacgcct gtgctgcaga cattgatgga    2520
gacggtatcc tcaatgaacg ggacaactgc cagtacgtct acaatgtgga ccagagagac    2580
actgatatgg atggggttgg agatcagtgt gacaattgcc ccttggaaca caatccggat    2640
cagctggact ctgactcaga ccgcattgga gatacctgtg acaacaatca ggatattgat    2700
gaagatggcc accagaacaa tctggacaac tgtccctatg tgcccaatgc caaccaggct    2760
gaccatgaca agatggcaa gggagatgcc tgtgaccacg atgatgacaa cgatggcatt    2820
cctgatgaca aggacaactg cagactcgtg cccaatcccg accagaagga ctctgacggc    2880
gatggtcgag gtgatgcctg caaagatgat tttgaccatg acagtgtgcc agacatcgat    2940
gacatctgtc ctgagaatgt tgacatcagt gagaccgatt ccgccgatt ccagatgatt    3000
cctctggacc ccaaagggac atcccaaaat gaccctaact gggttgtacg ccatcagggt    3060
aaagaactcg tccagactgt caactgtgat cctggactcg ctgtaggtta tgatgagttt    3120
aatgctgtgg acttcagtgg caccttcttc atcaacaccg aaagggacga tgactatgct    3180
ggatttgtct ttggctacca gtccagcagc cgcttttatg ttgtgatgtg aagcaagtc    3240
acccagtcct actgggacac caaccccacg agggctcagg gatactcggg cctttctgtg    3300
aaagttgtaa actccaccac agggcctggc gagcacctgc ggaacgccct gtggcacaca    3360
ggaaacaccc ctgccaggt gcgcaccctg tggcatgacc ctcgtcacat aggctggaaa    3420
gatttcaccg cctacagatg gcgtctcagc cacaggccaa agacgggttt cattagagtg    3480
gtgatgtatg aagggaagaa aatcatggct gactcaggac ccatctatga taaaacctat    3540
gctggtggta gactagggtt gtttgtcttc tctcaagaaa tggtgttctt ctctgacctg    3600
aaatacgaat gtagagatcc ctaatcatca aattgttgat tgaaagactg atcataaacc    3660
aatgctggta ttgcaccttc tggaactatg ggcttgagaa acccccagg atcacttctc    3720
cttggcttcc ttcttttctg tgcttgcatc agtgtggact cctagaacgt gcgacctgcc    3780
tcaagaaaat gcagttttca aaaacagact catcagcatt cagcctccaa tgaataagac    3840
atcttccaag catataaaca attgctttgg tttccttttg aaaagcatc tacttgcttc    3900
agttgggaag gtgcccattc cactctgcct ttgtcacaga gcagggtgct attgtgaggc    3960
catctctgag cagtggactc aaaagcattt tcaggcatgt cagagaaggg aggactcact    4020
agaattagca aacaaaacca ccctgacatc ctccttcagg aacacgggga gcagaggcca    4080
aagcactaag ggggggcgc atacccgaga cgattgtatg aagaaatat ggaggaactg    4140
ttacatgttc ggtactaagt cattttcagg ggattgaaag actattgctg gatttcatga    4200
tgctgactgg cgttagctga ttaacccatg taaataggca cttaaataga agcaggaaag    4260
```

-continued

```
ggagacaaag actggcttct ggacttcctc cctgatcccc acccttactc atcaccttgc      4320
agtggccaga attagggaat cagaatcaaa ccagtgtaag gcagtgctgg ctgccattgc      4380
ctggtcacat tgaaattggt ggcttcattc tagatgtagc ttgtgcagat gtagcaggaa      4440
aataggaaaa cctaccatct cagtgagcac cagctgcctc ccaaaggagg ggcagccgtg      4500
cttatatttt tatggttaca atggcacaaa attattatca acctaactaa acattcctt       4560 ttctctttt  tccgtaatta ctaggtagtt ttctaattct ctcttttgga agtatgattt      4620
ttttaaagtc tttacgatgt aaaatattta ttttttactt attctggaag atctggctga     4680
aggattattc atggaacagg aagaagcgta aagactatcc atgtcatctt tgttgagagt     4740
cttcgtgact gtaagattgt aaatacagat tatttattaa ctctgttctg cctggaaatt    4800
taggcttcat acggaaagtg tttgagagca agtagttgac atttatcagc aaatctcttg    4860
caagaacagc acaaggaaaa tcagtctaat aagctgctct gccccttgtg ctcagagtgg    4920
atgttatggg attcctttt  tctctgtttt atctttcaa  gtggaattag ttggttatcc    4980
atttgcaaat gttttaaatt gcaaagaaag ccatgaggtc ttcaatactg ttttacccca    5040
tcccttgtgc atatttccag ggagaaggaa agcatataca ctttttctt  tcattttcc     5100 aaaagagaaa aaaatgacaa aaggtgaaac ttacatacaa atattcctc  atttgttgtg    5160 tgactgagta aagaattttt ggatcaagcg gaaagagttt aagtgtctaa caaacttaaa    5220
gctactgtag tacctaaaaa gtcagtgttg tacatagcat aaaaactctg cagagaagta    5280
ttcccaataa ggaaatagca ttgaaatgtt aaatacaatt tctgaaagtt atgttttttt    5340
tctatcatct ggtataccat tgctttattt ttataaatta ttttctcatt gccattggaa    5400
tagaatattc agattgtgta gatatgctat ttaaataatt tatcaggaaa tactgcctgt    5460
agagttagta tttctattt  tatataatgt ttgcacactg aattgaagaa ttgttggttt    5520
tttctttttt ttgttttttt tttttttttt ttttttttg  cttttgacct cccatttta     5580 ctatttgcca ataccttttt ctaggaatgt gcttttttt  gtacacattt ttatccattt    5640
tacattctaa agcagtgtaa gttgtatatt actgtttctt atgtacaagg aacaacaata    5700
aatcatatgg aaatttatat tt                                              5722
```

<210> SEQ ID NO 2
<211> LENGTH: 1170
<212> TYPE: PRT
<213> ORGANISM: Homo sapiens

<400> SEQUENCE: 2

```
Met Gly Leu Ala Trp Gly Leu Gly Val Leu Phe Leu Met His Val Cys
  1               5                  10                  15

Gly Thr Asn Arg Ile Pro Glu Ser Gly Gly Asp Asn Ser Val Phe Asp
              20                  25                  30

Ile Phe Glu Leu Thr Gly Ala Ala Arg Lys Gly Ser Gly Arg Arg Leu
          35                  40                  45

Val Lys Gly Pro Asp Pro Ser Ser Pro Ala Phe Arg Ile Glu Asp Ala
      50                  55                  60

Asn Leu Ile Pro Pro Val Pro Asp Asp Lys Phe Gln Asp Leu Val Asp
  65                  70                  75                  80

Ala Val Arg Ala Glu Lys Gly Phe Leu Leu Leu Ala Ser Leu Arg Gln
                  85                  90                  95

Met Lys Lys Thr Arg Gly Thr Leu Leu Ala Leu Glu Arg Lys Asp His
             100                 105                 110
```

```
Ser Gly Gln Val Phe Ser Val Ser Asn Gly Lys Ala Gly Thr Leu
        115                 120                 125

Asp Leu Ser Leu Thr Val Gln Gly Lys Gln His Val Val Ser Val Glu
        130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Glu Lys Met Glu Asn
                165                 170                 175

Ala Glu Leu Asp Val Pro Ile Gln Ser Val Phe Thr Arg Asp Leu Ala
                180                 185                 190

Ser Ile Ala Arg Leu Arg Ile Ala Lys Gly Gly Val Asn Asp Asn Phe
        195                 200                 205

Gln Gly Val Leu Gln Asn Val Arg Phe Val Phe Gly Thr Thr Pro Glu
        210                 215                 220

Asp Ile Leu Arg Asn Lys Gly Cys Ser Ser Ser Thr Ser Val Leu Leu
225                 230                 235                 240

Thr Leu Asp Asn Asn Val Val Asn Gly Ser Ser Pro Ala Ile Arg Thr
                245                 250                 255

Asn Tyr Ile Gly His Lys Thr Lys Asp Leu Gln Ala Ile Cys Gly Ile
                260                 265                 270

Ser Cys Asp Glu Leu Ser Ser Met Val Leu Glu Leu Arg Gly Leu Arg
        275                 280                 285

Thr Ile Val Thr Thr Leu Gln Asp Ser Ile Arg Lys Val Thr Glu Glu
        290                 295                 300

Asn Lys Glu Leu Ala Asn Glu Leu Arg Arg Pro Pro Leu Cys Tyr His
305                 310                 315                 320

Asn Gly Val Gln Tyr Arg Asn Asn Glu Glu Trp Thr Val Asp Ser Cys
                325                 330                 335

Thr Glu Cys His Cys Gln Asn Ser Val Thr Ile Cys Lys Lys Val Ser
                340                 345                 350

Cys Pro Ile Met Pro Cys Ser Asn Ala Thr Val Pro Asp Gly Glu Cys
        355                 360                 365

Cys Pro Arg Cys Trp Pro Ser Asp Ser Ala Asp Asp Gly Trp Ser Pro
        370                 375                 380

Trp Ser Glu Trp Thr Ser Cys Ser Thr Ser Cys Gly Asn Gly Ile Gln
385                 390                 395                 400

Gln Arg Gly Arg Ser Cys Asp Ser Leu Asn Asn Arg Cys Glu Gly Ser
                405                 410                 415

Ser Val Gln Thr Arg Thr Cys His Ile Gln Glu Cys Asp Lys Arg Phe
                420                 425                 430

Lys Gln Asp Gly Gly Trp Ser His Trp Ser Pro Trp Ser Ser Cys Ser
        435                 440                 445

Val Thr Cys Gly Asp Gly Val Ile Thr Arg Ile Arg Leu Cys Asn Ser
        450                 455                 460

Pro Ser Pro Gln Met Asn Gly Lys Pro Cys Glu Gly Glu Ala Arg Glu
465                 470                 475                 480

Thr Lys Ala Cys Lys Lys Asp Ala Cys Pro Ile Asn Gly Gly Trp Gly
                485                 490                 495

Pro Trp Ser Pro Trp Asp Ile Cys Ser Val Thr Cys Gly Gly Gly Val
        500                 505                 510

Gln Lys Arg Ser Arg Leu Cys Asn Asn Pro Ala Pro Gln Phe Gly Gly
        515                 520                 525
```

-continued

```
Lys Asp Cys Val Gly Asp Val Thr Glu Asn Gln Ile Cys Asn Lys Gln
530                 535                 540

Asp Cys Pro Ile Asp Gly Cys Leu Ser Asn Pro Cys Phe Ala Gly Val
545                 550                 555                 560

Lys Cys Thr Ser Tyr Pro Asp Gly Ser Trp Lys Cys Gly Ala Cys Pro
                565                 570                 575

Pro Gly Tyr Ser Gly Asn Gly Ile Gln Cys Thr Asp Val Asp Glu Cys
                580                 585                 590

Lys Glu Val Pro Asp Ala Cys Phe Asn His Asn Gly Glu His Arg Cys
            595                 600                 605

Glu Asn Thr Asp Pro Gly Tyr Asn Cys Leu Pro Cys Pro Pro Arg Phe
610                 615                 620

Thr Gly Ser Gln Pro Phe Gly Gln Gly Val Glu His Ala Thr Ala Asn
625                 630                 635                 640

Lys Gln Val Cys Lys Pro Arg Asn Pro Cys Thr Asp Gly Thr His Asp
                645                 650                 655

Cys Asn Lys Asn Ala Lys Cys Asn Tyr Leu Gly His Tyr Ser Asp Pro
                660                 665                 670

Met Tyr Arg Cys Glu Cys Lys Pro Gly Tyr Ala Gly Asn Gly Ile Ile
            675                 680                 685

Cys Gly Glu Asp Thr Asp Leu Asp Gly Trp Pro Asn Glu Asn Leu Val
690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
                725                 730                 735

Ala Cys Asp Asp Asp Asp Asp Asn Asp Lys Ile Pro Asp Asp Arg Asp
            740                 745                 750

Asn Cys Pro Phe His Tyr Asn Pro Ala Gln Tyr Asp Tyr Asp Arg Asp
            755                 760                 765

Asp Val Gly Asp Arg Cys Asp Asn Cys Pro Tyr Asn His Asn Pro Asp
            770                 775                 780

Gln Ala Asp Thr Asp Asn Asn Gly Glu Gly Asp Ala Cys Ala Ala Asp
785                 790                 795                 800

Ile Asp Gly Asp Gly Ile Leu Asn Glu Arg Asp Asn Cys Gln Tyr Val
                805                 810                 815

Tyr Asn Val Asp Gln Arg Asp Thr Asp Met Asp Gly Val Gly Asp Gln
                820                 825                 830

Cys Asp Asn Cys Pro Leu Glu His Asn Pro Asp Gln Leu Asp Ser Asp
            835                 840                 845

Ser Asp Arg Ile Gly Asp Thr Cys Asp Asn Asn Gln Asp Ile Asp Glu
850                 855                 860

Asp Gly His Gln Asn Asn Leu Asp Asn Cys Pro Tyr Val Pro Asn Ala
865                 870                 875                 880

Asn Gln Ala Asp His Asp Lys Asp Gly Lys Gly Asp Ala Cys Asp His
                885                 890                 895

Asp Asp Asp Asn Asp Gly Ile Pro Asp Asp Lys Asp Asn Cys Arg Leu
            900                 905                 910

Val Pro Asn Pro Asp Gln Lys Asp Ser Asp Gly Asp Gly Arg Gly Asp
            915                 920                 925

Ala Cys Lys Asp Asp Phe Asp His Asp Ser Val Pro Asp Ile Asp Asp
930                 935                 940

Ile Cys Pro Glu Asn Val Asp Ile Ser Glu Thr Asp Phe Arg Arg Phe
```

```
                    945                 950                 955                 960

Gln Met Ile Pro Leu Asp Pro Lys Gly Thr Ser Gln Asn Asp Pro Asn
                965                 970                 975

Trp Val Arg His Gln Gly Lys Glu Leu Val Gln Thr Val Asn Cys
            980                 985                 990

Asp Pro Gly Leu Ala Val Gly Tyr Asp Glu Phe Asn Ala Val Asp Phe
            995                 1000                1005

Ser Gly Thr Phe Phe Ile Asn Thr Glu Arg Asp Asp Tyr Ala Gly
        1010                1015                1020

Phe Val Phe Gly Tyr Gln Ser Ser Ser Arg Phe Tyr Val Val Met Trp
1025                1030                1035                1040

Lys Gln Val Thr Gln Ser Tyr Trp Asp Thr Asn Pro Thr Arg Ala Gln
                1045                1050                1055

Gly Tyr Ser Gly Leu Ser Val Lys Val Val Asn Ser Thr Thr Gly Pro
                1060                1065                1070

Gly Glu His Leu Arg Asn Ala Leu Trp His Thr Gly Asn Thr Pro Gly
            1075                1080                1085

Gln Val Arg Thr Leu Trp His Asp Pro Arg His Ile Gly Trp Lys Asp
        1090                1095                1100

Phe Thr Ala Tyr Arg Trp Arg Leu Ser His Arg Pro Lys Thr Gly Phe
1105                1110                1115                1120

Ile Arg Val Val Met Tyr Glu Gly Lys Lys Ile Met Ala Asp Ser Gly
                1125                1130                1135

Pro Ile Tyr Asp Lys Thr Tyr Ala Gly Gly Arg Leu Gly Leu Phe Val
                1140                1145                1150

Phe Ser Gln Glu Met Val Phe Phe Ser Asp Leu Lys Tyr Glu Cys Arg
            1155                1160                1165

Asp Pro
    1170

<210> SEQ ID NO 3
<211> LENGTH: 3074
<212> TYPE: DNA
<213> ORGANISM: Homo sapiens

<400> SEQUENCE: 3
gaattccggg gagcaggaag agccaacatg ctggccccgc gcggagccgc cgtcctcctg      60
ctgcacctgg tcctgcagcg gtggctagcg gcaggcgccc aggccacccc ccaggtctttt    120 gaccttctcc catcttccag tcagaggcta aacccaggcg ctctgctgcc agtcctgaca    180
gaccccgccc tgaatgatct ctatgtgatt ccaccttca agctgcagac taaaagttca     240
gccaccatct tcggtctttta ctcttcaact gacaacagta aatattttga atttactgtg    300
atgggacgct taagcaaagc catcctccgt tacctgaaga acgatgggaa ggtgcatttg    360
gtggttttca caacctgca gctggcagac ggaaggcggc acaggatcct cctgaggctg    420
agcaatttgc agcgagggc cggctcccta gagctctacc tggactgcat ccaggtggat    480
tccgttcaca atctccccag ggcctttgct ggcccctccc agaaacctga gaccattgaa    540
ttgaggactt tccagaggaa gccacaggac ttcttggaag agctgaagct ggtggtgaga    600
ggctcactgt tccaggtggc cagcctgcaa gactgcttcc tgcagcagag tgagccactg    660
gctgccacag gcacagggga ctttaaccgg cagttcttgg gtcaaatgac acaattaaac    720
caactcctgg gagaggtgaa ggaccttctg agacagcagg ttaaggaaac atcattttttg   780 cgaaacacca tagctgaatg ccaggcttgc ggtcctctca gtttcagtc tccgaccccca    840
```

```
agcacggtgg tcgccccggc tcccctgca ccgccaacac gcccacctcg tcggtgtgac    900
tccaacccat gtttccgagg tgtccaatgt accgacagta gagatggctt ccagtgtggg    960
ccctgccccg agggctacac aggaaacggg atcacctgta ttgatgttga tgagtgcaaa   1020
taccatccct gctacccggg cgtgcactgc ataaatttgt ctcctggctt cagatgtgac   1080
gcctgcccag tgggcttcac agggcccatg gtgcaggtg ttgggatcag ttttgccaag    1140
tcaaacaagc aggtctgcac tgacattgat gagtgtcgaa atggagcgtg cgttcccaac   1200
tcgatctgcg ttaatacttt gggatcttac cgctgtgggc cttgtaagcc ggggtatact   1260
ggtgatcaga taaggggatg caaagtggaa agaaactgca gaaacccaga gctgaaccct   1320
tgcagtgtga atgcccagtg cattgaagag aggcaggggg atgtgacatg tgtgtgtgga   1380
gtcggttggg ctggagatgg ctatatctgt ggaaaggatg tggacatcga cagttacccc   1440
gacgaagaac tgccatgctc tgccaggaac tgtaaaaagg acaactgcaa atatgtgcca   1500
aattctggcc aagaagatgc agacagagat ggcattggcg acgcttgtga cgaggatgct   1560
gacggagatg ggatcctgaa tgagcaggat aactgtgtcc tgattcataa tgtgaccaa    1620 aggaacagcg ataaagatat ctttggggat gcctgtgata actgcctgag tgtcttaaat   1680
aacgaccaga agacaccga tggggatgga agaggagatg cctgtgatga tgacatggat    1740
ggagatggaa taaaaaacat tctggacaac tgcccaaaat ttcccaatcg tgaccaacgg   1800
gacaaggatg gtgatggtgt gggggatgcc tgtgacagtt gtcctgatgt cagcaaccct   1860
aaccagtctg atgtggataa tgatctggtt ggggactcct gtgacaccaa tcaggacagt   1920
gatggagatg ggcaccagga cagcacagac aactgcccca ccgtcattaa cagtgcccag   1980
ctggacaccg ataaggatgg aattggtgac gagtgtgatg atgatgatga caatgatggt   2040
atcccagacc tggtgccccc tggaccagac aactgccggc tggtcccaa cccagcccag    2100 gaggatagca acagcgacgg agtgggagac atctgtgagt ctgactttga ccaggaccag   2160
gtcatcgatc ggatcgacgt ctgcccagag aacgcagagg tcaccctgac cgacttcagg   2220
gcttaccaga ccgtgggcct ggatcctgaa ggggatgccc agatcgatcc caactgggtg   2280
gtcctgaacc agggcatgga gattgtacag accatgaaca gtgatcctgg cctggcagtg   2340
gggtacacag ctttaatgg agttgacttc gaagggacct tccatgtgaa tacccagaca    2400
gatgatgact atgcaggctt tatctttggc taccaagata gctccagctt ctacgtggtc   2460
atgtggaagc agacggagca gacatattgg caagccaccc cattccgagc agttgcagaa   2520
cctggcattc agctcaaggc tgtgaagtct aagacaggtc cagggagca ctccggaac    2580 tccctgtggc acacggggga caccagtgac caggtcaggc tgctgtggaa ggactccagg   2640
aatgtgggct ggaaggacaa ggtgtcctac cgctggttcc tacagcacag gccccaggtg   2700
ggctacatca gggtacgatt ttatgaaggc tctgagttgg tggctgactc tggcgtcacc   2760
atagacacca caatgcgtgg aggccgactt ggcgttttct gcttctctca agaaaacatc   2820
atctggtcca acctcaagta tcgctgcaat gacaccatcc ctgaggactt ccaagagttt   2880
caaacccaga atttcgaccg cttcgataat taaaccaagg aagcaatctg taactgcttt   2940
tcggaacact aaaaccatat atattttaac ttcaattttc tttagctttt accaacccaa   3000
atatatcaaa acgttttatg tgaatgtggc aataaggag aagagatcat ttttaaaaaa    3060
aaaaaaaaaa aaaa                                                    3074
```

<210> SEQ ID NO 4

```
<211> LENGTH: 961
<212> TYPE: PRT
<213> ORGANISM: Homo sapiens

<400> SEQUENCE: 4
```

| | | | | | | | | | | | | | | | |
|---|---|---|---|---|---|---|---|---|---|---|---|---|---|---|---|
| Met | Leu | Ala | Pro | Arg | Gly | Ala | Ala | Val | Leu | Leu | His | Leu | Val | Leu | |
| 1 | | | | 5 | | | | | 10 | | | | | 15 | |
| Gln | Arg | Trp | Leu | Ala | Ala | Gly | Ala | Gln | Ala | Thr | Pro | Gln | Val | Phe | Asp |
| | | | 20 | | | | | 25 | | | | | 30 | | |
| Leu | Leu | Pro | Ser | Ser | Ser | Gln | Arg | Leu | Asn | Pro | Gly | Ala | Leu | Leu | Pro |
| | | 35 | | | | | 40 | | | | | 45 | | | |
| Val | Leu | Thr | Asp | Pro | Ala | Leu | Asn | Asp | Leu | Tyr | Val | Ile | Ser | Thr | Phe |
| | 50 | | | | | 55 | | | | | 60 | | | | |
| Lys | Leu | Gln | Thr | Lys | Ser | Ser | Ala | Thr | Ile | Phe | Gly | Leu | Tyr | Ser | Ser |
| 65 | | | | | 70 | | | | | 75 | | | | | 80 |
| Thr | Asp | Asn | Ser | Lys | Tyr | Phe | Glu | Phe | Thr | Val | Met | Gly | Arg | Leu | Ser |
| | | | | 85 | | | | | 90 | | | | | 95 | |
| Lys | Ala | Ile | Leu | Arg | Tyr | Leu | Lys | Asn | Asp | Gly | Lys | Val | His | Leu | Val |
| | | | 100 | | | | | 105 | | | | | 110 | | |
| Val | Phe | Asn | Asn | Leu | Gln | Leu | Ala | Asp | Gly | Arg | Arg | His | Arg | Ile | Leu |
| | | 115 | | | | | 120 | | | | | 125 | | | |
| Leu | Arg | Leu | Ser | Asn | Leu | Gln | Arg | Gly | Ala | Gly | Ser | Leu | Glu | Leu | Tyr |
| | 130 | | | | | 135 | | | | | 140 | | | | |
| Leu | Asp | Cys | Ile | Gln | Val | Asp | Ser | Val | His | Asn | Leu | Pro | Arg | Ala | Phe |
| 145 | | | | | 150 | | | | | 155 | | | | | 160 |
| Ala | Gly | Pro | Ser | Gln | Lys | Pro | Glu | Thr | Ile | Glu | Leu | Arg | Thr | Phe | Gln |
| | | | | 165 | | | | | 170 | | | | | 175 | |
| Arg | Lys | Pro | Gln | Asp | Phe | Leu | Glu | Glu | Leu | Lys | Leu | Val | Val | Arg | Gly |
| | | | 180 | | | | | 185 | | | | | 190 | | |
| Ser | Leu | Phe | Gln | Val | Ala | Ser | Leu | Gln | Asp | Cys | Phe | Leu | Gln | Gln | Ser |
| | | 195 | | | | | 200 | | | | | 205 | | | |
| Glu | Pro | Leu | Ala | Ala | Thr | Gly | Thr | Gly | Asp | Phe | Asn | Arg | Gln | Phe | Leu |
| | 210 | | | | | 215 | | | | | 220 | | | | |
| Gly | Gln | Met | Thr | Gln | Leu | Asn | Gln | Leu | Leu | Gly | Glu | Val | Lys | Asp | Leu |
| 225 | | | | | 230 | | | | | 235 | | | | | 240 |
| Leu | Arg | Gln | Gln | Val | Lys | Glu | Thr | Ser | Phe | Leu | Arg | Asn | Thr | Ile | Ala |
| | | | | 245 | | | | | 250 | | | | | 255 | |
| Glu | Cys | Gln | Ala | Cys | Gly | Pro | Leu | Lys | Phe | Gln | Ser | Pro | Thr | Pro | Ser |
| | | | 260 | | | | | 265 | | | | | 270 | | |
| Thr | Val | Val | Ala | Pro | Ala | Pro | Ala | Pro | Thr | Arg | Pro | Pro | Arg | | |
| | | 275 | | | | | 280 | | | | | 285 | | | |
| Arg | Cys | Asp | Ser | Asn | Pro | Cys | Phe | Arg | Gly | Val | Gln | Cys | Thr | Asp | Ser |
| | 290 | | | | | 295 | | | | | 300 | | | | |
| Arg | Asp | Gly | Phe | Gln | Cys | Gly | Pro | Cys | Pro | Glu | Gly | Tyr | Thr | Gly | Asn |
| 305 | | | | | 310 | | | | | 315 | | | | | 320 |
| Gly | Ile | Thr | Cys | Ile | Asp | Val | Asp | Glu | Cys | Lys | Tyr | His | Pro | Cys | Tyr |
| | | | | 325 | | | | | 330 | | | | | 335 | |
| Pro | Gly | Val | His | Cys | Ile | Asn | Leu | Ser | Pro | Gly | Phe | Arg | Cys | Asp | Ala |
| | | | 340 | | | | | 345 | | | | | 350 | | |
| Cys | Pro | Val | Gly | Phe | Thr | Gly | Pro | Met | Val | Gln | Gly | Val | Gly | Ile | Ser |
| | | 355 | | | | | 360 | | | | | 365 | | | |
| Phe | Ala | Lys | Ser | Asn | Lys | Gln | Val | Cys | Thr | Asp | Ile | Asp | Glu | Cys | Arg |
| | 370 | | | | | 375 | | | | | 380 | | | | |
| Asn | Gly | Ala | Cys | Val | Pro | Asn | Ser | Ile | Cys | Val | Asn | Thr | Leu | Gly | Ser |

-continued

```
385                 390                 395                 400
Tyr Arg Cys Gly Pro Cys Lys Pro Gly Tyr Thr Gly Asp Gln Ile Arg
                405                 410                 415

Gly Cys Lys Val Glu Arg Asn Cys Arg Asn Pro Glu Leu Asn Pro Cys
            420                 425                 430

Ser Val Asn Ala Gln Cys Ile Glu Glu Arg Gln Gly Asp Val Thr Cys
        435                 440                 445

Val Cys Gly Val Gly Trp Ala Gly Asp Gly Tyr Ile Cys Gly Lys Asp
    450                 455                 460

Val Asp Ile Asp Ser Tyr Pro Asp Glu Glu Leu Pro Cys Ser Ala Arg
465                 470                 475                 480

Asn Cys Lys Lys Asp Asn Cys Lys Tyr Val Pro Asn Ser Gly Gln Glu
                485                 490                 495

Asp Ala Asp Arg Asp Gly Ile Gly Asp Ala Cys Asp Glu Asp Ala Asp
            500                 505                 510

Gly Asp Gly Ile Leu Asn Glu Gln Asp Asn Cys Val Leu Ile His Asn
        515                 520                 525

Val Asp Gln Arg Asn Ser Asp Lys Asp Ile Phe Gly Asp Ala Cys Asp
    530                 535                 540

Asn Cys Leu Ser Val Leu Asn Asn Asp Gln Lys Asp Thr Asp Gly Asp
545                 550                 555                 560

Gly Arg Gly Asp Ala Cys Asp Asp Met Asp Gly Asp Gly Ile Lys
                565                 570                 575

Asn Ile Leu Asp Asn Cys Pro Lys Phe Pro Asn Arg Asp Gln Arg Asp
                580                 585                 590

Lys Asp Gly Asp Gly Val Gly Asp Ala Cys Asp Ser Cys Pro Asp Val
            595                 600                 605

Ser Asn Pro Asn Gln Ser Asp Val Asp Asn Asp Leu Val Gly Asp Ser
        610                 615                 620

Cys Asp Thr Asn Gln Asp Ser Asp Gly Asp Gly His Gln Asp Ser Thr
625                 630                 635                 640

Asp Asn Cys Pro Thr Val Ile Asn Ser Ala Gln Leu Asp Thr Asp Lys
                645                 650                 655

Asp Gly Ile Gly Asp Glu Cys Asp Asp Asp Asp Asn Asp Gly Ile
            660                 665                 670

Pro Asp Leu Val Pro Pro Gly Pro Asp Asn Cys Arg Leu Val Pro Asn
        675                 680                 685

Pro Ala Gln Glu Asp Ser Asn Ser Asp Gly Val Gly Asp Ile Cys Glu
    690                 695                 700

Ser Asp Phe Asp Gln Asp Gln Val Ile Asp Arg Ile Asp Val Cys Pro
705                 710                 715                 720

Glu Asn Ala Glu Val Thr Leu Thr Asp Phe Arg Ala Tyr Gln Thr Val
                725                 730                 735

Gly Leu Asp Pro Glu Gly Asp Ala Gln Ile Asp Pro Asn Trp Val Val
            740                 745                 750

Leu Asn Gln Gly Met Glu Ile Val Gln Thr Met Asn Ser Asp Pro Gly
        755                 760                 765

Leu Ala Val Gly Tyr Thr Ala Phe Asn Gly Val Asp Phe Glu Gly Thr
    770                 775                 780

Phe His Val Asn Thr Gln Thr Asp Asp Tyr Ala Gly Phe Ile Phe
785                 790                 795                 800

Gly Tyr Gln Asp Ser Ser Ser Phe Tyr Val Val Met Trp Lys Gln Thr
                805                 810                 815
```

```
Glu Gln Thr Tyr Trp Gln Ala Thr Pro Phe Arg Ala Val Ala Glu Pro
            820                 825                 830
Gly Ile Gln Leu Lys Ala Val Lys Ser Lys Thr Gly Pro Gly Glu His
        835                 840                 845
Leu Arg Asn Ser Leu Trp His Thr Gly Asp Thr Ser Asp Gln Val Arg
    850                 855                 860
Leu Leu Trp Lys Asp Ser Arg Asn Val Gly Trp Lys Asp Lys Val Ser
865                 870                 875                 880
Tyr Arg Trp Phe Leu Gln His Arg Pro Gln Val Gly Tyr Ile Arg Val
                885                 890                 895
Arg Phe Tyr Glu Gly Ser Glu Leu Val Ala Asp Ser Gly Val Thr Ile
            900                 905                 910
Asp Thr Thr Met Arg Gly Gly Arg Leu Gly Val Phe Cys Phe Ser Gln
        915                 920                 925
Glu Asn Ile Ile Trp Ser Asn Leu Lys Tyr Arg Cys Asn Asp Thr Ile
    930                 935                 940
Pro Glu Asp Phe Gln Glu Phe Gln Thr Gln Asn Phe Asp Arg Phe Asp
945                 950                 955                 960
Asn

<210> SEQ ID NO 5
<211> LENGTH: 31
<212> TYPE: DNA
<213> ORGANISM: Homo sapiens

<400> SEQUENCE: 5
tggatggctg gcccartgag aacctggtgt g                           31

<210> SEQ ID NO 6
<211> LENGTH: 31
<212> TYPE: DNA
<213> ORGANISM: Homo sapiens

<400> SEQUENCE: 6
gagtgtcgaa atggascgtg cgttcccaac t                           31

<210> SEQ ID NO 7
<211> LENGTH: 21
<212> TYPE: DNA
<213> ORGANISM: Homo sapiens

<400> SEQUENCE: 7
ctgcaggagt rgctggatga a                                      21

<210> SEQ ID NO 8
<211> LENGTH: 21
<212> TYPE: DNA
<213> ORGANISM: Homo sapiens

<400> SEQUENCE: 8
catctggacc ytgctgggca a                                      21

<210> SEQ ID NO 9
<211> LENGTH: 21
<212> TYPE: DNA
<213> ORGANISM: Homo sapiens

<400> SEQUENCE: 9
gtgctggtgt scgcagccat c                                      21
```

<210> SEQ ID NO 10
<211> LENGTH: 21
<212> TYPE: DNA
<213> ORGANISM: Homo sapiens

<400> SEQUENCE: 10
tgcgcgccaa satgaccaac g                                    21

<210> SEQ ID NO 11
<211> LENGTH: 21
<212> TYPE: DNA
<213> ORGANISM: Homo sapiens

<400> SEQUENCE: 11
tgtgctccac ygcctccatc c                                    21

<210> SEQ ID NO 12
<211> LENGTH: 21
<212> TYPE: DNA
<213> ORGANISM: Homo sapiens

<400> SEQUENCE: 12
gcagagcacg ygcagagctg c                                    21

<210> SEQ ID NO 13
<211> LENGTH: 21
<212> TYPE: DNA
<213> ORGANISM: Homo sapiens

<400> SEQUENCE: 13
atggtcggcc yggcatggac c                                    21

<210> SEQ ID NO 14
<211> LENGTH: 21
<212> TYPE: DNA
<213> ORGANISM: Homo sapiens

<400> SEQUENCE: 14
gcaagatgac ycagcgcatg g                                    21

<210> SEQ ID NO 15
<211> LENGTH: 21
<212> TYPE: DNA
<213> ORGANISM: Homo sapiens

<400> SEQUENCE: 15
tcgctcatca rcttctacat c                                    21

<210> SEQ ID NO 16
<211> LENGTH: 21
<212> TYPE: DNA
<213> ORGANISM: Homo sapiens

<400> SEQUENCE: 16
ggggcgggct kgacctgcca a                                    21

<210> SEQ ID NO 17
<211> LENGTH: 21
<212> TYPE: DNA
<213> ORGANISM: Homo sapiens

<400> SEQUENCE: 17
agaccctgtc rgtgatcatg g    21

<210> SEQ ID NO 18
<211> LENGTH: 21
<212> TYPE: DNA
<213> ORGANISM: Homo sapiens

<400> SEQUENCE: 18
ggaggaggac ktttgggagc c    21

<210> SEQ ID NO 19
<211> LENGTH: 21
<212> TYPE: DNA
<213> ORGANISM: Homo sapiens

<400> SEQUENCE: 19
tttgggagcc ygacgtgaat g    21

<210> SEQ ID NO 20
<211> LENGTH: 21
<212> TYPE: DNA
<213> ORGANISM: Homo sapiens

<400> SEQUENCE: 20
ccgacgtgaa kgcagagaac t    21

<210> SEQ ID NO 21
<211> LENGTH: 21
<212> TYPE: DNA
<213> ORGANISM: Homo sapiens

<400> SEQUENCE: 21
acctacacgc rcatctaccg c    21

<210> SEQ ID NO 22
<211> LENGTH: 21
<212> TYPE: DNA
<213> ORGANISM: Homo sapiens

<400> SEQUENCE: 22
gtgcagccac ktctgctccc g    21

<210> SEQ ID NO 23
<211> LENGTH: 21
<212> TYPE: DNA
<213> ORGANISM: Homo sapiens

<400> SEQUENCE: 23
gaaatcgcag ytgcctacat c    21

<210> SEQ ID NO 24
<211> LENGTH: 21
<212> TYPE: DNA
<213> ORGANISM: Homo sapiens

<400> SEQUENCE: 24
accctgttgc wgagtctgtc t    21

<210> SEQ ID NO 25
<211> LENGTH: 21
<212> TYPE: DNA
<213> ORGANISM: Homo sapiens

<400> SEQUENCE: 25

```
tctcctacaa ycaagacatc g                                        21

<210> SEQ ID NO 26
<211> LENGTH: 21
<212> TYPE: DNA
<213> ORGANISM: Homo sapiens

<400> SEQUENCE: 26
cactcaaccc mgtcatctat g                                        21

<210> SEQ ID NO 27
<211> LENGTH: 21
<212> TYPE: DNA
<213> ORGANISM: Homo sapiens

<400> SEQUENCE: 27
acgccgactt ycagaaggtg t                                        21

<210> SEQ ID NO 28
<211> LENGTH: 21
<212> TYPE: DNA
<213> ORGANISM: Homo sapiens

<400> SEQUENCE: 28
cgaggaggag rgtcctttcg a                                        21

<210> SEQ ID NO 29
<211> LENGTH: 21
<212> TYPE: DNA
<213> ORGANISM: Homo sapiens

<400> SEQUENCE: 29
gatcgcatgt yccagatcta t                                        21

<210> SEQ ID NO 30
<211> LENGTH: 21
<212> TYPE: DNA
<213> ORGANISM: Homo sapiens

<400> SEQUENCE: 30
tgtctctggc ygtgtctgac c                                        21

<210> SEQ ID NO 31
<211> LENGTH: 21
<212> TYPE: DNA
<213> ORGANISM: Homo sapiens

<400> SEQUENCE: 31
tgccgccagg sagcaacggc a                                        21

<210> SEQ ID NO 32
<211> LENGTH: 21
<212> TYPE: DNA
<213> ORGANISM: Homo sapiens

<400> SEQUENCE: 32
ggcagttcgc kctataccag c                                        21

<210> SEQ ID NO 33
<211> LENGTH: 21
<212> TYPE: DNA
<213> ORGANISM: Homo sapiens
```

-continued

```
<400> SEQUENCE: 33
tggggccctc rcaggtggtc a                                              21

<210> SEQ ID NO 34
<211> LENGTH: 21
<212> TYPE: DNA
<213> ORGANISM: Homo sapiens

<400> SEQUENCE: 34
tggccggtta ytggcccttt g                                              21

<210> SEQ ID NO 35
<211> LENGTH: 21
<212> TYPE: DNA
<213> ORGANISM: Homo sapiens

<400> SEQUENCE: 35
cttcgacatc wtgtgctcca c                                              21

<210> SEQ ID NO 36
<211> LENGTH: 21
<212> TYPE: DNA
<213> ORGANISM: Homo sapiens

<400> SEQUENCE: 36
atcagcgtgg rccgctactg g                                              21

<210> SEQ ID NO 37
<211> LENGTH: 21
<212> TYPE: DNA
<213> ORGANISM: Homo sapiens

<400> SEQUENCE: 37
tgggcctttg ragcgttctg c                                              21

<210> SEQ ID NO 38
<211> LENGTH: 21
<212> TYPE: DNA
<213> ORGANISM: Homo sapiens

<400> SEQUENCE: 38
agcctgcgcg yttccatcaa g                                              21

<210> SEQ ID NO 39
<211> LENGTH: 21
<212> TYPE: DNA
<213> ORGANISM: Homo sapiens

<400> SEQUENCE: 39
ggttctcaag mccctgtcgg t                                              21

<210> SEQ ID NO 40
<211> LENGTH: 21
<212> TYPE: DNA
<213> ORGANISM: Homo sapiens

<400> SEQUENCE: 40
ctacatcccc rttgccatca t                                              21

<210> SEQ ID NO 41
<211> LENGTH: 21
<212> TYPE: DNA
<213> ORGANISM: Homo sapiens
```

<400> SEQUENCE: 41
gatttcctcc ytggagaggg c                                              21

<210> SEQ ID NO 42
<211> LENGTH: 21
<212> TYPE: DNA
<213> ORGANISM: Homo sapiens

<400> SEQUENCE: 42
ccctcaacgc ytcgttcctc c                                              21

<210> SEQ ID NO 43
<211> LENGTH: 21
<212> TYPE: DNA
<213> ORGANISM: Homo sapiens

<400> SEQUENCE: 43
gctgctcaag ytggcgtcgc c                                              21

<210> SEQ ID NO 44
<211> LENGTH: 21
<212> TYPE: DNA
<213> ORGANISM: Homo sapiens

<400> SEQUENCE: 44
tggagtccca rgagcggatc a                                              21

<210> SEQ ID NO 45
<211> LENGTH: 21
<212> TYPE: DNA
<213> ORGANISM: Homo sapiens

<400> SEQUENCE: 45
ccccagtggt rtacctgaag g                                              21

<210> SEQ ID NO 46
<211> LENGTH: 21
<212> TYPE: DNA
<213> ORGANISM: Homo sapiens

<400> SEQUENCE: 46
atgtgatgag wgagaaacat c                                              21

<210> SEQ ID NO 47
<211> LENGTH: 21
<212> TYPE: DNA
<213> ORGANISM: Homo sapiens

<400> SEQUENCE: 47
ccccaagatc mggacaagcc t                                              21

<210> SEQ ID NO 48
<211> LENGTH: 21
<212> TYPE: DNA
<213> ORGANISM: Homo sapiens

<400> SEQUENCE: 48
ccaactcagc yttcctgcat a                                              21

<210> SEQ ID NO 49
<211> LENGTH: 21
<212> TYPE: DNA

```
<213> ORGANISM: Homo sapiens

<400> SEQUENCE: 49
gccgctcaga ytccgaggat g                                      21

<210> SEQ ID NO 50
<211> LENGTH: 21
<212> TYPE: DNA
<213> ORGANISM: Homo sapiens

<400> SEQUENCE: 50
ggtacaagtt rcttaaccaa g                                      21

<210> SEQ ID NO 51
<211> LENGTH: 21
<212> TYPE: DNA
<213> ORGANISM: Homo sapiens

<400> SEQUENCE: 51
ctggcctgcc rtgtccggga g                                      21

<210> SEQ ID NO 52
<211> LENGTH: 21
<212> TYPE: DNA
<213> ORGANISM: Homo sapiens

<400> SEQUENCE: 52
agtgcaggga ygaaggcctc a                                      21

<210> SEQ ID NO 53
<211> LENGTH: 21
<212> TYPE: DNA
<213> ORGANISM: Homo sapiens

<400> SEQUENCE: 53
gctgccacgg yctcgtcccg c                                      21

<210> SEQ ID NO 54
<211> LENGTH: 21
<212> TYPE: DNA
<213> ORGANISM: Homo sapiens

<400> SEQUENCE: 54
agaagaatga ycaaatttac g                                      21

<210> SEQ ID NO 55
<211> LENGTH: 21
<212> TYPE: DNA
<213> ORGANISM: Homo sapiens

<400> SEQUENCE: 55
ggattttctg wcatcaagtc c                                      21

<210> SEQ ID NO 56
<211> LENGTH: 21
<212> TYPE: DNA
<213> ORGANISM: Homo sapiens

<400> SEQUENCE: 56
caagtgggtg racagcgaag g                                      21

<210> SEQ ID NO 57
<211> LENGTH: 21
```

-continued

```
<212> TYPE: DNA
<213> ORGANISM: Homo sapiens

<400> SEQUENCE: 57
tcccaagagc ytccagtaga c                                              21

<210> SEQ ID NO 58
<211> LENGTH: 21
<212> TYPE: DNA
<213> ORGANISM: Homo sapiens

<400> SEQUENCE: 58
tcatcaacaa ratgaaactg g                                              21

<210> SEQ ID NO 59
<211> LENGTH: 21
<212> TYPE: DNA
<213> ORGANISM: Homo sapiens

<400> SEQUENCE: 59
tcccatgtca mccggatgac c                                              21

<210> SEQ ID NO 60
<211> LENGTH: 21
<212> TYPE: DNA
<213> ORGANISM: Homo sapiens

<400> SEQUENCE: 60
gactatggga ycaaatttgc c                                              21

<210> SEQ ID NO 61
<211> LENGTH: 21
<212> TYPE: DNA
<213> ORGANISM: Homo sapiens

<400> SEQUENCE: 61
tgcacacatg maaggccccc a                                              21

<210> SEQ ID NO 62
<211> LENGTH: 21
<212> TYPE: DNA
<213> ORGANISM: Homo sapiens

<400> SEQUENCE: 62
cctgatgaat yttcacaaca a                                              21

<210> SEQ ID NO 63
<211> LENGTH: 21
<212> TYPE: DNA
<213> ORGANISM: Homo sapiens

<400> SEQUENCE: 63
gacatgctgg ytggccatgg c                                              21

<210> SEQ ID NO 64
<211> LENGTH: 21
<212> TYPE: DNA
<213> ORGANISM: Homo sapiens

<400> SEQUENCE: 64
actatgggat yaaatttgcc c                                              21

<210> SEQ ID NO 65
```

```
<211> LENGTH: 21
<212> TYPE: DNA
<213> ORGANISM: Homo sapiens

<400> SEQUENCE: 65
tgcaaaggaa rggaaaggaa a                                              21

<210> SEQ ID NO 66
<211> LENGTH: 21
<212> TYPE: DNA
<213> ORGANISM: Homo sapiens

<400> SEQUENCE: 66
atacttgcaa rgcccccaag a                                              21

<210> SEQ ID NO 67
<211> LENGTH: 21
<212> TYPE: DNA
<213> ORGANISM: Homo sapiens

<400> SEQUENCE: 67
ggcaagggga raatgttgcc g                                              21

<210> SEQ ID NO 68
<211> LENGTH: 21
<212> TYPE: DNA
<213> ORGANISM: Homo sapiens

<400> SEQUENCE: 68
ctggccaagc ygtggagtgc t                                              21

<210> SEQ ID NO 69
<211> LENGTH: 21
<212> TYPE: DNA
<213> ORGANISM: Homo sapiens

<400> SEQUENCE: 69
caaattgcga ktgggtatta a                                              21

<210> SEQ ID NO 70
<211> LENGTH: 21
<212> TYPE: DNA
<213> ORGANISM: Homo sapiens

<400> SEQUENCE: 70
gggacctaac yggcgtgcag a                                              21

<210> SEQ ID NO 71
<211> LENGTH: 21
<212> TYPE: DNA
<213> ORGANISM: Homo sapiens

<400> SEQUENCE: 71
gccctcatca rtgcagatga g                                              21

<210> SEQ ID NO 72
<211> LENGTH: 21
<212> TYPE: DNA
<213> ORGANISM: Homo sapiens

<400> SEQUENCE: 72
ctgaaggtct yatggcagag g                                              21
```

```
<210> SEQ ID NO 73
<211> LENGTH: 21
<212> TYPE: DNA
<213> ORGANISM: Homo sapiens

<400> SEQUENCE: 73
tccgtgaagc raatgaacta c                                              21

<210> SEQ ID NO 74
<211> LENGTH: 21
<212> TYPE: DNA
<213> ORGANISM: Homo sapiens

<400> SEQUENCE: 74
tgagacagac wtcaccgtcc a                                              21

<210> SEQ ID NO 75
<211> LENGTH: 21
<212> TYPE: DNA
<213> ORGANISM: Homo sapiens

<400> SEQUENCE: 75
catgaatgtt rcctgtgctg g                                              21

<210> SEQ ID NO 76
<211> LENGTH: 21
<212> TYPE: DNA
<213> ORGANISM: Homo sapiens

<400> SEQUENCE: 76
gccgccctgg rcgctattac g                                              21

<210> SEQ ID NO 77
<211> LENGTH: 21
<212> TYPE: DNA
<213> ORGANISM: Homo sapiens

<400> SEQUENCE: 77
aacattaaga sgtgccacca a                                              21

<210> SEQ ID NO 78
<211> LENGTH: 21
<212> TYPE: DNA
<213> ORGANISM: Homo sapiens

<400> SEQUENCE: 78
ctcatagatg yaaaaactgg a                                              21

<210> SEQ ID NO 79
<211> LENGTH: 21
<212> TYPE: DNA
<213> ORGANISM: Homo sapiens

<400> SEQUENCE: 79
gatagatttt yagaagttaa a                                              21

<210> SEQ ID NO 80
<211> LENGTH: 21
<212> TYPE: DNA
<213> ORGANISM: Homo sapiens

<400> SEQUENCE: 80
tcgagatgga rcagcggctg g                                              21
```

```
<210> SEQ ID NO 81
<211> LENGTH: 21
<212> TYPE: DNA
<213> ORGANISM: Homo sapiens

<400> SEQUENCE: 81
gggagcgccg mgccatcgag a                                              21

<210> SEQ ID NO 82
<211> LENGTH: 21
<212> TYPE: DNA
<213> ORGANISM: Homo sapiens

<400> SEQUENCE: 82
gggatcgcca ygggaactca a                                              21

<210> SEQ ID NO 83
<211> LENGTH: 21
<212> TYPE: DNA
<213> ORGANISM: Homo sapiens

<400> SEQUENCE: 83
ccctccttct ycaagaactt t                                              21

<210> SEQ ID NO 84
<211> LENGTH: 21
<212> TYPE: DNA
<213> ORGANISM: Homo sapiens

<400> SEQUENCE: 84
tctccaactt stacaaattc t                                              21

<210> SEQ ID NO 85
<211> LENGTH: 21
<212> TYPE: DNA
<213> ORGANISM: Homo sapiens

<400> SEQUENCE: 85
actgaatctg maggccagga t                                              21

<210> SEQ ID NO 86
<211> LENGTH: 21
<212> TYPE: DNA
<213> ORGANISM: Homo sapiens

<400> SEQUENCE: 86
aatttgagct wcttgataag g                                              21

<210> SEQ ID NO 87
<211> LENGTH: 21
<212> TYPE: DNA
<213> ORGANISM: Homo sapiens

<400> SEQUENCE: 87
tcagaatcat ytgatggatc t                                              21

<210> SEQ ID NO 88
<211> LENGTH: 21
<212> TYPE: DNA
<213> ORGANISM: Homo sapiens

<400> SEQUENCE: 88
ttcaagtgaa satgctgaaa g                                              21
```

<210> SEQ ID NO 89
<211> LENGTH: 21
<212> TYPE: DNA
<213> ORGANISM: Homo sapiens

<400> SEQUENCE: 89
ctcttgacga kgacgaagat g                                              21

<210> SEQ ID NO 90
<211> LENGTH: 21
<212> TYPE: DNA
<213> ORGANISM: Homo sapiens

<400> SEQUENCE: 90
ccggactctt ycagccatta a                                              21

<210> SEQ ID NO 91
<211> LENGTH: 21
<212> TYPE: DNA
<213> ORGANISM: Homo sapiens

<400> SEQUENCE: 91
ctgagaaaga ygcggaagat t                                              21

<210> SEQ ID NO 92
<211> LENGTH: 21
<212> TYPE: DNA
<213> ORGANISM: Homo sapiens

<400> SEQUENCE: 92
tggaacagaa ygaagacaga t                                              21

<210> SEQ ID NO 93
<211> LENGTH: 21
<212> TYPE: DNA
<213> ORGANISM: Homo sapiens

<400> SEQUENCE: 93
gtttcctgta ytaaagcaac t                                              21

<210> SEQ ID NO 94
<211> LENGTH: 21
<212> TYPE: DNA
<213> ORGANISM: Homo sapiens

<400> SEQUENCE: 94
agaacagctg ygaaagagcc a                                              21

<210> SEQ ID NO 95
<211> LENGTH: 21
<212> TYPE: DNA
<213> ORGANISM: Homo sapiens

<400> SEQUENCE: 95
gatgtgcaga ygggagggcc a                                              21

<210> SEQ ID NO 96
<211> LENGTH: 21
<212> TYPE: DNA
<213> ORGANISM: Homo sapiens

<400> SEQUENCE: 96

-continued aagaatttga kctacttgat a                                              21

<210> SEQ ID NO 97
<211> LENGTH: 21
<212> TYPE: DNA
<213> ORGANISM: Homo sapiens

<400> SEQUENCE: 97
acacttctga ytgcactccc g                                              21

<210> SEQ ID NO 98
<211> LENGTH: 21
<212> TYPE: DNA
<213> ORGANISM: Homo sapiens

<400> SEQUENCE: 98
gccaccccat kaacctggag g                                              21

<210> SEQ ID NO 99
<211> LENGTH: 21
<212> TYPE: DNA
<213> ORGANISM: Homo sapiens

<400> SEQUENCE: 99
gagtcaccac yttcacctta t                                              21

<210> SEQ ID NO 100
<211> LENGTH: 21
<212> TYPE: DNA
<213> ORGANISM: Homo sapiens

<400> SEQUENCE: 100
acgtacatca mtgcctcgac g                                              21

<210> SEQ ID NO 101
<211> LENGTH: 21
<212> TYPE: DNA
<213> ORGANISM: Homo sapiens

<400> SEQUENCE: 101
tctgtaccca yactcttgta c                                              21

<210> SEQ ID NO 102
<211> LENGTH: 21
<212> TYPE: DNA
<213> ORGANISM: Homo sapiens

<400> SEQUENCE: 102
aggcaacatg sgtgactgga g                                              21

<210> SEQ ID NO 103
<211> LENGTH: 21
<212> TYPE: DNA
<213> ORGANISM: Homo sapiens

<400> SEQUENCE: 103
tatgtgatgc raaaggaaga g                                              21

<210> SEQ ID NO 104
<211> LENGTH: 21
<212> TYPE: DNA
<213> ORGANISM: Homo sapiens

<400> SEQUENCE: 104

```
ttcattttcc raatcctgct g                                        21

<210> SEQ ID NO 105
<211> LENGTH: 21
<212> TYPE: DNA
<213> ORGANISM: Homo sapiens

<400> SEQUENCE: 105
caagcctact yaactgctgg a                                        21

<210> SEQ ID NO 106
<211> LENGTH: 21
<212> TYPE: DNA
<213> ORGANISM: Homo sapiens

<400> SEQUENCE: 106
agaaagagga rgaactcaag g                                        21

<210> SEQ ID NO 107
<211> LENGTH: 21
<212> TYPE: DNA
<213> ORGANISM: Homo sapiens

<400> SEQUENCE: 107
gcacttgaag magattgaga t                                        21

<210> SEQ ID NO 108
<211> LENGTH: 21
<212> TYPE: DNA
<213> ORGANISM: Homo sapiens

<400> SEQUENCE: 108
atgcacttga rgcagattga g                                        21

<210> SEQ ID NO 109
<211> LENGTH: 21
<212> TYPE: DNA
<213> ORGANISM: Homo sapiens

<400> SEQUENCE: 109
cgctgagccc ygccaaagac t                                        21

<210> SEQ ID NO 110
<211> LENGTH: 21
<212> TYPE: DNA
<213> ORGANISM: Homo sapiens

<400> SEQUENCE: 110
cctcaccaac ygctcccctc t                                        21

<210> SEQ ID NO 111
<211> LENGTH: 21
<212> TYPE: DNA
<213> ORGANISM: Homo sapiens

<400> SEQUENCE: 111
aagctggtta mtggcgacag a                                        21

<210> SEQ ID NO 112
<211> LENGTH: 21
<212> TYPE: DNA
<213> ORGANISM: Homo sapiens
```

```
<400> SEQUENCE: 112
ctaactccca ygcacagcct t                                              21

<210> SEQ ID NO 113
<211> LENGTH: 21
<212> TYPE: DNA
<213> ORGANISM: Homo sapiens

<400> SEQUENCE: 113
tggacatgaa ytacagccac t                                              21

<210> SEQ ID NO 114
<211> LENGTH: 21
<212> TYPE: DNA
<213> ORGANISM: Homo sapiens

<400> SEQUENCE: 114
ccgcaattac racaagcaag c                                              21

<210> SEQ ID NO 115
<211> LENGTH: 21
<212> TYPE: DNA
<213> ORGANISM: Homo sapiens

<400> SEQUENCE: 115
gtggaccagc raccttcaag c                                              21

<210> SEQ ID NO 116
<211> LENGTH: 21
<212> TYPE: DNA
<213> ORGANISM: Homo sapiens

<400> SEQUENCE: 116
tatttgtgtc ygtacccaca c                                              21

<210> SEQ ID NO 117
<211> LENGTH: 21
<212> TYPE: DNA
<213> ORGANISM: Homo sapiens

<400> SEQUENCE: 117
cgttaaggat ygggttaagg g                                              21

<210> SEQ ID NO 118
<211> LENGTH: 21
<212> TYPE: DNA
<213> ORGANISM: Homo sapiens

<400> SEQUENCE: 118
aactcttcta ygttttcttc a                                              21

<210> SEQ ID NO 119
<211> LENGTH: 21
<212> TYPE: DNA
<213> ORGANISM: Homo sapiens

<400> SEQUENCE: 119
agttcaagta yggtattgaa g                                              21

<210> SEQ ID NO 120
<211> LENGTH: 21
<212> TYPE: DNA
<213> ORGANISM: Homo sapiens
```

```
<400> SEQUENCE: 120
ccagcgacct kcaagcagag c                                              21

<210> SEQ ID NO 121
<211> LENGTH: 21
<212> TYPE: DNA
<213> ORGANISM: Homo sapiens

<400> SEQUENCE: 121
caacaagcaa rcaagtgagc a                                              21

<210> SEQ ID NO 122
<211> LENGTH: 21
<212> TYPE: DNA
<213> ORGANISM: Homo sapiens

<400> SEQUENCE: 122
caaaactggg staattacag t                                              21

<210> SEQ ID NO 123
<211> LENGTH: 21
<212> TYPE: DNA
<213> ORGANISM: Homo sapiens

<400> SEQUENCE: 123
agacctgtgc rtacaccaac c                                              21

<210> SEQ ID NO 124
<211> LENGTH: 21
<212> TYPE: DNA
<213> ORGANISM: Homo sapiens

<400> SEQUENCE: 124 gacacccag ygcccggcta c                                               21

<210> SEQ ID NO 125
<211> LENGTH: 21
<212> TYPE: DNA
<213> ORGANISM: Homo sapiens

<400> SEQUENCE: 125
tccactcgga satcgtgaaa c                                              21

<210> SEQ ID NO 126
<211> LENGTH: 21
<212> TYPE: DNA
<213> ORGANISM: Homo sapiens

<400> SEQUENCE: 126
ggggctggcc rataccatcg t                                              21

<210> SEQ ID NO 127
<211> LENGTH: 21
<212> TYPE: DNA
<213> ORGANISM: Homo sapiens

<400> SEQUENCE: 127
ccatgttcga ygtgcatgtg a                                              21

<210> SEQ ID NO 128
<211> LENGTH: 21
<212> TYPE: DNA
```

<213> ORGANISM: Homo sapiens

<400> SEQUENCE: 128
aggtggacca rctgtaccgg a    21

<210> SEQ ID NO 129
<211> LENGTH: 21
<212> TYPE: DNA
<213> ORGANISM: Homo sapiens

<400> SEQUENCE: 129
cccccgacgg ygtgaagtgg c    21

<210> SEQ ID NO 130
<211> LENGTH: 21
<212> TYPE: DNA
<213> ORGANISM: Homo sapiens

<400> SEQUENCE: 130
gcagaggagc rgcagaggat c    21

<210> SEQ ID NO 131
<211> LENGTH: 21
<212> TYPE: DNA
<213> ORGANISM: Homo sapiens

<400> SEQUENCE: 131
atgacggacc ygtgtgtgaa g    21

<210> SEQ ID NO 132
<211> LENGTH: 21
<212> TYPE: DNA
<213> ORGANISM: Homo sapiens

<400> SEQUENCE: 132
ccatcaccat ygccaaccag a    21

<210> SEQ ID NO 133
<211> LENGTH: 21
<212> TYPE: DNA
<213> ORGANISM: Homo sapiens

<400> SEQUENCE: 133
acgtggggtc yctgttgctc a    21

<210> SEQ ID NO 134
<211> LENGTH: 21
<212> TYPE: DNA
<213> ORGANISM: Homo sapiens

<400> SEQUENCE: 134
tagaagaaag rtattgcatc g    21

<210> SEQ ID NO 135
<211> LENGTH: 21
<212> TYPE: DNA
<213> ORGANISM: Homo sapiens

<400> SEQUENCE: 135
atccaagagt ygcatgtcag c    21

<210> SEQ ID NO 136
<211> LENGTH: 21

```
<212> TYPE: DNA
<213> ORGANISM: Homo sapiens

<400> SEQUENCE: 136
cacagaagag wcgtggcccg g                                              21

<210> SEQ ID NO 137
<211> LENGTH: 21
<212> TYPE: DNA
<213> ORGANISM: Homo sapiens

<400> SEQUENCE: 137
caagtggctg scectggaga g                                              21

<210> SEQ ID NO 138
<211> LENGTH: 21
<212> TYPE: DNA
<213> ORGANISM: Homo sapiens

<400> SEQUENCE: 138
ttggcgggaa ycgcctgaaa c                                              21

<210> SEQ ID NO 139
<211> LENGTH: 21
<212> TYPE: DNA
<213> ORGANISM: Homo sapiens

<400> SEQUENCE: 139
agagcctggc ygacaacctg t                                              21

<210> SEQ ID NO 140
<211> LENGTH: 21
<212> TYPE: DNA
<213> ORGANISM: Homo sapiens

<400> SEQUENCE: 140
ctctgagtga rgatgacttt g                                              21

<210> SEQ ID NO 141
<211> LENGTH: 21
<212> TYPE: DNA
<213> ORGANISM: Homo sapiens

<400> SEQUENCE: 141
ttgagacctt yggcaacagc a                                              21

<210> SEQ ID NO 142
<211> LENGTH: 21
<212> TYPE: DNA
<213> ORGANISM: Homo sapiens

<400> SEQUENCE: 142
catgatctgc ytgttccaaa t                                              21

<210> SEQ ID NO 143
<211> LENGTH: 21
<212> TYPE: DNA
<213> ORGANISM: Homo sapiens

<400> SEQUENCE: 143
aggtttggga raagtttgat c                                              21

<210> SEQ ID NO 144
```

```
<211> LENGTH: 21
<212> TYPE: DNA
<213> ORGANISM: Homo sapiens

<400> SEQUENCE: 144
gcaacagcat satctgcctg t                                              21

<210> SEQ ID NO 145
<211> LENGTH: 21
<212> TYPE: DNA
<213> ORGANISM: Homo sapiens

<400> SEQUENCE: 145
gctcagttaa rggagactgt g                                              21

<210> SEQ ID NO 146
<211> LENGTH: 21
<212> TYPE: DNA
<213> ORGANISM: Homo sapiens

<400> SEQUENCE: 146
tgtacatcgc sgtcatcctg g                                              21

<210> SEQ ID NO 147
<211> LENGTH: 21
<212> TYPE: DNA
<213> ORGANISM: Homo sapiens

<400> SEQUENCE: 147
atcaccctgg magctcagtt a                                              21

<210> SEQ ID NO 148
<211> LENGTH: 21
<212> TYPE: DNA
<213> ORGANISM: Homo sapiens

<400> SEQUENCE: 148
atggctacac ragctttgac a                                              21

<210> SEQ ID NO 149
<211> LENGTH: 21
<212> TYPE: DNA
<213> ORGANISM: Homo sapiens

<400> SEQUENCE: 149
tctgtgtgaa kgctggtaga a                                              21

<210> SEQ ID NO 150
<211> LENGTH: 21
<212> TYPE: DNA
<213> ORGANISM: Homo sapiens

<400> SEQUENCE: 150
tcccagctgt raccctctgt a                                              21

<210> SEQ ID NO 151
<211> LENGTH: 21
<212> TYPE: DNA
<213> ORGANISM: Homo sapiens

<400> SEQUENCE: 151
tctgtaacct saatggcttc c                                              21
```

-continued

```
<210> SEQ ID NO 152
<211> LENGTH: 21
<212> TYPE: DNA
<213> ORGANISM: Homo sapiens

<400> SEQUENCE: 152
tcaccaccaa ygacctgtac c                                              21

<210> SEQ ID NO 153
<211> LENGTH: 21
<212> TYPE: DNA
<213> ORGANISM: Homo sapiens

<400> SEQUENCE: 153
ccccatctgg mtgacccctc c                                              21

<210> SEQ ID NO 154
<211> LENGTH: 21
<212> TYPE: DNA
<213> ORGANISM: Homo sapiens

<400> SEQUENCE: 154
ccctgcggca raaggccaac t                                              21

<210> SEQ ID NO 155
<211> LENGTH: 21
<212> TYPE: DNA
<213> ORGANISM: Homo sapiens

<400> SEQUENCE: 155
cagtcaaagc rgctaaggga g                                              21

<210> SEQ ID NO 156
<211> LENGTH: 21
<212> TYPE: DNA
<213> ORGANISM: Homo sapiens

<400> SEQUENCE: 156
caaaggaagc sttggcagtc a                                              21

<210> SEQ ID NO 157
<211> LENGTH: 21
<212> TYPE: DNA
<213> ORGANISM: Homo sapiens

<400> SEQUENCE: 157
ctcccatgga kactgctcag a                                              21

<210> SEQ ID NO 158
<211> LENGTH: 21
<212> TYPE: DNA
<213> ORGANISM: Homo sapiens

<400> SEQUENCE: 158
ggaacctgtt magatagagc t                                              21

<210> SEQ ID NO 159
<211> LENGTH: 21
<212> TYPE: DNA
<213> ORGANISM: Homo sapiens

<400> SEQUENCE: 159
atgacacctc ygactgtgcc a                                              21
```

```
<210> SEQ ID NO 160
<211> LENGTH: 21
<212> TYPE: DNA
<213> ORGANISM: Homo sapiens

<400> SEQUENCE: 160
aagccaagga rtggtgggcc t                                              21

<210> SEQ ID NO 161
<211> LENGTH: 21
<212> TYPE: DNA
<213> ORGANISM: Homo sapiens

<400> SEQUENCE: 161
agtccctgta yggctttcca g                                              21

<210> SEQ ID NO 162
<211> LENGTH: 21
<212> TYPE: DNA
<213> ORGANISM: Homo sapiens

<400> SEQUENCE: 162
agtcattttg yacataaacg a                                              21

<210> SEQ ID NO 163
<211> LENGTH: 21
<212> TYPE: DNA
<213> ORGANISM: Homo sapiens

<400> SEQUENCE: 163
gaggaataca rcccattcct c                                              21

<210> SEQ ID NO 164
<211> LENGTH: 21
<212> TYPE: DNA
<213> ORGANISM: Homo sapiens

<400> SEQUENCE: 164
ctgcctactc rctccagatc t                                              21

<210> SEQ ID NO 165
<211> LENGTH: 21
<212> TYPE: DNA
<213> ORGANISM: Homo sapiens

<400> SEQUENCE: 165
cgtcctctga ragctctgtc a                                              21

<210> SEQ ID NO 166
<211> LENGTH: 21
<212> TYPE: DNA
<213> ORGANISM: Homo sapiens

<400> SEQUENCE: 166
actttgccga ygccctgtct g                                              21

<210> SEQ ID NO 167
<211> LENGTH: 21
<212> TYPE: DNA
<213> ORGANISM: Homo sapiens

<400> SEQUENCE: 167
gagcccatca ycaccacact c                                              21
```

<210> SEQ ID NO 168
<211> LENGTH: 21
<212> TYPE: DNA
<213> ORGANISM: Homo sapiens

<400> SEQUENCE: 168
gcgttcactt wccttcggga c                                          21

<210> SEQ ID NO 169
<211> LENGTH: 21
<212> TYPE: DNA
<213> ORGANISM: Homo sapiens

<400> SEQUENCE: 169
ccacagtgaa katctcgccg a                                          21

<210> SEQ ID NO 170
<211> LENGTH: 21
<212> TYPE: DNA
<213> ORGANISM: Homo sapiens

<400> SEQUENCE: 170
ggcctggctg kccaggacac a                                          21

<210> SEQ ID NO 171
<211> LENGTH: 21
<212> TYPE: DNA
<213> ORGANISM: Homo sapiens

<400> SEQUENCE: 171
aatgggcctc rgcccgcgg a                                           21

<210> SEQ ID NO 172
<211> LENGTH: 21
<212> TYPE: DNA
<213> ORGANISM: Homo sapiens

<400> SEQUENCE: 172
ttggcaagag ytacaaggag t                                          21

<210> SEQ ID NO 173
<211> LENGTH: 21
<212> TYPE: DNA
<213> ORGANISM: Homo sapiens

<400> SEQUENCE: 173
tggtcatgtt yatctactcc a                                          21

<210> SEQ ID NO 174
<211> LENGTH: 21
<212> TYPE: DNA
<213> ORGANISM: Homo sapiens

<400> SEQUENCE: 174
tcaacatgta satcgccatc a                                          21

<210> SEQ ID NO 175
<211> LENGTH: 21
<212> TYPE: DNA
<213> ORGANISM: Homo sapiens

<400> SEQUENCE: 175

-continued gtcaagggtg rctgcggcaa c 21

<210> SEQ ID NO 176
<211> LENGTH: 21
<212> TYPE: DNA
<213> ORGANISM: Homo sapiens

<400> SEQUENCE: 176
gtacatcgcc rtcatcctgg a 21

<210> SEQ ID NO 177
<211> LENGTH: 21
<212> TYPE: DNA
<213> ORGANISM: Homo sapiens

<400> SEQUENCE: 177
gttcatctac kccatcttcg g 21

<210> SEQ ID NO 178
<211> LENGTH: 21
<212> TYPE: DNA
<213> ORGANISM: Homo sapiens

<400> SEQUENCE: 178
tggtgaagat kactttgaga t 21

<210> SEQ ID NO 179
<211> LENGTH: 21
<212> TYPE: DNA
<213> ORGANISM: Homo sapiens

<400> SEQUENCE: 179
ttctggctga ycttcagcat c 21

<210> SEQ ID NO 180
<211> LENGTH: 21
<212> TYPE: DNA
<213> ORGANISM: Homo sapiens

<400> SEQUENCE: 180
ggagacagac raccagagcc a 21

<210> SEQ ID NO 181
<211> LENGTH: 21
<212> TYPE: DNA
<213> ORGANISM: Homo sapiens

<400> SEQUENCE: 181
tctgcttctt mtgcagctat a 21

<210> SEQ ID NO 182
<211> LENGTH: 21
<212> TYPE: DNA
<213> ORGANISM: Homo sapiens

<400> SEQUENCE: 182
cagggcagac kgtgcgccca g 21

<210> SEQ ID NO 183
<211> LENGTH: 21
<212> TYPE: DNA
<213> ORGANISM: Homo sapiens

<400> SEQUENCE: 183

```
cagggggacgc yggacccact a                                          21

<210> SEQ ID NO 184
<211> LENGTH: 21
<212> TYPE: DNA
<213> ORGANISM: Homo sapiens

<400> SEQUENCE: 184
cgctgctgct rccactattg c                                           21

<210> SEQ ID NO 185
<211> LENGTH: 21
<212> TYPE: DNA
<213> ORGANISM: Homo sapiens

<400> SEQUENCE: 185
tctgcgcgcg yagcccgcca t                                           21

<210> SEQ ID NO 186
<211> LENGTH: 21
<212> TYPE: DNA
<213> ORGANISM: Homo sapiens

<400> SEQUENCE: 186
cagcatgtgg ycgccgtgga t                                           21

<210> SEQ ID NO 187
<211> LENGTH: 21
<212> TYPE: DNA
<213> ORGANISM: Homo sapiens

<400> SEQUENCE: 187
atgagcgaaa rgtgaatgcg t                                           21

<210> SEQ ID NO 188
<211> LENGTH: 21
<212> TYPE: DNA
<213> ORGANISM: Homo sapiens

<400> SEQUENCE: 188
ggttcctgag rgccaagatg g                                           21

<210> SEQ ID NO 189
<211> LENGTH: 21
<212> TYPE: DNA
<213> ORGANISM: Homo sapiens

<400> SEQUENCE: 189
gtgaggctgt rtcgggtctg c                                           21

<210> SEQ ID NO 190
<211> LENGTH: 21
<212> TYPE: DNA
<213> ORGANISM: Homo sapiens

<400> SEQUENCE: 190
ccaagaaatt saagaggaaa t                                           21

<210> SEQ ID NO 191
<211> LENGTH: 21
<212> TYPE: DNA
<213> ORGANISM: Homo sapiens
```

<400> SEQUENCE: 191
atcagcctgg kgatgctgag g                                              21

<210> SEQ ID NO 192
<211> LENGTH: 21
<212> TYPE: DNA
<213> ORGANISM: Homo sapiens

<400> SEQUENCE: 192
gccacgggat ygtggaggtt g                                              21

<210> SEQ ID NO 193
<211> LENGTH: 21
<212> TYPE: DNA
<213> ORGANISM: Homo sapiens

<400> SEQUENCE: 193
ctttggcacc rtcatctgca a                                              21

<210> SEQ ID NO 194
<211> LENGTH: 21
<212> TYPE: DNA
<213> ORGANISM: Homo sapiens

<400> SEQUENCE: 194
gggtgtctgt ragtgtgtcc a                                              21

<210> SEQ ID NO 195
<211> LENGTH: 21
<212> TYPE: DNA
<213> ORGANISM: Homo sapiens

<400> SEQUENCE: 195
ctgctgcttc wgctcttgtt c                                              21

<210> SEQ ID NO 196
<211> LENGTH: 21
<212> TYPE: DNA
<213> ORGANISM: Homo sapiens

<400> SEQUENCE: 196
aaacgctgtg yatcatctgg t                                              21

<210> SEQ ID NO 197
<211> LENGTH: 21
<212> TYPE: DNA
<213> ORGANISM: Homo sapiens

<400> SEQUENCE: 197
gtgcgcttct ycgcctgccc c                                              21

<210> SEQ ID NO 198
<211> LENGTH: 21
<212> TYPE: DNA
<213> ORGANISM: Homo sapiens

<400> SEQUENCE: 198
atttcatcac sctgggcacc g                                              21

<210> SEQ ID NO 199
<211> LENGTH: 21
<212> TYPE: DNA
<213> ORGANISM: Homo sapiens

<400> SEQUENCE: 199
tgtgcatcat ytggttctcc t                                          21

<210> SEQ ID NO 200
<211> LENGTH: 21
<212> TYPE: DNA
<213> ORGANISM: Homo sapiens

<400> SEQUENCE: 200
tgaacatcat wgacattgtg g                                          21

<210> SEQ ID NO 201
<211> LENGTH: 21
<212> TYPE: DNA
<213> ORGANISM: Homo sapiens

<400> SEQUENCE: 201
cacagtgacc yggctctttt t                                          21

<210> SEQ ID NO 202
<211> LENGTH: 21
<212> TYPE: DNA
<213> ORGANISM: Homo sapiens

<400> SEQUENCE: 202
ccctggagga ygggttctac g                                          21

<210> SEQ ID NO 203
<211> LENGTH: 21
<212> TYPE: DNA
<213> ORGANISM: Homo sapiens

<400> SEQUENCE: 203
ataaatgccc rgagggaatt a                                          21

<210> SEQ ID NO 204
<211> LENGTH: 21
<212> TYPE: DNA
<213> ORGANISM: Homo sapiens

<400> SEQUENCE: 204
ttccgggcaa ytcagaagaa a                                          21

<210> SEQ ID NO 205
<211> LENGTH: 21
<212> TYPE: DNA
<213> ORGANISM: Homo sapiens

<400> SEQUENCE: 205
cactgtgcca ygtgcccttta t                                         21

<210> SEQ ID NO 206
<211> LENGTH: 21
<212> TYPE: DNA
<213> ORGANISM: Homo sapiens

<400> SEQUENCE: 206
acctcttcga yacagcagaa g                                          21

<210> SEQ ID NO 207
<211> LENGTH: 21
<212> TYPE: DNA

```
<213> ORGANISM: Homo sapiens

<400> SEQUENCE: 207
acctggccga wgagatcctg t                                              21

<210> SEQ ID NO 208
<211> LENGTH: 21
<212> TYPE: DNA
<213> ORGANISM: Homo sapiens

<400> SEQUENCE: 208
cgttactctg kggactactc c                                              21

<210> SEQ ID NO 209
<211> LENGTH: 21
<212> TYPE: DNA
<213> ORGANISM: Homo sapiens

<400> SEQUENCE: 209
gcttggctgc rtcttcatga a                                              21

<210> SEQ ID NO 210
<211> LENGTH: 21
<212> TYPE: DNA
<213> ORGANISM: Homo sapiens

<400> SEQUENCE: 210
cggtgatcgc yctgcgccac g                                              21

<210> SEQ ID NO 211
<211> LENGTH: 21
<212> TYPE: DNA
<213> ORGANISM: Homo sapiens

<400> SEQUENCE: 211
ggaccctgcc ragcccaggt a                                              21

<210> SEQ ID NO 212
<211> LENGTH: 21
<212> TYPE: DNA
<213> ORGANISM: Homo sapiens

<400> SEQUENCE: 212
gtggctcatc rccttcgccc a                                              21

<210> SEQ ID NO 213
<211> LENGTH: 21
<212> TYPE: DNA
<213> ORGANISM: Homo sapiens

<400> SEQUENCE: 213
tggactactc rcgttttcac a                                              21

<210> SEQ ID NO 214
<211> LENGTH: 21
<212> TYPE: DNA
<213> ORGANISM: Homo sapiens

<400> SEQUENCE: 214
ggccaccgct wtgagcctgt g                                              21

<210> SEQ ID NO 215
<211> LENGTH: 21
```

```
<212> TYPE: DNA
<213> ORGANISM: Homo sapiens

<400> SEQUENCE: 215
ggccaccgct wtgagcctgt g                                              21

<210> SEQ ID NO 216
<211> LENGTH: 21
<212> TYPE: DNA
<213> ORGANISM: Homo sapiens

<400> SEQUENCE: 216
cgcgggtcac ygaggagggc g                                              21

<210> SEQ ID NO 217
<211> LENGTH: 21
<212> TYPE: DNA
<213> ORGANISM: Homo sapiens

<400> SEQUENCE: 217
ctggtgtcgc ycatcaccat c                                              21

<210> SEQ ID NO 218
<211> LENGTH: 21
<212> TYPE: DNA
<213> ORGANISM: Homo sapiens

<400> SEQUENCE: 218
tctccatcga sacgcagacc a                                              21

<210> SEQ ID NO 219
<211> LENGTH: 21
<212> TYPE: DNA
<213> ORGANISM: Homo sapiens

<400> SEQUENCE: 219
cactccccag maagactggg g                                              21

<210> SEQ ID NO 220
<211> LENGTH: 21
<212> TYPE: DNA
<213> ORGANISM: Homo sapiens

<400> SEQUENCE: 220
cccagcaaga stgggggcag c                                              21

<210> SEQ ID NO 221
<211> LENGTH: 21
<212> TYPE: DNA
<213> ORGANISM: Homo sapiens

<400> SEQUENCE: 221
gagtgtgcca mgcttttgga c                                              21

<210> SEQ ID NO 222
<211> LENGTH: 21
<212> TYPE: DNA
<213> ORGANISM: Homo sapiens

<400> SEQUENCE: 222
acaaccccca rctgcccac g                                               21

<210> SEQ ID NO 223
```

```
<211> LENGTH: 21
<212> TYPE: DNA
<213> ORGANISM: Homo sapiens

<400> SEQUENCE: 223
tcctgggcaa raccttgcag g                                              21

<210> SEQ ID NO 224
<211> LENGTH: 21
<212> TYPE: DNA
<213> ORGANISM: Homo sapiens

<400> SEQUENCE: 224
cgagctgctc rtgcgcttct t                                              21

<210> SEQ ID NO 225
<211> LENGTH: 21
<212> TYPE: DNA
<213> ORGANISM: Homo sapiens

<400> SEQUENCE: 225
ctctgggtcc rcgcgggcca t                                              21

<210> SEQ ID NO 226
<211> LENGTH: 21
<212> TYPE: DNA
<213> ORGANISM: Homo sapiens

<400> SEQUENCE: 226
gttatcctca yctccatcat c                                              21

<210> SEQ ID NO 227
<211> LENGTH: 21
<212> TYPE: DNA
<213> ORGANISM: Homo sapiens

<400> SEQUENCE: 227
caaccagcca rtggaggagg c                                              21

<210> SEQ ID NO 228
<211> LENGTH: 21
<212> TYPE: DNA
<213> ORGANISM: Homo sapiens

<400> SEQUENCE: 228
catcatctgg ytctccttcg a                                              21

<210> SEQ ID NO 229
<211> LENGTH: 21
<212> TYPE: DNA
<213> ORGANISM: Homo sapiens

<400> SEQUENCE: 229
gtgtattctg wggattactc c                                              21

<210> SEQ ID NO 230
<211> LENGTH: 21
<212> TYPE: DNA
<213> ORGANISM: Homo sapiens

<400> SEQUENCE: 230
ttctctactt yggcttgcgg t                                              21
```

```
<210> SEQ ID NO 231
<211> LENGTH: 21
<212> TYPE: DNA
<213> ORGANISM: Homo sapiens

<400> SEQUENCE: 231
gtggtctgca yctttggcga c                                              21

<210> SEQ ID NO 232
<211> LENGTH: 21
<212> TYPE: DNA
<213> ORGANISM: Homo sapiens

<400> SEQUENCE: 232
gatgatactt sgctgcagga c                                              21

<210> SEQ ID NO 233
<211> LENGTH: 21
<212> TYPE: DNA
<213> ORGANISM: Homo sapiens

<400> SEQUENCE: 233
tcgtggtctg yatctttggc g                                              21

<210> SEQ ID NO 234
<211> LENGTH: 21
<212> TYPE: DNA
<213> ORGANISM: Homo sapiens

<400> SEQUENCE: 234
cactcatgag ygcgacgtac t                                              21

<210> SEQ ID NO 235
<211> LENGTH: 21
<212> TYPE: DNA
<213> ORGANISM: Homo sapiens

<400> SEQUENCE: 235
ggatgtttca ytggtgtgca c                                              21

<210> SEQ ID NO 236
<211> LENGTH: 21
<212> TYPE: DNA
<213> ORGANISM: Homo sapiens

<400> SEQUENCE: 236
catcctgact ygaagtgaag c                                              21

<210> SEQ ID NO 237
<211> LENGTH: 21
<212> TYPE: DNA
<213> ORGANISM: Homo sapiens

<400> SEQUENCE: 237
ctggcaatga ycagattgac a                                              21

<210> SEQ ID NO 238
<211> LENGTH: 21
<212> TYPE: DNA
<213> ORGANISM: Homo sapiens

<400> SEQUENCE: 238 agttttttgga ycaagacgat g                                             21
```

<210> SEQ ID NO 239
<211> LENGTH: 21
<212> TYPE: DNA
<213> ORGANISM: Homo sapiens

<400> SEQUENCE: 239
tgcacgggat rttacgtcaa c                                         21

<210> SEQ ID NO 240
<211> LENGTH: 21
<212> TYPE: DNA
<213> ORGANISM: Homo sapiens

<400> SEQUENCE: 240
tgctggtaat wgatgcatct a                                         21

<210> SEQ ID NO 241
<211> LENGTH: 21
<212> TYPE: DNA
<213> ORGANISM: Homo sapiens

<400> SEQUENCE: 241
tctacctgca yacagtcatt c                                         21

<210> SEQ ID NO 242
<211> LENGTH: 21
<212> TYPE: DNA
<213> ORGANISM: Homo sapiens

<400> SEQUENCE: 242
caaaggtata yagatgacaa c                                         21

<210> SEQ ID NO 243
<211> LENGTH: 21
<212> TYPE: DNA
<213> ORGANISM: Homo sapiens

<400> SEQUENCE: 243
cctgaaaatg ragccacctt c                                         21

<210> SEQ ID NO 244
<211> LENGTH: 21
<212> TYPE: DNA
<213> ORGANISM: Homo sapiens

<400> SEQUENCE: 244
tgaacatcag rtggagctac t                                         21

<210> SEQ ID NO 245
<211> LENGTH: 21
<212> TYPE: DNA
<213> ORGANISM: Homo sapiens

<400> SEQUENCE: 245
actatgagaa ratagagaga a                                         21

<210> SEQ ID NO 246
<211> LENGTH: 21
<212> TYPE: DNA
<213> ORGANISM: Homo sapiens

<400> SEQUENCE: 246
ctgaagaggg ygggtactca t                                         21

<210> SEQ ID NO 247
<211> LENGTH: 21
<212> TYPE: DNA
<213> ORGANISM: Homo sapiens

<400> SEQUENCE: 247
agacaagcca rtaaaaacag a                                              21

<210> SEQ ID NO 248
<211> LENGTH: 21
<212> TYPE: DNA
<213> ORGANISM: Homo sapiens

<400> SEQUENCE: 248
caccacagca rctgtcatgg c                                              21

<210> SEQ ID NO 249
<211> LENGTH: 21
<212> TYPE: DNA
<213> ORGANISM: Homo sapiens

<400> SEQUENCE: 249
gcccaatgag rttaaagtct c                                              21

<210> SEQ ID NO 250
<211> LENGTH: 21
<212> TYPE: DNA
<213> ORGANISM: Homo sapiens

<400> SEQUENCE: 250
gattttcacc ratcaagaga t                                              21

<210> SEQ ID NO 251
<211> LENGTH: 21
<212> TYPE: DNA
<213> ORGANISM: Homo sapiens

<400> SEQUENCE: 251
atcaagagat ygggggagtta c                                             21

<210> SEQ ID NO 252
<211> LENGTH: 21
<212> TYPE: DNA
<213> ORGANISM: Homo sapiens

<400> SEQUENCE: 252
tacttccaca yactgttacg a                                              21

<210> SEQ ID NO 253
<211> LENGTH: 21
<212> TYPE: DNA
<213> ORGANISM: Homo sapiens

<400> SEQUENCE: 253
tcactctcca stacctaaac a                                              21

<210> SEQ ID NO 254
<211> LENGTH: 21
<212> TYPE: DNA
<213> ORGANISM: Homo sapiens

<400> SEQUENCE: 254
aggtaatggt raaaaaagac a 21

<210> SEQ ID NO 255
<211> LENGTH: 21
<212> TYPE: DNA
<213> ORGANISM: Homo sapiens

<400> SEQUENCE: 255
gtcctgccga ktcccctgat g 21

<210> SEQ ID NO 256
<211> LENGTH: 21
<212> TYPE: DNA
<213> ORGANISM: Homo sapiens

<400> SEQUENCE: 256
cccctgatga rggaatcact a 21

<210> SEQ ID NO 257
<211> LENGTH: 21
<212> TYPE: DNA
<213> ORGANISM: Homo sapiens

<400> SEQUENCE: 257
agatgccact ratggcaagg a 21

<210> SEQ ID NO 258
<211> LENGTH: 21
<212> TYPE: DNA
<213> ORGANISM: Homo sapiens

<400> SEQUENCE: 258
caccgctcaa yggattttct g 21

<210> SEQ ID NO 259
<211> LENGTH: 21
<212> TYPE: DNA
<213> ORGANISM: Homo sapiens

<400> SEQUENCE: 259
ttccagagcc wacaacagat g 21

<210> SEQ ID NO 260
<211> LENGTH: 21
<212> TYPE: DNA
<213> ORGANISM: Homo sapiens

<400> SEQUENCE: 260
gcggcctcgt sctcaccagc a 21

<210> SEQ ID NO 261
<211> LENGTH: 21
<212> TYPE: DNA
<213> ORGANISM: Homo sapiens

<400> SEQUENCE: 261
tgtgggcgcc ktggtcgcct t 21

<210> SEQ ID NO 262
<211> LENGTH: 21
<212> TYPE: DNA
<213> ORGANISM: Homo sapiens

<400> SEQUENCE: 262
gccgtgtcac ycgaggatga t                                           21

<210> SEQ ID NO 263
<211> LENGTH: 21
<212> TYPE: DNA
<213> ORGANISM: Homo sapiens

<400> SEQUENCE: 263
aattccgatc kgatcctcag g                                           21

<210> SEQ ID NO 264
<211> LENGTH: 21
<212> TYPE: DNA
<213> ORGANISM: Homo sapiens

<400> SEQUENCE: 264
caagcttatc ragaccctct c                                           21

<210> SEQ ID NO 265
<211> LENGTH: 21
<212> TYPE: DNA
<213> ORGANISM: Homo sapiens

<400> SEQUENCE: 265
gcagatcact sttggcctcg t                                           21

<210> SEQ ID NO 266
<211> LENGTH: 21
<212> TYPE: DNA
<213> ORGANISM: Homo sapiens

<400> SEQUENCE: 266
tcttggcctc rtcttcctct g                                           21

<210> SEQ ID NO 267
<211> LENGTH: 21
<212> TYPE: DNA
<213> ORGANISM: Homo sapiens

<400> SEQUENCE: 267
tagagatagc ygcttacaga a                                           21

<210> SEQ ID NO 268
<211> LENGTH: 21
<212> TYPE: DNA
<213> ORGANISM: Homo sapiens

<400> SEQUENCE: 268
cagctgcaac yctaactatt c                                           21

<210> SEQ ID NO 269
<211> LENGTH: 21
<212> TYPE: DNA
<213> ORGANISM: Homo sapiens

<400> SEQUENCE: 269
gagcgaagca ygtgatcatg c                                           21

<210> SEQ ID NO 270
<211> LENGTH: 21
<212> TYPE: DNA
<213> ORGANISM: Homo sapiens -continued

```
<400> SEQUENCE: 270
atggagagaa yactgcccag t                                              21

<210> SEQ ID NO 271
<211> LENGTH: 21
<212> TYPE: DNA
<213> ORGANISM: Homo sapiens

<400> SEQUENCE: 271
taatgtcggc ygagagcccc a                                              21

<210> SEQ ID NO 272
<211> LENGTH: 21
<212> TYPE: DNA
<213> ORGANISM: Homo sapiens

<400> SEQUENCE: 272
gaccctgacc rctatgtctg t                                              21

<210> SEQ ID NO 273
<211> LENGTH: 21
<212> TYPE: DNA
<213> ORGANISM: Homo sapiens

<400> SEQUENCE: 273
acttctcacc rggagatttg g                                              21

<210> SEQ ID NO 274
<211> LENGTH: 21
<212> TYPE: DNA
<213> ORGANISM: Homo sapiens

<400> SEQUENCE: 274
aacgtgcaga ygaagcctta a                                              21

<210> SEQ ID NO 275
<211> LENGTH: 21
<212> TYPE: DNA
<213> ORGANISM: Homo sapiens

<400> SEQUENCE: 275
cccacgttag yggaggtggt g                                              21

<210> SEQ ID NO 276
<211> LENGTH: 21
<212> TYPE: DNA
<213> ORGANISM: Homo sapiens

<400> SEQUENCE: 276
cattgttcga ratttaggac t                                              21

<210> SEQ ID NO 277
<211> LENGTH: 21
<212> TYPE: DNA
<213> ORGANISM: Homo sapiens

<400> SEQUENCE: 277
gacagcaggg ytataatgta t                                              21

<210> SEQ ID NO 278
<211> LENGTH: 21
<212> TYPE: DNA
<213> ORGANISM: Homo sapiens
```

```
<400> SEQUENCE: 278
aagagtcaga wccacccaga c                                              21

<210> SEQ ID NO 279
<211> LENGTH: 21
<212> TYPE: DNA
<213> ORGANISM: Homo sapiens

<400> SEQUENCE: 279 cagtaattt yctcatcttg t                                               21

<210> SEQ ID NO 280
<211> LENGTH: 21
<212> TYPE: DNA
<213> ORGANISM: Homo sapiens

<400> SEQUENCE: 280
taatgaatga mattgcagat a                                              21

<210> SEQ ID NO 281
<211> LENGTH: 21
<212> TYPE: DNA
<213> ORGANISM: Homo sapiens

<400> SEQUENCE: 281
caatggaaga kgttcttgaa c                                              21

<210> SEQ ID NO 282
<211> LENGTH: 21
<212> TYPE: DNA
<213> ORGANISM: Homo sapiens

<400> SEQUENCE: 282
cacttatacc ycttgtgtat g                                              21

<210> SEQ ID NO 283
<211> LENGTH: 21
<212> TYPE: DNA
<213> ORGANISM: Homo sapiens

<400> SEQUENCE: 283
attcttggat ycagctattt g                                              21

<210> SEQ ID NO 284
<211> LENGTH: 21
<212> TYPE: DNA
<213> ORGANISM: Homo sapiens

<400> SEQUENCE: 284
gactttggca stgaccacca g                                              21

<210> SEQ ID NO 285
<211> LENGTH: 21
<212> TYPE: DNA
<213> ORGANISM: Homo sapiens

<400> SEQUENCE: 285
actactgctc rgaccaatac t                                              21

<210> SEQ ID NO 286
<211> LENGTH: 21
<212> TYPE: DNA
```

```
<213> ORGANISM: Homo sapiens

<400> SEQUENCE: 286
ttgaaggtgt yttcagaaga t                                              21

<210> SEQ ID NO 287
<211> LENGTH: 21
<212> TYPE: DNA
<213> ORGANISM: Homo sapiens

<400> SEQUENCE: 287
ccaaacacct ygtagaactc t                                              21

<210> SEQ ID NO 288
<211> LENGTH: 21
<212> TYPE: DNA
<213> ORGANISM: Homo sapiens

<400> SEQUENCE: 288
ttcaggagcc yatcatggct c                                              21

<210> SEQ ID NO 289
<211> LENGTH: 21
<212> TYPE: DNA
<213> ORGANISM: Homo sapiens

<400> SEQUENCE: 289
tatatattaa ktggcagaaa c                                              21

<210> SEQ ID NO 290
<211> LENGTH: 21
<212> TYPE: DNA
<213> ORGANISM: Homo sapiens

<400> SEQUENCE: 290
cattcagatt scaaacaagg a                                              21

<210> SEQ ID NO 291
<211> LENGTH: 21
<212> TYPE: DNA
<213> ORGANISM: Homo sapiens

<400> SEQUENCE: 291
ttccacatct rgtgattaga a                                              21

<210> SEQ ID NO 292
<211> LENGTH: 21
<212> TYPE: DNA
<213> ORGANISM: Homo sapiens

<400> SEQUENCE: 292
gagaaatatg magtcttcat g                                              21

<210> SEQ ID NO 293
<211> LENGTH: 21
<212> TYPE: DNA
<213> ORGANISM: Homo sapiens

<400> SEQUENCE: 293
aggagaaaag ytttaaaaaa t                                              21

<210> SEQ ID NO 294
<211> LENGTH: 21
```

<212> TYPE: DNA
<213> ORGANISM: Homo sapiens

<400> SEQUENCE: 294
ttcaaaatga rtggttacat a                                              21

<210> SEQ ID NO 295
<211> LENGTH: 21
<212> TYPE: DNA
<213> ORGANISM: Homo sapiens

<400> SEQUENCE: 295
cctgtgcact ycggtggtca c                                              21

<210> SEQ ID NO 296
<211> LENGTH: 21
<212> TYPE: DNA
<213> ORGANISM: Homo sapiens

<400> SEQUENCE: 296
ttgccaagaa rtccaagaac c                                              21

<210> SEQ ID NO 297
<211> LENGTH: 21
<212> TYPE: DNA
<213> ORGANISM: Homo sapiens

<400> SEQUENCE: 297
atgatccatg sgtagaacat g                                              21

<210> SEQ ID NO 298
<211> LENGTH: 21
<212> TYPE: DNA
<213> ORGANISM: Homo sapiens

<400> SEQUENCE: 298
ccaccagacc wgacgagggg c                                              21

<210> SEQ ID NO 299
<211> LENGTH: 21
<212> TYPE: DNA
<213> ORGANISM: Homo sapiens

<400> SEQUENCE: 299
tttgcaattc sttcaaggga g                                              21

<210> SEQ ID NO 300
<211> LENGTH: 21
<212> TYPE: DNA
<213> ORGANISM: Homo sapiens

<400> SEQUENCE: 300
ggcaggagtg yggagagcct g                                              21

<210> SEQ ID NO 301
<211> LENGTH: 21
<212> TYPE: DNA
<213> ORGANISM: Homo sapiens

<400> SEQUENCE: 301
tgcagcccac rgcagagaat g                                              21

<210> SEQ ID NO 302

```
<211> LENGTH: 21
<212> TYPE: DNA
<213> ORGANISM: Homo sapiens

<400> SEQUENCE: 302
ggtgtcaact sttagccacg c                                              21

<210> SEQ ID NO 303
<211> LENGTH: 21
<212> TYPE: DNA
<213> ORGANISM: Homo sapiens

<400> SEQUENCE: 303
acgcagatgc ygattgcttt g                                              21

<210> SEQ ID NO 304
<211> LENGTH: 21
<212> TYPE: DNA
<213> ORGANISM: Homo sapiens

<400> SEQUENCE: 304
actttattaa yggttcttac t                                              21

<210> SEQ ID NO 305
<211> LENGTH: 21
<212> TYPE: DNA
<213> ORGANISM: Homo sapiens

<400> SEQUENCE: 305
ttgcgtatgc ygataatagc c                                              21

<210> SEQ ID NO 306
<211> LENGTH: 21
<212> TYPE: DNA
<213> ORGANISM: Homo sapiens

<400> SEQUENCE: 306
attctgatga yggctgttta a                                              21

<210> SEQ ID NO 307
<211> LENGTH: 21
<212> TYPE: DNA
<213> ORGANISM: Homo sapiens

<400> SEQUENCE: 307
atttatgtgg watgctctca c                                              21

<210> SEQ ID NO 308
<211> LENGTH: 21
<212> TYPE: DNA
<213> ORGANISM: Homo sapiens

<400> SEQUENCE: 308
tcattcatta ycatggtgta g                                              21

<210> SEQ ID NO 309
<211> LENGTH: 21
<212> TYPE: DNA
<213> ORGANISM: Homo sapiens

<400> SEQUENCE: 309
cagcttttta ygactcactg a                                              21
```

```
<210> SEQ ID NO 310
<211> LENGTH: 21
<212> TYPE: DNA
<213> ORGANISM: Homo sapiens

<400> SEQUENCE: 310
atcctgttat ygagatgtta g                                              21

<210> SEQ ID NO 311
<211> LENGTH: 21
<212> TYPE: DNA
<213> ORGANISM: Homo sapiens

<400> SEQUENCE: 311
atttaatgga rgatccagac a                                              21

<210> SEQ ID NO 312
<211> LENGTH: 21
<212> TYPE: DNA
<213> ORGANISM: Homo sapiens

<400> SEQUENCE: 312
aaaatataac rgaatgcagg a                                              21

<210> SEQ ID NO 313
<211> LENGTH: 21
<212> TYPE: DNA
<213> ORGANISM: Homo sapiens

<400> SEQUENCE: 313
gaaataaagc mcaaactgta c                                              21

<210> SEQ ID NO 314
<211> LENGTH: 21
<212> TYPE: DNA
<213> ORGANISM: Homo sapiens

<400> SEQUENCE: 314
tatgtattac ygaaaaagcc t                                              21

<210> SEQ ID NO 315
<211> LENGTH: 21
<212> TYPE: DNA
<213> ORGANISM: Homo sapiens

<400> SEQUENCE: 315
ggatgaggat rtgaagctga t                                              21

<210> SEQ ID NO 316
<211> LENGTH: 21
<212> TYPE: DNA
<213> ORGANISM: Homo sapiens

<400> SEQUENCE: 316
atgaggagga ygagcagctg a                                              21

<210> SEQ ID NO 317
<211> LENGTH: 21
<212> TYPE: DNA
<213> ORGANISM: Homo sapiens

<400> SEQUENCE: 317
cactgagaat rgcaccagtc t                                              21
```

<210> SEQ ID NO 318
<211> LENGTH: 21
<212> TYPE: DNA
<213> ORGANISM: Homo sapiens

<400> SEQUENCE: 318
tggagatgag raaatgggtc c                                              21

<210> SEQ ID NO 319
<211> LENGTH: 21
<212> TYPE: DNA
<213> ORGANISM: Homo sapiens

<400> SEQUENCE: 319
tgaccatcaa yaaggaagat g                                              21

<210> SEQ ID NO 320
<211> LENGTH: 21
<212> TYPE: DNA
<213> ORGANISM: Homo sapiens

<400> SEQUENCE: 320
ataacaagga ygtgtcggtg a                                              21

<210> SEQ ID NO 321
<211> LENGTH: 21
<212> TYPE: DNA
<213> ORGANISM: Homo sapiens

<400> SEQUENCE: 321
cagatcaaga rtgacatcca g                                              21

<210> SEQ ID NO 322
<211> LENGTH: 21
<212> TYPE: DNA
<213> ORGANISM: Homo sapiens

<400> SEQUENCE: 322
atccctgccc yggacagcaa g                                              21

<210> SEQ ID NO 323
<211> LENGTH: 21
<212> TYPE: DNA
<213> ORGANISM: Homo sapiens

<400> SEQUENCE: 323
attgataatg raagctggcc a                                              21

<210> SEQ ID NO 324
<211> LENGTH: 21
<212> TYPE: DNA
<213> ORGANISM: Homo sapiens

<400> SEQUENCE: 324
agtttagaaa rccaagctac a                                              21

<210> SEQ ID NO 325
<211> LENGTH: 21
<212> TYPE: DNA
<213> ORGANISM: Homo sapiens

<400> SEQUENCE: 325
aaatgtagca matcagaagc c                                              21

<210> SEQ ID NO 326
<211> LENGTH: 21
<212> TYPE: DNA
<213> ORGANISM: Homo sapiens

<400> SEQUENCE: 326
cttataatca rctggcttca a                                            21

<210> SEQ ID NO 327
<211> LENGTH: 21
<212> TYPE: DNA
<213> ORGANISM: Homo sapiens

<400> SEQUENCE: 327
accatggttt yatatggaga c                                            21

<210> SEQ ID NO 328
<211> LENGTH: 21
<212> TYPE: DNA
<213> ORGANISM: Homo sapiens

<400> SEQUENCE: 328
gaaaaaaata wtgattacat g                                            21

<210> SEQ ID NO 329
<211> LENGTH: 21
<212> TYPE: DNA
<213> ORGANISM: Homo sapiens

<400> SEQUENCE: 329
agcatgtgag mccattgaga t                                            21

<210> SEQ ID NO 330
<211> LENGTH: 21
<212> TYPE: DNA
<213> ORGANISM: Homo sapiens

<400> SEQUENCE: 330
atgattctgt ygtttcaatg t                                            21

<210> SEQ ID NO 331
<211> LENGTH: 21
<212> TYPE: DNA
<213> ORGANISM: Homo sapiens

<400> SEQUENCE: 331
agtcagtgtg sagcatttga a                                            21

<210> SEQ ID NO 332
<211> LENGTH: 21
<212> TYPE: DNA
<213> ORGANISM: Homo sapiens

<400> SEQUENCE: 332
catctcaaga sgagctcatt a                                            21

<210> SEQ ID NO 333
<211> LENGTH: 21
<212> TYPE: DNA
<213> ORGANISM: Homo sapiens

<400> SEQUENCE: 333
tctcctgaac rtctaaaaga t                                           21

<210> SEQ ID NO 334
<211> LENGTH: 21
<212> TYPE: DNA
<213> ORGANISM: Homo sapiens

<400> SEQUENCE: 334
agcgtccaga raggagagct t                                           21

<210> SEQ ID NO 335
<211> LENGTH: 21
<212> TYPE: DNA
<213> ORGANISM: Homo sapiens

<400> SEQUENCE: 335
tatgggaagt rgtcatgcat c                                           21

<210> SEQ ID NO 336
<211> LENGTH: 21
<212> TYPE: DNA
<213> ORGANISM: Homo sapiens

<400> SEQUENCE: 336
atctgcccag rgtccagctg c                                           21

<210> SEQ ID NO 337
<211> LENGTH: 21
<212> TYPE: DNA
<213> ORGANISM: Homo sapiens

<400> SEQUENCE: 337
agtacaacca ratgccagtc a                                           21

<210> SEQ ID NO 338
<211> LENGTH: 21
<212> TYPE: DNA
<213> ORGANISM: Homo sapiens

<400> SEQUENCE: 338
tctccacaaa rtgtgaccac a                                           21

<210> SEQ ID NO 339
<211> LENGTH: 21
<212> TYPE: DNA
<213> ORGANISM: Homo sapiens

<400> SEQUENCE: 339
tccaggtccg yggcctggag a                                           21

<210> SEQ ID NO 340
<211> LENGTH: 21
<212> TYPE: DNA
<213> ORGANISM: Homo sapiens

<400> SEQUENCE: 340
tacaacacca rtaacggggc t                                           21

<210> SEQ ID NO 341
<211> LENGTH: 21
<212> TYPE: DNA
<213> ORGANISM: Homo sapiens

<400> SEQUENCE: 341
gcaatttgga yatctccaac a        21

<210> SEQ ID NO 342
<211> LENGTH: 21
<212> TYPE: DNA
<213> ORGANISM: Homo sapiens

<400> SEQUENCE: 342
tgaaatttct yagtgagaac a        21

<210> SEQ ID NO 343
<211> LENGTH: 21
<212> TYPE: DNA
<213> ORGANISM: Homo sapiens

<400> SEQUENCE: 343
ttcaccacac ytaaggagaa c        21

<210> SEQ ID NO 344
<211> LENGTH: 21
<212> TYPE: DNA
<213> ORGANISM: Homo sapiens

<400> SEQUENCE: 344
tttcttccct satcctgatc t        21

<210> SEQ ID NO 345
<211> LENGTH: 21
<212> TYPE: DNA
<213> ORGANISM: Homo sapiens

<400> SEQUENCE: 345
cagcaatgac mttcccatcg c        21

<210> SEQ ID NO 346
<211> LENGTH: 21
<212> TYPE: DNA
<213> ORGANISM: Homo sapiens

<400> SEQUENCE: 346
cagctgagaa ygctgccaag g        21

<210> SEQ ID NO 347
<211> LENGTH: 21
<212> TYPE: DNA
<213> ORGANISM: Homo sapiens

<400> SEQUENCE: 347
tgtccctagc ygaactcagg a        21

<210> SEQ ID NO 348
<211> LENGTH: 21
<212> TYPE: DNA
<213> ORGANISM: Homo sapiens

<400> SEQUENCE: 348
agcgaacgac rcttcgctat g        21

<210> SEQ ID NO 349
<211> LENGTH: 21
<212> TYPE: DNA
<213> ORGANISM: Homo sapiens -continued

```
<400> SEQUENCE: 349
aaagcaatgc ygagaggatg a                                              21

<210> SEQ ID NO 350
<211> LENGTH: 21
<212> TYPE: DNA
<213> ORGANISM: Homo sapiens

<400> SEQUENCE: 350
ttcgtgaatg rtctaaagcg g                                              21

<210> SEQ ID NO 351
<211> LENGTH: 21
<212> TYPE: DNA
<213> ORGANISM: Homo sapiens

<400> SEQUENCE: 351
agtgtgaccc rgactgcctc c                                              21

<210> SEQ ID NO 352
<211> LENGTH: 21
<212> TYPE: DNA
<213> ORGANISM: Homo sapiens

<400> SEQUENCE: 352
catgccaatt rcatcgttca c                                              21

<210> SEQ ID NO 353
<211> LENGTH: 21
<212> TYPE: DNA
<213> ORGANISM: Homo sapiens

<400> SEQUENCE: 353
ctgaagccga ycagttgggc a                                              21

<210> SEQ ID NO 354
<211> LENGTH: 21
<212> TYPE: DNA
<213> ORGANISM: Homo sapiens

<400> SEQUENCE: 354
tatgcaacac ytgtggacat g                                              21

<210> SEQ ID NO 355
<211> LENGTH: 21
<212> TYPE: DNA
<213> ORGANISM: Homo sapiens

<400> SEQUENCE: 355
ttctggtgac ragtggtgga a                                              21

<210> SEQ ID NO 356
<211> LENGTH: 21
<212> TYPE: DNA
<213> ORGANISM: Homo sapiens

<400> SEQUENCE: 356
tgattgggct rcctccagag g                                              21

<210> SEQ ID NO 357
<211> LENGTH: 21
<212> TYPE: DNA
<213> ORGANISM: Homo sapiens
```

<400> SEQUENCE: 357
ctcttatcta yataaggatg a                                              21

<210> SEQ ID NO 358
<211> LENGTH: 21
<212> TYPE: DNA
<213> ORGANISM: Homo sapiens

<400> SEQUENCE: 358
cagacctcag ygcctctctg g                                              21

<210> SEQ ID NO 359
<211> LENGTH: 21
<212> TYPE: DNA
<213> ORGANISM: Homo sapiens

<400> SEQUENCE: 359
gtgagtgatg maggtttgaa g                                              21

<210> SEQ ID NO 360
<211> LENGTH: 21
<212> TYPE: DNA
<213> ORGANISM: Homo sapiens

<400> SEQUENCE: 360
aaggtttgaa rggcaagatt a                                              21

<210> SEQ ID NO 361
<211> LENGTH: 21
<212> TYPE: DNA
<213> ORGANISM: Homo sapiens

<400> SEQUENCE: 361
gtcacagcca yggacaagag c                                              21

<210> SEQ ID NO 362
<211> LENGTH: 21
<212> TYPE: DNA
<213> ORGANISM: Homo sapiens

<400> SEQUENCE: 362
tgacgtttga yattgatgcc a                                              21

<210> SEQ ID NO 363
<211> LENGTH: 21
<212> TYPE: DNA
<213> ORGANISM: Homo sapiens

<400> SEQUENCE: 363
tgaccgtgga ygagggtgtc c                                              21

<210> SEQ ID NO 364
<211> LENGTH: 21
<212> TYPE: DNA
<213> ORGANISM: Homo sapiens

<400> SEQUENCE: 364
cccactgccg mttctatgag g                                              21

<210> SEQ ID NO 365
<211> LENGTH: 21
<212> TYPE: DNA

<213> ORGANISM: Homo sapiens

<400> SEQUENCE: 365
tcatctcccg mtttgagggc t                                              21

<210> SEQ ID NO 366
<211> LENGTH: 21
<212> TYPE: DNA
<213> ORGANISM: Homo sapiens

<400> SEQUENCE: 366
acctgtgttc wcaaagatgg c                                              21

<210> SEQ ID NO 367
<211> LENGTH: 21
<212> TYPE: DNA
<213> ORGANISM: Homo sapiens

<400> SEQUENCE: 367
actcaagcta ygaggaaaag a                                              21

<210> SEQ ID NO 368
<211> LENGTH: 21
<212> TYPE: DNA
<213> ORGANISM: Homo sapiens

<400> SEQUENCE: 368
ggggtactgg racatccgcg g                                              21

<210> SEQ ID NO 369
<211> LENGTH: 21
<212> TYPE: DNA
<213> ORGANISM: Homo sapiens

<400> SEQUENCE: 369
gattgatggg rctcacaaga t                                              21

<210> SEQ ID NO 370
<211> LENGTH: 21
<212> TYPE: DNA
<213> ORGANISM: Homo sapiens

<400> SEQUENCE: 370
cccagagcaa ygccatcctg c                                              21

<210> SEQ ID NO 371
<211> LENGTH: 21
<212> TYPE: DNA
<213> ORGANISM: Homo sapiens

<400> SEQUENCE: 371
gtatatttga scccaagtgc c                                              21

<210> SEQ ID NO 372
<211> LENGTH: 21
<212> TYPE: DNA
<213> ORGANISM: Homo sapiens

<400> SEQUENCE: 372
caacaagcct rtatgctgag c                                              21

<210> SEQ ID NO 373
<211> LENGTH: 21

```
<212> TYPE: DNA
<213> ORGANISM: Homo sapiens

<400> SEQUENCE: 373
ggctttcatg kgccgttttg a                                              21

<210> SEQ ID NO 374
<211> LENGTH: 21
<212> TYPE: DNA
<213> ORGANISM: Homo sapiens

<400> SEQUENCE: 374
cagagcaatg mcatcttgcg c                                              21

<210> SEQ ID NO 375
<211> LENGTH: 21
<212> TYPE: DNA
<213> ORGANISM: Homo sapiens

<400> SEQUENCE: 375
tggacgcctt yccaaatctg a                                              21

<210> SEQ ID NO 376
<211> LENGTH: 21
<212> TYPE: DNA
<213> ORGANISM: Homo sapiens

<400> SEQUENCE: 376
tggggctgga racggccgga g                                              21

<210> SEQ ID NO 377
<211> LENGTH: 21
<212> TYPE: DNA
<213> ORGANISM: Homo sapiens

<400> SEQUENCE: 377
ggccggggac rcccacctgg g                                              21

<210> SEQ ID NO 378
<211> LENGTH: 21
<212> TYPE: DNA
<213> ORGANISM: Homo sapiens

<400> SEQUENCE: 378
tcagcgaggc sgacaagaag a                                              21

<210> SEQ ID NO 379
<211> LENGTH: 21
<212> TYPE: DNA
<213> ORGANISM: Homo sapiens

<400> SEQUENCE: 379 acaagggga saccaaggca t                                               21

<210> SEQ ID NO 380
<211> LENGTH: 21
<212> TYPE: DNA
<213> ORGANISM: Homo sapiens

<400> SEQUENCE: 380
agctgctgca rgacttcttc a                                              21

<210> SEQ ID NO 381
```

<210> SEQ ID NO 381
<211> LENGTH: 21
<212> TYPE: DNA
<213> ORGANISM: Homo sapiens

<400> SEQUENCE: 381
attcctccga rgtcttttgt t                                              21

<210> SEQ ID NO 382
<211> LENGTH: 21
<212> TYPE: DNA
<213> ORGANISM: Homo sapiens

<400> SEQUENCE: 382
gacgccttcc yaaacttgaa g                                              21

<210> SEQ ID NO 383
<211> LENGTH: 21
<212> TYPE: DNA
<213> ORGANISM: Homo sapiens

<400> SEQUENCE: 383
ttggaaagtc rgctacatgg a                                              21

<210> SEQ ID NO 384
<211> LENGTH: 21
<212> TYPE: DNA
<213> ORGANISM: Homo sapiens

<400> SEQUENCE: 384
ctctcggcta ygaactgttt g                                              21

<210> SEQ ID NO 385
<211> LENGTH: 21
<212> TYPE: DNA
<213> ORGANISM: Homo sapiens

<400> SEQUENCE: 385
ggactgccat rgaccaggcc c                                              21

<210> SEQ ID NO 386
<211> LENGTH: 21
<212> TYPE: DNA
<213> ORGANISM: Homo sapiens

<400> SEQUENCE: 386
caggtgttgg rgccactcat t                                              21

<210> SEQ ID NO 387
<211> LENGTH: 21
<212> TYPE: DNA
<213> ORGANISM: Homo sapiens

<400> SEQUENCE: 387
tgttggggcc mctcattggg g                                              21

<210> SEQ ID NO 388
<211> LENGTH: 21
<212> TYPE: DNA
<213> ORGANISM: Homo sapiens

<400> SEQUENCE: 388
ccaggtgccc raggagaagg t                                              21

-continued

```
<210> SEQ ID NO 389
<211> LENGTH: 21
<212> TYPE: DNA
<213> ORGANISM: Homo sapiens

<400> SEQUENCE: 389
ccgcgttgac yctctggaga c                                              21

<210> SEQ ID NO 390
<211> LENGTH: 21
<212> TYPE: DNA
<213> ORGANISM: Homo sapiens

<400> SEQUENCE: 390
tggaccacta yaagaagggg a                                              21

<210> SEQ ID NO 391
<211> LENGTH: 21
<212> TYPE: DNA
<213> ORGANISM: Homo sapiens

<400> SEQUENCE: 391
tcatcgtggt ygccctgtat g                                              21

<210> SEQ ID NO 392
<211> LENGTH: 21
<212> TYPE: DNA
<213> ORGANISM: Homo sapiens

<400> SEQUENCE: 392
ccattcacca ygaagacctc a                                              21

<210> SEQ ID NO 393
<211> LENGTH: 21
<212> TYPE: DNA
<213> ORGANISM: Homo sapiens

<400> SEQUENCE: 393
ccctggccac scggaaggag g                                              21

<210> SEQ ID NO 394
<211> LENGTH: 21
<212> TYPE: DNA
<213> ORGANISM: Homo sapiens

<400> SEQUENCE: 394
ccagcgccag yccacactgt c                                              21

<210> SEQ ID NO 395
<211> LENGTH: 21
<212> TYPE: DNA
<213> ORGANISM: Homo sapiens

<400> SEQUENCE: 395
ccacgaagac ytcagcttcc a                                              21

<210> SEQ ID NO 396
<211> LENGTH: 21
<212> TYPE: DNA
<213> ORGANISM: Homo sapiens

<400> SEQUENCE: 396
gtgaattaag rgaaataatg a                                              21
```

<210> SEQ ID NO 397
<211> LENGTH: 21
<212> TYPE: DNA
<213> ORGANISM: Homo sapiens

<400> SEQUENCE: 397
gactgtgtga wttccctgat a                                              21

<210> SEQ ID NO 398
<211> LENGTH: 21
<212> TYPE: DNA
<213> ORGANISM: Homo sapiens

<400> SEQUENCE: 398
agatatggat yaggtggaaa a                                              21

<210> SEQ ID NO 399
<211> LENGTH: 21
<212> TYPE: DNA
<213> ORGANISM: Homo sapiens

<400> SEQUENCE: 399
gacagtttga wctgactact t                                              21

<210> SEQ ID NO 400
<211> LENGTH: 21
<212> TYPE: DNA
<213> ORGANISM: Homo sapiens

<400> SEQUENCE: 400
tcagctagat rctgttgtca g                                              21

<210> SEQ ID NO 401
<211> LENGTH: 21
<212> TYPE: DNA
<213> ORGANISM: Homo sapiens

<400> SEQUENCE: 401
gagtttctgg kctgagctca a                                              21

<210> SEQ ID NO 402
<211> LENGTH: 21
<212> TYPE: DNA
<213> ORGANISM: Homo sapiens

<400> SEQUENCE: 402
gcacgcgcac rcccgcaggg t                                              21

<210> SEQ ID NO 403
<211> LENGTH: 21
<212> TYPE: DNA
<213> ORGANISM: Homo sapiens

<400> SEQUENCE: 403
catcccgaat ycaggcatca c                                              21

<210> SEQ ID NO 404
<211> LENGTH: 21
<212> TYPE: DNA
<213> ORGANISM: Homo sapiens

<400> SEQUENCE: 404
gcgtggtccg yttcgccatg c                                              21

<210> SEQ ID NO 405
<211> LENGTH: 21
<212> TYPE: DNA
<213> ORGANISM: Homo sapiens

<400> SEQUENCE: 405
attttgccat kgttctgctc a                                              21

<210> SEQ ID NO 406
<211> LENGTH: 21
<212> TYPE: DNA
<213> ORGANISM: Homo sapiens

<400> SEQUENCE: 406
ctgccatggg yagctccgtg c                                              21

<210> SEQ ID NO 407
<211> LENGTH: 21
<212> TYPE: DNA
<213> ORGANISM: Homo sapiens

<400> SEQUENCE: 407
ccctcgaacc ygagacagca g                                              21

<210> SEQ ID NO 408
<211> LENGTH: 21
<212> TYPE: DNA
<213> ORGANISM: Homo sapiens

<400> SEQUENCE: 408
ctgctggttg yactgtcagt g                                              21

<210> SEQ ID NO 409
<211> LENGTH: 21
<212> TYPE: DNA
<213> ORGANISM: Homo sapiens

<400> SEQUENCE: 409
caccgttcac sttgctttgg c                                              21

<210> SEQ ID NO 410
<211> LENGTH: 21
<212> TYPE: DNA
<213> ORGANISM: Homo sapiens

<400> SEQUENCE: 410
tctactgaag rgcattctgg c                                              21

<210> SEQ ID NO 411
<211> LENGTH: 21
<212> TYPE: DNA
<213> ORGANISM: Homo sapiens

<400> SEQUENCE: 411
ccatcagcaa ygtcacagcc t                                              21

<210> SEQ ID NO 412
<211> LENGTH: 21
<212> TYPE: DNA
<213> ORGANISM: Homo sapiens

<400> SEQUENCE: 412
aaatactttt ytttctacaa c                                              21

<210> SEQ ID NO 413
<211> LENGTH: 21
<212> TYPE: DNA
<213> ORGANISM: Homo sapiens

<400> SEQUENCE: 413
ggacactctc rtcttttgct g                                              21

<210> SEQ ID NO 414
<211> LENGTH: 21
<212> TYPE: DNA
<213> ORGANISM: Homo sapiens

<400> SEQUENCE: 414
aagcactatg ytcctttcct c                                              21

<210> SEQ ID NO 415
<211> LENGTH: 21
<212> TYPE: DNA
<213> ORGANISM: Homo sapiens

<400> SEQUENCE: 415
tcttcatggc ygcgttaatc c                                              21

<210> SEQ ID NO 416
<211> LENGTH: 21
<212> TYPE: DNA
<213> ORGANISM: Homo sapiens

<400> SEQUENCE: 416
ggacatggaa raagacatct t                                              21

<210> SEQ ID NO 417
<211> LENGTH: 21
<212> TYPE: DNA
<213> ORGANISM: Homo sapiens

<400> SEQUENCE: 417
tgacattggc ratgcagctg a                                              21

<210> SEQ ID NO 418
<211> LENGTH: 21
<212> TYPE: DNA
<213> ORGANISM: Homo sapiens

<400> SEQUENCE: 418
cggaaaatga rtgccaggca g                                              21

<210> SEQ ID NO 419
<211> LENGTH: 21
<212> TYPE: DNA
<213> ORGANISM: Homo sapiens

<400> SEQUENCE: 419
tcataatgca ytaaaaacct c                                              21

<210> SEQ ID NO 420
<211> LENGTH: 21
<212> TYPE: DNA
<213> ORGANISM: Homo sapiens

<400> SEQUENCE: 420
ccactgtgac wttggcaatg c                                              21

<210> SEQ ID NO 421
<211> LENGTH: 21
<212> TYPE: DNA
<213> ORGANISM: Homo sapiens

<400> SEQUENCE: 421
gtcgctgact yggagagctc a                                              21

<210> SEQ ID NO 422
<211> LENGTH: 21
<212> TYPE: DNA
<213> ORGANISM: Homo sapiens

<400> SEQUENCE: 422
gaagtgtata rgaatcccaa t                                              21

<210> SEQ ID NO 423
<211> LENGTH: 21
<212> TYPE: DNA
<213> ORGANISM: Homo sapiens

<400> SEQUENCE: 423
ttctggctga mcctgtggag a                                              21

<210> SEQ ID NO 424
<211> LENGTH: 21
<212> TYPE: DNA
<213> ORGANISM: Homo sapiens

<400> SEQUENCE: 424
atctttacct saagatgaaa c                                              21

<210> SEQ ID NO 425
<211> LENGTH: 21
<212> TYPE: DNA
<213> ORGANISM: Homo sapiens

<400> SEQUENCE: 425
ctctgccgta rttttgcccc t                                              21

<210> SEQ ID NO 426
<211> LENGTH: 21
<212> TYPE: DNA
<213> ORGANISM: Homo sapiens

<400> SEQUENCE: 426
atcctgggct ycattgggtc t                                              21

<210> SEQ ID NO 427
<211> LENGTH: 21
<212> TYPE: DNA
<213> ORGANISM: Homo sapiens

<400> SEQUENCE: 427
ctgccgtagt yttgcccctg g                                              21

<210> SEQ ID NO 428
<211> LENGTH: 21
<212> TYPE: DNA
<213> ORGANISM: Homo sapiens

<400> SEQUENCE: 428
agctggatgt rcctgtggta a                                             21

<210> SEQ ID NO 429
<211> LENGTH: 21
<212> TYPE: DNA
<213> ORGANISM: Homo sapiens

<400> SEQUENCE: 429
cggcttcggc ytctccaact a                                             21

<210> SEQ ID NO 430
<211> LENGTH: 21
<212> TYPE: DNA
<213> ORGANISM: Homo sapiens

<400> SEQUENCE: 430
gccggggcca ygtgagattc c                                             21

<210> SEQ ID NO 431
<211> LENGTH: 21
<212> TYPE: DNA
<213> ORGANISM: Homo sapiens

<400> SEQUENCE: 431
tgtacggctt yggcctctcc a                                             21

<210> SEQ ID NO 432
<211> LENGTH: 21
<212> TYPE: DNA
<213> ORGANISM: Homo sapiens

<400> SEQUENCE: 432
tgatgggcaa rcagctggag a                                             21

<210> SEQ ID NO 433
<211> LENGTH: 21
<212> TYPE: DNA
<213> ORGANISM: Homo sapiens

<400> SEQUENCE: 433
gcaaagtccc ktttaacaaa a                                             21

<210> SEQ ID NO 434
<211> LENGTH: 21
<212> TYPE: DNA
<213> ORGANISM: Homo sapiens

<400> SEQUENCE: 434
tggcatacat ygagcggaag a                                             21

<210> SEQ ID NO 435
<211> LENGTH: 21
<212> TYPE: DNA
<213> ORGANISM: Homo sapiens

<400> SEQUENCE: 435
aaaggcttgg ygctgggcag t                                             21

<210> SEQ ID NO 436
<211> LENGTH: 21
<212> TYPE: DNA
<213> ORGANISM: Homo sapiens

```
<400> SEQUENCE: 436
agccacagaa rccatgggat a                                              21

<210> SEQ ID NO 437
<211> LENGTH: 21
<212> TYPE: DNA
<213> ORGANISM: Homo sapiens

<400> SEQUENCE: 437
cctgctattt waaagacttc t                                              21

<210> SEQ ID NO 438
<211> LENGTH: 21
<212> TYPE: DNA
<213> ORGANISM: Homo sapiens

<400> SEQUENCE: 438
acaaagttga yttagaagag a                                              21

<210> SEQ ID NO 439
<211> LENGTH: 21
<212> TYPE: DNA
<213> ORGANISM: Homo sapiens

<400> SEQUENCE: 439
tcatgagctt yggtatcctt a                                              21

<210> SEQ ID NO 440
<211> LENGTH: 21
<212> TYPE: DNA
<213> ORGANISM: Homo sapiens

<400> SEQUENCE: 440
tcatgtaaca raaaatcaaa t                                              21

<210> SEQ ID NO 441
<211> LENGTH: 21
<212> TYPE: DNA
<213> ORGANISM: Homo sapiens

<400> SEQUENCE: 441
aaaaaatcaa rtgtaataga t                                              21

<210> SEQ ID NO 442
<211> LENGTH: 21
<212> TYPE: DNA
<213> ORGANISM: Homo sapiens

<400> SEQUENCE: 442
ttaccatgta ragtaagtaa t                                              21

<210> SEQ ID NO 443
<211> LENGTH: 21
<212> TYPE: DNA
<213> ORGANISM: Homo sapiens

<400> SEQUENCE: 443
gaacgataca rtagtcaaat g                                              21

<210> SEQ ID NO 444
<211> LENGTH: 21
<212> TYPE: DNA
```

```
<213> ORGANISM: Homo sapiens

<400> SEQUENCE: 444
tttagaggat kcaacactac a                                              21

<210> SEQ ID NO 445
<211> LENGTH: 21
<212> TYPE: DNA
<213> ORGANISM: Homo sapiens

<400> SEQUENCE: 445
tttagacgtt wtatataaaa t                                              21

<210> SEQ ID NO 446
<211> LENGTH: 21
<212> TYPE: DNA
<213> ORGANISM: Homo sapiens

<400> SEQUENCE: 446
agacgtttta yataaaatga c                                              21

<210> SEQ ID NO 447
<211> LENGTH: 21
<212> TYPE: DNA
<213> ORGANISM: Homo sapiens

<400> SEQUENCE: 447
ataccaggag yttcaattac t                                              21

<210> SEQ ID NO 448
<211> LENGTH: 21
<212> TYPE: DNA
<213> ORGANISM: Homo sapiens

<400> SEQUENCE: 448
ttttctttct kaaaatcgat g                                              21

<210> SEQ ID NO 449
<211> LENGTH: 21
<212> TYPE: DNA
<213> ORGANISM: Homo sapiens

<400> SEQUENCE: 449
ctcagaaatc ytgatgacgt c                                              21

<210> SEQ ID NO 450
<211> LENGTH: 21
<212> TYPE: DNA
<213> ORGANISM: Homo sapiens

<400> SEQUENCE: 450
ctgccaggct rcaagggcca a                                              21

<210> SEQ ID NO 451
<211> LENGTH: 21
<212> TYPE: DNA
<213> ORGANISM: Homo sapiens

<400> SEQUENCE: 451
cacatgccag ygccaatccc c                                              21

<210> SEQ ID NO 452
<211> LENGTH: 21
```

```
<212> TYPE: DNA
<213> ORGANISM: Homo sapiens

<400> SEQUENCE: 452
ggggctcagc ygacggccct c                                    21

<210> SEQ ID NO 453
<211> LENGTH: 21
<212> TYPE: DNA
<213> ORGANISM: Homo sapiens

<400> SEQUENCE: 453
gacccctcag ycgtgcctgt g                                    21

<210> SEQ ID NO 454
<211> LENGTH: 21
<212> TYPE: DNA
<213> ORGANISM: Homo sapiens

<400> SEQUENCE: 454
ccggagccca rggactgcgt c                                    21

<210> SEQ ID NO 455
<211> LENGTH: 21
<212> TYPE: DNA
<213> ORGANISM: Homo sapiens

<400> SEQUENCE: 455
acggatgcac wgggccaggt c                                    21

<210> SEQ ID NO 456
<211> LENGTH: 21
<212> TYPE: DNA
<213> ORGANISM: Homo sapiens

<400> SEQUENCE: 456
gcgccgctgc stggccgccc g                                    21

<210> SEQ ID NO 457
<211> LENGTH: 21
<212> TYPE: DNA
<213> ORGANISM: Homo sapiens

<400> SEQUENCE: 457
ttggaattcc rggtcatgcc t                                    21

<210> SEQ ID NO 458
<211> LENGTH: 21
<212> TYPE: DNA
<213> ORGANISM: Homo sapiens

<400> SEQUENCE: 458
aatcaactac ycaggaaaaa c                                    21

<210> SEQ ID NO 459
<211> LENGTH: 21
<212> TYPE: DNA
<213> ORGANISM: Homo sapiens

<400> SEQUENCE: 459
cctgaggttg yggaaaagga a                                    21

<210> SEQ ID NO 460
```

-continued

<210> SEQ ID NO 460
<211> LENGTH: 21
<212> TYPE: DNA
<213> ORGANISM: Homo sapiens

<400> SEQUENCE: 460
agaagatgag wttatgcctg a                           21

<210> SEQ ID NO 461
<211> LENGTH: 21
<212> TYPE: DNA
<213> ORGANISM: Homo sapiens

<400> SEQUENCE: 461
gagaggccgc racccaacac c                           21

<210> SEQ ID NO 462
<211> LENGTH: 21
<212> TYPE: DNA
<213> ORGANISM: Homo sapiens

<400> SEQUENCE: 462
tgttccagga rtccagtatc t                           21

<210> SEQ ID NO 463
<211> LENGTH: 21
<212> TYPE: DNA
<213> ORGANISM: Homo sapiens

<400> SEQUENCE: 463
agcttcagat ytgcccggcg a                           21

<210> SEQ ID NO 464
<211> LENGTH: 21
<212> TYPE: DNA
<213> ORGANISM: Homo sapiens

<400> SEQUENCE: 464
gcagtggtcc rgcggccact c                           21

<210> SEQ ID NO 465
<211> LENGTH: 21
<212> TYPE: DNA
<213> ORGANISM: Homo sapiens

<400> SEQUENCE: 465
tcatggacaa sgtggtgcgg t                           21

<210> SEQ ID NO 466
<211> LENGTH: 21
<212> TYPE: DNA
<213> ORGANISM: Homo sapiens

<400> SEQUENCE: 466
ttgtgtcaga wcccaaagct g                           21

<210> SEQ ID NO 467
<211> LENGTH: 21
<212> TYPE: DNA
<213> ORGANISM: Homo sapiens

<400> SEQUENCE: 467
aatattcagt yccaggcgcc a                           21

```
<210> SEQ ID NO 468
<211> LENGTH: 21
<212> TYPE: DNA
<213> ORGANISM: Homo sapiens

<400> SEQUENCE: 468
ctaaagaata rcccacctta t                                              21

<210> SEQ ID NO 469
<211> LENGTH: 21
<212> TYPE: DNA
<213> ORGANISM: Homo sapiens

<400> SEQUENCE: 469
aactcatcct rgctacatgg c                                              21

<210> SEQ ID NO 470
<211> LENGTH: 21
<212> TYPE: DNA
<213> ORGANISM: Homo sapiens

<400> SEQUENCE: 470
tcgagaacct yatgagtcag g                                              21

<210> SEQ ID NO 471
<211> LENGTH: 21
<212> TYPE: DNA
<213> ORGANISM: Homo sapiens

<400> SEQUENCE: 471
tctttccaag yggactcttt c                                              21

<210> SEQ ID NO 472
<211> LENGTH: 21
<212> TYPE: DNA
<213> ORGANISM: Homo sapiens

<400> SEQUENCE: 472
ctctggatgg ygatcctaca a                                              21

<210> SEQ ID NO 473
<211> LENGTH: 21
<212> TYPE: DNA
<213> ORGANISM: Homo sapiens

<400> SEQUENCE: 473
ccggcactca yttccatttt c                                              21

<210> SEQ ID NO 474
<211> LENGTH: 21
<212> TYPE: DNA
<213> ORGANISM: Homo sapiens

<400> SEQUENCE: 474
agcggcccag yttcagcacc a                                              21

<210> SEQ ID NO 475
<211> LENGTH: 21
<212> TYPE: DNA
<213> ORGANISM: Homo sapiens

<400> SEQUENCE: 475
cccagcgggt yaagagtgac a                                              21
```

<210> SEQ ID NO 476
<211> LENGTH: 21
<212> TYPE: DNA
<213> ORGANISM: Homo sapiens

<400> SEQUENCE: 476 gaagccctg yatgagcagc t                                              21

<210> SEQ ID NO 477
<211> LENGTH: 21
<212> TYPE: DNA
<213> ORGANISM: Homo sapiens

<400> SEQUENCE: 477
gagaggaagc ygatggggtc t                                             21

<210> SEQ ID NO 478
<211> LENGTH: 21
<212> TYPE: DNA
<213> ORGANISM: Homo sapiens

<400> SEQUENCE: 478
ctgctggcat kgagtacctg g                                             21

<210> SEQ ID NO 479
<211> LENGTH: 21
<212> TYPE: DNA
<213> ORGANISM: Homo sapiens

<400> SEQUENCE: 479
gatggtctgc yccggcactt c                                             21

<210> SEQ ID NO 480
<211> LENGTH: 21
<212> TYPE: DNA
<213> ORGANISM: Homo sapiens

<400> SEQUENCE: 480
gtgacaaggc yaaggacaag t                                             21

<210> SEQ ID NO 481
<211> LENGTH: 21
<212> TYPE: DNA
<213> ORGANISM: Homo sapiens

<400> SEQUENCE: 481
tgggcaccgg ytgcttcggg g                                             21

<210> SEQ ID NO 482
<211> LENGTH: 21
<212> TYPE: DNA
<213> ORGANISM: Homo sapiens

<400> SEQUENCE: 482
cagaagctac rgggcagcag a                                             21

<210> SEQ ID NO 483
<211> LENGTH: 21
<212> TYPE: DNA
<213> ORGANISM: Homo sapiens

<400> SEQUENCE: 483
tggatcaaca raatcccgat g                                             21

<210> SEQ ID NO 484
<211> LENGTH: 21
<212> TYPE: DNA
<213> ORGANISM: Homo sapiens

<400> SEQUENCE: 484
actacaacgt ygatagaacc a                                              21

<210> SEQ ID NO 485
<211> LENGTH: 21
<212> TYPE: DNA
<213> ORGANISM: Homo sapiens

<400> SEQUENCE: 485
ggccaatcca rtttgtggta c                                              21

<210> SEQ ID NO 486
<211> LENGTH: 21
<212> TYPE: DNA
<213> ORGANISM: Homo sapiens

<400> SEQUENCE: 486
gtccaggctt ytaatgtaga t                                              21

<210> SEQ ID NO 487
<211> LENGTH: 21
<212> TYPE: DNA
<213> ORGANISM: Homo sapiens

<400> SEQUENCE: 487
gcatcacaat ytgcagaaat c                                              21

<210> SEQ ID NO 488
<211> LENGTH: 21
<212> TYPE: DNA
<213> ORGANISM: Homo sapiens

<400> SEQUENCE: 488
aaattctcag sagctattat c                                              21

<210> SEQ ID NO 489
<211> LENGTH: 21
<212> TYPE: DNA
<213> ORGANISM: Homo sapiens

<400> SEQUENCE: 489
aaccaatgca kcgacacctt t                                              21

<210> SEQ ID NO 490
<211> LENGTH: 21
<212> TYPE: DNA
<213> ORGANISM: Homo sapiens

<400> SEQUENCE: 490
gacactgaag ragctgtcag t                                              21

<210> SEQ ID NO 491
<211> LENGTH: 21
<212> TYPE: DNA
<213> ORGANISM: Homo sapiens

<400> SEQUENCE: 491

```
ttctcttcag yagaatgatg a                                              21

<210> SEQ ID NO 492
<211> LENGTH: 21
<212> TYPE: DNA
<213> ORGANISM: Homo sapiens

<400> SEQUENCE: 492
actgtgaagg wtctgctctg t                                              21

<210> SEQ ID NO 493
<211> LENGTH: 21
<212> TYPE: DNA
<213> ORGANISM: Homo sapiens

<400> SEQUENCE: 493
aaaatcagag yaacttaaaa a                                              21

<210> SEQ ID NO 494
<211> LENGTH: 21
<212> TYPE: DNA
<213> ORGANISM: Homo sapiens

<400> SEQUENCE: 494
agtactgggg ytcctcagtc t                                              21

<210> SEQ ID NO 495
<211> LENGTH: 21
<212> TYPE: DNA
<213> ORGANISM: Homo sapiens

<400> SEQUENCE: 495
gccagtctct stgcctcaat a                                              21

<210> SEQ ID NO 496
<211> LENGTH: 21
<212> TYPE: DNA
<213> ORGANISM: Homo sapiens

<400> SEQUENCE: 496
attctgggac kcccaaagac c                                              21

<210> SEQ ID NO 497
<211> LENGTH: 21
<212> TYPE: DNA
<213> ORGANISM: Homo sapiens

<400> SEQUENCE: 497
ggagtgaccc rgtggagcaa g                                              21

<210> SEQ ID NO 498
<211> LENGTH: 21
<212> TYPE: DNA
<213> ORGANISM: Homo sapiens

<400> SEQUENCE: 498
tccagaacca ytttgtggac g                                              21

<210> SEQ ID NO 499
<211> LENGTH: 21
<212> TYPE: DNA
<213> ORGANISM: Homo sapiens

<400> SEQUENCE: 499
```

```
gcatacctca stggctacta a                                               21

<210> SEQ ID NO 500
<211> LENGTH: 21
<212> TYPE: DNA
<213> ORGANISM: Homo sapiens

<400> SEQUENCE: 500
ccatcttggt ygtgaagatc c                                               21

<210> SEQ ID NO 501
<211> LENGTH: 21
<212> TYPE: DNA
<213> ORGANISM: Homo sapiens

<400> SEQUENCE: 501
agagccaggt rtcggagcag c                                               21

<210> SEQ ID NO 502
<211> LENGTH: 21
<212> TYPE: DNA
<213> ORGANISM: Homo sapiens

<400> SEQUENCE: 502
gtcgccgggg mccagcaaat a                                               21

<210> SEQ ID NO 503
<211> LENGTH: 21
<212> TYPE: DNA
<213> ORGANISM: Homo sapiens

<400> SEQUENCE: 503
cctcccaaag ygctgggatt a                                               21

<210> SEQ ID NO 504
<211> LENGTH: 21
<212> TYPE: DNA
<213> ORGANISM: Homo sapiens

<400> SEQUENCE: 504
gacgcagggt ytcccatgac c                                               21

<210> SEQ ID NO 505
<211> LENGTH: 21
<212> TYPE: DNA
<213> ORGANISM: Homo sapiens

<400> SEQUENCE: 505
tatgatccat yttaactgag g                                               21

<210> SEQ ID NO 506
<211> LENGTH: 21
<212> TYPE: DNA
<213> ORGANISM: Homo sapiens

<400> SEQUENCE: 506
tgcaactcct rctattaaga c                                               21

<210> SEQ ID NO 507
<211> LENGTH: 21
<212> TYPE: DNA
<213> ORGANISM: Homo sapiens
```

```
<400> SEQUENCE: 507
taccgtgtaa ygtgaaccag c                                               21

<210> SEQ ID NO 508
<211> LENGTH: 21
<212> TYPE: DNA
<213> ORGANISM: Homo sapiens

<400> SEQUENCE: 508
ttctgctgct ratggagcga g                                               21

<210> SEQ ID NO 509
<211> LENGTH: 21
<212> TYPE: DNA
<213> ORGANISM: Homo sapiens

<400> SEQUENCE: 509
tgattcatga stgtcctcat c                                               21

<210> SEQ ID NO 510
<211> LENGTH: 21
<212> TYPE: DNA
<213> ORGANISM: Homo sapiens

<400> SEQUENCE: 510
tagaggacat raacgagttc a                                               21

<210> SEQ ID NO 511
<211> LENGTH: 21
<212> TYPE: DNA
<213> ORGANISM: Homo sapiens

<400> SEQUENCE: 511
gaattcagga ygttgtaccg t                                               21

<210> SEQ ID NO 512
<211> LENGTH: 21
<212> TYPE: DNA
<213> ORGANISM: Homo sapiens

<400> SEQUENCE: 512
actcatgaag yagcttaatg c                                               21

<210> SEQ ID NO 513
<211> LENGTH: 21
<212> TYPE: DNA
<213> ORGANISM: Homo sapiens

<400> SEQUENCE: 513
tttatgacat saagcggggc t                                               21

<210> SEQ ID NO 514
<211> LENGTH: 21
<212> TYPE: DNA
<213> ORGANISM: Homo sapiens

<400> SEQUENCE: 514
tggaagactt ygagacgatt g                                               21

<210> SEQ ID NO 515
<211> LENGTH: 21
<212> TYPE: DNA
<213> ORGANISM: Homo sapiens
```

<400> SEQUENCE: 515
aagacgcagt ytatcatgat g                                              21

<210> SEQ ID NO 516
<211> LENGTH: 21
<212> TYPE: DNA
<213> ORGANISM: Homo sapiens

<400> SEQUENCE: 516
ttcaggcaaa ygagatcatg t                                              21

<210> SEQ ID NO 517
<211> LENGTH: 21
<212> TYPE: DNA
<213> ORGANISM: Homo sapiens

<400> SEQUENCE: 517
tatgttgtat ytcgagagta a                                              21

<210> SEQ ID NO 518
<211> LENGTH: 21
<212> TYPE: DNA
<213> ORGANISM: Homo sapiens

<400> SEQUENCE: 518
tctcgacccc ygtggtgctc t                                              21

<210> SEQ ID NO 519
<211> LENGTH: 21
<212> TYPE: DNA
<213> ORGANISM: Homo sapiens

<400> SEQUENCE: 519
ggctgtgggg rctacgcaag a                                              21

<210> SEQ ID NO 520
<211> LENGTH: 21
<212> TYPE: DNA
<213> ORGANISM: Homo sapiens

<400> SEQUENCE: 520
aggcccaggc rgtttggcac g                                              21

<210> SEQ ID NO 521
<211> LENGTH: 21
<212> TYPE: DNA
<213> ORGANISM: Homo sapiens

<400> SEQUENCE: 521
gctgggacct sttccacaaa t                                              21

<210> SEQ ID NO 522
<211> LENGTH: 21
<212> TYPE: DNA
<213> ORGANISM: Homo sapiens

<400> SEQUENCE: 522
tacatcccca rtcgtggccc t                                              21

<210> SEQ ID NO 523
<211> LENGTH: 21
<212> TYPE: DNA

```
<213> ORGANISM: Homo sapiens

<400> SEQUENCE: 523
aaaacctcaa rgttataaag g                                              21

<210> SEQ ID NO 524
<211> LENGTH: 21
<212> TYPE: DNA
<213> ORGANISM: Homo sapiens

<400> SEQUENCE: 524
tgcattccag rgacacgtgg c                                              21

<210> SEQ ID NO 525
<211> LENGTH: 21
<212> TYPE: DNA
<213> ORGANISM: Homo sapiens

<400> SEQUENCE: 525
gggagccatc rtaaggaccc a                                              21

<210> SEQ ID NO 526
<211> LENGTH: 21
<212> TYPE: DNA
<213> ORGANISM: Homo sapiens

<400> SEQUENCE: 526
agcttgccag yggcatcctc a                                              21

<210> SEQ ID NO 527
<211> LENGTH: 21
<212> TYPE: DNA
<213> ORGANISM: Homo sapiens

<400> SEQUENCE: 527
cccatttgag magctgtgag c                                              21

<210> SEQ ID NO 528
<211> LENGTH: 21
<212> TYPE: DNA
<213> ORGANISM: Homo sapiens

<400> SEQUENCE: 528
atgacctcag rgactttcca a                                              21

<210> SEQ ID NO 529
<211> LENGTH: 21
<212> TYPE: DNA
<213> ORGANISM: Homo sapiens

<400> SEQUENCE: 529
gggacgcgaa stgcgcagcc a                                              21

<210> SEQ ID NO 530
<211> LENGTH: 21
<212> TYPE: DNA
<213> ORGANISM: Homo sapiens

<400> SEQUENCE: 530
aagcggtcta ytccagggat t                                              21

<210> SEQ ID NO 531
<211> LENGTH: 21
```

-continued

```
<212> TYPE: DNA
<213> ORGANISM: Homo sapiens

<400> SEQUENCE: 531
cctattgatc rgaagtcagt c                                              21

<210> SEQ ID NO 532
<211> LENGTH: 21
<212> TYPE: DNA
<213> ORGANISM: Homo sapiens

<400> SEQUENCE: 532
gagtggatct yattgaagtt t                                              21

<210> SEQ ID NO 533
<211> LENGTH: 21
<212> TYPE: DNA
<213> ORGANISM: Homo sapiens

<400> SEQUENCE: 533 tgcccctag ygactccgtg t                                               21

<210> SEQ ID NO 534
<211> LENGTH: 21
<212> TYPE: DNA
<213> ORGANISM: Homo sapiens

<400> SEQUENCE: 534
gaaagcgcct raaactgacg a                                              21

<210> SEQ ID NO 535
<211> LENGTH: 21
<212> TYPE: DNA
<213> ORGANISM: Homo sapiens

<400> SEQUENCE: 535
actcggggca yggcagcact t                                              21

<210> SEQ ID NO 536
<211> LENGTH: 21
<212> TYPE: DNA
<213> ORGANISM: Homo sapiens

<400> SEQUENCE: 536
tcgcaggaac rtgtggactc t                                              21

<210> SEQ ID NO 537
<211> LENGTH: 21
<212> TYPE: DNA
<213> ORGANISM: Homo sapiens

<400> SEQUENCE: 537
cgtcctgaga yctcagaaag a                                              21

<210> SEQ ID NO 538
<211> LENGTH: 21
<212> TYPE: DNA
<213> ORGANISM: Homo sapiens

<400> SEQUENCE: 538
ggactgctct yaacacaagc g                                              21

<210> SEQ ID NO 539
```

<211> LENGTH: 21
<212> TYPE: DNA
<213> ORGANISM: Homo sapiens

<400> SEQUENCE: 539
tgagctgttc sgatgctctg c                                              21

<210> SEQ ID NO 540
<211> LENGTH: 21
<212> TYPE: DNA
<213> ORGANISM: Homo sapiens

<400> SEQUENCE: 540
catcccagac rcgggcagtc a                                              21

<210> SEQ ID NO 541
<211> LENGTH: 21
<212> TYPE: DNA
<213> ORGANISM: Homo sapiens

<400> SEQUENCE: 541
ccttcggacc ycaggacgtc g                                              21

<210> SEQ ID NO 542
<211> LENGTH: 21
<212> TYPE: DNA
<213> ORGANISM: Homo sapiens

<400> SEQUENCE: 542
actagtaaaa rctggacctt c                                              21

<210> SEQ ID NO 543
<211> LENGTH: 21
<212> TYPE: DNA
<213> ORGANISM: Homo sapiens

<400> SEQUENCE: 543
atatttgcga yaagtaggat a                                              21

<210> SEQ ID NO 544
<211> LENGTH: 21
<212> TYPE: DNA
<213> ORGANISM: Homo sapiens

<400> SEQUENCE: 544
cacacaaggt sgtgttatat t                                              21

<210> SEQ ID NO 545
<211> LENGTH: 21
<212> TYPE: DNA
<213> ORGANISM: Homo sapiens

<400> SEQUENCE: 545
ttgaacacct ycctcgccgt g                                              21

<210> SEQ ID NO 546
<211> LENGTH: 21
<212> TYPE: DNA
<213> ORGANISM: Homo sapiens

<400> SEQUENCE: 546
tttgtggcac yagcttggag c                                              21

-continued

```
<210> SEQ ID NO 547
<211> LENGTH: 21
<212> TYPE: DNA
<213> ORGANISM: Homo sapiens

<400> SEQUENCE: 547
ttctatgaca yctaccatgc t                                              21

<210> SEQ ID NO 548
<211> LENGTH: 21
<212> TYPE: DNA
<213> ORGANISM: Homo sapiens

<400> SEQUENCE: 548
agaaagcaac ycaaagtggg a                                              21

<210> SEQ ID NO 549
<211> LENGTH: 21
<212> TYPE: DNA
<213> ORGANISM: Homo sapiens

<400> SEQUENCE: 549
tctgcaacga rcgcttcact c                                              21

<210> SEQ ID NO 550
<211> LENGTH: 21
<212> TYPE: DNA
<213> ORGANISM: Homo sapiens

<400> SEQUENCE: 550
agacacggga stgcatctac t                                              21

<210> SEQ ID NO 551
<211> LENGTH: 21
<212> TYPE: DNA
<213> ORGANISM: Homo sapiens

<400> SEQUENCE: 551
cctcacggat yacctcaagg g                                              21

<210> SEQ ID NO 552
<211> LENGTH: 21
<212> TYPE: DNA
<213> ORGANISM: Homo sapiens

<400> SEQUENCE: 552
ggctcctgag rtgctcgagg g                                              21

<210> SEQ ID NO 553
<211> LENGTH: 21
<212> TYPE: DNA
<213> ORGANISM: Homo sapiens

<400> SEQUENCE: 553
tgctgaagag ygacctcaca g                                              21

<210> SEQ ID NO 554
<211> LENGTH: 21
<212> TYPE: DNA
<213> ORGANISM: Homo sapiens

<400> SEQUENCE: 554
ccagagacag ygcgacccgg a                                              21
```

<210> SEQ ID NO 555
<211> LENGTH: 21
<212> TYPE: DNA
<213> ORGANISM: Homo sapiens

<400> SEQUENCE: 555
acctggccat ygtccacgcc a                                              21

<210> SEQ ID NO 556
<211> LENGTH: 21
<212> TYPE: DNA
<213> ORGANISM: Homo sapiens

<400> SEQUENCE: 556
agtgcttgac wgacatttac c                                              21

<210> SEQ ID NO 557
<211> LENGTH: 21
<212> TYPE: DNA
<213> ORGANISM: Homo sapiens

<400> SEQUENCE: 557
catgctggtc rtcctcatct t                                              21

<210> SEQ ID NO 558
<211> LENGTH: 21
<212> TYPE: DNA
<213> ORGANISM: Homo sapiens

<400> SEQUENCE: 558
acatccacgc mgctcgaggg a                                              21

<210> SEQ ID NO 559
<211> LENGTH: 21
<212> TYPE: DNA
<213> ORGANISM: Homo sapiens

<400> SEQUENCE: 559
ggtgctagtc ygcgccatca a                                              21

<210> SEQ ID NO 560
<211> LENGTH: 21
<212> TYPE: DNA
<213> ORGANISM: Homo sapiens

<400> SEQUENCE: 560
cacctacctg stctggacct g                                              21

<210> SEQ ID NO 561
<211> LENGTH: 21
<212> TYPE: DNA
<213> ORGANISM: Homo sapiens

<400> SEQUENCE: 561
cggtacacag ygacaattga g                                              21

<210> SEQ ID NO 562
<211> LENGTH: 21
<212> TYPE: DNA
<213> ORGANISM: Homo sapiens

<400> SEQUENCE: 562
gagcacgggt ycctgtttga t                                              21

<210> SEQ ID NO 563
<211> LENGTH: 21
<212> TYPE: DNA
<213> ORGANISM: Homo sapiens

<400> SEQUENCE: 563
cagagttatg wggcactgcg g                                              21

<210> SEQ ID NO 564
<211> LENGTH: 21
<212> TYPE: DNA
<213> ORGANISM: Homo sapiens

<400> SEQUENCE: 564
tatattggga sattgctcga a                                              21

<210> SEQ ID NO 565
<211> LENGTH: 21
<212> TYPE: DNA
<213> ORGANISM: Homo sapiens

<400> SEQUENCE: 565
gagatgtgtc yctccaaaga c                                              21

<210> SEQ ID NO 566
<211> LENGTH: 21
<212> TYPE: DNA
<213> ORGANISM: Homo sapiens

<400> SEQUENCE: 566
agctgtactt ycaacagtta t                                              21

<210> SEQ ID NO 567
<211> LENGTH: 21
<212> TYPE: DNA
<213> ORGANISM: Homo sapiens

<400> SEQUENCE: 567
ggggaaacca rtgaaaagcg t                                              21

<210> SEQ ID NO 568
<211> LENGTH: 21
<212> TYPE: DNA
<213> ORGANISM: Homo sapiens

<400> SEQUENCE: 568
tcacctgctg ytataacttc a                                              21

<210> SEQ ID NO 569
<211> LENGTH: 21
<212> TYPE: DNA
<213> ORGANISM: Homo sapiens

<400> SEQUENCE: 569
tgaaagaagt rgcaacgctg t                                              21

<210> SEQ ID NO 570
<211> LENGTH: 21
<212> TYPE: DNA
<213> ORGANISM: Homo sapiens

<400> SEQUENCE: 570
gcatctctgc ygaagccaag g                    21

<210> SEQ ID NO 571
<211> LENGTH: 21
<212> TYPE: DNA
<213> ORGANISM: Homo sapiens

<400> SEQUENCE: 571
tgaccagcct ycgccgctcg g                    21

<210> SEQ ID NO 572
<211> LENGTH: 21
<212> TYPE: DNA
<213> ORGANISM: Homo sapiens

<400> SEQUENCE: 572
cagagtgcaa rcgcagccac a                    21

<210> SEQ ID NO 573
<211> LENGTH: 21
<212> TYPE: DNA
<213> ORGANISM: Homo sapiens

<400> SEQUENCE: 573
ataacaaccc yatctggtca g                    21

<210> SEQ ID NO 574
<211> LENGTH: 21
<212> TYPE: DNA
<213> ORGANISM: Homo sapiens

<400> SEQUENCE: 574
tgaagctctt ytttggtggc c                    21

<210> SEQ ID NO 575
<211> LENGTH: 21
<212> TYPE: DNA
<213> ORGANISM: Homo sapiens

<400> SEQUENCE: 575
cggcgggagg yactgaggag g                    21

<210> SEQ ID NO 576
<211> LENGTH: 21
<212> TYPE: DNA
<213> ORGANISM: Homo sapiens

<400> SEQUENCE: 576
gcagctcttc rccaatgggg a                    21

<210> SEQ ID NO 577
<211> LENGTH: 21
<212> TYPE: DNA
<213> ORGANISM: Homo sapiens

<400> SEQUENCE: 577
tcactgtcca rgtgcccagc a                    21

<210> SEQ ID NO 578
<211> LENGTH: 21
<212> TYPE: DNA
<213> ORGANISM: Homo sapiens

<400> SEQUENCE: 578
gactggccag mccagcctca g 21

<210> SEQ ID NO 579
<211> LENGTH: 21
<212> TYPE: DNA
<213> ORGANISM: Homo sapiens

<400> SEQUENCE: 579
ggcttctgca kacagtcaag c 21

<210> SEQ ID NO 580
<211> LENGTH: 21
<212> TYPE: DNA
<213> ORGANISM: Homo sapiens

<400> SEQUENCE: 580
ttttacaaat ragcagagaa t 21

<210> SEQ ID NO 581
<211> LENGTH: 21
<212> TYPE: DNA
<213> ORGANISM: Homo sapiens

<400> SEQUENCE: 581
gctgtgtttc sggatgcaag c 21

<210> SEQ ID NO 582
<211> LENGTH: 21
<212> TYPE: DNA
<213> ORGANISM: Homo sapiens

<400> SEQUENCE: 582
cagtaacatg ygcatctact g 21

<210> SEQ ID NO 583
<211> LENGTH: 21
<212> TYPE: DNA
<213> ORGANISM: Homo sapiens

<400> SEQUENCE: 583
agcgccaggc mccgagcagt g 21

<210> SEQ ID NO 584
<211> LENGTH: 21
<212> TYPE: DNA
<213> ORGANISM: Homo sapiens

<400> SEQUENCE: 584
ggtggctggc rtcctggttc t 21

<210> SEQ ID NO 585
<211> LENGTH: 21
<212> TYPE: DNA
<213> ORGANISM: Homo sapiens

<400> SEQUENCE: 585
tgaagccgga rgacagtggc a 21

<210> SEQ ID NO 586
<211> LENGTH: 21
<212> TYPE: DNA
<213> ORGANISM: Homo sapiens -continued

<400> SEQUENCE: 586
ctgcatgatc ktcgggagcc c　　　　　　　　　　　　　　　　　　　　　21

<210> SEQ ID NO 587
<211> LENGTH: 21
<212> TYPE: DNA
<213> ORGANISM: Homo sapiens

<400> SEQUENCE: 587
tctgggattc ygcaaaaggg a　　　　　　　　　　　　　　　　　　　　　21

<210> SEQ ID NO 588
<211> LENGTH: 21
<212> TYPE: DNA
<213> ORGANISM: Homo sapiens

<400> SEQUENCE: 588
gagtggccat scacctgtgc t　　　　　　　　　　　　　　　　　　　　　21

<210> SEQ ID NO 589
<211> LENGTH: 21
<212> TYPE: DNA
<213> ORGANISM: Homo sapiens

<400> SEQUENCE: 589
ttgtagcccc rtcacccttg g　　　　　　　　　　　　　　　　　　　　　21

<210> SEQ ID NO 590
<211> LENGTH: 21
<212> TYPE: DNA
<213> ORGANISM: Homo sapiens

<400> SEQUENCE: 590
ctgtgtgtga ygtgcatggg a　　　　　　　　　　　　　　　　　　　　　21

<210> SEQ ID NO 591
<211> LENGTH: 21
<212> TYPE: DNA
<213> ORGANISM: Homo sapiens

<400> SEQUENCE: 591
ggtggtaacc rtcgggctag a　　　　　　　　　　　　　　　　　　　　　21

<210> SEQ ID NO 592
<211> LENGTH: 21
<212> TYPE: DNA
<213> ORGANISM: Homo sapiens

<400> SEQUENCE: 592
ctgatgggat sctatggaac c　　　　　　　　　　　　　　　　　　　　　21

<210> SEQ ID NO 593
<211> LENGTH: 21
<212> TYPE: DNA
<213> ORGANISM: Homo sapiens

<400> SEQUENCE: 593
atgatgccat ygatgccctc g　　　　　　　　　　　　　　　　　　　　　21

<210> SEQ ID NO 594
<211> LENGTH: 21
<212> TYPE: DNA
<213> ORGANISM: Homo sapiens

<400> SEQUENCE: 594
ctgtctctgg ytggccaaag g                                               21

<210> SEQ ID NO 595
<211> LENGTH: 21
<212> TYPE: DNA
<213> ORGANISM: Homo sapiens

<400> SEQUENCE: 595
agaaagggat macctgccgc a                                               21

<210> SEQ ID NO 596
<211> LENGTH: 21
<212> TYPE: DNA
<213> ORGANISM: Homo sapiens

<400> SEQUENCE: 596
agaggccgca ygtcggatct c                                               21

<210> SEQ ID NO 597
<211> LENGTH: 21
<212> TYPE: DNA
<213> ORGANISM: Homo sapiens

<400> SEQUENCE: 597
ccgtttgcct rcctcgtcca g                                               21

<210> SEQ ID NO 598
<211> LENGTH: 21
<212> TYPE: DNA
<213> ORGANISM: Homo sapiens

<400> SEQUENCE: 598
gtttgactgt rgaccagctg c                                               21

<210> SEQ ID NO 599
<211> LENGTH: 21
<212> TYPE: DNA
<213> ORGANISM: Homo sapiens

<400> SEQUENCE: 599
gtgtctgaga ractccggac c                                               21

<210> SEQ ID NO 600
<211> LENGTH: 21
<212> TYPE: DNA
<213> ORGANISM: Homo sapiens

<400> SEQUENCE: 600
gggactaaga sctgggaaga a                                               21

<210> SEQ ID NO 601
<211> LENGTH: 21
<212> TYPE: DNA
<213> ORGANISM: Homo sapiens

<400> SEQUENCE: 601
tctccgatga yacactcttt c                                               21

<210> SEQ ID NO 602
<211> LENGTH: 21
<212> TYPE: DNA

```
<213> ORGANISM: Homo sapiens

<400> SEQUENCE: 602
gctgctctcc yggagatggc a                                              21

<210> SEQ ID NO 603
<211> LENGTH: 21
<212> TYPE: DNA
<213> ORGANISM: Homo sapiens

<400> SEQUENCE: 603
gtggccttct ycaccaatgg g                                              21

<210> SEQ ID NO 604
<211> LENGTH: 21
<212> TYPE: DNA
<213> ORGANISM: Homo sapiens

<400> SEQUENCE: 604
acagccctcc rtgtgctacc t                                              21

<210> SEQ ID NO 605
<211> LENGTH: 21
<212> TYPE: DNA
<213> ORGANISM: Homo sapiens

<400> SEQUENCE: 605
tgcctggaac yttggctggg c                                              21

<210> SEQ ID NO 606
<211> LENGTH: 21
<212> TYPE: DNA
<213> ORGANISM: Homo sapiens

<400> SEQUENCE: 606
agattcactc rggctctgtc a                                              21

<210> SEQ ID NO 607
<211> LENGTH: 21
<212> TYPE: DNA
<213> ORGANISM: Homo sapiens

<400> SEQUENCE: 607
ccattgctgc yttcttgccg g                                              21

<210> SEQ ID NO 608
<211> LENGTH: 21
<212> TYPE: DNA
<213> ORGANISM: Homo sapiens

<400> SEQUENCE: 608
tggccaataa matcttggcc a                                              21

<210> SEQ ID NO 609
<211> LENGTH: 21
<212> TYPE: DNA
<213> ORGANISM: Homo sapiens

<400> SEQUENCE: 609
atgacggaca ratttgccca g                                              21

<210> SEQ ID NO 610
<211> LENGTH: 21
```

-continued

<212> TYPE: DNA
<213> ORGANISM: Homo sapiens

<400> SEQUENCE: 610
agcagcttcg katggcaatg a                                              21

<210> SEQ ID NO 611
<211> LENGTH: 21
<212> TYPE: DNA
<213> ORGANISM: Homo sapiens

<400> SEQUENCE: 611
tcacgagggc rgagcaggtg g                                              21

<210> SEQ ID NO 612
<211> LENGTH: 21
<212> TYPE: DNA
<213> ORGANISM: Homo sapiens

<400> SEQUENCE: 612
ggcgcagcat ycggcttttc a                                              21

<210> SEQ ID NO 613
<211> LENGTH: 21
<212> TYPE: DNA
<213> ORGANISM: Homo sapiens

<400> SEQUENCE: 613
gcccctcacc rtatcagcct t                                              21

<210> SEQ ID NO 614
<211> LENGTH: 21
<212> TYPE: DNA
<213> ORGANISM: Homo sapiens

<400> SEQUENCE: 614
tcagggcgct ytgtgacaga g                                              21

<210> SEQ ID NO 615
<211> LENGTH: 21
<212> TYPE: DNA
<213> ORGANISM: Homo sapiens

<400> SEQUENCE: 615
caaggtggca ycattagtct t                                              21

<210> SEQ ID NO 616
<211> LENGTH: 21
<212> TYPE: DNA
<213> ORGANISM: Homo sapiens

<400> SEQUENCE: 616
tttcgaagtt ycttaccaac c                                              21

<210> SEQ ID NO 617
<211> LENGTH: 21
<212> TYPE: DNA
<213> ORGANISM: Homo sapiens

<400> SEQUENCE: 617
ctccagcatg sgaagtcggt g                                              21

<210> SEQ ID NO 618

```
<211> LENGTH: 21
<212> TYPE: DNA
<213> ORGANISM: Homo sapiens

<400> SEQUENCE: 618
acagtgcaac rgctgatgct g                                              21

<210> SEQ ID NO 619
<211> LENGTH: 21
<212> TYPE: DNA
<213> ORGANISM: Homo sapiens

<400> SEQUENCE: 619
gtctgagaga ytccggaccc t                                              21

<210> SEQ ID NO 620
<211> LENGTH: 21
<212> TYPE: DNA
<213> ORGANISM: Homo sapiens

<400> SEQUENCE: 620
ggagggccct ytggagcgcc c                                              21

<210> SEQ ID NO 621
<211> LENGTH: 21
<212> TYPE: DNA
<213> ORGANISM: Homo sapiens

<400> SEQUENCE: 621
tggttgtcgg ktgctgcaga c                                              21

<210> SEQ ID NO 622
<211> LENGTH: 21
<212> TYPE: DNA
<213> ORGANISM: Homo sapiens

<400> SEQUENCE: 622
agctgctgac rcggccacac a                                              21

<210> SEQ ID NO 623
<211> LENGTH: 21
<212> TYPE: DNA
<213> ORGANISM: Homo sapiens

<400> SEQUENCE: 623
tagtgagcca rcaccacatc t                                              21

<210> SEQ ID NO 624
<211> LENGTH: 21
<212> TYPE: DNA
<213> ORGANISM: Homo sapiens

<400> SEQUENCE: 624
catcgatggg rctgataggt t                                              21

<210> SEQ ID NO 625
<211> LENGTH: 21
<212> TYPE: DNA
<213> ORGANISM: Homo sapiens

<400> SEQUENCE: 625
tgagtgggat sgtggaaggg a                                              21
```

```
<210> SEQ ID NO 626
<211> LENGTH: 21
<212> TYPE: DNA
<213> ORGANISM: Homo sapiens

<400> SEQUENCE: 626
gtggaaggga racacacttg g                                              21

<210> SEQ ID NO 627
<211> LENGTH: 21
<212> TYPE: DNA
<213> ORGANISM: Homo sapiens

<400> SEQUENCE: 627 gagggaaga raatgaggtg t                                               21

<210> SEQ ID NO 628
<211> LENGTH: 21
<212> TYPE: DNA
<213> ORGANISM: Homo sapiens

<400> SEQUENCE: 628
aagaaatata yacttgagtg g                                              21

<210> SEQ ID NO 629
<211> LENGTH: 21
<212> TYPE: DNA
<213> ORGANISM: Homo sapiens

<400> SEQUENCE: 629
tgatcgctat stagcaaccc t                                              21

<210> SEQ ID NO 630
<211> LENGTH: 21
<212> TYPE: DNA
<213> ORGANISM: Homo sapiens

<400> SEQUENCE: 630
tcttaaaatt sacatggacc a                                              21

<210> SEQ ID NO 631
<211> LENGTH: 21
<212> TYPE: DNA
<213> ORGANISM: Homo sapiens

<400> SEQUENCE: 631
cactgggagt ygccatatct g                                              21

<210> SEQ ID NO 632
<211> LENGTH: 21
<212> TYPE: DNA
<213> ORGANISM: Homo sapiens

<400> SEQUENCE: 632
agattatgag yctccatttg g                                              21

<210> SEQ ID NO 633
<211> LENGTH: 21
<212> TYPE: DNA
<213> ORGANISM: Homo sapiens

<400> SEQUENCE: 633
tgggaactgc ragatacatg g                                              21
```

<210> SEQ ID NO 634
<211> LENGTH: 21
<212> TYPE: DNA
<213> ORGANISM: Homo sapiens

<400> SEQUENCE: 634
tactccagtt sctgacggct g                                    21

<210> SEQ ID NO 635
<211> LENGTH: 21
<212> TYPE: DNA
<213> ORGANISM: Homo sapiens

<400> SEQUENCE: 635
tcgtgaagaa ygacctaacc t                                    21

<210> SEQ ID NO 636
<211> LENGTH: 21
<212> TYPE: DNA
<213> ORGANISM: Homo sapiens

<400> SEQUENCE: 636
tgtcatcatc mtcttctact g                                    21

<210> SEQ ID NO 637
<211> LENGTH: 21
<212> TYPE: DNA
<213> ORGANISM: Homo sapiens

<400> SEQUENCE: 637
cctccacagt ratcacactc c                                    21

<210> SEQ ID NO 638
<211> LENGTH: 21
<212> TYPE: DNA
<213> ORGANISM: Homo sapiens

<400> SEQUENCE: 638
cctgtctgac ratcctggac t                                    21

<210> SEQ ID NO 639
<211> LENGTH: 21
<212> TYPE: DNA
<213> ORGANISM: Homo sapiens

<400> SEQUENCE: 639
gaagccacag racttgcact t                                    21

<210> SEQ ID NO 640
<211> LENGTH: 21
<212> TYPE: DNA
<213> ORGANISM: Homo sapiens

<400> SEQUENCE: 640
agataaataa yggcggctgt t                                    21

<210> SEQ ID NO 641
<211> LENGTH: 21
<212> TYPE: DNA
<213> ORGANISM: Homo sapiens

<400> SEQUENCE: 641
gggtggatgt yttcacccaa c                                    21

<210> SEQ ID NO 642
<211> LENGTH: 21
<212> TYPE: DNA
<213> ORGANISM: Homo sapiens

<400> SEQUENCE: 642
ctgagacgta yggacccccag t                                        21

<210> SEQ ID NO 643
<211> LENGTH: 21
<212> TYPE: DNA
<213> ORGANISM: Homo sapiens

<400> SEQUENCE: 643
tggttatggg mcaaatggat g                                         21

<210> SEQ ID NO 644
<211> LENGTH: 21
<212> TYPE: DNA
<213> ORGANISM: Homo sapiens

<400> SEQUENCE: 644
tctgggttat saaaactgaa a                                         21

<210> SEQ ID NO 645
<211> LENGTH: 21
<212> TYPE: DNA
<213> ORGANISM: Homo sapiens

<400> SEQUENCE: 645
gcctttcact yacaccaggc a                                         21

<210> SEQ ID NO 646
<211> LENGTH: 21
<212> TYPE: DNA
<213> ORGANISM: Homo sapiens

<400> SEQUENCE: 646
gcaaggtgcc rggaaacttc a                                         21

<210> SEQ ID NO 647
<211> LENGTH: 21
<212> TYPE: DNA
<213> ORGANISM: Homo sapiens

<400> SEQUENCE: 647
agaggagtgc rtctccctca c                                         21

<210> SEQ ID NO 648
<211> LENGTH: 21
<212> TYPE: DNA
<213> ORGANISM: Homo sapiens

<400> SEQUENCE: 648
caggtatctt rgaagttttg c                                         21

<210> SEQ ID NO 649
<211> LENGTH: 21
<212> TYPE: DNA
<213> ORGANISM: Homo sapiens

<400> SEQUENCE: 649
tagaagccat ygtcagcagt g                                    21

<210> SEQ ID NO 650
<211> LENGTH: 21
<212> TYPE: DNA
<213> ORGANISM: Homo sapiens

<400> SEQUENCE: 650
acatgggagg ycctgaaact c                                    21

<210> SEQ ID NO 651
<211> LENGTH: 21
<212> TYPE: DNA
<213> ORGANISM: Homo sapiens

<400> SEQUENCE: 651
tactatattg ratttcggta c                                    21

<210> SEQ ID NO 652
<211> LENGTH: 21
<212> TYPE: DNA
<213> ORGANISM: Homo sapiens

<400> SEQUENCE: 652
agaagacgct rtccatttc a                                     21

<210> SEQ ID NO 653
<211> LENGTH: 21
<212> TYPE: DNA
<213> ORGANISM: Homo sapiens

<400> SEQUENCE: 653
atcgtggaga rcggcggggc a                                    21

<210> SEQ ID NO 654
<211> LENGTH: 21
<212> TYPE: DNA
<213> ORGANISM: Homo sapiens

<400> SEQUENCE: 654
gggcctcacg ytctttgcag t                                    21

<210> SEQ ID NO 655
<211> LENGTH: 21
<212> TYPE: DNA
<213> ORGANISM: Homo sapiens

<400> SEQUENCE: 655
tgaaaatggc yttggaggca g                                    21

<210> SEQ ID NO 656
<211> LENGTH: 21
<212> TYPE: DNA
<213> ORGANISM: Homo sapiens

<400> SEQUENCE: 656
aggagacgac yttctacacg c                                    21

<210> SEQ ID NO 657
<211> LENGTH: 21
<212> TYPE: DNA
<213> ORGANISM: Homo sapiens

<400> SEQUENCE: 657
ggtgtgcctg rcatgggcct g         21

<210> SEQ ID NO 658
<211> LENGTH: 21
<212> TYPE: DNA
<213> ORGANISM: Homo sapiens

<400> SEQUENCE: 658
catgttgcca ragccaacgt c         21

<210> SEQ ID NO 659
<211> LENGTH: 21
<212> TYPE: DNA
<213> ORGANISM: Homo sapiens

<400> SEQUENCE: 659
ctatgtctgc sgagtcagca t         21

<210> SEQ ID NO 660
<211> LENGTH: 21
<212> TYPE: DNA
<213> ORGANISM: Homo sapiens

<400> SEQUENCE: 660
agggcacggg ytccgaggcg t         21

<210> SEQ ID NO 661
<211> LENGTH: 21
<212> TYPE: DNA
<213> ORGANISM: Homo sapiens

<400> SEQUENCE: 661
cctcactgcc kccagccctc t         21

<210> SEQ ID NO 662
<211> LENGTH: 21
<212> TYPE: DNA
<213> ORGANISM: Homo sapiens

<400> SEQUENCE: 662
acagccaaga mctgggaact c         21

<210> SEQ ID NO 663
<211> LENGTH: 21
<212> TYPE: DNA
<213> ORGANISM: Homo sapiens

<400> SEQUENCE: 663
acctgcacct kcgctgcagc g         21

<210> SEQ ID NO 664
<211> LENGTH: 21
<212> TYPE: DNA
<213> ORGANISM: Homo sapiens

<400> SEQUENCE: 664
cctggctcta ytctcctgga c         21

<210> SEQ ID NO 665
<211> LENGTH: 21
<212> TYPE: DNA
<213> ORGANISM: Homo sapiens

```
<400> SEQUENCE: 665
tcctgaatcc ytggattact g                                              21

<210> SEQ ID NO 666
<211> LENGTH: 21
<212> TYPE: DNA
<213> ORGANISM: Homo sapiens

<400> SEQUENCE: 666
gccactgaag racaggcaaa t                                              21

<210> SEQ ID NO 667
<211> LENGTH: 21
<212> TYPE: DNA
<213> ORGANISM: Homo sapiens

<400> SEQUENCE: 667
cgctgaagac rccccacggg g                                              21

<210> SEQ ID NO 668
<211> LENGTH: 21
<212> TYPE: DNA
<213> ORGANISM: Homo sapiens

<400> SEQUENCE: 668
agagctgccc ragaagctcc c                                              21

<210> SEQ ID NO 669
<211> LENGTH: 21
<212> TYPE: DNA
<213> ORGANISM: Homo sapiens

<400> SEQUENCE: 669
tccgagaggc racaaggttt g                                              21

<210> SEQ ID NO 670
<211> LENGTH: 21
<212> TYPE: DNA
<213> ORGANISM: Homo sapiens

<400> SEQUENCE: 670
ccagtgtgga mgaactaaag g                                              21

<210> SEQ ID NO 671
<211> LENGTH: 21
<212> TYPE: DNA
<213> ORGANISM: Homo sapiens

<400> SEQUENCE: 671
tcttcagggg rcccaatggt g                                              21

<210> SEQ ID NO 672
<211> LENGTH: 21
<212> TYPE: DNA
<213> ORGANISM: Homo sapiens

<400> SEQUENCE: 672
gttccttttg matttctccc g                                              21

<210> SEQ ID NO 673
<211> LENGTH: 21
<212> TYPE: DNA
<213> ORGANISM: Homo sapiens
```

-continued

```
<400> SEQUENCE: 673
ccagggcctg ygggtagagt c                                              21

<210> SEQ ID NO 674
<211> LENGTH: 21
<212> TYPE: DNA
<213> ORGANISM: Homo sapiens

<400> SEQUENCE: 674
tcaagaacca yacagagatc g                                              21

<210> SEQ ID NO 675
<211> LENGTH: 21
<212> TYPE: DNA
<213> ORGANISM: Homo sapiens

<400> SEQUENCE: 675
tgcaattcaa rgatggtaca g                                              21

<210> SEQ ID NO 676
<211> LENGTH: 21
<212> TYPE: DNA
<213> ORGANISM: Homo sapiens

<400> SEQUENCE: 676
cggcgcagac racactggtg g                                              21

<210> SEQ ID NO 677
<211> LENGTH: 21
<212> TYPE: DNA
<213> ORGANISM: Homo sapiens

<400> SEQUENCE: 677
atgggcacaa ygtgtgggcc c                                              21

<210> SEQ ID NO 678
<211> LENGTH: 21
<212> TYPE: DNA
<213> ORGANISM: Homo sapiens

<400> SEQUENCE: 678
gcatctttgg ygatgaggat g                                              21

<210> SEQ ID NO 679
<211> LENGTH: 21
<212> TYPE: DNA
<213> ORGANISM: Homo sapiens

<400> SEQUENCE: 679
gctcgctgct yatcgtgcag a                                              21

<210> SEQ ID NO 680
<211> LENGTH: 21
<212> TYPE: DNA
<213> ORGANISM: Homo sapiens

<400> SEQUENCE: 680
agcctgagtg yttcggaccc g                                              21

<210> SEQ ID NO 681
<211> LENGTH: 21
<212> TYPE: DNA
```

```
<213> ORGANISM: Homo sapiens

<400> SEQUENCE: 681
accacaaggc rtccatggtg c                                              21

<210> SEQ ID NO 682
<211> LENGTH: 21
<212> TYPE: DNA
<213> ORGANISM: Homo sapiens

<400> SEQUENCE: 682
cagacgcccc rgctgtggtc a                                              21

<210> SEQ ID NO 683
<211> LENGTH: 21
<212> TYPE: DNA
<213> ORGANISM: Homo sapiens

<400> SEQUENCE: 683
tccaaagaag raggaagctg g                                              21

<210> SEQ ID NO 684
<211> LENGTH: 21
<212> TYPE: DNA
<213> ORGANISM: Homo sapiens

<400> SEQUENCE: 684
acatcccagc rcgccgaaac c                                              21

<210> SEQ ID NO 685
<211> LENGTH: 21
<212> TYPE: DNA
<213> ORGANISM: Homo sapiens

<400> SEQUENCE: 685
tgaagatcgc rcagggtgtc t                                              21

<210> SEQ ID NO 686
<211> LENGTH: 21
<212> TYPE: DNA
<213> ORGANISM: Homo sapiens

<400> SEQUENCE: 686
cccctacagg yatgtggtgg t                                              21

<210> SEQ ID NO 687
<211> LENGTH: 21
<212> TYPE: DNA
<213> ORGANISM: Homo sapiens

<400> SEQUENCE: 687
tgaacatgat yctcccggac t                                              21

<210> SEQ ID NO 688
<211> LENGTH: 21
<212> TYPE: DNA
<213> ORGANISM: Homo sapiens

<400> SEQUENCE: 688
gcaggccatc ycggaggcag g                                              21

<210> SEQ ID NO 689
<211> LENGTH: 21
```

```
<212> TYPE: DNA
<213> ORGANISM: Homo sapiens

<400> SEQUENCE: 689
ggcctgcctg yggctgacct g                                              21

<210> SEQ ID NO 690
<211> LENGTH: 21
<212> TYPE: DNA
<213> ORGANISM: Homo sapiens

<400> SEQUENCE: 690
gcagctgcct yaatgactgc c                                              21

<210> SEQ ID NO 691
<211> LENGTH: 21
<212> TYPE: DNA
<213> ORGANISM: Homo sapiens

<400> SEQUENCE: 691
gttcgaatgt kagaacctct a                                              21

<210> SEQ ID NO 692
<211> LENGTH: 21
<212> TYPE: DNA
<213> ORGANISM: Homo sapiens

<400> SEQUENCE: 692
tgaccagttt yccgcacatg g                                              21

<210> SEQ ID NO 693
<211> LENGTH: 21
<212> TYPE: DNA
<213> ORGANISM: Homo sapiens

<400> SEQUENCE: 693
ctgacatcta ygtgctaggc t                                              21

<210> SEQ ID NO 694
<211> LENGTH: 21
<212> TYPE: DNA
<213> ORGANISM: Homo sapiens

<400> SEQUENCE: 694
tgcgggcacg scagatgcac c                                              21

<210> SEQ ID NO 695
<211> LENGTH: 21
<212> TYPE: DNA
<213> ORGANISM: Homo sapiens

<400> SEQUENCE: 695
tgctggcaat ygctgtggac c                                              21

<210> SEQ ID NO 696
<211> LENGTH: 21
<212> TYPE: DNA
<213> ORGANISM: Homo sapiens

<400> SEQUENCE: 696
tggcaattgc kgtggaccgc t                                              21

<210> SEQ ID NO 697
```

```
<211> LENGTH: 21
<212> TYPE: DNA
<213> ORGANISM: Homo sapiens

<400> SEQUENCE: 697
cctagatctc rggagttaat g                                              21

<210> SEQ ID NO 698
<211> LENGTH: 21
<212> TYPE: DNA
<213> ORGANISM: Homo sapiens

<400> SEQUENCE: 698
tctcctctgt yccataggt t                                               21

<210> SEQ ID NO 699
<211> LENGTH: 21
<212> TYPE: DNA
<213> ORGANISM: Homo sapiens

<400> SEQUENCE: 699
ttgatgtgga yggcaaccga a                                              21

<210> SEQ ID NO 700
<211> LENGTH: 21
<212> TYPE: DNA
<213> ORGANISM: Homo sapiens

<400> SEQUENCE: 700
atcaccatgg yctgcggctc c                                              21

<210> SEQ ID NO 701
<211> LENGTH: 21
<212> TYPE: DNA
<213> ORGANISM: Homo sapiens

<400> SEQUENCE: 701
tggacgaggt mcagaccgga g                                              21

<210> SEQ ID NO 702
<211> LENGTH: 21
<212> TYPE: DNA
<213> ORGANISM: Homo sapiens

<400> SEQUENCE: 702
attatgatgg rcctctgatg a                                              21

<210> SEQ ID NO 703
<211> LENGTH: 21
<212> TYPE: DNA
<213> ORGANISM: Homo sapiens

<400> SEQUENCE: 703
tgttctcgaa rgaatgccaa g                                              21

<210> SEQ ID NO 704
<211> LENGTH: 21
<212> TYPE: DNA
<213> ORGANISM: Homo sapiens

<400> SEQUENCE: 704
gcctaaacct stgtgaaccc a                                              21
```

```
<210> SEQ ID NO 705
<211> LENGTH: 21
<212> TYPE: DNA
<213> ORGANISM: Homo sapiens

<400> SEQUENCE: 705
taccaggaaa yctgtggagg a                                              21

<210> SEQ ID NO 706
<211> LENGTH: 21
<212> TYPE: DNA
<213> ORGANISM: Homo sapiens

<400> SEQUENCE: 706
tggccaggta yggtgtgaag c                                              21

<210> SEQ ID NO 707
<211> LENGTH: 21
<212> TYPE: DNA
<213> ORGANISM: Homo sapiens

<400> SEQUENCE: 707
tgaggtggca ytggcgtatg c                                              21

<210> SEQ ID NO 708
<211> LENGTH: 21
<212> TYPE: DNA
<213> ORGANISM: Homo sapiens

<400> SEQUENCE: 708
tgagtgaaaa yggagcattc c                                              21

<210> SEQ ID NO 709
<211> LENGTH: 21
<212> TYPE: DNA
<213> ORGANISM: Homo sapiens

<400> SEQUENCE: 709
ctctggtccc rtatctggta g                                              21

<210> SEQ ID NO 710
<211> LENGTH: 21
<212> TYPE: DNA
<213> ORGANISM: Homo sapiens

<400> SEQUENCE: 710 caggcccta yggcgccaac a                                               21

<210> SEQ ID NO 711
<211> LENGTH: 21
<212> TYPE: DNA
<213> ORGANISM: Homo sapiens

<400> SEQUENCE: 711
gacaaggact kgaatatttt c                                              21

<210> SEQ ID NO 712
<211> LENGTH: 21
<212> TYPE: DNA
<213> ORGANISM: Homo sapiens

<400> SEQUENCE: 712
aagagcatga yaaggcctgc g                                              21
```

<210> SEQ ID NO 713
<211> LENGTH: 21
<212> TYPE: DNA
<213> ORGANISM: Homo sapiens

<400> SEQUENCE: 713
cagtgacccg kcctctgtct c                                              21

<210> SEQ ID NO 714
<211> LENGTH: 21
<212> TYPE: DNA
<213> ORGANISM: Homo sapiens

<400> SEQUENCE: 714
ttgatttgga yaattctggt t                                              21

<210> SEQ ID NO 715
<211> LENGTH: 21
<212> TYPE: DNA
<213> ORGANISM: Homo sapiens

<400> SEQUENCE: 715
atgtgtgact yttatcagag a                                              21

<210> SEQ ID NO 716
<211> LENGTH: 21
<212> TYPE: DNA
<213> ORGANISM: Homo sapiens

<400> SEQUENCE: 716
caccacaaca ygcagacctt c                                              21

<210> SEQ ID NO 717
<211> LENGTH: 21
<212> TYPE: DNA
<213> ORGANISM: Homo sapiens

<400> SEQUENCE: 717
gtgctccggc rcgcctggac t                                              21

<210> SEQ ID NO 718
<211> LENGTH: 21
<212> TYPE: DNA
<213> ORGANISM: Homo sapiens

<400> SEQUENCE: 718
tgtgctccgg ygcgcctgga c                                              21

<210> SEQ ID NO 719
<211> LENGTH: 21
<212> TYPE: DNA
<213> ORGANISM: Homo sapiens

<400> SEQUENCE: 719
gcaaagctcc rccacaacat g                                              21

<210> SEQ ID NO 720
<211> LENGTH: 21
<212> TYPE: DNA
<213> ORGANISM: Homo sapiens

<400> SEQUENCE: 720
agttatcatc rtccaagttt a                                              21

<210> SEQ ID NO 721
<211> LENGTH: 21
<212> TYPE: DNA
<213> ORGANISM: Homo sapiens

<400> SEQUENCE: 721
gctggccttc rcgaccacac t                                              21

<210> SEQ ID NO 722
<211> LENGTH: 21
<212> TYPE: DNA
<213> ORGANISM: Homo sapiens

<400> SEQUENCE: 722
ctgctgccca ygggtcacac c                                              21

<210> SEQ ID NO 723
<211> LENGTH: 21
<212> TYPE: DNA
<213> ORGANISM: Homo sapiens

<400> SEQUENCE: 723
gctccaggcg ktgcttgttc c                                              21

<210> SEQ ID NO 724
<211> LENGTH: 21
<212> TYPE: DNA
<213> ORGANISM: Homo sapiens

<400> SEQUENCE: 724
cagaggtttg ytgggactcc c                                              21

<210> SEQ ID NO 725
<211> LENGTH: 21
<212> TYPE: DNA
<213> ORGANISM: Homo sapiens

<400> SEQUENCE: 725
ggatctggag ygagtggagt g                                              21

<210> SEQ ID NO 726
<211> LENGTH: 21
<212> TYPE: DNA
<213> ORGANISM: Homo sapiens

<400> SEQUENCE: 726
cgatgggacc rggacaggcc g                                              21

<210> SEQ ID NO 727
<211> LENGTH: 21
<212> TYPE: DNA
<213> ORGANISM: Homo sapiens

<400> SEQUENCE: 727
gggacaggcc rtggaagtgg a                                              21

<210> SEQ ID NO 728
<211> LENGTH: 21
<212> TYPE: DNA
<213> ORGANISM: Homo sapiens

<400> SEQUENCE: 728

-continued ccagaacctg sagtgcttct t                                              21

<210> SEQ ID NO 729
<211> LENGTH: 21
<212> TYPE: DNA
<213> ORGANISM: Homo sapiens

<400> SEQUENCE: 729
ccccacagcc mgagggcctc c                                              21

<210> SEQ ID NO 730
<211> LENGTH: 21
<212> TYPE: DNA
<213> ORGANISM: Homo sapiens

<400> SEQUENCE: 730
gccgtggaga mggtgaacat c                                              21

<210> SEQ ID NO 731
<211> LENGTH: 21
<212> TYPE: DNA
<213> ORGANISM: Homo sapiens

<400> SEQUENCE: 731
ctgctgaacc kcctggcaga c                                              21

<210> SEQ ID NO 732
<211> LENGTH: 21
<212> TYPE: DNA
<213> ORGANISM: Homo sapiens

<400> SEQUENCE: 732
tatggcccaa sagcaggtgc g                                              21

<210> SEQ ID NO 733
<211> LENGTH: 21
<212> TYPE: DNA
<213> ORGANISM: Homo sapiens

<400> SEQUENCE: 733
gcccgggaag ycttccgcct g                                              21

<210> SEQ ID NO 734
<211> LENGTH: 21
<212> TYPE: DNA
<213> ORGANISM: Homo sapiens

<400> SEQUENCE: 734
accctaccac yggggaggtc a                                              21

<210> SEQ ID NO 735
<211> LENGTH: 21
<212> TYPE: DNA
<213> ORGANISM: Homo sapiens

<400> SEQUENCE: 735
gggaggtcat ygggcacgtg g                                              21

<210> SEQ ID NO 736
<211> LENGTH: 21
<212> TYPE: DNA
<213> ORGANISM: Homo sapiens

<400> SEQUENCE: 736
cggggtatgg yccaacagca g                                                21

<210> SEQ ID NO 737
<211> LENGTH: 21
<212> TYPE: DNA
<213> ORGANISM: Homo sapiens

<400> SEQUENCE: 737
cgcccagcac rtggatgttg a                                                21

<210> SEQ ID NO 738
<211> LENGTH: 21
<212> TYPE: DNA
<213> ORGANISM: Homo sapiens

<400> SEQUENCE: 738
ccctcatcaa sgaggcaggc t                                                21

<210> SEQ ID NO 739
<211> LENGTH: 21
<212> TYPE: DNA
<213> ORGANISM: Homo sapiens

<400> SEQUENCE: 739
tgccacagac rattttgcgg a                                                21

<210> SEQ ID NO 740
<211> LENGTH: 21
<212> TYPE: DNA
<213> ORGANISM: Homo sapiens

<400> SEQUENCE: 740
accagcctga rgtgtctcag g                                                21

<210> SEQ ID NO 741
<211> LENGTH: 21
<212> TYPE: DNA
<213> ORGANISM: Homo sapiens

<400> SEQUENCE: 741
cagaccatgg ygtgtgacat c                                                21

<210> SEQ ID NO 742
<211> LENGTH: 21
<212> TYPE: DNA
<213> ORGANISM: Homo sapiens

<400> SEQUENCE: 742
tatattggca ygggctatta t                                                21

<210> SEQ ID NO 743
<211> LENGTH: 21
<212> TYPE: DNA
<213> ORGANISM: Homo sapiens

<400> SEQUENCE: 743
gtgccacaga sgattttgcg g                                                21

<210> SEQ ID NO 744
<211> LENGTH: 21
<212> TYPE: DNA
<213> ORGANISM: Homo sapiens

```
<400> SEQUENCE: 744
ctgcatgcca yttcaagcaa a                                              21

<210> SEQ ID NO 745
<211> LENGTH: 21
<212> TYPE: DNA
<213> ORGANISM: Homo sapiens

<400> SEQUENCE: 745
ggaaatttct ygttgatccc c                                              21

<210> SEQ ID NO 746
<211> LENGTH: 21
<212> TYPE: DNA
<213> ORGANISM: Homo sapiens

<400> SEQUENCE: 746
cattgtggct rctcagtgaa g                                              21

<210> SEQ ID NO 747
<211> LENGTH: 21
<212> TYPE: DNA
<213> ORGANISM: Homo sapiens

<400> SEQUENCE: 747
aaactgaaca rttcgtctga a                                              21

<210> SEQ ID NO 748
<211> LENGTH: 21
<212> TYPE: DNA
<213> ORGANISM: Homo sapiens

<400> SEQUENCE: 748
gacaggtcta yctagacggg g                                              21

<210> SEQ ID NO 749
<211> LENGTH: 21
<212> TYPE: DNA
<213> ORGANISM: Homo sapiens

<400> SEQUENCE: 749
ggtgggaatc wgtcgccctg g                                              21

<210> SEQ ID NO 750
<211> LENGTH: 21
<212> TYPE: DNA
<213> ORGANISM: Homo sapiens

<400> SEQUENCE: 750
ttagtcctct stccctaagt t                                              21

<210> SEQ ID NO 751
<211> LENGTH: 21
<212> TYPE: DNA
<213> ORGANISM: Homo sapiens

<400> SEQUENCE: 751
tggtgtatgt stctgactcc g                                              21

<210> SEQ ID NO 752
<211> LENGTH: 21
<212> TYPE: DNA
<213> ORGANISM: Homo sapiens
```

```
<400> SEQUENCE: 752
tgcctagtgg ycattggcag a                                              21

<210> SEQ ID NO 753
<211> LENGTH: 21
<212> TYPE: DNA
<213> ORGANISM: Homo sapiens

<400> SEQUENCE: 753
acctcacttc rtggtggtcc a                                              21

<210> SEQ ID NO 754
<211> LENGTH: 21
<212> TYPE: DNA
<213> ORGANISM: Homo sapiens

<400> SEQUENCE: 754
ttgctggtac wcttctatcc a                                              21

<210> SEQ ID NO 755
<211> LENGTH: 21
<212> TYPE: DNA
<213> ORGANISM: Homo sapiens

<400> SEQUENCE: 755
ttacccacga satgaggcag g                                              21

<210> SEQ ID NO 756
<211> LENGTH: 21
<212> TYPE: DNA
<213> ORGANISM: Homo sapiens

<400> SEQUENCE: 756
cccccagtcc scggtgatgc a                                              21

<210> SEQ ID NO 757
<211> LENGTH: 21
<212> TYPE: DNA
<213> ORGANISM: Homo sapiens

<400> SEQUENCE: 757
ggcaagaaga rcttcgagac t                                              21

<210> SEQ ID NO 758
<211> LENGTH: 21
<212> TYPE: DNA
<213> ORGANISM: Homo sapiens

<400> SEQUENCE: 758
tacgataaga wgcaaacgtg g                                              21

<210> SEQ ID NO 759
<211> LENGTH: 21
<212> TYPE: DNA
<213> ORGANISM: Homo sapiens

<400> SEQUENCE: 759
ccactcaaac ytttcaacaa a                                              21

<210> SEQ ID NO 760
<211> LENGTH: 21
<212> TYPE: DNA
```

<210> SEQ ID NO 760
<211> LENGTH: 21
<212> TYPE: DNA
<213> ORGANISM: Homo sapiens

<400> SEQUENCE: 760
tggcgggcaa ygtgctggtg t                                          21

<210> SEQ ID NO 761
<211> LENGTH: 21
<212> TYPE: DNA
<213> ORGANISM: Homo sapiens

<400> SEQUENCE: 761
gcagcctgcc rgagatcgac a                                          21

<210> SEQ ID NO 762
<211> LENGTH: 21
<212> TYPE: DNA
<213> ORGANISM: Homo sapiens

<400> SEQUENCE: 762
tcctggctgc rgtcaccacc a                                          21

<210> SEQ ID NO 763
<211> LENGTH: 21
<212> TYPE: DNA
<213> ORGANISM: Homo sapiens

<400> SEQUENCE: 763
aaggagcctg ycggggagaa c                                          21

<210> SEQ ID NO 764
<211> LENGTH: 21
<212> TYPE: DNA
<213> ORGANISM: Homo sapiens

<400> SEQUENCE: 764
agaccaaggc yggccgcatc a                                          21

<210> SEQ ID NO 765
<211> LENGTH: 21
<212> TYPE: DNA
<213> ORGANISM: Homo sapiens

<400> SEQUENCE: 765
gccgccgctc rgatgaggac t                                          21

<210> SEQ ID NO 766
<211> LENGTH: 21
<212> TYPE: DNA
<213> ORGANISM: Homo sapiens

<400> SEQUENCE: 766
actatggact yacagcagcc g                                          21

<210> SEQ ID NO 767
<211> LENGTH: 21
<212> TYPE: DNA
<213> ORGANISM: Homo sapiens

<400> SEQUENCE: 767
ataaaaagag ygaatagcac c                                          21

<210> SEQ ID NO 768
<211> LENGTH: 21

```
<212> TYPE: DNA
<213> ORGANISM: Homo sapiens

<400> SEQUENCE: 768
atagccagtg sagtgctgga g                                              21

<210> SEQ ID NO 769
<211> LENGTH: 21
<212> TYPE: DNA
<213> ORGANISM: Homo sapiens

<400> SEQUENCE: 769
accctaccgc yttcgttgtc a                                              21

<210> SEQ ID NO 770
<211> LENGTH: 21
<212> TYPE: DNA
<213> ORGANISM: Homo sapiens

<400> SEQUENCE: 770
cctgccggga sttgccttgt t                                              21

<210> SEQ ID NO 771
<211> LENGTH: 21
<212> TYPE: DNA
<213> ORGANISM: Homo sapiens

<400> SEQUENCE: 771
tggtggtcct stcctctctt g                                              21

<210> SEQ ID NO 772
<211> LENGTH: 21
<212> TYPE: DNA
<213> ORGANISM: Homo sapiens

<400> SEQUENCE: 772
tagtatttca kgtatgctgc t                                              21

<210> SEQ ID NO 773
<211> LENGTH: 21
<212> TYPE: DNA
<213> ORGANISM: Homo sapiens

<400> SEQUENCE: 773
agagtcccag rcccggccgg g                                              21

<210> SEQ ID NO 774
<211> LENGTH: 21
<212> TYPE: DNA
<213> ORGANISM: Homo sapiens

<400> SEQUENCE: 774
aacatcatgt ytcgggtaac a                                              21

<210> SEQ ID NO 775
<211> LENGTH: 21
<212> TYPE: DNA
<213> ORGANISM: Homo sapiens

<400> SEQUENCE: 775
ggtcaccctg rtcaccctgc c                                              21

<210> SEQ ID NO 776
```

<211> LENGTH: 21
<212> TYPE: DNA
<213> ORGANISM: Homo sapiens

<400> SEQUENCE: 776
ccaaaccgcc yagatgtctt a                                              21

<210> SEQ ID NO 777
<211> LENGTH: 21
<212> TYPE: DNA
<213> ORGANISM: Homo sapiens

<400> SEQUENCE: 777
cttgcggtga ragcgaattc c                                              21

<210> SEQ ID NO 778
<211> LENGTH: 21
<212> TYPE: DNA
<213> ORGANISM: Homo sapiens

<400> SEQUENCE: 778
tgcttaagga rcattccata c                                              21

<210> SEQ ID NO 779
<211> LENGTH: 21
<212> TYPE: DNA
<213> ORGANISM: Homo sapiens

<400> SEQUENCE: 779
agccaaatat sagcgatggc t                                              21

<210> SEQ ID NO 780
<211> LENGTH: 21
<212> TYPE: DNA
<213> ORGANISM: Homo sapiens

<400> SEQUENCE: 780
ctgaagttta raatgggtat c                                              21

<210> SEQ ID NO 781
<211> LENGTH: 21
<212> TYPE: DNA
<213> ORGANISM: Homo sapiens

<400> SEQUENCE: 781
tttaagaaaa rtggattgat t                                              21

<210> SEQ ID NO 782
<211> LENGTH: 21
<212> TYPE: DNA
<213> ORGANISM: Homo sapiens

<400> SEQUENCE: 782
tctgcgctgt wcctcaggtg t                                              21

<210> SEQ ID NO 783
<211> LENGTH: 21
<212> TYPE: DNA
<213> ORGANISM: Homo sapiens

<400> SEQUENCE: 783
cccgcaggga rttgcgtggt g                                              21

```
<210> SEQ ID NO 784
<211> LENGTH: 21
<212> TYPE: DNA
<213> ORGANISM: Homo sapiens

<400> SEQUENCE: 784
aaggagatcc rctacccacc c                                              21

<210> SEQ ID NO 785
<211> LENGTH: 21
<212> TYPE: DNA
<213> ORGANISM: Homo sapiens

<400> SEQUENCE: 785
tgccgggcgc rcctctcgct g                                              21

<210> SEQ ID NO 786
<211> LENGTH: 21
<212> TYPE: DNA
<213> ORGANISM: Homo sapiens

<400> SEQUENCE: 786
gtgccgccga rgaaaaagtg c                                              21

<210> SEQ ID NO 787
<211> LENGTH: 21
<212> TYPE: DNA
<213> ORGANISM: Homo sapiens

<400> SEQUENCE: 787
gttatcttgc wgagatctct g                                              21

<210> SEQ ID NO 788
<211> LENGTH: 21
<212> TYPE: DNA
<213> ORGANISM: Homo sapiens

<400> SEQUENCE: 788
tgcaaaatat ycaggagacc g                                              21

<210> SEQ ID NO 789
<211> LENGTH: 21
<212> TYPE: DNA
<213> ORGANISM: Homo sapiens

<400> SEQUENCE: 789
tggagttgat ytttcagtgc t                                              21

<210> SEQ ID NO 790
<211> LENGTH: 21
<212> TYPE: DNA
<213> ORGANISM: Homo sapiens

<400> SEQUENCE: 790
tctactggct stctaactaa t                                              21

<210> SEQ ID NO 791
<211> LENGTH: 21
<212> TYPE: DNA
<213> ORGANISM: Homo sapiens

<400> SEQUENCE: 791
ttgtcaaggc wgaatattac t                                              21
```

<210> SEQ ID NO 792
<211> LENGTH: 21
<212> TYPE: DNA
<213> ORGANISM: Homo sapiens

<400> SEQUENCE: 792
ggtcccgatg yacaccttgc a                                              21

<210> SEQ ID NO 793
<211> LENGTH: 21
<212> TYPE: DNA
<213> ORGANISM: Homo sapiens

<400> SEQUENCE: 793
aagaagtaat kgcaccgtct c                                              21

<210> SEQ ID NO 794
<211> LENGTH: 21
<212> TYPE: DNA
<213> ORGANISM: Homo sapiens

<400> SEQUENCE: 794
tcgctgtcat rttcctggct a                                              21

<210> SEQ ID NO 795
<211> LENGTH: 21
<212> TYPE: DNA
<213> ORGANISM: Homo sapiens

<400> SEQUENCE: 795
ggcatctaca rctgcattca t                                              21

<210> SEQ ID NO 796
<211> LENGTH: 21
<212> TYPE: DNA
<213> ORGANISM: Homo sapiens

<400> SEQUENCE: 796
ctatgtattc yagggacaac a                                              21

<210> SEQ ID NO 797
<211> LENGTH: 21
<212> TYPE: DNA
<213> ORGANISM: Homo sapiens

<400> SEQUENCE: 797
ggacattgac racatggcgg g                                              21

<210> SEQ ID NO 798
<211> LENGTH: 21
<212> TYPE: DNA
<213> ORGANISM: Homo sapiens

<400> SEQUENCE: 798
aggtgtccaa rctggagtgg c                                              21

<210> SEQ ID NO 799
<211> LENGTH: 21
<212> TYPE: DNA
<213> ORGANISM: Homo sapiens

<400> SEQUENCE: 799
ggtcacccgc raggtgaccg t                                              21

<210> SEQ ID NO 800
<211> LENGTH: 21
<212> TYPE: DNA
<213> ORGANISM: Homo sapiens

<400> SEQUENCE: 800
gaccagccca wgttgttggg c                                              21

<210> SEQ ID NO 801
<211> LENGTH: 21
<212> TYPE: DNA
<213> ORGANISM: Homo sapiens

<400> SEQUENCE: 801
ttggcatggt kgtaatccat a                                              21

<210> SEQ ID NO 802
<211> LENGTH: 21
<212> TYPE: DNA
<213> ORGANISM: Homo sapiens

<400> SEQUENCE: 802
aaatggtata waattcaaaa t                                              21

<210> SEQ ID NO 803
<211> LENGTH: 21
<212> TYPE: DNA
<213> ORGANISM: Homo sapiens

<400> SEQUENCE: 803
ttatctacca stgcttctca a                                              21

<210> SEQ ID NO 804
<211> LENGTH: 21
<212> TYPE: DNA
<213> ORGANISM: Homo sapiens

<400> SEQUENCE: 804
attgatcaaa rccaatcttt g                                              21

<210> SEQ ID NO 805
<211> LENGTH: 21
<212> TYPE: DNA
<213> ORGANISM: Homo sapiens

<400> SEQUENCE: 805
atttaaggac ragaccagca g                                              21

<210> SEQ ID NO 806
<211> LENGTH: 21
<212> TYPE: DNA
<213> ORGANISM: Homo sapiens

<400> SEQUENCE: 806
caagtcaaca ytggatattg t                                              21

<210> SEQ ID NO 807
<211> LENGTH: 21
<212> TYPE: DNA
<213> ORGANISM: Homo sapiens

<400> SEQUENCE: 807
tgcatgtgat yaagcgagat g                    21

<210> SEQ ID NO 808
<211> LENGTH: 21
<212> TYPE: DNA
<213> ORGANISM: Homo sapiens

<400> SEQUENCE: 808
caacacagct mgatatgtgg a                    21

<210> SEQ ID NO 809
<211> LENGTH: 21
<212> TYPE: DNA
<213> ORGANISM: Homo sapiens

<400> SEQUENCE: 809
gaagattgca magtatggta t                    21

<210> SEQ ID NO 810
<211> LENGTH: 21
<212> TYPE: DNA
<213> ORGANISM: Homo sapiens

<400> SEQUENCE: 810
gagtatgaaa satgacagca t                    21

<210> SEQ ID NO 811
<211> LENGTH: 21
<212> TYPE: DNA
<213> ORGANISM: Homo sapiens

<400> SEQUENCE: 811
tcagcactgg saatccctga a                    21

<210> SEQ ID NO 812
<211> LENGTH: 21
<212> TYPE: DNA
<213> ORGANISM: Homo sapiens

<400> SEQUENCE: 812
tcgctgcgcc kccactatgc t                    21

<210> SEQ ID NO 813
<211> LENGTH: 21
<212> TYPE: DNA
<213> ORGANISM: Homo sapiens

<400> SEQUENCE: 813
ttgacctctc saaggacatt c                    21

<210> SEQ ID NO 814
<211> LENGTH: 21
<212> TYPE: DNA
<213> ORGANISM: Homo sapiens

<400> SEQUENCE: 814
ccttgatggc rtatatttca g                    21

<210> SEQ ID NO 815
<211> LENGTH: 21
<212> TYPE: DNA
<213> ORGANISM: Homo sapiens

<400> SEQUENCE: 815

```
ctgtagaccg yggcttcttc a                                              21

<210> SEQ ID NO 816
<211> LENGTH: 21
<212> TYPE: DNA
<213> ORGANISM: Homo sapiens

<400> SEQUENCE: 816
tcagaactag ygagacgggc a                                              21

<210> SEQ ID NO 817
<211> LENGTH: 21
<212> TYPE: DNA
<213> ORGANISM: Homo sapiens

<400> SEQUENCE: 817
ggggtgatca raagaaagct c                                              21

<210> SEQ ID NO 818
<211> LENGTH: 21
<212> TYPE: DNA
<213> ORGANISM: Homo sapiens

<400> SEQUENCE: 818
caattgtggc yattgcatca t                                              21

<210> SEQ ID NO 819
<211> LENGTH: 21
<212> TYPE: DNA
<213> ORGANISM: Homo sapiens

<400> SEQUENCE: 819
tggtggacaa ygagctgcct g                                              21

<210> SEQ ID NO 820
<211> LENGTH: 21
<212> TYPE: DNA
<213> ORGANISM: Homo sapiens

<400> SEQUENCE: 820
tgaatcttag ygtgacaact c                                              21

<210> SEQ ID NO 821
<211> LENGTH: 21
<212> TYPE: DNA
<213> ORGANISM: Homo sapiens

<400> SEQUENCE: 821
ctgaatacaa yaacttcaag t                                              21

<210> SEQ ID NO 822
<211> LENGTH: 21
<212> TYPE: DNA
<213> ORGANISM: Homo sapiens

<400> SEQUENCE: 822
agctgcgcta yggcgaagac g                                              21

<210> SEQ ID NO 823
<211> LENGTH: 21
<212> TYPE: DNA
<213> ORGANISM: Homo sapiens
```

```
<400> SEQUENCE: 823
tgggccagtc ygctcgagat g                                              21

<210> SEQ ID NO 824
<211> LENGTH: 21
<212> TYPE: DNA
<213> ORGANISM: Homo sapiens

<400> SEQUENCE: 824
tgcctgactt ygatgtggcc c                                              21

<210> SEQ ID NO 825
<211> LENGTH: 21
<212> TYPE: DNA
<213> ORGANISM: Homo sapiens

<400> SEQUENCE: 825
cccagagcac rgtggtggca g                                              21

<210> SEQ ID NO 826
<211> LENGTH: 21
<212> TYPE: DNA
<213> ORGANISM: Homo sapiens

<400> SEQUENCE: 826
ctgtgtcttc stgatctgca g                                              21

<210> SEQ ID NO 827
<211> LENGTH: 21
<212> TYPE: DNA
<213> ORGANISM: Homo sapiens

<400> SEQUENCE: 827
tggataagac ycgagctttg a                                              21

<210> SEQ ID NO 828
<211> LENGTH: 21
<212> TYPE: DNA
<213> ORGANISM: Homo sapiens

<400> SEQUENCE: 828
gatgctatta rgaaagccca c                                              21

<210> SEQ ID NO 829
<211> LENGTH: 21
<212> TYPE: DNA
<213> ORGANISM: Homo sapiens

<400> SEQUENCE: 829
cccagatata ytacaactca a                                              21

<210> SEQ ID NO 830
<211> LENGTH: 21
<212> TYPE: DNA
<213> ORGANISM: Homo sapiens

<400> SEQUENCE: 830
aactatctat raaaagccaa a                                              21

<210> SEQ ID NO 831
<211> LENGTH: 21
<212> TYPE: DNA
<213> ORGANISM: Homo sapiens
```

<400> SEQUENCE: 831
aactattggg waatgtgttc a                                              21

<210> SEQ ID NO 832
<211> LENGTH: 21
<212> TYPE: DNA
<213> ORGANISM: Homo sapiens

<400> SEQUENCE: 832
aatctgttca rtacagggat t                                              21

<210> SEQ ID NO 833
<211> LENGTH: 21
<212> TYPE: DNA
<213> ORGANISM: Homo sapiens

<400> SEQUENCE: 833
ctgtcagatt rtagcaatga a                                              21

<210> SEQ ID NO 834
<211> LENGTH: 21
<212> TYPE: DNA
<213> ORGANISM: Homo sapiens

<400> SEQUENCE: 834
tatagagata yacggaattc c                                              21

<210> SEQ ID NO 835
<211> LENGTH: 21
<212> TYPE: DNA
<213> ORGANISM: Homo sapiens

<400> SEQUENCE: 835
ttgaagggcc raggagatct g                                              21

<210> SEQ ID NO 836
<211> LENGTH: 21
<212> TYPE: DNA
<213> ORGANISM: Homo sapiens

<400> SEQUENCE: 836
gggccaagga ratctgttga a                                              21

<210> SEQ ID NO 837
<211> LENGTH: 21
<212> TYPE: DNA
<213> ORGANISM: Homo sapiens

<400> SEQUENCE: 837 acattttttga ycctgagcaa a                                             21

<210> SEQ ID NO 838
<211> LENGTH: 21
<212> TYPE: DNA
<213> ORGANISM: Homo sapiens

<400> SEQUENCE: 838
aagttgcctt ytgatccaga t                                              21

<210> SEQ ID NO 839
<211> LENGTH: 21
<212> TYPE: DNA

<210> SEQ ID NO 839
<211> LENGTH: 21
<212> TYPE: DNA
<213> ORGANISM: Homo sapiens

<400> SEQUENCE: 839
aattaaaaag watgatcatt g                      21

<210> SEQ ID NO 840
<211> LENGTH: 21
<212> TYPE: DNA
<213> ORGANISM: Homo sapiens

<400> SEQUENCE: 840
aggtctttgg yaataaactc t                      21

<210> SEQ ID NO 841
<211> LENGTH: 21
<212> TYPE: DNA
<213> ORGANISM: Homo sapiens

<400> SEQUENCE: 841
ttcatatcaa ratcatcagt g                      21

<210> SEQ ID NO 842
<211> LENGTH: 21
<212> TYPE: DNA
<213> ORGANISM: Homo sapiens

<400> SEQUENCE: 842
tgaatgtttg yagcctggat a                      21

<210> SEQ ID NO 843
<211> LENGTH: 21
<212> TYPE: DNA
<213> ORGANISM: Homo sapiens

<400> SEQUENCE: 843
ctcatcacca rtgacaatac t                      21

<210> SEQ ID NO 844
<211> LENGTH: 21
<212> TYPE: DNA
<213> ORGANISM: Homo sapiens

<400> SEQUENCE: 844
ttgatgacat ytttaaaata g                      21

<210> SEQ ID NO 845
<211> LENGTH: 21
<212> TYPE: DNA
<213> ORGANISM: Homo sapiens

<400> SEQUENCE: 845
tagaaatggc rgacacagtc c                      21

<210> SEQ ID NO 846
<211> LENGTH: 21
<212> TYPE: DNA
<213> ORGANISM: Homo sapiens

<400> SEQUENCE: 846
tgacatcttt waaatagcgg t                      21

<210> SEQ ID NO 847
<211> LENGTH: 21

```
<212> TYPE: DNA
<213> ORGANISM: Homo sapiens

<400> SEQUENCE: 847
tctgtcatct yggctcatca c                                          21

<210> SEQ ID NO 848
<211> LENGTH: 21
<212> TYPE: DNA
<213> ORGANISM: Homo sapiens

<400> SEQUENCE: 848
gagggctgcc yggaacgtct c                                          21

<210> SEQ ID NO 849
<211> LENGTH: 21
<212> TYPE: DNA
<213> ORGANISM: Homo sapiens

<400> SEQUENCE: 849
atgggagcca ygtggactac a                                          21

<210> SEQ ID NO 850
<211> LENGTH: 21
<212> TYPE: DNA
<213> ORGANISM: Homo sapiens

<400> SEQUENCE: 850
ggcttgaata ytgcctcaag g                                          21

<210> SEQ ID NO 851
<211> LENGTH: 21
<212> TYPE: DNA
<213> ORGANISM: Homo sapiens

<400> SEQUENCE: 851
tcagtgcgga yaactataca c                                          21

<210> SEQ ID NO 852
<211> LENGTH: 21
<212> TYPE: DNA
<213> ORGANISM: Homo sapiens

<400> SEQUENCE: 852
catgccttct yccaccttcg g                                          21

<210> SEQ ID NO 853
<211> LENGTH: 21
<212> TYPE: DNA
<213> ORGANISM: Homo sapiens

<400> SEQUENCE: 853
agtggctatc rggagtttgt a                                          21

<210> SEQ ID NO 854
<211> LENGTH: 21
<212> TYPE: DNA
<213> ORGANISM: Homo sapiens

<400> SEQUENCE: 854
tgttataatg sacaagccat a                                          21

<210> SEQ ID NO 855
```

```
<211> LENGTH: 21
<212> TYPE: DNA
<213> ORGANISM: Homo sapiens

<400> SEQUENCE: 855
cctgagtgtc rtctatcggg a                                              21

<210> SEQ ID NO 856
<211> LENGTH: 21
<212> TYPE: DNA
<213> ORGANISM: Homo sapiens

<400> SEQUENCE: 856
ttttaatgca ygatgtagct t                                              21

<210> SEQ ID NO 857
<211> LENGTH: 21
<212> TYPE: DNA
<213> ORGANISM: Homo sapiens

<400> SEQUENCE: 857
tcctcgtggg yctcagcggg g                                              21

<210> SEQ ID NO 858
<211> LENGTH: 21
<212> TYPE: DNA
<213> ORGANISM: Homo sapiens

<400> SEQUENCE: 858
agtcaagcat yctgggcctg c                                              21

<210> SEQ ID NO 859
<211> LENGTH: 21
<212> TYPE: DNA
<213> ORGANISM: Homo sapiens

<400> SEQUENCE: 859
gcctccgtgt stcccaccga g                                              21

<210> SEQ ID NO 860
<211> LENGTH: 21
<212> TYPE: DNA
<213> ORGANISM: Homo sapiens

<400> SEQUENCE: 860
acgatcgccc kgccagagat a                                              21

<210> SEQ ID NO 861
<211> LENGTH: 21
<212> TYPE: DNA
<213> ORGANISM: Homo sapiens

<400> SEQUENCE: 861
aggaggtggc ragaggcgtg c                                              21

<210> SEQ ID NO 862
<211> LENGTH: 21
<212> TYPE: DNA
<213> ORGANISM: Homo sapiens

<400> SEQUENCE: 862
cattgccatt rttctgaggt t                                              21
```

<210> SEQ ID NO 863
<211> LENGTH: 21
<212> TYPE: DNA
<213> ORGANISM: Homo sapiens

<400> SEQUENCE: 863
ccagtgcaag mttcttcttc a                                    21

<210> SEQ ID NO 864
<211> LENGTH: 21
<212> TYPE: DNA
<213> ORGANISM: Homo sapiens

<400> SEQUENCE: 864
ctactaataa wgacgatgat a                                    21

<210> SEQ ID NO 865
<211> LENGTH: 21
<212> TYPE: DNA
<213> ORGANISM: Homo sapiens

<400> SEQUENCE: 865
ttccccagat rgctggctgg g                                    21

<210> SEQ ID NO 866
<211> LENGTH: 21
<212> TYPE: DNA
<213> ORGANISM: Homo sapiens

<400> SEQUENCE: 866
atacagacta yttcttcccc a                                    21

<210> SEQ ID NO 867
<211> LENGTH: 21
<212> TYPE: DNA
<213> ORGANISM: Homo sapiens

<400> SEQUENCE: 867
tcagagggtc rtcacacaca a                                    21

<210> SEQ ID NO 868
<211> LENGTH: 21
<212> TYPE: DNA
<213> ORGANISM: Homo sapiens

<400> SEQUENCE: 868
ggaagcccca mcaaattcca g                                    21

<210> SEQ ID NO 869
<211> LENGTH: 21
<212> TYPE: DNA
<213> ORGANISM: Homo sapiens

<400> SEQUENCE: 869
ctggagacaa ragcccacag a                                    21

<210> SEQ ID NO 870
<211> LENGTH: 21
<212> TYPE: DNA
<213> ORGANISM: Homo sapiens

<400> SEQUENCE: 870
cctcttgatg rtctttgtgg c                                    21

<210> SEQ ID NO 871
<211> LENGTH: 21
<212> TYPE: DNA
<213> ORGANISM: Homo sapiens

<400> SEQUENCE: 871
atcatggtgc ytggctgcca g                                              21

<210> SEQ ID NO 872
<211> LENGTH: 21
<212> TYPE: DNA
<213> ORGANISM: Homo sapiens

<400> SEQUENCE: 872
aaagtccaat scagccagtg g                                              21

<210> SEQ ID NO 873
<211> LENGTH: 21
<212> TYPE: DNA
<213> ORGANISM: Homo sapiens

<400> SEQUENCE: 873
acgatgaccc rccagagatc c                                              21

<210> SEQ ID NO 874
<211> LENGTH: 21
<212> TYPE: DNA
<213> ORGANISM: Homo sapiens

<400> SEQUENCE: 874
aaatgaccca ygggaagaca a                                              21

<210> SEQ ID NO 875
<211> LENGTH: 21
<212> TYPE: DNA
<213> ORGANISM: Homo sapiens

<400> SEQUENCE: 875
agccccagct matatgcaca g                                              21

<210> SEQ ID NO 876
<211> LENGTH: 21
<212> TYPE: DNA
<213> ORGANISM: Homo sapiens

<400> SEQUENCE: 876
ctggtagtag sccctcagtg c                                              21

<210> SEQ ID NO 877
<211> LENGTH: 21
<212> TYPE: DNA
<213> ORGANISM: Homo sapiens

<400> SEQUENCE: 877
cctgccagtg ycctcaccgg t                                              21

<210> SEQ ID NO 878
<211> LENGTH: 21
<212> TYPE: DNA
<213> ORGANISM: Homo sapiens

<400> SEQUENCE: 878
tgatgctgag yttgaaactg g                                              21

<210> SEQ ID NO 879
<211> LENGTH: 21
<212> TYPE: DNA
<213> ORGANISM: Homo sapiens

<400> SEQUENCE: 879
cacgtgattg rcaagttcct a                                              21

<210> SEQ ID NO 880
<211> LENGTH: 21
<212> TYPE: DNA
<213> ORGANISM: Homo sapiens

<400> SEQUENCE: 880
cttcgagccc rcgtgattga c                                              21

<210> SEQ ID NO 881
<211> LENGTH: 21
<212> TYPE: DNA
<213> ORGANISM: Homo sapiens

<400> SEQUENCE: 881
gctggcgggc raatacgcag a                                              21

<210> SEQ ID NO 882
<211> LENGTH: 21
<212> TYPE: DNA
<213> ORGANISM: Homo sapiens

<400> SEQUENCE: 882
actgatgtcc rtcctttgta t                                              21

<210> SEQ ID NO 883
<211> LENGTH: 21
<212> TYPE: DNA
<213> ORGANISM: Homo sapiens

<400> SEQUENCE: 883
ccttactgaa rgtttctagt t                                              21

<210> SEQ ID NO 884
<211> LENGTH: 21
<212> TYPE: DNA
<213> ORGANISM: Homo sapiens

<400> SEQUENCE: 884
ctgttctccc raaaccagac t                                              21

<210> SEQ ID NO 885
<211> LENGTH: 21
<212> TYPE: DNA
<213> ORGANISM: Homo sapiens

<400> SEQUENCE: 885
ccagaagaca rtgaaagtca c                                              21

<210> SEQ ID NO 886
<211> LENGTH: 21
<212> TYPE: DNA
<213> ORGANISM: Homo sapiens

<400> SEQUENCE: 886

-continued ttaagaacat rgcttcccat c                                              21

<210> SEQ ID NO 887
<211> LENGTH: 21
<212> TYPE: DNA
<213> ORGANISM: Homo sapiens

<400> SEQUENCE: 887
tacattctaa rcattggagc a                                              21

<210> SEQ ID NO 888
<211> LENGTH: 21
<212> TYPE: DNA
<213> ORGANISM: Homo sapiens

<400> SEQUENCE: 888
gtttgcacac rgaacaccta t                                              21

<210> SEQ ID NO 889
<211> LENGTH: 21
<212> TYPE: DNA
<213> ORGANISM: Homo sapiens

<400> SEQUENCE: 889
accctccaat yattgctcga t                                              21

<210> SEQ ID NO 890
<211> LENGTH: 21
<212> TYPE: DNA
<213> ORGANISM: Homo sapiens

<400> SEQUENCE: 890
gagaattatc rcttccatgc a                                              21

<210> SEQ ID NO 891
<211> LENGTH: 21
<212> TYPE: DNA
<213> ORGANISM: Homo sapiens

<400> SEQUENCE: 891
tgacagtaca rgaatttgct c                                              21

<210> SEQ ID NO 892
<211> LENGTH: 21
<212> TYPE: DNA
<213> ORGANISM: Homo sapiens

<400> SEQUENCE: 892
tttttcacca kctttgatga g                                              21

<210> SEQ ID NO 893
<211> LENGTH: 21
<212> TYPE: DNA
<213> ORGANISM: Homo sapiens

<400> SEQUENCE: 893
accacaattc yagaaaatga c                                              21

<210> SEQ ID NO 894
<211> LENGTH: 21
<212> TYPE: DNA
<213> ORGANISM: Homo sapiens

<400> SEQUENCE: 894
tgcaagtgga yttccagaag a 21

<210> SEQ ID NO 895
<211> LENGTH: 21
<212> TYPE: DNA
<213> ORGANISM: Homo sapiens

<400> SEQUENCE: 895
cagagaatat mcaacgcttt c 21

<210> SEQ ID NO 896
<211> LENGTH: 21
<212> TYPE: DNA
<213> ORGANISM: Homo sapiens

<400> SEQUENCE: 896
gagaatatac macgctttct c 21

<210> SEQ ID NO 897
<211> LENGTH: 21
<212> TYPE: DNA
<213> ORGANISM: Homo sapiens

<400> SEQUENCE: 897
cgcctttctt matcatccag a 21

<210> SEQ ID NO 898
<211> LENGTH: 21
<212> TYPE: DNA
<213> ORGANISM: Homo sapiens

<400> SEQUENCE: 898
tcggcatgtt ygcgtcggcc t 21

<210> SEQ ID NO 899
<211> LENGTH: 21
<212> TYPE: DNA
<213> ORGANISM: Homo sapiens

<400> SEQUENCE: 899
gcctggccga yctggccgtg g 21

<210> SEQ ID NO 900
<211> LENGTH: 21
<212> TYPE: DNA
<213> ORGANISM: Homo sapiens

<400> SEQUENCE: 900
tctctccgcc rgtcccgacg c 21

<210> SEQ ID NO 901
<211> LENGTH: 21
<212> TYPE: DNA
<213> ORGANISM: Homo sapiens

<400> SEQUENCE: 901
agactctgca rcagcccgcg c 21

<210> SEQ ID NO 902
<211> LENGTH: 21
<212> TYPE: DNA
<213> ORGANISM: Homo sapiens

```
<400> SEQUENCE: 902
ccttgaatag mtgctgtaat c                                            21

<210> SEQ ID NO 903
<211> LENGTH: 21
<212> TYPE: DNA
<213> ORGANISM: Homo sapiens

<400> SEQUENCE: 903
tgtaatccct rgatatacat g                                            21

<210> SEQ ID NO 904
<211> LENGTH: 21
<212> TYPE: DNA
<213> ORGANISM: Homo sapiens

<400> SEQUENCE: 904
aatatcctgt rgaaaaacta a                                            21

<210> SEQ ID NO 905
<211> LENGTH: 21
<212> TYPE: DNA
<213> ORGANISM: Homo sapiens

<400> SEQUENCE: 905
ttgtggaagc rgatacccca g                                            21

<210> SEQ ID NO 906
<211> LENGTH: 21
<212> TYPE: DNA
<213> ORGANISM: Homo sapiens

<400> SEQUENCE: 906
ctcttccaga yatttgttat c                                            21

<210> SEQ ID NO 907
<211> LENGTH: 21
<212> TYPE: DNA
<213> ORGANISM: Homo sapiens

<400> SEQUENCE: 907
ctctgaagac wtggagatac t                                            21

<210> SEQ ID NO 908
<211> LENGTH: 21
<212> TYPE: DNA
<213> ORGANISM: Homo sapiens

<400> SEQUENCE: 908
ctcatacgca rcctcaatgt c                                            21

<210> SEQ ID NO 909
<211> LENGTH: 21
<212> TYPE: DNA
<213> ORGANISM: Homo sapiens

<400> SEQUENCE: 909
agcgactgca wcttcctccc g                                            21

<210> SEQ ID NO 910
<211> LENGTH: 21
<212> TYPE: DNA
<213> ORGANISM: Homo sapiens
```

```
<400> SEQUENCE: 910
agtgcaacat maattagcag a                                              21

<210> SEQ ID NO 911
<211> LENGTH: 21
<212> TYPE: DNA
<213> ORGANISM: Homo sapiens

<400> SEQUENCE: 911
aaggacttat ytggagacaa a                                              21

<210> SEQ ID NO 912
<211> LENGTH: 21
<212> TYPE: DNA
<213> ORGANISM: Homo sapiens

<400> SEQUENCE: 912 tgagggtct rgagggaaac t                                               21

<210> SEQ ID NO 913
<211> LENGTH: 21
<212> TYPE: DNA
<213> ORGANISM: Homo sapiens

<400> SEQUENCE: 913
ggttctctgg mccctgcatt c                                              21

<210> SEQ ID NO 914
<211> LENGTH: 21
<212> TYPE: DNA
<213> ORGANISM: Homo sapiens

<400> SEQUENCE: 914
aaaggagcga wcccacaatg t                                              21

<210> SEQ ID NO 915
<211> LENGTH: 21
<212> TYPE: DNA
<213> ORGANISM: Homo sapiens

<400> SEQUENCE: 915
cgcactggct rgcctgcatc t                                              21

<210> SEQ ID NO 916
<211> LENGTH: 21
<212> TYPE: DNA
<213> ORGANISM: Homo sapiens

<400> SEQUENCE: 916
acttcacctt yagcagcctc a                                              21

<210> SEQ ID NO 917
<211> LENGTH: 21
<212> TYPE: DNA
<213> ORGANISM: Homo sapiens

<400> SEQUENCE: 917
ccggccgcat ygccgtccac t                                              21

<210> SEQ ID NO 918
<211> LENGTH: 21
<212> TYPE: DNA
```

```
<213> ORGANISM: Homo sapiens

<400> SEQUENCE: 918
ccctcatgta ygctagcatc t                                              21

<210> SEQ ID NO 919
<211> LENGTH: 21
<212> TYPE: DNA
<213> ORGANISM: Homo sapiens

<400> SEQUENCE: 919
ccctgctctg rtcaccaccc g                                              21

<210> SEQ ID NO 920
<211> LENGTH: 21
<212> TYPE: DNA
<213> ORGANISM: Homo sapiens

<400> SEQUENCE: 920
accagcttac rcacaccgag g                                              21

<210> SEQ ID NO 921
<211> LENGTH: 21
<212> TYPE: DNA
<213> ORGANISM: Homo sapiens

<400> SEQUENCE: 921
gtggagagac yctgcatagc t                                              21

<210> SEQ ID NO 922
<211> LENGTH: 21
<212> TYPE: DNA
<213> ORGANISM: Homo sapiens

<400> SEQUENCE: 922
gagccatctt mcagcctgtt t                                              21

<210> SEQ ID NO 923
<211> LENGTH: 21
<212> TYPE: DNA
<213> ORGANISM: Homo sapiens

<400> SEQUENCE: 923
tattccatat rttaaagaaa g                                              21

<210> SEQ ID NO 924
<211> LENGTH: 21
<212> TYPE: DNA
<213> ORGANISM: Homo sapiens

<400> SEQUENCE: 924
cagaagaaac yagtacgtgt a                                              21

<210> SEQ ID NO 925
<211> LENGTH: 21
<212> TYPE: DNA
<213> ORGANISM: Homo sapiens

<400> SEQUENCE: 925
tgggaacgtt kcaatgaatt a                                              21

<210> SEQ ID NO 926
<211> LENGTH: 21
```

```
<212> TYPE: DNA
<213> ORGANISM: Homo sapiens

<400> SEQUENCE: 926
acatggcttc rgacatcctg c                                               21

<210> SEQ ID NO 927
<211> LENGTH: 21
<212> TYPE: DNA
<213> ORGANISM: Homo sapiens

<400> SEQUENCE: 927
gcacaagagg mggcttccgg a                                               21

<210> SEQ ID NO 928
<211> LENGTH: 21
<212> TYPE: DNA
<213> ORGANISM: Homo sapiens

<400> SEQUENCE: 928
atgacatgga ygaggaggac t                                               21

<210> SEQ ID NO 929
<211> LENGTH: 21
<212> TYPE: DNA
<213> ORGANISM: Homo sapiens

<400> SEQUENCE: 929
agttttccgg ragtccctac a                                               21

<210> SEQ ID NO 930
<211> LENGTH: 21
<212> TYPE: DNA
<213> ORGANISM: Homo sapiens

<400> SEQUENCE: 930
gctcccccta ytattatagc g                                               21

<210> SEQ ID NO 931
<211> LENGTH: 21
<212> TYPE: DNA
<213> ORGANISM: Homo sapiens

<400> SEQUENCE: 931
gtcctgcccc mctcatcagc a                                               21

<210> SEQ ID NO 932
<211> LENGTH: 21
<212> TYPE: DNA
<213> ORGANISM: Homo sapiens

<400> SEQUENCE: 932
tggcctctcc rgcagagtca g                                               21

<210> SEQ ID NO 933
<211> LENGTH: 21
<212> TYPE: DNA
<213> ORGANISM: Homo sapiens

<400> SEQUENCE: 933
catagagggt yccaggtccc c                                               21

<210> SEQ ID NO 934
```

```
<211> LENGTH: 21
<212> TYPE: DNA
<213> ORGANISM: Homo sapiens

<400> SEQUENCE: 934
ccggacagga rgtgcattcc c                                              21

<210> SEQ ID NO 935
<211> LENGTH: 21
<212> TYPE: DNA
<213> ORGANISM: Homo sapiens

<400> SEQUENCE: 935
atgcagccat ygaactgcct a                                              21

<210> SEQ ID NO 936
<211> LENGTH: 21
<212> TYPE: DNA
<213> ORGANISM: Homo sapiens

<400> SEQUENCE: 936
aactctttca ytgttgtttc a                                              21

<210> SEQ ID NO 937
<211> LENGTH: 21
<212> TYPE: DNA
<213> ORGANISM: Homo sapiens

<400> SEQUENCE: 937
ccatggtgcc rgtggcaggc c                                              21

<210> SEQ ID NO 938
<211> LENGTH: 21
<212> TYPE: DNA
<213> ORGANISM: Homo sapiens

<400> SEQUENCE: 938
actctgaagt rattcgttat g                                              21

<210> SEQ ID NO 939
<211> LENGTH: 21
<212> TYPE: DNA
<213> ORGANISM: Homo sapiens

<400> SEQUENCE: 939
gttccaatgc rcatctgggc g                                              21

<210> SEQ ID NO 940
<211> LENGTH: 21
<212> TYPE: DNA
<213> ORGANISM: Homo sapiens

<400> SEQUENCE: 940
acttgctctg raaatgaatt c                                              21

<210> SEQ ID NO 941
<211> LENGTH: 21
<212> TYPE: DNA
<213> ORGANISM: Homo sapiens

<400> SEQUENCE: 941
actccttatg scatcactgt t                                              21
```

-continued

<210> SEQ ID NO 942
<211> LENGTH: 21
<212> TYPE: DNA
<213> ORGANISM: Homo sapiens

<400> SEQUENCE: 942
ttgcttggaa racaatggtg g                                              21

<210> SEQ ID NO 943
<211> LENGTH: 21
<212> TYPE: DNA
<213> ORGANISM: Homo sapiens

<400> SEQUENCE: 943
tacacaaaat rtcataattc a                                              21

<210> SEQ ID NO 944
<211> LENGTH: 21
<212> TYPE: DNA
<213> ORGANISM: Homo sapiens

<400> SEQUENCE: 944
catctttgaa saccagttat a                                              21

<210> SEQ ID NO 945
<211> LENGTH: 21
<212> TYPE: DNA
<213> ORGANISM: Homo sapiens

<400> SEQUENCE: 945
tcatggccac rgaccccag t                                               21

<210> SEQ ID NO 946
<211> LENGTH: 21
<212> TYPE: DNA
<213> ORGANISM: Homo sapiens

<400> SEQUENCE: 946
agtggctggc rgtgggcatg g                                              21

<210> SEQ ID NO 947
<211> LENGTH: 21
<212> TYPE: DNA
<213> ORGANISM: Homo sapiens

<400> SEQUENCE: 947
ccatggcaga rttgaatgcc a                                              21

<210> SEQ ID NO 948
<211> LENGTH: 21
<212> TYPE: DNA
<213> ORGANISM: Homo sapiens

<400> SEQUENCE: 948
atcgccaaga rattgaatac g                                              21

<210> SEQ ID NO 949
<211> LENGTH: 21
<212> TYPE: DNA
<213> ORGANISM: Homo sapiens

<400> SEQUENCE: 949
gccacacaga yggagccagc t                                              21

<210> SEQ ID NO 950
<211> LENGTH: 21
<212> TYPE: DNA
<213> ORGANISM: Homo sapiens

<400> SEQUENCE: 950
ccgcctgcta ygccctggcc a                                    21

<210> SEQ ID NO 951
<211> LENGTH: 21
<212> TYPE: DNA
<213> ORGANISM: Homo sapiens

<400> SEQUENCE: 951
acaaatacat ygtgacaggc t                                    21

<210> SEQ ID NO 952
<211> LENGTH: 21
<212> TYPE: DNA
<213> ORGANISM: Homo sapiens

<400> SEQUENCE: 952
cggacagcgt ygccctgagg a                                    21

<210> SEQ ID NO 953
<211> LENGTH: 21
<212> TYPE: DNA
<213> ORGANISM: Homo sapiens

<400> SEQUENCE: 953
ctgagttgtg wcatctccag a                                    21

<210> SEQ ID NO 954
<211> LENGTH: 21
<212> TYPE: DNA
<213> ORGANISM: Homo sapiens

<400> SEQUENCE: 954
tgtcaccctc sgaaagcctc c                                    21

<210> SEQ ID NO 955
<211> LENGTH: 21
<212> TYPE: DNA
<213> ORGANISM: Homo sapiens

<400> SEQUENCE: 955
tggacaacac rgtgcgctcc t                                    21

<210> SEQ ID NO 956
<211> LENGTH: 21
<212> TYPE: DNA
<213> ORGANISM: Homo sapiens

<400> SEQUENCE: 956
acctggcctc rcccacgccc c                                    21

<210> SEQ ID NO 957
<211> LENGTH: 21
<212> TYPE: DNA
<213> ORGANISM: Homo sapiens

<400> SEQUENCE: 957
ggcttcgcca rcgccaacct g                                    21

-continued

<210> SEQ ID NO 958
<211> LENGTH: 21
<212> TYPE: DNA
<213> ORGANISM: Homo sapiens

<400> SEQUENCE: 958
cagcgccaac ytgcagggca g                                              21

<210> SEQ ID NO 959
<211> LENGTH: 21
<212> TYPE: DNA
<213> ORGANISM: Homo sapiens

<400> SEQUENCE: 959
gccgtggata ycggcgtccc t                                              21

<210> SEQ ID NO 960
<211> LENGTH: 21
<212> TYPE: DNA
<213> ORGANISM: Homo sapiens

<400> SEQUENCE: 960
agtggtttta ygaatatggg a                                              21

<210> SEQ ID NO 961
<211> LENGTH: 21
<212> TYPE: DNA
<213> ORGANISM: Homo sapiens

<400> SEQUENCE: 961
gagagaagcc stacgaatgt g                                              21

<210> SEQ ID NO 962
<211> LENGTH: 21
<212> TYPE: DNA
<213> ORGANISM: Homo sapiens

<400> SEQUENCE: 962
agccagcagt ygcagctggt t                                              21

<210> SEQ ID NO 963
<211> LENGTH: 21
<212> TYPE: DNA
<213> ORGANISM: Homo sapiens

<400> SEQUENCE: 963
gaggcagcgg ycccgggcct g                                              21

<210> SEQ ID NO 964
<211> LENGTH: 21
<212> TYPE: DNA
<213> ORGANISM: Homo sapiens

<400> SEQUENCE: 964
taaaagagag rgcggattcc c                                              21

<210> SEQ ID NO 965
<211> LENGTH: 21
<212> TYPE: DNA
<213> ORGANISM: Homo sapiens

<400> SEQUENCE: 965

```
cccttcgacc mgtcgggttt g                                    21

<210> SEQ ID NO 966
<211> LENGTH: 21
<212> TYPE: DNA
<213> ORGANISM: Homo sapiens

<400> SEQUENCE: 966
cactgcttac rttgccatga t                                    21

<210> SEQ ID NO 967
<211> LENGTH: 21
<212> TYPE: DNA
<213> ORGANISM: Homo sapiens

<400> SEQUENCE: 967
ctctaaaaga sagggcggat t                                    21

<210> SEQ ID NO 968
<211> LENGTH: 21
<212> TYPE: DNA
<213> ORGANISM: Homo sapiens

<400> SEQUENCE: 968
tgtggagact ygcagacatc g                                    21

<210> SEQ ID NO 969
<211> LENGTH: 21
<212> TYPE: DNA
<213> ORGANISM: Homo sapiens

<400> SEQUENCE: 969
tggtgccact kggacccgaa t                                    21

<210> SEQ ID NO 970
<211> LENGTH: 21
<212> TYPE: DNA
<213> ORGANISM: Homo sapiens

<400> SEQUENCE: 970
aaaagactca rtacttggcc t                                    21

<210> SEQ ID NO 971
<211> LENGTH: 21
<212> TYPE: DNA
<213> ORGANISM: Homo sapiens

<400> SEQUENCE: 971
gtgccttcaa rgaaccttcc a                                    21

<210> SEQ ID NO 972
<211> LENGTH: 21
<212> TYPE: DNA
<213> ORGANISM: Homo sapiens

<400> SEQUENCE: 972
gctgcagcaa rcaatatgac a                                    21

<210> SEQ ID NO 973
<211> LENGTH: 21
<212> TYPE: DNA
<213> ORGANISM: Homo sapiens

<400> SEQUENCE: 973
```
ggccaaactc rgcgcccacc a                          21

<210> SEQ ID NO 974
<211> LENGTH: 21
<212> TYPE: DNA
<213> ORGANISM: Homo sapiens

<400> SEQUENCE: 974
agtcgcacga yaaactgcgg c                          21

<210> SEQ ID NO 975
<211> LENGTH: 21
<212> TYPE: DNA
<213> ORGANISM: Homo sapiens

<400> SEQUENCE: 975
acttcgaacc ygagaggcct t                          21

<210> SEQ ID NO 976
<211> LENGTH: 21
<212> TYPE: DNA
<213> ORGANISM: Homo sapiens

<400> SEQUENCE: 976
caggttctct rctcgcagta g                          21

<210> SEQ ID NO 977
<211> LENGTH: 21
<212> TYPE: DNA
<213> ORGANISM: Homo sapiens

<400> SEQUENCE: 977
tgactccttc kagcaccctt t                          21

<210> SEQ ID NO 978
<211> LENGTH: 21
<212> TYPE: DNA
<213> ORGANISM: Homo sapiens

<400> SEQUENCE: 978
ttatgcgaat rctttatttt c                          21

<210> SEQ ID NO 979
<211> LENGTH: 21
<212> TYPE: DNA
<213> ORGANISM: Homo sapiens

<400> SEQUENCE: 979
gggactcgga yttggcggcc g                          21

<210> SEQ ID NO 980
<211> LENGTH: 21
<212> TYPE: DNA
<213> ORGANISM: Homo sapiens

<400> SEQUENCE: 980
agaccctgga rctggagaag g                          21

<210> SEQ ID NO 981
<211> LENGTH: 21
<212> TYPE: DNA
<213> ORGANISM: Homo sapiens -continued

<400> SEQUENCE: 981
tcagactcag rgaaaactgc g                                              21

<210> SEQ ID NO 982
<211> LENGTH: 21
<212> TYPE: DNA
<213> ORGANISM: Homo sapiens

<400> SEQUENCE: 982
ggcgtgaaca rtcctcgagc a                                              21

<210> SEQ ID NO 983
<211> LENGTH: 21
<212> TYPE: DNA
<213> ORGANISM: Homo sapiens

<400> SEQUENCE: 983
atggagctgg rgcccgacaa c                                              21

<210> SEQ ID NO 984
<211> LENGTH: 21
<212> TYPE: DNA
<213> ORGANISM: Homo sapiens

<400> SEQUENCE: 984
gcgagctctg ygaccagtgc t                                              21

<210> SEQ ID NO 985
<211> LENGTH: 21
<212> TYPE: DNA
<213> ORGANISM: Homo sapiens

<400> SEQUENCE: 985
gcctgccccg yattgaggca g                                              21

<210> SEQ ID NO 986
<211> LENGTH: 21
<212> TYPE: DNA
<213> ORGANISM: Homo sapiens

<400> SEQUENCE: 986
ctggatcgca rgcaacatct a                                              21

<210> SEQ ID NO 987
<211> LENGTH: 21
<212> TYPE: DNA
<213> ORGANISM: Homo sapiens

<400> SEQUENCE: 987
aaggcaccaa ygtgtgcgcg g                                              21

<210> SEQ ID NO 988
<211> LENGTH: 21
<212> TYPE: DNA
<213> ORGANISM: Homo sapiens

<400> SEQUENCE: 988
ggctgaagga ygacggccgg a                                              21

<210> SEQ ID NO 989
<211> LENGTH: 21
<212> TYPE: DNA
<213> ORGANISM: Homo sapiens

```
<400> SEQUENCE: 989
actgcatgga yggctcagat g                                              21

<210> SEQ ID NO 990
<211> LENGTH: 21
<212> TYPE: DNA
<213> ORGANISM: Homo sapiens

<400> SEQUENCE: 990
acccgacctg yggccccagt g                                              21

<210> SEQ ID NO 991
<211> LENGTH: 21
<212> TYPE: DNA
<213> ORGANISM: Homo sapiens

<400> SEQUENCE: 991
ccctgcgctg yaacatgttc g                                              21

<210> SEQ ID NO 992
<211> LENGTH: 21
<212> TYPE: DNA
<213> ORGANISM: Homo sapiens

<400> SEQUENCE: 992
gaccagtatg rgaagccggg t                                              21

<210> SEQ ID NO 993
<211> LENGTH: 21
<212> TYPE: DNA
<213> ORGANISM: Homo sapiens

<400> SEQUENCE: 993
agaagcgcat yctttggatt g                                              21

<210> SEQ ID NO 994
<211> LENGTH: 21
<212> TYPE: DNA
<213> ORGANISM: Homo sapiens

<400> SEQUENCE: 994
ttggccgtgt sgagggcatt g                                              21

<210> SEQ ID NO 995
<211> LENGTH: 21
<212> TYPE: DNA
<213> ORGANISM: Homo sapiens

<400> SEQUENCE: 995
ctgtcggcat ygacttccac g                                              21

<210> SEQ ID NO 996
<211> LENGTH: 21
<212> TYPE: DNA
<213> ORGANISM: Homo sapiens

<400> SEQUENCE: 996
acgcctcaga ygagatgaac t                                              21

<210> SEQ ID NO 997
<211> LENGTH: 21
<212> TYPE: DNA
```

```
<213> ORGANISM: Homo sapiens

<400> SEQUENCE: 997
acggcagcga ygaggaggcc t                                              21

<210> SEQ ID NO 998
<211> LENGTH: 21
<212> TYPE: DNA
<213> ORGANISM: Homo sapiens

<400> SEQUENCE: 998
acgtctttga rgattacatc t                                              21

<210> SEQ ID NO 999
<211> LENGTH: 21
<212> TYPE: DNA
<213> ORGANISM: Homo sapiens

<400> SEQUENCE: 999
acggatctga ygaggcccct g                                              21

<210> SEQ ID NO 1000
<211> LENGTH: 21
<212> TYPE: DNA
<213> ORGANISM: Homo sapiens

<400> SEQUENCE: 1000
gccgccttgt ytactgggca g                                              21

<210> SEQ ID NO 1001
<211> LENGTH: 21
<212> TYPE: DNA
<213> ORGANISM: Homo sapiens

<400> SEQUENCE: 1001
gatgcctatc kggactatat t                                              21

<210> SEQ ID NO 1002
<211> LENGTH: 21
<212> TYPE: DNA
<213> ORGANISM: Homo sapiens

<400> SEQUENCE: 1002
caccagctac ytcattggcc g                                              21

<210> SEQ ID NO 1003
<211> LENGTH: 21
<212> TYPE: DNA
<213> ORGANISM: Homo sapiens

<400> SEQUENCE: 1003
gatggctcca rgaggatcac c                                              21

<210> SEQ ID NO 1004
<211> LENGTH: 21
<212> TYPE: DNA
<213> ORGANISM: Homo sapiens

<400> SEQUENCE: 1004
ctctgacgag rtcccttgca a                                              21

<210> SEQ ID NO 1005
<211> LENGTH: 21
```

```
<212> TYPE: DNA
<213> ORGANISM: Homo sapiens

<400> SEQUENCE: 1005
gtgcgcaccg rgaaagcggc c                                    21

<210> SEQ ID NO 1006
<211> LENGTH: 21
<212> TYPE: DNA
<213> ORGANISM: Homo sapiens

<400> SEQUENCE: 1006
tggggatcca rcctccaaaa g                                    21

<210> SEQ ID NO 1007
<211> LENGTH: 21
<212> TYPE: DNA
<213> ORGANISM: Homo sapiens

<400> SEQUENCE: 1007
ataagggagc rtgaggagtc t                                    21

<210> SEQ ID NO 1008
<211> LENGTH: 21
<212> TYPE: DNA
<213> ORGANISM: Homo sapiens

<400> SEQUENCE: 1008
atcttcaatt rtgggttcct t                                    21

<210> SEQ ID NO 1009
<211> LENGTH: 21
<212> TYPE: DNA
<213> ORGANISM: Homo sapiens

<400> SEQUENCE: 1009
agagaaggct rtgcagcttg c                                    21

<210> SEQ ID NO 1010
<211> LENGTH: 21
<212> TYPE: DNA
<213> ORGANISM: Homo sapiens

<400> SEQUENCE: 1010
tgtaccagac rcccttgcac t                                    21

<210> SEQ ID NO 1011
<211> LENGTH: 21
<212> TYPE: DNA
<213> ORGANISM: Homo sapiens

<400> SEQUENCE: 1011
agctgcagct stataagtta c                                    21

<210> SEQ ID NO 1012
<211> LENGTH: 21
<212> TYPE: DNA
<213> ORGANISM: Homo sapiens

<400> SEQUENCE: 1012
aacagccccg kaagtggcac c                                    21

<210> SEQ ID NO 1013
```

```
<211> LENGTH: 21
<212> TYPE: DNA
<213> ORGANISM: Homo sapiens

<400> SEQUENCE: 1013
cgccaaatga ktcagctggc a                                              21

<210> SEQ ID NO 1014
<211> LENGTH: 21
<212> TYPE: DNA
<213> ORGANISM: Homo sapiens

<400> SEQUENCE: 1014
ctcaccctaa raacacacag c                                              21

<210> SEQ ID NO 1015
<211> LENGTH: 21
<212> TYPE: DNA
<213> ORGANISM: Homo sapiens

<400> SEQUENCE: 1015
gtgccgaggg rcggccacac t                                              21

<210> SEQ ID NO 1016
<211> LENGTH: 21
<212> TYPE: DNA
<213> ORGANISM: Homo sapiens

<400> SEQUENCE: 1016
tccgtttcct ygagagcctg c                                              21

<210> SEQ ID NO 1017
<211> LENGTH: 21
<212> TYPE: DNA
<213> ORGANISM: Homo sapiens

<400> SEQUENCE: 1017
ggattaagaa rgcagccgaa g                                              21

<210> SEQ ID NO 1018
<211> LENGTH: 21
<212> TYPE: DNA
<213> ORGANISM: Homo sapiens

<400> SEQUENCE: 1018
tccaagaaga ygaaattcca g                                              21

<210> SEQ ID NO 1019
<211> LENGTH: 21
<212> TYPE: DNA
<213> ORGANISM: Homo sapiens

<400> SEQUENCE: 1019
agtggagcgt ygccgccgag a                                              21

<210> SEQ ID NO 1020
<211> LENGTH: 21
<212> TYPE: DNA
<213> ORGANISM: Homo sapiens

<400> SEQUENCE: 1020
cccttgtcat ygagttcacc g                                              21
```

<210> SEQ ID NO 1021
<211> LENGTH: 21
<212> TYPE: DNA
<213> ORGANISM: Homo sapiens

<400> SEQUENCE: 1021
tggcggccca maagtacctg c                                              21

<210> SEQ ID NO 1022
<211> LENGTH: 21
<212> TYPE: DNA
<213> ORGANISM: Homo sapiens

<400> SEQUENCE: 1022
ggacggtcat ygattacaac g                                              21

<210> SEQ ID NO 1023
<211> LENGTH: 21
<212> TYPE: DNA
<213> ORGANISM: Homo sapiens

<400> SEQUENCE: 1023
aacattgcaa yggcattttg a                                              21

<210> SEQ ID NO 1024
<211> LENGTH: 21
<212> TYPE: DNA
<213> ORGANISM: Homo sapiens

<400> SEQUENCE: 1024
taggcccttc yggctttgga c                                              21

<210> SEQ ID NO 1025
<211> LENGTH: 21
<212> TYPE: DNA
<213> ORGANISM: Homo sapiens

<400> SEQUENCE: 1025
cctcgtcgtc rtcttcagac a                                              21

<210> SEQ ID NO 1026
<211> LENGTH: 21
<212> TYPE: DNA
<213> ORGANISM: Homo sapiens

<400> SEQUENCE: 1026
tctcttctgt stcacacaca g                                              21

<210> SEQ ID NO 1027
<211> LENGTH: 21
<212> TYPE: DNA
<213> ORGANISM: Homo sapiens

<400> SEQUENCE: 1027
gttaaaacat kgcaatggca t                                              21

<210> SEQ ID NO 1028
<211> LENGTH: 21
<212> TYPE: DNA
<213> ORGANISM: Homo sapiens

<400> SEQUENCE: 1028
ctggggccga ygaagatgac a                                              21

<210> SEQ ID NO 1029
<211> LENGTH: 21
<212> TYPE: DNA
<213> ORGANISM: Homo sapiens

<400> SEQUENCE: 1029
cttggccgac rgctggcccc g                                    21

<210> SEQ ID NO 1030
<211> LENGTH: 21
<212> TYPE: DNA
<213> ORGANISM: Homo sapiens

<400> SEQUENCE: 1030
cagagtacag ygagccccac g                                    21

<210> SEQ ID NO 1031
<211> LENGTH: 21
<212> TYPE: DNA
<213> ORGANISM: Homo sapiens

<400> SEQUENCE: 1031
agactgctct ygaggctcat a                                    21

<210> SEQ ID NO 1032
<211> LENGTH: 21
<212> TYPE: DNA
<213> ORGANISM: Homo sapiens

<400> SEQUENCE: 1032
ctctgtctgc ratgctctta g                                    21

<210> SEQ ID NO 1033
<211> LENGTH: 21
<212> TYPE: DNA
<213> ORGANISM: Homo sapiens

<400> SEQUENCE: 1033
ggggactcca katgaaagga g                                    21

<210> SEQ ID NO 1034
<211> LENGTH: 21
<212> TYPE: DNA
<213> ORGANISM: Homo sapiens

<400> SEQUENCE: 1034
gcttttccca yctaccccca a                                    21

<210> SEQ ID NO 1035
<211> LENGTH: 21
<212> TYPE: DNA
<213> ORGANISM: Homo sapiens

<400> SEQUENCE: 1035
tctggagatc yatatgaggt c                                    21

<210> SEQ ID NO 1036
<211> LENGTH: 21
<212> TYPE: DNA
<213> ORGANISM: Homo sapiens

<400> SEQUENCE: 1036
agaccttgcc rgctcagcta c                                    21

<210> SEQ ID NO 1037
<211> LENGTH: 21
<212> TYPE: DNA
<213> ORGANISM: Homo sapiens

<400> SEQUENCE: 1037
caaggtttac rgactaccag c                                              21

<210> SEQ ID NO 1038
<211> LENGTH: 21
<212> TYPE: DNA
<213> ORGANISM: Homo sapiens

<400> SEQUENCE: 1038
gaagaccaac mctccccagc a                                              21

<210> SEQ ID NO 1039
<211> LENGTH: 21
<212> TYPE: DNA
<213> ORGANISM: Homo sapiens

<400> SEQUENCE: 1039
tccaacctcc mcaatgaaca c                                              21

<210> SEQ ID NO 1040
<211> LENGTH: 21
<212> TYPE: DNA
<213> ORGANISM: Homo sapiens

<400> SEQUENCE: 1040
ccctgcaggc ygcgttgact t                                              21

<210> SEQ ID NO 1041
<211> LENGTH: 21
<212> TYPE: DNA
<213> ORGANISM: Homo sapiens

<400> SEQUENCE: 1041
ccaacagacg mctattcgga g                                              21

<210> SEQ ID NO 1042
<211> LENGTH: 21
<212> TYPE: DNA
<213> ORGANISM: Homo sapiens

<400> SEQUENCE: 1042
tggtgtggtt ycagaatgcc c                                              21

<210> SEQ ID NO 1043
<211> LENGTH: 21
<212> TYPE: DNA
<213> ORGANISM: Homo sapiens

<400> SEQUENCE: 1043
accaggcttt wctccttatt a                                              21

<210> SEQ ID NO 1044
<211> LENGTH: 21
<212> TYPE: DNA
<213> ORGANISM: Homo sapiens

<400> SEQUENCE: 1044
gcagcctgtc rgaggacgag t 21

<210> SEQ ID NO 1045
<211> LENGTH: 21
<212> TYPE: DNA
<213> ORGANISM: Homo sapiens

<400> SEQUENCE: 1045
gccttccaga rgaggacgag g 21

<210> SEQ ID NO 1046
<211> LENGTH: 21
<212> TYPE: DNA
<213> ORGANISM: Homo sapiens

<400> SEQUENCE: 1046
ctctactgcc rtccactttg a 21

<210> SEQ ID NO 1047
<211> LENGTH: 21
<212> TYPE: DNA
<213> ORGANISM: Homo sapiens

<400> SEQUENCE: 1047
cgttgcgcta rccctgctcg t 21

<210> SEQ ID NO 1048
<211> LENGTH: 21
<212> TYPE: DNA
<213> ORGANISM: Homo sapiens

<400> SEQUENCE: 1048
agaaatatga rcaggcatgt a 21

<210> SEQ ID NO 1049
<211> LENGTH: 21
<212> TYPE: DNA
<213> ORGANISM: Homo sapiens

<400> SEQUENCE: 1049
gtaacttcag yaaacaggcc a 21

<210> SEQ ID NO 1050
<211> LENGTH: 21
<212> TYPE: DNA
<213> ORGANISM: Homo sapiens

<400> SEQUENCE: 1050
cctgcgaggc ygtgatgatc c 21

<210> SEQ ID NO 1051
<211> LENGTH: 21
<212> TYPE: DNA
<213> ORGANISM: Homo sapiens

<400> SEQUENCE: 1051
gaggccagat stacagccca c 21

<210> SEQ ID NO 1052
<211> LENGTH: 21
<212> TYPE: DNA
<213> ORGANISM: Homo sapiens

<400> SEQUENCE: 1052

```
acgcatggtg rgcatcatcc a                                          21

<210> SEQ ID NO 1053
<211> LENGTH: 21
<212> TYPE: DNA
<213> ORGANISM: Homo sapiens

<400> SEQUENCE: 1053
gtaacttcag yaaacaggcc a                                          21

<210> SEQ ID NO 1054
<211> LENGTH: 21
<212> TYPE: DNA
<213> ORGANISM: Homo sapiens

<400> SEQUENCE: 1054
agaagtatga rcaggcatgt a                                          21

<210> SEQ ID NO 1055
<211> LENGTH: 21
<212> TYPE: DNA
<213> ORGANISM: Homo sapiens

<400> SEQUENCE: 1055
atggacggag scttgaagat g                                          21

<210> SEQ ID NO 1056
<211> LENGTH: 21
<212> TYPE: DNA
<213> ORGANISM: Homo sapiens

<400> SEQUENCE: 1056
gggatgatga ygcccacggt g                                          21

<210> SEQ ID NO 1057
<211> LENGTH: 21
<212> TYPE: DNA
<213> ORGANISM: Homo sapiens

<400> SEQUENCE: 1057
ggcattgagc ytcccaaggg c                                          21

<210> SEQ ID NO 1058
<211> LENGTH: 21
<212> TYPE: DNA
<213> ORGANISM: Homo sapiens

<400> SEQUENCE: 1058
tgctggagct ygagagagac g                                          21

<210> SEQ ID NO 1059
<211> LENGTH: 21
<212> TYPE: DNA
<213> ORGANISM: Homo sapiens

<400> SEQUENCE: 1059
tggagttcat sgccagcaag a                                          21

<210> SEQ ID NO 1060
<211> LENGTH: 21
<212> TYPE: DNA
<213> ORGANISM: Homo sapiens
```

```
<400> SEQUENCE: 1060
gggacctgct rcgtccacca g                                              21

<210> SEQ ID NO 1061
<211> LENGTH: 21
<212> TYPE: DNA
<213> ORGANISM: Homo sapiens

<400> SEQUENCE: 1061
acgacagttc ygggaaggg a                                               21

<210> SEQ ID NO 1062
<211> LENGTH: 21
<212> TYPE: DNA
<213> ORGANISM: Homo sapiens

<400> SEQUENCE: 1062
tttgatgagt yccacgattt c                                              21

<210> SEQ ID NO 1063
<211> LENGTH: 21
<212> TYPE: DNA
<213> ORGANISM: Homo sapiens

<400> SEQUENCE: 1063
atacgggtcc rcggcagctc t                                              21

<210> SEQ ID NO 1064
<211> LENGTH: 21
<212> TYPE: DNA
<213> ORGANISM: Homo sapiens

<400> SEQUENCE: 1064
tcaggagcgc rcagggggcag c                                             21

<210> SEQ ID NO 1065
<211> LENGTH: 21
<212> TYPE: DNA
<213> ORGANISM: Homo sapiens

<400> SEQUENCE: 1065
ggggcagccc rccagcaagg a                                              21

<210> SEQ ID NO 1066
<211> LENGTH: 21
<212> TYPE: DNA
<213> ORGANISM: Homo sapiens

<400> SEQUENCE: 1066
tgtggcacta ygtcccctc c                                               21

<210> SEQ ID NO 1067
<211> LENGTH: 21
<212> TYPE: DNA
<213> ORGANISM: Homo sapiens

<400> SEQUENCE: 1067
tcttgtcacc rcgtcaacac c                                              21

<210> SEQ ID NO 1068
<211> LENGTH: 21
<212> TYPE: DNA
<213> ORGANISM: Homo sapiens
```

<400> SEQUENCE: 1068
ttcttggtac yggacagtcc c                                        21

<210> SEQ ID NO 1069
<211> LENGTH: 21
<212> TYPE: DNA
<213> ORGANISM: Homo sapiens

<400> SEQUENCE: 1069
ttatccggca kcacaacatc c                                        21

<210> SEQ ID NO 1070
<211> LENGTH: 21
<212> TYPE: DNA
<213> ORGANISM: Homo sapiens

<400> SEQUENCE: 1070
caaatccatg saccgcctag c                                        21

<210> SEQ ID NO 1071
<211> LENGTH: 21
<212> TYPE: DNA
<213> ORGANISM: Homo sapiens

<400> SEQUENCE: 1071
ttgacagcat rtctaattcg c                                        21

<210> SEQ ID NO 1072
<211> LENGTH: 21
<212> TYPE: DNA
<213> ORGANISM: Homo sapiens

<400> SEQUENCE: 1072
ccagctgata rttcatcaac a                                        21

<210> SEQ ID NO 1073
<211> LENGTH: 21
<212> TYPE: DNA
<213> ORGANISM: Homo sapiens

<400> SEQUENCE: 1073
caaagtcaac rgccagtcac t                                        21

<210> SEQ ID NO 1074
<211> LENGTH: 21
<212> TYPE: DNA
<213> ORGANISM: Homo sapiens

<400> SEQUENCE: 1074
cataggaata yggtcacaga a                                        21

<210> SEQ ID NO 1075
<211> LENGTH: 21
<212> TYPE: DNA
<213> ORGANISM: Homo sapiens

<400> SEQUENCE: 1075
ttctgcagca rccatctgaa c                                        21

<210> SEQ ID NO 1076
<211> LENGTH: 21
<212> TYPE: DNA

<213> ORGANISM: Homo sapiens

<400> SEQUENCE: 1076
cagaactgag yaccttgtca c                                              21

<210> SEQ ID NO 1077
<211> LENGTH: 21
<212> TYPE: DNA
<213> ORGANISM: Homo sapiens

<400> SEQUENCE: 1077
tgaaacttta ytaaaatcaa g                                              21

<210> SEQ ID NO 1078
<211> LENGTH: 21
<212> TYPE: DNA
<213> ORGANISM: Homo sapiens

<400> SEQUENCE: 1078
tcttctgtct rtaccttcac t                                              21

<210> SEQ ID NO 1079
<211> LENGTH: 21
<212> TYPE: DNA
<213> ORGANISM: Homo sapiens

<400> SEQUENCE: 1079
gcggtctgca rcctcagatt c                                              21

<210> SEQ ID NO 1080
<211> LENGTH: 21
<212> TYPE: DNA
<213> ORGANISM: Homo sapiens

<400> SEQUENCE: 1080
cctaaacata rtgttaccat a                                              21

<210> SEQ ID NO 1081
<211> LENGTH: 21
<212> TYPE: DNA
<213> ORGANISM: Homo sapiens

<400> SEQUENCE: 1081
tgggtcttct raaagtgagg a                                              21

<210> SEQ ID NO 1082
<211> LENGTH: 21
<212> TYPE: DNA
<213> ORGANISM: Homo sapiens

<400> SEQUENCE: 1082
ccgctctgta yacctggtac g                                              21

<210> SEQ ID NO 1083
<211> LENGTH: 21
<212> TYPE: DNA
<213> ORGANISM: Homo sapiens

<400> SEQUENCE: 1083
gggccgagcc ygacaccaag c                                              21

<210> SEQ ID NO 1084
<211> LENGTH: 21

```
<212> TYPE: DNA
<213> ORGANISM: Homo sapiens

<400> SEQUENCE: 1084
ccagttctcc yagcagctgc a                                              21

<210> SEQ ID NO 1085
<211> LENGTH: 21
<212> TYPE: DNA
<213> ORGANISM: Homo sapiens

<400> SEQUENCE: 1085
gaatgagtgt ragttgcaga a                                              21

<210> SEQ ID NO 1086
<211> LENGTH: 21
<212> TYPE: DNA
<213> ORGANISM: Homo sapiens

<400> SEQUENCE: 1086
cgccttcttc kcccgaggac a                                              21

<210> SEQ ID NO 1087
<211> LENGTH: 21
<212> TYPE: DNA
<213> ORGANISM: Homo sapiens

<400> SEQUENCE: 1087
ccttggacca kctcatccag a                                              21

<210> SEQ ID NO 1088
<211> LENGTH: 21
<212> TYPE: DNA
<213> ORGANISM: Homo sapiens

<400> SEQUENCE: 1088
ctgaggacaa rgccaacaag a                                              21

<210> SEQ ID NO 1089
<211> LENGTH: 21
<212> TYPE: DNA
<213> ORGANISM: Homo sapiens

<400> SEQUENCE: 1089
gtccctgtta yggctaccag t                                              21

<210> SEQ ID NO 1090
<211> LENGTH: 21
<212> TYPE: DNA
<213> ORGANISM: Homo sapiens

<400> SEQUENCE: 1090
tcatattcat yagaggaaat g                                              21

<210> SEQ ID NO 1091
<211> LENGTH: 21
<212> TYPE: DNA
<213> ORGANISM: Homo sapiens

<400> SEQUENCE: 1091
tactccagag rtcaagtcca a                                              21

<210> SEQ ID NO 1092
```

```
<211> LENGTH: 21
<212> TYPE: DNA
<213> ORGANISM: Homo sapiens

<400> SEQUENCE: 1092
tgacatccta ygtgctcctc g                                              21

<210> SEQ ID NO 1093
<211> LENGTH: 21
<212> TYPE: DNA
<213> ORGANISM: Homo sapiens

<400> SEQUENCE: 1093
atatcaccat ygcccttctg g                                              21

<210> SEQ ID NO 1094
<211> LENGTH: 21
<212> TYPE: DNA
<213> ORGANISM: Homo sapiens

<400> SEQUENCE: 1094
ccaagctcga kcctacatct t                                              21

<210> SEQ ID NO 1095
<211> LENGTH: 21
<212> TYPE: DNA
<213> ORGANISM: Homo sapiens

<400> SEQUENCE: 1095
tcacactttc racagggaat t                                              21

<210> SEQ ID NO 1096
<211> LENGTH: 21
<212> TYPE: DNA
<213> ORGANISM: Homo sapiens

<400> SEQUENCE: 1096
tttctggggg rttcccaggt t                                              21

<210> SEQ ID NO 1097
<211> LENGTH: 21
<212> TYPE: DNA
<213> ORGANISM: Homo sapiens

<400> SEQUENCE: 1097
agtgccggga rgaacccttg g                                              21

<210> SEQ ID NO 1098
<211> LENGTH: 21
<212> TYPE: DNA
<213> ORGANISM: Homo sapiens

<400> SEQUENCE: 1098
tggggaaaca saattcctca a                                              21

<210> SEQ ID NO 1099
<211> LENGTH: 21
<212> TYPE: DNA
<213> ORGANISM: Homo sapiens

<400> SEQUENCE: 1099
ctcaccacaa ygacattgcc t                                              21
```

```
<210> SEQ ID NO 1100
<211> LENGTH: 21
<212> TYPE: DNA
<213> ORGANISM: Homo sapiens

<400> SEQUENCE: 1100
ggcctaaagc ygcttgtcca a                                              21

<210> SEQ ID NO 1101
<211> LENGTH: 21
<212> TYPE: DNA
<213> ORGANISM: Homo sapiens

<400> SEQUENCE: 1101
tgattaccca magaaggagg a                                              21

<210> SEQ ID NO 1102
<211> LENGTH: 21
<212> TYPE: DNA
<213> ORGANISM: Homo sapiens

<400> SEQUENCE: 1102
acatcacaaa rcaacctgtg g                                              21

<210> SEQ ID NO 1103
<211> LENGTH: 21
<212> TYPE: DNA
<213> ORGANISM: Homo sapiens

<400> SEQUENCE: 1103
catgcgtgtg ractcagaca a                                              21

<210> SEQ ID NO 1104
<211> LENGTH: 21
<212> TYPE: DNA
<213> ORGANISM: Homo sapiens

<400> SEQUENCE: 1104
atgagaaagg kttcattgaa a                                              21

<210> SEQ ID NO 1105
<211> LENGTH: 21
<212> TYPE: DNA
<213> ORGANISM: Homo sapiens

<400> SEQUENCE: 1105
ggagatccac ycccgagaca g                                              21

<210> SEQ ID NO 1106
<211> LENGTH: 21
<212> TYPE: DNA
<213> ORGANISM: Homo sapiens

<400> SEQUENCE: 1106
ctcgcaacgt yctcctggca c                                              21

<210> SEQ ID NO 1107
<211> LENGTH: 21
<212> TYPE: DNA
<213> ORGANISM: Homo sapiens

<400> SEQUENCE: 1107
tcagggagga rctggctgcc c                                              21
```

<210> SEQ ID NO 1108
<211> LENGTH: 21
<212> TYPE: DNA
<213> ORGANISM: Homo sapiens

<400> SEQUENCE: 1108
ccagaggata rctggctact c               21

<210> SEQ ID NO 1109
<211> LENGTH: 21
<212> TYPE: DNA
<213> ORGANISM: Homo sapiens

<400> SEQUENCE: 1109
gcctgcctca ygcaatggga a               21

<210> SEQ ID NO 1110
<211> LENGTH: 21
<212> TYPE: DNA
<213> ORGANISM: Homo sapiens

<400> SEQUENCE: 1110
ctctgcgggg yttcccttca g               21

<210> SEQ ID NO 1111
<211> LENGTH: 21
<212> TYPE: DNA
<213> ORGANISM: Homo sapiens

<400> SEQUENCE: 1111
atgcctctga ygaggcagcc c               21

<210> SEQ ID NO 1112
<211> LENGTH: 21
<212> TYPE: DNA
<213> ORGANISM: Homo sapiens

<400> SEQUENCE: 1112
cttcaaaaga raataacgtt t               21

<210> SEQ ID NO 1113
<211> LENGTH: 21
<212> TYPE: DNA
<213> ORGANISM: Homo sapiens

<400> SEQUENCE: 1113
acagaatgtt yaacttcaag c               21

<210> SEQ ID NO 1114
<211> LENGTH: 21
<212> TYPE: DNA
<213> ORGANISM: Homo sapiens

<400> SEQUENCE: 1114
tgttttgtgg yaaaagattc a               21

<210> SEQ ID NO 1115
<211> LENGTH: 21
<212> TYPE: DNA
<213> ORGANISM: Homo sapiens

<400> SEQUENCE: 1115
agcagctcac rgaggaactg a               21

<210> SEQ ID NO 1116
<211> LENGTH: 21
<212> TYPE: DNA
<213> ORGANISM: Homo sapiens

<400> SEQUENCE: 1116
ccagcacgcc stcgcccccc g                                              21

<210> SEQ ID NO 1117
<211> LENGTH: 21
<212> TYPE: DNA
<213> ORGANISM: Homo sapiens

<400> SEQUENCE: 1117
tgcacagcga rgggaagccc t                                              21

<210> SEQ ID NO 1118
<211> LENGTH: 21
<212> TYPE: DNA
<213> ORGANISM: Homo sapiens

<400> SEQUENCE: 1118
tgttcggacc rgaagcaccc a                                              21

<210> SEQ ID NO 1119
<211> LENGTH: 21
<212> TYPE: DNA
<213> ORGANISM: Homo sapiens

<400> SEQUENCE: 1119
atcctagacg scttcgagga g                                              21

<210> SEQ ID NO 1120
<211> LENGTH: 21
<212> TYPE: DNA
<213> ORGANISM: Homo sapiens

<400> SEQUENCE: 1120
tgagcgacac rgtggcgctg t                                              21

<210> SEQ ID NO 1121
<211> LENGTH: 21
<212> TYPE: DNA
<213> ORGANISM: Homo sapiens

<400> SEQUENCE: 1121
tgcacagcac rtgcggaccg g                                              21

<210> SEQ ID NO 1122
<211> LENGTH: 21
<212> TYPE: DNA
<213> ORGANISM: Homo sapiens

<400> SEQUENCE: 1122
ttctgctcat yctagacgcc t                                              21

<210> SEQ ID NO 1123
<211> LENGTH: 21
<212> TYPE: DNA
<213> ORGANISM: Homo sapiens

<400> SEQUENCE: 1123

```
tactctagag ragcctgttg g                                                   21

<210> SEQ ID NO 1124
<211> LENGTH: 21
<212> TYPE: DNA
<213> ORGANISM: Homo sapiens

<400> SEQUENCE: 1124
gaaactccag ktcaaagact t                                                   21

<210> SEQ ID NO 1125
<211> LENGTH: 21
<212> TYPE: DNA
<213> ORGANISM: Homo sapiens

<400> SEQUENCE: 1125
ctgcttgaat ycatgtatga r                                                   21

<210> SEQ ID NO 1126
<211> LENGTH: 21
<212> TYPE: DNA
<213> ORGANISM: Homo sapiens

<400> SEQUENCE: 1126
ccaacttcga ygctataaga g                                                   21

<210> SEQ ID NO 1127
<211> LENGTH: 21
<212> TYPE: DNA
<213> ORGANISM: Homo sapiens

<400> SEQUENCE: 1127
ttgaccttgt rcaaataaaa c                                                   21

<210> SEQ ID NO 1128
<211> LENGTH: 21
<212> TYPE: DNA
<213> ORGANISM: Homo sapiens

<400> SEQUENCE: 1128
gtcagaagtc rgccctaatt g                                                   21

<210> SEQ ID NO 1129
<211> LENGTH: 21
<212> TYPE: DNA
<213> ORGANISM: Homo sapiens

<400> SEQUENCE: 1129
cccgacagct yattaagaaa g                                                   21

<210> SEQ ID NO 1130
<211> LENGTH: 21
<212> TYPE: DNA
<213> ORGANISM: Homo sapiens

<400> SEQUENCE: 1130
acttctgtga ygtccagcgc t                                                   21

<210> SEQ ID NO 1131
<211> LENGTH: 21
<212> TYPE: DNA
<213> ORGANISM: Homo sapiens

<400> SEQUENCE: 1131
```

-continued

```
tgtgaatgcc ygcctggcca t                                           21

<210> SEQ ID NO 1132
<211> LENGTH: 21
<212> TYPE: DNA
<213> ORGANISM: Homo sapiens

<400> SEQUENCE: 1132
agatagctcc ktcctgtggc t                                           21

<210> SEQ ID NO 1133
<211> LENGTH: 21
<212> TYPE: DNA
<213> ORGANISM: Homo sapiens

<400> SEQUENCE: 1133
gatctgcaat matggacgct g                                           21

<210> SEQ ID NO 1134
<211> LENGTH: 21
<212> TYPE: DNA
<213> ORGANISM: Homo sapiens

<400> SEQUENCE: 1134
gaactgcaca sacattgacg a                                           21

<210> SEQ ID NO 1135
<211> LENGTH: 21
<212> TYPE: DNA
<213> ORGANISM: Homo sapiens

<400> SEQUENCE: 1135
tctgcatgaa ygggcgttgc g                                           21

<210> SEQ ID NO 1136
<211> LENGTH: 21
<212> TYPE: DNA
<213> ORGANISM: Homo sapiens

<400> SEQUENCE: 1136
gcaaacacaa yggaatgtgg c                                           21

<210> SEQ ID NO 1137
<211> LENGTH: 21
<212> TYPE: DNA
<213> ORGANISM: Homo sapiens

<400> SEQUENCE: 1137
aagccagaca wtcagccctt t                                           21

<210> SEQ ID NO 1138
<211> LENGTH: 21
<212> TYPE: DNA
<213> ORGANISM: Homo sapiens

<400> SEQUENCE: 1138
ccactattgc ycatgtcctg c                                           21

<210> SEQ ID NO 1139
<211> LENGTH: 21
<212> TYPE: DNA
<213> ORGANISM: Homo sapiens
```

-continued

```
<400> SEQUENCE: 1139
gcccaaagac rttctcataa t                                              21

<210> SEQ ID NO 1140
<211> LENGTH: 21
<212> TYPE: DNA
<213> ORGANISM: Homo sapiens

<400> SEQUENCE: 1140
gtgcctgggc ygcagaagtg a                                              21

<210> SEQ ID NO 1141
<211> LENGTH: 21
<212> TYPE: DNA
<213> ORGANISM: Homo sapiens

<400> SEQUENCE: 1141 cctggggtg yctgggctgc a                                               21

<210> SEQ ID NO 1142
<211> LENGTH: 21
<212> TYPE: DNA
<213> ORGANISM: Homo sapiens

<400> SEQUENCE: 1142
ttctttggcc rtggtgcgga g                                              21

<210> SEQ ID NO 1143
<211> LENGTH: 21
<212> TYPE: DNA
<213> ORGANISM: Homo sapiens

<400> SEQUENCE: 1143
tatccagaga ytctttggcc a                                              21

<210> SEQ ID NO 1144
<211> LENGTH: 21
<212> TYPE: DNA
<213> ORGANISM: Homo sapiens

<400> SEQUENCE: 1144
cttggtcctg rgtgtcagca g                                              21

<210> SEQ ID NO 1145
<211> LENGTH: 21
<212> TYPE: DNA
<213> ORGANISM: Homo sapiens

<400> SEQUENCE: 1145
ctgaccttca ycaagagcgc c                                              21

<210> SEQ ID NO 1146
<211> LENGTH: 21
<212> TYPE: DNA
<213> ORGANISM: Homo sapiens

<400> SEQUENCE: 1146
tatgcccgga maccatgaac a                                              21

<210> SEQ ID NO 1147
<211> LENGTH: 21
<212> TYPE: DNA
<213> ORGANISM: Homo sapiens
```

```
<400> SEQUENCE: 1147
gttcatgctc rgcttcctcc g                                              21

<210> SEQ ID NO 1148
<211> LENGTH: 21
<212> TYPE: DNA
<213> ORGANISM: Homo sapiens

<400> SEQUENCE: 1148
ccataaaaag yataagccag c                                              21

<210> SEQ ID NO 1149
<211> LENGTH: 21
<212> TYPE: DNA
<213> ORGANISM: Homo sapiens

<400> SEQUENCE: 1149
cagcctggac ragagcccca t                                              21

<210> SEQ ID NO 1150
<211> LENGTH: 21
<212> TYPE: DNA
<213> ORGANISM: Homo sapiens

<400> SEQUENCE: 1150
gggcatcagc wtctatgagg a                                              21

<210> SEQ ID NO 1151
<211> LENGTH: 21
<212> TYPE: DNA
<213> ORGANISM: Homo sapiens

<400> SEQUENCE: 1151
actttgccaa ygtgcaggag c                                              21

<210> SEQ ID NO 1152
<211> LENGTH: 21
<212> TYPE: DNA
<213> ORGANISM: Homo sapiens

<400> SEQUENCE: 1152
gggcggtgct rcagaacacg t                                              21

<210> SEQ ID NO 1153
<211> LENGTH: 21
<212> TYPE: DNA
<213> ORGANISM: Homo sapiens

<400> SEQUENCE: 1153
gttcttgctg raatggtcct t                                              21

<210> SEQ ID NO 1154
<211> LENGTH: 21
<212> TYPE: DNA
<213> ORGANISM: Homo sapiens

<400> SEQUENCE: 1154
aaggccaaca yagctgcagg c                                              21

<210> SEQ ID NO 1155
<211> LENGTH: 21
<212> TYPE: DNA
```

```
<213> ORGANISM: Homo sapiens

<400> SEQUENCE: 1155
cagcaacatt rtcaagactg a                                              21

<210> SEQ ID NO 1156
<211> LENGTH: 21
<212> TYPE: DNA
<213> ORGANISM: Homo sapiens

<400> SEQUENCE: 1156
gggtgcagtt rgtctatgtg t                                              21

<210> SEQ ID NO 1157
<211> LENGTH: 21
<212> TYPE: DNA
<213> ORGANISM: Homo sapiens

<400> SEQUENCE: 1157
tttttgtgga yttccgtgag a                                              21

<210> SEQ ID NO 1158
<211> LENGTH: 21
<212> TYPE: DNA
<213> ORGANISM: Homo sapiens

<400> SEQUENCE: 1158
caggccagga ratcactgaa a                                              21

<210> SEQ ID NO 1159
<211> LENGTH: 21
<212> TYPE: DNA
<213> ORGANISM: Homo sapiens

<400> SEQUENCE: 1159
tcaacaacct ygtgaacgcc a                                              21

<210> SEQ ID NO 1160
<211> LENGTH: 21
<212> TYPE: DNA
<213> ORGANISM: Homo sapiens

<400> SEQUENCE: 1160
agaagcacgt ktgccacatc c                                              21

<210> SEQ ID NO 1161
<211> LENGTH: 21
<212> TYPE: DNA
<213> ORGANISM: Homo sapiens

<400> SEQUENCE: 1161
tgtggtgaag ytgacaggtg g                                              21

<210> SEQ ID NO 1162
<211> LENGTH: 21
<212> TYPE: DNA
<213> ORGANISM: Homo sapiens

<400> SEQUENCE: 1162
cccactcccg yggcagcatg a                                              21

<210> SEQ ID NO 1163
<211> LENGTH: 21
```

-continued

```
<212> TYPE: DNA
<213> ORGANISM: Homo sapiens

<400> SEQUENCE: 1163
tcggatgcaa rtccaggccc a                                              21

<210> SEQ ID NO 1164
<211> LENGTH: 21
<212> TYPE: DNA
<213> ORGANISM: Homo sapiens

<400> SEQUENCE: 1164
aaagagtttc rgtcagagtt c                                              21

<210> SEQ ID NO 1165
<211> LENGTH: 21
<212> TYPE: DNA
<213> ORGANISM: Homo sapiens

<400> SEQUENCE: 1165
aaactcttac rgccattgca g                                              21

<210> SEQ ID NO 1166
<211> LENGTH: 21
<212> TYPE: DNA
<213> ORGANISM: Homo sapiens

<400> SEQUENCE: 1166
tagatgtagt saacaaccca g                                              21

<210> SEQ ID NO 1167
<211> LENGTH: 21
<212> TYPE: DNA
<213> ORGANISM: Homo sapiens

<400> SEQUENCE: 1167
atttgcggga sggcaacatc a                                              21

<210> SEQ ID NO 1168
<211> LENGTH: 21
<212> TYPE: DNA
<213> ORGANISM: Homo sapiens

<400> SEQUENCE: 1168
acagccggcc ractttggag g                                              21

<210> SEQ ID NO 1169
<211> LENGTH: 21
<212> TYPE: DNA
<213> ORGANISM: Homo sapiens

<400> SEQUENCE: 1169
tcttggatca sctgaactat g                                              21

<210> SEQ ID NO 1170
<211> LENGTH: 21
<212> TYPE: DNA
<213> ORGANISM: Homo sapiens

<400> SEQUENCE: 1170
caaaaagcct scatcagagc t                                              21

<210> SEQ ID NO 1171
```

```
<211> LENGTH: 21
<212> TYPE: DNA
<213> ORGANISM: Homo sapiens

<400> SEQUENCE: 1171
ccacaatggt rtcagaggag g                                              21

<210> SEQ ID NO 1172
<211> LENGTH: 21
<212> TYPE: DNA
<213> ORGANISM: Homo sapiens

<400> SEQUENCE: 1172
agaggattta saggaagatg a                                              21

<210> SEQ ID NO 1173
<211> LENGTH: 21
<212> TYPE: DNA
<213> ORGANISM: Homo sapiens

<400> SEQUENCE: 1173
acctgagccc ygaggagaag g                                              21

<210> SEQ ID NO 1174
<211> LENGTH: 21
<212> TYPE: DNA
<213> ORGANISM: Homo sapiens

<400> SEQUENCE: 1174
tacattggcc mcaagacaaa g                                              21

<210> SEQ ID NO 1175
<211> LENGTH: 21
<212> TYPE: DNA
<213> ORGANISM: Homo sapiens

<400> SEQUENCE: 1175
tcacagccct ycggccaggg t                                              21

<210> SEQ ID NO 1176
<211> LENGTH: 21
<212> TYPE: DNA
<213> ORGANISM: Homo sapiens

<400> SEQUENCE: 1176
cccagatgaa ygggaaaccc t                                              21

<210> SEQ ID NO 1177
<211> LENGTH: 21
<212> TYPE: DNA
<213> ORGANISM: Homo sapiens

<400> SEQUENCE: 1177
ggctggccca rtgagaacct g                                              21

<210> SEQ ID NO 1178
<211> LENGTH: 21
<212> TYPE: DNA
<213> ORGANISM: Homo sapiens

<400> SEQUENCE: 1178
gtgagaccga yttccgccga t                                              21
```

<210> SEQ ID NO 1179
<211> LENGTH: 21
<212> TYPE: DNA
<213> ORGANISM: Homo sapiens

<400> SEQUENCE: 1179
tgtcactgtc rgaactcagt t                     21

<210> SEQ ID NO 1180
<211> LENGTH: 21
<212> TYPE: DNA
<213> ORGANISM: Homo sapiens

<400> SEQUENCE: 1180
agtggaaatg rcatccagtg c                     21

<210> SEQ ID NO 1181
<211> LENGTH: 21
<212> TYPE: DNA
<213> ORGANISM: Homo sapiens

<400> SEQUENCE: 1181
gcagtgccca yggcgagctg g                     21

<210> SEQ ID NO 1182
<211> LENGTH: 21
<212> TYPE: DNA
<213> ORGANISM: Homo sapiens

<400> SEQUENCE: 1182
gagcagtatg mcagcaaggt t                     21

<210> SEQ ID NO 1183
<211> LENGTH: 21
<212> TYPE: DNA
<213> ORGANISM: Homo sapiens

<400> SEQUENCE: 1183
caccaggtga yggtacagaa a                     21

<210> SEQ ID NO 1184
<211> LENGTH: 21
<212> TYPE: DNA
<213> ORGANISM: Homo sapiens

<400> SEQUENCE: 1184
gaagagccac kttcgtaccc a                     21

<210> SEQ ID NO 1185
<211> LENGTH: 21
<212> TYPE: DNA
<213> ORGANISM: Homo sapiens

<400> SEQUENCE: 1185
agctgtggaa rggcctttgc c                     21

<210> SEQ ID NO 1186
<211> LENGTH: 21
<212> TYPE: DNA
<213> ORGANISM: Homo sapiens

<400> SEQUENCE: 1186
agctgtcgca ytcggacgag a                     21

<210> SEQ ID NO 1187
<211> LENGTH: 21
<212> TYPE: DNA
<213> ORGANISM: Homo sapiens

<400> SEQUENCE: 1187
ttcgattttc yaaagaacaa c                                             21

<210> SEQ ID NO 1188
<211> LENGTH: 21
<212> TYPE: DNA
<213> ORGANISM: Homo sapiens

<400> SEQUENCE: 1188
ggcgtgctga stgccctggg a                                             21

<210> SEQ ID NO 1189
<211> LENGTH: 21
<212> TYPE: DNA
<213> ORGANISM: Homo sapiens

<400> SEQUENCE: 1189
ttataacgtt katgtagctg a                                             21

<210> SEQ ID NO 1190
<211> LENGTH: 21
<212> TYPE: DNA
<213> ORGANISM: Homo sapiens

<400> SEQUENCE: 1190
ctcggaactg rgactgaggc c                                             21

<210> SEQ ID NO 1191
<211> LENGTH: 21
<212> TYPE: DNA
<213> ORGANISM: Homo sapiens

<400> SEQUENCE: 1191
tctcacggat rgcaccatca c                                             21

<210> SEQ ID NO 1192
<211> LENGTH: 21
<212> TYPE: DNA
<213> ORGANISM: Homo sapiens

<400> SEQUENCE: 1192
atctaatgac maaaagtgac a                                             21

<210> SEQ ID NO 1193
<211> LENGTH: 21
<212> TYPE: DNA
<213> ORGANISM: Homo sapiens

<400> SEQUENCE: 1193
gatgatgaac rgtttgtccc a                                             21

<210> SEQ ID NO 1194
<211> LENGTH: 21
<212> TYPE: DNA
<213> ORGANISM: Homo sapiens

<400> SEQUENCE: 1194
tcagcaagtc yctttatgg t                                              21

<210> SEQ ID NO 1195
<211> LENGTH: 21
<212> TYPE: DNA
<213> ORGANISM: Homo sapiens

<400> SEQUENCE: 1195
gactggaagg saaagtcaaa c                                                 21

<210> SEQ ID NO 1196
<211> LENGTH: 21
<212> TYPE: DNA
<213> ORGANISM: Homo sapiens

<400> SEQUENCE: 1196
ttacctcctg racatggacc g                                                 21

<210> SEQ ID NO 1197
<211> LENGTH: 21
<212> TYPE: DNA
<213> ORGANISM: Homo sapiens

<400> SEQUENCE: 1197
tcccagattt ycagtctgat a                                                 21

<210> SEQ ID NO 1198
<211> LENGTH: 21
<212> TYPE: DNA
<213> ORGANISM: Homo sapiens

<400> SEQUENCE: 1198
ctggaaggca ragtcaaaca g                                                 21

<210> SEQ ID NO 1199
<211> LENGTH: 21
<212> TYPE: DNA
<213> ORGANISM: Homo sapiens

<400> SEQUENCE: 1199
agagcatgtc maatgttcca t                                                 21

<210> SEQ ID NO 1200
<211> LENGTH: 21
<212> TYPE: DNA
<213> ORGANISM: Homo sapiens

<400> SEQUENCE: 1200
atctcaatcg rcacaagctc t                                                 21

<210> SEQ ID NO 1201
<211> LENGTH: 21
<212> TYPE: DNA
<213> ORGANISM: Homo sapiens

<400> SEQUENCE: 1201
aaaggagaca kgacggcagg a                                                 21

<210> SEQ ID NO 1202
<211> LENGTH: 21
<212> TYPE: DNA
<213> ORGANISM: Homo sapiens

<400> SEQUENCE: 1202

-continued tgaagctcac wctttataat c        21

<210> SEQ ID NO 1203
<211> LENGTH: 21
<212> TYPE: DNA
<213> ORGANISM: Homo sapiens

<400> SEQUENCE: 1203
ctcaacagac rgcttccttg a        21

<210> SEQ ID NO 1204
<211> LENGTH: 21
<212> TYPE: DNA
<213> ORGANISM: Homo sapiens

<400> SEQUENCE: 1204
agagccagag ytctacctcg a        21

<210> SEQ ID NO 1205
<211> LENGTH: 21
<212> TYPE: DNA
<213> ORGANISM: Homo sapiens

<400> SEQUENCE: 1205
gctcagacag rgaaccctga g        21

<210> SEQ ID NO 1206
<211> LENGTH: 21
<212> TYPE: DNA
<213> ORGANISM: Homo sapiens

<400> SEQUENCE: 1206
aaaagcctta ygtgtgccgg g        21

<210> SEQ ID NO 1207
<211> LENGTH: 21
<212> TYPE: DNA
<213> ORGANISM: Homo sapiens

<400> SEQUENCE: 1207
ctggggatcc rggcccaggg g        21

<210> SEQ ID NO 1208
<211> LENGTH: 21
<212> TYPE: DNA
<213> ORGANISM: Homo sapiens

<400> SEQUENCE: 1208
gggaaaagcc ktatgtgtgc c        21

<210> SEQ ID NO 1209
<211> LENGTH: 21
<212> TYPE: DNA
<213> ORGANISM: Homo sapiens

<400> SEQUENCE: 1209
cagctctaat yacacacaag c        21

<210> SEQ ID NO 1210
<211> LENGTH: 21
<212> TYPE: DNA
<213> ORGANISM: Homo sapiens

<400> SEQUENCE: 1210
agcattgtat rtggagaagt c                                              21

<210> SEQ ID NO 1211
<211> LENGTH: 21
<212> TYPE: DNA
<213> ORGANISM: Homo sapiens

<400> SEQUENCE: 1211
cacagctcct ygctcagcca g                                              21

<210> SEQ ID NO 1212
<211> LENGTH: 21
<212> TYPE: DNA
<213> ORGANISM: Homo sapiens

<400> SEQUENCE: 1212
tcagccagca ygaaaggacg c                                              21

<210> SEQ ID NO 1213
<211> LENGTH: 21
<212> TYPE: DNA
<213> ORGANISM: Homo sapiens

<400> SEQUENCE: 1213
agtcacagct ygtccctcac c                                              21

<210> SEQ ID NO 1214
<211> LENGTH: 21
<212> TYPE: DNA
<213> ORGANISM: Homo sapiens

<400> SEQUENCE: 1214
gcgaatccac rctggggaga a                                              21

<210> SEQ ID NO 1215
<211> LENGTH: 21
<212> TYPE: DNA
<213> ORGANISM: Homo sapiens

<400> SEQUENCE: 1215
caggagagaa rccctatgaa t                                              21

<210> SEQ ID NO 1216
<211> LENGTH: 21
<212> TYPE: DNA
<213> ORGANISM: Homo sapiens

<400> SEQUENCE: 1216
aaagccgtat sggtgcaatg a                                              21

<210> SEQ ID NO 1217
<211> LENGTH: 21
<212> TYPE: DNA
<213> ORGANISM: Homo sapiens

<400> SEQUENCE: 1217
caccaaacat yagcgaatcc a                                              21

<210> SEQ ID NO 1218
<211> LENGTH: 21
<212> TYPE: DNA
<213> ORGANISM: Homo sapiens -continued
<210> SEQ ID NO 1219
<211> LENGTH: 21
<212> TYPE: DNA
<213> ORGANISM: Homo sapiens

<400> SEQUENCE: 1219
tccccaagtg ractcgcccc g                                              21

<210> SEQ ID NO 1220
<211> LENGTH: 21
<212> TYPE: DNA
<213> ORGANISM: Homo sapiens

<400> SEQUENCE: 1220
gagctggcct rtactttagc a                                              21

<210> SEQ ID NO 1221
<211> LENGTH: 21
<212> TYPE: DNA
<213> ORGANISM: Homo sapiens

<400> SEQUENCE: 1221
tgctgtgggc rtaagcaccc t                                              21

<210> SEQ ID NO 1222
<211> LENGTH: 21
<212> TYPE: DNA
<213> ORGANISM: Homo sapiens

<400> SEQUENCE: 1222
tgagtcctct ktttcatcag c                                              21

<210> SEQ ID NO 1223
<211> LENGTH: 21
<212> TYPE: DNA
<213> ORGANISM: Homo sapiens

<400> SEQUENCE: 1223
aaacatcatt ygattgaaca c                                              21

<210> SEQ ID NO 1224
<211> LENGTH: 21
<212> TYPE: DNA
<213> ORGANISM: Homo sapiens

<400> SEQUENCE: 1224
agatattcca waagagtagt t                                              21

<210> SEQ ID NO 1225
<211> LENGTH: 21
<212> TYPE: DNA
<213> ORGANISM: Homo sapiens

<400> SEQUENCE: 1225
agagaaggga mtgctaagaa c                                              21

<210> SEQ ID NO 1226
<211> LENGTH: 21
<212> TYPE: DNA
<213> ORGANISM: Homo sapiens

<400> SEQUENCE: 1218
cctatgggcc rttcaccacg g                                              21

<400> SEQUENCE: 1226
tgccaacaga ycagacagtg t                                               21

<210> SEQ ID NO 1227
<211> LENGTH: 21
<212> TYPE: DNA
<213> ORGANISM: Homo sapiens

<400> SEQUENCE: 1227
ataactttag ytgctccctg t                                               21

<210> SEQ ID NO 1228
<211> LENGTH: 21
<212> TYPE: DNA
<213> ORGANISM: Homo sapiens

<400> SEQUENCE: 1228
cagttttacc rgtgggatca a                                               21

<210> SEQ ID NO 1229
<211> LENGTH: 21
<212> TYPE: DNA
<213> ORGANISM: Homo sapiens

<400> SEQUENCE: 1229
cttgccaaca rtccaaaata g                                               21

<210> SEQ ID NO 1230
<211> LENGTH: 21
<212> TYPE: DNA
<213> ORGANISM: Homo sapiens

<400> SEQUENCE: 1230
acaagtatct statgccatg c                                               21

<210> SEQ ID NO 1231
<211> LENGTH: 21
<212> TYPE: DNA
<213> ORGANISM: Homo sapiens

<400> SEQUENCE: 1231
tgacgatgtc rgaaccatg c                                                21

<210> SEQ ID NO 1232
<211> LENGTH: 21
<212> TYPE: DNA
<213> ORGANISM: Homo sapiens

<400> SEQUENCE: 1232
gccattccca ygccaaaatg t                                               21

<210> SEQ ID NO 1233
<211> LENGTH: 21
<212> TYPE: DNA
<213> ORGANISM: Homo sapiens

<400> SEQUENCE: 1233
agagtaccag stgttggtgg a                                               21

<210> SEQ ID NO 1234
<211> LENGTH: 10
<212> TYPE: DNA

<213> ORGANISM: Homo sapiens

<400> SEQUENCE: 1234 attgttcccs                                                          10

<210> SEQ ID NO 1235
<211> LENGTH: 21
<212> TYPE: DNA
<213> ORGANISM: Homo sapiens

<400> SEQUENCE: 1235
tgctggcaga rtcagatgaa t                                             21

<210> SEQ ID NO 1236
<211> LENGTH: 21
<212> TYPE: DNA
<213> ORGANISM: Homo sapiens

<400> SEQUENCE: 1236
tggccaaggc maaagctgtg a                                             21

<210> SEQ ID NO 1237
<211> LENGTH: 21
<212> TYPE: DNA
<213> ORGANISM: Homo sapiens

<400> SEQUENCE: 1237
aactgcctga rtgtcttaaa t                                             21

<210> SEQ ID NO 1238
<211> LENGTH: 21
<212> TYPE: DNA
<213> ORGANISM: Homo sapiens

<400> SEQUENCE: 1238
tcgaaatgga scgtgcgttc c                                             21

<210> SEQ ID NO 1239
<211> LENGTH: 21
<212> TYPE: DNA
<213> ORGANISM: Homo sapiens

<400> SEQUENCE: 1239
actgccccac sgtcattaac a                                             21

<210> SEQ ID NO 1240
<211> LENGTH: 21
<212> TYPE: DNA
<213> ORGANISM: Homo sapiens

<400> SEQUENCE: 1240
ctgccccacc rtcattaaca g                                             21

<210> SEQ ID NO 1241
<211> LENGTH: 21
<212> TYPE: DNA
<213> ORGANISM: Homo sapiens

<400> SEQUENCE: 1241
aagagactat yacagccctc t                                             21

<210> SEQ ID NO 1242
<211> LENGTH: 21

```
<212> TYPE: DNA
<213> ORGANISM: Homo sapiens

<400> SEQUENCE: 1242
ccgccaccag yagtaccggg t                                              21

<210> SEQ ID NO 1243
<211> LENGTH: 21
<212> TYPE: DNA
<213> ORGANISM: Homo sapiens

<400> SEQUENCE: 1243
ggagcgcaga stcggcaggc a                                              21

<210> SEQ ID NO 1244
<211> LENGTH: 21
<212> TYPE: DNA
<213> ORGANISM: Homo sapiens

<400> SEQUENCE: 1244
gccctcaagg rctgaaaata a                                              21

<210> SEQ ID NO 1245
<211> LENGTH: 21
<212> TYPE: DNA
<213> ORGANISM: Homo sapiens

<400> SEQUENCE: 1245
atgagtacga ygagcttcca g                                              21

<210> SEQ ID NO 1246
<211> LENGTH: 21
<212> TYPE: DNA
<213> ORGANISM: Homo sapiens

<400> SEQUENCE: 1246
tcatgggtct rgatggggcc a                                              21

<210> SEQ ID NO 1247
<211> LENGTH: 21
<212> TYPE: DNA
<213> ORGANISM: Homo sapiens

<400> SEQUENCE: 1247
ctcagatcca ytggacactt t                                              21

<210> SEQ ID NO 1248
<211> LENGTH: 21
<212> TYPE: DNA
<213> ORGANISM: Homo sapiens

<400> SEQUENCE: 1248
cgcaggctga rgtgggagta c                                              21

<210> SEQ ID NO 1249
<211> LENGTH: 21
<212> TYPE: DNA
<213> ORGANISM: Homo sapiens

<400> SEQUENCE: 1249
aggccttgtc yccttttctat t                                             21

<210> SEQ ID NO 1250
```

```
<211> LENGTH: 21
<212> TYPE: DNA
<213> ORGANISM: Homo sapiens

<400> SEQUENCE: 1250
cttctaacga raccactttt g                                              21

<210> SEQ ID NO 1251
<211> LENGTH: 21
<212> TYPE: DNA
<213> ORGANISM: Homo sapiens

<400> SEQUENCE: 1251
gcttacattc kgaattactt a                                              21

<210> SEQ ID NO 1252
<211> LENGTH: 21
<212> TYPE: DNA
<213> ORGANISM: Homo sapiens

<400> SEQUENCE: 1252
tggctcacta ygacaccacc g                                              21

<210> SEQ ID NO 1253
<211> LENGTH: 21
<212> TYPE: DNA
<213> ORGANISM: Homo sapiens

<400> SEQUENCE: 1253
tcatccccac rgtgctggac a                                              21

<210> SEQ ID NO 1254
<211> LENGTH: 21
<212> TYPE: DNA
<213> ORGANISM: Homo sapiens

<400> SEQUENCE: 1254
ggcacccaat rgaagccatg c                                              21

<210> SEQ ID NO 1255
<211> LENGTH: 21
<212> TYPE: DNA
<213> ORGANISM: Homo sapiens

<400> SEQUENCE: 1255
tcatgggcct rgcagtggtg c                                              21

<210> SEQ ID NO 1256
<211> LENGTH: 21
<212> TYPE: DNA
<213> ORGANISM: Homo sapiens

<400> SEQUENCE: 1256
cgtcacgcag saaagggacg a                                              21

<210> SEQ ID NO 1257
<211> LENGTH: 21
<212> TYPE: DNA
<213> ORGANISM: Homo sapiens

<400> SEQUENCE: 1257
aggcctatgg saatggctac t                                              21
```

<210> SEQ ID NO 1258
<211> LENGTH: 21
<212> TYPE: DNA
<213> ORGANISM: Homo sapiens

<400> SEQUENCE: 1258
cactctctgg rtatgaagag c					21

<210> SEQ ID NO 1259
<211> LENGTH: 21
<212> TYPE: DNA
<213> ORGANISM: Homo sapiens

<400> SEQUENCE: 1259
gcagaaacta ycagaggccg t					21

<210> SEQ ID NO 1260
<211> LENGTH: 21
<212> TYPE: DNA
<213> ORGANISM: Homo sapiens

<400> SEQUENCE: 1260
gcctccttca yggcctacag c					21

<210> SEQ ID NO 1261
<211> LENGTH: 21
<212> TYPE: DNA
<213> ORGANISM: Homo sapiens

<400> SEQUENCE: 1261
agatccagac rgagaggagg g					21

<210> SEQ ID NO 1262
<211> LENGTH: 21
<212> TYPE: DNA
<213> ORGANISM: Homo sapiens

<400> SEQUENCE: 1262
gcatcatcga ygtaatcaca c					21

<210> SEQ ID NO 1263
<211> LENGTH: 21
<212> TYPE: DNA
<213> ORGANISM: Homo sapiens

<400> SEQUENCE: 1263
atcatccata ygacgcagca c					21

<210> SEQ ID NO 1264
<211> LENGTH: 21
<212> TYPE: DNA
<213> ORGANISM: Homo sapiens

<400> SEQUENCE: 1264
aaaattctcc rttgaaggat t					21

<210> SEQ ID NO 1265
<211> LENGTH: 21
<212> TYPE: DNA
<213> ORGANISM: Homo sapiens

<400> SEQUENCE: 1265
tcaccaagtg yttctctagc a					21

<210> SEQ ID NO 1266
<211> LENGTH: 21
<212> TYPE: DNA
<213> ORGANISM: Homo sapiens

<400> SEQUENCE: 1266
caatatcaag ygaaatattc a                                              21

<210> SEQ ID NO 1267
<211> LENGTH: 21
<212> TYPE: DNA
<213> ORGANISM: Homo sapiens

<400> SEQUENCE: 1267
cagagaataa ycttcaattc c                                              21

<210> SEQ ID NO 1268
<211> LENGTH: 21
<212> TYPE: DNA
<213> ORGANISM: Homo sapiens

<400> SEQUENCE: 1268
ttctgacaag ygttgggtct a                                              21

<210> SEQ ID NO 1269
<211> LENGTH: 21
<212> TYPE: DNA
<213> ORGANISM: Homo sapiens

<400> SEQUENCE: 1269
ctatgaaaaa sgagaaaaat g                                              21

<210> SEQ ID NO 1270
<211> LENGTH: 21
<212> TYPE: DNA
<213> ORGANISM: Homo sapiens

<400> SEQUENCE: 1270
tcatctactc sagcccaggc g                                              21

<210> SEQ ID NO 1271
<211> LENGTH: 21
<212> TYPE: DNA
<213> ORGANISM: Homo sapiens

<400> SEQUENCE: 1271
ggagaactgg ytgtctgagt g                                              21

<210> SEQ ID NO 1272
<211> LENGTH: 21
<212> TYPE: DNA
<213> ORGANISM: Homo sapiens

<400> SEQUENCE: 1272
tggagctcca magaaggatg t                                              21

<210> SEQ ID NO 1273
<211> LENGTH: 21
<212> TYPE: DNA
<213> ORGANISM: Homo sapiens

<400> SEQUENCE: 1273
cacctcccac rtcccggagg t                                              21

```
<210> SEQ ID NO 1274
<211> LENGTH: 21
<212> TYPE: DNA
<213> ORGANISM: Homo sapiens

<400> SEQUENCE: 1274
ctggacaggg ygacccgaga g                                    21

<210> SEQ ID NO 1275
<211> LENGTH: 21
<212> TYPE: DNA
<213> ORGANISM: Homo sapiens

<400> SEQUENCE: 1275
caagagctac rtcatcgctg g                                    21

<210> SEQ ID NO 1276
<211> LENGTH: 21
<212> TYPE: DNA
<213> ORGANISM: Homo sapiens

<400> SEQUENCE: 1276
tggcacacat yctgggcatc c                                    21

<210> SEQ ID NO 1277
<211> LENGTH: 21
<212> TYPE: DNA
<213> ORGANISM: Homo sapiens

<400> SEQUENCE: 1277
ggggcatcaa ygtcctgctg a                                    21

<210> SEQ ID NO 1278
<211> LENGTH: 21
<212> TYPE: DNA
<213> ORGANISM: Homo sapiens

<400> SEQUENCE: 1278
acatggccca rgggaagcac a                                    21

<210> SEQ ID NO 1279
<211> LENGTH: 21
<212> TYPE: DNA
<213> ORGANISM: Homo sapiens

<400> SEQUENCE: 1279
ggacccggct yccgtccgtg a                                    21

<210> SEQ ID NO 1280
<211> LENGTH: 21
<212> TYPE: DNA
<213> ORGANISM: Homo sapiens

<400> SEQUENCE: 1280
cacctttgtg rtgataccaa c                                    21

<210> SEQ ID NO 1281
<211> LENGTH: 21
<212> TYPE: DNA
<213> ORGANISM: Homo sapiens

<400> SEQUENCE: 1281
```

-continued tctacctgga yggcaggtgt g                                             21

<210> SEQ ID NO 1282
<211> LENGTH: 21
<212> TYPE: DNA
<213> ORGANISM: Homo sapiens

<400> SEQUENCE: 1282
ggcaggatgc rtgtggttcc a                                             21

<210> SEQ ID NO 1283
<211> LENGTH: 21
<212> TYPE: DNA
<213> ORGANISM: Homo sapiens

<400> SEQUENCE: 1283
gcgtgcccac ragtccggag g                                             21

<210> SEQ ID NO 1284
<211> LENGTH: 21
<212> TYPE: DNA
<213> ORGANISM: Homo sapiens

<400> SEQUENCE: 1284
agcagcgggc raggctcccc c                                             21

<210> SEQ ID NO 1285
<211> LENGTH: 21
<212> TYPE: DNA
<213> ORGANISM: Homo sapiens

<400> SEQUENCE: 1285
atgacagtgc rggaaagcag c                                             21

<210> SEQ ID NO 1286
<211> LENGTH: 21
<212> TYPE: DNA
<213> ORGANISM: Homo sapiens

<400> SEQUENCE: 1286
atcacagaca stctggttgc a                                             21

<210> SEQ ID NO 1287
<211> LENGTH: 21
<212> TYPE: DNA
<213> ORGANISM: Homo sapiens

<400> SEQUENCE: 1287
cactctccag sagctccgtg c                                             21

<210> SEQ ID NO 1288
<211> LENGTH: 21
<212> TYPE: DNA
<213> ORGANISM: Homo sapiens

<400> SEQUENCE: 1288
gctgctgccg scaacctaca a                                             21

<210> SEQ ID NO 1289
<211> LENGTH: 21
<212> TYPE: DNA
<213> ORGANISM: Homo sapiens

<400> SEQUENCE: 1289

```
ctccagaaat rctgaggaac a                                      21

<210> SEQ ID NO 1290
<211> LENGTH: 21
<212> TYPE: DNA
<213> ORGANISM: Homo sapiens

<400> SEQUENCE: 1290
ttgctcgtgc sgtggacaca c                                      21

<210> SEQ ID NO 1291
<211> LENGTH: 21
<212> TYPE: DNA
<213> ORGANISM: Homo sapiens

<400> SEQUENCE: 1291
aggacctgga sgtgattctc c                                      21

<210> SEQ ID NO 1292
<211> LENGTH: 21
<212> TYPE: DNA
<213> ORGANISM: Homo sapiens

<400> SEQUENCE: 1292
gcccctgaga rcaaggcctt c                                      21

<210> SEQ ID NO 1293
<211> LENGTH: 21
<212> TYPE: DNA
<213> ORGANISM: Homo sapiens

<400> SEQUENCE: 1293
tggcctcaac ygccaccaat g                                      21

<210> SEQ ID NO 1294
<211> LENGTH: 21
<212> TYPE: DNA
<213> ORGANISM: Homo sapiens

<400> SEQUENCE: 1294
actgtaccat ragtggagtc c                                      21

<210> SEQ ID NO 1295
<211> LENGTH: 21
<212> TYPE: DNA
<213> ORGANISM: Homo sapiens

<400> SEQUENCE: 1295
gctcgagtgt rccaaaacgt g                                      21

<210> SEQ ID NO 1296
<211> LENGTH: 21
<212> TYPE: DNA
<213> ORGANISM: Homo sapiens

<400> SEQUENCE: 1296
gccagaacta ygacctggag t                                      21

<210> SEQ ID NO 1297
<211> LENGTH: 21
<212> TYPE: DNA
<213> ORGANISM: Homo sapiens
```

```
<400> SEQUENCE: 1297
tctcggaacc rccgttgcac g                                              21

<210> SEQ ID NO 1298
<211> LENGTH: 21
<212> TYPE: DNA
<213> ORGANISM: Homo sapiens

<400> SEQUENCE: 1298
aactttgtcc rctacgtcca g                                              21

<210> SEQ ID NO 1299
<211> LENGTH: 21
<212> TYPE: DNA
<213> ORGANISM: Homo sapiens

<400> SEQUENCE: 1299
gccctaatgc yaacgtgcag g                                              21

<210> SEQ ID NO 1300
<211> LENGTH: 21
<212> TYPE: DNA
<213> ORGANISM: Homo sapiens

<400> SEQUENCE: 1300
ttaccagtga ygtcttccag g                                              21

<210> SEQ ID NO 1301
<211> LENGTH: 21
<212> TYPE: DNA
<213> ORGANISM: Homo sapiens

<400> SEQUENCE: 1301
acatggtgac ygtggagtac c                                              21

<210> SEQ ID NO 1302
<211> LENGTH: 21
<212> TYPE: DNA
<213> ORGANISM: Homo sapiens

<400> SEQUENCE: 1302
caggagcaag ragttcatgg a                                              21

<210> SEQ ID NO 1303
<211> LENGTH: 21
<212> TYPE: DNA
<213> ORGANISM: Homo sapiens

<400> SEQUENCE: 1303
cctgcagcgg ktgcgagaga t                                              21

<210> SEQ ID NO 1304
<211> LENGTH: 21
<212> TYPE: DNA
<213> ORGANISM: Homo sapiens

<400> SEQUENCE: 1304
tcagcgaggc mcagtccaaa g                                              21

<210> SEQ ID NO 1305
<211> LENGTH: 21
<212> TYPE: DNA
<213> ORGANISM: Homo sapiens
```

```
<400> SEQUENCE: 1305
aaacaaggag yaggacctgg a                                              21

<210> SEQ ID NO 1306
<211> LENGTH: 21
<212> TYPE: DNA
<213> ORGANISM: Homo sapiens

<400> SEQUENCE: 1306
tcaccttggt yacatcttca c                                              21

<210> SEQ ID NO 1307
<211> LENGTH: 21
<212> TYPE: DNA
<213> ORGANISM: Homo sapiens

<400> SEQUENCE: 1307
caggtgtgca rccagctgga g                                              21

<210> SEQ ID NO 1308
<211> LENGTH: 21
<212> TYPE: DNA
<213> ORGANISM: Homo sapiens

<400> SEQUENCE: 1308
accaaccaca ytgtgatgac c                                              21

<210> SEQ ID NO 1309
<211> LENGTH: 21
<212> TYPE: DNA
<213> ORGANISM: Homo sapiens

<400> SEQUENCE: 1309
tcactgccga ycagctcagg a                                              21

<210> SEQ ID NO 1310
<211> LENGTH: 21
<212> TYPE: DNA
<213> ORGANISM: Homo sapiens

<400> SEQUENCE: 1310
catctacaac wtgataggat a                                              21

<210> SEQ ID NO 1311
<211> LENGTH: 21
<212> TYPE: DNA
<213> ORGANISM: Homo sapiens

<400> SEQUENCE: 1311
tgaagaagct rgtataccto t                                              21

<210> SEQ ID NO 1312
<211> LENGTH: 21
<212> TYPE: DNA
<213> ORGANISM: Homo sapiens

<400> SEQUENCE: 1312
ttcttggcgg yggccttgac a                                              21

<210> SEQ ID NO 1313
<211> LENGTH: 21
<212> TYPE: DNA
```

<213> ORGANISM: Homo sapiens

<400> SEQUENCE: 1313
aggtccacgc rccactcagc c          21

<210> SEQ ID NO 1314
<211> LENGTH: 21
<212> TYPE: DNA
<213> ORGANISM: Homo sapiens

<400> SEQUENCE: 1314
gaggcaccac yatgtaccct g          21

<210> SEQ ID NO 1315
<211> LENGTH: 21
<212> TYPE: DNA
<213> ORGANISM: Homo sapiens

<400> SEQUENCE: 1315
cgaggctgac ygagagcgag g          21

<210> SEQ ID NO 1316
<211> LENGTH: 21
<212> TYPE: DNA
<213> ORGANISM: Homo sapiens

<400> SEQUENCE: 1316
ggtgcccagc ygtgaccaga c          21

<210> SEQ ID NO 1317
<211> LENGTH: 21
<212> TYPE: DNA
<213> ORGANISM: Homo sapiens

<400> SEQUENCE: 1317
acaccgtcta yagcatggag c          21

<210> SEQ ID NO 1318
<211> LENGTH: 21
<212> TYPE: DNA
<213> ORGANISM: Homo sapiens

<400> SEQUENCE: 1318
gatcttggca rgagacaaga a          21

<210> SEQ ID NO 1319
<211> LENGTH: 21
<212> TYPE: DNA
<213> ORGANISM: Homo sapiens

<400> SEQUENCE: 1319
ggctgctctc rgagatccgg c          21

<210> SEQ ID NO 1320
<211> LENGTH: 21
<212> TYPE: DNA
<213> ORGANISM: Homo sapiens

<400> SEQUENCE: 1320
tgctgctgcc kgatgactac c          21

<210> SEQ ID NO 1321
<211> LENGTH: 21

<212> TYPE: DNA
<213> ORGANISM: Homo sapiens

<400> SEQUENCE: 1321
tgtactaccg yggtgccaac c                                    21

<210> SEQ ID NO 1322
<211> LENGTH: 21
<212> TYPE: DNA
<213> ORGANISM: Homo sapiens

<400> SEQUENCE: 1322
agctggtctc ygaagccaag g                                    21

<210> SEQ ID NO 1323
<211> LENGTH: 21
<212> TYPE: DNA
<213> ORGANISM: Homo sapiens

<400> SEQUENCE: 1323
agagtgtcat yggcagcgtg c                                    21

<210> SEQ ID NO 1324
<211> LENGTH: 21
<212> TYPE: DNA
<213> ORGANISM: Homo sapiens

<400> SEQUENCE: 1324
acgccagtga ygacggcagc g                                    21

<210> SEQ ID NO 1325
<211> LENGTH: 21
<212> TYPE: DNA
<213> ORGANISM: Homo sapiens

<400> SEQUENCE: 1325
cttgccaacc wggccgacct g                                    21

<210> SEQ ID NO 1326
<211> LENGTH: 21
<212> TYPE: DNA
<213> ORGANISM: Homo sapiens

<400> SEQUENCE: 1326
tcatgggtga yggcctggcc a                                    21

<210> SEQ ID NO 1327
<211> LENGTH: 21
<212> TYPE: DNA
<213> ORGANISM: Homo sapiens

<400> SEQUENCE: 1327
gacctctgcg sccggaaggt c                                    21

<210> SEQ ID NO 1328
<211> LENGTH: 21
<212> TYPE: DNA
<213> ORGANISM: Homo sapiens

<400> SEQUENCE: 1328
gtgacgacgg yagcggctcg g                                    21

<210> SEQ ID NO 1329

```
<211> LENGTH: 21
<212> TYPE: DNA
<213> ORGANISM: Homo sapiens

<400> SEQUENCE: 1329
tgacctctgc rgccggaagg t                                              21

<210> SEQ ID NO 1330
<211> LENGTH: 21
<212> TYPE: DNA
<213> ORGANISM: Homo sapiens

<400> SEQUENCE: 1330
tctggcactt ygccgacaac c                                              21

<210> SEQ ID NO 1331
<211> LENGTH: 21
<212> TYPE: DNA
<213> ORGANISM: Homo sapiens

<400> SEQUENCE: 1331
gctccgtggc ycaggttgtg c                                              21

<210> SEQ ID NO 1332
<211> LENGTH: 21
<212> TYPE: DNA
<213> ORGANISM: Homo sapiens

<400> SEQUENCE: 1332
ccctcatcct sgtgatgttt g                                              21

<210> SEQ ID NO 1333
<211> LENGTH: 21
<212> TYPE: DNA
<213> ORGANISM: Homo sapiens

<400> SEQUENCE: 1333
tgtgtgccca ygaggagctc c                                              21

<210> SEQ ID NO 1334
<211> LENGTH: 21
<212> TYPE: DNA
<213> ORGANISM: Homo sapiens

<400> SEQUENCE: 1334
ccatacacag kccttgcaaa c                                              21

<210> SEQ ID NO 1335
<211> LENGTH: 21
<212> TYPE: DNA
<213> ORGANISM: Homo sapiens

<400> SEQUENCE: 1335
ggagatctgt kttcgtacag t                                              21

<210> SEQ ID NO 1336
<211> LENGTH: 21
<212> TYPE: DNA
<213> ORGANISM: Homo sapiens

<400> SEQUENCE: 1336
tggctgctgt ycatgccgaa a                                              21
```

<210> SEQ ID NO 1337
<211> LENGTH: 21
<212> TYPE: DNA
<213> ORGANISM: Homo sapiens

<400> SEQUENCE: 1337
cccggggcag yggtgtcaat g                                    21

<210> SEQ ID NO 1338
<211> LENGTH: 21
<212> TYPE: DNA
<213> ORGANISM: Homo sapiens

<400> SEQUENCE: 1338
acgagctgat rgtgcgccgc g                                    21

<210> SEQ ID NO 1339
<211> LENGTH: 21
<212> TYPE: DNA
<213> ORGANISM: Homo sapiens

<400> SEQUENCE: 1339
gctggaggtg wcagtcactt a                                    21

<210> SEQ ID NO 1340
<211> LENGTH: 21
<212> TYPE: DNA
<213> ORGANISM: Homo sapiens

<400> SEQUENCE: 1340
ggtggcagtc mcagaatgat g                                    21

<210> SEQ ID NO 1341
<211> LENGTH: 21
<212> TYPE: DNA
<213> ORGANISM: Homo sapiens

<400> SEQUENCE: 1341
cttcatctac ytgtggactg a                                    21

<210> SEQ ID NO 1342
<211> LENGTH: 21
<212> TYPE: DNA
<213> ORGANISM: Homo sapiens

<400> SEQUENCE: 1342
gaggctactg yaatcgctac c                                    21

<210> SEQ ID NO 1343
<211> LENGTH: 21
<212> TYPE: DNA
<213> ORGANISM: Homo sapiens

<400> SEQUENCE: 1343
gaccaggcag wtgattaggg c                                    21

<210> SEQ ID NO 1344
<211> LENGTH: 21
<212> TYPE: DNA
<213> ORGANISM: Homo sapiens

<400> SEQUENCE: 1344
tttctccgag yttcatctac c                                    21

<210> SEQ ID NO 1345
<211> LENGTH: 21
<212> TYPE: DNA
<213> ORGANISM: Homo sapiens

<400> SEQUENCE: 1345
cacggccatg ytgatcgctg c                                              21

<210> SEQ ID NO 1346
<211> LENGTH: 21
<212> TYPE: DNA
<213> ORGANISM: Homo sapiens

<400> SEQUENCE: 1346
agtgtgatcc rgatggggca g                                              21

<210> SEQ ID NO 1347
<211> LENGTH: 21
<212> TYPE: DNA
<213> ORGANISM: Homo sapiens

<400> SEQUENCE: 1347
ctatggagac rtggccacag g                                              21

<210> SEQ ID NO 1348
<211> LENGTH: 21
<212> TYPE: DNA
<213> ORGANISM: Homo sapiens

<400> SEQUENCE: 1348
ggctgtgaac ygtgtgcctg c                                              21

<210> SEQ ID NO 1349
<211> LENGTH: 21
<212> TYPE: DNA
<213> ORGANISM: Homo sapiens

<400> SEQUENCE: 1349
cctgacagga ytggagaagc g                                              21

<210> SEQ ID NO 1350
<211> LENGTH: 21
<212> TYPE: DNA
<213> ORGANISM: Homo sapiens

<400> SEQUENCE: 1350
tgctgcgctc rgcggacctg a                                              21

<210> SEQ ID NO 1351
<211> LENGTH: 21
<212> TYPE: DNA
<213> ORGANISM: Homo sapiens

<400> SEQUENCE: 1351
tggagcagga kaagcaccgg c                                              21

<210> SEQ ID NO 1352
<211> LENGTH: 21
<212> TYPE: DNA
<213> ORGANISM: Homo sapiens

<400> SEQUENCE: 1352
cgtttggcag rgcagccagg c                                              21

<210> SEQ ID NO 1353
<211> LENGTH: 21
<212> TYPE: DNA
<213> ORGANISM: Homo sapiens

<400> SEQUENCE: 1353
ggtcccaatg rgcaaggagc c                                           21

<210> SEQ ID NO 1354
<211> LENGTH: 21
<212> TYPE: DNA
<213> ORGANISM: Homo sapiens

<400> SEQUENCE: 1354
ccacagagat ycctgacttc a                                           21

<210> SEQ ID NO 1355
<211> LENGTH: 21
<212> TYPE: DNA
<213> ORGANISM: Homo sapiens

<400> SEQUENCE: 1355
tttgggatga ytccagctgc c                                           21

<210> SEQ ID NO 1356
<211> LENGTH: 21
<212> TYPE: DNA
<213> ORGANISM: Homo sapiens

<400> SEQUENCE: 1356
ttcaggctta yggtatgaag c                                           21

<210> SEQ ID NO 1357
<211> LENGTH: 21
<212> TYPE: DNA
<213> ORGANISM: Homo sapiens

<400> SEQUENCE: 1357
agattgacaa rttcgagttt g                                           21

<210> SEQ ID NO 1358
<211> LENGTH: 21
<212> TYPE: DNA
<213> ORGANISM: Homo sapiens

<400> SEQUENCE: 1358
gcaaagtcgg ygggcgctgg a                                           21

<210> SEQ ID NO 1359
<211> LENGTH: 21
<212> TYPE: DNA
<213> ORGANISM: Homo sapiens

<400> SEQUENCE: 1359
ggagctctgg sagaccctgc a                                           21

<210> SEQ ID NO 1360
<211> LENGTH: 21
<212> TYPE: DNA
<213> ORGANISM: Homo sapiens

<400> SEQUENCE: 1360

| | |
|---|---|
| gattctcctc rggcatcaca g | 21 |

<210> SEQ ID NO 1361
<211> LENGTH: 21
<212> TYPE: DNA
<213> ORGANISM: Homo sapiens

<400> SEQUENCE: 1361

| | |
|---|---|
| ttgagttcca ytgtgctgtg c | 21 |

<210> SEQ ID NO 1362
<211> LENGTH: 21
<212> TYPE: DNA
<213> ORGANISM: Homo sapiens

<400> SEQUENCE: 1362

| | |
|---|---|
| aatgctatga yagctcccca t | 21 |

<210> SEQ ID NO 1363
<211> LENGTH: 21
<212> TYPE: DNA
<213> ORGANISM: Homo sapiens

<400> SEQUENCE: 1363

| | |
|---|---|
| tggctgtgcc ygaggaaacc g | 21 |

<210> SEQ ID NO 1364
<211> LENGTH: 21
<212> TYPE: DNA
<213> ORGANISM: Homo sapiens

<400> SEQUENCE: 1364

| | |
|---|---|
| gtgccgctgg yggccagcat c | 21 |

<210> SEQ ID NO 1365
<211> LENGTH: 21
<212> TYPE: DNA
<213> ORGANISM: Homo sapiens

<400> SEQUENCE: 1365

| | |
|---|---|
| ggacagccac rcggtgctgc a | 21 |

<210> SEQ ID NO 1366
<211> LENGTH: 21
<212> TYPE: DNA
<213> ORGANISM: Homo sapiens

<400> SEQUENCE: 1366

| | |
|---|---|
| caaagaaatc rattcagtcg g | 21 |

<210> SEQ ID NO 1367
<211> LENGTH: 21
<212> TYPE: DNA
<213> ORGANISM: Homo sapiens

<400> SEQUENCE: 1367

| | |
|---|---|
| atctaaacag yctgcctcac a | 21 |

<210> SEQ ID NO 1368
<211> LENGTH: 21
<212> TYPE: DNA
<213> ORGANISM: Homo sapiens

<400> SEQUENCE: 1368

```
ctaaggttgt rtctcagtat c                                              21

<210> SEQ ID NO 1369
<211> LENGTH: 21
<212> TYPE: DNA
<213> ORGANISM: Homo sapiens

<400> SEQUENCE: 1369
tacagcgtgg ygaagacgga t                                              21

<210> SEQ ID NO 1370
<211> LENGTH: 21
<212> TYPE: DNA
<213> ORGANISM: Homo sapiens

<400> SEQUENCE: 1370
attattgctg mccggaagca g                                              21

<210> SEQ ID NO 1371
<211> LENGTH: 21
<212> TYPE: DNA
<213> ORGANISM: Homo sapiens

<400> SEQUENCE: 1371
agatgtcctt rctggctaca a                                              21

<210> SEQ ID NO 1372
<211> LENGTH: 21
<212> TYPE: DNA
<213> ORGANISM: Homo sapiens

<400> SEQUENCE: 1372
agagagttaa kgccctggag g                                              21

<210> SEQ ID NO 1373
<211> LENGTH: 21
<212> TYPE: DNA
<213> ORGANISM: Homo sapiens

<400> SEQUENCE: 1373
aacttcacca raacatggca a                                              21

<210> SEQ ID NO 1374
<211> LENGTH: 21
<212> TYPE: DNA
<213> ORGANISM: Homo sapiens

<400> SEQUENCE: 1374
tcgatgtggc rggcaacctg g                                              21

<210> SEQ ID NO 1375
<211> LENGTH: 21
<212> TYPE: DNA
<213> ORGANISM: Homo sapiens

<400> SEQUENCE: 1375
ttcaccatgt ytctgaacct g                                              21

<210> SEQ ID NO 1376
<211> LENGTH: 21
<212> TYPE: DNA
<213> ORGANISM: Homo sapiens
```

```
<400> SEQUENCE: 1376
gaggtggacc rgatgttcca g                                              21

<210> SEQ ID NO 1377
<211> LENGTH: 21
<212> TYPE: DNA
<213> ORGANISM: Homo sapiens

<400> SEQUENCE: 1377
tcgagaacct rcggcggcga t                                              21

<210> SEQ ID NO 1378
<211> LENGTH: 21
<212> TYPE: DNA
<213> ORGANISM: Homo sapiens

<400> SEQUENCE: 1378
tcgctggcat rctggcagta g                                              21

<210> SEQ ID NO 1379
<211> LENGTH: 21
<212> TYPE: DNA
<213> ORGANISM: Homo sapiens

<400> SEQUENCE: 1379
aacccaacac rccatttgcc g                                              21

<210> SEQ ID NO 1380
<211> LENGTH: 21
<212> TYPE: DNA
<213> ORGANISM: Homo sapiens

<400> SEQUENCE: 1380
actcgtactc sttccgggtc t                                              21

<210> SEQ ID NO 1381
<211> LENGTH: 21
<212> TYPE: DNA
<213> ORGANISM: Homo sapiens

<400> SEQUENCE: 1381
agagagggag sctcggagtg g                                              21

<210> SEQ ID NO 1382
<211> LENGTH: 21
<212> TYPE: DNA
<213> ORGANISM: Homo sapiens

<400> SEQUENCE: 1382
ctgtcgacga yccctacgcc a                                              21

<210> SEQ ID NO 1383
<211> LENGTH: 21
<212> TYPE: DNA
<213> ORGANISM: Homo sapiens

<400> SEQUENCE: 1383
gaaagatgag ytttgccgtc a                                              21

<210> SEQ ID NO 1384
<211> LENGTH: 21
<212> TYPE: DNA
<213> ORGANISM: Homo sapiens
```

-continued

```
<400> SEQUENCE: 1384
atgacttggc ytccctcagt g                                              21

<210> SEQ ID NO 1385
<211> LENGTH: 21
<212> TYPE: DNA
<213> ORGANISM: Homo sapiens

<400> SEQUENCE: 1385
aagatcctaa yctggtgaat g                                              21

<210> SEQ ID NO 1386
<211> LENGTH: 21
<212> TYPE: DNA
<213> ORGANISM: Homo sapiens

<400> SEQUENCE: 1386
gctgctactt ygacatcgag t                                              21

<210> SEQ ID NO 1387
<211> LENGTH: 21
<212> TYPE: DNA
<213> ORGANISM: Homo sapiens

<400> SEQUENCE: 1387
gaaatatacc rtaagtatgg a                                              21

<210> SEQ ID NO 1388
<211> LENGTH: 21
<212> TYPE: DNA
<213> ORGANISM: Homo sapiens

<400> SEQUENCE: 1388
gtataataaa ytcctggagt t                                              21

<210> SEQ ID NO 1389
<211> LENGTH: 21
<212> TYPE: DNA
<213> ORGANISM: Homo sapiens

<400> SEQUENCE: 1389
agcagcctta rgcatcttgg a                                              21

<210> SEQ ID NO 1390
<211> LENGTH: 21
<212> TYPE: DNA
<213> ORGANISM: Homo sapiens

<400> SEQUENCE: 1390
tcaaccagct ktctgtgcct t                                              21

<210> SEQ ID NO 1391
<211> LENGTH: 21
<212> TYPE: DNA
<213> ORGANISM: Homo sapiens

<400> SEQUENCE: 1391
aaaaaggcaa wactgttcct g                                              21

<210> SEQ ID NO 1392
<211> LENGTH: 21
<212> TYPE: DNA
```

<213> ORGANISM: Homo sapiens

<400> SEQUENCE: 1392
tttttaatta yatttactcc a                                              21

<210> SEQ ID NO 1393
<211> LENGTH: 21
<212> TYPE: DNA
<213> ORGANISM: Homo sapiens

<400> SEQUENCE: 1393
ttagtaaaac yggagctgaa g                                              21

<210> SEQ ID NO 1394
<211> LENGTH: 21
<212> TYPE: DNA
<213> ORGANISM: Homo sapiens

<400> SEQUENCE: 1394
gctcattggc rtcaacctga t                                              21

<210> SEQ ID NO 1395
<211> LENGTH: 21
<212> TYPE: DNA
<213> ORGANISM: Homo sapiens

<400> SEQUENCE: 1395
ctgtccatgt kccagttcag c                                              21

<210> SEQ ID NO 1396
<211> LENGTH: 21
<212> TYPE: DNA
<213> ORGANISM: Homo sapiens

<400> SEQUENCE: 1396
actacaacac rtccagcaaa g                                              21

<210> SEQ ID NO 1397
<211> LENGTH: 21
<212> TYPE: DNA
<213> ORGANISM: Homo sapiens

<400> SEQUENCE: 1397
ctggtcccca rgggcattgg t                                              21

<210> SEQ ID NO 1398
<211> LENGTH: 21
<212> TYPE: DNA
<213> ORGANISM: Homo sapiens

<400> SEQUENCE: 1398
cagcctcctc rgagacctcc a                                              21

<210> SEQ ID NO 1399
<211> LENGTH: 21
<212> TYPE: DNA
<213> ORGANISM: Homo sapiens

<400> SEQUENCE: 1399
aatccaccga yggaagccgc a                                              21

<210> SEQ ID NO 1400
<211> LENGTH: 21

<212> TYPE: DNA
<213> ORGANISM: Homo sapiens

<400> SEQUENCE: 1400
ccggcaaacc ygacagccag t                                              21

<210> SEQ ID NO 1401
<211> LENGTH: 21
<212> TYPE: DNA
<213> ORGANISM: Homo sapiens

<400> SEQUENCE: 1401
tctcggacac ygtggctttt g                                              21

<210> SEQ ID NO 1402
<211> LENGTH: 21
<212> TYPE: DNA
<213> ORGANISM: Homo sapiens

<400> SEQUENCE: 1402
gctgcgttct yttccgcact c                                              21

<210> SEQ ID NO 1403
<211> LENGTH: 21
<212> TYPE: DNA
<213> ORGANISM: Homo sapiens

<400> SEQUENCE: 1403
ctggattacg ytgcgttctc t                                              21

<210> SEQ ID NO 1404
<211> LENGTH: 21
<212> TYPE: DNA
<213> ORGANISM: Homo sapiens

<400> SEQUENCE: 1404
gagtgcactt ycctatcccg c                                              21

<210> SEQ ID NO 1405
<211> LENGTH: 21
<212> TYPE: DNA
<213> ORGANISM: Homo sapiens

<400> SEQUENCE: 1405
agaagacgtt yaccaagccc c                                              21

<210> SEQ ID NO 1406
<211> LENGTH: 21
<212> TYPE: DNA
<213> ORGANISM: Homo sapiens

<400> SEQUENCE: 1406
aatttctcca ycaattttcc a                                              21

<210> SEQ ID NO 1407
<211> LENGTH: 21
<212> TYPE: DNA
<213> ORGANISM: Homo sapiens

<400> SEQUENCE: 1407
tgtgtgaact ktcacctgtc a                                              21

<210> SEQ ID NO 1408

```
<211> LENGTH: 21
<212> TYPE: DNA
<213> ORGANISM: Homo sapiens

<400> SEQUENCE: 1408
ctgatgagct yctgtttagc c                                        21

<210> SEQ ID NO 1409
<211> LENGTH: 21
<212> TYPE: DNA
<213> ORGANISM: Homo sapiens

<400> SEQUENCE: 1409
agctacggat yctgctggac c                                        21

<210> SEQ ID NO 1410
<211> LENGTH: 21
<212> TYPE: DNA
<213> ORGANISM: Homo sapiens

<400> SEQUENCE: 1410
tcttgaagtg maaaaagtct g                                        21

<210> SEQ ID NO 1411
<211> LENGTH: 21
<212> TYPE: DNA
<213> ORGANISM: Homo sapiens

<400> SEQUENCE: 1411
cctcctgagc yacggatcct g                                        21

<210> SEQ ID NO 1412
<211> LENGTH: 21
<212> TYPE: DNA
<213> ORGANISM: Homo sapiens

<400> SEQUENCE: 1412
atgttgaggt rtctgttact a                                        21

<210> SEQ ID NO 1413
<211> LENGTH: 21
<212> TYPE: DNA
<213> ORGANISM: Homo sapiens

<400> SEQUENCE: 1413
ctctgcgcgg yttttttgagc g                                       21

<210> SEQ ID NO 1414
<211> LENGTH: 21
<212> TYPE: DNA
<213> ORGANISM: Homo sapiens

<400> SEQUENCE: 1414
agacagcgat ygcctcggag g                                        21

<210> SEQ ID NO 1415
<211> LENGTH: 21
<212> TYPE: DNA
<213> ORGANISM: Homo sapiens

<400> SEQUENCE: 1415
accttctgga rtggattgaa c                                        21
```

```
<210> SEQ ID NO 1416
<211> LENGTH: 21
<212> TYPE: DNA
<213> ORGANISM: Homo sapiens

<400> SEQUENCE: 1416
agctcgaggc ygagaattac c                                      21

<210> SEQ ID NO 1417
<211> LENGTH: 21
<212> TYPE: DNA
<213> ORGANISM: Homo sapiens

<400> SEQUENCE: 1417
acatcaagaa ygagatcgac a                                      21

<210> SEQ ID NO 1418
<211> LENGTH: 21
<212> TYPE: DNA
<213> ORGANISM: Homo sapiens

<400> SEQUENCE: 1418
ccaagcacat ygcggaagag g                                      21

<210> SEQ ID NO 1419
<211> LENGTH: 21
<212> TYPE: DNA
<213> ORGANISM: Homo sapiens

<400> SEQUENCE: 1419
aaggccagac katgcccta t                                       21

<210> SEQ ID NO 1420
<211> LENGTH: 21
<212> TYPE: DNA
<213> ORGANISM: Homo sapiens

<400> SEQUENCE: 1420
ccaacaaagc kgttaagggc a                                      21

<210> SEQ ID NO 1421
<211> LENGTH: 21
<212> TYPE: DNA
<213> ORGANISM: Homo sapiens

<400> SEQUENCE: 1421
ctatggagtc ytcagatgag g                                      21

<210> SEQ ID NO 1422
<211> LENGTH: 21
<212> TYPE: DNA
<213> ORGANISM: Homo sapiens

<400> SEQUENCE: 1422
gggtccattg mccatgcatc t                                      21

<210> SEQ ID NO 1423
<211> LENGTH: 21
<212> TYPE: DNA
<213> ORGANISM: Homo sapiens

<400> SEQUENCE: 1423
atgaccacac rtcagaaaag t                                      21
```

<210> SEQ ID NO 1424
<211> LENGTH: 21
<212> TYPE: DNA
<213> ORGANISM: Homo sapiens

<400> SEQUENCE: 1424
tccatccagc rtctcctccc c                                           21

<210> SEQ ID NO 1425
<211> LENGTH: 21
<212> TYPE: DNA
<213> ORGANISM: Homo sapiens

<400> SEQUENCE: 1425
agggtgaaca yataagggaa a                                           21

<210> SEQ ID NO 1426
<211> LENGTH: 21
<212> TYPE: DNA
<213> ORGANISM: Homo sapiens

<400> SEQUENCE: 1426
ccatcctgaa rgaggagggt g                                           21

<210> SEQ ID NO 1427
<211> LENGTH: 21
<212> TYPE: DNA
<213> ORGANISM: Homo sapiens

<400> SEQUENCE: 1427
tgatcctaaa saaagagatg a                                           21

<210> SEQ ID NO 1428
<211> LENGTH: 21
<212> TYPE: DNA
<213> ORGANISM: Homo sapiens

<400> SEQUENCE: 1428
ccatctcccc ratggtgatg g                                           21

<210> SEQ ID NO 1429
<211> LENGTH: 21
<212> TYPE: DNA
<213> ORGANISM: Homo sapiens

<400> SEQUENCE: 1429
gggatgaaga ygcctgggcc a                                           21

<210> SEQ ID NO 1430
<211> LENGTH: 21
<212> TYPE: DNA
<213> ORGANISM: Homo sapiens

<400> SEQUENCE: 1430
aagcacagcg rtggattgat a                                           21

<210> SEQ ID NO 1431
<211> LENGTH: 21
<212> TYPE: DNA
<213> ORGANISM: Homo sapiens

<400> SEQUENCE: 1431
gccagggtgg ytacaaagat a                                           21

<210> SEQ ID NO 1432
<211> LENGTH: 21
<212> TYPE: DNA
<213> ORGANISM: Homo sapiens

<400> SEQUENCE: 1432
gaattcttca rtccttaaaa c                                              21

<210> SEQ ID NO 1433
<211> LENGTH: 21
<212> TYPE: DNA
<213> ORGANISM: Homo sapiens

<400> SEQUENCE: 1433
ttagacctgc mgaaatcctg a                                              21

<210> SEQ ID NO 1434
<211> LENGTH: 21
<212> TYPE: DNA
<213> ORGANISM: Homo sapiens

<400> SEQUENCE: 1434
agtgttctag mtattctgaa a                                              21

<210> SEQ ID NO 1435
<211> LENGTH: 21
<212> TYPE: DNA
<213> ORGANISM: Homo sapiens

<400> SEQUENCE: 1435
cttttggcaa ygtggagcct g                                              21

<210> SEQ ID NO 1436
<211> LENGTH: 21
<212> TYPE: DNA
<213> ORGANISM: Homo sapiens

<400> SEQUENCE: 1436
ctctggaaca rctcctaatt c                                              21

<210> SEQ ID NO 1437
<211> LENGTH: 21
<212> TYPE: DNA
<213> ORGANISM: Homo sapiens

<400> SEQUENCE: 1437
aaccttatta ytttatgtga g                                              21

<210> SEQ ID NO 1438
<211> LENGTH: 21
<212> TYPE: DNA
<213> ORGANISM: Homo sapiens

<400> SEQUENCE: 1438
attagatgac yttgttgaaa c                                              21

<210> SEQ ID NO 1439
<211> LENGTH: 21
<212> TYPE: DNA
<213> ORGANISM: Homo sapiens

<400> SEQUENCE: 1439

```
gtggtcccag rtgcacttcc t                                              21
```

<210> SEQ ID NO 1440
<211> LENGTH: 21
<212> TYPE: DNA
<213> ORGANISM: Homo sapiens

<400> SEQUENCE: 1440

```
cagacaagtg yaatatgatt a                                              21
```

<210> SEQ ID NO 1441
<211> LENGTH: 21
<212> TYPE: DNA
<213> ORGANISM: Homo sapiens

<400> SEQUENCE: 1441

```
agatgacttt rttgaaacgg g                                              21
```

<210> SEQ ID NO 1442
<211> LENGTH: 21
<212> TYPE: DNA
<213> ORGANISM: Homo sapiens

<400> SEQUENCE: 1442

```
atgcctccaa raaagatggg g                                              21
```

<210> SEQ ID NO 1443
<211> LENGTH: 21
<212> TYPE: DNA
<213> ORGANISM: Homo sapiens

<400> SEQUENCE: 1443

```
ggaactttgc rtactgggct g                                              21
```

<210> SEQ ID NO 1444
<211> LENGTH: 21
<212> TYPE: DNA
<213> ORGANISM: Homo sapiens

<400> SEQUENCE: 1444

```
ccgaggaggc yactggcgtc g                                              21
```

<210> SEQ ID NO 1445
<211> LENGTH: 21
<212> TYPE: DNA
<213> ORGANISM: Homo sapiens

<400> SEQUENCE: 1445

```
gctgctgctg ytcttcgtag g                                              21
```

<210> SEQ ID NO 1446
<211> LENGTH: 21
<212> TYPE: DNA
<213> ORGANISM: Homo sapiens

<400> SEQUENCE: 1446

```
ccataacctg mtgacatttc a                                              21
```

<210> SEQ ID NO 1447
<211> LENGTH: 21
<212> TYPE: DNA
<213> ORGANISM: Homo sapiens

<400> SEQUENCE: 1447

```
agctggaggt raagatccgt g                                              21

<210> SEQ ID NO 1448
<211> LENGTH: 21
<212> TYPE: DNA
<213> ORGANISM: Homo sapiens

<400> SEQUENCE: 1448
acaggacaat ygaggagctg c                                              21

<210> SEQ ID NO 1449
<211> LENGTH: 21
<212> TYPE: DNA
<213> ORGANISM: Homo sapiens

<400> SEQUENCE: 1449
ggaggaggcc racactgagc t                                              21

<210> SEQ ID NO 1450
<211> LENGTH: 21
<212> TYPE: DNA
<213> ORGANISM: Homo sapiens

<400> SEQUENCE: 1450
ctggctgctg mtgacttccg c                                              21

<210> SEQ ID NO 1451
<211> LENGTH: 21
<212> TYPE: DNA
<213> ORGANISM: Homo sapiens

<400> SEQUENCE: 1451
atcgattgca stcagagcct g                                              21

<210> SEQ ID NO 1452
<211> LENGTH: 21
<212> TYPE: DNA
<213> ORGANISM: Homo sapiens

<400> SEQUENCE: 1452
gtcctatcag yactgagagg c                                              21

<210> SEQ ID NO 1453
<211> LENGTH: 21
<212> TYPE: DNA
<213> ORGANISM: Homo sapiens

<400> SEQUENCE: 1453
acacccggga rctgtttctc a                                              21

<210> SEQ ID NO 1454
<211> LENGTH: 21
<212> TYPE: DNA
<213> ORGANISM: Homo sapiens

<400> SEQUENCE: 1454
acctgaagag ygtgatgctg c                                              21

<210> SEQ ID NO 1455
<211> LENGTH: 21
<212> TYPE: DNA
<213> ORGANISM: Homo sapiens
```

-continued

<210> SEQ ID NO 1456
<211> LENGTH: 21
<212> TYPE: DNA
<213> ORGANISM: Homo sapiens

<400> SEQUENCE: 1456
agttccacag raaataccgg a                    21

<210> SEQ ID NO 1457
<211> LENGTH: 21
<212> TYPE: DNA
<213> ORGANISM: Homo sapiens

<400> SEQUENCE: 1457
cctccttcct rcgggcaccc a                    21

<210> SEQ ID NO 1458
<211> LENGTH: 21
<212> TYPE: DNA
<213> ORGANISM: Homo sapiens

<400> SEQUENCE: 1458
ccagccgcct ytttgaccag t                    21

<210> SEQ ID NO 1459
<211> LENGTH: 21
<212> TYPE: DNA
<213> ORGANISM: Homo sapiens

<400> SEQUENCE: 1459
ggatcccagc ygatgtagac c                    21

<210> SEQ ID NO 1460
<211> LENGTH: 21
<212> TYPE: DNA
<213> ORGANISM: Homo sapiens

<400> SEQUENCE: 1460
tagagttggc rttggaaaca t                    21

<210> SEQ ID NO 1461
<211> LENGTH: 21
<212> TYPE: DNA
<213> ORGANISM: Homo sapiens

<400> SEQUENCE: 1461
tatttagtag ygaaaccaaa t                    21

<210> SEQ ID NO 1462
<211> LENGTH: 21
<212> TYPE: DNA
<213> ORGANISM: Homo sapiens

<400> SEQUENCE: 1462
tcattatcac rcaaggtaac t                    21

<210> SEQ ID NO 1463
<211> LENGTH: 21
<212> TYPE: DNA
<213> ORGANISM: Homo sapiens Beginning of page (SEQUENCE 1455):

tcgaggagaa stctggcatg g                    21

```
<400> SEQUENCE: 1463
cggtcagtgg yttccagcca g                                              21

<210> SEQ ID NO 1464
<211> LENGTH: 21
<212> TYPE: DNA
<213> ORGANISM: Homo sapiens

<400> SEQUENCE: 1464
catgctgatg rtcacacacc t                                              21

<210> SEQ ID NO 1465
<211> LENGTH: 21
<212> TYPE: DNA
<213> ORGANISM: Homo sapiens

<400> SEQUENCE: 1465
agcctcctga wgctgatggt g                                              21

<210> SEQ ID NO 1466
<211> LENGTH: 21
<212> TYPE: DNA
<213> ORGANISM: Homo sapiens

<400> SEQUENCE: 1466
tacatcaact ytttggagat g                                              21

<210> SEQ ID NO 1467
<211> LENGTH: 21
<212> TYPE: DNA
<213> ORGANISM: Homo sapiens

<400> SEQUENCE: 1467
gctttgccta yattgcccgc c                                              21

<210> SEQ ID NO 1468
<211> LENGTH: 21
<212> TYPE: DNA
<213> ORGANISM: Homo sapiens

<400> SEQUENCE: 1468
gtcactggga ytgctgtagc g                                              21

<210> SEQ ID NO 1469
<211> LENGTH: 21
<212> TYPE: DNA
<213> ORGANISM: Homo sapiens

<400> SEQUENCE: 1469
gggagtacac rtgccagact g                                              21

<210> SEQ ID NO 1470
<211> LENGTH: 21
<212> TYPE: DNA
<213> ORGANISM: Homo sapiens

<400> SEQUENCE: 1470
tacacgctgt wctcatccaa g                                              21

<210> SEQ ID NO 1471
<211> LENGTH: 21
<212> TYPE: DNA
```

```
<213> ORGANISM: Homo sapiens

<400> SEQUENCE: 1471
ttacgtccat rctttatcat c                                              21

<210> SEQ ID NO 1472
<211> LENGTH: 21
<212> TYPE: DNA
<213> ORGANISM: Homo sapiens

<400> SEQUENCE: 1472
gagtgtcctg rctccttta c                                               21

<210> SEQ ID NO 1473
<211> LENGTH: 21
<212> TYPE: DNA
<213> ORGANISM: Homo sapiens

<400> SEQUENCE: 1473
gccagcaagg wcttctctcc g                                              21

<210> SEQ ID NO 1474
<211> LENGTH: 21
<212> TYPE: DNA
<213> ORGANISM: Homo sapiens

<400> SEQUENCE: 1474
ccagggaaag rcgcttactt g                                              21

<210> SEQ ID NO 1475
<211> LENGTH: 21
<212> TYPE: DNA
<213> ORGANISM: Homo sapiens

<400> SEQUENCE: 1475
accgtgtgtg rctgcaggaa g                                              21

<210> SEQ ID NO 1476
<211> LENGTH: 21
<212> TYPE: DNA
<213> ORGANISM: Homo sapiens

<400> SEQUENCE: 1476
ttattggagt raaaacctt t                                               21

<210> SEQ ID NO 1477
<211> LENGTH: 21
<212> TYPE: DNA
<213> ORGANISM: Homo sapiens

<400> SEQUENCE: 1477
tgctaaagct ragagggctg c                                              21

<210> SEQ ID NO 1478
<211> LENGTH: 21
<212> TYPE: DNA
<213> ORGANISM: Homo sapiens

<400> SEQUENCE: 1478
caggctgcag rcagttcagc g                                              21

<210> SEQ ID NO 1479
<211> LENGTH: 21
```

-continued

```
<212> TYPE: DNA
<213> ORGANISM: Homo sapiens

<400> SEQUENCE: 1479
tgcccagctc yaggagggac a                                              21

<210> SEQ ID NO 1480
<211> LENGTH: 21
<212> TYPE: DNA
<213> ORGANISM: Homo sapiens

<400> SEQUENCE: 1480
gaacaacatt rcttatgggc t                                              21

<210> SEQ ID NO 1481
<211> LENGTH: 21
<212> TYPE: DNA
<213> ORGANISM: Homo sapiens

<400> SEQUENCE: 1481 aagggctga ygtttaccct a                                               21

<210> SEQ ID NO 1482
<211> LENGTH: 21
<212> TYPE: DNA
<213> ORGANISM: Homo sapiens

<400> SEQUENCE: 1482
tgcacttggg kgtgcagatg c                                              21

<210> SEQ ID NO 1483
<211> LENGTH: 21
<212> TYPE: DNA
<213> ORGANISM: Homo sapiens

<400> SEQUENCE: 1483
gtacctgctc rtaaggaggg t                                              21

<210> SEQ ID NO 1484
<211> LENGTH: 21
<212> TYPE: DNA
<213> ORGANISM: Homo sapiens

<400> SEQUENCE: 1484
tgctcagcaa ygtgggagct g                                              21

<210> SEQ ID NO 1485
<211> LENGTH: 21
<212> TYPE: DNA
<213> ORGANISM: Homo sapiens

<400> SEQUENCE: 1485
cccgcctggt kcagcagcgg c                                              21

<210> SEQ ID NO 1486
<211> LENGTH: 21
<212> TYPE: DNA
<213> ORGANISM: Homo sapiens

<400> SEQUENCE: 1486
tgataaggtg rtggcggctg c                                              21

<210> SEQ ID NO 1487
```

<211> LENGTH: 21
<212> TYPE: DNA
<213> ORGANISM: Homo sapiens

<400> SEQUENCE: 1487
gccaatcaaa kgagggctca c                                              21

<210> SEQ ID NO 1488
<211> LENGTH: 21
<212> TYPE: DNA
<213> ORGANISM: Homo sapiens

<400> SEQUENCE: 1488
ccgcccaccc rggcccggag t                                              21

<210> SEQ ID NO 1489
<211> LENGTH: 21
<212> TYPE: DNA
<213> ORGANISM: Homo sapiens

<400> SEQUENCE: 1489
accgccacgt ygcagatggg g                                              21

<210> SEQ ID NO 1490
<211> LENGTH: 21
<212> TYPE: DNA
<213> ORGANISM: Homo sapiens

<400> SEQUENCE: 1490
acaaaaaact yatcatgtat t                                              21

<210> SEQ ID NO 1491
<211> LENGTH: 21
<212> TYPE: DNA
<213> ORGANISM: Homo sapiens

<400> SEQUENCE: 1491
atcacatgaa ragagcaact c                                              21

<210> SEQ ID NO 1492
<211> LENGTH: 21
<212> TYPE: DNA
<213> ORGANISM: Homo sapiens

<400> SEQUENCE: 1492
agaattgtca kaattgtccc t                                              21

<210> SEQ ID NO 1493
<211> LENGTH: 21
<212> TYPE: DNA
<213> ORGANISM: Homo sapiens

<400> SEQUENCE: 1493
gtgcccggct sctgaaagcc g                                              21

<210> SEQ ID NO 1494
<211> LENGTH: 21
<212> TYPE: DNA
<213> ORGANISM: Homo sapiens

<400> SEQUENCE: 1494
ggctgtctgt ragaccctg g                                               21

```
<210> SEQ ID NO 1495
<211> LENGTH: 21
<212> TYPE: DNA
<213> ORGANISM: Homo sapiens

<400> SEQUENCE: 1495
acacagtctt ygctcccaca a                                              21

<210> SEQ ID NO 1496
<211> LENGTH: 21
<212> TYPE: DNA
<213> ORGANISM: Homo sapiens

<400> SEQUENCE: 1496
gtaatagcct ytgcattgag a                                              21

<210> SEQ ID NO 1497
<211> LENGTH: 21
<212> TYPE: DNA
<213> ORGANISM: Homo sapiens

<400> SEQUENCE: 1497
gctgaccaat raggccaccc t                                              21

<210> SEQ ID NO 1498
<211> LENGTH: 21
<212> TYPE: DNA
<213> ORGANISM: Homo sapiens

<400> SEQUENCE: 1498
tgcccgagac ygaggacgag a                                              21

<210> SEQ ID NO 1499
<211> LENGTH: 21
<212> TYPE: DNA
<213> ORGANISM: Homo sapiens

<400> SEQUENCE: 1499
gcaaaacaag rgcatcagtg c                                              21

<210> SEQ ID NO 1500
<211> LENGTH: 21
<212> TYPE: DNA
<213> ORGANISM: Homo sapiens

<400> SEQUENCE: 1500
tgacctggcg ygctgccatg c                                              21

<210> SEQ ID NO 1501
<211> LENGTH: 21
<212> TYPE: DNA
<213> ORGANISM: Homo sapiens

<400> SEQUENCE: 1501
tcattatatt ygagcagatt c                                              21

<210> SEQ ID NO 1502
<211> LENGTH: 21
<212> TYPE: DNA
<213> ORGANISM: Homo sapiens

<400> SEQUENCE: 1502
tttcagttcc ytattttctg t                                              21
```

<210> SEQ ID NO 1503
<211> LENGTH: 21
<212> TYPE: DNA
<213> ORGANISM: Homo sapiens

<400> SEQUENCE: 1503
ttttctgttt saacattggc g                                           21

<210> SEQ ID NO 1504
<211> LENGTH: 21
<212> TYPE: DNA
<213> ORGANISM: Homo sapiens

<400> SEQUENCE: 1504
ggggttatgt ygctatgaag t                                           21

<210> SEQ ID NO 1505
<211> LENGTH: 21
<212> TYPE: DNA
<213> ORGANISM: Homo sapiens

<400> SEQUENCE: 1505
tccagccaac ratgaccagt c                                           21

<210> SEQ ID NO 1506
<211> LENGTH: 21
<212> TYPE: DNA
<213> ORGANISM: Homo sapiens

<400> SEQUENCE: 1506
ttcagtcctc rgcctctcca g                                           21

<210> SEQ ID NO 1507
<211> LENGTH: 21
<212> TYPE: DNA
<213> ORGANISM: Homo sapiens

<400> SEQUENCE: 1507
gctaaataaa racatgacct a                                           21

<210> SEQ ID NO 1508
<211> LENGTH: 21
<212> TYPE: DNA
<213> ORGANISM: Homo sapiens

<400> SEQUENCE: 1508
ccagcctctc raatgggcac a                                           21

<210> SEQ ID NO 1509
<211> LENGTH: 21
<212> TYPE: DNA
<213> ORGANISM: Homo sapiens

<400> SEQUENCE: 1509
caactcgacg rtccaggcct c                                           21

<210> SEQ ID NO 1510
<211> LENGTH: 21
<212> TYPE: DNA
<213> ORGANISM: Homo sapiens

<400> SEQUENCE: 1510
gatttctgga ytccactgtt g                                           21

<210> SEQ ID NO 1511
<211> LENGTH: 21
<212> TYPE: DNA
<213> ORGANISM: Homo sapiens

<400> SEQUENCE: 1511
acctgaagaa rtttatagaa a                                              21

<210> SEQ ID NO 1512
<211> LENGTH: 21
<212> TYPE: DNA
<213> ORGANISM: Homo sapiens

<400> SEQUENCE: 1512
gatgtctgca rtgggaagag t                                              21

<210> SEQ ID NO 1513
<211> LENGTH: 21
<212> TYPE: DNA
<213> ORGANISM: Homo sapiens

<400> SEQUENCE: 1513
aatttacaaa yttcaatctt t                                              21

<210> SEQ ID NO 1514
<211> LENGTH: 21
<212> TYPE: DNA
<213> ORGANISM: Homo sapiens

<400> SEQUENCE: 1514
ctccaggtca rccctgcca c                                               21

<210> SEQ ID NO 1515
<211> LENGTH: 21
<212> TYPE: DNA
<213> ORGANISM: Homo sapiens

<400> SEQUENCE: 1515
cacatcgacc rggctctgga t                                              21

<210> SEQ ID NO 1516
<211> LENGTH: 21
<212> TYPE: DNA
<213> ORGANISM: Homo sapiens

<400> SEQUENCE: 1516
tcatcgtgcc rctgctgatc a                                              21

<210> SEQ ID NO 1517
<211> LENGTH: 21
<212> TYPE: DNA
<213> ORGANISM: Homo sapiens

<400> SEQUENCE: 1517
gccatggact yctcaagatt c                                              21

<210> SEQ ID NO 1518
<211> LENGTH: 21
<212> TYPE: DNA
<213> ORGANISM: Homo sapiens

<400> SEQUENCE: 1518
atggagagtg rcagctttga a                                              21

<210> SEQ ID NO 1519
<211> LENGTH: 21
<212> TYPE: DNA
<213> ORGANISM: Homo sapiens

<400> SEQUENCE: 1519
gctatgccag yccggagatg t                                              21

<210> SEQ ID NO 1520
<211> LENGTH: 21
<212> TYPE: DNA
<213> ORGANISM: Homo sapiens

<400> SEQUENCE: 1520
atggcggcag ytgtggctgt g                                              21

<210> SEQ ID NO 1521
<211> LENGTH: 21
<212> TYPE: DNA
<213> ORGANISM: Homo sapiens

<400> SEQUENCE: 1521
agcttgacaa ratggtgaca g                                              21

<210> SEQ ID NO 1522
<211> LENGTH: 21
<212> TYPE: DNA
<213> ORGANISM: Homo sapiens

<400> SEQUENCE: 1522
tggtcaacct rcccttggtg a                                              21

<210> SEQ ID NO 1523
<211> LENGTH: 21
<212> TYPE: DNA
<213> ORGANISM: Homo sapiens

<400> SEQUENCE: 1523
tctggagaca ytacttccag a                                              21

<210> SEQ ID NO 1524
<211> LENGTH: 21
<212> TYPE: DNA
<213> ORGANISM: Homo sapiens

<400> SEQUENCE: 1524
cgagatcttt ktcataatcc t                                              21

<210> SEQ ID NO 1525
<211> LENGTH: 21
<212> TYPE: DNA
<213> ORGANISM: Homo sapiens

<400> SEQUENCE: 1525
tcctcataaa rtacaggagg c                                              21

<210> SEQ ID NO 1526
<211> LENGTH: 21
<212> TYPE: DNA
<213> ORGANISM: Homo sapiens

<400> SEQUENCE: 1526

```
gcaagaagat mctgctgccc g                                        21

<210> SEQ ID NO 1527
<211> LENGTH: 21
<212> TYPE: DNA
<213> ORGANISM: Homo sapiens

<400> SEQUENCE: 1527
tagaagggca ygtggtgatt c                                        21

<210> SEQ ID NO 1528
<211> LENGTH: 21
<212> TYPE: DNA
<213> ORGANISM: Homo sapiens

<400> SEQUENCE: 1528
ccctgctcaa rcccaacatg g                                        21

<210> SEQ ID NO 1529
<211> LENGTH: 21
<212> TYPE: DNA
<213> ORGANISM: Homo sapiens

<400> SEQUENCE: 1529
tgaagccttc scatgtaatt t                                        21

<210> SEQ ID NO 1530
<211> LENGTH: 21
<212> TYPE: DNA
<213> ORGANISM: Homo sapiens

<400> SEQUENCE: 1530
ttttctcaac rcattacttc c                                        21

<210> SEQ ID NO 1531
<211> LENGTH: 21
<212> TYPE: DNA
<213> ORGANISM: Homo sapiens

<400> SEQUENCE: 1531
tgcaaggtaa rgccaattgg a                                        21

<210> SEQ ID NO 1532
<211> LENGTH: 21
<212> TYPE: DNA
<213> ORGANISM: Homo sapiens

<400> SEQUENCE: 1532
ctcctcgcca sgtctctgca a                                        21

<210> SEQ ID NO 1533
<211> LENGTH: 21
<212> TYPE: DNA
<213> ORGANISM: Homo sapiens

<400> SEQUENCE: 1533
gtggagcaga ratcttcgtt g                                        21

<210> SEQ ID NO 1534
<211> LENGTH: 21
<212> TYPE: DNA
<213> ORGANISM: Homo sapiens
```

```
<400> SEQUENCE: 1534
agttcccacg saaatgagag g                                              21

<210> SEQ ID NO 1535
<211> LENGTH: 21
<212> TYPE: DNA
<213> ORGANISM: Homo sapiens

<400> SEQUENCE: 1535
ggtgacttgg sagcctccca g                                              21

<210> SEQ ID NO 1536
<211> LENGTH: 21
<212> TYPE: DNA
<213> ORGANISM: Homo sapiens

<400> SEQUENCE: 1536
tctaaactgg stacggagtc g                                              21

<210> SEQ ID NO 1537
<211> LENGTH: 21
<212> TYPE: DNA
<213> ORGANISM: Homo sapiens

<400> SEQUENCE: 1537
ccagtgtccc ygagctggtc g                                              21

<210> SEQ ID NO 1538
<211> LENGTH: 21
<212> TYPE: DNA
<213> ORGANISM: Homo sapiens

<400> SEQUENCE: 1538
acaacaacac yaagctcgca a                                              21

<210> SEQ ID NO 1539
<211> LENGTH: 21
<212> TYPE: DNA
<213> ORGANISM: Homo sapiens

<400> SEQUENCE: 1539
gctgaaagtg magaaagtca t                                              21

<210> SEQ ID NO 1540
<211> LENGTH: 21
<212> TYPE: DNA
<213> ORGANISM: Homo sapiens

<400> SEQUENCE: 1540
gaagaaatat rtccgcaggg a                                              21

<210> SEQ ID NO 1541
<211> LENGTH: 21
<212> TYPE: DNA
<213> ORGANISM: Homo sapiens

<400> SEQUENCE: 1541
ttcaagccac rgagcttgcc a                                              21

<210> SEQ ID NO 1542
<211> LENGTH: 21
<212> TYPE: DNA
<213> ORGANISM: Homo sapiens
```

<400> SEQUENCE: 1542
acaaactggc ygagtcctgt g                                              21

<210> SEQ ID NO 1543
<211> LENGTH: 21
<212> TYPE: DNA
<213> ORGANISM: Homo sapiens

<400> SEQUENCE: 1543
gcctcaatga kcctggtcca t                                              21

<210> SEQ ID NO 1544
<211> LENGTH: 21
<212> TYPE: DNA
<213> ORGANISM: Homo sapiens

<400> SEQUENCE: 1544
tggatgtgca ygcggacagg a                                              21

<210> SEQ ID NO 1545
<211> LENGTH: 21
<212> TYPE: DNA
<213> ORGANISM: Homo sapiens

<400> SEQUENCE: 1545
cactttccat ygctttgaca a                                              21

<210> SEQ ID NO 1546
<211> LENGTH: 21
<212> TYPE: DNA
<213> ORGANISM: Homo sapiens

<400> SEQUENCE: 1546
tgcgggaggt ytttgagagc a                                              21

<210> SEQ ID NO 1547
<211> LENGTH: 21
<212> TYPE: DNA
<213> ORGANISM: Homo sapiens

<400> SEQUENCE: 1547
gtaccaaggg ycagctggcc a                                              21

<210> SEQ ID NO 1548
<211> LENGTH: 21
<212> TYPE: DNA
<213> ORGANISM: Homo sapiens

<400> SEQUENCE: 1548
cctggggagt ygctccaaca a                                              21

<210> SEQ ID NO 1549
<211> LENGTH: 21
<212> TYPE: DNA
<213> ORGANISM: Homo sapiens

<400> SEQUENCE: 1549
aggccatcat ygactgcctg g                                              21

<210> SEQ ID NO 1550
<211> LENGTH: 21
<212> TYPE: DNA

-continued

```
<213> ORGANISM: Homo sapiens

<400> SEQUENCE: 1550
tccaaattta ytctgctgac a                                              21

<210> SEQ ID NO 1551
<211> LENGTH: 21
<212> TYPE: DNA
<213> ORGANISM: Homo sapiens

<400> SEQUENCE: 1551
aaggctatga ygtcattgcc t                                              21

<210> SEQ ID NO 1552
<211> LENGTH: 21
<212> TYPE: DNA
<213> ORGANISM: Homo sapiens

<400> SEQUENCE: 1552
ggccctgcat ygcccgcaaa c                                              21

<210> SEQ ID NO 1553
<211> LENGTH: 21
<212> TYPE: DNA
<213> ORGANISM: Homo sapiens

<400> SEQUENCE: 1553
aatcccagac rctatgtcca g                                              21

<210> SEQ ID NO 1554
<211> LENGTH: 21
<212> TYPE: DNA
<213> ORGANISM: Homo sapiens

<400> SEQUENCE: 1554
tggacacctc stgcatcctc g                                              21

<210> SEQ ID NO 1555
<211> LENGTH: 21
<212> TYPE: DNA
<213> ORGANISM: Homo sapiens

<400> SEQUENCE: 1555
agtttgtgga rgagttcatc t                                              21

<210> SEQ ID NO 1556
<211> LENGTH: 21
<212> TYPE: DNA
<213> ORGANISM: Homo sapiens

<400> SEQUENCE: 1556
aggcactgaa rcttggggcc a                                              21

<210> SEQ ID NO 1557
<211> LENGTH: 21
<212> TYPE: DNA
<213> ORGANISM: Homo sapiens

<400> SEQUENCE: 1557
ccagtccagc rcactgtatg a                                              21

<210> SEQ ID NO 1558
<211> LENGTH: 21
```

```
<210> SEQ ID NO 1558
<211> LENGTH: 21
<212> TYPE: DNA
<213> ORGANISM: Homo sapiens

<400> SEQUENCE: 1558
tgtcccacgg ygccacagga a                                          21

<210> SEQ ID NO 1559
<211> LENGTH: 21
<212> TYPE: DNA
<213> ORGANISM: Homo sapiens

<400> SEQUENCE: 1559
gaattctaca rccggttcaa g                                          21

<210> SEQ ID NO 1560
<211> LENGTH: 21
<212> TYPE: DNA
<213> ORGANISM: Homo sapiens

<400> SEQUENCE: 1560
ttctcgagat ygagttcaaa a                                          21

<210> SEQ ID NO 1561
<211> LENGTH: 21
<212> TYPE: DNA
<213> ORGANISM: Homo sapiens

<400> SEQUENCE: 1561
atgctcattt rgacatcgag g                                          21

<210> SEQ ID NO 1562
<211> LENGTH: 21
<212> TYPE: DNA
<213> ORGANISM: Homo sapiens

<400> SEQUENCE: 1562
cagttttcca ygagcaacat c                                          21

<210> SEQ ID NO 1563
<211> LENGTH: 21
<212> TYPE: DNA
<213> ORGANISM: Homo sapiens

<400> SEQUENCE: 1563
ttcagtggaa ygcaggctca g                                          21

<210> SEQ ID NO 1564
<211> LENGTH: 21
<212> TYPE: DNA
<213> ORGANISM: Homo sapiens

<400> SEQUENCE: 1564
ggtttcttct stgtctccgc g                                          21

<210> SEQ ID NO 1565
<211> LENGTH: 21
<212> TYPE: DNA
<213> ORGANISM: Homo sapiens

<400> SEQUENCE: 1565
ccacgagtgc rttcctgggg a                                          21

<210> SEQ ID NO 1566
```

```
<211> LENGTH: 21
<212> TYPE: DNA
<213> ORGANISM: Homo sapiens

<400> SEQUENCE: 1566
cgagtgattg ragagcccac g                                        21

<210> SEQ ID NO 1567
<211> LENGTH: 21
<212> TYPE: DNA
<213> ORGANISM: Homo sapiens

<400> SEQUENCE: 1567
gggtgctccc rgccggccga g                                        21

<210> SEQ ID NO 1568
<211> LENGTH: 21
<212> TYPE: DNA
<213> ORGANISM: Homo sapiens

<400> SEQUENCE: 1568
agccgtgctg yggacatttc c                                        21

<210> SEQ ID NO 1569
<211> LENGTH: 21
<212> TYPE: DNA
<213> ORGANISM: Homo sapiens

<400> SEQUENCE: 1569
gcaagaatct ygcagcagca t                                        21

<210> SEQ ID NO 1570
<211> LENGTH: 21
<212> TYPE: DNA
<213> ORGANISM: Homo sapiens

<400> SEQUENCE: 1570
acaacaccac ytctaacatg g                                        21

<210> SEQ ID NO 1571
<211> LENGTH: 21
<212> TYPE: DNA
<213> ORGANISM: Homo sapiens

<400> SEQUENCE: 1571
aagttgatta yccccgggat g                                        21

<210> SEQ ID NO 1572
<211> LENGTH: 21
<212> TYPE: DNA
<213> ORGANISM: Homo sapiens

<400> SEQUENCE: 1572
catcatttca rtgaaggaaa a                                        21

<210> SEQ ID NO 1573
<211> LENGTH: 21
<212> TYPE: DNA
<213> ORGANISM: Homo sapiens

<400> SEQUENCE: 1573
accctgctac rtttatctga t                                        21
```

<210> SEQ ID NO 1574
<211> LENGTH: 21
<212> TYPE: DNA
<213> ORGANISM: Homo sapiens

<400> SEQUENCE: 1574
acccaggtca rcacgcaggc c                      21

<210> SEQ ID NO 1575
<211> LENGTH: 21
<212> TYPE: DNA
<213> ORGANISM: Homo sapiens

<400> SEQUENCE: 1575
acacgcaggc ygagcagctg c                      21

<210> SEQ ID NO 1576
<211> LENGTH: 21
<212> TYPE: DNA
<213> ORGANISM: Homo sapiens

<400> SEQUENCE: 1576
ctcaattgct rttgacacaa t                      21

<210> SEQ ID NO 1577
<211> LENGTH: 21
<212> TYPE: DNA
<213> ORGANISM: Homo sapiens

<400> SEQUENCE: 1577
atctttcatt kctgcaagga a                      21

<210> SEQ ID NO 1578
<211> LENGTH: 21
<212> TYPE: DNA
<213> ORGANISM: Homo sapiens

<400> SEQUENCE: 1578
tccatcgcag ygaacgccga c                      21

<210> SEQ ID NO 1579
<211> LENGTH: 21
<212> TYPE: DNA
<213> ORGANISM: Homo sapiens

<400> SEQUENCE: 1579
ctgccgccca ygctgctggg g                      21

<210> SEQ ID NO 1580
<211> LENGTH: 21
<212> TYPE: DNA
<213> ORGANISM: Homo sapiens

<400> SEQUENCE: 1580
ttttgccttt raagtggatg g                      21

<210> SEQ ID NO 1581
<211> LENGTH: 21
<212> TYPE: DNA
<213> ORGANISM: Homo sapiens

<400> SEQUENCE: 1581
agccggagcc rgagctggaa c                      21

-continued

<210> SEQ ID NO 1582
<211> LENGTH: 21
<212> TYPE: DNA
<213> ORGANISM: Homo sapiens

<400> SEQUENCE: 1582
cagggcctgg kcgtcacacc c                                           21

<210> SEQ ID NO 1583
<211> LENGTH: 21
<212> TYPE: DNA
<213> ORGANISM: Homo sapiens

<400> SEQUENCE: 1583
agctgacact sgttcgcgtg a                                           21

<210> SEQ ID NO 1584
<211> LENGTH: 21
<212> TYPE: DNA
<213> ORGANISM: Homo sapiens

<400> SEQUENCE: 1584
accccaaacc ygaggttgct g                                           21

<210> SEQ ID NO 1585
<211> LENGTH: 21
<212> TYPE: DNA
<213> ORGANISM: Homo sapiens

<400> SEQUENCE: 1585
tttggcagaa raagccacgt t                                           21

<210> SEQ ID NO 1586
<211> LENGTH: 21
<212> TYPE: DNA
<213> ORGANISM: Homo sapiens

<400> SEQUENCE: 1586
gttacatgat ygacaacgtg a                                           21

<210> SEQ ID NO 1587
<211> LENGTH: 21
<212> TYPE: DNA
<213> ORGANISM: Homo sapiens

<400> SEQUENCE: 1587
taaaggtttc yaacaccctg g                                           21

<210> SEQ ID NO 1588
<211> LENGTH: 21
<212> TYPE: DNA
<213> ORGANISM: Homo sapiens

<400> SEQUENCE: 1588
tcactaccaa yctgatcaat t                                           21

<210> SEQ ID NO 1589
<211> LENGTH: 21
<212> TYPE: DNA
<213> ORGANISM: Homo sapiens

<400> SEQUENCE: 1589
aggtatacgg yattgaaggt c                                           21

<210> SEQ ID NO 1590
<211> LENGTH: 21
<212> TYPE: DNA
<213> ORGANISM: Homo sapiens

<400> SEQUENCE: 1590
atcacagcaa ragagaggtt c                                      21

<210> SEQ ID NO 1591
<211> LENGTH: 21
<212> TYPE: DNA
<213> ORGANISM: Homo sapiens

<400> SEQUENCE: 1591
tgccctggac rcccaccagc a                                      21

<210> SEQ ID NO 1592
<211> LENGTH: 21
<212> TYPE: DNA
<213> ORGANISM: Homo sapiens

<400> SEQUENCE: 1592
cgcaatgtct ytgacggcat c                                      21

<210> SEQ ID NO 1593
<211> LENGTH: 21
<212> TYPE: DNA
<213> ORGANISM: Homo sapiens

<400> SEQUENCE: 1593
gcactatctg ygtggcctac c                                      21

<210> SEQ ID NO 1594
<211> LENGTH: 21
<212> TYPE: DNA
<213> ORGANISM: Homo sapiens

<400> SEQUENCE: 1594
caggaccatg wtgaagaaca t                                      21

<210> SEQ ID NO 1595
<211> LENGTH: 21
<212> TYPE: DNA
<213> ORGANISM: Homo sapiens

<400> SEQUENCE: 1595
tgcactgacc yagattaatg t                                      21

<210> SEQ ID NO 1596
<211> LENGTH: 21
<212> TYPE: DNA
<213> ORGANISM: Homo sapiens

<400> SEQUENCE: 1596
atgtcacgct yatcatcctg g                                      21

<210> SEQ ID NO 1597
<211> LENGTH: 21
<212> TYPE: DNA
<213> ORGANISM: Homo sapiens

<400> SEQUENCE: 1597

-continued agctgcgttc ragggatgca c					21

<210> SEQ ID NO 1598
<211> LENGTH: 21
<212> TYPE: DNA
<213> ORGANISM: Homo sapiens

<400> SEQUENCE: 1598
tgatccaagg raatgatctg a					21

<210> SEQ ID NO 1599
<211> LENGTH: 21
<212> TYPE: DNA
<213> ORGANISM: Homo sapiens

<400> SEQUENCE: 1599
tactagcact rttgaaggaa a					21

<210> SEQ ID NO 1600
<211> LENGTH: 21
<212> TYPE: DNA
<213> ORGANISM: Homo sapiens

<400> SEQUENCE: 1600
cctggcggct kcgccggtcc a					21

<210> SEQ ID NO 1601
<211> LENGTH: 21
<212> TYPE: DNA
<213> ORGANISM: Homo sapiens

<400> SEQUENCE: 1601
cagaccgtga raatagatgc c					21

<210> SEQ ID NO 1602
<211> LENGTH: 21
<212> TYPE: DNA
<213> ORGANISM: Homo sapiens

<400> SEQUENCE: 1602
tgaaaggcaa kccctccaga g					21

<210> SEQ ID NO 1603
<211> LENGTH: 21
<212> TYPE: DNA
<213> ORGANISM: Homo sapiens

<400> SEQUENCE: 1603
cgaggctgct rttacggctc a					21

<210> SEQ ID NO 1604
<211> LENGTH: 21
<212> TYPE: DNA
<213> ORGANISM: Homo sapiens

<400> SEQUENCE: 1604
cagtgacggg racaaaggtc t					21

<210> SEQ ID NO 1605
<211> LENGTH: 21
<212> TYPE: DNA
<213> ORGANISM: Homo sapiens

<400> SEQUENCE: 1605
accgccgagg mtgctgttac g    21

<210> SEQ ID NO 1606
<211> LENGTH: 21
<212> TYPE: DNA
<213> ORGANISM: Homo sapiens

<400> SEQUENCE: 1606
tttccccagg ygaatgggct g    21

<210> SEQ ID NO 1607
<211> LENGTH: 21
<212> TYPE: DNA
<213> ORGANISM: Homo sapiens

<400> SEQUENCE: 1607
tgcctcatgc rtacgtccca c    21

<210> SEQ ID NO 1608
<211> LENGTH: 21
<212> TYPE: DNA
<213> ORGANISM: Homo sapiens

<400> SEQUENCE: 1608
acaaatctct yactgaagaa g    21

<210> SEQ ID NO 1609
<211> LENGTH: 21
<212> TYPE: DNA
<213> ORGANISM: Homo sapiens

<400> SEQUENCE: 1609
ccagtgtcag yttgtgattc a    21

<210> SEQ ID NO 1610
<211> LENGTH: 21
<212> TYPE: DNA
<213> ORGANISM: Homo sapiens

<400> SEQUENCE: 1610
tgagcctttg saggccccag a    21

<210> SEQ ID NO 1611
<211> LENGTH: 21
<212> TYPE: DNA
<213> ORGANISM: Homo sapiens

<400> SEQUENCE: 1611
ctgtactcac yctttgggaa a    21

<210> SEQ ID NO 1612
<211> LENGTH: 21
<212> TYPE: DNA
<213> ORGANISM: Homo sapiens

<400> SEQUENCE: 1612
cggacaacct kacgctgcgg t    21

<210> SEQ ID NO 1613
<211> LENGTH: 21
<212> TYPE: DNA
<213> ORGANISM: Homo sapiens -continued

<400> SEQUENCE: 1613
cggcctccgg stacctcttg c                                               21

<210> SEQ ID NO 1614
<211> LENGTH: 21
<212> TYPE: DNA
<213> ORGANISM: Homo sapiens

<400> SEQUENCE: 1614
tgccacaaga ragcaggagt t                                               21

<210> SEQ ID NO 1615
<211> LENGTH: 21
<212> TYPE: DNA
<213> ORGANISM: Homo sapiens

<400> SEQUENCE: 1615
aactacaact kgtcacttac a                                               21

<210> SEQ ID NO 1616
<211> LENGTH: 21
<212> TYPE: DNA
<213> ORGANISM: Homo sapiens

<400> SEQUENCE: 1616
agggctgagc mttcaggcag c                                               21

<210> SEQ ID NO 1617
<211> LENGTH: 21
<212> TYPE: DNA
<213> ORGANISM: Homo sapiens

<400> SEQUENCE: 1617
agtatgatct rtctgacatg c                                               21

<210> SEQ ID NO 1618
<211> LENGTH: 21
<212> TYPE: DNA
<213> ORGANISM: Homo sapiens

<400> SEQUENCE: 1618
atttctttaa yaactacaag a                                               21

<210> SEQ ID NO 1619
<211> LENGTH: 21
<212> TYPE: DNA
<213> ORGANISM: Homo sapiens

<400> SEQUENCE: 1619
gtgcagaaga mtatctatcc g                                               21

<210> SEQ ID NO 1620
<211> LENGTH: 21
<212> TYPE: DNA
<213> ORGANISM: Homo sapiens

<400> SEQUENCE: 1620
aagactatct mtccgtggtc c                                               21

<210> SEQ ID NO 1621
<211> LENGTH: 21
<212> TYPE: DNA
<213> ORGANISM: Homo sapiens

```
<400> SEQUENCE: 1621
ttgttgagct ygtgaaacac a                                              21

<210> SEQ ID NO 1622
<211> LENGTH: 21
<212> TYPE: DNA
<213> ORGANISM: Homo sapiens

<400> SEQUENCE: 1622
cagggcggac yttgccaagt a                                              21

<210> SEQ ID NO 1623
<211> LENGTH: 21
<212> TYPE: DNA
<213> ORGANISM: Homo sapiens

<400> SEQUENCE: 1623
tatctatccg wggtcctgaa c                                              21

<210> SEQ ID NO 1624
<211> LENGTH: 21
<212> TYPE: DNA
<213> ORGANISM: Homo sapiens

<400> SEQUENCE: 1624
ccagaatgcg ytattagttc g                                              21

<210> SEQ ID NO 1625
<211> LENGTH: 21
<212> TYPE: DNA
<213> ORGANISM: Homo sapiens

<400> SEQUENCE: 1625
cctaggaaaa rtgggcagca a                                              21

<210> SEQ ID NO 1626
<211> LENGTH: 21
<212> TYPE: DNA
<213> ORGANISM: Homo sapiens

<400> SEQUENCE: 1626
accagcccrt yctcatcgag g                                              21

<210> SEQ ID NO 1627
<211> LENGTH: 21
<212> TYPE: DNA
<213> ORGANISM: Homo sapiens

<400> SEQUENCE: 1627
gctagccact sctcagtaat g                                              21

<210> SEQ ID NO 1628
<211> LENGTH: 21
<212> TYPE: DNA
<213> ORGANISM: Homo sapiens

<400> SEQUENCE: 1628
tgttcttcac yaccttcatg c                                              21

<210> SEQ ID NO 1629
<211> LENGTH: 21
<212> TYPE: DNA
```

```
<213> ORGANISM: Homo sapiens

<400> SEQUENCE: 1629
agaatgggca ygtggatata g                                              21

<210> SEQ ID NO 1630
<211> LENGTH: 21
<212> TYPE: DNA
<213> ORGANISM: Homo sapiens

<400> SEQUENCE: 1630
aaagtatgaa rttcctgaag g                                              21

<210> SEQ ID NO 1631
<211> LENGTH: 21
<212> TYPE: DNA
<213> ORGANISM: Homo sapiens

<400> SEQUENCE: 1631
aagaaaagta ygtgaacagg a                                              21

<210> SEQ ID NO 1632
<211> LENGTH: 21
<212> TYPE: DNA
<213> ORGANISM: Homo sapiens

<400> SEQUENCE: 1632
tcgtacccga ygtctcctac g                                              21

<210> SEQ ID NO 1633
<211> LENGTH: 21
<212> TYPE: DNA
<213> ORGANISM: Homo sapiens

<400> SEQUENCE: 1633
aggatggcca rgcctctgga g                                              21

<210> SEQ ID NO 1634
<211> LENGTH: 21
<212> TYPE: DNA
<213> ORGANISM: Homo sapiens

<400> SEQUENCE: 1634
tgctgcagaa rgagctggcc a                                              21

<210> SEQ ID NO 1635
<211> LENGTH: 21
<212> TYPE: DNA
<213> ORGANISM: Homo sapiens

<400> SEQUENCE: 1635
tctactgcca ygagtacttc a                                              21

<210> SEQ ID NO 1636
<211> LENGTH: 21
<212> TYPE: DNA
<213> ORGANISM: Homo sapiens

<400> SEQUENCE: 1636
acggggtcca ygccactaag c                                              21

<210> SEQ ID NO 1637
<211> LENGTH: 21
```

-continued

```
<212> TYPE: DNA
<213> ORGANISM: Homo sapiens

<400> SEQUENCE: 1637
ggaggccata ytggacataa t                                              21

<210> SEQ ID NO 1638
<211> LENGTH: 21
<212> TYPE: DNA
<213> ORGANISM: Homo sapiens

<400> SEQUENCE: 1638
cagacacacc yagtggagac a                                              21

<210> SEQ ID NO 1639
<211> LENGTH: 21
<212> TYPE: DNA
<213> ORGANISM: Homo sapiens

<400> SEQUENCE: 1639
aaggaggact rtcacaagtc c                                              21

<210> SEQ ID NO 1640
<211> LENGTH: 21
<212> TYPE: DNA
<213> ORGANISM: Homo sapiens

<400> SEQUENCE: 1640
tggtggagaa rtcagtgaca g                                              21

<210> SEQ ID NO 1641
<211> LENGTH: 21
<212> TYPE: DNA
<213> ORGANISM: Homo sapiens

<400> SEQUENCE: 1641
attggctacc yagtgatgat c                                              21

<210> SEQ ID NO 1642
<211> LENGTH: 21
<212> TYPE: DNA
<213> ORGANISM: Homo sapiens

<400> SEQUENCE: 1642
tggagaagtc mgtgacaggt t                                              21

<210> SEQ ID NO 1643
<211> LENGTH: 21
<212> TYPE: DNA
<213> ORGANISM: Homo sapiens

<400> SEQUENCE: 1643
gacaccattg rctacccagt g                                              21

<210> SEQ ID NO 1644
<211> LENGTH: 21
<212> TYPE: DNA
<213> ORGANISM: Homo sapiens

<400> SEQUENCE: 1644
agcctgtttt kaatatcaca a                                              21

<210> SEQ ID NO 1645
```

```
<211> LENGTH: 21
<212> TYPE: DNA
<213> ORGANISM: Homo sapiens

<400> SEQUENCE: 1645
cacaaaggcc yttgctatga c                                              21

<210> SEQ ID NO 1646
<211> LENGTH: 21
<212> TYPE: DNA
<213> ORGANISM: Homo sapiens

<400> SEQUENCE: 1646
aaagctacca mcattacatc a                                              21

<210> SEQ ID NO 1647
<211> LENGTH: 21
<212> TYPE: DNA
<213> ORGANISM: Homo sapiens

<400> SEQUENCE: 1647
gtgccaacgt yccctcaaccg t                                             21

<210> SEQ ID NO 1648
<211> LENGTH: 21
<212> TYPE: DNA
<213> ORGANISM: Homo sapiens

<400> SEQUENCE: 1648
agcagtgccc rccaggcctg c                                              21

<210> SEQ ID NO 1649
<211> LENGTH: 21
<212> TYPE: DNA
<213> ORGANISM: Homo sapiens

<400> SEQUENCE: 1649
ttttgttccg matgtctgag g                                              21

<210> SEQ ID NO 1650
<211> LENGTH: 21
<212> TYPE: DNA
<213> ORGANISM: Homo sapiens

<400> SEQUENCE: 1650
ggccatcgcc yggactccga g                                              21

<210> SEQ ID NO 1651
<211> LENGTH: 21
<212> TYPE: DNA
<213> ORGANISM: Homo sapiens

<400> SEQUENCE: 1651
tcgcctggac wccgagactc c                                              21

<210> SEQ ID NO 1652
<211> LENGTH: 21
<212> TYPE: DNA
<213> ORGANISM: Homo sapiens

<400> SEQUENCE: 1652
ttcgtgactt ygctggccgc a                                              21
```

<210> SEQ ID NO 1653
<211> LENGTH: 21
<212> TYPE: DNA
<213> ORGANISM: Homo sapiens

<400> SEQUENCE: 1653
tgcgccgccg yccgcccggc c                                              21

<210> SEQ ID NO 1654
<211> LENGTH: 21
<212> TYPE: DNA
<213> ORGANISM: Homo sapiens

<400> SEQUENCE: 1654
tctgttgatc mgaacctgtg g                                              21

<210> SEQ ID NO 1655
<211> LENGTH: 21
<212> TYPE: DNA
<213> ORGANISM: Homo sapiens

<400> SEQUENCE: 1655
tggtggccac rcagcaggag a                                              21

<210> SEQ ID NO 1656
<211> LENGTH: 21
<212> TYPE: DNA
<213> ORGANISM: Homo sapiens

<400> SEQUENCE: 1656
tctggggcca sccccaaaga g                                              21

<210> SEQ ID NO 1657
<211> LENGTH: 21
<212> TYPE: DNA
<213> ORGANISM: Homo sapiens

<400> SEQUENCE: 1657
acgacctcgc ygggctcggc a                                              21

<210> SEQ ID NO 1658
<211> LENGTH: 21
<212> TYPE: DNA
<213> ORGANISM: Homo sapiens

<400> SEQUENCE: 1658
gatggtggcc ytattgacgg g                                              21

<210> SEQ ID NO 1659
<211> LENGTH: 21
<212> TYPE: DNA
<213> ORGANISM: Homo sapiens

<400> SEQUENCE: 1659
ataagcggag rcggagcgtg a                                              21

<210> SEQ ID NO 1660
<211> LENGTH: 21
<212> TYPE: DNA
<213> ORGANISM: Homo sapiens

<400> SEQUENCE: 1660
agagccccat ygcgccctgt a                                              21

<210> SEQ ID NO 1661
<211> LENGTH: 21
<212> TYPE: DNA
<213> ORGANISM: Homo sapiens

<400> SEQUENCE: 1661
aaatccaaac mgatcggcag a                                              21

<210> SEQ ID NO 1662
<211> LENGTH: 21
<212> TYPE: DNA
<213> ORGANISM: Homo sapiens

<400> SEQUENCE: 1662
tatagcctga wttttgtgtt g                                              21

<210> SEQ ID NO 1663
<211> LENGTH: 21
<212> TYPE: DNA
<213> ORGANISM: Homo sapiens

<400> SEQUENCE: 1663
aaggatgcag yggtgtcctt t                                              21

<210> SEQ ID NO 1664
<211> LENGTH: 21
<212> TYPE: DNA
<213> ORGANISM: Homo sapiens

<400> SEQUENCE: 1664
tgtgttgggc ytcagcggga a                                              21

<210> SEQ ID NO 1665
<211> LENGTH: 21
<212> TYPE: DNA
<213> ORGANISM: Homo sapiens

<400> SEQUENCE: 1665
aaaatagctg yagccttggt g                                              21

<210> SEQ ID NO 1666
<211> LENGTH: 21
<212> TYPE: DNA
<213> ORGANISM: Homo sapiens

<400> SEQUENCE: 1666
tctgagaact mccctaacaa g                                              21

<210> SEQ ID NO 1667
<211> LENGTH: 21
<212> TYPE: DNA
<213> ORGANISM: Homo sapiens

<400> SEQUENCE: 1667
aggctgagga mccgggccaa g                                              21

<210> SEQ ID NO 1668
<211> LENGTH: 21
<212> TYPE: DNA
<213> ORGANISM: Homo sapiens

<400> SEQUENCE: 1668
gatggttgag rtctatctgc t                                              21

```
<210> SEQ ID NO 1669
<211> LENGTH: 21
<212> TYPE: DNA
<213> ORGANISM: Homo sapiens

<400> SEQUENCE: 1669
atgagcctgg rcaagtacct g                                              21

<210> SEQ ID NO 1670
<211> LENGTH: 21
<212> TYPE: DNA
<213> ORGANISM: Homo sapiens

<400> SEQUENCE: 1670
cagggccggg ytttaaaaat a                                              21

<210> SEQ ID NO 1671
<211> LENGTH: 21
<212> TYPE: DNA
<213> ORGANISM: Homo sapiens

<400> SEQUENCE: 1671
ttccagatgt kaccagtcaa c                                              21

<210> SEQ ID NO 1672
<211> LENGTH: 21
<212> TYPE: DNA
<213> ORGANISM: Homo sapiens

<400> SEQUENCE: 1672
tccaccccag yggggccata g                                              21

<210> SEQ ID NO 1673
<211> LENGTH: 21
<212> TYPE: DNA
<213> ORGANISM: Homo sapiens

<400> SEQUENCE: 1673
ttcctaacac rgtgactgtg g                                              21

<210> SEQ ID NO 1674
<211> LENGTH: 21
<212> TYPE: DNA
<213> ORGANISM: Homo sapiens

<400> SEQUENCE: 1674
cctgccctat yaccgacgcc c                                              21

<210> SEQ ID NO 1675
<211> LENGTH: 21
<212> TYPE: DNA
<213> ORGANISM: Homo sapiens

<400> SEQUENCE: 1675
atattgtcca yaagcatgga g                                              21

<210> SEQ ID NO 1676
<211> LENGTH: 21
<212> TYPE: DNA
<213> ORGANISM: Homo sapiens

<400> SEQUENCE: 1676
```
gggacagaag yacatgaccg c                    21

<210> SEQ ID NO 1677
<211> LENGTH: 21
<212> TYPE: DNA
<213> ORGANISM: Homo sapiens

<400> SEQUENCE: 1677
tggtgaagct sttcgggccc t                    21

<210> SEQ ID NO 1678
<211> LENGTH: 21
<212> TYPE: DNA
<213> ORGANISM: Homo sapiens

<400> SEQUENCE: 1678
tgaagtacta yaccctagag g                    21

<210> SEQ ID NO 1679
<211> LENGTH: 21
<212> TYPE: DNA
<213> ORGANISM: Homo sapiens

<400> SEQUENCE: 1679
agaatttcgt mgttgggaag t                    21

<210> SEQ ID NO 1680
<211> LENGTH: 21
<212> TYPE: DNA
<213> ORGANISM: Homo sapiens

<400> SEQUENCE: 1680
ctgttgatcc ygatgaacct g                    21

<210> SEQ ID NO 1681
<211> LENGTH: 21
<212> TYPE: DNA
<213> ORGANISM: Homo sapiens

<400> SEQUENCE: 1681
tggatttcaa kaatatacca t                    21

<210> SEQ ID NO 1682
<211> LENGTH: 21
<212> TYPE: DNA
<213> ORGANISM: Homo sapiens

<400> SEQUENCE: 1682
acacttactc rgagtggcac a                    21

<210> SEQ ID NO 1683
<211> LENGTH: 21
<212> TYPE: DNA
<213> ORGANISM: Homo sapiens

<400> SEQUENCE: 1683
gggaaagtgc rtgtgagcgg c                    21

<210> SEQ ID NO 1684
<211> LENGTH: 21
<212> TYPE: DNA
<213> ORGANISM: Homo sapiens

<400> SEQUENCE: 1684

-continued ctggcaaaag ktggcctatt g                                             21

<210> SEQ ID NO 1685
<211> LENGTH: 21
<212> TYPE: DNA
<213> ORGANISM: Homo sapiens

<400> SEQUENCE: 1685
gttattttct ycttaccctg g                                             21

<210> SEQ ID NO 1686
<211> LENGTH: 21
<212> TYPE: DNA
<213> ORGANISM: Homo sapiens

<400> SEQUENCE: 1686
aatgaaacca matccgtggt t                                             21

<210> SEQ ID NO 1687
<211> LENGTH: 21
<212> TYPE: DNA
<213> ORGANISM: Homo sapiens

<400> SEQUENCE: 1687
ccctgcacca ygccttggaa c                                             21

<210> SEQ ID NO 1688
<211> LENGTH: 21
<212> TYPE: DNA
<213> ORGANISM: Homo sapiens

<400> SEQUENCE: 1688
ctgacgtctt yctggaggca t                                             21

<210> SEQ ID NO 1689
<211> LENGTH: 21
<212> TYPE: DNA
<213> ORGANISM: Homo sapiens

<400> SEQUENCE: 1689
ccttcccgac rtgaacaaga t                                             21

<210> SEQ ID NO 1690
<211> LENGTH: 21
<212> TYPE: DNA
<213> ORGANISM: Homo sapiens

<400> SEQUENCE: 1690
cgagctggcc rtgatggtga t                                             21

<210> SEQ ID NO 1691
<211> LENGTH: 21
<212> TYPE: DNA
<213> ORGANISM: Homo sapiens

<400> SEQUENCE: 1691
ttaccagcat kccagacacc t                                             21

<210> SEQ ID NO 1692
<211> LENGTH: 21
<212> TYPE: DNA
<213> ORGANISM: Homo sapiens -continued

<400> SEQUENCE: 1692
gtttttcatt mtgcctgcca a                                            21

<210> SEQ ID NO 1693
<211> LENGTH: 21
<212> TYPE: DNA
<213> ORGANISM: Homo sapiens

<400> SEQUENCE: 1693
gcttgaatgt kaagaaattt t                                            21

<210> SEQ ID NO 1694
<211> LENGTH: 21
<212> TYPE: DNA
<213> ORGANISM: Homo sapiens

<400> SEQUENCE: 1694
catcacagtg rtggtgtttt t                                            21

<210> SEQ ID NO 1695
<211> LENGTH: 21
<212> TYPE: DNA
<213> ORGANISM: Homo sapiens

<400> SEQUENCE: 1695
gaaaagtttg raaaaaaact c                                            21

<210> SEQ ID NO 1696
<211> LENGTH: 21
<212> TYPE: DNA
<213> ORGANISM: Homo sapiens

<400> SEQUENCE: 1696
tgagagatac ratgaggaag a                                            21

<210> SEQ ID NO 1697
<211> LENGTH: 21
<212> TYPE: DNA
<213> ORGANISM: Homo sapiens

<400> SEQUENCE: 1697
tacttaggca satattacca g                                            21

<210> SEQ ID NO 1698
<211> LENGTH: 21
<212> TYPE: DNA
<213> ORGANISM: Homo sapiens

<400> SEQUENCE: 1698
cttacggtat ytacatcgtt g                                            21

<210> SEQ ID NO 1699
<211> LENGTH: 21
<212> TYPE: DNA
<213> ORGANISM: Homo sapiens

<400> SEQUENCE: 1699
gcgctcacgt sttccaccacg g                                           21

<210> SEQ ID NO 1700
<211> LENGTH: 21
<212> TYPE: DNA
<213> ORGANISM: Homo sapiens

```
<400> SEQUENCE: 1700
tgcaatcagc ygactaagtt t                                              21

<210> SEQ ID NO 1701
<211> LENGTH: 21
<212> TYPE: DNA
<213> ORGANISM: Homo sapiens

<400> SEQUENCE: 1701
catcaaagtg rttggcaatg g                                              21

<210> SEQ ID NO 1702
<211> LENGTH: 21
<212> TYPE: DNA
<213> ORGANISM: Homo sapiens

<400> SEQUENCE: 1702
aacccgggaa yaaatccgag a                                              21

<210> SEQ ID NO 1703
<211> LENGTH: 21
<212> TYPE: DNA
<213> ORGANISM: Homo sapiens

<400> SEQUENCE: 1703
aagaagtggc rgcacaagtc g                                              21

<210> SEQ ID NO 1704
<211> LENGTH: 21
<212> TYPE: DNA
<213> ORGANISM: Homo sapiens

<400> SEQUENCE: 1704
atggcgagcc ytccggagag c                                              21

<210> SEQ ID NO 1705
<211> LENGTH: 21
<212> TYPE: DNA
<213> ORGANISM: Homo sapiens

<400> SEQUENCE: 1705
agaaaccatt rtcatcaccc t                                              21

<210> SEQ ID NO 1706
<211> LENGTH: 21
<212> TYPE: DNA
<213> ORGANISM: Homo sapiens

<400> SEQUENCE: 1706
cgcgctggtg ktggccacca t                                              21

<210> SEQ ID NO 1707
<211> LENGTH: 21
<212> TYPE: DNA
<213> ORGANISM: Homo sapiens

<400> SEQUENCE: 1707
gaccctgccg ygggcgcggc a                                              21

<210> SEQ ID NO 1708
<211> LENGTH: 21
<212> TYPE: DNA
```

```
<213> ORGANISM: Homo sapiens

<400> SEQUENCE: 1708
aggtgctgac rtgctcctgg t                                              21

<210> SEQ ID NO 1709
<211> LENGTH: 21
<212> TYPE: DNA
<213> ORGANISM: Homo sapiens

<400> SEQUENCE: 1709
cgggagcaac ktgctggaga c                                              21

<210> SEQ ID NO 1710
<211> LENGTH: 21
<212> TYPE: DNA
<213> ORGANISM: Homo sapiens

<400> SEQUENCE: 1710
cttataggta ytttcagcca t                                              21

<210> SEQ ID NO 1711
<211> LENGTH: 21
<212> TYPE: DNA
<213> ORGANISM: Homo sapiens

<400> SEQUENCE: 1711
tgaaagccat yctcgttaca c                                              21

<210> SEQ ID NO 1712
<211> LENGTH: 21
<212> TYPE: DNA
<213> ORGANISM: Homo sapiens

<400> SEQUENCE: 1712
cgattccacg ygaagacatt g                                              21

<210> SEQ ID NO 1713
<211> LENGTH: 21
<212> TYPE: DNA
<213> ORGANISM: Homo sapiens

<400> SEQUENCE: 1713
attggtgaga ragacataaa g                                              21

<210> SEQ ID NO 1714
<211> LENGTH: 21
<212> TYPE: DNA
<213> ORGANISM: Homo sapiens

<400> SEQUENCE: 1714
attgcaaagc rccctaatgt t                                              21

<210> SEQ ID NO 1715
<211> LENGTH: 21
<212> TYPE: DNA
<213> ORGANISM: Homo sapiens

<400> SEQUENCE: 1715
tccctgccac rgtctgagag c                                              21

<210> SEQ ID NO 1716
<211> LENGTH: 21
```

<212> TYPE: DNA
<213> ORGANISM: Homo sapiens

<400> SEQUENCE: 1716
cccctgaacc rtccgcagct c					21

<210> SEQ ID NO 1717
<211> LENGTH: 21
<212> TYPE: DNA
<213> ORGANISM: Homo sapiens

<400> SEQUENCE: 1717
catgatcagc ygggccaaga a					21

<210> SEQ ID NO 1718
<211> LENGTH: 21
<212> TYPE: DNA
<213> ORGANISM: Homo sapiens

<400> SEQUENCE: 1718
ggaagtgtta ygaagtggga a					21

<210> SEQ ID NO 1719
<211> LENGTH: 21
<212> TYPE: DNA
<213> ORGANISM: Homo sapiens

<400> SEQUENCE: 1719
aggcctgccg rcttcggaag t					21

<210> SEQ ID NO 1720
<211> LENGTH: 21
<212> TYPE: DNA
<213> ORGANISM: Homo sapiens

<400> SEQUENCE: 1720
gctttgaagg rctatagcat g					21

<210> SEQ ID NO 1721
<211> LENGTH: 21
<212> TYPE: DNA
<213> ORGANISM: Homo sapiens

<400> SEQUENCE: 1721
gcaacatcaa rcaagtgcag g					21

<210> SEQ ID NO 1722
<211> LENGTH: 21
<212> TYPE: DNA
<213> ORGANISM: Homo sapiens

<400> SEQUENCE: 1722
gaggacatac rtcatgatgg t					21

<210> SEQ ID NO 1723
<211> LENGTH: 21
<212> TYPE: DNA
<213> ORGANISM: Homo sapiens

<400> SEQUENCE: 1723
cctgtatgaa mttcgattaa a					21

<210> SEQ ID NO 1724

```
<211> LENGTH: 21
<212> TYPE: DNA
<213> ORGANISM: Homo sapiens

<400> SEQUENCE: 1724
cactgttggc rtgtacaatg g                                         21

<210> SEQ ID NO 1725
<211> LENGTH: 21
<212> TYPE: DNA
<213> ORGANISM: Homo sapiens

<400> SEQUENCE: 1725
ccaatgtcaa rgagatcaag g                                         21

<210> SEQ ID NO 1726
<211> LENGTH: 21
<212> TYPE: DNA
<213> ORGANISM: Homo sapiens

<400> SEQUENCE: 1726
ccaacatgat ygtggaggag t                                         21

<210> SEQ ID NO 1727
<211> LENGTH: 21
<212> TYPE: DNA
<213> ORGANISM: Homo sapiens

<400> SEQUENCE: 1727
cttattttcc rgagatggaa g                                         21

<210> SEQ ID NO 1728
<211> LENGTH: 21
<212> TYPE: DNA
<213> ORGANISM: Homo sapiens

<400> SEQUENCE: 1728
cagcttgcat kgctgacttt g                                         21

<210> SEQ ID NO 1729
<211> LENGTH: 21
<212> TYPE: DNA
<213> ORGANISM: Homo sapiens

<400> SEQUENCE: 1729
ctgactttgg sttggcctta a                                         21

<210> SEQ ID NO 1730
<211> LENGTH: 21
<212> TYPE: DNA
<213> ORGANISM: Homo sapiens

<400> SEQUENCE: 1730
tctcttggaa ygaactgtgt c                                         21

<210> SEQ ID NO 1731
<211> LENGTH: 21
<212> TYPE: DNA
<213> ORGANISM: Homo sapiens

<400> SEQUENCE: 1731
tgagcgggaa ygcgtgtgtg c                                         21
```

<210> SEQ ID NO 1732
<211> LENGTH: 21
<212> TYPE: DNA
<213> ORGANISM: Homo sapiens

<400> SEQUENCE: 1732
tctggcagaa yttgcggctc a                                              21

<210> SEQ ID NO 1733
<211> LENGTH: 21
<212> TYPE: DNA
<213> ORGANISM: Homo sapiens

<400> SEQUENCE: 1733
tggacagcct rccccaggca g                                              21

<210> SEQ ID NO 1734
<211> LENGTH: 21
<212> TYPE: DNA
<213> ORGANISM: Homo sapiens

<400> SEQUENCE: 1734
aagccactgt sgcttctggc a                                              21

<210> SEQ ID NO 1735
<211> LENGTH: 21
<212> TYPE: DNA
<213> ORGANISM: Homo sapiens

<400> SEQUENCE: 1735
ccagcgaccc rgcaggacct a                                              21

<210> SEQ ID NO 1736
<211> LENGTH: 21
<212> TYPE: DNA
<213> ORGANISM: Homo sapiens

<400> SEQUENCE: 1736
tatgcagctg ytaccctcca g                                              21

<210> SEQ ID NO 1737
<211> LENGTH: 21
<212> TYPE: DNA
<213> ORGANISM: Homo sapiens

<400> SEQUENCE: 1737
gggatcccag ytttgaggag g                                              21

<210> SEQ ID NO 1738
<211> LENGTH: 21
<212> TYPE: DNA
<213> ORGANISM: Homo sapiens

<400> SEQUENCE: 1738
aaccccaacc rcgttcgcat g                                              21

<210> SEQ ID NO 1739
<211> LENGTH: 21
<212> TYPE: DNA
<213> ORGANISM: Homo sapiens

<400> SEQUENCE: 1739
gcttcctcaa yggggaggtg c                                              21

<210> SEQ ID NO 1740
<211> LENGTH: 21
<212> TYPE: DNA
<213> ORGANISM: Homo sapiens

<400> SEQUENCE: 1740
agcagagcca rggcacctgc a                                              21

<210> SEQ ID NO 1741
<211> LENGTH: 21
<212> TYPE: DNA
<213> ORGANISM: Homo sapiens

<400> SEQUENCE: 1741
atgctcttcg sgtgcctcca c                                              21

<210> SEQ ID NO 1742
<211> LENGTH: 21
<212> TYPE: DNA
<213> ORGANISM: Homo sapiens

<400> SEQUENCE: 1742
atgaggagga rgaagagcca c                                              21

<210> SEQ ID NO 1743
<211> LENGTH: 21
<212> TYPE: DNA
<213> ORGANISM: Homo sapiens

<400> SEQUENCE: 1743
gcctggccaa ygctgctgcc t                                              21

<210> SEQ ID NO 1744
<211> LENGTH: 21
<212> TYPE: DNA
<213> ORGANISM: Homo sapiens

<400> SEQUENCE: 1744
gcagcagagt ygccacatca t                                              21

<210> SEQ ID NO 1745
<211> LENGTH: 21
<212> TYPE: DNA
<213> ORGANISM: Homo sapiens

<400> SEQUENCE: 1745
gacgcttgtg yttgccctgg c                                              21

<210> SEQ ID NO 1746
<211> LENGTH: 21
<212> TYPE: DNA
<213> ORGANISM: Homo sapiens

<400> SEQUENCE: 1746
acagggaggt rgccgagatc c                                              21

<210> SEQ ID NO 1747
<211> LENGTH: 21
<212> TYPE: DNA
<213> ORGANISM: Homo sapiens

<400> SEQUENCE: 1747
tcatgctggc ygtgggagga g                                              21

```
<210> SEQ ID NO 1748
<211> LENGTH: 21
<212> TYPE: DNA
<213> ORGANISM: Homo sapiens

<400> SEQUENCE: 1748
ccatcgcgct rgcactgctg g                                              21

<210> SEQ ID NO 1749
<211> LENGTH: 21
<212> TYPE: DNA
<213> ORGANISM: Homo sapiens

<400> SEQUENCE: 1749
agtgaagatc magaagacaa g                                              21

<210> SEQ ID NO 1750
<211> LENGTH: 21
<212> TYPE: DNA
<213> ORGANISM: Homo sapiens

<400> SEQUENCE: 1750
atgatcgttt ycttagtcag t                                              21

<210> SEQ ID NO 1751
<211> LENGTH: 21
<212> TYPE: DNA
<213> ORGANISM: Homo sapiens

<400> SEQUENCE: 1751
tagtagcagt yttagaatac a                                              21

<210> SEQ ID NO 1752
<211> LENGTH: 21
<212> TYPE: DNA
<213> ORGANISM: Homo sapiens

<400> SEQUENCE: 1752
ctcagccccg magtgcttca g                                              21

<210> SEQ ID NO 1753
<211> LENGTH: 21
<212> TYPE: DNA
<213> ORGANISM: Homo sapiens

<400> SEQUENCE: 1753
gttgtaatga rtttataatg g                                              21

<210> SEQ ID NO 1754
<211> LENGTH: 21
<212> TYPE: DNA
<213> ORGANISM: Homo sapiens

<400> SEQUENCE: 1754
atttataatg raaggaactc t                                              21

<210> SEQ ID NO 1755
<211> LENGTH: 21
<212> TYPE: DNA
<213> ORGANISM: Homo sapiens

<400> SEQUENCE: 1755
```
aagcaggaac yggccaagta c　　　　　　　　　　　　　　　　21

<210> SEQ ID NO 1756
<211> LENGTH: 21
<212> TYPE: DNA
<213> ORGANISM: Homo sapiens

<400> SEQUENCE: 1756
agtattgtcc rtatcagacc t　　　　　　　　　　　　　　　　21

<210> SEQ ID NO 1757
<211> LENGTH: 21
<212> TYPE: DNA
<213> ORGANISM: Homo sapiens

<400> SEQUENCE: 1757
ccattgacat sgccacggaa a　　　　　　　　　　　　　　　　21

<210> SEQ ID NO 1758
<211> LENGTH: 21
<212> TYPE: DNA
<213> ORGANISM: Homo sapiens

<400> SEQUENCE: 1758
gctacattgc ygagcagaac a　　　　　　　　　　　　　　　　21

<210> SEQ ID NO 1759
<211> LENGTH: 21
<212> TYPE: DNA
<213> ORGANISM: Homo sapiens

<400> SEQUENCE: 1759
gctgcagcaa rtgctcgccg g　　　　　　　　　　　　　　　　21

<210> SEQ ID NO 1760
<211> LENGTH: 21
<212> TYPE: DNA
<213> ORGANISM: Homo sapiens

<400> SEQUENCE: 1760
tctgcacctg yaggcccggc t　　　　　　　　　　　　　　　　21

<210> SEQ ID NO 1761
<211> LENGTH: 21
<212> TYPE: DNA
<213> ORGANISM: Homo sapiens

<400> SEQUENCE: 1761
gatctgtaac rtggtggcca t　　　　　　　　　　　　　　　　21

<210> SEQ ID NO 1762
<211> LENGTH: 21
<212> TYPE: DNA
<213> ORGANISM: Homo sapiens

<400> SEQUENCE: 1762
aatgcaagca kggatgcagt c　　　　　　　　　　　　　　　　21

<210> SEQ ID NO 1763
<211> LENGTH: 21
<212> TYPE: DNA
<213> ORGANISM: Homo sapiens

<400> SEQUENCE: 1763
ccaagcacct ycttcctgct c            21

<210> SEQ ID NO 1764
<211> LENGTH: 21
<212> TYPE: DNA
<213> ORGANISM: Homo sapiens

<400> SEQUENCE: 1764
gccgctgccc rctcatgctg a            21

<210> SEQ ID NO 1765
<211> LENGTH: 21
<212> TYPE: DNA
<213> ORGANISM: Homo sapiens

<400> SEQUENCE: 1765
cgcgctacag ycagcgccca g            21

<210> SEQ ID NO 1766
<211> LENGTH: 21
<212> TYPE: DNA
<213> ORGANISM: Homo sapiens

<400> SEQUENCE: 1766
tcggcctcta ygactccgtc a            21

<210> SEQ ID NO 1767
<211> LENGTH: 21
<212> TYPE: DNA
<213> ORGANISM: Homo sapiens

<400> SEQUENCE: 1767
tgcaccacag ragccatggc g            21

<210> SEQ ID NO 1768
<211> LENGTH: 21
<212> TYPE: DNA
<213> ORGANISM: Homo sapiens

<400> SEQUENCE: 1768
tacgggaatc rccgttttga a            21

<210> SEQ ID NO 1769
<211> LENGTH: 21
<212> TYPE: DNA
<213> ORGANISM: Homo sapiens

<400> SEQUENCE: 1769
atcctgacca yggtgcggac t            21

<210> SEQ ID NO 1770
<211> LENGTH: 21
<212> TYPE: DNA
<213> ORGANISM: Homo sapiens

<400> SEQUENCE: 1770
actgtggcat mgagatatac t            21

<210> SEQ ID NO 1771
<211> LENGTH: 21
<212> TYPE: DNA
<213> ORGANISM: Homo sapiens

<400> SEQUENCE: 1771
atattaactt satggctgca a                                              21

<210> SEQ ID NO 1772
<211> LENGTH: 21
<212> TYPE: DNA
<213> ORGANISM: Homo sapiens

<400> SEQUENCE: 1772
cctgtagtga mtcggccgct g                                              21

<210> SEQ ID NO 1773
<211> LENGTH: 21
<212> TYPE: DNA
<213> ORGANISM: Homo sapiens

<400> SEQUENCE: 1773
cgctgcagcg mctggtggag g                                              21

<210> SEQ ID NO 1774
<211> LENGTH: 21
<212> TYPE: DNA
<213> ORGANISM: Homo sapiens

<400> SEQUENCE: 1774
ggaccgctac stggccgtgg t                                              21

<210> SEQ ID NO 1775
<211> LENGTH: 21
<212> TYPE: DNA
<213> ORGANISM: Homo sapiens

<400> SEQUENCE: 1775
tggccgtggt rcatcccatc a                                              21

<210> SEQ ID NO 1776
<211> LENGTH: 21
<212> TYPE: DNA
<213> ORGANISM: Homo sapiens

<400> SEQUENCE: 1776
tgcagctggt yaacgtgttt g                                              21

<210> SEQ ID NO 1777
<211> LENGTH: 21
<212> TYPE: DNA
<213> ORGANISM: Homo sapiens

<400> SEQUENCE: 1777
gccacggagc ygcgtccaga c                                              21

<210> SEQ ID NO 1778
<211> LENGTH: 21
<212> TYPE: DNA
<213> ORGANISM: Homo sapiens

<400> SEQUENCE: 1778
acgtgtcggc rggcccaagc c                                              21

<210> SEQ ID NO 1779
<211> LENGTH: 21
<212> TYPE: DNA
<213> ORGANISM: Homo sapiens -continued

```
<400> SEQUENCE: 1779
ccacccgctc rgcccgctgg c                                              21

<210> SEQ ID NO 1780
<211> LENGTH: 21
<212> TYPE: DNA
<213> ORGANISM: Homo sapiens

<400> SEQUENCE: 1780
agctgaatga yactcaccct c                                              21

<210> SEQ ID NO 1781
<211> LENGTH: 21
<212> TYPE: DNA
<213> ORGANISM: Homo sapiens

<400> SEQUENCE: 1781
agctgatcac ytcagtggca g                                              21

<210> SEQ ID NO 1782
<211> LENGTH: 21
<212> TYPE: DNA
<213> ORGANISM: Homo sapiens

<400> SEQUENCE: 1782
tgtacaaccg yattaagaaa g                                              21

<210> SEQ ID NO 1783
<211> LENGTH: 21
<212> TYPE: DNA
<213> ORGANISM: Homo sapiens

<400> SEQUENCE: 1783
aagcaagttg raagtcatct t                                              21

<210> SEQ ID NO 1784
<211> LENGTH: 21
<212> TYPE: DNA
<213> ORGANISM: Homo sapiens

<400> SEQUENCE: 1784
gatgtggacc stctgagaag g                                              21

<210> SEQ ID NO 1785
<211> LENGTH: 21
<212> TYPE: DNA
<213> ORGANISM: Homo sapiens

<400> SEQUENCE: 1785
ccggggaagc kgccgtctaa a                                              21

<210> SEQ ID NO 1786
<211> LENGTH: 21
<212> TYPE: DNA
<213> ORGANISM: Homo sapiens

<400> SEQUENCE: 1786
ggacgactcc ragctgccta c                                              21

<210> SEQ ID NO 1787
<211> LENGTH: 21
<212> TYPE: DNA
```

-continued

<213> ORGANISM: Homo sapiens

<400> SEQUENCE: 1787
tgggaggcac rgtgattgga a                                               21

<210> SEQ ID NO 1788
<211> LENGTH: 21
<212> TYPE: DNA
<213> ORGANISM: Homo sapiens

<400> SEQUENCE: 1788
tgattggaag ygcccggtgc a                                               21

<210> SEQ ID NO 1789
<211> LENGTH: 21
<212> TYPE: DNA
<213> ORGANISM: Homo sapiens

<400> SEQUENCE: 1789
cgtgggatca scaatctctg t                                               21

<210> SEQ ID NO 1790
<211> LENGTH: 21
<212> TYPE: DNA
<213> ORGANISM: Homo sapiens

<400> SEQUENCE: 1790
cactgtggat rcctggccct t                                               21

<210> SEQ ID NO 1791
<211> LENGTH: 21
<212> TYPE: DNA
<213> ORGANISM: Homo sapiens

<400> SEQUENCE: 1791
atggcagcct yacaggtgcc a                                               21

<210> SEQ ID NO 1792
<211> LENGTH: 21
<212> TYPE: DNA
<213> ORGANISM: Homo sapiens

<400> SEQUENCE: 1792
cagcgttctt ygtgacgtta g                                               21

<210> SEQ ID NO 1793
<211> LENGTH: 21
<212> TYPE: DNA
<213> ORGANISM: Homo sapiens

<400> SEQUENCE: 1793
aatatctcgc ygtggagtcc c                                               21

<210> SEQ ID NO 1794
<211> LENGTH: 21
<212> TYPE: DNA
<213> ORGANISM: Homo sapiens

<400> SEQUENCE: 1794
acttcaaacg katgacagca c                                               21

<210> SEQ ID NO 1795
<211> LENGTH: 21

-continued

<212> TYPE: DNA
<213> ORGANISM: Homo sapiens

<400> SEQUENCE: 1795
cctcacatac saggcctcca t                                              21

<210> SEQ ID NO 1796
<211> LENGTH: 21
<212> TYPE: DNA
<213> ORGANISM: Homo sapiens

<400> SEQUENCE: 1796
tccgggatct yagtaagcca g                                              21

<210> SEQ ID NO 1797
<211> LENGTH: 21
<212> TYPE: DNA
<213> ORGANISM: Homo sapiens

<400> SEQUENCE: 1797
aagtatatca ktttcaaata t                                              21

<210> SEQ ID NO 1798
<211> LENGTH: 21
<212> TYPE: DNA
<213> ORGANISM: Homo sapiens

<400> SEQUENCE: 1798
gtagccatgc ytacgcaaat c                                              21

<210> SEQ ID NO 1799
<211> LENGTH: 21
<212> TYPE: DNA
<213> ORGANISM: Homo sapiens

<400> SEQUENCE: 1799
cacgagcact rtaaaatcca c                                              21

<210> SEQ ID NO 1800
<211> LENGTH: 21
<212> TYPE: DNA
<213> ORGANISM: Homo sapiens

<400> SEQUENCE: 1800
ccatgcttac rcaaatcttg g                                              21

<210> SEQ ID NO 1801
<211> LENGTH: 21
<212> TYPE: DNA
<213> ORGANISM: Homo sapiens

<400> SEQUENCE: 1801
tgccattcag sgattgtatg t                                              21

<210> SEQ ID NO 1802
<211> LENGTH: 21
<212> TYPE: DNA
<213> ORGANISM: Homo sapiens

<400> SEQUENCE: 1802
attctgcatc rtgggactct a                                              21

<210> SEQ ID NO 1803

```
<211> LENGTH: 21
<212> TYPE: DNA
<213> ORGANISM: Homo sapiens

<400> SEQUENCE: 1803
ttgtgaaatc wattcgaagt a                                              21

<210> SEQ ID NO 1804
<211> LENGTH: 21
<212> TYPE: DNA
<213> ORGANISM: Homo sapiens

<400> SEQUENCE: 1804
cgaagtaatg ytcagcgcca g                                              21

<210> SEQ ID NO 1805
<211> LENGTH: 21
<212> TYPE: DNA
<213> ORGANISM: Homo sapiens

<400> SEQUENCE: 1805
attgcttcaa sgacacctga a                                              21

<210> SEQ ID NO 1806
<211> LENGTH: 21
<212> TYPE: DNA
<213> ORGANISM: Homo sapiens

<400> SEQUENCE: 1806
gagtagtcgc yatggcacag g                                              21

<210> SEQ ID NO 1807
<211> LENGTH: 21
<212> TYPE: DNA
<213> ORGANISM: Homo sapiens

<400> SEQUENCE: 1807
gtaatgctca scgccaggaa a                                              21

<210> SEQ ID NO 1808
<211> LENGTH: 21
<212> TYPE: DNA
<213> ORGANISM: Homo sapiens

<400> SEQUENCE: 1808
tgcaagatta yaggctgttg c                                              21

<210> SEQ ID NO 1809
<211> LENGTH: 21
<212> TYPE: DNA
<213> ORGANISM: Homo sapiens

<400> SEQUENCE: 1809
ccctcagtca ygattcttta a                                              21

<210> SEQ ID NO 1810
<211> LENGTH: 21
<212> TYPE: DNA
<213> ORGANISM: Homo sapiens

<400> SEQUENCE: 1810
gttggcagtt wccagctccc a                                              21
```

```
<210> SEQ ID NO 1811
<211> LENGTH: 21
<212> TYPE: DNA
<213> ORGANISM: Homo sapiens

<400> SEQUENCE: 1811
gcagtactca rtctgaaaag c                                              21

<210> SEQ ID NO 1812
<211> LENGTH: 21
<212> TYPE: DNA
<213> ORGANISM: Homo sapiens

<400> SEQUENCE: 1812
tcctgaacca kggctttctg g                                              21

<210> SEQ ID NO 1813
<211> LENGTH: 21
<212> TYPE: DNA
<213> ORGANISM: Homo sapiens

<400> SEQUENCE: 1813
actatattac rtgcttcaaa a                                              21

<210> SEQ ID NO 1814
<211> LENGTH: 21
<212> TYPE: DNA
<213> ORGANISM: Homo sapiens

<400> SEQUENCE: 1814
acaatagcca yatgggaaat a                                              21

<210> SEQ ID NO 1815
<211> LENGTH: 21
<212> TYPE: DNA
<213> ORGANISM: Homo sapiens

<400> SEQUENCE: 1815
atcaaatgga rttccccacc a                                              21

<210> SEQ ID NO 1816
<211> LENGTH: 21
<212> TYPE: DNA
<213> ORGANISM: Homo sapiens

<400> SEQUENCE: 1816
atttgtcccc rcacagaagt a                                              21

<210> SEQ ID NO 1817
<211> LENGTH: 21
<212> TYPE: DNA
<213> ORGANISM: Homo sapiens

<400> SEQUENCE: 1817
tgcggtccat yttggtcaag g                                              21

<210> SEQ ID NO 1818
<211> LENGTH: 21
<212> TYPE: DNA
<213> ORGANISM: Homo sapiens

<400> SEQUENCE: 1818
accaacctgc mcttccaggc c                                              21
```

<210> SEQ ID NO 1819
<211> LENGTH: 21
<212> TYPE: DNA
<213> ORGANISM: Homo sapiens

<400> SEQUENCE: 1819
ccatctcata macgggcgac g                                              21

<210> SEQ ID NO 1820
<211> LENGTH: 21
<212> TYPE: DNA
<213> ORGANISM: Homo sapiens

<400> SEQUENCE: 1820
gggacctatg ytgataaact g                                              21

<210> SEQ ID NO 1821
<211> LENGTH: 21
<212> TYPE: DNA
<213> ORGANISM: Homo sapiens

<400> SEQUENCE: 1821
cctgttaata ytaggagtaa g                                              21

<210> SEQ ID NO 1822
<211> LENGTH: 21
<212> TYPE: DNA
<213> ORGANISM: Homo sapiens

<400> SEQUENCE: 1822
ggtaatgaag kcacgtgtgt t                                              21

<210> SEQ ID NO 1823
<211> LENGTH: 21
<212> TYPE: DNA
<213> ORGANISM: Homo sapiens

<400> SEQUENCE: 1823
gtacctttgt yatccaggcc a                                              21

<210> SEQ ID NO 1824
<211> LENGTH: 21
<212> TYPE: DNA
<213> ORGANISM: Homo sapiens

<400> SEQUENCE: 1824
ccaggcagat sgaggcctta c                                              21

<210> SEQ ID NO 1825
<211> LENGTH: 21
<212> TYPE: DNA
<213> ORGANISM: Homo sapiens

<400> SEQUENCE: 1825
gagtaatcat wgaagatgtg g                                              21

<210> SEQ ID NO 1826
<211> LENGTH: 21
<212> TYPE: DNA
<213> ORGANISM: Homo sapiens

<400> SEQUENCE: 1826
tccaataatc wgtcaacttt a                                              21

<210> SEQ ID NO 1827
<211> LENGTH: 21
<212> TYPE: DNA
<213> ORGANISM: Homo sapiens

<400> SEQUENCE: 1827
ttcaaaagca wttcaatcaa a                                              21

<210> SEQ ID NO 1828
<211> LENGTH: 21
<212> TYPE: DNA
<213> ORGANISM: Homo sapiens

<400> SEQUENCE: 1828
tattcagctc rtccgtatcc t                                              21

<210> SEQ ID NO 1829
<211> LENGTH: 21
<212> TYPE: DNA
<213> ORGANISM: Homo sapiens

<400> SEQUENCE: 1829
atctttacct yggtgctatg a                                              21

<210> SEQ ID NO 1830
<211> LENGTH: 21
<212> TYPE: DNA
<213> ORGANISM: Homo sapiens

<400> SEQUENCE: 1830
gtggaaatcc rtactacctg t                                              21

<210> SEQ ID NO 1831
<211> LENGTH: 21
<212> TYPE: DNA
<213> ORGANISM: Homo sapiens

<400> SEQUENCE: 1831
ttgtggcatt sctagcagac a                                              21

<210> SEQ ID NO 1832
<211> LENGTH: 21
<212> TYPE: DNA
<213> ORGANISM: Homo sapiens

<400> SEQUENCE: 1832
atccatctat ygtaaatggc a                                              21

<210> SEQ ID NO 1833
<211> LENGTH: 21
<212> TYPE: DNA
<213> ORGANISM: Homo sapiens

<400> SEQUENCE: 1833
ctatggacct yagataactg t                                              21

<210> SEQ ID NO 1834
<211> LENGTH: 21
<212> TYPE: DNA
<213> ORGANISM: Homo sapiens

<400> SEQUENCE: 1834

-continued accatcacag rgatgtgcca g 21

<210> SEQ ID NO 1835
<211> LENGTH: 21
<212> TYPE: DNA
<213> ORGANISM: Homo sapiens

<400> SEQUENCE: 1835
ccctttacga rgcagcatta t 21

<210> SEQ ID NO 1836
<211> LENGTH: 21
<212> TYPE: DNA
<213> ORGANISM: Homo sapiens

<400> SEQUENCE: 1836
tatgtgggag rcacccattg c 21

<210> SEQ ID NO 1837
<211> LENGTH: 21
<212> TYPE: DNA
<213> ORGANISM: Homo sapiens

<400> SEQUENCE: 1837
aagagctcct ytgggagaat a 21

<210> SEQ ID NO 1838
<211> LENGTH: 21
<212> TYPE: DNA
<213> ORGANISM: Homo sapiens

<400> SEQUENCE: 1838
gtctttgcaa ygatgtcatt c 21

<210> SEQ ID NO 1839
<211> LENGTH: 21
<212> TYPE: DNA
<213> ORGANISM: Homo sapiens

<400> SEQUENCE: 1839
gctcattgcg rtatcttctt g 21

<210> SEQ ID NO 1840
<211> LENGTH: 21
<212> TYPE: DNA
<213> ORGANISM: Homo sapiens

<400> SEQUENCE: 1840
tatcttcttg watggataga a 21

<210> SEQ ID NO 1841
<211> LENGTH: 21
<212> TYPE: DNA
<213> ORGANISM: Homo sapiens

<400> SEQUENCE: 1841
agaagtcagc rttcacacgg t 21

<210> SEQ ID NO 1842
<211> LENGTH: 21
<212> TYPE: DNA
<213> ORGANISM: Homo sapiens

<400> SEQUENCE: 1842
cctgtgtgtt wgacatggaa g                      21

<210> SEQ ID NO 1843
<211> LENGTH: 21
<212> TYPE: DNA
<213> ORGANISM: Homo sapiens

<400> SEQUENCE: 1843
ggggttctct yttcggcaga t                      21

<210> SEQ ID NO 1844
<211> LENGTH: 21
<212> TYPE: DNA
<213> ORGANISM: Homo sapiens

<400> SEQUENCE: 1844
cagctcagca wctcgtgcgc a                      21

<210> SEQ ID NO 1845
<211> LENGTH: 21
<212> TYPE: DNA
<213> ORGANISM: Homo sapiens

<400> SEQUENCE: 1845
ctttgttgta rcacaggccc t                      21

<210> SEQ ID NO 1846
<211> LENGTH: 21
<212> TYPE: DNA
<213> ORGANISM: Homo sapiens

<400> SEQUENCE: 1846
agaactgtct scctgaccct g                      21

<210> SEQ ID NO 1847
<211> LENGTH: 21
<212> TYPE: DNA
<213> ORGANISM: Homo sapiens

<400> SEQUENCE: 1847
ttaaaccaca ytttggcagt g                      21

<210> SEQ ID NO 1848
<211> LENGTH: 21
<212> TYPE: DNA
<213> ORGANISM: Homo sapiens

<400> SEQUENCE: 1848
acgtggacaa ygccgagggc t                      21

<210> SEQ ID NO 1849
<211> LENGTH: 21
<212> TYPE: DNA
<213> ORGANISM: Homo sapiens

<400> SEQUENCE: 1849
attccccatt ygccggggca c                      21

<210> SEQ ID NO 1850
<211> LENGTH: 21
<212> TYPE: DNA
<213> ORGANISM: Homo sapiens -continued

<400> SEQUENCE: 1850
ggcaaggtga rgcagcagca g					21

<210> SEQ ID NO 1851
<211> LENGTH: 21
<212> TYPE: DNA
<213> ORGANISM: Homo sapiens

<400> SEQUENCE: 1851
atgctcccat ygtctccgaa a					21

<210> SEQ ID NO 1852
<211> LENGTH: 21
<212> TYPE: DNA
<213> ORGANISM: Homo sapiens

<400> SEQUENCE: 1852
tccagaggaa yaggacactg c					21

<210> SEQ ID NO 1853
<211> LENGTH: 21
<212> TYPE: DNA
<213> ORGANISM: Homo sapiens

<400> SEQUENCE: 1853
cactcctcaa ytggataaat g					21

<210> SEQ ID NO 1854
<211> LENGTH: 21
<212> TYPE: DNA
<213> ORGANISM: Homo sapiens

<400> SEQUENCE: 1854
tggagaacca rgtgctggta a					21

<210> SEQ ID NO 1855
<211> LENGTH: 21
<212> TYPE: DNA
<213> ORGANISM: Homo sapiens

<400> SEQUENCE: 1855
gtaaatggac rgttaataga g					21

<210> SEQ ID NO 1856
<211> LENGTH: 21
<212> TYPE: DNA
<213> ORGANISM: Homo sapiens

<400> SEQUENCE: 1856
agcatatcat stcccgagtg g					21

<210> SEQ ID NO 1857
<211> LENGTH: 21
<212> TYPE: DNA
<213> ORGANISM: Homo sapiens

<400> SEQUENCE: 1857
agtcatcagc yttgtgccac c					21

<210> SEQ ID NO 1858
<211> LENGTH: 21
<212> TYPE: DNA
<213> ORGANISM: Homo sapiens

```
<400> SEQUENCE: 1858
ctcagtacca ygatcctgat g                                              21

<210> SEQ ID NO 1859
<211> LENGTH: 21
<212> TYPE: DNA
<213> ORGANISM: Homo sapiens

<400> SEQUENCE: 1859
ccgagccata ygatgagagc g                                              21

<210> SEQ ID NO 1860
<211> LENGTH: 21
<212> TYPE: DNA
<213> ORGANISM: Homo sapiens

<400> SEQUENCE: 1860
aaatctcctc rgaacacgcc c                                              21

<210> SEQ ID NO 1861
<211> LENGTH: 21
<212> TYPE: DNA
<213> ORGANISM: Homo sapiens

<400> SEQUENCE: 1861
gccccagaag racctgagca g                                              21

<210> SEQ ID NO 1862
<211> LENGTH: 21
<212> TYPE: DNA
<213> ORGANISM: Homo sapiens

<400> SEQUENCE: 1862
tcctggttta ycagctgctg c                                              21

<210> SEQ ID NO 1863
<211> LENGTH: 21
<212> TYPE: DNA
<213> ORGANISM: Homo sapiens

<400> SEQUENCE: 1863
tttgcatgca ragaacatca t                                              21

<210> SEQ ID NO 1864
<211> LENGTH: 21
<212> TYPE: DNA
<213> ORGANISM: Homo sapiens

<400> SEQUENCE: 1864
gacagtctaa rgaaagcact g                                              21

<210> SEQ ID NO 1865
<211> LENGTH: 21
<212> TYPE: DNA
<213> ORGANISM: Homo sapiens

<400> SEQUENCE: 1865
ccaaacagag rattttagtc t                                              21

<210> SEQ ID NO 1866
<211> LENGTH: 21
<212> TYPE: DNA
```

```
<213> ORGANISM: Homo sapiens

<400> SEQUENCE: 1866
aggaagaggc rtccttagca g                                        21

<210> SEQ ID NO 1867
<211> LENGTH: 21
<212> TYPE: DNA
<213> ORGANISM: Homo sapiens

<400> SEQUENCE: 1867
aagaagacaa kaggtttctt c                                        21

<210> SEQ ID NO 1868
<211> LENGTH: 21
<212> TYPE: DNA
<213> ORGANISM: Homo sapiens

<400> SEQUENCE: 1868
gcatatacct sgagtatgtg a                                        21

<210> SEQ ID NO 1869
<211> LENGTH: 21
<212> TYPE: DNA
<213> ORGANISM: Homo sapiens

<400> SEQUENCE: 1869
ataacaatta yggctgtgtc c                                        21

<210> SEQ ID NO 1870
<211> LENGTH: 21
<212> TYPE: DNA
<213> ORGANISM: Homo sapiens

<400> SEQUENCE: 1870
tgaaattcag rgaattgacc c                                        21

<210> SEQ ID NO 1871
<211> LENGTH: 21
<212> TYPE: DNA
<213> ORGANISM: Homo sapiens

<400> SEQUENCE: 1871
gaagctcaac ytggactcga t                                        21

<210> SEQ ID NO 1872
<211> LENGTH: 21
<212> TYPE: DNA
<213> ORGANISM: Homo sapiens

<400> SEQUENCE: 1872
aagacggcta ygagttcttt g                                        21

<210> SEQ ID NO 1873
<211> LENGTH: 21
<212> TYPE: DNA
<213> ORGANISM: Homo sapiens

<400> SEQUENCE: 1873
cattgaacca macagttca a                                         21

<210> SEQ ID NO 1874
<211> LENGTH: 21
```

```
<212> TYPE: DNA
<213> ORGANISM: Homo sapiens

<400> SEQUENCE: 1874
atcagaaatt ygtacaacag c                                              21

<210> SEQ ID NO 1875
<211> LENGTH: 21
<212> TYPE: DNA
<213> ORGANISM: Homo sapiens

<400> SEQUENCE: 1875
aggagtacct stcctttcgt t                                              21

<210> SEQ ID NO 1876
<211> LENGTH: 21
<212> TYPE: DNA
<213> ORGANISM: Homo sapiens

<400> SEQUENCE: 1876
aaaactgtct yttgaaagga a                                              21

<210> SEQ ID NO 1877
<211> LENGTH: 21
<212> TYPE: DNA
<213> ORGANISM: Homo sapiens

<400> SEQUENCE: 1877
agcacggaca ygcaggcccg g                                              21

<210> SEQ ID NO 1878
<211> LENGTH: 21
<212> TYPE: DNA
<213> ORGANISM: Homo sapiens

<400> SEQUENCE: 1878
tgaccctcac rtgagtagta a                                              21

<210> SEQ ID NO 1879
<211> LENGTH: 21
<212> TYPE: DNA
<213> ORGANISM: Homo sapiens

<400> SEQUENCE: 1879
ttctggggaa raagctgaag c                                              21

<210> SEQ ID NO 1880
<211> LENGTH: 21
<212> TYPE: DNA
<213> ORGANISM: Homo sapiens

<400> SEQUENCE: 1880
taagcattgc rgagacgcca a                                              21

<210> SEQ ID NO 1881
<211> LENGTH: 21
<212> TYPE: DNA
<213> ORGANISM: Homo sapiens

<400> SEQUENCE: 1881
ccctgaaagc mctgaggctc t                                              21

<210> SEQ ID NO 1882
```

```
<210> SEQ ID NO 1882
<211> LENGTH: 21
<212> TYPE: DNA
<213> ORGANISM: Homo sapiens

<400> SEQUENCE: 1882
tggtgttccc rcctggactg g                                              21

<210> SEQ ID NO 1883
<211> LENGTH: 21
<212> TYPE: DNA
<213> ORGANISM: Homo sapiens

<400> SEQUENCE: 1883
tgaggctctc ycgtcagcgg t                                              21

<210> SEQ ID NO 1884
<211> LENGTH: 21
<212> TYPE: DNA
<213> ORGANISM: Homo sapiens

<400> SEQUENCE: 1884
gacgccaagt ktgaaggaac t                                              21

<210> SEQ ID NO 1885
<211> LENGTH: 21
<212> TYPE: DNA
<213> ORGANISM: Homo sapiens

<400> SEQUENCE: 1885
tctggagatg rtactgacta t                                              21

<210> SEQ ID NO 1886
<211> LENGTH: 21
<212> TYPE: DNA
<213> ORGANISM: Homo sapiens

<400> SEQUENCE: 1886
tgatcttgga ygaaggacac a                                              21

<210> SEQ ID NO 1887
<211> LENGTH: 21
<212> TYPE: DNA
<213> ORGANISM: Homo sapiens

<400> SEQUENCE: 1887
ctaacatatc ygtaaatgat g                                              21

<210> SEQ ID NO 1888
<211> LENGTH: 21
<212> TYPE: DNA
<213> ORGANISM: Homo sapiens

<400> SEQUENCE: 1888
gggcacctgc rggaagcttc t                                              21

<210> SEQ ID NO 1889
<211> LENGTH: 21
<212> TYPE: DNA
<213> ORGANISM: Homo sapiens

<400> SEQUENCE: 1889
tatcatggaa wtagatgaca c                                              21
```

```
<210> SEQ ID NO 1890
<211> LENGTH: 21
<212> TYPE: DNA
<213> ORGANISM: Homo sapiens

<400> SEQUENCE: 1890
cctcatgtta sacggcgcac c                                              21

<210> SEQ ID NO 1891
<211> LENGTH: 21
<212> TYPE: DNA
<213> ORGANISM: Homo sapiens

<400> SEQUENCE: 1891
ttttatgatg ratgtctgcg a                                              21

<210> SEQ ID NO 1892
<211> LENGTH: 21
<212> TYPE: DNA
<213> ORGANISM: Homo sapiens

<400> SEQUENCE: 1892
ttcatggaca rtatacagat t                                              21

<210> SEQ ID NO 1893
<211> LENGTH: 21
<212> TYPE: DNA
<213> ORGANISM: Homo sapiens

<400> SEQUENCE: 1893
cattctggag rattactagc a                                              21

<210> SEQ ID NO 1894
<211> LENGTH: 21
<212> TYPE: DNA
<213> ORGANISM: Homo sapiens

<400> SEQUENCE: 1894 agggtatga wcacaaagca a                                               21

<210> SEQ ID NO 1895
<211> LENGTH: 21
<212> TYPE: DNA
<213> ORGANISM: Homo sapiens

<400> SEQUENCE: 1895
ccaattattg yggagagttt g                                              21

<210> SEQ ID NO 1896
<211> LENGTH: 21
<212> TYPE: DNA
<213> ORGANISM: Homo sapiens

<400> SEQUENCE: 1896
gatcttatat ktagagccca t                                              21

<210> SEQ ID NO 1897
<211> LENGTH: 21
<212> TYPE: DNA
<213> ORGANISM: Homo sapiens

<400> SEQUENCE: 1897
aaagatgcag rtctgaactc t                                              21
```

<210> SEQ ID NO 1898
<211> LENGTH: 21
<212> TYPE: DNA
<213> ORGANISM: Homo sapiens

<400> SEQUENCE: 1898
cgatgggaac kccccatcct t                                    21

<210> SEQ ID NO 1899
<211> LENGTH: 21
<212> TYPE: DNA
<213> ORGANISM: Homo sapiens

<400> SEQUENCE: 1899
cgccccatcc yttggtttac t                                    21

<210> SEQ ID NO 1900
<211> LENGTH: 21
<212> TYPE: DNA
<213> ORGANISM: Homo sapiens

<400> SEQUENCE: 1900
acttaaagga yattgcagga g                                    21

<210> SEQ ID NO 1901
<211> LENGTH: 21
<212> TYPE: DNA
<213> ORGANISM: Homo sapiens

<400> SEQUENCE: 1901
taaagatgtg yttggacatc t                                    21

<210> SEQ ID NO 1902
<211> LENGTH: 21
<212> TYPE: DNA
<213> ORGANISM: Homo sapiens

<400> SEQUENCE: 1902
atgttcaggg ytgcaggggg a                                    21

<210> SEQ ID NO 1903
<211> LENGTH: 21
<212> TYPE: DNA
<213> ORGANISM: Homo sapiens

<400> SEQUENCE: 1903
attatggcag yaacttacag a                                    21

<210> SEQ ID NO 1904
<211> LENGTH: 21
<212> TYPE: DNA
<213> ORGANISM: Homo sapiens

<400> SEQUENCE: 1904
caaagatgca ratctgaact c                                    21

<210> SEQ ID NO 1905
<211> LENGTH: 21
<212> TYPE: DNA
<213> ORGANISM: Homo sapiens

<400> SEQUENCE: 1905 accttttgtct yatagaaact c                                   21

<210> SEQ ID NO 1906
<211> LENGTH: 21
<212> TYPE: DNA
<213> ORGANISM: Homo sapiens

<400> SEQUENCE: 1906
tgcaagtggc yaacaccacc a                                          21

<210> SEQ ID NO 1907
<211> LENGTH: 21
<212> TYPE: DNA
<213> ORGANISM: Homo sapiens

<400> SEQUENCE: 1907
gtcatgcaag yggccaacac c                                          21

<210> SEQ ID NO 1908
<211> LENGTH: 21
<212> TYPE: DNA
<213> ORGANISM: Homo sapiens

<400> SEQUENCE: 1908
acaaggacgt rgagcccggc a                                          21

<210> SEQ ID NO 1909
<211> LENGTH: 21
<212> TYPE: DNA
<213> ORGANISM: Homo sapiens

<400> SEQUENCE: 1909
tccacgacgg mgagtgcatg c                                          21

<210> SEQ ID NO 1910
<211> LENGTH: 21
<212> TYPE: DNA
<213> ORGANISM: Homo sapiens

<400> SEQUENCE: 1910
cttctgctca satgctccaa g                                          21

<210> SEQ ID NO 1911
<211> LENGTH: 21
<212> TYPE: DNA
<213> ORGANISM: Homo sapiens

<400> SEQUENCE: 1911
agaaggagca ratgacattc c                                          21

<210> SEQ ID NO 1912
<211> LENGTH: 21
<212> TYPE: DNA
<213> ORGANISM: Homo sapiens

<400> SEQUENCE: 1912
aagtggccgg macctgagaa t                                          21

<210> SEQ ID NO 1913
<211> LENGTH: 21
<212> TYPE: DNA
<213> ORGANISM: Homo sapiens

<400> SEQUENCE: 1913
ctccaccacc wcgtcgaaga a                                              21

<210> SEQ ID NO 1914
<211> LENGTH: 21
<212> TYPE: DNA
<213> ORGANISM: Homo sapiens

<400> SEQUENCE: 1914
caccacgtcg ragaatcgca t                                              21

<210> SEQ ID NO 1915
<211> LENGTH: 21
<212> TYPE: DNA
<213> ORGANISM: Homo sapiens

<400> SEQUENCE: 1915
cccctgacta yagggatctc a                                              21

<210> SEQ ID NO 1916
<211> LENGTH: 21
<212> TYPE: DNA
<213> ORGANISM: Homo sapiens

<400> SEQUENCE: 1916
tctgcagact yttcaggaga g                                              21

<210> SEQ ID NO 1917
<211> LENGTH: 21
<212> TYPE: DNA
<213> ORGANISM: Homo sapiens

<400> SEQUENCE: 1917
aagcattaga rgccttacag a                                              21

<210> SEQ ID NO 1918
<211> LENGTH: 21
<212> TYPE: DNA
<213> ORGANISM: Homo sapiens

<400> SEQUENCE: 1918
caaatatcca ygtggactaa a                                              21

<210> SEQ ID NO 1919
<211> LENGTH: 21
<212> TYPE: DNA
<213> ORGANISM: Homo sapiens

<400> SEQUENCE: 1919
ttctgctgtg kcgctccatc c                                              21

<210> SEQ ID NO 1920
<211> LENGTH: 21
<212> TYPE: DNA
<213> ORGANISM: Homo sapiens

<400> SEQUENCE: 1920
cttgcccaga kcatgcaact t                                              21

<210> SEQ ID NO 1921
<211> LENGTH: 21
<212> TYPE: DNA
<213> ORGANISM: Homo sapiens

<400> SEQUENCE: 1921
gcaccaagca rtggacagtt g                                              21

<210> SEQ ID NO 1922
<211> LENGTH: 21
<212> TYPE: DNA
<213> ORGANISM: Homo sapiens

<400> SEQUENCE: 1922
tgaagacgtg ratgaatgtg c                                              21

<210> SEQ ID NO 1923
<211> LENGTH: 21
<212> TYPE: DNA
<213> ORGANISM: Homo sapiens

<400> SEQUENCE: 1923
ttactattgc rcttgcaaac a                                              21

<210> SEQ ID NO 1924
<211> LENGTH: 21
<212> TYPE: DNA
<213> ORGANISM: Homo sapiens

<400> SEQUENCE: 1924
tcaccagcag sgtctgccct g                                              21

<210> SEQ ID NO 1925
<211> LENGTH: 21
<212> TYPE: DNA
<213> ORGANISM: Homo sapiens

<400> SEQUENCE: 1925
ctcagcaaat rtcactccgg c                                              21

<210> SEQ ID NO 1926
<211> LENGTH: 21
<212> TYPE: DNA
<213> ORGANISM: Homo sapiens

<400> SEQUENCE: 1926
acactggcat ytttttggaa a                                              21

<210> SEQ ID NO 1927
<211> LENGTH: 21
<212> TYPE: DNA
<213> ORGANISM: Homo sapiens

<400> SEQUENCE: 1927
gacaacaaga ygggctgcgc c                                              21

<210> SEQ ID NO 1928
<211> LENGTH: 21
<212> TYPE: DNA
<213> ORGANISM: Homo sapiens

<400> SEQUENCE: 1928
tgcctcccta ygccttcttc t                                              21

<210> SEQ ID NO 1929
<211> LENGTH: 21
<212> TYPE: DNA
<213> ORGANISM: Homo sapiens

```
<400> SEQUENCE: 1929
aacgtgagcc rggagcagcg t                                              21

<210> SEQ ID NO 1930
<211> LENGTH: 21
<212> TYPE: DNA
<213> ORGANISM: Homo sapiens

<400> SEQUENCE: 1930
attgttttta rggtgagaaa t                                              21

<210> SEQ ID NO 1931
<211> LENGTH: 21
<212> TYPE: DNA
<213> ORGANISM: Homo sapiens

<400> SEQUENCE: 1931
ctcgccgaac raccctgtca c                                              21

<210> SEQ ID NO 1932
<211> LENGTH: 21
<212> TYPE: DNA
<213> ORGANISM: Homo sapiens

<400> SEQUENCE: 1932
tcctgccgct ygatttctcc a                                              21

<210> SEQ ID NO 1933
<211> LENGTH: 21
<212> TYPE: DNA
<213> ORGANISM: Homo sapiens

<400> SEQUENCE: 1933
ggccatgggc rtgaagcggg a                                              21

<210> SEQ ID NO 1934
<211> LENGTH: 21
<212> TYPE: DNA
<213> ORGANISM: Homo sapiens

<400> SEQUENCE: 1934
gacaaacagc ytttcaccct g                                              21

<210> SEQ ID NO 1935
<211> LENGTH: 21
<212> TYPE: DNA
<213> ORGANISM: Homo sapiens

<400> SEQUENCE: 1935
aggagaaagc yctcaaagca t                                              21

<210> SEQ ID NO 1936
<211> LENGTH: 21
<212> TYPE: DNA
<213> ORGANISM: Homo sapiens

<400> SEQUENCE: 1936
ccttcagcaa ygggaggaaa a                                              21

<210> SEQ ID NO 1937
<211> LENGTH: 21
<212> TYPE: DNA
<213> ORGANISM: Homo sapiens
```

<400> SEQUENCE: 1937
cctatcctta mcctcggtac a                      21

<210> SEQ ID NO 1938
<211> LENGTH: 21
<212> TYPE: DNA
<213> ORGANISM: Homo sapiens

<400> SEQUENCE: 1938
tttctgctgc ygccaacaac a                      21

<210> SEQ ID NO 1939
<211> LENGTH: 21
<212> TYPE: DNA
<213> ORGANISM: Homo sapiens

<400> SEQUENCE: 1939
tctatgacct yggagatgtg c                      21

<210> SEQ ID NO 1940
<211> LENGTH: 21
<212> TYPE: DNA
<213> ORGANISM: Homo sapiens

<400> SEQUENCE: 1940
ccttcatgac kcagagctcc c                      21

<210> SEQ ID NO 1941
<211> LENGTH: 21
<212> TYPE: DNA
<213> ORGANISM: Homo sapiens

<400> SEQUENCE: 1941
ttcatgactc rgagctcccc t                      21

<210> SEQ ID NO 1942
<211> LENGTH: 21
<212> TYPE: DNA
<213> ORGANISM: Homo sapiens

<400> SEQUENCE: 1942
tcacccagga ygcccagctg a                      21

<210> SEQ ID NO 1943
<211> LENGTH: 21
<212> TYPE: DNA
<213> ORGANISM: Homo sapiens

<400> SEQUENCE: 1943
cgccacgcgc rcctgcggcc t                      21

<210> SEQ ID NO 1944
<211> LENGTH: 21
<212> TYPE: DNA
<213> ORGANISM: Homo sapiens

<400> SEQUENCE: 1944
ggccgcgcca scgaggtccc c                      21

<210> SEQ ID NO 1945
<211> LENGTH: 21
<212> TYPE: DNA

-continued

<213> ORGANISM: Homo sapiens

<400> SEQUENCE: 1945
tcgatgccta maaacaggtg a                                      21

<210> SEQ ID NO 1946
<211> LENGTH: 21
<212> TYPE: DNA
<213> ORGANISM: Homo sapiens

<400> SEQUENCE: 1946
tgcctacaaa maggtgaaat t                                      21

<210> SEQ ID NO 1947
<211> LENGTH: 21
<212> TYPE: DNA
<213> ORGANISM: Homo sapiens

<400> SEQUENCE: 1947
tgtctccagt rcagaaggag g                                      21

<210> SEQ ID NO 1948
<211> LENGTH: 21
<212> TYPE: DNA
<213> ORGANISM: Homo sapiens

<400> SEQUENCE: 1948
cgagcctggg ragccccggg g                                      21

<210> SEQ ID NO 1949
<211> LENGTH: 21
<212> TYPE: DNA
<213> ORGANISM: Homo sapiens

<400> SEQUENCE: 1949
ggctcgccga wttgcccaga t                                      21

<210> SEQ ID NO 1950
<211> LENGTH: 21
<212> TYPE: DNA
<213> ORGANISM: Homo sapiens

<400> SEQUENCE: 1950
actgccaggc rttcagtggc a                                      21

<210> SEQ ID NO 1951
<211> LENGTH: 21
<212> TYPE: DNA
<213> ORGANISM: Homo sapiens

<400> SEQUENCE: 1951
ttggaaaaac wctaggagaa g                                      21

<210> SEQ ID NO 1952
<211> LENGTH: 21
<212> TYPE: DNA
<213> ORGANISM: Homo sapiens

<400> SEQUENCE: 1952
cgagtgagct kcgagacctg c                                      21

<210> SEQ ID NO 1953
<211> LENGTH: 21

-continued

```
<212> TYPE: DNA
<213> ORGANISM: Homo sapiens

<400> SEQUENCE: 1953
tcggctggaa wgaatggata a                                                 21

<210> SEQ ID NO 1954
<211> LENGTH: 21
<212> TYPE: DNA
<213> ORGANISM: Homo sapiens

<400> SEQUENCE: 1954
ctgtggagca rtggaaagcc c                                                 21

<210> SEQ ID NO 1955
<211> LENGTH: 21
<212> TYPE: DNA
<213> ORGANISM: Homo sapiens

<400> SEQUENCE: 1955
tgtgactgct scatgcactg t                                                 21

<210> SEQ ID NO 1956
<211> LENGTH: 21
<212> TYPE: DNA
<213> ORGANISM: Homo sapiens

<400> SEQUENCE: 1956
agcacctact ycatgctggg c                                                 21

<210> SEQ ID NO 1957
<211> LENGTH: 21
<212> TYPE: DNA
<213> ORGANISM: Homo sapiens

<400> SEQUENCE: 1957
aggaaatgat ygaggaactc c                                                 21

<210> SEQ ID NO 1958
<211> LENGTH: 21
<212> TYPE: DNA
<213> ORGANISM: Homo sapiens

<400> SEQUENCE: 1958
aagtgcacac yataccagcc a                                                 21

<210> SEQ ID NO 1959
<211> LENGTH: 21
<212> TYPE: DNA
<213> ORGANISM: Homo sapiens

<400> SEQUENCE: 1959
gtttatcagg kgctccagga g                                                 21

<210> SEQ ID NO 1960
<211> LENGTH: 21
<212> TYPE: DNA
<213> ORGANISM: Homo sapiens

<400> SEQUENCE: 1960
aggtgctcca rgagcacttg g                                                 21

<210> SEQ ID NO 1961
```

```
<211> LENGTH: 21
<212> TYPE: DNA
<213> ORGANISM: Homo sapiens

<400> SEQUENCE: 1961
ggctggctgg kgtttgacat c                                              21

<210> SEQ ID NO 1962
<211> LENGTH: 21
<212> TYPE: DNA
<213> ORGANISM: Homo sapiens

<400> SEQUENCE: 1962
ggcctgcagc kctcggtgga g                                              21

<210> SEQ ID NO 1963
<211> LENGTH: 21
<212> TYPE: DNA
<213> ORGANISM: Homo sapiens

<400> SEQUENCE: 1963
atctacaagg rctacatccg g                                              21

<210> SEQ ID NO 1964
<211> LENGTH: 21
<212> TYPE: DNA
<213> ORGANISM: Homo sapiens

<400> SEQUENCE: 1964
gccactagct yctccgagaa t                                              21

<210> SEQ ID NO 1965
<211> LENGTH: 21
<212> TYPE: DNA
<213> ORGANISM: Homo sapiens

<400> SEQUENCE: 1965
gttcccttta kgattatctg a                                              21

<210> SEQ ID NO 1966
<211> LENGTH: 21
<212> TYPE: DNA
<213> ORGANISM: Homo sapiens

<400> SEQUENCE: 1966
gctaaatcaa ygctgaagtt a                                              21

<210> SEQ ID NO 1967
<211> LENGTH: 21
<212> TYPE: DNA
<213> ORGANISM: Homo sapiens

<400> SEQUENCE: 1967
tatcagacag kgttgatgag g                                              21

<210> SEQ ID NO 1968
<211> LENGTH: 21
<212> TYPE: DNA
<213> ORGANISM: Homo sapiens

<400> SEQUENCE: 1968
tccttatcat racctagtgc c                                              21
```

```
<210> SEQ ID NO 1969
<211> LENGTH: 21
<212> TYPE: DNA
<213> ORGANISM: Homo sapiens

<400> SEQUENCE: 1969
gttacgcccc kcattcccaa a                                              21

<210> SEQ ID NO 1970
<211> LENGTH: 21
<212> TYPE: DNA
<213> ORGANISM: Homo sapiens

<400> SEQUENCE: 1970
tgttggacga ragcttgaac a                                              21

<210> SEQ ID NO 1971
<211> LENGTH: 21
<212> TYPE: DNA
<213> ORGANISM: Homo sapiens

<400> SEQUENCE: 1971
aaatttggca rcaagcacaa a                                              21

<210> SEQ ID NO 1972
<211> LENGTH: 21
<212> TYPE: DNA
<213> ORGANISM: Homo sapiens

<400> SEQUENCE: 1972
tggagttgcc wagatgaata c                                              21

<210> SEQ ID NO 1973
<211> LENGTH: 21
<212> TYPE: DNA
<213> ORGANISM: Homo sapiens

<400> SEQUENCE: 1973
atgatcagga yggcaatgga t                                              21

<210> SEQ ID NO 1974
<211> LENGTH: 21
<212> TYPE: DNA
<213> ORGANISM: Homo sapiens

<400> SEQUENCE: 1974
gggcacaatt scagctgatg a                                              21

<210> SEQ ID NO 1975
<211> LENGTH: 21
<212> TYPE: DNA
<213> ORGANISM: Homo sapiens

<400> SEQUENCE: 1975
tacctgtgga yacctttctg a                                              21

<210> SEQ ID NO 1976
<211> LENGTH: 21
<212> TYPE: DNA
<213> ORGANISM: Homo sapiens

<400> SEQUENCE: 1976
ttacggatat yctacaatgt g                                              21
```

<210> SEQ ID NO 1977
<211> LENGTH: 21
<212> TYPE: DNA
<213> ORGANISM: Homo sapiens

<400> SEQUENCE: 1977
cctacaatgt ktacttagca g                                    21

<210> SEQ ID NO 1978
<211> LENGTH: 21
<212> TYPE: DNA
<213> ORGANISM: Homo sapiens

<400> SEQUENCE: 1978
ggagagggct yttcaccaat g                                    21

<210> SEQ ID NO 1979
<211> LENGTH: 21
<212> TYPE: DNA
<213> ORGANISM: Homo sapiens

<400> SEQUENCE: 1979
tacggatatc ytacaatgtg t                                    21

<210> SEQ ID NO 1980
<211> LENGTH: 21
<212> TYPE: DNA
<213> ORGANISM: Homo sapiens

<400> SEQUENCE: 1980
tcgtgctctg yatctcatgc a                                    21

<210> SEQ ID NO 1981
<211> LENGTH: 21
<212> TYPE: DNA
<213> ORGANISM: Homo sapiens

<400> SEQUENCE: 1981
tgtcctcctg rtgtttgagg c                                    21

<210> SEQ ID NO 1982
<211> LENGTH: 21
<212> TYPE: DNA
<213> ORGANISM: Homo sapiens

<400> SEQUENCE: 1982
tctcccgcaa scggtccagc a                                    21

<210> SEQ ID NO 1983
<211> LENGTH: 21
<212> TYPE: DNA
<213> ORGANISM: Homo sapiens

<400> SEQUENCE: 1983
tcctattcat wttggagtag c                                    21

<210> SEQ ID NO 1984
<211> LENGTH: 21
<212> TYPE: DNA
<213> ORGANISM: Homo sapiens

<400> SEQUENCE: 1984
cattccagcc katgccagca c                                    21

<210> SEQ ID NO 1985
<211> LENGTH: 21
<212> TYPE: DNA
<213> ORGANISM: Homo sapiens

<400> SEQUENCE: 1985
agggatatct rcatcgactt c                                              21

<210> SEQ ID NO 1986
<211> LENGTH: 21
<212> TYPE: DNA
<213> ORGANISM: Homo sapiens

<400> SEQUENCE: 1986
gatatttgcc rtagaggaga t                                              21

<210> SEQ ID NO 1987
<211> LENGTH: 21
<212> TYPE: DNA
<213> ORGANISM: Homo sapiens

<400> SEQUENCE: 1987
ttctggtcca rtgagaacca c                                              21

<210> SEQ ID NO 1988
<211> LENGTH: 21
<212> TYPE: DNA
<213> ORGANISM: Homo sapiens

<400> SEQUENCE: 1988
agctggagga ygagatcatc t                                              21

<210> SEQ ID NO 1989
<211> LENGTH: 21
<212> TYPE: DNA
<213> ORGANISM: Homo sapiens

<400> SEQUENCE: 1989
tcagcaactc sacggcgcgc a                                              21

<210> SEQ ID NO 1990
<211> LENGTH: 21
<212> TYPE: DNA
<213> ORGANISM: Homo sapiens

<400> SEQUENCE: 1990
cggcgccctg ytagtcaacg c                                              21

<210> SEQ ID NO 1991
<211> LENGTH: 21
<212> TYPE: DNA
<213> ORGANISM: Homo sapiens

<400> SEQUENCE: 1991
gcggctccct rctattcatt g                                              21

<210> SEQ ID NO 1992
<211> LENGTH: 21
<212> TYPE: DNA
<213> ORGANISM: Homo sapiens

<400> SEQUENCE: 1992

-continued aacgatgttg magcaggaac t                                    21

<210> SEQ ID NO 1993
<211> LENGTH: 21
<212> TYPE: DNA
<213> ORGANISM: Homo sapiens

<400> SEQUENCE: 1993
tggacaaatt wtacccagtg t                                    21

<210> SEQ ID NO 1994
<211> LENGTH: 21
<212> TYPE: DNA
<213> ORGANISM: Homo sapiens

<400> SEQUENCE: 1994
aggcattcca rgattccctg g                                    21

<210> SEQ ID NO 1995
<211> LENGTH: 21
<212> TYPE: DNA
<213> ORGANISM: Homo sapiens

<400> SEQUENCE: 1995
tgccaaccag sgggtaacag g                                    21

<210> SEQ ID NO 1996
<211> LENGTH: 21
<212> TYPE: DNA
<213> ORGANISM: Homo sapiens

<400> SEQUENCE: 1996
cataccacgt scatgtgaaa g                                    21

<210> SEQ ID NO 1997
<211> LENGTH: 21
<212> TYPE: DNA
<213> ORGANISM: Homo sapiens

<400> SEQUENCE: 1997
agtcatgcct sagggtttta t                                    21

<210> SEQ ID NO 1998
<211> LENGTH: 21
<212> TYPE: DNA
<213> ORGANISM: Homo sapiens

<400> SEQUENCE: 1998
agaagaaaac wgtgacaatg a                                    21

<210> SEQ ID NO 1999
<211> LENGTH: 21
<212> TYPE: DNA
<213> ORGANISM: Homo sapiens

<400> SEQUENCE: 1999
tgacaatgat wgttgattgt a                                    21

<210> SEQ ID NO 2000
<211> LENGTH: 21
<212> TYPE: DNA
<213> ORGANISM: Homo sapiens

<400> SEQUENCE: 2000
tagtccagac wgtgactctt c                                              21

<210> SEQ ID NO 2001
<211> LENGTH: 21
<212> TYPE: DNA
<213> ORGANISM: Homo sapiens

<400> SEQUENCE: 2001
agactgtgac wcttcagcac c                                              21

<210> SEQ ID NO 2002
<211> LENGTH: 21
<212> TYPE: DNA
<213> ORGANISM: Homo sapiens

<400> SEQUENCE: 2002
tgacgggaag wggcatcggg t                                              21

<210> SEQ ID NO 2003
<211> LENGTH: 21
<212> TYPE: DNA
<213> ORGANISM: Homo sapiens

<400> SEQUENCE: 2003
tggcatcggg wagcaatcag c                                              21

<210> SEQ ID NO 2004
<211> LENGTH: 21
<212> TYPE: DNA
<213> ORGANISM: Homo sapiens

<400> SEQUENCE: 2004
cgtcctggct yaccagggc t                                               21

<210> SEQ ID NO 2005
<211> LENGTH: 21
<212> TYPE: DNA
<213> ORGANISM: Homo sapiens

<400> SEQUENCE: 2005
tgggtttcca rgtgccaatg g                                              21

<210> SEQ ID NO 2006
<211> LENGTH: 21
<212> TYPE: DNA
<213> ORGANISM: Homo sapiens

<400> SEQUENCE: 2006
gtccagaagg wcttcggggc a                                              21

<210> SEQ ID NO 2007
<211> LENGTH: 21
<212> TYPE: DNA
<213> ORGANISM: Homo sapiens

<400> SEQUENCE: 2007 gaaaaggtg wccgagggct c                                               21

<210> SEQ ID NO 2008
<211> LENGTH: 21
<212> TYPE: DNA
<213> ORGANISM: Homo sapiens

<400> SEQUENCE: 2008
gctaaggggg magcaggtgc a                    21

<210> SEQ ID NO 2009
<211> LENGTH: 21
<212> TYPE: DNA
<213> ORGANISM: Homo sapiens

<400> SEQUENCE: 2009
agacatactg raggcatgca a                    21

<210> SEQ ID NO 2010
<211> LENGTH: 21
<212> TYPE: DNA
<213> ORGANISM: Homo sapiens

<400> SEQUENCE: 2010
aacaagacat ygagcatatg a                    21

<210> SEQ ID NO 2011
<211> LENGTH: 21
<212> TYPE: DNA
<213> ORGANISM: Homo sapiens

<400> SEQUENCE: 2011
aagcactaga ktttcacaat t                    21

<210> SEQ ID NO 2012
<211> LENGTH: 21
<212> TYPE: DNA
<213> ORGANISM: Homo sapiens

<400> SEQUENCE: 2012
gggagcctgg scctccaggt c                    21

<210> SEQ ID NO 2013
<211> LENGTH: 21
<212> TYPE: DNA
<213> ORGANISM: Homo sapiens

<400> SEQUENCE: 2013
aattgatcaa rtacctattg t                    21

<210> SEQ ID NO 2014
<211> LENGTH: 21
<212> TYPE: DNA
<213> ORGANISM: Homo sapiens

<400> SEQUENCE: 2014
ggagttcaag rtcctgttgg t                    21

<210> SEQ ID NO 2015
<211> LENGTH: 21
<212> TYPE: DNA
<213> ORGANISM: Homo sapiens

<400> SEQUENCE: 2015
gagatgtcct wtgacaataa t                    21

<210> SEQ ID NO 2016
<211> LENGTH: 21
<212> TYPE: DNA
<213> ORGANISM: Homo sapiens

<400> SEQUENCE: 2016
tcccctgaga ytccgtgggg c                                               21

<210> SEQ ID NO 2017
<211> LENGTH: 21
<212> TYPE: DNA
<213> ORGANISM: Homo sapiens

<400> SEQUENCE: 2017
caatggcgct ratggcccac a                                               21

<210> SEQ ID NO 2018
<211> LENGTH: 21
<212> TYPE: DNA
<213> ORGANISM: Homo sapiens

<400> SEQUENCE: 2018
gcctggctca racgacccc c                                                21

<210> SEQ ID NO 2019
<211> LENGTH: 21
<212> TYPE: DNA
<213> ORGANISM: Homo sapiens

<400> SEQUENCE: 2019
gcctctcctc ytgcagagac c                                               21

<210> SEQ ID NO 2020
<211> LENGTH: 21
<212> TYPE: DNA
<213> ORGANISM: Homo sapiens

<400> SEQUENCE: 2020
tgttggacaa raaatgacaa c                                               21

<210> SEQ ID NO 2021
<211> LENGTH: 21
<212> TYPE: DNA
<213> ORGANISM: Homo sapiens

<400> SEQUENCE: 2021
gcttgttgca wgctgtggca a                                               21

<210> SEQ ID NO 2022
<211> LENGTH: 21
<212> TYPE: DNA
<213> ORGANISM: Homo sapiens

<400> SEQUENCE: 2022
attccaccag mccgggatgt a                                               21

<210> SEQ ID NO 2023
<211> LENGTH: 21
<212> TYPE: DNA
<213> ORGANISM: Homo sapiens

<400> SEQUENCE: 2023
aagaagtaaa racattattt t                                               21

<210> SEQ ID NO 2024
<211> LENGTH: 21
<212> TYPE: DNA

<213> ORGANISM: Homo sapiens

<400> SEQUENCE: 2024
tggctcctat wgcattggga t                                              21

<210> SEQ ID NO 2025
<211> LENGTH: 21
<212> TYPE: DNA
<213> ORGANISM: Homo sapiens

<400> SEQUENCE: 2025
attacttgga ytcaagctcc a                                              21

<210> SEQ ID NO 2026
<211> LENGTH: 21
<212> TYPE: DNA
<213> ORGANISM: Homo sapiens

<400> SEQUENCE: 2026
cagataagat rgagaccatc t                                              21

<210> SEQ ID NO 2027
<211> LENGTH: 21
<212> TYPE: DNA
<213> ORGANISM: Homo sapiens

<400> SEQUENCE: 2027
gagcccatgg wagcctttgt t                                              21

<210> SEQ ID NO 2028
<211> LENGTH: 21
<212> TYPE: DNA
<213> ORGANISM: Homo sapiens

<400> SEQUENCE: 2028
ccaggatgag rtcaagaagg c                                              21

<210> SEQ ID NO 2029
<211> LENGTH: 21
<212> TYPE: DNA
<213> ORGANISM: Homo sapiens

<400> SEQUENCE: 2029
acctcggggg stgcctgggc c                                              21

<210> SEQ ID NO 2030
<211> LENGTH: 21
<212> TYPE: DNA
<213> ORGANISM: Homo sapiens

<400> SEQUENCE: 2030 tcggggctg yctgggcccc c                                               21

<210> SEQ ID NO 2031
<211> LENGTH: 21
<212> TYPE: DNA
<213> ORGANISM: Homo sapiens

<400> SEQUENCE: 2031 cccctggcc rtcctggaaa c                                               21

<210> SEQ ID NO 2032
<211> LENGTH: 21

```
<212> TYPE: DNA
<213> ORGANISM: Homo sapiens

<400> SEQUENCE: 2032
cagtatttgc macttacagc a                                          21

<210> SEQ ID NO 2033
<211> LENGTH: 21
<212> TYPE: DNA
<213> ORGANISM: Homo sapiens

<400> SEQUENCE: 2033
tgtgactgta sttcccgttt a                                          21

<210> SEQ ID NO 2034
<211> LENGTH: 21
<212> TYPE: DNA
<213> ORGANISM: Homo sapiens

<400> SEQUENCE: 2034
aggaaacaag kgctccatgg g                                          21

<210> SEQ ID NO 2035
<211> LENGTH: 21
<212> TYPE: DNA
<213> ORGANISM: Homo sapiens

<400> SEQUENCE: 2035
tccagggact ycagggaatg a                                          21

<210> SEQ ID NO 2036
<211> LENGTH: 21
<212> TYPE: DNA
<213> ORGANISM: Homo sapiens

<400> SEQUENCE: 2036
tgtgggtcca rgcagtgaag a                                          21

<210> SEQ ID NO 2037
<211> LENGTH: 21
<212> TYPE: DNA
<213> ORGANISM: Homo sapiens

<400> SEQUENCE: 2037
atattccaat rtactccttt g                                          21

<210> SEQ ID NO 2038
<211> LENGTH: 21
<212> TYPE: DNA
<213> ORGANISM: Homo sapiens

<400> SEQUENCE: 2038
ccatttgcaa katctgtcca c                                          21

<210> SEQ ID NO 2039
<211> LENGTH: 21
<212> TYPE: DNA
<213> ORGANISM: Homo sapiens

<400> SEQUENCE: 2039
ccagcagcac ycgtggtggc g                                          21

<210> SEQ ID NO 2040
```

```
<211> LENGTH: 21
<212> TYPE: DNA
<213> ORGANISM: Homo sapiens

<400> SEQUENCE: 2040
aaggcgacca rggagcccag g                                             21

<210> SEQ ID NO 2041
<211> LENGTH: 21
<212> TYPE: DNA
<213> ORGANISM: Homo sapiens

<400> SEQUENCE: 2041
ggcgaccagg ratttcaagg c                                             21

<210> SEQ ID NO 2042
<211> LENGTH: 21
<212> TYPE: DNA
<213> ORGANISM: Homo sapiens

<400> SEQUENCE: 2042
ccatgaaaac yatgaagggg c                                             21

<210> SEQ ID NO 2043
<211> LENGTH: 21
<212> TYPE: DNA
<213> ORGANISM: Homo sapiens

<400> SEQUENCE: 2043
ccaaaggtga maaagggggac a                                            21

<210> SEQ ID NO 2044
<211> LENGTH: 21
<212> TYPE: DNA
<213> ORGANISM: Homo sapiens

<400> SEQUENCE: 2044
gcccacgcga mgagtattcc c                                             21

<210> SEQ ID NO 2045
<211> LENGTH: 21
<212> TYPE: DNA
<213> ORGANISM: Homo sapiens

<400> SEQUENCE: 2045
ggggtctccc rgaggagttt g                                             21

<210> SEQ ID NO 2046
<211> LENGTH: 21
<212> TYPE: DNA
<213> ORGANISM: Homo sapiens

<400> SEQUENCE: 2046
ctcatgaaga mgtctgccat c                                             21

<210> SEQ ID NO 2047
<211> LENGTH: 21
<212> TYPE: DNA
<213> ORGANISM: Homo sapiens

<400> SEQUENCE: 2047
cctggtcctc ygggattgcc a                                             21
```

<210> SEQ ID NO 2048
<211> LENGTH: 21
<212> TYPE: DNA
<213> ORGANISM: Homo sapiens

<400> SEQUENCE: 2048
tcctggctgt kttgggagcc c                                    21

<210> SEQ ID NO 2049
<211> LENGTH: 21
<212> TYPE: DNA
<213> ORGANISM: Homo sapiens

<400> SEQUENCE: 2049
acctcatcca ycgactcagc c                                    21

<210> SEQ ID NO 2050
<211> LENGTH: 21
<212> TYPE: DNA
<213> ORGANISM: Homo sapiens

<400> SEQUENCE: 2050
acaggcgaga rgggccagaa a                                    21

<210> SEQ ID NO 2051
<211> LENGTH: 21
<212> TYPE: DNA
<213> ORGANISM: Homo sapiens

<400> SEQUENCE: 2051
gtcaggagct ytgggaccct c                                    21

<210> SEQ ID NO 2052
<211> LENGTH: 21
<212> TYPE: DNA
<213> ORGANISM: Homo sapiens

<400> SEQUENCE: 2052
tcctggtgaa saaggtccct c                                    21

<210> SEQ ID NO 2053
<211> LENGTH: 21
<212> TYPE: DNA
<213> ORGANISM: Homo sapiens

<400> SEQUENCE: 2053
atgaggagac yggcaacctg a                                    21

<210> SEQ ID NO 2054
<211> LENGTH: 21
<212> TYPE: DNA
<213> ORGANISM: Homo sapiens

<400> SEQUENCE: 2054
ggtgcaatcg rcagtccagg a                                    21

<210> SEQ ID NO 2055
<211> LENGTH: 21
<212> TYPE: DNA
<213> ORGANISM: Homo sapiens

<400> SEQUENCE: 2055
ggtgtcaagg rtgaaagtgg g                                    21

<210> SEQ ID NO 2056
<211> LENGTH: 21
<212> TYPE: DNA
<213> ORGANISM: Homo sapiens

<400> SEQUENCE: 2056
tcttggtcag ycctatgcgg a                                              21

<210> SEQ ID NO 2057
<211> LENGTH: 21
<212> TYPE: DNA
<213> ORGANISM: Homo sapiens

<400> SEQUENCE: 2057
ctggacctca rggaccccca g                                              21

<210> SEQ ID NO 2058
<211> LENGTH: 21
<212> TYPE: DNA
<213> ORGANISM: Homo sapiens

<400> SEQUENCE: 2058
tagaggtgga rctggtcccc c                                              21

<210> SEQ ID NO 2059
<211> LENGTH: 21
<212> TYPE: DNA
<213> ORGANISM: Homo sapiens

<400> SEQUENCE: 2059
gggattggag rtgaaaaagc t                                              21

<210> SEQ ID NO 2060
<211> LENGTH: 21
<212> TYPE: DNA
<213> ORGANISM: Homo sapiens

<400> SEQUENCE: 2060
gagattggcg ygactggtga t                                              21

<210> SEQ ID NO 2061
<211> LENGTH: 21
<212> TYPE: DNA
<213> ORGANISM: Homo sapiens

<400> SEQUENCE: 2061
ctcgtggaaa raaaggtccc c                                              21

<210> SEQ ID NO 2062
<211> LENGTH: 21
<212> TYPE: DNA
<213> ORGANISM: Homo sapiens

<400> SEQUENCE: 2062
gaaaggacca rtgggattcc c                                              21

<210> SEQ ID NO 2063
<211> LENGTH: 21
<212> TYPE: DNA
<213> ORGANISM: Homo sapiens

<400> SEQUENCE: 2063
atgatgtggg rccacctggt c                                              21

<210> SEQ ID NO 2064
<211> LENGTH: 21
<212> TYPE: DNA
<213> ORGANISM: Homo sapiens

<400> SEQUENCE: 2064
accaggaaag matggtgcct c                    21

<210> SEQ ID NO 2065
<211> LENGTH: 21
<212> TYPE: DNA
<213> ORGANISM: Homo sapiens

<400> SEQUENCE: 2065
ctgtttgcca ytgtgttcct g                    21

<210> SEQ ID NO 2066
<211> LENGTH: 21
<212> TYPE: DNA
<213> ORGANISM: Homo sapiens

<400> SEQUENCE: 2066
tccaggggat satgaagatg c                    21

<210> SEQ ID NO 2067
<211> LENGTH: 21
<212> TYPE: DNA
<213> ORGANISM: Homo sapiens

<400> SEQUENCE: 2067
gccttcccgt rtttagcacg c                    21

<210> SEQ ID NO 2068
<211> LENGTH: 21
<212> TYPE: DNA
<213> ORGANISM: Homo sapiens

<400> SEQUENCE: 2068
ctggaccacc rgggtgccca g                    21

<210> SEQ ID NO 2069
<211> LENGTH: 21
<212> TYPE: DNA
<213> ORGANISM: Homo sapiens

<400> SEQUENCE: 2069
ggagcatccg sagagcaggg c                    21

<210> SEQ ID NO 2070
<211> LENGTH: 21
<212> TYPE: DNA
<213> ORGANISM: Homo sapiens

<400> SEQUENCE: 2070
ctggtcttcc rggtcccaga g                    21

<210> SEQ ID NO 2071
<211> LENGTH: 21
<212> TYPE: DNA
<213> ORGANISM: Homo sapiens

<400> SEQUENCE: 2071

```
gccactttt mgcaaataag t                                              21

<210> SEQ ID NO 2072
<211> LENGTH: 21
<212> TYPE: DNA
<213> ORGANISM: Homo sapiens

<400> SEQUENCE: 2072
gacttgcctg ygatgtggtc t                                             21

<210> SEQ ID NO 2073
<211> LENGTH: 21
<212> TYPE: DNA
<213> ORGANISM: Homo sapiens

<400> SEQUENCE: 2073
ttcaaggttt wctgcaactt c                                             21

<210> SEQ ID NO 2074
<211> LENGTH: 21
<212> TYPE: DNA
<213> ORGANISM: Homo sapiens

<400> SEQUENCE: 2074
aacagggtat yactggtcct t                                             21

<210> SEQ ID NO 2075
<211> LENGTH: 21
<212> TYPE: DNA
<213> ORGANISM: Homo sapiens

<400> SEQUENCE: 2075
tcggtcctcc sggtgaacag g                                             21

<210> SEQ ID NO 2076
<211> LENGTH: 21
<212> TYPE: DNA
<213> ORGANISM: Homo sapiens

<400> SEQUENCE: 2076
acggcctggc wgggttgcca g                                             21

<210> SEQ ID NO 2077
<211> LENGTH: 21
<212> TYPE: DNA
<213> ORGANISM: Homo sapiens

<400> SEQUENCE: 2077
gtgaccctgg yccttccggc c                                             21

<210> SEQ ID NO 2078
<211> LENGTH: 21
<212> TYPE: DNA
<213> ORGANISM: Homo sapiens

<400> SEQUENCE: 2078
cgggcagaaa rgtgatgaag g                                             21

<210> SEQ ID NO 2079
<211> LENGTH: 21
<212> TYPE: DNA
<213> ORGANISM: Homo sapiens

<400> SEQUENCE: 2079
```

```
atggactgga rccagatact g                                              21

<210> SEQ ID NO 2080
<211> LENGTH: 21
<212> TYPE: DNA
<213> ORGANISM: Homo sapiens

<400> SEQUENCE: 2080
tatcctggcg rccactcaga g                                              21

<210> SEQ ID NO 2081
<211> LENGTH: 21
<212> TYPE: DNA
<213> ORGANISM: Homo sapiens

<400> SEQUENCE: 2081
gactcggtga ytttggcctg g                                              21

<210> SEQ ID NO 2082
<211> LENGTH: 21
<212> TYPE: DNA
<213> ORGANISM: Homo sapiens

<400> SEQUENCE: 2082
cggactatga kgtgaccgtg a                                              21

<210> SEQ ID NO 2083
<211> LENGTH: 21
<212> TYPE: DNA
<213> ORGANISM: Homo sapiens

<400> SEQUENCE: 2083
ccaagtgact ktgattgccc t                                              21

<210> SEQ ID NO 2084
<211> LENGTH: 21
<212> TYPE: DNA
<213> ORGANISM: Homo sapiens

<400> SEQUENCE: 2084
cgccgggagc yggaaactcc a                                              21

<210> SEQ ID NO 2085
<211> LENGTH: 21
<212> TYPE: DNA
<213> ORGANISM: Homo sapiens

<400> SEQUENCE: 2085
gcttagctac wctgtgcggg t                                              21

<210> SEQ ID NO 2086
<211> LENGTH: 21
<212> TYPE: DNA
<213> ORGANISM: Homo sapiens

<400> SEQUENCE: 2086
tgtccgccgg ragccggaaa c                                              21

<210> SEQ ID NO 2087
<211> LENGTH: 21
<212> TYPE: DNA
<213> ORGANISM: Homo sapiens
```

<400> SEQUENCE: 2087
gggccctgct rcagtcatcg t                                              21

<210> SEQ ID NO 2088
<211> LENGTH: 21
<212> TYPE: DNA
<213> ORGANISM: Homo sapiens

<400> SEQUENCE: 2088
gagccagata ytgagtatac g                                              21

<210> SEQ ID NO 2089
<211> LENGTH: 21
<212> TYPE: DNA
<213> ORGANISM: Homo sapiens

<400> SEQUENCE: 2089
tcatctgtca ycattacctg g                                              21

<210> SEQ ID NO 2090
<211> LENGTH: 21
<212> TYPE: DNA
<213> ORGANISM: Homo sapiens

<400> SEQUENCE: 2090
accaggagag ygtggtatgg c                                              21

<210> SEQ ID NO 2091
<211> LENGTH: 21
<212> TYPE: DNA
<213> ORGANISM: Homo sapiens

<400> SEQUENCE: 2091
gggtgaccga kgctttgacg g                                              21

<210> SEQ ID NO 2092
<211> LENGTH: 21
<212> TYPE: DNA
<213> ORGANISM: Homo sapiens

<400> SEQUENCE: 2092
cgccatccgt ragcttagct a                                              21

<210> SEQ ID NO 2093
<211> LENGTH: 21
<212> TYPE: DNA
<213> ORGANISM: Homo sapiens

<400> SEQUENCE: 2093
aggatccgtg wcatgcccta c                                              21

<210> SEQ ID NO 2094
<211> LENGTH: 21
<212> TYPE: DNA
<213> ORGANISM: Homo sapiens

<400> SEQUENCE: 2094
acggagaacc ygggggaccct g                                             21

<210> SEQ ID NO 2095
<211> LENGTH: 21
<212> TYPE: DNA
<213> ORGANISM: Homo sapiens -continued

<400> SEQUENCE: 2095
tgccagggcc scgaggcgag a                                              21

<210> SEQ ID NO 2096
<211> LENGTH: 21
<212> TYPE: DNA
<213> ORGANISM: Homo sapiens

<400> SEQUENCE: 2096
gcttggatgg ygacaaagga c                                              21

<210> SEQ ID NO 2097
<211> LENGTH: 21
<212> TYPE: DNA
<213> ORGANISM: Homo sapiens

<400> SEQUENCE: 2097
accgtggttc ycactggacc a                                              21

<210> SEQ ID NO 2098
<211> LENGTH: 21
<212> TYPE: DNA
<213> ORGANISM: Homo sapiens

<400> SEQUENCE: 2098
tcctagggcc rgctggagaa g                                              21

<210> SEQ ID NO 2099
<211> LENGTH: 21
<212> TYPE: DNA
<213> ORGANISM: Homo sapiens

<400> SEQUENCE: 2099
ccagggagat yctggagagg a                                              21

<210> SEQ ID NO 2100
<211> LENGTH: 21
<212> TYPE: DNA
<213> ORGANISM: Homo sapiens

<400> SEQUENCE: 2100
atcttgcaaa rgatccgtga c                                              21

<210> SEQ ID NO 2101
<211> LENGTH: 21
<212> TYPE: DNA
<213> ORGANISM: Homo sapiens

<400> SEQUENCE: 2101
atgggcaagg ragccgttcc c                                              21

<210> SEQ ID NO 2102
<211> LENGTH: 21
<212> TYPE: DNA
<213> ORGANISM: Homo sapiens

<400> SEQUENCE: 2102
caggcgggac rgcccggaag t                                              21

<210> SEQ ID NO 2103
<211> LENGTH: 21
<212> TYPE: DNA

```
<213> ORGANISM: Homo sapiens

<400> SEQUENCE: 2103
aagggagaga ygggccctca t                                              21

<210> SEQ ID NO 2104
<211> LENGTH: 21
<212> TYPE: DNA
<213> ORGANISM: Homo sapiens

<400> SEQUENCE: 2104
aagtgggtga yccaggggtg g                                              21

<210> SEQ ID NO 2105
<211> LENGTH: 21
<212> TYPE: DNA
<213> ORGANISM: Homo sapiens

<400> SEQUENCE: 2105
ccaccagggc stagcgggtg t                                              21

<210> SEQ ID NO 2106
<211> LENGTH: 10
<212> TYPE: DNA
<213> ORGANISM: Homo sapiens

<400> SEQUENCE: 2106 tgctccctgk                                                           10

<210> SEQ ID NO 2107
<211> LENGTH: 21
<212> TYPE: DNA
<213> ORGANISM: Homo sapiens

<400> SEQUENCE: 2107
atggagagct raagtccaag a                                              21

<210> SEQ ID NO 2108
<211> LENGTH: 21
<212> TYPE: DNA
<213> ORGANISM: Homo sapiens

<400> SEQUENCE: 2108
gcgccgaggg rccaaatgag a                                              21

<210> SEQ ID NO 2109
<211> LENGTH: 21
<212> TYPE: DNA
<213> ORGANISM: Homo sapiens

<400> SEQUENCE: 2109
tgctgaagtt rtggaaacat c                                              21

<210> SEQ ID NO 2110
<211> LENGTH: 21
<212> TYPE: DNA
<213> ORGANISM: Homo sapiens

<400> SEQUENCE: 2110
gtatcagaag ytatttttag a                                              21

<210> SEQ ID NO 2111
<211> LENGTH: 21
```

```
<212> TYPE: DNA
<213> ORGANISM: Homo sapiens

<400> SEQUENCE: 2111
ccctggagac mctcgagacc a                                              21

<210> SEQ ID NO 2112
<211> LENGTH: 21
<212> TYPE: DNA
<213> ORGANISM: Homo sapiens

<400> SEQUENCE: 2112
ctcagcaaga rgccctgcct g                                              21

<210> SEQ ID NO 2113
<211> LENGTH: 21
<212> TYPE: DNA
<213> ORGANISM: Homo sapiens

<400> SEQUENCE: 2113
ccttcaggga yggaggcaat g                                              21

<210> SEQ ID NO 2114
<211> LENGTH: 21
<212> TYPE: DNA
<213> ORGANISM: Homo sapiens

<400> SEQUENCE: 2114
ccgcgctgat ygaggccatc c                                              21

<210> SEQ ID NO 2115
<211> LENGTH: 21
<212> TYPE: DNA
<213> ORGANISM: Homo sapiens

<400> SEQUENCE: 2115
ttgaccggaa ygtgccccgg a                                              21

<210> SEQ ID NO 2116
<211> LENGTH: 21
<212> TYPE: DNA
<213> ORGANISM: Homo sapiens

<400> SEQUENCE: 2116
atcacctcac wcatggaaag c                                              21

<210> SEQ ID NO 2117
<211> LENGTH: 21
<212> TYPE: DNA
<213> ORGANISM: Homo sapiens

<400> SEQUENCE: 2117
aagatgatga rgaccatgtg g                                              21

<210> SEQ ID NO 2118
<211> LENGTH: 21
<212> TYPE: DNA
<213> ORGANISM: Homo sapiens

<400> SEQUENCE: 2118
ccattgactc raacgactct g                                              21

<210> SEQ ID NO 2119
```

-continued

```
<211> LENGTH: 21
<212> TYPE: DNA
<213> ORGANISM: Homo sapiens

<400> SEQUENCE: 2119
taaacaggct rattctggaa g                                              21

<210> SEQ ID NO 2120
<211> LENGTH: 21
<212> TYPE: DNA
<213> ORGANISM: Homo sapiens

<400> SEQUENCE: 2120
ccaggacctg macgcgcctt c                                              21

<210> SEQ ID NO 2121
<211> LENGTH: 21
<212> TYPE: DNA
<213> ORGANISM: Homo sapiens

<400> SEQUENCE: 2121
catacaaggc matcccgtt g                                               21

<210> SEQ ID NO 2122
<211> LENGTH: 21
<212> TYPE: DNA
<213> ORGANISM: Homo sapiens

<400> SEQUENCE: 2122
gacagcagtc sggatgccgc c                                              21

<210> SEQ ID NO 2123
<211> LENGTH: 21
<212> TYPE: DNA
<213> ORGANISM: Homo sapiens

<400> SEQUENCE: 2123
cggccattga rgcagagctg g                                              21

<210> SEQ ID NO 2124
<211> LENGTH: 21
<212> TYPE: DNA
<213> ORGANISM: Homo sapiens

<400> SEQUENCE: 2124
ggacaaccgg racagttcca t                                              21

<210> SEQ ID NO 2125
<211> LENGTH: 21
<212> TYPE: DNA
<213> ORGANISM: Homo sapiens

<400> SEQUENCE: 2125
gtacaatgcc rtgtccaacg c                                              21

<210> SEQ ID NO 2126
<211> LENGTH: 21
<212> TYPE: DNA
<213> ORGANISM: Homo sapiens

<400> SEQUENCE: 2126
cagttcctcc rcctgtcctc t                                              21
```

<210> SEQ ID NO 2127
<211> LENGTH: 21
<212> TYPE: DNA
<213> ORGANISM: Homo sapiens

<400> SEQUENCE: 2127
cctgcaggcc mccaacatct t					21

<210> SEQ ID NO 2128
<211> LENGTH: 21
<212> TYPE: DNA
<213> ORGANISM: Homo sapiens

<400> SEQUENCE: 2128
gaactgaatt yggcctgaag t					21

<210> SEQ ID NO 2129
<211> LENGTH: 21
<212> TYPE: DNA
<213> ORGANISM: Homo sapiens

<400> SEQUENCE: 2129
tcatcgactt ygtgtggatc a					21

<210> SEQ ID NO 2130
<211> LENGTH: 21
<212> TYPE: DNA
<213> ORGANISM: Homo sapiens

<400> SEQUENCE: 2130
aagcagctca scatcagaaa a					21

<210> SEQ ID NO 2131
<211> LENGTH: 21
<212> TYPE: DNA
<213> ORGANISM: Homo sapiens

<400> SEQUENCE: 2131
gatgcttcac sagcagaggt c					21

<210> SEQ ID NO 2132
<211> LENGTH: 21
<212> TYPE: DNA
<213> ORGANISM: Homo sapiens

<400> SEQUENCE: 2132
acctgcattg kcatgtgcaa g					21

<210> SEQ ID NO 2133
<211> LENGTH: 21
<212> TYPE: DNA
<213> ORGANISM: Homo sapiens

<400> SEQUENCE: 2133
cgggaaccca ygtcggccga g					21

<210> SEQ ID NO 2134
<211> LENGTH: 21
<212> TYPE: DNA
<213> ORGANISM: Homo sapiens

<400> SEQUENCE: 2134
cctctttgag ygtcactggc a					21

<210> SEQ ID NO 2135
<211> LENGTH: 21
<212> TYPE: DNA
<213> ORGANISM: Homo sapiens

<400> SEQUENCE: 2135
atggcgtctg racagctcag c                                              21

<210> SEQ ID NO 2136
<211> LENGTH: 21
<212> TYPE: DNA
<213> ORGANISM: Homo sapiens

<400> SEQUENCE: 2136
cgtggaggtg sagctgctac a                                              21

<210> SEQ ID NO 2137
<211> LENGTH: 21
<212> TYPE: DNA
<213> ORGANISM: Homo sapiens

<400> SEQUENCE: 2137
taggagctgg yttgctaatg g                                              21

<210> SEQ ID NO 2138
<211> LENGTH: 21
<212> TYPE: DNA
<213> ORGANISM: Homo sapiens

<400> SEQUENCE: 2138
agaagaaagt raccttggaa a                                              21

<210> SEQ ID NO 2139
<211> LENGTH: 21
<212> TYPE: DNA
<213> ORGANISM: Homo sapiens

<400> SEQUENCE: 2139
caaatcatca kgtggcctag a                                              21

<210> SEQ ID NO 2140
<211> LENGTH: 21
<212> TYPE: DNA
<213> ORGANISM: Homo sapiens

<400> SEQUENCE: 2140
gaagattcca ycagatccca t                                              21

<210> SEQ ID NO 2141
<211> LENGTH: 21
<212> TYPE: DNA
<213> ORGANISM: Homo sapiens

<400> SEQUENCE: 2141
ctgggccctt ycctgatgaa c                                              21

<210> SEQ ID NO 2142
<211> LENGTH: 21
<212> TYPE: DNA
<213> ORGANISM: Homo sapiens

<400> SEQUENCE: 2142
tgccatcact yctgctgttg g                                              21

<210> SEQ ID NO 2143
<211> LENGTH: 21
<212> TYPE: DNA
<213> ORGANISM: Homo sapiens

<400> SEQUENCE: 2143
tgtttgaact yaaacatatg a                                              21

<210> SEQ ID NO 2144
<211> LENGTH: 21
<212> TYPE: DNA
<213> ORGANISM: Homo sapiens

<400> SEQUENCE: 2144
ccccgttact ktctctttgg g                                              21

<210> SEQ ID NO 2145
<211> LENGTH: 21
<212> TYPE: DNA
<213> ORGANISM: Homo sapiens

<400> SEQUENCE: 2145
gagcgccaag ygctcatgct c                                              21

<210> SEQ ID NO 2146
<211> LENGTH: 21
<212> TYPE: DNA
<213> ORGANISM: Homo sapiens

<400> SEQUENCE: 2146
gtccccgtgg ragcctgcag g                                              21

<210> SEQ ID NO 2147
<211> LENGTH: 21
<212> TYPE: DNA
<213> ORGANISM: Homo sapiens

<400> SEQUENCE: 2147
gctggcacaa rgctgcgggc a                                              21

<210> SEQ ID NO 2148
<211> LENGTH: 21
<212> TYPE: DNA
<213> ORGANISM: Homo sapiens

<400> SEQUENCE: 2148
tgatggccac rtcccggaaa t                                              21

<210> SEQ ID NO 2149
<211> LENGTH: 21
<212> TYPE: DNA
<213> ORGANISM: Homo sapiens

<400> SEQUENCE: 2149
cccactgcac magtgtgaca t                                              21

<210> SEQ ID NO 2150
<211> LENGTH: 21
<212> TYPE: DNA
<213> ORGANISM: Homo sapiens

<400> SEQUENCE: 2150

```
tcccccttcag ytacctcgtc g                                      21

<210> SEQ ID NO 2151
<211> LENGTH: 21
<212> TYPE: DNA
<213> ORGANISM: Homo sapiens

<400> SEQUENCE: 2151
tcaggtactt ygtcagcttc a                                       21

<210> SEQ ID NO 2152
<211> LENGTH: 21
<212> TYPE: DNA
<213> ORGANISM: Homo sapiens

<400> SEQUENCE: 2152
agcccctcta yctgaacctc c                                       21

<210> SEQ ID NO 2153
<211> LENGTH: 21
<212> TYPE: DNA
<213> ORGANISM: Homo sapiens

<400> SEQUENCE: 2153
tcagcagcag ygtgtcctca g                                       21

<210> SEQ ID NO 2154
<211> LENGTH: 21
<212> TYPE: DNA
<213> ORGANISM: Homo sapiens

<400> SEQUENCE: 2154
cctttgtgct rctcatgttg c                                       21

<210> SEQ ID NO 2155
<211> LENGTH: 21
<212> TYPE: DNA
<213> ORGANISM: Homo sapiens

<400> SEQUENCE: 2155
ctagcaagat ygactttgtg c                                       21

<210> SEQ ID NO 2156
<211> LENGTH: 21
<212> TYPE: DNA
<213> ORGANISM: Homo sapiens

<400> SEQUENCE: 2156
tcgtcatcct sgcctgggcc a                                       21

<210> SEQ ID NO 2157
<211> LENGTH: 21
<212> TYPE: DNA
<213> ORGANISM: Homo sapiens

<400> SEQUENCE: 2157
tgtttgggag yggcctgcct g                                       21

<210> SEQ ID NO 2158
<211> LENGTH: 21
<212> TYPE: DNA
<213> ORGANISM: Homo sapiens

<400> SEQUENCE: 2158
```
ccttgttctc yggtatcggc t                                21

<210> SEQ ID NO 2159
<211> LENGTH: 21
<212> TYPE: DNA
<213> ORGANISM: Homo sapiens

<400> SEQUENCE: 2159
tagaagacct yatcaaacct c                                21

<210> SEQ ID NO 2160
<211> LENGTH: 21
<212> TYPE: DNA
<213> ORGANISM: Homo sapiens

<400> SEQUENCE: 2160
gattgttgtg stgggacctc g                                21

<210> SEQ ID NO 2161
<211> LENGTH: 21
<212> TYPE: DNA
<213> ORGANISM: Homo sapiens

<400> SEQUENCE: 2161
ggcttttcct rgcctgtgct t                                21

<210> SEQ ID NO 2162
<211> LENGTH: 21
<212> TYPE: DNA
<213> ORGANISM: Homo sapiens

<400> SEQUENCE: 2162
atacaatatc rgccagcctg g                                21

<210> SEQ ID NO 2163
<211> LENGTH: 21
<212> TYPE: DNA
<213> ORGANISM: Homo sapiens

<400> SEQUENCE: 2163
ctgagctggg yaagccgcgg c                                21

<210> SEQ ID NO 2164
<211> LENGTH: 21
<212> TYPE: DNA
<213> ORGANISM: Homo sapiens

<400> SEQUENCE: 2164
agagccccct racctatgag g                                21

<210> SEQ ID NO 2165
<211> LENGTH: 21
<212> TYPE: DNA
<213> ORGANISM: Homo sapiens

<400> SEQUENCE: 2165
ctcgtgagat ygccaagtcc c                                21

<210> SEQ ID NO 2166
<211> LENGTH: 21
<212> TYPE: DNA
<213> ORGANISM: Homo sapiens

```
<400> SEQUENCE: 2166
atctcgtctc ygaagacatc t                                              21

<210> SEQ ID NO 2167
<211> LENGTH: 21
<212> TYPE: DNA
<213> ORGANISM: Homo sapiens

<400> SEQUENCE: 2167
atgtgaacga yggtgcgatg c                                              21

<210> SEQ ID NO 2168
<211> LENGTH: 21
<212> TYPE: DNA
<213> ORGANISM: Homo sapiens

<400> SEQUENCE: 2168
gtatctcaat ktgttcatcc c                                              21

<210> SEQ ID NO 2169
<211> LENGTH: 21
<212> TYPE: DNA
<213> ORGANISM: Homo sapiens

<400> SEQUENCE: 2169
atgggcctcc ygagcaggtc t                                              21

<210> SEQ ID NO 2170
<211> LENGTH: 21
<212> TYPE: DNA
<213> ORGANISM: Homo sapiens

<400> SEQUENCE: 2170
aggatgtcca rtgcttttcc g                                              21

<210> SEQ ID NO 2171
<211> LENGTH: 21
<212> TYPE: DNA
<213> ORGANISM: Homo sapiens

<400> SEQUENCE: 2171
ctagtggtat sccagcaact a                                              21

<210> SEQ ID NO 2172
<211> LENGTH: 21
<212> TYPE: DNA
<213> ORGANISM: Homo sapiens

<400> SEQUENCE: 2172
gcctggcagt ragctggaca a                                              21

<210> SEQ ID NO 2173
<211> LENGTH: 21
<212> TYPE: DNA
<213> ORGANISM: Homo sapiens

<400> SEQUENCE: 2173
ctctgaggcc yggagtacca a                                              21

<210> SEQ ID NO 2174
<211> LENGTH: 21
<212> TYPE: DNA
<213> ORGANISM: Homo sapiens
```

```
<400> SEQUENCE: 2174
ccaacgactc yggcccccgc c                                              21

<210> SEQ ID NO 2175
<211> LENGTH: 21
<212> TYPE: DNA
<213> ORGANISM: Homo sapiens

<400> SEQUENCE: 2175
gaaaattata yttagaacga g                                              21

<210> SEQ ID NO 2176
<211> LENGTH: 21
<212> TYPE: DNA
<213> ORGANISM: Homo sapiens

<400> SEQUENCE: 2176
cagctggaac rtgaagaggg c                                              21

<210> SEQ ID NO 2177
<211> LENGTH: 21
<212> TYPE: DNA
<213> ORGANISM: Homo sapiens

<400> SEQUENCE: 2177
ggaagctttt saaagaatgt t                                              21

<210> SEQ ID NO 2178
<211> LENGTH: 21
<212> TYPE: DNA
<213> ORGANISM: Homo sapiens

<400> SEQUENCE: 2178
gcgtgtgcac rgaagctggc a                                              21

<210> SEQ ID NO 2179
<211> LENGTH: 21
<212> TYPE: DNA
<213> ORGANISM: Homo sapiens

<400> SEQUENCE: 2179
ctcacggagg rttccccaac a                                              21

<210> SEQ ID NO 2180
<211> LENGTH: 21
<212> TYPE: DNA
<213> ORGANISM: Homo sapiens

<400> SEQUENCE: 2180
ggttgtgatc ytagggaaac a                                              21

<210> SEQ ID NO 2181
<211> LENGTH: 21
<212> TYPE: DNA
<213> ORGANISM: Homo sapiens

<400> SEQUENCE: 2181
gctactggaa ygagtatgaa a                                              21

<210> SEQ ID NO 2182
<211> LENGTH: 21
<212> TYPE: DNA
```

<213> ORGANISM: Homo sapiens

<400> SEQUENCE: 2182
tcttttccta rtcagcaggt t    21

<210> SEQ ID NO 2183
<211> LENGTH: 21
<212> TYPE: DNA
<213> ORGANISM: Homo sapiens

<400> SEQUENCE: 2183
gctacaacgt rtatggaaca g    21

<210> SEQ ID NO 2184
<211> LENGTH: 21
<212> TYPE: DNA
<213> ORGANISM: Homo sapiens

<400> SEQUENCE: 2184
ctcagcatta rgaacgcctg t    21

<210> SEQ ID NO 2185
<211> LENGTH: 21
<212> TYPE: DNA
<213> ORGANISM: Homo sapiens

<400> SEQUENCE: 2185
tgcagacgac raccatgtgc a    21

<210> SEQ ID NO 2186
<211> LENGTH: 21
<212> TYPE: DNA
<213> ORGANISM: Homo sapiens

<400> SEQUENCE: 2186
cacagactgc rcctcaacag g    21

<210> SEQ ID NO 2187
<211> LENGTH: 21
<212> TYPE: DNA
<213> ORGANISM: Homo sapiens

<400> SEQUENCE: 2187
gtggtcttgg sctgtttgtt t    21

<210> SEQ ID NO 2188
<211> LENGTH: 21
<212> TYPE: DNA
<213> ORGANISM: Homo sapiens

<400> SEQUENCE: 2188
atcctgtttc raccccagaa g    21

<210> SEQ ID NO 2189
<211> LENGTH: 21
<212> TYPE: DNA
<213> ORGANISM: Homo sapiens

<400> SEQUENCE: 2189
acacccttgg ycaaagcatc g    21

<210> SEQ ID NO 2190
<211> LENGTH: 21

<212> TYPE: DNA
<213> ORGANISM: Homo sapiens

<400> SEQUENCE: 2190
ccctgctgac yaagacaaac t								21

<210> SEQ ID NO 2191
<211> LENGTH: 21
<212> TYPE: DNA
<213> ORGANISM: Homo sapiens

<400> SEQUENCE: 2191
gcgccaatgc ytccttcacc t								21

<210> SEQ ID NO 2192
<211> LENGTH: 21
<212> TYPE: DNA
<213> ORGANISM: Homo sapiens

<400> SEQUENCE: 2192
caacaaatgc ytggaactgg c								21

<210> SEQ ID NO 2193
<211> LENGTH: 21
<212> TYPE: DNA
<213> ORGANISM: Homo sapiens

<400> SEQUENCE: 2193
agggtatact ycaaggatgc a								21

<210> SEQ ID NO 2194
<211> LENGTH: 21
<212> TYPE: DNA
<213> ORGANISM: Homo sapiens

<400> SEQUENCE: 2194
gcgtggccca yggatgcacc a								21

<210> SEQ ID NO 2195
<211> LENGTH: 21
<212> TYPE: DNA
<213> ORGANISM: Homo sapiens

<400> SEQUENCE: 2195
agctgatggc rtcttcgacc c								21

<210> SEQ ID NO 2196
<211> LENGTH: 21
<212> TYPE: DNA
<213> ORGANISM: Homo sapiens

<400> SEQUENCE: 2196
cctcatggaa yaaataacac t								21

<210> SEQ ID NO 2197
<211> LENGTH: 21
<212> TYPE: DNA
<213> ORGANISM: Homo sapiens

<400> SEQUENCE: 2197
tttacctgct rgcggtgctg g								21

<210> SEQ ID NO 2198

```
<211> LENGTH: 21
<212> TYPE: DNA
<213> ORGANISM: Homo sapiens

<400> SEQUENCE: 2198
ctgggcctgg rgggtggagg t                                              21

<210> SEQ ID NO 2199
<211> LENGTH: 21
<212> TYPE: DNA
<213> ORGANISM: Homo sapiens

<400> SEQUENCE: 2199
tcactgatgg kcacataaaa g                                              21

<210> SEQ ID NO 2200
<211> LENGTH: 21
<212> TYPE: DNA
<213> ORGANISM: Homo sapiens

<400> SEQUENCE: 2200
gcaagccact sgaggttaat t                                              21

<210> SEQ ID NO 2201
<211> LENGTH: 21
<212> TYPE: DNA
<213> ORGANISM: Homo sapiens

<400> SEQUENCE: 2201
acactacccg ragaattggt c                                              21

<210> SEQ ID NO 2202
<211> LENGTH: 21
<212> TYPE: DNA
<213> ORGANISM: Homo sapiens

<400> SEQUENCE: 2202
accaaaatca rtgatggcca g                                              21

<210> SEQ ID NO 2203
<211> LENGTH: 21
<212> TYPE: DNA
<213> ORGANISM: Homo sapiens

<400> SEQUENCE: 2203
ctctgtgact rcttcctccc t                                              21

<210> SEQ ID NO 2204
<211> LENGTH: 21
<212> TYPE: DNA
<213> ORGANISM: Homo sapiens

<400> SEQUENCE: 2204
gtcagtcctc rggtggaaga t                                              21

<210> SEQ ID NO 2205
<211> LENGTH: 21
<212> TYPE: DNA
<213> ORGANISM: Homo sapiens

<400> SEQUENCE: 2205
tgtgagagcc ytggatggac c                                              21
```

<210> SEQ ID NO 2206
<211> LENGTH: 21
<212> TYPE: DNA
<213> ORGANISM: Homo sapiens

<400> SEQUENCE: 2206
aagtaacagc rgtgttgcca a                                              21

<210> SEQ ID NO 2207
<211> LENGTH: 21
<212> TYPE: DNA
<213> ORGANISM: Homo sapiens

<400> SEQUENCE: 2207
ggcgaggaac yctacatcat c                                              21

<210> SEQ ID NO 2208
<211> LENGTH: 21
<212> TYPE: DNA
<213> ORGANISM: Homo sapiens

<400> SEQUENCE: 2208
gccgtcaggg matctcccct a                                              21

<210> SEQ ID NO 2209
<211> LENGTH: 21
<212> TYPE: DNA
<213> ORGANISM: Homo sapiens

<400> SEQUENCE: 2209
ttggagttcc rgccatgtct a                                              21

<210> SEQ ID NO 2210
<211> LENGTH: 21
<212> TYPE: DNA
<213> ORGANISM: Homo sapiens

<400> SEQUENCE: 2210
tgaccttcgc ygaggcccag g                                              21

<210> SEQ ID NO 2211
<211> LENGTH: 21
<212> TYPE: DNA
<213> ORGANISM: Homo sapiens

<400> SEQUENCE: 2211
gaggtgacag rtgttgtgtt c                                              21

<210> SEQ ID NO 2212
<211> LENGTH: 21
<212> TYPE: DNA
<213> ORGANISM: Homo sapiens

<400> SEQUENCE: 2212
acaggatatc rccgatgcca g                                              21

<210> SEQ ID NO 2213
<211> LENGTH: 21
<212> TYPE: DNA
<213> ORGANISM: Homo sapiens

<400> SEQUENCE: 2213
agcgcagccc sagatgcccc t                                              21

<210> SEQ ID NO 2214
<211> LENGTH: 21
<212> TYPE: DNA
<213> ORGANISM: Homo sapiens

<400> SEQUENCE: 2214
gctttgcccg rgagctgggg g                                      21

<210> SEQ ID NO 2215
<211> LENGTH: 21
<212> TYPE: DNA
<213> ORGANISM: Homo sapiens

<400> SEQUENCE: 2215
acattgatga ytgcctctgc a                                      21

<210> SEQ ID NO 2216
<211> LENGTH: 21
<212> TYPE: DNA
<213> ORGANISM: Homo sapiens

<400> SEQUENCE: 2216
gccaagcgca rcccgagatg c                                      21

<210> SEQ ID NO 2217
<211> LENGTH: 21
<212> TYPE: DNA
<213> ORGANISM: Homo sapiens

<400> SEQUENCE: 2217
atgaaaacac rtggatcggc c                                      21

<210> SEQ ID NO 2218
<211> LENGTH: 21
<212> TYPE: DNA
<213> ORGANISM: Homo sapiens

<400> SEQUENCE: 2218
ccagggcaga sttcagagaa a                                      21

<210> SEQ ID NO 2219
<211> LENGTH: 21
<212> TYPE: DNA
<213> ORGANISM: Homo sapiens

<400> SEQUENCE: 2219
atatcaccga kgccagcgaa a                                      21

<210> SEQ ID NO 2220
<211> LENGTH: 21
<212> TYPE: DNA
<213> ORGANISM: Homo sapiens

<400> SEQUENCE: 2220
acaggacttg yccatcctgg t                                      21

<210> SEQ ID NO 2221
<211> LENGTH: 21
<212> TYPE: DNA
<213> ORGANISM: Homo sapiens

<400> SEQUENCE: 2221
gcatgagcaa rccagccgga t                                      21

<210> SEQ ID NO 2222
<211> LENGTH: 21
<212> TYPE: DNA
<213> ORGANISM: Homo sapiens

<400> SEQUENCE: 2222
ataaggatac macaagaagg a                                              21

<210> SEQ ID NO 2223
<211> LENGTH: 21
<212> TYPE: DNA
<213> ORGANISM: Homo sapiens

<400> SEQUENCE: 2223
ggcagcaaat katgacatgg t                                              21

<210> SEQ ID NO 2224
<211> LENGTH: 21
<212> TYPE: DNA
<213> ORGANISM: Homo sapiens

<400> SEQUENCE: 2224
cagacgaagg kcaatgctgg c                                              21

<210> SEQ ID NO 2225
<211> LENGTH: 21
<212> TYPE: DNA
<213> ORGANISM: Homo sapiens

<400> SEQUENCE: 2225
atctcccaga mactgaatgt t                                              21

<210> SEQ ID NO 2226
<211> LENGTH: 21
<212> TYPE: DNA
<213> ORGANISM: Homo sapiens

<400> SEQUENCE: 2226
gaagcctgaa racagtgaat g                                              21

<210> SEQ ID NO 2227
<211> LENGTH: 21
<212> TYPE: DNA
<213> ORGANISM: Homo sapiens

<400> SEQUENCE: 2227
taccggaaaa wtccagggga c                                              21

<210> SEQ ID NO 2228
<211> LENGTH: 21
<212> TYPE: DNA
<213> ORGANISM: Homo sapiens

<400> SEQUENCE: 2228
aactttttga rtccggaaaa a                                              21

<210> SEQ ID NO 2229
<211> LENGTH: 21
<212> TYPE: DNA
<213> ORGANISM: Homo sapiens

<400> SEQUENCE: 2229

```
tcgagactat rttgtgacca a                                      21

<210> SEQ ID NO 2230
<211> LENGTH: 21
<212> TYPE: DNA
<213> ORGANISM: Homo sapiens

<400> SEQUENCE: 2230
gaggaagcct saaaacagtg a                                      21

<210> SEQ ID NO 2231
<211> LENGTH: 21
<212> TYPE: DNA
<213> ORGANISM: Homo sapiens

<400> SEQUENCE: 2231
aagtaaaaga yttgaaaaag a                                      21

<210> SEQ ID NO 2232
<211> LENGTH: 21
<212> TYPE: DNA
<213> ORGANISM: Homo sapiens

<400> SEQUENCE: 2232
tccatgaata wcagcatttg g                                      21

<210> SEQ ID NO 2233
<211> LENGTH: 21
<212> TYPE: DNA
<213> ORGANISM: Homo sapiens

<400> SEQUENCE: 2233
cctggagcta rgtccatgaa t                                      21

<210> SEQ ID NO 2234
<211> LENGTH: 21
<212> TYPE: DNA
<213> ORGANISM: Homo sapiens

<400> SEQUENCE: 2234
tgaccaagac rtatgccact g                                      21

<210> SEQ ID NO 2235
<211> LENGTH: 21
<212> TYPE: DNA
<213> ORGANISM: Homo sapiens

<400> SEQUENCE: 2235
accttctacc ycaatcacaa a                                      21

<210> SEQ ID NO 2236
<211> LENGTH: 21
<212> TYPE: DNA
<213> ORGANISM: Homo sapiens

<400> SEQUENCE: 2236
cgtcagtgtc wgggaactgg a                                      21

<210> SEQ ID NO 2237
<211> LENGTH: 21
<212> TYPE: DNA
<213> ORGANISM: Homo sapiens

<400> SEQUENCE: 2237
```

```
catgtctgac rgatacaagc t                                              21

<210> SEQ ID NO 2238
<211> LENGTH: 21
<212> TYPE: DNA
<213> ORGANISM: Homo sapiens

<400> SEQUENCE: 2238
tgtccaacgc rgtcaagcag a                                              21

<210> SEQ ID NO 2239
<211> LENGTH: 21
<212> TYPE: DNA
<213> ORGANISM: Homo sapiens

<400> SEQUENCE: 2239
ttaaagtaga rcaggccgaa t                                              21

<210> SEQ ID NO 2240
<211> LENGTH: 21
<212> TYPE: DNA
<213> ORGANISM: Homo sapiens

<400> SEQUENCE: 2240
ccaaccccga ygagaagacg a                                              21

<210> SEQ ID NO 2241
<211> LENGTH: 21
<212> TYPE: DNA
<213> ORGANISM: Homo sapiens

<400> SEQUENCE: 2241
tacacgacat kttcatggac a                                              21

<210> SEQ ID NO 2242
<211> LENGTH: 21
<212> TYPE: DNA
<213> ORGANISM: Homo sapiens

<400> SEQUENCE: 2242
tatgacagag racagaggat g                                              21

<210> SEQ ID NO 2243
<211> LENGTH: 21
<212> TYPE: DNA
<213> ORGANISM: Homo sapiens

<400> SEQUENCE: 2243
gcatccacat sgtgacaggt c                                              21

<210> SEQ ID NO 2244
<211> LENGTH: 21
<212> TYPE: DNA
<213> ORGANISM: Homo sapiens

<400> SEQUENCE: 2244
ctaactggtc kggattacag a                                              21

<210> SEQ ID NO 2245
<211> LENGTH: 21
<212> TYPE: DNA
<213> ORGANISM: Homo sapiens
```

-continued

<400> SEQUENCE: 2245
gaaatgaaac rgattgttga g　　　　　　　　　　　　　　　　21

<210> SEQ ID NO 2246
<211> LENGTH: 21
<212> TYPE: DNA
<213> ORGANISM: Homo sapiens

<400> SEQUENCE: 2246
gagtttttca ytgcactcaa t　　　　　　　　　　　　　　　　21

<210> SEQ ID NO 2247
<211> LENGTH: 21
<212> TYPE: DNA
<213> ORGANISM: Homo sapiens

<400> SEQUENCE: 2247
tgtgagacac rgttcagatc c　　　　　　　　　　　　　　　　21

<210> SEQ ID NO 2248
<211> LENGTH: 21
<212> TYPE: DNA
<213> ORGANISM: Homo sapiens

<400> SEQUENCE: 2248
tataatccat mtacacggag t　　　　　　　　　　　　　　　　21

<210> SEQ ID NO 2249
<211> LENGTH: 21
<212> TYPE: DNA
<213> ORGANISM: Homo sapiens

<400> SEQUENCE: 2249
gattacctgc maacaggaat g　　　　　　　　　　　　　　　　21

<210> SEQ ID NO 2250
<211> LENGTH: 21
<212> TYPE: DNA
<213> ORGANISM: Homo sapiens

<400> SEQUENCE: 2250
ccttctatac yccagagcca g　　　　　　　　　　　　　　　　21

<210> SEQ ID NO 2251
<211> LENGTH: 21
<212> TYPE: DNA
<213> ORGANISM: Homo sapiens

<400> SEQUENCE: 2251
tcctgaaaga yaccaagagc a　　　　　　　　　　　　　　　　21

<210> SEQ ID NO 2252
<211> LENGTH: 21
<212> TYPE: DNA
<213> ORGANISM: Homo sapiens

<400> SEQUENCE: 2252
cagacggaaa ktgctcacac c　　　　　　　　　　　　　　　　21

<210> SEQ ID NO 2253
<211> LENGTH: 21
<212> TYPE: DNA
<213> ORGANISM: Homo sapiens

```
<400> SEQUENCE: 2253
tggtgggaca yggataaagc t                                              21

<210> SEQ ID NO 2254
<211> LENGTH: 21
<212> TYPE: DNA
<213> ORGANISM: Homo sapiens

<400> SEQUENCE: 2254
gaaaagcttt ytatcgaaac a                                              21

<210> SEQ ID NO 2255
<211> LENGTH: 21
<212> TYPE: DNA
<213> ORGANISM: Homo sapiens

<400> SEQUENCE: 2255
aatgactacg ycaacggctt c                                              21

<210> SEQ ID NO 2256
<211> LENGTH: 21
<212> TYPE: DNA
<213> ORGANISM: Homo sapiens

<400> SEQUENCE: 2256
actgggcaga yggaaagtgc t                                              21

<210> SEQ ID NO 2257
<211> LENGTH: 21
<212> TYPE: DNA
<213> ORGANISM: Homo sapiens

<400> SEQUENCE: 2257
actacgccaa mggcttcatg g                                              21

<210> SEQ ID NO 2258
<211> LENGTH: 21
<212> TYPE: DNA
<213> ORGANISM: Homo sapiens

<400> SEQUENCE: 2258
gctcagatac yagcagcctg g                                              21

<210> SEQ ID NO 2259
<211> LENGTH: 21
<212> TYPE: DNA
<213> ORGANISM: Homo sapiens

<400> SEQUENCE: 2259
tctttgacaa rtcctgcagc g                                              21

<210> SEQ ID NO 2260
<211> LENGTH: 21
<212> TYPE: DNA
<213> ORGANISM: Homo sapiens

<400> SEQUENCE: 2260
cttgattggg sagaacgaga a                                              21

<210> SEQ ID NO 2261
<211> LENGTH: 21
<212> TYPE: DNA
```

<213> ORGANISM: Homo sapiens

<400> SEQUENCE: 2261
gatggctatg rcctggagat c                    21

<210> SEQ ID NO 2262
<211> LENGTH: 21
<212> TYPE: DNA
<213> ORGANISM: Homo sapiens

<400> SEQUENCE: 2262
cctgagacca raagaaacgc a                    21

<210> SEQ ID NO 2263
<211> LENGTH: 21
<212> TYPE: DNA
<213> ORGANISM: Homo sapiens

<400> SEQUENCE: 2263
ccgcagggat ytactgagac t                    21

<210> SEQ ID NO 2264
<211> LENGTH: 21
<212> TYPE: DNA
<213> ORGANISM: Homo sapiens

<400> SEQUENCE: 2264
agattaccaa rcccaacgtg t                    21

<210> SEQ ID NO 2265
<211> LENGTH: 21
<212> TYPE: DNA
<213> ORGANISM: Homo sapiens

<400> SEQUENCE: 2265
tgtcctgcag kgacaagatt g                    21

<210> SEQ ID NO 2266
<211> LENGTH: 21
<212> TYPE: DNA
<213> ORGANISM: Homo sapiens

<400> SEQUENCE: 2266
gggttggagg yccgtgactg c                    21

<210> SEQ ID NO 2267
<211> LENGTH: 21
<212> TYPE: DNA
<213> ORGANISM: Homo sapiens

<400> SEQUENCE: 2267
atgatgaccc rtctcttgaa g                    21

<210> SEQ ID NO 2268
<211> LENGTH: 21
<212> TYPE: DNA
<213> ORGANISM: Homo sapiens

<400> SEQUENCE: 2268
aagctggtct rccagatctt c                    21

<210> SEQ ID NO 2269
<211> LENGTH: 21

-continued

<212> TYPE: DNA
<213> ORGANISM: Homo sapiens

<400> SEQUENCE: 2269
aaatccacag rtttctgatg a    21

<210> SEQ ID NO 2270
<211> LENGTH: 21
<212> TYPE: DNA
<213> ORGANISM: Homo sapiens

<400> SEQUENCE: 2270
aattccgact ygacctatga g    21

<210> SEQ ID NO 2271
<211> LENGTH: 21
<212> TYPE: DNA
<213> ORGANISM: Homo sapiens

<400> SEQUENCE: 2271
gggccacgtc rgaccctctg g    21

<210> SEQ ID NO 2272
<211> LENGTH: 21
<212> TYPE: DNA
<213> ORGANISM: Homo sapiens

<400> SEQUENCE: 2272
gttcttcctc ytggagaatg t    21

<210> SEQ ID NO 2273
<211> LENGTH: 21
<212> TYPE: DNA
<213> ORGANISM: Homo sapiens

<400> SEQUENCE: 2273
aggacctgat maacaagatc g    21

<210> SEQ ID NO 2274
<211> LENGTH: 21
<212> TYPE: DNA
<213> ORGANISM: Homo sapiens

<400> SEQUENCE: 2274
agacattcac wggacacaga g    21

<210> SEQ ID NO 2275
<211> LENGTH: 21
<212> TYPE: DNA
<213> ORGANISM: Homo sapiens

<400> SEQUENCE: 2275
cctctggctc mgtgttccga g    21

<210> SEQ ID NO 2276
<211> LENGTH: 21
<212> TYPE: DNA
<213> ORGANISM: Homo sapiens

<400> SEQUENCE: 2276
actcactttg wtgagctcca g    21

<210> SEQ ID NO 2277

―continued

```
<211> LENGTH: 21
<212> TYPE: DNA
<213> ORGANISM: Homo sapiens

<400> SEQUENCE: 2277
gaaccttcac rccatctatg a                                              21

<210> SEQ ID NO 2278
<211> LENGTH: 21
<212> TYPE: DNA
<213> ORGANISM: Homo sapiens

<400> SEQUENCE: 2278
tgaccaggag wtggaggagc t                                              21

<210> SEQ ID NO 2279
<211> LENGTH: 21
<212> TYPE: DNA
<213> ORGANISM: Homo sapiens

<400> SEQUENCE: 2279
aacgacgtgg rcggccagcg c                                              21

<210> SEQ ID NO 2280
<211> LENGTH: 21
<212> TYPE: DNA
<213> ORGANISM: Homo sapiens

<400> SEQUENCE: 2280
gtcctgccca ytgggggggcg c                                             21

<210> SEQ ID NO 2281
<211> LENGTH: 21
<212> TYPE: DNA
<213> ORGANISM: Homo sapiens

<400> SEQUENCE: 2281
cgcagctggg rcccaagctc t                                              21

<210> SEQ ID NO 2282
<211> LENGTH: 21
<212> TYPE: DNA
<213> ORGANISM: Homo sapiens

<400> SEQUENCE: 2282
caggcagctg rtctgcaacg t                                              21

<210> SEQ ID NO 2283
<211> LENGTH: 21
<212> TYPE: DNA
<213> ORGANISM: Homo sapiens

<400> SEQUENCE: 2283
ctcaggcaaa yggagtaagc c                                              21

<210> SEQ ID NO 2284
<211> LENGTH: 21
<212> TYPE: DNA
<213> ORGANISM: Homo sapiens

<400> SEQUENCE: 2284
accgtctgaa sttgtaggga g                                              21
```

```
<210> SEQ ID NO 2285
<211> LENGTH: 21
<212> TYPE: DNA
<213> ORGANISM: Homo sapiens

<400> SEQUENCE: 2285
caagggtacc rcgtcgatgc t                                          21

<210> SEQ ID NO 2286
<211> LENGTH: 21
<212> TYPE: DNA
<213> ORGANISM: Homo sapiens

<400> SEQUENCE: 2286
ttttggcttc stggcctttg g                                          21

<210> SEQ ID NO 2287
<211> LENGTH: 21
<212> TYPE: DNA
<213> ORGANISM: Homo sapiens

<400> SEQUENCE: 2287
cccagttcat kgatggtgcc c                                          21

<210> SEQ ID NO 2288
<211> LENGTH: 21
<212> TYPE: DNA
<213> ORGANISM: Homo sapiens

<400> SEQUENCE: 2288
ctgtgagtgg satttgtttt g                                          21

<210> SEQ ID NO 2289
<211> LENGTH: 21
<212> TYPE: DNA
<213> ORGANISM: Homo sapiens

<400> SEQUENCE: 2289
ggtctgcagt kgccacctga a                                          21

<210> SEQ ID NO 2290
<211> LENGTH: 21
<212> TYPE: DNA
<213> ORGANISM: Homo sapiens

<400> SEQUENCE: 2290
gtgtaacaga mgacgggggt t                                          21

<210> SEQ ID NO 2291
<211> LENGTH: 21
<212> TYPE: DNA
<213> ORGANISM: Homo sapiens

<400> SEQUENCE: 2291
aggccatcaa satggggcag t                                          21

<210> SEQ ID NO 2292
<211> LENGTH: 21
<212> TYPE: DNA
<213> ORGANISM: Homo sapiens

<400> SEQUENCE: 2292
gtcaacagta rcctggtgtg c                                          21
```

<210> SEQ ID NO 2293
<211> LENGTH: 21
<212> TYPE: DNA
<213> ORGANISM: Homo sapiens

<400> SEQUENCE: 2293
ccttcactta ygaggatccc a                                          21

<210> SEQ ID NO 2294
<211> LENGTH: 21
<212> TYPE: DNA
<213> ORGANISM: Homo sapiens

<400> SEQUENCE: 2294
acctgtgtgg ytcatgcaga g                                          21

<210> SEQ ID NO 2295
<211> LENGTH: 21
<212> TYPE: DNA
<213> ORGANISM: Homo sapiens

<400> SEQUENCE: 2295
ctttgggata ytcatgtggg a                                          21

<210> SEQ ID NO 2296
<211> LENGTH: 21
<212> TYPE: DNA
<213> ORGANISM: Homo sapiens

<400> SEQUENCE: 2296
gagaccttca yccttacta c                                           21

<210> SEQ ID NO 2297
<211> LENGTH: 21
<212> TYPE: DNA
<213> ORGANISM: Homo sapiens

<400> SEQUENCE: 2297
tttgaggtgc maggctcagc a                                          21

<210> SEQ ID NO 2298
<211> LENGTH: 21
<212> TYPE: DNA
<213> ORGANISM: Homo sapiens

<400> SEQUENCE: 2298
ctatgaccag rcagaagacg a                                          21

<210> SEQ ID NO 2299
<211> LENGTH: 21
<212> TYPE: DNA
<213> ORGANISM: Homo sapiens

<400> SEQUENCE: 2299
ggggctttgg scttcctcct g                                          21

<210> SEQ ID NO 2300
<211> LENGTH: 21
<212> TYPE: DNA
<213> ORGANISM: Homo sapiens

<400> SEQUENCE: 2300
ggccatccag rccctgtggg c                                          21

<210> SEQ ID NO 2301
<211> LENGTH: 21
<212> TYPE: DNA
<213> ORGANISM: Homo sapiens

<400> SEQUENCE: 2301
ggaggtcatt sggacaggct c                                              21

<210> SEQ ID NO 2302
<211> LENGTH: 21
<212> TYPE: DNA
<213> ORGANISM: Homo sapiens

<400> SEQUENCE: 2302
ttcctcaggc rgcgggaggg c                                              21

<210> SEQ ID NO 2303
<211> LENGTH: 21
<212> TYPE: DNA
<213> ORGANISM: Homo sapiens

<400> SEQUENCE: 2303
agccattgga ytggagtgct a                                              21

<210> SEQ ID NO 2304
<211> LENGTH: 21
<212> TYPE: DNA
<213> ORGANISM: Homo sapiens

<400> SEQUENCE: 2304
agctgaacct sctgacagag t                                              21

<210> SEQ ID NO 2305
<211> LENGTH: 21
<212> TYPE: DNA
<213> ORGANISM: Homo sapiens

<400> SEQUENCE: 2305
tttggtgttc ratagcatat t                                              21

<210> SEQ ID NO 2306
<211> LENGTH: 21
<212> TYPE: DNA
<213> ORGANISM: Homo sapiens

<400> SEQUENCE: 2306
tgaagcaaat scagatactt c                                              21

<210> SEQ ID NO 2307
<211> LENGTH: 21
<212> TYPE: DNA
<213> ORGANISM: Homo sapiens

<400> SEQUENCE: 2307
gcatcagcca ygatggtaga a                                              21

<210> SEQ ID NO 2308
<211> LENGTH: 21
<212> TYPE: DNA
<213> ORGANISM: Homo sapiens

<400> SEQUENCE: 2308
tacagaacag rctactcggg t                                      21

<210> SEQ ID NO 2309
<211> LENGTH: 21
<212> TYPE: DNA
<213> ORGANISM: Homo sapiens

<400> SEQUENCE: 2309
cagcaatggg yatcccctcg g                                      21

<210> SEQ ID NO 2310
<211> LENGTH: 21
<212> TYPE: DNA
<213> ORGANISM: Homo sapiens

<400> SEQUENCE: 2310
aaatcccgta rtgaatccaa g                                      21

<210> SEQ ID NO 2311
<211> LENGTH: 21
<212> TYPE: DNA
<213> ORGANISM: Homo sapiens

<400> SEQUENCE: 2311
taacaggaaa ygtgcagttt a                                      21

<210> SEQ ID NO 2312
<211> LENGTH: 21
<212> TYPE: DNA
<213> ORGANISM: Homo sapiens

<400> SEQUENCE: 2312
agatcagcag kgtagcccgt g                                      21

<210> SEQ ID NO 2313
<211> LENGTH: 21
<212> TYPE: DNA
<213> ORGANISM: Homo sapiens

<400> SEQUENCE: 2313
cagaagagtc sttcacagct g                                      21

<210> SEQ ID NO 2314
<211> LENGTH: 21
<212> TYPE: DNA
<213> ORGANISM: Homo sapiens

<400> SEQUENCE: 2314
ctagagaaat wctactttgc t                                      21

<210> SEQ ID NO 2315
<211> LENGTH: 21
<212> TYPE: DNA
<213> ORGANISM: Homo sapiens

<400> SEQUENCE: 2315
aagtcagtac rgtggatgcc a                                      21

<210> SEQ ID NO 2316
<211> LENGTH: 21
<212> TYPE: DNA
<213> ORGANISM: Homo sapiens

<400> SEQUENCE: 2316
gaacatgaca raagagtcct t  21

<210> SEQ ID NO 2317
<211> LENGTH: 21
<212> TYPE: DNA
<213> ORGANISM: Homo sapiens

<400> SEQUENCE: 2317
ggaagatcat rgaagttgaa g  21

<210> SEQ ID NO 2318
<211> LENGTH: 21
<212> TYPE: DNA
<213> ORGANISM: Homo sapiens

<400> SEQUENCE: 2318
ttctcttaac saagccatca t  21

<210> SEQ ID NO 2319
<211> LENGTH: 21
<212> TYPE: DNA
<213> ORGANISM: Homo sapiens

<400> SEQUENCE: 2319
tgttggctta ytcattcacg c  21

<210> SEQ ID NO 2320
<211> LENGTH: 21
<212> TYPE: DNA
<213> ORGANISM: Homo sapiens

<400> SEQUENCE: 2320
ggctgccatt ktcattgctc a  21

<210> SEQ ID NO 2321
<211> LENGTH: 21
<212> TYPE: DNA
<213> ORGANISM: Homo sapiens

<400> SEQUENCE: 2321
aaacccttgg rtttttattg g  21

<210> SEQ ID NO 2322
<211> LENGTH: 21
<212> TYPE: DNA
<213> ORGANISM: Homo sapiens

<400> SEQUENCE: 2322
ctgttggagc maccattaac a  21

<210> SEQ ID NO 2323
<211> LENGTH: 21
<212> TYPE: DNA
<213> ORGANISM: Homo sapiens

<400> SEQUENCE: 2323
gactttgtgc ycaacgtcaa g  21

<210> SEQ ID NO 2324
<211> LENGTH: 21
<212> TYPE: DNA
<213> ORGANISM: Homo sapiens -continued

<400> SEQUENCE: 2324
cttctatgtc rcctccagtg a                                              21

<210> SEQ ID NO 2325
<211> LENGTH: 21
<212> TYPE: DNA
<213> ORGANISM: Homo sapiens

<400> SEQUENCE: 2325
atgcaagtat kttgggctcg c                                              21

<210> SEQ ID NO 2326
<211> LENGTH: 21
<212> TYPE: DNA
<213> ORGANISM: Homo sapiens

<400> SEQUENCE: 2326
cccagtttgt ycccactgtt t                                              21

<210> SEQ ID NO 2327
<211> LENGTH: 21
<212> TYPE: DNA
<213> ORGANISM: Homo sapiens

<400> SEQUENCE: 2327
acaggtggcc rtctgcctgg c                                              21

<210> SEQ ID NO 2328
<211> LENGTH: 21
<212> TYPE: DNA
<213> ORGANISM: Homo sapiens

<400> SEQUENCE: 2328
gtgcttggct kcctctttgc g                                              21

<210> SEQ ID NO 2329
<211> LENGTH: 21
<212> TYPE: DNA
<213> ORGANISM: Homo sapiens

<400> SEQUENCE: 2329
cctcttccag ycgcagaaga a                                              21

<210> SEQ ID NO 2330
<211> LENGTH: 21
<212> TYPE: DNA
<213> ORGANISM: Homo sapiens

<400> SEQUENCE: 2330
agcccgacct kggcacctgc t                                              21

<210> SEQ ID NO 2331
<211> LENGTH: 21
<212> TYPE: DNA
<213> ORGANISM: Homo sapiens

<400> SEQUENCE: 2331
ggacctgtcg ytcatctgcc t                                              21

<210> SEQ ID NO 2332
<211> LENGTH: 21
<212> TYPE: DNA
<213> ORGANISM: Homo sapiens

<400> SEQUENCE: 2332
accagcggac rctcgacccc c          21

<210> SEQ ID NO 2333
<211> LENGTH: 21
<212> TYPE: DNA
<213> ORGANISM: Homo sapiens

<400> SEQUENCE: 2333
atcgcaaatg macaggacag g          21

<210> SEQ ID NO 2334
<211> LENGTH: 21
<212> TYPE: DNA
<213> ORGANISM: Homo sapiens

<400> SEQUENCE: 2334
tcctgtcttc ytggcaatgt t          21

<210> SEQ ID NO 2335
<211> LENGTH: 21
<212> TYPE: DNA
<213> ORGANISM: Homo sapiens

<400> SEQUENCE: 2335
tgtgcacact rccatgtaag c          21

<210> SEQ ID NO 2336
<211> LENGTH: 21
<212> TYPE: DNA
<213> ORGANISM: Homo sapiens

<400> SEQUENCE: 2336
tgtgctgact wccggggtgt c          21

<210> SEQ ID NO 2337
<211> LENGTH: 21
<212> TYPE: DNA
<213> ORGANISM: Homo sapiens

<400> SEQUENCE: 2337
aagccagagg rgttctcaag t          21

<210> SEQ ID NO 2338
<211> LENGTH: 21
<212> TYPE: DNA
<213> ORGANISM: Homo sapiens

<400> SEQUENCE: 2338
tcatagacta ygatgaacac a          21

<210> SEQ ID NO 2339
<211> LENGTH: 21
<212> TYPE: DNA
<213> ORGANISM: Homo sapiens

<400> SEQUENCE: 2339
cgaactcttg mcaataatcg a          21

<210> SEQ ID NO 2340
<211> LENGTH: 21
<212> TYPE: DNA

```
<213> ORGANISM: Homo sapiens

<400> SEQUENCE: 2340
aaacaaaccg yatccaccga a                                              21

<210> SEQ ID NO 2341
<211> LENGTH: 21
<212> TYPE: DNA
<213> ORGANISM: Homo sapiens

<400> SEQUENCE: 2341
gagggcttca rgacgcgaac t                                              21

<210> SEQ ID NO 2342
<211> LENGTH: 21
<212> TYPE: DNA
<213> ORGANISM: Homo sapiens

<400> SEQUENCE: 2342
attagtccag satctcagct g                                              21

<210> SEQ ID NO 2343
<211> LENGTH: 21
<212> TYPE: DNA
<213> ORGANISM: Homo sapiens

<400> SEQUENCE: 2343
ttttctctgt kattcaatca c                                              21

<210> SEQ ID NO 2344
<211> LENGTH: 21
<212> TYPE: DNA
<213> ORGANISM: Homo sapiens

<400> SEQUENCE: 2344
ttaccatgta yaccacctgc a                                              21

<210> SEQ ID NO 2345
<211> LENGTH: 21
<212> TYPE: DNA
<213> ORGANISM: Homo sapiens

<400> SEQUENCE: 2345
aactcaggcc mcagcagagc c                                              21

<210> SEQ ID NO 2346
<211> LENGTH: 21
<212> TYPE: DNA
<213> ORGANISM: Homo sapiens

<400> SEQUENCE: 2346
gaagtcgctc wacaactgcc g                                              21

<210> SEQ ID NO 2347
<211> LENGTH: 21
<212> TYPE: DNA
<213> ORGANISM: Homo sapiens

<400> SEQUENCE: 2347
gtctgagaat raaattccca c                                              21

<210> SEQ ID NO 2348
<211> LENGTH: 21
```

<212> TYPE: DNA
<213> ORGANISM: Homo sapiens

<400> SEQUENCE: 2348
gcgtgtccaa ygatgtctgc a                                    21

<210> SEQ ID NO 2349
<211> LENGTH: 21
<212> TYPE: DNA
<213> ORGANISM: Homo sapiens

<400> SEQUENCE: 2349
tgggcaatcc rtttacatgc t                                    21

<210> SEQ ID NO 2350
<211> LENGTH: 21
<212> TYPE: DNA
<213> ORGANISM: Homo sapiens

<400> SEQUENCE: 2350
ggatcaagac wctccaagag g                                    21

<210> SEQ ID NO 2351
<211> LENGTH: 21
<212> TYPE: DNA
<213> ORGANISM: Homo sapiens

<400> SEQUENCE: 2351
gcaaatctgg ycgcacctaa c                                    21

<210> SEQ ID NO 2352
<211> LENGTH: 21
<212> TYPE: DNA
<213> ORGANISM: Homo sapiens

<400> SEQUENCE: 2352
ctccaagttt rgcatgaaag g                                    21

<210> SEQ ID NO 2353
<211> LENGTH: 21
<212> TYPE: DNA
<213> ORGANISM: Homo sapiens

<400> SEQUENCE: 2353
gtcggtggcc rcacaatgct g                                    21

<210> SEQ ID NO 2354
<211> LENGTH: 21
<212> TYPE: DNA
<213> ORGANISM: Homo sapiens

<400> SEQUENCE: 2354
tccttaagga yaactaacat t                                    21

<210> SEQ ID NO 2355
<211> LENGTH: 21
<212> TYPE: DNA
<213> ORGANISM: Homo sapiens

<400> SEQUENCE: 2355
aggatgccag ygacaatgca c                                    21

<210> SEQ ID NO 2356

```
<211> LENGTH: 21
<212> TYPE: DNA
<213> ORGANISM: Homo sapiens

<400> SEQUENCE: 2356
ggacctcaac magttcctca g                                          21

<210> SEQ ID NO 2357
<211> LENGTH: 21
<212> TYPE: DNA
<213> ORGANISM: Homo sapiens

<400> SEQUENCE: 2357
agcatgggga yctcaacaag t                                          21

<210> SEQ ID NO 2358
<211> LENGTH: 21
<212> TYPE: DNA
<213> ORGANISM: Homo sapiens

<400> SEQUENCE: 2358
gtaatgaaat yccttccaca g                                          21

<210> SEQ ID NO 2359
<211> LENGTH: 21
<212> TYPE: DNA
<213> ORGANISM: Homo sapiens

<400> SEQUENCE: 2359
tactaaaata yatgttacca a                                          21

<210> SEQ ID NO 2360
<211> LENGTH: 21
<212> TYPE: DNA
<213> ORGANISM: Homo sapiens

<400> SEQUENCE: 2360
catttgttca scacatcaag c                                          21

<210> SEQ ID NO 2361
<211> LENGTH: 21
<212> TYPE: DNA
<213> ORGANISM: Homo sapiens

<400> SEQUENCE: 2361
cacgcaagga yttccaccgt g                                          21

<210> SEQ ID NO 2362
<211> LENGTH: 21
<212> TYPE: DNA
<213> ORGANISM: Homo sapiens

<400> SEQUENCE: 2362
ctgtcattat yggaatgacc a                                          21

<210> SEQ ID NO 2363
<211> LENGTH: 21
<212> TYPE: DNA
<213> ORGANISM: Homo sapiens

<400> SEQUENCE: 2363
attggaatga scaagatccc t                                          21
```

<210> SEQ ID NO 2364
<211> LENGTH: 21
<212> TYPE: DNA
<213> ORGANISM: Homo sapiens

<400> SEQUENCE: 2364
ccagtacttt kgcatcacca a                                              21

<210> SEQ ID NO 2365
<211> LENGTH: 21
<212> TYPE: DNA
<213> ORGANISM: Homo sapiens

<400> SEQUENCE: 2365
gacataacat kgttctgaaa a                                              21

<210> SEQ ID NO 2366
<211> LENGTH: 21
<212> TYPE: DNA
<213> ORGANISM: Homo sapiens

<400> SEQUENCE: 2366
aaatctggcc kcacctaacc t                                              21

<210> SEQ ID NO 2367
<211> LENGTH: 21
<212> TYPE: DNA
<213> ORGANISM: Homo sapiens

<400> SEQUENCE: 2367
tgctgcccat ycgctggatg c                                              21

<210> SEQ ID NO 2368
<211> LENGTH: 21
<212> TYPE: DNA
<213> ORGANISM: Homo sapiens

<400> SEQUENCE: 2368
gatgctgcat wtagcccagc a                                              21

<210> SEQ ID NO 2369
<211> LENGTH: 21
<212> TYPE: DNA
<213> ORGANISM: Homo sapiens

<400> SEQUENCE: 2369
cgtcccagca mttcgtgcac c                                              21

<210> SEQ ID NO 2370
<211> LENGTH: 21
<212> TYPE: DNA
<213> ORGANISM: Homo sapiens

<400> SEQUENCE: 2370
cccattcgct rgatgcctcc a                                              21

<210> SEQ ID NO 2371
<211> LENGTH: 21
<212> TYPE: DNA
<213> ORGANISM: Homo sapiens

<400> SEQUENCE: 2371
tttggccacc mggaactgcc t                                              21

<210> SEQ ID NO 2372
<211> LENGTH: 21
<212> TYPE: DNA
<213> ORGANISM: Homo sapiens

<400> SEQUENCE: 2372
ggagaacttg ytggtgaaaa t                                              21

<210> SEQ ID NO 2373
<211> LENGTH: 21
<212> TYPE: DNA
<213> ORGANISM: Homo sapiens

<400> SEQUENCE: 2373
gggatgtcgt yctggataag g                                              21

<210> SEQ ID NO 2374
<211> LENGTH: 21
<212> TYPE: DNA
<213> ORGANISM: Homo sapiens

<400> SEQUENCE: 2374
tgtattggga ygttggtaac c                                              21

<210> SEQ ID NO 2375
<211> LENGTH: 21
<212> TYPE: DNA
<213> ORGANISM: Homo sapiens

<400> SEQUENCE: 2375
ggtataagag ycgccctgtc g                                              21

<210> SEQ ID NO 2376
<211> LENGTH: 21
<212> TYPE: DNA
<213> ORGANISM: Homo sapiens

<400> SEQUENCE: 2376
ccggagctgc rggaggccta c                                              21

<210> SEQ ID NO 2377
<211> LENGTH: 21
<212> TYPE: DNA
<213> ORGANISM: Homo sapiens

<400> SEQUENCE: 2377
tgcaattcaa ygcagtccga a                                              21

<210> SEQ ID NO 2378
<211> LENGTH: 21
<212> TYPE: DNA
<213> ORGANISM: Homo sapiens

<400> SEQUENCE: 2378
tgcacacagt rgaccacgtg g                                              21

<210> SEQ ID NO 2379
<211> LENGTH: 21
<212> TYPE: DNA
<213> ORGANISM: Homo sapiens

<400> SEQUENCE: 2379
acgtccggaa maaactgaag a                                              21

<210> SEQ ID NO 2380
<211> LENGTH: 21
<212> TYPE: DNA
<213> ORGANISM: Homo sapiens

<400> SEQUENCE: 2380
agcaagccct yagtgagatt g                                              21

<210> SEQ ID NO 2381
<211> LENGTH: 21
<212> TYPE: DNA
<213> ORGANISM: Homo sapiens

<400> SEQUENCE: 2381
gctgaattaa ragtggccta a                                              21

<210> SEQ ID NO 2382
<211> LENGTH: 21
<212> TYPE: DNA
<213> ORGANISM: Homo sapiens

<400> SEQUENCE: 2382
attgaggaaa ytcggcttaa c                                              21

<210> SEQ ID NO 2383
<211> LENGTH: 21
<212> TYPE: DNA
<213> ORGANISM: Homo sapiens

<400> SEQUENCE: 2383
cagctgacac rggatgatga t                                              21

<210> SEQ ID NO 2384
<211> LENGTH: 21
<212> TYPE: DNA
<213> ORGANISM: Homo sapiens

<400> SEQUENCE: 2384
ccggaagaaa ytgataatta t                                              21

<210> SEQ ID NO 2385
<211> LENGTH: 21
<212> TYPE: DNA
<213> ORGANISM: Homo sapiens

<400> SEQUENCE: 2385
tacagtatca ytctctctgc a                                              21

<210> SEQ ID NO 2386
<211> LENGTH: 21
<212> TYPE: DNA
<213> ORGANISM: Homo sapiens

<400> SEQUENCE: 2386
acttccagtc wgtcacctcc a                                              21

<210> SEQ ID NO 2387
<211> LENGTH: 21
<212> TYPE: DNA
<213> ORGANISM: Homo sapiens

<400> SEQUENCE: 2387
atttcgtgag rgccaagggc a                                    21

<210> SEQ ID NO 2388
<211> LENGTH: 21
<212> TYPE: DNA
<213> ORGANISM: Homo sapiens

<400> SEQUENCE: 2388
tccagatcaa ygttatcccc a                                    21

<210> SEQ ID NO 2389
<211> LENGTH: 21
<212> TYPE: DNA
<213> ORGANISM: Homo sapiens

<400> SEQUENCE: 2389
attctggcct wgatgaagtg g                                    21

<210> SEQ ID NO 2390
<211> LENGTH: 21
<212> TYPE: DNA
<213> ORGANISM: Homo sapiens

<400> SEQUENCE: 2390
agtccctgtc sccttcagga t                                    21

<210> SEQ ID NO 2391
<211> LENGTH: 21
<212> TYPE: DNA
<213> ORGANISM: Homo sapiens

<400> SEQUENCE: 2391
aagggaagaa rgtctggata g                                    21

<210> SEQ ID NO 2392
<211> LENGTH: 21
<212> TYPE: DNA
<213> ORGANISM: Homo sapiens

<400> SEQUENCE: 2392
gggagagcct rcgacaggga a                                    21

<210> SEQ ID NO 2393
<211> LENGTH: 21
<212> TYPE: DNA
<213> ORGANISM: Homo sapiens

<400> SEQUENCE: 2393
gcccaaatac kggaaataaa a                                    21

<210> SEQ ID NO 2394
<211> LENGTH: 21
<212> TYPE: DNA
<213> ORGANISM: Homo sapiens

<400> SEQUENCE: 2394
tcgtgcgcaa ygtgccctgg g                                    21

<210> SEQ ID NO 2395
<211> LENGTH: 21
<212> TYPE: DNA
<213> ORGANISM: Homo sapiens

<400> SEQUENCE: 2395

```
ctggggccac rtgccccaca g                                             21

<210> SEQ ID NO 2396
<211> LENGTH: 21
<212> TYPE: DNA
<213> ORGANISM: Homo sapiens

<400> SEQUENCE: 2396
gcagtgctgc maagctaaag a                                             21

<210> SEQ ID NO 2397
<211> LENGTH: 21
<212> TYPE: DNA
<213> ORGANISM: Homo sapiens

<400> SEQUENCE: 2397
ttaccttggt rttcccattg t                                             21

<210> SEQ ID NO 2398
<211> LENGTH: 21
<212> TYPE: DNA
<213> ORGANISM: Homo sapiens

<400> SEQUENCE: 2398
acagcttgtt raaaaaaagc t                                             21

<210> SEQ ID NO 2399
<211> LENGTH: 21
<212> TYPE: DNA
<213> ORGANISM: Homo sapiens

<400> SEQUENCE: 2399
gagcagtttt yggaggccag c                                             21

<210> SEQ ID NO 2400
<211> LENGTH: 21
<212> TYPE: DNA
<213> ORGANISM: Homo sapiens

<400> SEQUENCE: 2400
cggaggagtt sgtgcccag g                                              21

<210> SEQ ID NO 2401
<211> LENGTH: 21
<212> TYPE: DNA
<213> ORGANISM: Homo sapiens

<400> SEQUENCE: 2401
gagctcagaa ygtctctaag g                                             21

<210> SEQ ID NO 2402
<211> LENGTH: 21
<212> TYPE: DNA
<213> ORGANISM: Homo sapiens

<400> SEQUENCE: 2402
agagccagcg rgttgtgctg c                                             21

<210> SEQ ID NO 2403
<211> LENGTH: 21
<212> TYPE: DNA
<213> ORGANISM: Homo sapiens
```

-continued

```
<400> SEQUENCE: 2403
gaccacttaa ytgagcgact a                                              21

<210> SEQ ID NO 2404
<211> LENGTH: 21
<212> TYPE: DNA
<213> ORGANISM: Homo sapiens

<400> SEQUENCE: 2404
ctgcaaggca rcctggaaac t                                              21

<210> SEQ ID NO 2405
<211> LENGTH: 21
<212> TYPE: DNA
<213> ORGANISM: Homo sapiens

<400> SEQUENCE: 2405
tggtggtgat ycctgcagag g                                              21

<210> SEQ ID NO 2406
<211> LENGTH: 21
<212> TYPE: DNA
<213> ORGANISM: Homo sapiens

<400> SEQUENCE: 2406
gctggagcca statctggcc t                                              21

<210> SEQ ID NO 2407
<211> LENGTH: 21
<212> TYPE: DNA
<213> ORGANISM: Homo sapiens

<400> SEQUENCE: 2407
aaggatgaga rggaccactt a                                              21

<210> SEQ ID NO 2408
<211> LENGTH: 21
<212> TYPE: DNA
<213> ORGANISM: Homo sapiens

<400> SEQUENCE: 2408
actgcgcacc ygaaattctt a                                              21

<210> SEQ ID NO 2409
<211> LENGTH: 21
<212> TYPE: DNA
<213> ORGANISM: Homo sapiens

<400> SEQUENCE: 2409
agagccacaa rgctagccga g                                              21

<210> SEQ ID NO 2410
<211> LENGTH: 21
<212> TYPE: DNA
<213> ORGANISM: Homo sapiens

<400> SEQUENCE: 2410
catgttcagg wgaattctga a                                              21

<210> SEQ ID NO 2411
<211> LENGTH: 21
<212> TYPE: DNA
<213> ORGANISM: Homo sapiens
```

```
<400> SEQUENCE: 2411
tggcctcttc scgcctggga a                                              21

<210> SEQ ID NO 2412
<211> LENGTH: 21
<212> TYPE: DNA
<213> ORGANISM: Homo sapiens

<400> SEQUENCE: 2412
atgacattcc ygatcgtcca g                                              21

<210> SEQ ID NO 2413
<211> LENGTH: 21
<212> TYPE: DNA
<213> ORGANISM: Homo sapiens

<400> SEQUENCE: 2413
atagccttcc ytaatccata c                                              21

<210> SEQ ID NO 2414
<211> LENGTH: 21
<212> TYPE: DNA
<213> ORGANISM: Homo sapiens

<400> SEQUENCE: 2414
cattggagcg rtcgcaggaa g                                              21

<210> SEQ ID NO 2415
<211> LENGTH: 21
<212> TYPE: DNA
<213> ORGANISM: Homo sapiens

<400> SEQUENCE: 2415
atattttccg raagctggga c                                              21

<210> SEQ ID NO 2416
<211> LENGTH: 21
<212> TYPE: DNA
<213> ORGANISM: Homo sapiens

<400> SEQUENCE: 2416
gccattgaag yttcgaagca t                                              21

<210> SEQ ID NO 2417
<211> LENGTH: 21
<212> TYPE: DNA
<213> ORGANISM: Homo sapiens

<400> SEQUENCE: 2417
tcccttagct ktcctgacac a                                              21

<210> SEQ ID NO 2418
<211> LENGTH: 21
<212> TYPE: DNA
<213> ORGANISM: Homo sapiens

<400> SEQUENCE: 2418
catcatcaga rgttacttgg g                                              21

<210> SEQ ID NO 2419
<211> LENGTH: 21
<212> TYPE: DNA
```

```
<213> ORGANISM: Homo sapiens

<400> SEQUENCE: 2419
agtagtaaca ytaacaggat t                                              21

<210> SEQ ID NO 2420
<211> LENGTH: 21
<212> TYPE: DNA
<213> ORGANISM: Homo sapiens

<400> SEQUENCE: 2420
caatggagat ygtggtggat a                                              21

<210> SEQ ID NO 2421
<211> LENGTH: 21
<212> TYPE: DNA
<213> ORGANISM: Homo sapiens

<400> SEQUENCE: 2421
gagaggttga ycaggaaata c                                              21

<210> SEQ ID NO 2422
<211> LENGTH: 21
<212> TYPE: DNA
<213> ORGANISM: Homo sapiens

<400> SEQUENCE: 2422
ccctcccagg ytaagctgcg g                                              21

<210> SEQ ID NO 2423
<211> LENGTH: 21
<212> TYPE: DNA
<213> ORGANISM: Homo sapiens

<400> SEQUENCE: 2423
ctcacgcaag scgaagacca g                                              21

<210> SEQ ID NO 2424
<211> LENGTH: 21
<212> TYPE: DNA
<213> ORGANISM: Homo sapiens

<400> SEQUENCE: 2424
tcaacacctc ytccttgctg g                                              21

<210> SEQ ID NO 2425
<211> LENGTH: 21
<212> TYPE: DNA
<213> ORGANISM: Homo sapiens

<400> SEQUENCE: 2425
gagctaagcc rgggcaagct c                                              21

<210> SEQ ID NO 2426
<211> LENGTH: 21
<212> TYPE: DNA
<213> ORGANISM: Homo sapiens

<400> SEQUENCE: 2426
ctaagccggg kcaagctcta t                                              21

<210> SEQ ID NO 2427
<211> LENGTH: 21
```

-continued

<212> TYPE: DNA
<213> ORGANISM: Homo sapiens

<400> SEQUENCE: 2427
tcttcacggg rtactacggg a					21

<210> SEQ ID NO 2428
<211> LENGTH: 21
<212> TYPE: DNA
<213> ORGANISM: Homo sapiens

<400> SEQUENCE: 2428
gggtcatgag ygtctgtctg c					21

<210> SEQ ID NO 2429
<211> LENGTH: 21
<212> TYPE: DNA
<213> ORGANISM: Homo sapiens

<400> SEQUENCE: 2429
tgctgcccat ycgctggatg g					21

<210> SEQ ID NO 2430
<211> LENGTH: 21
<212> TYPE: DNA
<213> ORGANISM: Homo sapiens

<400> SEQUENCE: 2430
aagatctggt yagtcttgat t					21

<210> SEQ ID NO 2431
<211> LENGTH: 21
<212> TYPE: DNA
<213> ORGANISM: Homo sapiens

<400> SEQUENCE: 2431
taccaggagc yccggcctcg t					21

<210> SEQ ID NO 2432
<211> LENGTH: 21
<212> TYPE: DNA
<213> ORGANISM: Homo sapiens

<400> SEQUENCE: 2432
cgccccactc ygctccctgt g					21

<210> SEQ ID NO 2433
<211> LENGTH: 21
<212> TYPE: DNA
<213> ORGANISM: Homo sapiens

<400> SEQUENCE: 2433
tggagaacgg ygacctcaac c					21

<210> SEQ ID NO 2434
<211> LENGTH: 21
<212> TYPE: DNA
<213> ORGANISM: Homo sapiens

<400> SEQUENCE: 2434
tgaaagcttt kacctggagc c					21

<210> SEQ ID NO 2435

```
<211> LENGTH: 21
<212> TYPE: DNA
<213> ORGANISM: Homo sapiens

<400> SEQUENCE: 2435
ccacgcgatt satcaggatc t                                              21

<210> SEQ ID NO 2436
<211> LENGTH: 21
<212> TYPE: DNA
<213> ORGANISM: Homo sapiens

<400> SEQUENCE: 2436
gaccttctgg yatcacatgt c                                              21

<210> SEQ ID NO 2437
<211> LENGTH: 21
<212> TYPE: DNA
<213> ORGANISM: Homo sapiens

<400> SEQUENCE: 2437
ttcccaagct kacgaaaatc a                                              21

<210> SEQ ID NO 2438
<211> LENGTH: 21
<212> TYPE: DNA
<213> ORGANISM: Homo sapiens

<400> SEQUENCE: 2438 tttttacac ygacagcgcg a                                               21

<210> SEQ ID NO 2439
<211> LENGTH: 21
<212> TYPE: DNA
<213> ORGANISM: Homo sapiens

<400> SEQUENCE: 2439
acttgggcct yctgcgcttt g                                              21

<210> SEQ ID NO 2440
<211> LENGTH: 21
<212> TYPE: DNA
<213> ORGANISM: Homo sapiens

<400> SEQUENCE: 2440
gaaatctggg mtggattccc t                                              21

<210> SEQ ID NO 2441
<211> LENGTH: 21
<212> TYPE: DNA
<213> ORGANISM: Homo sapiens

<400> SEQUENCE: 2441
cagaatggag stgctgggct g                                              21

<210> SEQ ID NO 2442
<211> LENGTH: 21
<212> TYPE: DNA
<213> ORGANISM: Homo sapiens

<400> SEQUENCE: 2442
ttgtctttgc rccaaagatg t                                              21
```

```
<210> SEQ ID NO 2443
<211> LENGTH: 21
<212> TYPE: DNA
<213> ORGANISM: Homo sapiens

<400> SEQUENCE: 2443
tgggtcccac rtcggcacac t                                              21

<210> SEQ ID NO 2444
<211> LENGTH: 21
<212> TYPE: DNA
<213> ORGANISM: Homo sapiens

<400> SEQUENCE: 2444
ggattgctaa ygaacagatc a                                              21

<210> SEQ ID NO 2445
<211> LENGTH: 21
<212> TYPE: DNA
<213> ORGANISM: Homo sapiens

<400> SEQUENCE: 2445
atgacacccc kgacatccga a                                              21

<210> SEQ ID NO 2446
<211> LENGTH: 21
<212> TYPE: DNA
<213> ORGANISM: Homo sapiens

<400> SEQUENCE: 2446
tggcactcag rtatcgccct c                                              21

<210> SEQ ID NO 2447
<211> LENGTH: 21
<212> TYPE: DNA
<213> ORGANISM: Homo sapiens

<400> SEQUENCE: 2447
atggctacta ygtcaaatcc t                                              21

<210> SEQ ID NO 2448
<211> LENGTH: 21
<212> TYPE: DNA
<213> ORGANISM: Homo sapiens

<400> SEQUENCE: 2448
gttcatcgac rgggatcctc t                                              21

<210> SEQ ID NO 2449
<211> LENGTH: 21
<212> TYPE: DNA
<213> ORGANISM: Homo sapiens

<400> SEQUENCE: 2449
gcaacctcag kgtctggcgc c                                              21

<210> SEQ ID NO 2450
<211> LENGTH: 21
<212> TYPE: DNA
<213> ORGANISM: Homo sapiens

<400> SEQUENCE: 2450
gctatatcac ytctcccggt t                                              21
```

<210> SEQ ID NO 2451
<211> LENGTH: 21
<212> TYPE: DNA
<213> ORGANISM: Homo sapiens

<400> SEQUENCE: 2451
cttttgcagt kgacatccca g                                              21

<210> SEQ ID NO 2452
<211> LENGTH: 21
<212> TYPE: DNA
<213> ORGANISM: Homo sapiens

<400> SEQUENCE: 2452
ttgcagtgga satcccagaa a                                              21

<210> SEQ ID NO 2453
<211> LENGTH: 21
<212> TYPE: DNA
<213> ORGANISM: Homo sapiens

<400> SEQUENCE: 2453
aaggatatga rgatgaaatt g                                              21

<210> SEQ ID NO 2454
<211> LENGTH: 21
<212> TYPE: DNA
<213> ORGANISM: Homo sapiens

<400> SEQUENCE: 2454
agatgaaatt katgatgaat a                                              21

<210> SEQ ID NO 2455
<211> LENGTH: 21
<212> TYPE: DNA
<213> ORGANISM: Homo sapiens

<400> SEQUENCE: 2455
tcgttcatcg wcggggatcc t                                              21

<210> SEQ ID NO 2456
<211> LENGTH: 21
<212> TYPE: DNA
<213> ORGANISM: Homo sapiens

<400> SEQUENCE: 2456
atggcggtgg ycaaggatgg c                                              21

<210> SEQ ID NO 2457
<211> LENGTH: 21
<212> TYPE: DNA
<213> ORGANISM: Homo sapiens

<400> SEQUENCE: 2457
acaatgggaa raaatcagta g                                              21

<210> SEQ ID NO 2458
<211> LENGTH: 21
<212> TYPE: DNA
<213> ORGANISM: Homo sapiens

<400> SEQUENCE: 2458
actggttcat rgccgtctgt t                                              21

-continued

<210> SEQ ID NO 2459
<211> LENGTH: 21
<212> TYPE: DNA
<213> ORGANISM: Homo sapiens

<400> SEQUENCE: 2459
tgtcagcaag rttgacaaaa t                                              21

<210> SEQ ID NO 2460
<211> LENGTH: 21
<212> TYPE: DNA
<213> ORGANISM: Homo sapiens

<400> SEQUENCE: 2460
caaaagaaag rcatcaaagc c                                              21

<210> SEQ ID NO 2461
<211> LENGTH: 21
<212> TYPE: DNA
<213> ORGANISM: Homo sapiens

<400> SEQUENCE: 2461
agaacaaatg mtttggttca c                                              21

<210> SEQ ID NO 2462
<211> LENGTH: 21
<212> TYPE: DNA
<213> ORGANISM: Homo sapiens

<400> SEQUENCE: 2462
aattacgatg yttcagctgc a                                              21

<210> SEQ ID NO 2463
<211> LENGTH: 21
<212> TYPE: DNA
<213> ORGANISM: Homo sapiens

<400> SEQUENCE: 2463
aaggctatga yattcgtctg a                                              21

<210> SEQ ID NO 2464
<211> LENGTH: 21
<212> TYPE: DNA
<213> ORGANISM: Homo sapiens

<400> SEQUENCE: 2464
ctctgggtgc ytgataccta t                                              21

<210> SEQ ID NO 2465
<211> LENGTH: 21
<212> TYPE: DNA
<213> ORGANISM: Homo sapiens

<400> SEQUENCE: 2465
ctggatggaa sctacagtga g                                              21

<210> SEQ ID NO 2466
<211> LENGTH: 21
<212> TYPE: DNA
<213> ORGANISM: Homo sapiens

<400> SEQUENCE: 2466

-continued accaccatca ycacgggcgt g                                              21

<210> SEQ ID NO 2467
<211> LENGTH: 21
<212> TYPE: DNA
<213> ORGANISM: Homo sapiens

<400> SEQUENCE: 2467
cgtctcctac rtcaaggccg t                                              21

<210> SEQ ID NO 2468
<211> LENGTH: 21
<212> TYPE: DNA
<213> ORGANISM: Homo sapiens

<400> SEQUENCE: 2468
gtcctgctcc mgttcaccac t                                              21

<210> SEQ ID NO 2469
<211> LENGTH: 21
<212> TYPE: DNA
<213> ORGANISM: Homo sapiens

<400> SEQUENCE: 2469
gataacagca mgccacattt g                                              21

<210> SEQ ID NO 2470
<211> LENGTH: 21
<212> TYPE: DNA
<213> ORGANISM: Homo sapiens

<400> SEQUENCE: 2470
ctgggtagtg yaacgtgcaa g                                              21

<210> SEQ ID NO 2471
<211> LENGTH: 21
<212> TYPE: DNA
<213> ORGANISM: Homo sapiens

<400> SEQUENCE: 2471
ctggcctctt yaccgtggag a                                              21

<210> SEQ ID NO 2472
<211> LENGTH: 21
<212> TYPE: DNA
<213> ORGANISM: Homo sapiens

<400> SEQUENCE: 2472
ctaccccaac mcagaaacta c                                              21

<210> SEQ ID NO 2473
<211> LENGTH: 21
<212> TYPE: DNA
<213> ORGANISM: Homo sapiens

<400> SEQUENCE: 2473
gtgtgcccca ragtccgagc c                                              21

<210> SEQ ID NO 2474
<211> LENGTH: 21
<212> TYPE: DNA
<213> ORGANISM: Homo sapiens

<400> SEQUENCE: 2474
atcagcttct rcatgctctg t                                              21

<210> SEQ ID NO 2475
<211> LENGTH: 21
<212> TYPE: DNA
<213> ORGANISM: Homo sapiens

<400> SEQUENCE: 2475
accacctgga ygagtttaaa a                                              21

<210> SEQ ID NO 2476
<211> LENGTH: 21
<212> TYPE: DNA
<213> ORGANISM: Homo sapiens

<400> SEQUENCE: 2476
ccggctccaa ygccaacatc a                                              21

<210> SEQ ID NO 2477
<211> LENGTH: 21
<212> TYPE: DNA
<213> ORGANISM: Homo sapiens

<400> SEQUENCE: 2477
cttcacatag yccttttggt a                                              21

<210> SEQ ID NO 2478
<211> LENGTH: 21
<212> TYPE: DNA
<213> ORGANISM: Homo sapiens

<400> SEQUENCE: 2478
aagaggaccc wgctccatgt g                                              21

<210> SEQ ID NO 2479
<211> LENGTH: 21
<212> TYPE: DNA
<213> ORGANISM: Homo sapiens

<400> SEQUENCE: 2479
gctggacaga ygtgctctac t                                              21

<210> SEQ ID NO 2480
<211> LENGTH: 21
<212> TYPE: DNA
<213> ORGANISM: Homo sapiens

<400> SEQUENCE: 2480
ggcaagttta wttttgatga a                                              21

<210> SEQ ID NO 2481
<211> LENGTH: 21
<212> TYPE: DNA
<213> ORGANISM: Homo sapiens

<400> SEQUENCE: 2481
tgctgagcag ygctgccctg g                                              21

<210> SEQ ID NO 2482
<211> LENGTH: 21
<212> TYPE: DNA
<213> ORGANISM: Homo sapiens

```
<400> SEQUENCE: 2482
ttgaagatga yaacttttgg a                                              21

<210> SEQ ID NO 2483
<211> LENGTH: 21
<212> TYPE: DNA
<213> ORGANISM: Homo sapiens

<400> SEQUENCE: 2483
actgggttac yttgactatg c                                              21

<210> SEQ ID NO 2484
<211> LENGTH: 21
<212> TYPE: DNA
<213> ORGANISM: Homo sapiens

<400> SEQUENCE: 2484
tgcctctcaa yagtgacggg a                                              21

<210> SEQ ID NO 2485
<211> LENGTH: 21
<212> TYPE: DNA
<213> ORGANISM: Homo sapiens

<400> SEQUENCE: 2485
tgctttggtt ygaacggctc t                                              21

<210> SEQ ID NO 2486
<211> LENGTH: 21
<212> TYPE: DNA
<213> ORGANISM: Homo sapiens

<400> SEQUENCE: 2486
cagatatcgt rgctgaagag g                                              21

<210> SEQ ID NO 2487
<211> LENGTH: 21
<212> TYPE: DNA
<213> ORGANISM: Homo sapiens

<400> SEQUENCE: 2487
accaagcgga kcacctttga c                                              21

<210> SEQ ID NO 2488
<211> LENGTH: 21
<212> TYPE: DNA
<213> ORGANISM: Homo sapiens

<400> SEQUENCE: 2488
tcaccttttt ycgtcttttc c                                              21

<210> SEQ ID NO 2489
<211> LENGTH: 21
<212> TYPE: DNA
<213> ORGANISM: Homo sapiens

<400> SEQUENCE: 2489
gctacagcga ygaagagcca g                                              21

<210> SEQ ID NO 2490
<211> LENGTH: 21
<212> TYPE: DNA
<213> ORGANISM: Homo sapiens
```

```
<400> SEQUENCE: 2490
cccgagccaa yggggatgtg g                                          21

<210> SEQ ID NO 2491
<211> LENGTH: 21
<212> TYPE: DNA
<213> ORGANISM: Homo sapiens

<400> SEQUENCE: 2491
tacatcgagc rtgcttcatg a                                          21

<210> SEQ ID NO 2492
<211> LENGTH: 21
<212> TYPE: DNA
<213> ORGANISM: Homo sapiens

<400> SEQUENCE: 2492
gccactacat ygtgaacctg c                                          21

<210> SEQ ID NO 2493
<211> LENGTH: 21
<212> TYPE: DNA
<213> ORGANISM: Homo sapiens

<400> SEQUENCE: 2493
atgtagatca ygagaaaaac a                                          21

<210> SEQ ID NO 2494
<211> LENGTH: 21
<212> TYPE: DNA
<213> ORGANISM: Homo sapiens

<400> SEQUENCE: 2494
agaacgagaa ygaacgctgc g                                          21

<210> SEQ ID NO 2495
<211> LENGTH: 21
<212> TYPE: DNA
<213> ORGANISM: Homo sapiens

<400> SEQUENCE: 2495
tatggacccc rccgatgacg g                                          21

<210> SEQ ID NO 2496
<211> LENGTH: 21
<212> TYPE: DNA
<213> ORGANISM: Homo sapiens

<400> SEQUENCE: 2496
atgacggaca kttccaagaa c                                          21

<210> SEQ ID NO 2497
<211> LENGTH: 21
<212> TYPE: DNA
<213> ORGANISM: Homo sapiens

<400> SEQUENCE: 2497
gctggcagga rgccttgatg a                                          21

<210> SEQ ID NO 2498
<211> LENGTH: 21
<212> TYPE: DNA
```

```
<213> ORGANISM: Homo sapiens

<400> SEQUENCE: 2498
ccctcctttc ytacagctcc c                                              21

<210> SEQ ID NO 2499
<211> LENGTH: 21
<212> TYPE: DNA
<213> ORGANISM: Homo sapiens

<400> SEQUENCE: 2499
aacgctttgg saaccaacaa a                                              21

<210> SEQ ID NO 2500
<211> LENGTH: 21
<212> TYPE: DNA
<213> ORGANISM: Homo sapiens

<400> SEQUENCE: 2500
tgacttcatc rccgtgattg g                                              21

<210> SEQ ID NO 2501
<211> LENGTH: 21
<212> TYPE: DNA
<213> ORGANISM: Homo sapiens

<400> SEQUENCE: 2501
ttgatgccct ytgatgaggc c                                              21

<210> SEQ ID NO 2502
<211> LENGTH: 21
<212> TYPE: DNA
<213> ORGANISM: Homo sapiens

<400> SEQUENCE: 2502
tggacaggat yttcacagcg t                                              21

<210> SEQ ID NO 2503
<211> LENGTH: 21
<212> TYPE: DNA
<213> ORGANISM: Homo sapiens

<400> SEQUENCE: 2503
aggctctctt ygacttcctc a                                              21

<210> SEQ ID NO 2504
<211> LENGTH: 21
<212> TYPE: DNA
<213> ORGANISM: Homo sapiens

<400> SEQUENCE: 2504
catgcggcct rtggtgctgg t                                              21

<210> SEQ ID NO 2505
<211> LENGTH: 21
<212> TYPE: DNA
<213> ORGANISM: Homo sapiens

<400> SEQUENCE: 2505
actctgccta ygtagagcca a                                              21

<210> SEQ ID NO 2506
<211> LENGTH: 21
```

<210> SEQ ID NO 2506
<211> LENGTH: 21
<212> TYPE: DNA
<213> ORGANISM: Homo sapiens

<400> SEQUENCE: 2506
catttgactc rgaaacccag g                                    21

<210> SEQ ID NO 2507
<211> LENGTH: 21
<212> TYPE: DNA
<213> ORGANISM: Homo sapiens

<400> SEQUENCE: 2507
ccaattgaaa racgaagtct a                                    21

<210> SEQ ID NO 2508
<211> LENGTH: 21
<212> TYPE: DNA
<213> ORGANISM: Homo sapiens

<400> SEQUENCE: 2508
ggagcaggtt kaaaagatcc g                                    21

<210> SEQ ID NO 2509
<211> LENGTH: 21
<212> TYPE: DNA
<213> ORGANISM: Homo sapiens

<400> SEQUENCE: 2509
acacttacaa rccccatagg a                                    21

<210> SEQ ID NO 2510
<211> LENGTH: 21
<212> TYPE: DNA
<213> ORGANISM: Homo sapiens

<400> SEQUENCE: 2510
tcctgcacgg ygggcaaccc c                                    21

<210> SEQ ID NO 2511
<211> LENGTH: 21
<212> TYPE: DNA
<213> ORGANISM: Homo sapiens

<400> SEQUENCE: 2511
acacacacca ycgctcaccc a                                    21

<210> SEQ ID NO 2512
<211> LENGTH: 21
<212> TYPE: DNA
<213> ORGANISM: Homo sapiens

<400> SEQUENCE: 2512
aagattttta yagaagacat t                                    21

<210> SEQ ID NO 2513
<211> LENGTH: 21
<212> TYPE: DNA
<213> ORGANISM: Homo sapiens

<400> SEQUENCE: 2513
acacttcaga ygtggtgatt g                                    21

<210> SEQ ID NO 2514

```
<211> LENGTH: 21
<212> TYPE: DNA
<213> ORGANISM: Homo sapiens

<400> SEQUENCE: 2514
ctggaacccc rctgattttg g                                              21

<210> SEQ ID NO 2515
<211> LENGTH: 21
<212> TYPE: DNA
<213> ORGANISM: Homo sapiens

<400> SEQUENCE: 2515
aagttatacg ygttccttca g                                              21

<210> SEQ ID NO 2516
<211> LENGTH: 21
<212> TYPE: DNA
<213> ORGANISM: Homo sapiens

<400> SEQUENCE: 2516
ccattagata matttcgaga c                                              21

<210> SEQ ID NO 2517
<211> LENGTH: 21
<212> TYPE: DNA
<213> ORGANISM: Homo sapiens

<400> SEQUENCE: 2517
gatactactc rgcgctgcga c                                              21

<210> SEQ ID NO 2518
<211> LENGTH: 21
<212> TYPE: DNA
<213> ORGANISM: Homo sapiens

<400> SEQUENCE: 2518
gaaaacgatc yagcccagag a                                              21

<210> SEQ ID NO 2519
<211> LENGTH: 21
<212> TYPE: DNA
<213> ORGANISM: Homo sapiens

<400> SEQUENCE: 2519
gcgactgggg ytgtccggac t                                              21

<210> SEQ ID NO 2520
<211> LENGTH: 21
<212> TYPE: DNA
<213> ORGANISM: Homo sapiens

<400> SEQUENCE: 2520
tggtcttcat ygtcacttcc t                                              21

<210> SEQ ID NO 2521
<211> LENGTH: 21
<212> TYPE: DNA
<213> ORGANISM: Homo sapiens

<400> SEQUENCE: 2521
tgatgtgtgt ractgtgagg c                                              21
```

```
<210> SEQ ID NO 2522
<211> LENGTH: 21
<212> TYPE: DNA
<213> ORGANISM: Homo sapiens

<400> SEQUENCE: 2522
gccgctgacc kccgtctaca c                                        21

<210> SEQ ID NO 2523
<211> LENGTH: 21
<212> TYPE: DNA
<213> ORGANISM: Homo sapiens

<400> SEQUENCE: 2523
tggaggagtc rgagcatctg c                                        21

<210> SEQ ID NO 2524
<211> LENGTH: 21
<212> TYPE: DNA
<213> ORGANISM: Homo sapiens

<400> SEQUENCE: 2524
cctccacctg ygtcaaccca t                                        21

<210> SEQ ID NO 2525
<211> LENGTH: 21
<212> TYPE: DNA
<213> ORGANISM: Homo sapiens

<400> SEQUENCE: 2525
agttcctggc rgataaggtg g                                        21

<210> SEQ ID NO 2526
<211> LENGTH: 21
<212> TYPE: DNA
<213> ORGANISM: Homo sapiens

<400> SEQUENCE: 2526
gggcttcatc ytggtctgtt a                                        21

<210> SEQ ID NO 2527
<211> LENGTH: 21
<212> TYPE: DNA
<213> ORGANISM: Homo sapiens

<400> SEQUENCE: 2527
catctaccgg ygcctgcaga g                                        21

<210> SEQ ID NO 2528
<211> LENGTH: 21
<212> TYPE: DNA
<213> ORGANISM: Homo sapiens

<400> SEQUENCE: 2528
gtgatggtgg wggcctttgc c                                        21

<210> SEQ ID NO 2529
<211> LENGTH: 21
<212> TYPE: DNA
<213> ORGANISM: Homo sapiens

<400> SEQUENCE: 2529
tggcctttgc ygtgctctgg c                                        21
```

<210> SEQ ID NO 2530
<211> LENGTH: 21
<212> TYPE: DNA
<213> ORGANISM: Homo sapiens

<400> SEQUENCE: 2530
caacagcctg raagactggc a                                              21

<210> SEQ ID NO 2531
<211> LENGTH: 21
<212> TYPE: DNA
<213> ORGANISM: Homo sapiens

<400> SEQUENCE: 2531
ccatctgcca ygggaacctc a                                              21

<210> SEQ ID NO 2532
<211> LENGTH: 21
<212> TYPE: DNA
<213> ORGANISM: Homo sapiens

<400> SEQUENCE: 2532
tgactcatgc ytactggggc a                                              21

<210> SEQ ID NO 2533
<211> LENGTH: 21
<212> TYPE: DNA
<213> ORGANISM: Homo sapiens

<400> SEQUENCE: 2533
accacccagc rtctaataca a                                              21

<210> SEQ ID NO 2534
<211> LENGTH: 21
<212> TYPE: DNA
<213> ORGANISM: Homo sapiens

<400> SEQUENCE: 2534
gagcccttcc rcaacctctc t                                              21

<210> SEQ ID NO 2535
<211> LENGTH: 21
<212> TYPE: DNA
<213> ORGANISM: Homo sapiens

<400> SEQUENCE: 2535
aaggtacttg ygttcagaaa a                                              21

<210> SEQ ID NO 2536
<211> LENGTH: 21
<212> TYPE: DNA
<213> ORGANISM: Homo sapiens

<400> SEQUENCE: 2536
tccacactct kcctgtgtca g                                              21

<210> SEQ ID NO 2537
<211> LENGTH: 21
<212> TYPE: DNA
<213> ORGANISM: Homo sapiens

<400> SEQUENCE: 2537
taaggaccag raagacaagg c                                              21

<210> SEQ ID NO 2538
<211> LENGTH: 21
<212> TYPE: DNA
<213> ORGANISM: Homo sapiens

<400> SEQUENCE: 2538
gggcctattc kcattgccgg a                                              21

<210> SEQ ID NO 2539
<211> LENGTH: 21
<212> TYPE: DNA
<213> ORGANISM: Homo sapiens

<400> SEQUENCE: 2539
cttagatggc racctgtccg a                                              21

<210> SEQ ID NO 2540
<211> LENGTH: 21
<212> TYPE: DNA
<213> ORGANISM: Homo sapiens

<400> SEQUENCE: 2540
atgtatgaga kttgggtgcc a                                              21

<210> SEQ ID NO 2541
<211> LENGTH: 21
<212> TYPE: DNA
<213> ORGANISM: Homo sapiens

<400> SEQUENCE: 2541
gacaggatgt rgcccggttt a                                              21

<210> SEQ ID NO 2542
<211> LENGTH: 21
<212> TYPE: DNA
<213> ORGANISM: Homo sapiens

<400> SEQUENCE: 2542
tggaggagga rtttaactac c                                              21

<210> SEQ ID NO 2543
<211> LENGTH: 21
<212> TYPE: DNA
<213> ORGANISM: Homo sapiens

<400> SEQUENCE: 2543
caaataagac mtactccttc c                                              21

<210> SEQ ID NO 2544
<211> LENGTH: 21
<212> TYPE: DNA
<213> ORGANISM: Homo sapiens

<400> SEQUENCE: 2544
caatctgggc katgagatca a                                              21

<210> SEQ ID NO 2545
<211> LENGTH: 21
<212> TYPE: DNA
<213> ORGANISM: Homo sapiens

<400> SEQUENCE: 2545

```
-continued cagaattact rgcctcgatc c                                      21

<210> SEQ ID NO 2546
<211> LENGTH: 21
<212> TYPE: DNA
<213> ORGANISM: Homo sapiens

<400> SEQUENCE: 2546
ctggtcgaag mattggaatc c                                      21

<210> SEQ ID NO 2547
<211> LENGTH: 21
<212> TYPE: DNA
<213> ORGANISM: Homo sapiens

<400> SEQUENCE: 2547
gacttggaga wgtggaccag c                                      21

<210> SEQ ID NO 2548
<211> LENGTH: 21
<212> TYPE: DNA
<213> ORGANISM: Homo sapiens

<400> SEQUENCE: 2548
aataagaagt saggctgaaa c                                      21

<210> SEQ ID NO 2549
<211> LENGTH: 21
<212> TYPE: DNA
<213> ORGANISM: Homo sapiens

<400> SEQUENCE: 2549
taagaagtca rgctgaaact g                                      21

<210> SEQ ID NO 2550
<211> LENGTH: 21
<212> TYPE: DNA
<213> ORGANISM: Homo sapiens

<400> SEQUENCE: 2550
aggctgaaac ygggcgaatc t                                      21

<210> SEQ ID NO 2551
<211> LENGTH: 21
<212> TYPE: DNA
<213> ORGANISM: Homo sapiens

<400> SEQUENCE: 2551
gaaactgggc raatctacag a                                      21
```